US011999974B2

(12) United States Patent
Abeliovich et al.

(10) Patent No.: US 11,999,974 B2
(45) Date of Patent: Jun. 4, 2024

(54) GENE THERAPIES FOR LYSOSOMAL DISORDERS

(71) Applicant: Prevail Therapeutics, Inc., New York, NY (US)

(72) Inventors: Asa Abeliovich, New York, NY (US); Laura Heckman, New York, NY (US); Herve Rhinn, New York, NY (US); Li Chin Wong, New York, NY (US); Hsuan-Ni Lin, New York, NY (US); Franz Hefti, New York, NY (US)

(73) Assignee: Prevail Therapeutics, Inc., New York, NY (US)

( * ) Notice: Subject to any disclaimer, the term of this patent is extended or adjusted under 35 U.S.C. 154(b) by 722 days.

(21) Appl. No.: 16/846,065

(22) Filed: Apr. 10, 2020

(65) Prior Publication Data

US 2020/0332265 A1 Oct. 22, 2020

Related U.S. Application Data

(60) Provisional application No. 62/988,665, filed on Mar. 12, 2020, provisional application No. 62/960,471, filed on Jan. 13, 2020, provisional application No. 62/954,089, filed on Dec. 27, 2019, provisional application No. 62/934,450, filed on Nov. 12, 2019, provisional application No. 62/831,846, filed on Apr. 10, 2019.

(51) Int. Cl.

| | |
|---|---|
| ***C12N 7/00*** | (2006.01) |
| ***A61K 48/00*** | (2006.01) |
| ***A61P 25/28*** | (2006.01) |
| ***C07K 14/435*** | (2006.01) |
| ***C12N 9/02*** | (2006.01) |
| ***G01N 33/68*** | (2006.01) |

(52) U.S. Cl.

CPC ............ *C12N 7/00* (2013.01); *A61K 48/0075* (2013.01); *A61K 48/0083* (2013.01); *A61P 25/28* (2018.01); *C07K 14/435* (2013.01); *C12N 9/0071* (2013.01); *C12Y 114/18001* (2013.01); *G01N 33/6803* (2013.01); *C12N 2750/14132* (2013.01); *C12N 2750/14133* (2013.01); *C12N 2750/14143* (2013.01); *G01N 2333/435* (2013.01)

(58) Field of Classification Search

CPC ...................... C12N 7/00; C12N 15/86; C12N 2750/14143; C12N 2750/14132; C12N 9/0071; C12N 2750/14133; A61P 25/28; A61K 48/0075; A61K 48/0083; C07K 14/435; C12Y 114/18001; G01N 33/6803

See application file for complete search history.

(56) References Cited

U.S. PATENT DOCUMENTS

| | | | |
|---|---|---|---|
| 7,452,716 B2 | 11/2008 | Yew | |
| 8,486,635 B2 | 7/2013 | Hutton et al. | |
| 9,034,836 B2 | 5/2015 | Dodge et al. | |
| 9,486,541 B2 | 11/2016 | Hutton et al. | |
| 10,689,625 B2 | 6/2020 | Abeliovich et al. | |
| 11,655,460 B2 | 5/2023 | Abeliovich et al. | |
| 11,661,585 B2 | 5/2023 | Abeliovich et al. | |
| 2003/0133924 A1 | 7/2003 | Canfield | |
| 2006/0292117 A1 | 12/2006 | Loiler et al. | |
| 2008/0003204 A1 | 1/2008 | Flotte et al. | |
| 2013/0287736 A1 | 10/2013 | Passini et al. | |
| 2015/0284472 A1 | 8/2015 | Sardi et al. | |
| 2017/0246263 A1 | 8/2017 | Concino et al. | |
| 2018/0147300 A1 | 5/2018 | Park et al. | |
| 2019/0282662 A1 | 9/2019 | Kay et al. | |
| 2019/0328906 A1 | 10/2019 | Chen Plotkin et al. | |
| 2019/0388507 A1 | 12/2019 | Kay | |
| 2020/0231970 A1 | 7/2020 | Abeliovich et al. | |
| 2020/0308554 A1 | 10/2020 | Abeliovich et al. | |
| 2020/0318115 A1 | 10/2020 | Abeliovich et al. | |
| 2020/0338148 A1 | 10/2020 | Abeliovich et al. | |
| 2021/0317474 A1* | 10/2021 | Kaspar | A61K 39/12 |
| 2021/0332385 A1 | 10/2021 | Abeliovich et al. | |
| 2023/0287358 A1 | 9/2023 | Abeliovich | |
| 2023/0346979 A1 | 11/2023 | Abeliovich et al. | |

FOREIGN PATENT DOCUMENTS

| | | |
|---|---|---|
| EP | 2687223 A1 | 1/2014 |
| WO | WO-0183692 A2 | 11/2001 |
| WO | WO-2009079399 A2 | 6/2009 |
| WO | WO-2009120978 A2 | 10/2009 |
| WO | WO 2014/071282 A1 | 5/2014 |
| WO | WO 2014/186579 A1 | 11/2014 |
| WO | WO 2016/081927 A2 | 3/2016 |

(Continued)

OTHER PUBLICATIONS

Button et al. Power failure: why small sample size undermines the reliability of neuroscience. Nat Rev Neurosci. May 2013;14(5):365-76. doi: 10.1038/nrn3475. Epub Apr. 10, 2013.*

(Continued)

*Primary Examiner* — Olga N Chernyshev

(74) *Attorney, Agent, or Firm* — COOLEY LLP; Ivor Elrifi

(57) ABSTRACT

The disclosure relates to compositions and methods for treatment of diseases associated with aberrant lysosomal function, such as fronto-temporal dementia (FTD). The disclosure also provides expression constructs comprising a transgene encoding progranulin or a portion thereof. The disclosure provides methods of treating FTD by administering such expression constructs to a subject in need thereof.

13 Claims, 83 Drawing Sheets

Specification includes a Sequence Listing.

(56) References Cited

FOREIGN PATENT DOCUMENTS

| | | | |
|---|---|---|---|
| WO | WO 2017/136202 | A1 | 8/2017 |
| WO | WO 2019/070891 | A1 | 4/2019 |
| WO | WO 2019/070893 | A1 | 4/2019 |
| WO | WO 2019/070894 | A1 | 4/2019 |
| WO | WO-2019084068 | A1 | 5/2019 |
| WO | WO 2020/210615 | A1 | 10/2020 |

OTHER PUBLICATIONS

Gorski One reason mouse studies often don't translate to humans very well. Science-Based Medicine.org. Aug. 26, 2019. pp. 1-11. Retrieved from https://sciencebasedmedicine.org/one-reason-mouse-studies-often-dont-translate-to-humans-very-well/on Feb. 10, 2023.*
Mayo Clinic (Frontotemporal Dementia—Diagnosis and treatment. Retrieved from https://www.mayoclinic.org/diseases-conditions/frontotemporal-dementia/diagnosis-treatment/drc-20354741#.~:text=There's%20currently%20no%20cure%20or,the%20symptoms%20of%20frontotemporal%20dementia on Feb. 10, 2023).*
Anderson, et al. "Human pathology in NCL." Biochim Biophys Acta. Nov. 2013;1832(11):1807-26. doi: 10.1016/j.bbadis.2012.11.014.
Bond, et al. "Use of model organisms for the study of neuronal ceroid lipofuscinosis." Biochim Biophys Acta. Nov. 2013;1832(11):1842-65. doi: 10.1016/j.bbadis.2013.01.009.
Gotz, et al. "Animal models for Alzheimer's disease and frontotemporal dementia: a perspective." ASN Neuro. Nov. 9, 2009;1(4):e00019. doi: 10.1042/AN20090042.
Xu, et al. "Extracellular progranulin protects cortical neurons from toxic insults by activating survival signaling." Neurobiol Aging. Dec. 2011;32(12):2326.e5-16. doi: 10.1016/j.neurobiolaging.2011.06.017.
Yu, et al. "The spectrum of mutations in progranulin: a collaborative study screening 545 cases of neurodegeneration." Arch Neurol. Feb. 2010;67(2):161-70. doi: 10.1001/archneurol.2009.328.
Arrant, et al. "Progranulin Gene Therapy Improves Lysosomal Dysfunction and Microglial Pathology Associated with Frontotemporal Dementia and Neuronal Ceroid Lipofuscinosis." J. Neurosci. Feb. 28, 2018;38(9):2341-2358. doi: 10.1523/JNEUROSCI.3081-17.2018.
Ciesielska, et al. "Cerebral infusion of AAV9 vector-encoding non-self proteins can elicit cell-mediated immune responses." Mol Ther. Jan. 2013;21(1):158-66. doi: 10.1038/mt.2012.167.
GenBank Accession No. AAP36904.1 "*Homo sapiens* glucosidase, beta; acid (includes glucosylceramidase), partial [synthetic construct]" Jul. 25, 2016 [online].
GenBank Accession No. BT008212.1 "Synthetic construct *Homo sapiens* glucosidase, beta; acid (includes glucosylceramidase) mRNA, partial cds" Jul. 25, 2016 [online].
GenBank Accession No. NP_000148.2 "Lysosomal acid glucosylceramidase isoform 1 precursor [*Homo sapiens*]" Jan. 8, 2020 [online].
GenBank Accession No. NP_005497.1 "Lysosome membrane protein 2 isoform 1 precursor [*Homo sapiens*]" Jan. 1, 2020 [online].
GenBank Accession No. NP_002769.1 "Prosaposin isoform a preproprotein [*Homo sapiens*]" Sep. 27, 2019 [online].
GenBank Accession No. NP_001191184.1 "Lysosome membrane protein 2 isoform 2 precursor [*Homo sapiens*]" Jan. 4, 2020 [online].
GenBank Accession No. AAH01503.1 "Prosaposin [*Homo sapiens*]" Aug. 4, 2008 [online].
GenBank Accession No. AAH07612.1 "Prosaposin [*Homo sapiens*]" Aug. 4, 2008 [online].
GenBank Accession No. AAH04275.1 "Prosaposin [*Homo sapiens*]" Aug. 4, 2008 [online].
GenBank Accession No. AAA60303.1 "Prosaposin [*Homo sapiens*]" Jan. 9, 1995 [online].
GenBank Accession No. NP_001005742.1 "Lysosomal acid glucosylceramidase isoform 1 precursor [*Homo sapiens*]" Nov. 11, 2019 [online].
GenBank Accession No. NP_001165282.1 "Lysosomal acid glucosylceramidase isoform 2 [*Homo sapiens*]" Nov. 11, 2019 [online].
GenBank Accession No. NP_001165283.1 "Lysosomal acid glucosylceramidase isoform 3 [*Homo sapiens*]" Nov. 11, 2019 [online].
GenBank Accession No. NP_065995.1 "Non-lysosomal glucosylceramidase isoform 1 [*Homo sapiens*]" Aug. 22, 2019 [online].
GenBank Accession No. NP_000144.2 "Galactocerebrosidase isoform a precursor [*Homo sapiens*]" Sep. 26, 2019 [online].
GenBank Accession No. NP_001899.1 "Cathepsin B isoform 1 preproprotein [*Homo sapiens*]" Jan. 27, 2020 [online].
GenBank Accession No. NP_000534.3 "Sphingomyelin phosphodiesterase isoform 1 precursor [*Homo sapiens*]" Jan. 13, 2020 [online].
GenBank Accession No. NP_003920.1 "Ras-related protein Rab-7L1 isoform 1 [*Homo sapiens*]" Dec. 31, 2019 [online].
GenBank Accession No. NP_060676.2 "Vacuolar protein sorting-associated protein 35 [*Homo sapiens*]" Oct. 11, 2019 [online].
GenBank Accession No. NP_689669.2 "Interleukin-34 isoform 1 precursor [*Homo sapiens*]" Dec. 25, 2019 [online].
GenBank Accession No. NP_061838.1 "Triggering receptor expressed on myeloid cells 2 precursor isoform 1 precursor [*Homo sapiens*]" Feb. 2, 2020 [online].
GenBank Accession No. NP_060844.2 "Transmembrane protein 106B [*Homo sapiens*]" Jul. 28, 2019 [online].
GenBank Accession No. NP_002078.1 "Progranulin precursor [*Homo sapiens*]" Jan. 21, 2020 [online].
GenBank Accession No. NP_001317589.1 "Non-lysosomal glucosylceramidase isoform 2 [*Homo sapiens*]" Aug. 7, 2019 [online].
GenBank Accession No. EAW81359.1 "Galactosylceramidase, isoform CRA_a [*Homo sapiens*]" Mar. 23, 2015 [online].
GenBank Accession No. EAW81360.1 "Galactosylceramidase, isoform CRA_b [*Homo sapiens*]" Mar. 23, 2015 [online].
GenBank Accession No. EAW81362.1 "Galactosylceramidase, isoform CRA_c [*Homo sapiens*]" Mar. 23, 2015 [online].
GenBank Accession No. EAW68726.1 "Sphingomyelin phosphodiesterase 1, acid lysosomal (acid sphingomyelinase), isoform CRA_a [*Homo sapiens*]" Mar. 23, 2015 [online].
GenBank Accession No. EAW68727.1 "Sphingomyelin phosphodiesterase 1, acid lysosomal (acid sphingomyelinase), isoform CRA_b [*Homo sapiens*]" Mar. 23, 2015 [online].
GenBank Accession No. EAW68728.1 "Sphingomyelin phosphodiesterase 1, acid lysosomal (acid sphingomyelinase), isoform CRA_c [*Homo sapiens*]" Mar. 23, 2015 [online].
GenBank Accession No. EAW68729.1 "Sphingomyelin phosphodiesterase 1, acid lysosomal (acid sphingomyelinase), isoform CRA_d [*Homo sapiens*]" Mar. 23, 2015 [online].
GenBank Accession No. AAC37547.1 "Cathepsin B [*Homo sapiens*]" Apr. 7, 1994 [online].
GenBank Accession No. AAH95408.1 "Cathepsin B [*Homo sapiens*]" Jul. 17, 2006 [online].
GenBank Accession No. AAH10240.1 "Cathepsin B [*Homo sapiens*]" Jul. 15, 2006 [online].
GenBank Accession No. AAH02585.1 "RAB7, member RAS oncogene family-like 1 [*Homo sapiens*]" Jul. 15, 2006 [online].
GenBank Accession No. AAH25415.1 "GTP cyclohydrolase 1 [*Homo sapiens*]" Aug. 7, 2008 [online].
GenBank Accession No. AAH29804.1 "Interleukin 34 [*Homo sapiens*]" Jun. 9, 2008 [online].
GenBank Accession No. AAF69824.1 "Triggering receptor expressed on myeloid cells 2 [*Homo sapiens*]" May 23, 2000 [online].
GenBank Accession No. NP_002087.1 "General transcription factor IIF, polypeptide 1, 74kDa [*Homo sapiens*]" Jun. 3, 2007 [online].
GenBank Accession No. NP_000152.1 "GTP cyclohydrolase 1 isoform 1 [*Homo sapiens*]" Dec. 30, 2019 [online].
Samaranch, et al. "AAV9-mediated expression of a non-self protein in nonhuman primate central nervous system triggers widespread neuroinflammation driven by antigen-presenting cell transduction." Mol Ther. Feb. 2014;22(2):329-337. doi: 10.1038/mt.2013.266.
Database Accession No. Q14108, "Lysosome membrane protein II," Nov. 1, 1997, https://www.uniprot.org/Q14108.txt, 1-10.

(56) References Cited

OTHER PUBLICATIONS

Database Accession No. BDA66566, "Adeno-associated virus—2 (AAV2) ITR S-sequence, SEQ ID 3," Jul. 14, 2016, http://ibis.internal.epo.org/exam/dbfetch.jsp?id=GSN:BDA66566, 1 page.

Renaud-Gabardos, et al., "Internal ribosome entry site-based vectors for combined gene therapy," World Journal of Experimental Medicine, Feb. 20, 2015, 5(1), 11-20.

Rothaug, et al., "LIMP-2 expression is critical for β-glucocerebrosidase activity and α-synuclein clearance," PNAS, Oct. 28, 2014, 111(43), 15573-15578.

Supplemental European Search Report issued in EP application No. 18864729.1 dated July 2, 2021, 1-12.

Tamargo, et al., "The role of saposin C in Gaucher disease," Molecular Genetics and Metabolism, Apr. 29, 2012, 106, 257-263.

Choi et al., "Optimization of AAV expression cassettes to improve packaging capacity and transgene expression in neurons," Molecular Brain, 2014, 7(17):1-10.

François, A., et al., "The Cellular TATA Binding Protein is Required for Rep-Dependent Replication of a Minimal Adeno-associated Virus Type 2 p5 Element," Journal of Virology, Sep. 2005, 79(17):11082-11094.

G0345, pFBAAVCAGmcsBgHpA Viral Vector Core updated Feb. 22, 2017 [retrieved from the internet on Jun. 10, 2022] URL: https://medicine.uiowa.edu/vectorcore/sites/medicine.uiowa.edu.vectorcore/files/wysiwyg_uploads/Manual_G0345_pFBAAVCAGmcsBgHpA_0.pdf, 7 pages.

Ge, J., et al., "Optimization of eGFP Expression using a Modified Baculovirus Expression System," Journal of biotechnology, 2014, 173:41-6.

Huang, W., et al., "Targeting Visceral Fat by Intraperitoneal Delivery of Novel AAV Serotype Vector Restricting Off-Target Transduction in Liver," Molecular Therapy—Methods & Clinical Development, Sep. 2017, 6:68-78.

Jian, J., et al., "Association Between Progranulin and Gaucher Disease," EBioMedicine, 2016, 11:127-37.

Sikora, J., et al., "Neurolysosomal pathology in human prosaposin deficiency suggests essential neurotrophic function of prosaposin," Acta Neuropathol., Feb. 2007, 113(2):163-175.

Wang, L., et al., "Enhancing Transgene Expression from Recombinant AAV8 Vectors in Different Tissues Using Woodchuck Hepatitis Virus Post-Transcriptional Regulatory Element," International Journal of Medical Sciences, 2016, 13(4):286-291.

[Author Unknown] "Optimization of use frequency of codons for high level expression of a plant-derived fatty acid desaturase in mammalian cells". Mem. School. B. O. S. T. Kinki University, 2008, No. 22, pp. 33-41.

Cenik, B. et al. "Suberoylanilide Hydroxamic Acid (Vorinostat) Up-regulates Progranulin Transcription," The Journal of Biological Chemistry, May 6, 2011, 286(18):16101-16108.

Fath, S. et al., "Multiparameter RNA and Codon Optimization: A Standardized Tool to Assess and Enhance Autologous Mammalian Gene Expression," PLoS ONE, Mar. 3, 2011, 6(3):e17596:1-14.

Heckman, L. et al. "Preclinical development of PR006, a gene therapy for the treatment of frontotemporal dementia with progranulin mutations," Alzheimer's & Dementia, Dec. 7, 2020, 16(Supp. 2):e043632, 2 pages.

Lu, et al., "Complete correction of hemophilia A with adeno-associated viral vectors containing a full-size expression cassette." Hum Gene Ther. Jun. 2008, 19(6):648-654. doi: 10.1089/hum.2007.0182.

NCBI Reference Sequence: "*Homo sapiens* granulin precursor (GRN), mRNA," NCBI Reference Sequence: NM_002087.3, Feb. 26, 2020, 5 pages.

Savy, et al., "Impact of Inverted Terminal Repeat Integrity on rAAV8 Production Using the Baculovirus/Sf9 Cells System," Human Gene Therapy Methods, 2017, 28(5):277-289.

Valdez, C. et al. "Progranulin-mediated deficiency of cathepsin D results in FTD and NCL-like phenotypes in neurons derived from FTD patients," Human Molecular Genetics, 2017, 26(24):4861-4872.

Amado et al. "AAV-Mediated Progranulin Delivery to a Mouse Model of Progranulin Deficiency Causes T Cell-Mediated Toxicity," Molecular Therapy, Feb. 2019, 27(2):465-478.

* cited by examiner

| PR001B dose | Total vg | vg/g brain | Ratio to clinical* |
|---|---|---|---|
| max | 8.8e9 | 5.9e10 | 0.8x |

updated_38.GRN_PW aligned both VM and P (1)

10,870 bp

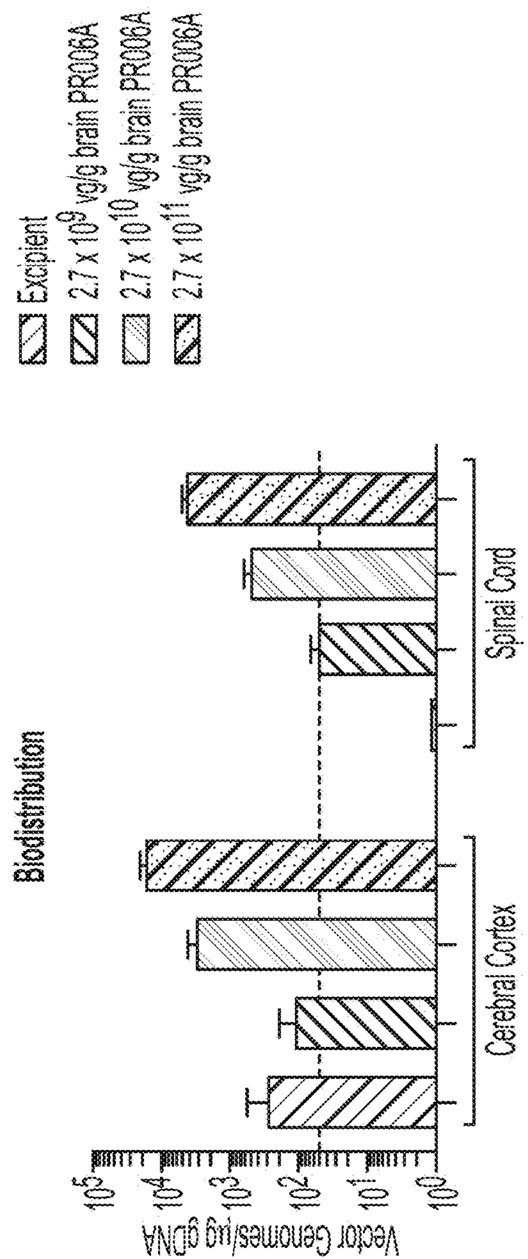
FIG. 53A
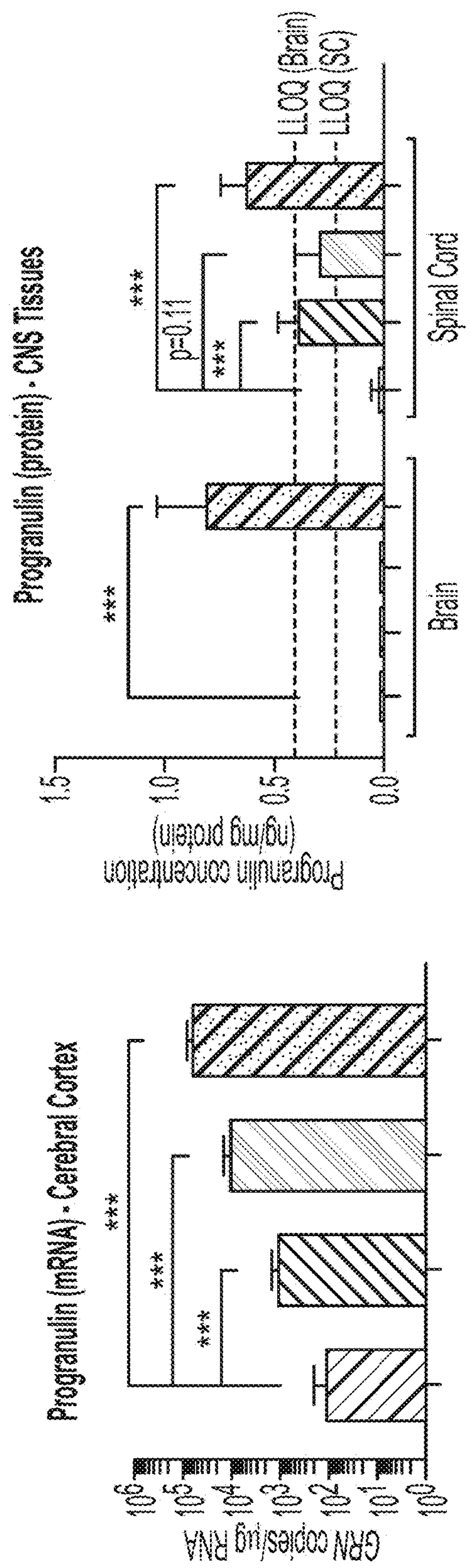
FIG. 53B
FIG. 53C

Lipofuscin Score
0 (Normal; no finding)
1 (Minimal)
2 (Mild)
3 (Moderate)

WT
*Grn* KO + excipient
*Grn* KO + 2.7 x $10^9$ vg/g brain PR006A
*Grn* KO + 2.7 x $10^{10}$ vg/g brain PR006A
*Grn* KO + 2.7 x $10^{11}$ vg/g brain PR006A

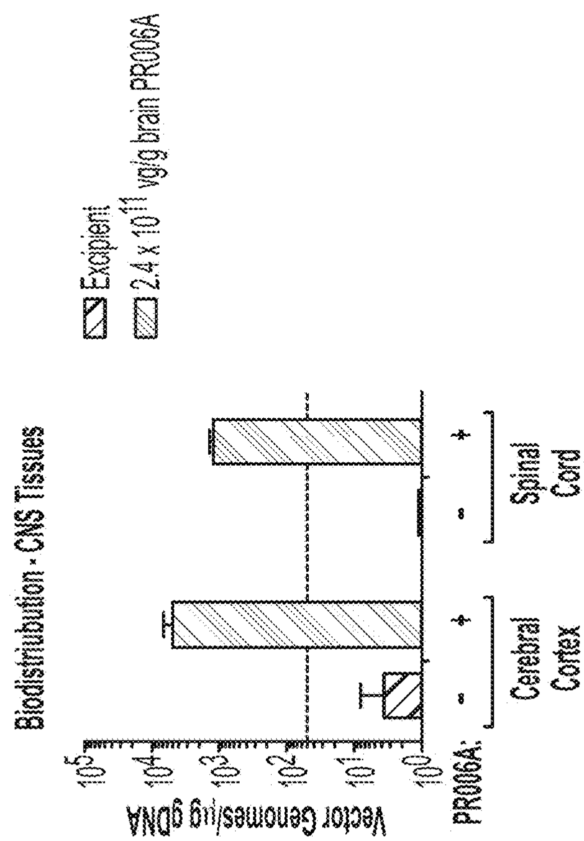
FIG. 59A
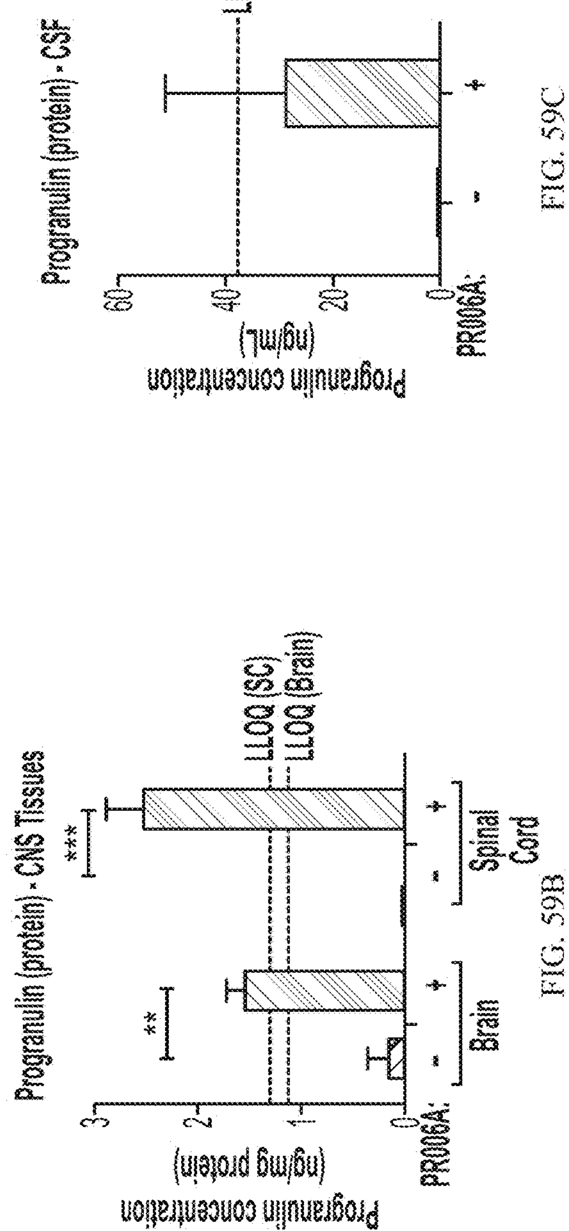
FIG. 59C
FIG. 59B

| PR006A dose | Total vg | vg / g brain |
|---|---|---|
| single | $9.7 \times 10^{10}$ | $2.4 \times 10^{11}$ |

| PR006A dose | Total vg | vg / g brain |
|---|---|---|
| Low | $1.1 \times 10^{9}$ | $2.7 \times 10^{9}$ |
| Medium | $1.1 \times 10^{10}$ | $2.7 \times 10^{10}$ |
| High | $1.1 \times 10^{11}$ | $2.7 \times 10^{11}$ |

SEQUENCE LISTING

```
<160> NUMBER OF SEQ ID NOS: 91

<210> SEQ ID NO 1
<211> LENGTH: 10697
<212> TYPE: DNA
<213> ORGANISM: Artificial sequence
<220> FEATURE:
<223> OTHER INFORMATION: Synthetic polynucleotide

<400> SEQUENCE: 1

ttggccactc cctctctgcg cgctcgctcg ctcactgagg ccgggcgacc aaaggtcgcc      60

cgacgcccgg gctttgcccg ggcggcctca gtgagcgagc gagcgcgcag agagggagtg     120
```

```
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg aattcggtac    300
cctagttatt aatagtaatc aattacgggg tcattagttc atagcccata tatggagttc    360
cgcgttacat aacttacggt aaatggcccg cctggctgac cgcccaacga cccccgccca    420
ttgacgtcaa taatgacgta tgttcccata gtaacgccaa tagggacttt ccattgacgt    480
caatgggtgg actatttacg gtaaactgcc cacttggcag tacatcaagt gtatcatatg    540
ccaagtacgc cccctattga cgtcaatgac ggtaaatggc ccgcctggca ttatgcccag    600
tacatgacct tatgggactt tcctacttgg cagtacatct acgtattagt catcgctatt    660
accatggtcg aggtgagccc cacgttctgc ttcactctcc ccatctcccc cccctcccca    720
cccccaattt tgtatttatt tatttttaa ttattttgtg cagcgatggg ggcgggggg    780
gggggggggc gcgcgccagg cggggcgggg cggggcgagg ggcggggcgg ggcgaggcgg    840
agaggtgcgg cggcagccaa tcagagcggc gcgctccgaa agtttccttt tatggcgagg    900
cggcggcggc ggcggcccta taaaaagcga agcgcgcggc gggcgggagt cgctgcgacg    960
ctgccttcgc cccgtgcccc gctccgccgc cgcctcgcgc cgcccgcccc ggctctgact   1020
gaccgcgtta ctcccacagg tgagcgggcg ggacggccct tctcctccgg gctgtaatta   1080
gcgcttggtt taatgacggc ttgtttctg tggctgcgtg aaagccttga ggggctccgg    1140
gagctagagc ctctgctaac catgttcatg ccttcttctt tttcctacag ctcctgggca   1200
acgtgctggt tattgtgctg tctcatcatt ttggcaaaga attcctcgaa gatccgaagg   1260
gaaagtcttc cacgactgtg ggatccgttc gaagatatca ccggttgagc caccatggaa   1320
ttcagcagcc ccagcagaga ggaatgcccc aagcctctga gccgggtgtc aatcatggcc   1380
ggatctctga caggactgct gctgcttcag gccgtgtctt gggcttctgg cgctagacct   1440
tgcatcccca agagcttcgg ctacagcagc gtcgtgtgcg tgtgcaatgc cacctactgc   1500
gacagcttcg accctcctac ctttcctgct ctgggcacct tcagcagata cgagagcacc   1560
agatccggca gacggatgga actgagcatg ggacccatcc aggccaatca cacaggcact   1620
ggcctgctgc tgacactgca gcctgagcag aaattccaga aagtgaaagg cttcggcgga   1680
gccatgacag atgccgccgc tctgaatatc ctggctctgt ctccaccagc tcagaacctg   1740
ctgctcaaga gctacttcag cgaggaaggc atcggctaca acatcatcag agtgcccatg   1800
gccagctgcg acttcagcat caggacctac acctacgccg acacacccga cgatttccag   1860
ctgcacaact tcagcctgcc tgaagaggac accaagctga agatccctct gatccacaga   1920
gccctgcagc tggcacaaag acccgtgtca ctgctggcct ctccatggac atctcccacc   1980
tggctgaaaa caaatggcgc cgtgaatggc aagggcagcc tgaaaggcca acctggcgac   2040
atctaccacc agacctgggc cagatacttc gtgaagttcc tggacgccta tgccgagcac   2100
aagctgcagt tttgggccgt gacagccgag aacgaacctt ctgctggact gctgagcggc   2160
taccccttc agtgcctggg ctttacaccc gagcaccagc gggactttat cgcccgtgat    2220
ctgggaccca cactggccaa tagcacccac cataatgtgc ggctgctgat gctggacgac   2280
cagagactgc ttctgcccca ctgggctaaa gtggtgctga cagatcctga ggccgccaaa   2340
tacgtgcacg gaatcgccgt gcactggtat ctggactttc tggcccctgc caaggccaca   2400
ctgggagaga cacacagact gttccccaac accatgctgt tcgccagcga agcctgtgtg   2460
ggcagcaagt tttgggaaca gagcgtgcgg ctcggcagct gggatagagg catgcagtac   2520
```

```
agccacagca tcatcaccaa cctgctgtac cacgtcgtcg gctggaccga ctggaatctg   2580
gccctgaatc ctgaaggcgg ccctaactgg gtccgaaact tcgtggacag ccccatcatc   2640
gtggacatca ccaaggacac cttctacaag cagcccatgt tctaccacct gggacacttc   2700
agcaagttca tccccgaggg ctctcagcgc gttggactgg tggcttccca gaagaacgat   2760
ctggacgccg tggctctgat gcaccctgat ggatctgctg tggtggtggt cctgaaccgc   2820
agcagcaaag atgtgcccct gaccatcaag gatcccgccg tgggattcct ggaaacaatc   2880
agccctggct actccatcca cacctacctg tggcgtagac agtgacaatt gttaattaag   2940
tttaaaccct cgaggccgca agcttatcga taatcaacct ctggattaca aaatttgtga   3000
aagattgact ggtattctta actatgttgc tccttttacg ctatgtggat acgctgcttt   3060
aatgcctttg tatcatgcta ttgcttcccg tatggctttc attttctcct ccttgtataa   3120
atcctggttg ctgtctcttt atgaggagtt gtggcccgtt gtcaggcaac gtggcgtggt   3180
gtgcactgtg tttgctgacg caacccccac tggttggggc attgccacca cctgtcagct   3240
cctttccggg actttcgctt tccccctccc tattgccacg gcggaactca tcgccgcctg   3300
ccttgcccgc tgctggacag gggctcggct gttgggcact gacaattccg tggtgttgtc   3360
ggggaaatca tcgtcctttc cttggctgct cgcctgtgtt gccacctgga ttctgcgcgg   3420
gacgtccttc tgctacgtcc cttcggccct caatccagcg gaccttcctt cccgcggcct   3480
gctgccggct ctgcggcctc ttccgcgtct tcgccttcgc cctcagacga gtcggatctc   3540
cctttgggcc gcctccccgc atcgataccg tcgactagag ctcgctgatc agcctcgact   3600
gtgccttcta gttgccagcc atctgttgtt tgcccctccc ccgtgccttc cttgaccctg   3660
gaaggtgcca ctcccactgt cctttcctaa taaaatgagg aaattgcatc gcattgtctg   3720
agtaggtgtc attctattct ggggggtggg gtggggcagg acagcaaggg ggaggattgg   3780
gaagacaata gcaggcatgc tggggagaga tccacgataa caaacagctt ttttggggtg   3840
aacatattga ctgaattccc tgcaggttgg ccactccctc tctgcgcgct cgctcgctca   3900
ctgaggccgc ccgggcaaag cccgggcgtc gggcgacctt tggtcgcccg gcctcagtga   3960
gcgagcgagc gcgcagagag ggagtggcca actccatcac taggggttcc tgcggccgct   4020
cgtacggtct cgaggaattc ctgcaggata acttgccaac ctcattctaa aatgtatata   4080
gaagcccaaa agacaataac aaaaatattc ttgtagaaca aaatgggaaa gaatgttcca   4140
ctaaatatca agatttagag caaagcatga gatgtgtggg gatagacagt gaggctgata   4200
aaatagagta gagctcagaa acagacccat tgatatatgt aagtgaccta tgaaaaaaat   4260
atggcatttt acaatgggaa aatgatggtc tttttctttt ttagaaaaac agggaaatat   4320
atttatatgt aaaaaataaa agggaaccca tatgtcatac catacacaca aaaaaattcc   4380
agtgaattat aagtctaaat ggagaaggca aaactttaaa tcttttagaa aataatatag   4440
aagcatgcag accagcctgg ccaacatgat gaaaccctct ctactaataa taaaatcagt   4500
agaactactc aggactactt tgagtgggaa gtccttttct atgaagactt ctttggccaa   4560
aattaggctc taaatgcaag gagatagtgc atcatgcctg gctgcactta ctgataaatg   4620
atgttatcac catctttaac caaatgcaca ggaacaagtt atggtactga tgtgctggat   4680
tgagaaggag ctctacttcc ttgacaggac acatttgtat caacttaaaa aagcagattt   4740
ttgccagcag aactattcat tcagaggtag gaaacttaga atagatgatg tcactgatta   4800
gcatggcttc cccatctcca cagctgcttc ccacccaggt tgcccacagt tgagtttgtc   4860
```

-continued

```
cagtgctcag ggctgcccac tctcagtaag aagccccaca ccagcccctc tccaaatatg   4920
ttggctgttc cttccattaa agtgacccca ctttagagca gcaagtggat ttctgtttct   4980
tacagttcag gaaggaggag tcagctgtga gaacctggag cctgagatgc ttctaagtcc   5040
cactgctact ggggtcaggg aagccagact ccagcatcag cagtcaggag cactaagccc   5100
ttgccaacat cctgtttctc agagaaactg cttccattat aatggttgtc ctttttttaag   5160
ctatcaagcc aaacaaccag tgtctaccat tattctcatc acctgaagcc aagggttcta   5220
gcaaaagtca agctgtcttg taatggttga tgtgcctcca gcttctgtct tcagtcactc   5280
cactcttagc ctgctctgaa tcaactctga ccacagttcc ctggagcccc tgccacctgc   5340
tgcccctgcc accttctcca tctgcagtgc tgtgcagcct tctgcactct tgcagagcta   5400
ataggtggag acttgaagga agaggaggaa agtttctcat aatagccttg ctgcaagctc   5460
aaatgggagg tgggcactgt gcccaggagc cttggagcaa aggctgtgcc caacctctga   5520
ctgcatccag gtttggtctt gacagagata agaagccctg gcttttggag ccaaaatcta   5580
ggtcagactt aggcaggatt ctcaaagttt atcagcagaa catgaggcag aagacccttt   5640
ctgctccagc ttcttcaggc tcaaccttca tcagaataga tagaaagaga ggctgtgagg   5700
gttcttaaaa cagaagcaaa tctgactcag agaataaaca acctcctagt aaactacagc   5760
ttagacagag catctggtgg tgagtgtgct cagtgtccta ctcaactgtc tggtatcagc   5820
cctcatgagg acttctcttc tttccctcat agacctccat ctctgttttc cttagcctgc   5880
agaaatctgg atggctattc acagaatgcc tgtgctttca gagttgcatt ttttctctgg   5940
tattctggtt caagcatttg aaggtaggaa aggttctcca agtgcaagaa agccagccct   6000
gagcctcaac tgcctggcta gtgtggtcag taggatgcaa aggctgttga atgccacaag   6060
gccaaacttt aacctgtgta ccacaagcct agcagcagag gcagctctgc tcactggaac   6120
tctctgtctt ctttctcctg agccttttct tttcctgagt tttctagctc tcctcaacct   6180
tacctctgcc ctacccagga caaacccaag agccactgtt tctgtgatgt cctctccagc   6240
cctaattagg catcatgact tcagcctgac cttccatgct cagaagcagt gctaatccac   6300
ttcagatgag ctgctctatg caacacaggc agagcctaca aacctttgca ccagagccct   6360
ccacatatca gtgtttgttc atactcactt caacagcaaa tgtgactgct gagattaaga   6420
ttttacacaa gatggtctgt aatttcacag ttagttttat cccattaggt atgaaagaat   6480
tagcataatt ccccttaaac atgaatgaat cttagatttt ttaataaata gttttggaag   6540
taaagacaga gacatcagga gcacaaggaa tagcctgaga ggacaaacag aacaagaaag   6600
agtctggaaa tacacaggat gttcttggcc tcctcaaagc aagtgcaagc agatagtacc   6660
agcagcccca ggctatcaga gcccagtgaa gagaagtacc atgaaagcca cagctctaac   6720
caccctgttc cagagtgaca gacagtcccc aagacaagcc agcctgagcc agagagagaa   6780
ctgcaagaga aagtttctaa tttaggttct gttagattca gacaagtgca ggtcatcctc   6840
tctccacagc tactcacctc tccagcctaa caaagcctgc agtccacact ccaaccctgg   6900
tgtctcacct cctagcctct cccaacatcc tgctctctga ccatcttctg catctctcat   6960
ctcaccatct cccactgtct acagcctact cttgcaacta ccatctcatt ttctgacatc   7020
ctgtctacat cttctgccat actctgccat ctaccatacc acctcttacc atctaccaca   7080
ccatctttta tctccatccc tctcagaagc ctccaagctg aatcctgctt tatgtgttca   7140
tctcagcccc tgcatggaaa gctgacccca gaggcagaac tattcccaga gagcttggcc   7200
aagaaaaaca aaactaccag cctggccagg ctcaggagta gtaagctgca gtgtctgttg   7260
```

```
tgttctagct tcaacagctg caggagttcc actctcaaat gctccacatt tctcacatcc   7320
tcctgattct ggtcactacc catcttcaaa gaacagaata tctcacatca gcatactgtg   7380
aaggactagt catgggtgca gctgctcaga gctgcaaagt cattctggat ggtggagagc   7440
ttacaaacat ttcatgatgc tccccccgct ctgatggctg gagcccaatc cctacacaga   7500
ctcctgctgt atgtgttttc ctttcactct gagccacagc cagagggcag gcattcagtc   7560
tcctcttcag gctggggctg gggcactgag aactcaccca acaccttgct ctcactcctt   7620
ctgcaaaaca agaaagagct ttgtgctgca gtagccatga agaatgaaag gaaggcttta   7680
actaaaaaat gtcagagatt attttcaacc ccttactgtg gatcaccagc aaggaggaaa   7740
cacaacacag agacattttt tcccctcaaa ttatcaaaag aatcactgca tttgttaaag   7800
agagcaactg aatcaggaag cagagttttg aacatatcag aagttaggaa tctgcatcag   7860
agacaaatgc agtcatggtt gtttgctgca taccagccct aatcattaga agcctcatgg   7920
acttcaaaca tcattccctc tgacaagatg ctctagccta actccatgag ataaaataaa   7980
tctgcctttc agagccaaag aagagtccac cagcttcttc tcagtgtgaa caagagctcc   8040
agtcaggtta gtcagtccag tgcagtagag gagaccagtc tgcatcctct aattttcaaa   8100
ggcaagaaga tttgtttacc ctggacacca ggcacaagtg aggtcacaga gctcttagat   8160
atgcagtcct catgagtgag gagactaaag cgcatgccat caagacttca gtgtagagaa   8220
aacctccaaa aaagcctcct cactacttct ggaatagctc agaggccgag gcggcctcgg   8280
cctctgcata aataaaaaaa attagtcagc catggggcgg agaatgggcg gaactgggcg   8340
gagttagggg cgggatgggc ggagttaggg gcgggactat ggttgctgac taattgagat   8400
gcatgctttg catacttctg cctgctgggg agcctgggga ctttccacac ctggttgctg   8460
actaattgag atgcatgctt tgcatacttc tgcctgctgg ggagcctggg gactttccac   8520
accctaactg acacacattc cacagctgca ttaatgaatc ggccaacgcg cggggagagg   8580
cggtttgcgt attgggcgct cttccgcttc ctcgctcact gactcgctgc gctcggtcgt   8640
tcggctgcgg cgagcggtat cagctcactc aaaggcggta atacggttat ccacagaatc   8700
aggggataac gcaggaaaga acatgtgagc aaaaggccag caaaaggcca ggaaccgtaa   8760
aaaggccgcg ttgctggcgt ttttccatag gctccgcccc cctgacgagc atcacaaaaa   8820
tcgacgctca agtcagaggt ggcgaaaccc gacaggacta taaagatacc aggcgtttcc   8880
ccctggaagc tccctcgtgc gctctcctgt tccgaccctg ccgcttaccg gatacctgtc   8940
cgcctttctc ccttcgggaa gcgtggcgct ttctcatagc tcacgctgta ggtatctcag   9000
ttcggtgtag gtcgttcgct ccaagctggg ctgtgtgcac gaaccccccg ttcagcccga   9060
ccgctgcgcc ttatccggta actatcgtct tgagtccaac ccggtaagac acgacttatc   9120
gccactggca gcagccactg gtaacaggat tagcagagcg aggtatgtag gcggtgctac   9180
agagttcttg aagtggtggc ctaactacgg ctacactaga agaacagtat ttggtatctg   9240
cgctctgctg aagccagtta ccttcggaaa aagagttggt agctcttgat ccggcaaaca   9300
aaccaccgct ggtagcggtg gtttttttgt ttgcaagcag cagattacgc gcagaaaaaa   9360
aggatctcaa gaagatcctt tgatcttttc tacggggtct gacgctcagt ggaacgaaaa   9420
ctcacgttaa gggattttgg tcatgagatt atcaaaaagg atcttcacct agatcctttt   9480
aaattaaaaa tgaagtttta aatcaatcta aagtatatat gagtaaactt ggtctgacag   9540
ttaccaatgc ttaatcagtg aggcacctat ctcagcgatc tgtctatttc gttcatccat   9600
```

-continued

```
agttgcctga ctcctgcaaa ccacgttgtg tctcaaaatc tctgatgtta cattgcacaa   9660

gataaaaata tatcatcatg aacaataaaa ctgtctgctt acataaacag taatacaagg   9720

ggtgttatga gccatattca acgggaaacg tcttgctcga ggccgcgatt aaattccaac   9780

atggatgctg atttatatgg gtataaatgg gctcgcgata atgtcgggca atcaggtgcg   9840

acaatctatc gattgtatgg gaagcccgat gcgccagagt tgtttctgaa acatggcaaa   9900

ggtagcgttg ccaatgatgt tacagatgag atggtcagac taaactggct gacggaattt   9960

atgcctcttc cgaccatcaa gcattttatc cgtactcctg atgatgcatg gttactcacc  10020

actgcgatcc ccgggaaaac agcattccag gtattagaag aatatcctga ttcaggtgaa  10080

aatattgttg atgcgctggc agtgttcctg cgccggttgc attcgattcc tgtttgtaat  10140

tgtcctttta acagcgatcg cgtatttcgt ctcgctcagg cgcaatcacg aatgaataac  10200

ggtttggttg atgcgagtga ttttgatgac gagcgtaatg gctggcctgt tgaacaagtc  10260

tggaaagaaa tgcataagct tttgccattc tcaccggatt cagtcgtcac tcatggtgat  10320

ttctcacttg ataaccttat ttttgacgag gggaaattaa taggttgtat tgatgttgga  10380

cgagtcggaa tcgcagaccg ataccaggat cttgccatcc tatggaactg cctcggtgag  10440

ttttctcctt cattacagaa acggcttttt caaaaatatg gtattgataa tcctgatatg  10500

aataaattgc agtttcattt gatgctcgat gagtttttct aagggcggcc tgccaccata  10560

cccacgccga aacaagcgct catgagcccg aagtggcgag cccgatcttc cccatcggtg  10620

atgtcggcga tataggcgcc agcaaccgca cctgtggcgc cggtgatgag ggcgcgccaa  10680

gtcgacgtcc ggcagtc                                                 10697
```

<210> SEQ ID NO 2
<211> LENGTH: 11355
<212> TYPE: DNA
<213> ORGANISM: Artificial sequence
<220> FEATURE:
<223> OTHER INFORMATION: Synthetic polynucleotide

<400> SEQUENCE: 2

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg agggcggagt    300

tagggcggag ccaatcagcg tgcgccgttc cgaaagttgc cttttatggc tgggcggaga    360

atgggcggtg aacgccgatg attatataag gacgcgccgg gtgtggcaca gctagttccg    420

tcgcagccgg gatttgggtc gcggttcttg tttgtggatc cctgtgatcg tcacttggta    480

agtcactgac tgtctatgcc tgggaaaggg tgggcaggag atggggcagt gcaggaaaag    540

tggcactatg aaccctgcag ccctaggaat gcatctagac aattgtacta accttcttct    600

ctttcctctc ctgacagtcc ggaaagccac catgggccgc tgctgcttct acaccgccgg    660

caccctgagc ctgctgctgc tggtgaccag cgtgaccctg ctggtggccc gcgtgttcca    720

gaaggccgtg gaccagagca tcgagaagaa gatcgtgctg cgcaacggca ccgaggcctt    780

cgacagctgg gagaagcccc ccctgcccgt gtacacccag ttctacttct tcaacgtgac    840

caaccccgag gagatcctgc gcggcgagac cccccgcgtg gaggaggtgg gcccctacac    900

ctaccgcgag ctgcgcaaca aggccaacat ccagttcggc gacaacggca ccaccatcag    960
```

-continued

```
cgccgtgagc aacaaggcct acgtgttcga gcgcgaccag agcgtgggcg accccaagat   1020
cgacctgatc cgcaccctga acatccccgt gctgaccgtg atcgagtgga gccaggtgca   1080
cttcctgcgc gagatcatcg aggccatgct gaaggcctac cagcagaagc tgttcgtgac   1140
ccacaccgtg gacgagctgc tgtggggcta caaggacgag atcctgagcc tgatccacgt   1200
gttccgcccc gacatcagcc cctacttcgg cctgttctac gagaagaacg gcaccaacga   1260
cggcgactac gtgttcctga ccggcgagga cagctacctg aacttcacca agatcgtgga   1320
gtggaacggc aagaccagcc tggactggtg gatcaccgac aagtgcaaca tgatcaacgg   1380
caccgacggc gacagcttcc accccctgat caccaaggac gaggtgctgt acgtgttccc   1440
cagcgacttc tgccgcagcg tgtacatcac cttcagcgac tacgagagcg tgcagggcct   1500
gcccgccttc cgctacaagg tgcccgccga gatcctggcc aacaccagcg acaacgccgg   1560
cttctgcatc cccgagggca actgcctggg cagcggcgtg ctgaacgtga gcatctgcaa   1620
gaacggcgcc cccatcatca tgagcttccc ccacttctac caggccgacg agcgcttcgt   1680
gagcgccatc gagggcatgc accccaacca ggaggaccac gagaccttcg tggacatcaa   1740
cccccctgacc ggcatcatcc tgaaggccgc caagcgcttc cagatcaaca tctacgtgaa   1800
gaagctggac gacttcgtgg agaccggcga catccgcacc atggtgttcc ccgtgatgta   1860
cctgaacgag agcgtgcaca tcgacaagga gaccgccagc cgcctgaaga gcatgatcaa   1920
caccaccctg atcatcacca acatccccta catcatcatg gccctgggcg tgttcttcgg   1980
cctggtgttc acctggctgg cctgcaaggg ccagggcagc atggacgagg gcaccgccga   2040
cgagcgcgcc cccctgatcc gcacctgatt gtggccgaac cgccgaactc agaggccggc   2100
cccagaaaac ccgagcgagt agggggcggc gcgcaggagg gaggagaact gggggcgcgg   2160
gaggctggtg ggtgtggggg gtggagatgt agaagatgtg acgccgcggc ccggcgggtg   2220
ccagattagc ggacgcggtg cccgcggttg caacgggatc ccgggcgctg cagcttggga   2280
ggcggctctc cccaggcggc gtccgcggag acacccatcc gtgaacccca ggtcccgggc   2340
cgccggctcg ccgcgcacca ggggccggcg gacagaagag cggccgagcg gctcgaggct   2400
gggggaccgc gggcgcggcc gcgcgctgcc gggcgggagg ctgggggccc ggggccgggg   2460
ccgtgccccg gagcgggtcg gaggccgggg ccggggccgg gggacggcgg ctccccgcgc   2520
ggctccagcg gctcggggat cccggccggg ccccgcaggg accatgatgg aattcagcag   2580
ccccagcaga gaggaatgcc ccaagcctct gagccgggtg tcaatcatgg ccggatctct   2640
gacaggactg ctgctgcttc aggccgtgtc ttgggcttct ggcgctagac cttgcatccc   2700
caagagcttc ggctacagca gcgtcgtgtg cgtgtgcaat gccacctact gcgacagctt   2760
cgaccctcct acctttcctg ctctgggcac cttcagcaga tacgagagca ccagatccgg   2820
cagacggatg gaactgagca tgggacccat ccaggccaat cacacaggca ctggcctgct   2880
gctgacactg cagcctgagc agaaattcca gaaagtgaaa ggcttcggcg gagccatgac   2940
agatgccgcc gctctgaata tcctggctct gtctccacca gctcagaacc tgctgctcaa   3000
gagctacttc agcgaggaag gcatcggcta caacatcatc agagtgccca tggccagctg   3060
cgacttcagc atcaggacct acacctacgc cgacacaccc gacgatttcc agctgcacaa   3120
cttcagcctg cctgaagagg acaccaagct gaagatccct ctgatccaca gagccctgca   3180
gctggcacaa agacccgtgt cactgctggc ctctccatgg acatctccca cctggctgaa   3240
aacaaatggc gccgtgaatg gcaagggcag cctgaaaggc caacctggcg acatctacca   3300
```

```
ccagacctgg gccagatact tcgtgaagtt cctggacgcc tatgccgagc acaagctgca   3360
gttttgggcc gtgacagccg agaacgaacc ttctgctgga ctgctgagcg gctacccctt   3420
tcagtgcctg ggctttacac ccgagcacca gcgggacttt atcgcccgtg atctgggacc   3480
cacactggcc aatagcaccc accataatgt gcggctgctg atgctggacg accagagact   3540
gcttctgccc cactgggcta aagtggtgct gacagatcct gaggccgcca aatacgtgca   3600
cggaatcgcc gtgcactggt atctggactt tctggcccct gccaaggcca cactgggaga   3660
gacacacaga ctgttcccca acaccatgct gttcgccagc gaagcctgtg tgggcagcaa   3720
gttttgggaa cagagcgtgc ggctcggcag ctgggataga ggcatgcagt acagccacag   3780
catcatcacc aacctgctgt accacgtcgt cggctggacc gactggaatc tggccctgaa   3840
tcctgaaggc ggccctaact gggtccgaaa cttcgtggac agccccatca tcgtggacat   3900
caccaaggac accttctaca agcagcccat gttctaccac ctgggacact tcagcaagtt   3960
catccccgag ggctctcagc gcgttggact ggtggcttcc cagaagaacg atctggacgc   4020
cgtggctctg atgcaccctg atggatctgc tgtggtggtg gtcctgaacc gcagcagcaa   4080
agatgtgccc ctgaccatca aggatcccgc cgtgggattc ctggaaacaa tcagccctgg   4140
ctactccatc cacacctacc tgtggcgtag acagtgacaa ttgttaatta agtttaaacc   4200
ctcgaggccg caagccgcat cgataccgtc gactagagct cgctgatcag cctcgactgt   4260
gccttctagt tgccagccat ctgttgtttg cccctccccc gtgccttcct tgaccctgga   4320
aggtgccact cccactgtcc tttcctaata aaatgaggaa attgcatcgc attgtctgag   4380
taggtgtcat tctattctgg ggggtggggt ggggcaggac agcaaggggg aggattggga   4440
agacaatagc aggcatgctg gggagagatc cacgataaca aacagctttt ttggggtgaa   4500
catattgact gaattccctg caggttggcc actccctctc tgcgcgctcg ctcgctcact   4560
gaggccgccc gggcaaagcc cgggcgtcgg gcgacctttg gtcgcccggc ctcagtgagc   4620
gagcgagcgc gcagagaggg agtggccaac tccatcacta ggggttcctg cggccgctcg   4680
tacggtctcg aggaattcct gcaggataac ttgccaacct cattctaaaa tgtatataga   4740
agcccaaaag acaataacaa aaatattctt gtagaacaaa atgggaaaga atgttccact   4800
aaatatcaag atttagagca aagcatgaga tgtgtgggga tagacagtga ggctgataaa   4860
atagagtaga gctcagaaac agacccattg atatatgtaa gtgacctatg aaaaaaatat   4920
ggcattttac aatgggaaaa tgatggtctt tttctttttt agaaaaacag ggaaatatat   4980
ttatatgtaa aaaataaaag ggaacccata tgtcatacca tacacacaaa aaaattccag   5040
tgaattataa gtctaaatgg agaaggcaaa actttaaatc ttttagaaaa taatatagaa   5100
gcatgcagac cagcctggcc aacatgatga aaccctctct actaataata aaatcagtag   5160
aactactcag gactactttg agtgggaagt ccttttctat gaagacttct ttggccaaaa   5220
ttaggctcta aatgcaagga gatagtgcat catgcctggc tgcacttact gataaatgat   5280
gttatcacca tctttaacca aatgcacagg aacaagttat ggtactgatg tgctggattg   5340
agaaggagct ctacttcctt gacaggacac atttgtatca acttaaaaaa gcagattttt   5400
gccagcagaa ctattcattc agaggtagga aacttagaat agatgatgtc actgattagc   5460
atggcttccc catctccaca gctgcttccc acccaggttg cccacagttg agtttgtcca   5520
gtgctcaggg ctgcccactc tcagtaagaa gccccacacc agcccctctc caaatatgtt   5580
ggctgttcct tccattaaag tgaccccact ttagagcagc aagtggattt ctgtttctta   5640
cagttcagga aggaggagtc agctgtgaga acctggagcc tgagatgctt ctaagtccca   5700
```

```
ctgctactgg ggtcagggaa gccagactcc agcatcagca gtcaggagca ctaagccctt   5760
gccaacatcc tgtttctcag agaaactgct tccattataa tggttgtcct tttttaagct   5820
atcaagccaa acaaccagtg tctaccatta ttctcatcac ctgaagccaa gggttctagc   5880
aaaagtcaag ctgtcttgta atggttgatg tgcctccagc ttctgtcttc agtcactcca   5940
ctcttagcct gctctgaatc aactctgacc acagttccct ggagcccctg ccacctgctg   6000
cccctgccac cttctccatc tgcagtgctg tgcagccttc tgcactcttg cagagctaat   6060
aggtggagac ttgaaggaag aggaggaaag tttctcataa tagccttgct gcaagctcaa   6120
atgggaggtg ggcactgtgc ccaggagcct tggagcaaag gctgtgccca acctctgact   6180
gcatccaggt ttggtcttga cagagataag aagccctggc ttttggagcc aaaatctagg   6240
tcagacttag gcaggattct caaagtttat cagcagaaca tgaggcagaa gaccctttct   6300
gctccagctt cttcaggctc aaccttcatc agaatagata gaaagagagg ctgtgagggt   6360
tcttaaaaca gaagcaaatc tgactcagag aataaacaac ctcctagtaa actacagctt   6420
agacagagca tctggtggtg agtgtgctca gtgtcctact caactgtctg gtatcagccc   6480
tcatgaggac ttctcttctt tccctcatag acctccatct ctgttttcct tagcctgcag   6540
aaatctggat ggctattcac agaatgcctg tgctttcaga gttgcatttt ttctctggta   6600
ttctggttca agcatttgaa ggtaggaaag gttctccaag tgcaagaaag ccagccctga   6660
gcctcaactg cctggctagt gtggtcagta ggatgcaaag gctgttgaat gccacaaggc   6720
caaactttaa cctgtgtacc acaagcctag cagcagaggc agctctgctc actggaactc   6780
tctgtcttct ttctcctgag ccttttcttt tcctgagttt tctagctctc ctcaacctta   6840
cctctgccct acccaggaca aacccaagag ccactgtttc tgtgatgtcc tctccagccc   6900
taattaggca tcatgacttc agcctgacct tccatgctca gaagcagtgc taatccactt   6960
cagatgagct gctctatgca acacaggcag agcctacaaa cctttgcacc agagccctcc   7020
acatatcagt gtttgttcat actcacttca acagcaaatg tgactgctga gattaagatt   7080
ttacacaaga tggtctgtaa tttcacagtt agttttatcc cattaggtat gaaagaatta   7140
gcataattcc ccttaaacat gaatgaatct tagatttttt aataaatagt tttggaagta   7200
aagacagaga catcaggagc acaaggaata gcctgagagg acaaacagaa caagaaagag   7260
tctggaaata cacaggatgt tcttggcctc ctcaaagcaa gtgcaagcag atagtaccag   7320
cagccccagg ctatcagagc ccagtgaaga gaagtaccat gaaagccaca gctctaacca   7380
ccctgttcca gagtgacaga cagtccccaa gacaagccag cctgagccag agagagaact   7440
gcaagagaaa gtttctaatt taggttctgt tagattcaga caagtgcagg tcatcctctc   7500
tccacagcta ctcacctctc cagcctaaca aagcctgcag tccacactcc aaccctggtg   7560
tctcacctcc tagcctctcc caacatcctg ctctctgacc atcttctgca tctctcatct   7620
caccatctcc cactgtctac agcctactct tgcaactacc atctcatttt ctgacatcct   7680
gtctacatct tctgccatac tctgccatct accataccac ctcttaccat ctaccacacc   7740
atcttttatc tccatccctc tcagaagcct ccaagctgaa tcctgcttta tgtgttcatc   7800
tcagcccctg catggaaagc tgaccccaga ggcagaacta ttcccagaga gcttggccaa   7860
gaaaaacaaa actaccagcc tggccaggct caggagtagt aagctgcagt gtctgttgtg   7920
ttctagcttc aacagctgca ggagttccac tctcaaatgc tccacatttc tcacatcctc   7980
ctgattctgg tcactaccca tcttcaaaga acagaatatc tcacatcagc atactgtgaa   8040
```

```
ggactagtca tgggtgcagc tgctcagagc tgcaaagtca ttctggatgg tggagagctt   8100
acaaacattt catgatgctc cccccgctct gatggctgga gcccaatccc tacacagact   8160
cctgctgtat gtgttttcct ttcactctga gccacagcca gagggcaggc attcagtctc   8220
ctcttcaggc tggggctggg gcactgagaa ctcacccaac accttgctct cactccttct   8280
gcaaaacaag aaagagcttt gtgctgcagt agccatgaag aatgaaagga aggctttaac   8340
taaaaaatgt cagagattat tttcaacccc ttactgtgga tcaccagcaa ggaggaaaca   8400
caacacagag acatttttc ccctcaaatt atcaaaagaa tcactgcatt tgttaaagag   8460
agcaactgaa tcaggaagca gagttttgaa catatcagaa gttaggaatc tgcatcagag   8520
acaaatgcag tcatggttgt ttgctgcata ccagccctaa tcattagaag cctcatggac   8580
ttcaaacatc attccctctg acaagatgct ctagcctaac tccatgagat aaaataaatc   8640
tgcctttcag agccaaagaa gagtccacca gcttcttctc agtgtgaaca agagctccag   8700
tcaggttagt cagtccagtg cagtagagga gaccagtctg catcctctaa ttttcaaagg   8760
caagaagatt tgtttaccct ggacaccagg cacaagtgag gtcacagagc tcttagatat   8820
gcagtcctca tgagtgagga gactaaagcg catgccatca agacttcagt gtagagaaaa   8880
cctccaaaaa agcctcctca ctacttctgg aatagctcag aggccgaggc ggcctcggcc   8940
tctgcataaa taaaaaaaat tagtcagcca tggggcggag aatgggcgga actgggcgga   9000
gttaggggcg ggatgggcgg agttaggggc gggactatgg ttgctgacta attgagatgc   9060
atgctttgca tacttctgcc tgctggggag cctggggact ttccacacct ggttgctgac   9120
taattgagat gcatgctttg catacttctg cctgctgggg agcctgggga ctttccacac   9180
cctaactgac acacattcca cagctgcatt aatgaatcgg ccaacgcgcg gggagaggcg   9240
gtttgcgtat tgggcgctct tccgcttcct cgctcactga ctcgctgcgc tcggtcgttc   9300
ggctgcggcg agcggtatca gctcactcaa aggcggtaat acggttatcc acagaatcag   9360
gggataacgc aggaaagaac atgtgagcaa aaggccagca aaaggccagg aaccgtaaaa   9420
aggccgcgtt gctggcgttt ttccataggc tccgcccccc tgacgagcat cacaaaaatc   9480
gacgctcaag tcagaggtgg cgaaacccga caggactata aagataccag gcgtttcccc   9540
ctggaagctc cctcgtgcgc tctcctgttc cgaccctgcc gcttaccgga tacctgtccg   9600
cctttctccc ttcgggaagc gtggcgcttt ctcatagctc acgctgtagg tatctcagtt   9660
cggtgtaggt cgttcgctcc aagctgggct gtgtgcacga accccccgtt cagcccgacc   9720
gctgcgcctt atccggtaac tatcgtcttg agtccaaccc ggtaagacac gacttatcgc   9780
cactggcagc agccactggt aacaggatta gcagagcgag gtatgtaggc ggtgctacag   9840
agttcttgaa gtggtggcct aactacggct acactagaag aacagtattt ggtatctgcg   9900
ctctgctgaa gccagttacc ttcggaaaaa gagttggtag ctcttgatcc ggcaaacaaa   9960
ccaccgctgg tagcggtggt ttttttgttt gcaagcagca gattacgcgc agaaaaaaag  10020
gatctcaaga agatcctttg atcttttcta cggggtctga cgctcagtgg aacgaaaact  10080
cacgttaagg gattttggtc atgagattat caaaaaggat cttcacctag atccttttaa  10140
attaaaaatg aagttttaaa tcaatctaaa gtatatatga gtaaacttgg tctgacagtt  10200
accaatgctt aatcagtgag gcacctatct cagcgatctg tctatttcgt tcatccatag  10260
ttgcctgact cctgcaaacc acgttgtgtc tcaaaatctc tgatgttaca ttgcacaaga  10320
taaaaatata tcatcatgaa caataaaact gtctgcttac ataaacagta atacaagggg  10380
tgttatgagc catattcaac gggaaacgtc ttgctcgagg ccgcgattaa attccaacat  10440
```

ggatgctgat ttatatgggt ataaatgggc tcgcgataat gtcgggcaat caggtgcgac 10500
aatctatcga ttgtatggga agcccgatgc gccagagttg tttctgaaac atggcaaagg 10560
tagcgttgcc aatgatgtta cagatgagat ggtcagacta aactggctga cggaatttat 10620
gcctcttccg accatcaagc attttatccg tactcctgat gatgcatggt tactcaccac 10680
tgcgatcccc gggaaaacag cattccaggt attagaagaa tatcctgatt caggtgaaaa 10740
tattgttgat gcgctggcag tgttcctgcg ccggttgcat tcgattcctg tttgtaattg 10800
tccttttaac agcgatcgcg tatttcgtct cgctcaggcg caatcacgaa tgaataacgg 10860
tttggttgat gcgagtgatt ttgatgacga gcgtaatggc tggcctgttg aacaagtctg 10920
gaaagaaatg cataagcttt tgccattctc accggattca gtcgtcactc atggtgattt 10980
ctcacttgat aaccttattt ttgacgaggg gaaattaata ggttgtattg atgttggacg 11040
agtcggaatc gcagaccgat accaggatct tgccatccta tggaactgcc tcggtgagtt 11100
ttctccttca ttacagaaac ggctttttca aaaatatggt attgataatc ctgatatgaa 11160
taaattgcag tttcatttga tgctcgatga gtttttctaa gggcggcctg ccaccatacc 11220
cacgccgaaa caagcgctca tgagcccgaa gtggcgagcc cgatcttccc catcggtgat 11280
gtcggcgata taggcgccag caaccgcacc tgtggcgccg gtgatgaggg cgcgccaagt 11340
cgacgtccgg cagtc 11355

<210> SEQ ID NO 3
<211> LENGTH: 11420
<212> TYPE: DNA
<213> ORGANISM: Artificial sequence
<220> FEATURE:
<223> OTHER INFORMATION: Synthetic polynucleotide

<400> SEQUENCE: 3
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg agggcggagt 300
tagggcggag ccaatcagcg tgcgccgttc cgaaagttgc cttttatggc tgggcggaga 360
atgggcggtg aacgccgatg attatataag gacgcgccgg gtgtggcaca gctagttccg 420
tcgcagccgg gatttgggtc gcggttcttg tttgtggatc cctgtgatcg tcacttggta 480
agtcactgac tgtctatgcc tgggaaaggg tgggcaggag atggggcagt gcaggaaaag 540
tggcactatg aaccctgcag ccctaggaat gcatctagac aattgtacta accttcttct 600
ctttcctctc ctgacagtcc ggaaagccac catggaattc agcagcccca gcagagagga 660
atgccccaag cctctgagcc gggtgtcaat catggccgga tctctgacag gactgctgct 720
gcttcaggcc gtgtcttggg cttctggcgc tagaccttgc atccccaaga gcttcggcta 780
cagcagcgtc gtgtgcgtgt gcaatgccac ctactgcgac agcttcgacc ctcctacctt 840
tcctgctctg ggcaccttca gcagatacga gagcaccaga tccggcagac ggatggaact 900
gagcatggga cccatccagg ccaatcacac aggcactggc ctgctgctga cactgcagcc 960
tgagcagaaa ttccagaaag tgaaaggctt cggcggagcc atgacagatg ccgccgctct 1020
gaatatcctg gctctgtctc caccagctca gaacctgctg ctcaagagct acttcagcga 1080

-continued

```
ggaaggcatc ggctacaaca tcatcagagt gcccatggcc agctgcgact tcagcatcag   1140
gacctacacc tacgccgaca cacccgacga tttccagctg cacaacttca gcctgcctga   1200
agaggacacc aagctgaaga tccctctgat ccacagagcc ctgcagctgg cacaaagacc   1260
cgtgtcactg ctggcctctc catggacatc tcccacctgg ctgaaaacaa atggcgccgt   1320
gaatggcaag ggcagcctga aaggccaacc tggcgacatc taccaccaga cctgggccag   1380
atacttcgtg aagttcctgg acgcctatgc cgagcacaag ctgcagtttt gggccgtgac   1440
agccgagaac gaaccttctg ctggactgct gagcggctac ccctttcagt gcctgggctt   1500
tacacccgag caccagcggg actttatcgc ccgtgatctg ggacccacac tggccaatag   1560
cacccaccat aatgtgcggc tgctgatgct ggacgaccag agactgcttc tgccccactg   1620
ggctaaagtg gtgctgacag atcctgaggc cgccaaatac gtgcacggaa tcgccgtgca   1680
ctggtatctg gactttctgg cccctgccaa ggccacactg ggagagacac acagactgtt   1740
ccccaacacc atgctgttcg ccagcgaagc ctgtgtgggc agcaagtttt gggaacagag   1800
cgtgcggctc ggcagctggg atagaggcat gcagtacagc cacagcatca tcaccaacct   1860
gctgtaccac gtcgtcggct ggaccgactg gaatctggcc ctgaatcctg aaggcggccc   1920
taactgggtc cgaaacttcg tggacagccc catcatcgtg gacatcacca aggacacctt   1980
ctacaagcag cccatgttct accacctggg acacttcagc aagttcatcc ccgagggctc   2040
tcagcgcgtt ggactggtgg cttcccagaa gaacgatctg gacgccgtgg ctctgatgca   2100
ccctgatgga tctgctgtgg tggtggtcct gaaccgcagc agcaaagatg tgcccctgac   2160
catcaaggat cccgccgtgg gattcctgga aacaatcagc cctggctact ccatccacac   2220
ctacctgtgg cgtagacagt gacaattgtt aattaagttt catcgatacc gtcgactaga   2280
gctcgctgat cagcctcgac tgtgccttct agttgccagc catctgttgt ttgcccctcc   2340
cccgtgcctt ccttgaccct ggaaggtgcc actcccactg tcctttccta ataaaatgag   2400
gaaattgcat cgcattgtct gagtaggtgt cattctattc tggggggtgg ggtggggcag   2460
gacagcaagg gggaggattg ggaagacaat agcaggcatg ctggggagag atccacgata   2520
acaaacagct tttttggggg ggcggagtta gggcggagcc aatcagcgtg cgccgttccg   2580
aaagttgcct tttatggctg ggcggagaat gggcggtgaa cgccgatgat tatataagga   2640
cgcgccgggt gtggcacagc tagttccgtc gcagccggga tttgggtcgc ggttcttgtt   2700
tgtggatccc tgtgatcgtc acttggtaag tcactgactg tctatgcctg ggaaagggtg   2760
ggcaggagat ggggcagtgc aggaaaagtg gcactatgaa ccctgcagcc ctaggaatgc   2820
atctagacaa ttgtactaac cttcttctct ttcctctcct gacagtccgg aaagccacca   2880
tgggccgctg ctgcttctac accgccggca ccctgagcct gctgctgctg gtgaccagcg   2940
tgaccctgct ggtggcccgc gtgttccaga aggccgtgga ccagagcatc gagaagaaga   3000
tcgtgctgcg caacggcacc gaggccttcg acagctggga gaagcccccc ctgcccgtgt   3060
acacccagtt ctacttcttc aacgtgacca accccgagga gatcctgcgc ggcgagaccc   3120
cccgcgtgga ggaggtgggc ccctacacct accgcgagct gcgcaacaag gccaacatcc   3180
agttcggcga caacggcacc accatcagcg ccgtgagcaa caaggcctac gtgttcgagc   3240
gcgaccagag cgtgggcgac cccaagatcg acctgatccg caccctgaac atccccgtgc   3300
tgaccgtgat cgagtggagc caggtgcact tcctgcgcga gatcatcgag gccatgctga   3360
aggcctacca gcagaagctg ttcgtgaccc acaccgtgga cgagctgctg tggggctaca   3420
aggacgagat cctgagcctg atccacgtgt tccgccccga catcagcccc tacttcggcc   3480
```

```
tgttctacga gaagaacggc accaacgacg gcgactacgt gttcctgacc ggcgaggaca   3540
gctacctgaa cttcaccaag atcgtggagt ggaacggcaa gaccagcctg gactggtgga   3600
tcaccgacaa gtgcaacatg atcaacggca ccgacggcga cagcttccac cccctgatca   3660
ccaaggacga ggtgctgtac gtgttcccca gcgacttctg ccgcagcgtg tacatcacct   3720
tcagcgacta cgagagcgtg cagggcctgc ccgccttccg ctacaaggtg cccgccgaga   3780
tcctggccaa caccagcgac aacgccggct tctgcatccc cgagggcaac tgcctgggca   3840
gcggcgtgct gaacgtgagc atctgcaaga acggcgcccc catcatcatg agcttccccc   3900
acttctacca ggccgacgag cgcttcgtga gcgccatcga gggcatgcac cccaaccagg   3960
aggaccacga gaccttcgtg gacatcaacc ccctgaccgg catcatcctg aaggccgcca   4020
agcgcttcca gatcaacatc tacgtgaaga agctggacga cttcgtggag accggcgaca   4080
tccgcaccat ggtgttcccc gtgatgtacc tgaacgagag cgtgcacatc gacaaggaga   4140
ccgccagccg cctgaagagc atgatcaaca ccaccctgat catcaccaac atcccctaca   4200
tcatcatggc cctgggcgtg ttcttcggcc tggtgttcac ctggctggcc tgcaagggcc   4260
agggcagcat ggacgagggc accgccgacg agcgcgcccc cctgatccgc acctgaccca   4320
ggggactcaa tcagcctcga agacatgata agatacattg atgagtttgg acaaaccaca   4380
acaagaatgc agtgaaaaaa atgctttatt tgtgaaattt gtgatgctat tgctttattt   4440
gtaaccatta taagctgcaa taaacaagtt aacaacaaca attgcattca ttttatgttt   4500
caggttcagg gggagatgtg ggaggttttt taaagcaagt aaaacctcta caaatgtggt   4560
atgaacatat tgactgaatt ccctgcaggt tggccactcc ctctctgcgc gctcgctcgc   4620
tcactgaggc cgcccgggca aagcccgggc gtcgggcgac ctttggtcgc ccggcctcag   4680
tgagcgagcg agcgcgcaga gagggagtgg ccaactccat cactaggggt tcctgcggcc   4740
gctcgtacgg tctcgaggaa ttcctgcagg ataacttgcc aacctcattc taaaatgtat   4800
atagaagccc aaaagacaat aacaaaaata ttcttgtaga acaaaatggg aaagaatgtt   4860
ccactaaata tcaagattta gagcaaagca tgagatgtgt ggggatagac agtgaggctg   4920
ataaaataga gtagagctca gaaacagacc cattgatata tgtaagtgac ctatgaaaaa   4980
aatatggcat tttacaatgg gaaaatgatg gtctttttct tttttagaaa aacagggaaa   5040
tatatttata tgtaaaaaat aaaagggaac ccatatgtca taccatacac acaaaaaaat   5100
tccagtgaat tataagtcta aatggagaag gcaaaacttt aaatctttta gaaaataata   5160
tagaagcatg cagaccagcc tggccaacat gatgaaaccc tctctactaa taataaaatc   5220
agtagaacta ctcaggacta ctttgagtgg gaagtccttt tctatgaaga cttctttggc   5280
caaaattagg ctctaaatgc aaggagatag tgcatcatgc ctggctgcac ttactgataa   5340
atgatgttat caccatcttt aaccaaatgc acaggaacaa gttatggtac tgatgtgctg   5400
gattgagaag gagctctact tccttgacag gacacatttg tatcaactta aaaaagcaga   5460
tttttgccag cagaactatt cattcagagg taggaaactt agaatagatg atgtcactga   5520
ttagcatggc ttccccatct ccacagctgc ttcccaccca ggttgcccac agttgagttt   5580
gtccagtgct cagggctgcc cactctcagt aagaagcccc acaccagccc ctctccaaat   5640
atgttggctg ttccttccat taaagtgacc ccactttaga gcagcaagtg gatttctgtt   5700
tcttacagtt caggaaggag gagtcagctg tgagaacctg gagcctgaga tgcttctaag   5760
tcccactgct actggggtca gggaagccag actccagcat cagcagtcag gagcactaag   5820
```

```
cccttgccaa catcctgttt ctcagagaaa ctgcttccat tataatggtt gtcctttttt   5880
aagctatcaa gccaaacaac cagtgtctac cattattctc atcacctgaa gccaagggtt   5940
ctagcaaaag tcaagctgtc ttgtaatggt tgatgtgcct ccagcttctg tcttcagtca   6000
ctccactctt agcctgctct gaatcaactc tgaccacagt tccctggagc cctgccacc    6060
tgctgcccct gccaccttct ccatctgcag tgctgtgcag ccttctgcac tcttgcagag   6120
ctaataggtg gagacttgaa ggaagaggag gaaagtttct cataatagcc ttgctgcaag   6180
ctcaaatggg aggtgggcac tgtgcccagg agccttggag caaaggctgt gcccaacctc   6240
tgactgcatc caggtttggt cttgacagag ataagaagcc ctggcttttg gagccaaaat   6300
ctaggtcaga cttaggcagg attctcaaag tttatcagca gaacatgagg cagaagaccc   6360
tttctgctcc agcttcttca ggctcaacct tcatcagaat agatagaaag agaggctgtg   6420
agggttctta aaacagaagc aaatctgact cagagaataa acaacctcct agtaaactac   6480
agcttagaca gagcatctgg tggtgagtgt gctcagtgtc ctactcaact gtctggtatc   6540
agccctcatg aggacttctc ttctttccct catagacctc catctctgtt ttccttagcc   6600
tgcagaaatc tggatggcta ttcacagaat gcctgtgctt tcagagttgc atttttttctc  6660
tggtattctg gttcaagcat ttgaaggtag gaaaggttct ccaagtgcaa gaaagccagc   6720
cctgagcctc aactgcctgg ctagtgtggt cagtaggatg caaaggctgt tgaatgccac   6780
aaggccaaac tttaacctgt gtaccacaag cctagcagca gaggcagctc tgctcactgg   6840
aactctctgt cttctttctc ctgagccttt tcttttcctg agttttctag ctctcctcaa   6900
ccttacctct gccctaccca ggacaaaccc aagagccact gtttctgtga tgtcctctcc   6960
agccctaatt aggcatcatg acttcagcct gaccttccat gctcagaagc agtgctaatc   7020
cacttcagat gagctgctct atgcaacaca ggcagagcct acaaaccttt gcaccagagc   7080
cctccacata tcagtgtttg ttcatactca cttcaacagc aaatgtgact gctgagatta   7140
agattttaca caagatggtc tgtaatttca cagttagttt tatcccatta ggtatgaaag   7200
aattagcata attcccctta aacatgaatg aatcttagat tttttaataa atagttttgg   7260
aagtaaagac agagacatca ggagcacaag gaatagcctg agaggacaaa cagaacaaga   7320
aagagtctgg aaatacacag gatgttcttg gcctcctcaa agcaagtgca agcagatagt   7380
accagcagcc ccaggctatc agagcccagt gaagagaagt accatgaaag ccacagctct   7440
aaccaccctg ttccagagtg acagacagtc cccaagacaa gccagcctga gccagagaga   7500
gaactgcaag agaaagtttc taatttaggt tctgttagat tcagacaagt gcaggtcatc   7560
ctctctccac agctactcac ctctccagcc taacaaagcc tgcagtccac actccaaccc   7620
tggtgtctca cctcctagcc tctcccaaca tcctgctctc tgaccatctt ctgcatctct   7680
catctcacca tctcccactg tctacagcct actcttgcaa ctaccatctc attttctgac   7740
atcctgtcta catcttctgc catactctgc catctaccat accacctctt accatctacc   7800
acaccatctt ttatctccat ccctctcaga agcctccaag ctgaatcctg ctttatgtgt   7860
tcatctcagc ccctgcatgg aaagctgacc ccagaggcag aactattccc agagagcttg   7920
gccaagaaaa acaaaactac cagcctggcc aggctcagga gtagtaagct gcagtgtctg   7980
ttgtgttcta gcttcaacag ctgcaggagt tccactctca aatgctccac atttctcaca   8040
tcctcctgat tctggtcact acccatcttc aaagaacaga atatctcaca tcagcatact   8100
gtgaaggact agtcatgggt gcagctgctc agagctgcaa agtcattctg gatggtggag   8160
agcttacaaa catttcatga tgctcccccc gctctgatgg ctggagccca atccctacac   8220
```

```
agactcctgc tgtatgtgtt ttcctttcac tctgagccac agccagaggg caggcattca   8280
gtctcctctt caggctgggg ctggggcact gagaactcac ccaacacctt gctctcactc   8340
cttctgcaaa acaagaaaga gctttgtgct gcagtagcca tgaagaatga aaggaaggct   8400
ttaactaaaa aatgtcagag attattttca accccttact gtggatcacc agcaaggagg   8460
aaacacaaca cagagacatt ttttcccctc aaattatcaa aagaatcact gcatttgtta   8520
aagagagcaa ctgaatcagg aagcagagtt ttgaacatat cagaagttag gaatctgcat   8580
cagagacaaa tgcagtcatg gttgtttgct gcataccagc cctaatcatt agaagcctca   8640
tggacttcaa acatcattcc ctctgacaag atgctctagc ctaactccat gagataaaat   8700
aaatctgcct ttcagagcca aagaagagtc caccagcttc ttctcagtgt gaacaagagc   8760
tccagtcagg ttagtcagtc cagtgcagta gaggagacca gtctgcatcc tctaattttc   8820
aaaggcaaga agatttgttt accctggaca ccaggcacaa gtgaggtcac agagctctta   8880
gatatgcagt cctcatgagt gaggagacta aagcgcatgc catcaagact tcagtgtaga   8940
gaaaacctcc aaaaaagcct cctcactact tctggaatag ctcagaggcc gaggcggcct   9000
cggcctctgc ataaataaaa aaaattagtc agccatgggg cggagaatgg gcggaactgg   9060
gcggagttag gggcgggatg ggcggagtta ggggcgggac tatggttgct gactaattga   9120
gatgcatgct ttgcatactt ctgcctgctg gggagcctgg ggactttcca cacctggttg   9180
ctgactaatt gagatgcatg ctttgcatac ttctgcctgc tggggagcct ggggactttc   9240
cacaccctaa ctgacacaca ttccacagct gcattaatga atcggccaac gcgcggggag   9300
aggcggtttg cgtattgggc gctcttccgc ttcctcgctc actgactcgc tgcgctcggt   9360
cgttcggctg cggcgagcgg tatcagctca ctcaaaggcg gtaatacggt tatccacaga   9420
atcaggggat aacgcaggaa agaacatgtg agcaaaaggc cagcaaaagg ccaggaaccg   9480
taaaaaggcc gcgttgctgg cgtttttcca taggctccgc ccccctgacg agcatcacaa   9540
aaatcgacgc tcaagtcaga ggtggcgaaa cccgacagga ctataaagat accaggcgtt   9600
tccccctgga agctccctcg tgcgctctcc tgttccgacc ctgccgctta ccggatacct   9660
gtccgccttt ctcccttcgg gaagcgtggc gctttctcat agctcacgct gtaggtatct   9720
cagttcggtg taggtcgttc gctccaagct gggctgtgtg cacgaacccc ccgttcagcc   9780
cgaccgctgc gccttatccg gtaactatcg tcttgagtcc aacccggtaa gacacgactt   9840
atcgccactg gcagcagcca ctggtaacag gattagcaga gcgaggtatg taggcggtgc   9900
tacagagttc ttgaagtggt ggcctaacta cggctacact agaagaacag tatttggtat   9960
ctgcgctctg ctgaagccag ttaccttcgg aaaaagagtt ggtagctctt gatccggcaa  10020
acaaaccacc gctggtagcg gtggtttttt tgtttgcaag cagcagatta cgcgcagaaa  10080
aaaaggatct caagaagatc ctttgatctt ttctacgggg tctgacgctc agtggaacga  10140
aaactcacgt taagggattt tggtcatgag attatcaaaa aggatcttca cctagatcct  10200
tttaaattaa aaatgaagtt ttaaatcaat ctaaagtata tatgagtaaa cttggtctga  10260
cagttaccaa tgcttaatca gtgaggcacc tatctcagcg atctgtctat ttcgttcatc  10320
catagttgcc tgactcctgc aaaccacgtt gtgtctcaaa atctctgatg ttacattgca  10380
caagataaaa atatatcatc atgaacaata aaactgtctg cttacataaa cagtaataca  10440
aggggtgtta tgagccatat tcaacgggaa acgtcttgct cgaggccgcg attaaattcc  10500
aacatggatg ctgatttata tgggtataaa tgggctcgcg ataatgtcgg gcaatcaggt  10560
```

```
gcgacaatct atcgattgta tgggaagccc gatgcgccag agttgtttct gaaacatggc  10620

aaaggtagcg ttgccaatga tgttacagat gagatggtca gactaaactg gctgacggaa  10680

tttatgcctc ttccgaccat caagcatttt atccgtactc ctgatgatgc atggttactc  10740

accactgcga tccccgggaa aacagcattc caggtattag aagaatatcc tgattcaggt  10800

gaaaatattg ttgatgcgct ggcagtgttc ctgcgccggt tgcattcgat tcctgtttgt  10860

aattgtcctt ttaacagcga tcgcgtattt cgtctcgctc aggcgcaatc acgaatgaat  10920

aacggtttgg ttgatgcgag tgattttgat gacgagcgta atggctggcc tgttgaacaa  10980

gtctggaaag aaatgcataa gcttttgcca ttctcaccgg attcagtcgt cactcatggt  11040

gatttctcac ttgataacct tatttttgac gaggggaaat taataggttg tattgatgtt  11100

ggacgagtcg gaatcgcaga ccgataccag gatcttgcca tcctatggaa ctgcctcggt  11160

gagttttctc cttcattaca gaaacggctt tttcaaaaat atggtattga taatcctgat  11220

atgaataaat tgcagtttca tttgatgctc gatgagtttt tctaagggcg gcctgccacc  11280

atacccacgc cgaaacaagc gctcatgagc ccgaagtggc gagcccgatc ttccccatcg  11340

gtgatgtcgg cgatataggc gccagcaacc gcacctgtgg cgccggtgat gagggcgcgc  11400

caagtcgacg tccggcagtc                                              11420
```

```
<210> SEQ ID NO 4
<211> LENGTH: 11171
<212> TYPE: DNA
<213> ORGANISM: Artificial sequence
<220> FEATURE:
<223> OTHER INFORMATION: Synthetic polynucleotide

<400> SEQUENCE: 4

ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg agggcggagt    300

tagggcggag ccaatcagcg tgcgccgttc cgaaagttgc cttttatggc tgggcggaga    360

atgggcggtg aacgccgatg attatataag gacgcgccgg gtgtggcaca gctagttccg    420

tcgcagccgg gatttgggtc gcggttcttg tttgtggatc cctgtgatcg tcacttggta    480

agtcactgac tgtctatgcc tgggaaaggg tgggcaggag atggggcagt gcaggaaaag    540

tggcactatg aaccctcctg gtggcgaggg gaggggggtg gtcctcgaac gccttgcaga    600

actggcctgg atacagagtg gaccggctgg ccccatctgg aagacttcga gatacactgt    660

tgtcttactg cgctcaacag tgtatctcga agtcttccaa atggtgccag ccatcgcagc    720

ggggtgcagg aaatgggggc agcccccctt tttggctatc cttccacgtg ttcttttttg    780

tatcttttgt gtttcctaga aacatctcca gtcaccaccg cagccctagg aatgcatcta    840

gacaattgta ctaaccttct tctctttcct ctcctgacag tccggaaagc caccatgggc    900

cgctgctgct tctacaccgc cggcaccctg agcctgctgc tgctggtgac cagcgtgacc    960

ctgctggtgg cccgcgtgtt ccagaaggcc gtggaccaga gcatcgagaa gaagatcgtg   1020

ctgcgcaacg gcaccgaggc cttcgacagc tgggagaagc ccccccctgcc cgtgtacacc   1080

cagttctact tcttcaacgt gaccaacccc gaggagatcc tgcgcggcga gacccccccgc  1140

gtggaggagg tgggccccta cacctaccgc gagctgcgca acaaggccaa catccagttc   1200
```

```
ggcgacaacg gcaccaccat cagcgccgtg agcaacaagg cctacgtgtt cgagcgcgac   1260
cagagcgtgg gcgaccccaa gatcgacctg atccgcaccc tgaacatccc cgtgctgacc   1320
gtgatcgagt ggagccaggt gcacttcctg cgcgagatca tcgaggccat gctgaaggcc   1380
taccagcaga agctgttcgt gacccacacc gtggacgagc tgctgtgggg ctacaaggac   1440
gagatcctga gcctgatcca cgtgttccgc cccgacatca gcccctactt cggcctgttc   1500
tacgagaaga acggcaccaa cgacggcgac tacgtgttcc tgaccggcga ggacagctac   1560
ctgaacttca ccaagatcgt ggagtggaac ggcaagacca gcctggactg gtggatcacc   1620
gacaagtgca acatgatcaa cggcaccgac ggcgacagct tccacccccct gatcaccaag   1680
gacgaggtgc tgtacgtgtt ccccagcgac ttctgccgca gcgtgtacat caccttcagc   1740
gactacgaga gcgtgcaggg cctgcccgcc ttccgctaca aggtgcccgc cgagatcctg   1800
gccaacacca gcgacaacgc cggcttctgc atccccgagg gcaactgcct gggcagcggc   1860
gtgctgaacg tgagcatctg caagaacggc gcccccatca tcatgagctt cccccacttc   1920
taccaggccg acgagcgctt cgtgagcgcc atcgagggca tgcaccccaa ccaggaggac   1980
cacgagacct tcgtggacat caaccccctg accggcatca tcctgaaggc cgccaagcgc   2040
ttccagatca acatctacgt gaagaagctg gacgacttcg tggagaccgg cgacatccgc   2100
accatggtgt tccccgtgat gtacctgaac gagagcgtgc acatcgacaa ggagaccgcc   2160
agccgcctga agagcatgat caacaccacc ctgatcatca ccaacatccc ctacatcatc   2220
atggccctgg gcgtgttctt cggcctggtg ttcacctggc tggcctgcaa gggccagggc   2280
agcatggacg agggcaccgc cgacgagcgc gccccccctga tccgcaccga gggcagagga   2340
agtcttctga catgcggaga cgtggaagag aatcccggcc ctatggaatt cagcagcccc   2400
agcagagagg aatgccccaa gcctctgagc cgggtgtcaa tcatggccgg atctctgaca   2460
ggactgctgc tgcttcaggc cgtgtcttgg gcttctggcg ctagaccttg catccccaag   2520
agcttcggct acagcagcgt cgtgtgcgtg tgcaatgcca cctactgcga cagcttcgac   2580
cctcctacct ttcctgctct gggcaccttc agcagatacg agagcaccag atccggcaga   2640
cggatggaac tgagcatggg acccatccag gccaatcaca caggcactgg cctgctgctg   2700
acactgcagc ctgagcagaa attccagaaa gtgaaaggct tcggcggagc catgacagat   2760
gccgccgctc tgaatatcct ggctctgtct ccaccagctc agaacctgct gctcaagagc   2820
tacttcagcg aggaaggcat cggctacaac atcatcagag tgcccatggc cagctgcgac   2880
ttcagcatca ggacctacac ctacgccgac acacccgacg atttccagct gcacaacttc   2940
agcctgcctg aagaggacac caagctgaag atccctctga tccacagagc cctgcagctg   3000
gcacaaagac ccgtgtcact gctggcctct ccatggacat ctcccacctg gctgaaaaca   3060
aatggcgccg tgaatggcaa gggcagcctg aaaggccaac ctggcgacat ctaccaccag   3120
acctgggcca gatacttcgt gaagttcctg gacgcctatg ccgagcacaa gctgcagttt   3180
tgggccgtga cagccgagaa cgaaccttct gctggactgc tgagcggcta cccctttcag   3240
tgcctgggct ttacacccga gcaccagcgg gactttatcg cccgtgatct gggacccaca   3300
ctggccaata gcacccacca taatgtgcgg ctgctgatgc tggacgacca gagactgctt   3360
ctgccccact gggctaaagt ggtgctgaca gatcctgagg ccgccaaata cgtgcacgga   3420
atcgccgtgc actggtatct ggactttctg gcccctgcca aggccacact gggagagaca   3480
cacagactgt tccccaacac catgctgttc gccagcgaag cctgtgtggg cagcaagttt   3540
```

```
tgggaacaga gcgtgcggct cggcagctgg gatagaggca tgcagtacag ccacagcatc   3600
atcaccaacc tgctgtacca cgtcgtcggc tggaccgact ggaatctggc cctgaatcct   3660
gaaggcggcc ctaactgggt ccgaaacttc gtggacagcc ccatcatcgt ggacatcacc   3720
aaggacacct tctacaagca gcccatgttc taccacctgg gacacttcag caagttcatc   3780
cccgagggct ctcagcgcgt tggactggtg gcttcccaga agaacgatct ggacgccgtg   3840
gctctgatgc accctgatgg atctgctgtg gtggtggtcc tgaaccgcag cagcaaagat   3900
gtgcccctga ccatcaagga tcccgccgtg ggattcctgg aaacaatcag ccctggctac   3960
tccatccaca cctacctgtg gcgtagacag tgacaattgt taattaagtt taaaccctcg   4020
aggccgcaag ccgcatcgat accgtcgact agagctcgct gatcagcctc gactgtgcct   4080
tctagttgcc agccatctgt tgtttgcccc tcccccgtgc cttccttgac cctggaaggt   4140
gccactccca ctgtcctttc ctaataaaat gaggaaattg catcgcattg tctgagtagg   4200
tgtcattcta ttctgggggg tggggtgggg caggacagca agggggagga ttgggaagac   4260
aatagcaggc atgctgggga gagatccacg ataacaaaca gctttttttgg ggtgaacata   4320
ttgactgaat tccctgcagg ttggccactc cctctctgcg cgctcgctcg ctcactgagg   4380
ccgcccgggc aaagcccggg cgtcgggcga cctttggtcg cccggcctca gtgagcgagc   4440
gagcgcgcag agagggagtg gccaactcca tcactagggg ttcctgcggc cgctcgtacg   4500
gtctcgagga attcctgcag gataacttgc caacctcatt ctaaaatgta tatagaagcc   4560
caaaagacaa taacaaaaat attcttgtag aacaaaatgg gaaagaatgt tccactaaat   4620
atcaagattt agagcaaagc atgagatgtg tggggataga cagtgaggct gataaaatag   4680
agtagagctc agaaacagac ccattgatat atgtaagtga cctatgaaaa aaatatggca   4740
ttttacaatg ggaaaatgat ggtctttttc tttttagaa aaacagggaa atatatttat   4800
atgtaaaaaa taaaagggaa cccatatgtc ataccataca cacaaaaaaa ttccagtgaa   4860
ttataagtct aaatggagaa ggcaaaactt taaatctttt agaaaataat atagaagcat   4920
gcagaccagc ctggccaaca tgatgaaacc ctctctacta ataataaaat cagtagaact   4980
actcaggact actttgagtg ggaagtcctt ttctatgaag acttctttgg ccaaaattag   5040
gctctaaatg caaggagata gtgcatcatg cctggctgca cttactgata aatgatgtta   5100
tcaccatctt taaccaaatg cacaggaaca agttatggta ctgatgtgct ggattgagaa   5160
ggagctctac ttccttgaca ggacacattt gtatcaactt aaaaaagcag atttttgcca   5220
gcagaactat tcattcagag gtaggaaact tagaatagat gatgtcactg attagcatgg   5280
cttccccatc tccacagctg cttcccaccc aggttgccca cagttgagtt tgtccagtgc   5340
tcagggctgc ccactctcag taagaagccc cacaccagcc cctctccaaa tatgttggct   5400
gttccttcca ttaaagtgac cccactttag agcagcaagt ggatttctgt ttcttacagt   5460
tcaggaagga ggagtcagct gtgagaacct ggagcctgag atgcttctaa gtcccactgc   5520
tactggggtc agggaagcca gactccagca tcagcagtca ggagcactaa gcccttgcca   5580
acatcctgtt tctcagagaa actgcttcca ttataatggt tgtccttttt taagctatca   5640
agccaaacaa ccagtgtcta ccattattct catcacctga agccaagggt tctagcaaaa   5700
gtcaagctgt cttgtaatgg ttgatgtgcc tccagcttct gtcttcagtc actccactct   5760
tagcctgctc tgaatcaact ctgaccacag ttccctggag cccctgccac ctgctgcccc   5820
tgccaccttc tccatctgca gtgctgtgca gccttctgca ctcttgcaga gctaataggt   5880
ggagacttga aggaagagga ggaaagtttc tcataatagc cttgctgcaa gctcaaatgg   5940
```

```
gaggtgggca ctgtgcccag gagccttgga gcaaaggctg tgcccaacct ctgactgcat   6000
ccaggtttgg tcttgacaga gataagaagc cctggctttt ggagccaaaa tctaggtcag   6060
acttaggcag gattctcaaa gtttatcagc agaacatgag gcagaagacc ctttctgctc   6120
cagcttcttc aggctcaacc ttcatcagaa tagatagaaa gagaggctgt gagggttctt   6180
aaaacagaag caaatctgac tcagagaata aacaacctcc tagtaaacta cagcttagac   6240
agagcatctg gtggtgagtg tgctcagtgt cctactcaac tgtctggtat cagccctcat   6300
gaggacttct cttctttccc tcatagacct ccatctctgt tttccttagc ctgcagaaat   6360
ctggatggct attcacagaa tgcctgtgct ttcagagttg catttttttct ctggtattct   6420
ggttcaagca tttgaaggta ggaaaggttc tccaagtgca agaaagccag ccctgagcct   6480
caactgcctg gctagtgtgg tcagtaggat gcaaaggctg ttgaatgcca caaggccaaa   6540
ctttaacctg tgtaccacaa gcctagcagc agaggcagct ctgctcactg gaactctctg   6600
tcttctttct cctgagcctt ttcttttcct gagttttcta gctctcctca accttacctc   6660
tgccctaccc aggacaaacc caagagccac tgtttctgtg atgtcctctc cagccctaat   6720
taggcatcat gacttcagcc tgaccttcca tgctcagaag cagtgctaat ccacttcaga   6780
tgagctgctc tatgcaacac aggcagagcc tacaaacctt tgcaccagag ccctccacat   6840
atcagtgttt gttcatactc acttcaacag caaatgtgac tgctgagatt aagattttac   6900
acaagatggt ctgtaatttc acagttagtt ttatcccatt aggtatgaaa gaattagcat   6960
aattcccctt aaacatgaat gaatcttaga ttttttaata aatagttttg gaagtaaaga   7020
cagagacatc aggagcacaa ggaatagcct gagaggacaa acagaacaag aaagagtctg   7080
gaaatacaca ggatgttctt ggcctcctca aagcaagtgc aagcagatag taccagcagc   7140
cccaggctat cagagcccag tgaagagaag taccatgaaa gccacagctc taaccaccct   7200
gttccagagt gacagacagt ccccaagaca agccagcctg agccagagag agaactgcaa   7260
gagaaagttt ctaatttagg ttctgttaga ttcagacaag tgcaggtcat cctctctcca   7320
cagctactca cctctccagc ctaacaaagc ctgcagtcca cactccaacc ctggtgtctc   7380
acctcctagc ctctcccaac atcctgctct ctgaccatct tctgcatctc tcatctcacc   7440
atctcccact gtctacagcc tactcttgca actaccatct cattttctga catcctgtct   7500
acatcttctg ccatactctg ccatctacca taccacctct taccatctac cacaccatct   7560
tttatctcca tccctctcag aagcctccaa gctgaatcct gctttatgtg ttcatctcag   7620
cccctgcatg gaaagctgac cccagaggca gaactattcc cagagagctt ggccaagaaa   7680
aacaaaacta ccagcctggc caggctcagg agtagtaagc tgcagtgtct gttgtgttct   7740
agcttcaaca gctgcaggag ttccactctc aaatgctcca catttctcac atcctcctga   7800
ttctggtcac tacccatctt caaagaacag aatatctcac atcagcatac tgtgaaggac   7860
tagtcatggg tgcagctgct cagagctgca aagtcattct ggatggtgga gagcttacaa   7920
acatttcatg atgctccccc cgctctgatg gctggagccc aatccctaca cagactcctg   7980
ctgtatgtgt tttcctttca ctctgagcca cagccagagg gcaggcattc agtctcctct   8040
tcaggctggg gctggggcac tgagaactca cccaacacct tgctctcact ccttctgcaa   8100
aacaagaaag agctttgtgc tgcagtagcc atgaagaatg aaaggaaggc tttaactaaa   8160
aaatgtcaga gattattttc aacccccttac tgtggatcac cagcaaggag gaaacacaac   8220
acagagacat tttttcccct caaattatca aaagaatcac tgcatttgtt aaagagagca   8280
```

```
actgaatcag gaagcagagt tttgaacata tcagaagtta ggaatctgca tcagagacaa   8340
atgcagtcat ggttgtttgc tgcataccag ccctaatcat tagaagcctc atggacttca   8400
aacatcattc cctctgacaa gatgctctag cctaactcca tgagataaaa taaatctgcc   8460
tttcagagcc aaagaagagt ccaccagctt cttctcagtg tgaacaagag ctccagtcag   8520
gttagtcagt ccagtgcagt agaggagacc agtctgcatc ctctaatttt caaaggcaag   8580
aagatttgtt taccctggac accaggcaca agtgaggtca cagagctctt agatatgcag   8640
tcctcatgag tgaggagact aaagcgcatg ccatcaagac ttcagtgtag agaaaacctc   8700
caaaaaagcc tcctcactac ttctggaata gctcagaggc cgaggcggcc tcggcctctg   8760
cataaataaa aaaaattagt cagccatggg gcggagaatg ggcggaactg ggcggagtta   8820
ggggcgggat gggcggagtt aggggcggga ctatggttgc tgactaattg agatgcatgc   8880
tttgcatact tctgcctgct ggggagcctg gggactttcc acacctggtt gctgactaat   8940
tgagatgcat gctttgcata cttctgcctg ctggggagcc tggggacttt ccacacccta   9000
actgacacac attccacagc tgcattaatg aatcggccaa cgcgcgggga gaggcggttt   9060
gcgtattggg cgctcttccg cttcctcgct cactgactcg ctgcgctcgg tcgttcggct   9120
gcggcgagcg gtatcagctc actcaaaggc ggtaatacgg ttatccacag aatcagggga   9180
taacgcagga aagaacatgt gagcaaaagg ccagcaaaag gccaggaacc gtaaaaaggc   9240
cgcgttgctg gcgtttttcc ataggctccg cccccctgac gagcatcaca aaaatcgacg   9300
ctcaagtcag aggtggcgaa acccgacagg actataaaga taccaggcgt ttccccctgg   9360
aagctccctc gtgcgctctc ctgttccgac cctgccgctt accggatacc tgtccgcctt   9420
tctcccttcg ggaagcgtgg cgctttctca tagctcacgc tgtaggtatc tcagttcggt   9480
gtaggtcgtt cgctccaagc tgggctgtgt gcacgaaccc cccgttcagc ccgaccgctg   9540
cgccttatcc ggtaactatc gtcttgagtc caacccggta agacacgact tatcgccact   9600
ggcagcagcc actggtaaca ggattagcag agcgaggtat gtaggcggtg ctacagagtt   9660
cttgaagtgg tggcctaact acggctacac tagaagaaca gtatttggta tctgcgctct   9720
gctgaagcca gttaccttcg gaaaaagagt tggtagctct tgatccggca aacaaaccac   9780
cgctggtagc ggtggttttt ttgtttgcaa gcagcagatt acgcgcagaa aaaaaggatc   9840
tcaagaagat cctttgatct tttctacggg gtctgacgct cagtggaacg aaaactcacg   9900
ttaagggatt ttggtcatga gattatcaaa aaggatcttc acctagatcc ttttaaatta   9960
aaaatgaagt tttaaatcaa tctaaagtat atatgagtaa acttggtctg acagttacca  10020
atgcttaatc agtgaggcac ctatctcagc gatctgtcta tttcgttcat ccatagttgc  10080
ctgactcctg caaaccacgt tgtgtctcaa aatctctgat gttacattgc acaagataaa  10140
aatatatcat catgaacaat aaaactgtct gcttacataa acagtaatac aaggggtgtt  10200
atgagccata ttcaacggga aacgtcttgc tcgaggccgc gattaaattc caacatggat  10260
gctgatttat atgggtataa atgggctcgc gataatgtcg ggcaatcagg tgcgacaatc  10320
tatcgattgt atgggaagcc cgatgcgcca gagttgtttc tgaaacatgg caaaggtagc  10380
gttgccaatg atgttacaga tgagatggtc agactaaact ggctgacgga atttatgcct  10440
cttccgacca tcaagcattt tatccgtact cctgatgatg catggttact caccactgcg  10500
atccccggga aaacagcatt ccaggtatta gaagaatatc ctgattcagg tgaaaatatt  10560
gttgatgcgc tggcagtgtt cctgcgccgg ttgcattcga ttcctgtttg taattgtcct  10620
tttaacagcg atcgcgtatt tcgtctcgct caggcgcaat cacgaatgaa taacggtttg  10680
```

```
gttgatgcga gtgattttga tgacgagcgt aatggctggc ctgttgaaca agtctggaaa  10740

gaaatgcata agcttttgcc attctcaccg gattcagtcg tcactcatgg tgatttctca  10800

cttgataacc ttatttttga cgaggggaaa ttaataggtt gtattgatgt tggacgagtc  10860

ggaatcgcag accgatacca ggatcttgcc atcctatgga actgcctcgg tgagttttct  10920

ccttcattac agaaacggct ttttcaaaaa tatggtattg ataatcctga tatgaataaa  10980

ttgcagtttc atttgatgct cgatgagttt ttctaagggc ggcctgccac catacccacg  11040

ccgaaacaag cgctcatgag cccgaagtgg cgagcccgat cttccccatc ggtgatgtcg  11100

gcgatatagg cgccagcaac cgcacctgtg gcgccggtga tgagggcgcg ccaagtcgac  11160

gtccggcagt c                                                       11171
```

<210> SEQ ID NO 5
<211> LENGTH: 11309
<212> TYPE: DNA
<213> ORGANISM: Artificial sequence
<220> FEATURE:
<223> OTHER INFORMATION: Synthetic polynucleotide

<400> SEQUENCE: 5

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg agggcggagt    300

tagggcggag ccaatcagcg tgcgccgttc cgaaagttgc cttttatggc tgggcggaga    360

atgggcggtg aacgccgatg attatataag gacgcgccgg gtgtggcaca gctagttccg    420

tcgcagccgg gatttgggtc gcggttcttg tttgtggatc cctgtgatcg tcacttggta    480

agtcactgac tgtctatgcc tgggaaaggg tgggcaggag atggggcagt gcaggaaaag    540

tggcactatg aaccctcctg gtggcgaggg gagggggtg gtcctcgaac gccttgcaga     600

actggcctgg atacagagtg gaccggctgg ccccatctgg aagacttcga gatacactgt    660

tgtcttactg cgctcaacag tgtatctcga agtcttccaa atggtgccag ccatcgcagc    720

ggggtgcagg aaatgggggc agcccccctt tttggctatc cttccacgtg ttcttttttg    780

tatcttttgt gtttcctaga aaacatctca gtcaccaccg cagccctagg aatgcatcta    840

gacaattgta ctaaccttct tctctttcct ctcctgacag tccggaaagc caccatgtac    900

gccctgttcc tgctggccag cctgctgggc gccgccctgg ccggccccgt gctgggcctg    960

aaggagtgca cccgcggcag cgccgtgtgg tgccagaacg tgaagaccgc cagcgactgc   1020

ggcgccgtga agcactgcct gcagaccgtg tggaacaagc ccaccgtgaa gagcctgccc   1080

tgcgacatct gcaaggacgt ggtgaccgcc gccggcgaca tgctgaagga caacgccacc   1140

gaggaggaga tcctggtgta cctggagaag acctgcgact ggctgcccaa gcccaacatg   1200

agcgccagct gcaaggagat cgtggacagc tacctgcccg tgatcctgga catcatcaag   1260

ggcgagatga gccgccccgg cgaggtgtgc agcgccctga acctgtgcga gagcctgcag   1320

aagcacctgg ccgagctgaa ccaccagaag cagctggaga gcaacaagat ccccgagctg   1380

gacatgaccg aggtggtggc cccctcatg gccaacatcc ccctgctgct gtacccccag    1440

gacggccccc gcagcaagcc ccagcccaag gacaacggcg acgtgtgcca ggactgcatc   1500
```

-continued

```
cagatggtga ccgacatcca gaccgccgtg cgcaccaaca gcaccttcgt gcaggccctg   1560
gtggagcacg tgaaggagga gtgcgaccgc ctgggccccg gcatggccga catctgcaag   1620
aactacatca gccagtacag cgagatcgcc atccagatga tgatgcacat gcagcccaag   1680
gagatctgcg ccctggtggg cttctgcgac gaggtgaagg agatgcccat gcagaccctg   1740
gtgcccgcca aggtggccag caagaacgtg atccccgccc tggagctggt ggagcccatc   1800
aagaagcacg aggtgcccgc caagagcgac gtgtactgcg aggtgtgcga gttcctggtg   1860
aaggaggtga ccaagctgat cgacaacaac aagaccgaga aggagatcct ggacgccttc   1920
gacaagatgt gcagcaagct gcccaagagc ctgagcgagg agtgccagga ggtggtggac   1980
acctacggca gcagcatcct gagcatcctg ctggaggagg tgagccccga gctggtgtgc   2040
agcatgctgc acctgtgcag cggcacccgc ctgcccgccc tgaccgtgca cgtgacccag   2100
cccaaggacg gcggcttctg cgaggtgtgc aagaagctgg tgggctacct ggaccgcaac   2160
ctggagaaga acagcaccaa gcaggagatc ctggccgccc tggagaaggg ctgcagcttc   2220
ctgcccgacc cctaccagaa gcagtgcgac cagttcgtgg ccgagtacga gcccgtgctg   2280
atcgagatcc tggtggaggt gatggacccc agcttcgtgt gcctgaagat cggcgcctgc   2340
cccagcgccc acaagcccct gctgggcacc gagaagtgca tctggggccc cagctactgg   2400
tgccagaaca ccgagaccgc cgcccagtgc aacgccgtgg agcactgcaa gcgccacgtg   2460
tggaacgagg gcagaggaag tcttctgaca tgcggagacg tggaagagaa tcccggccct   2520
atggaattca gcagccccag cagagaggaa tgccccaagc ctctgagccg ggtgtcaatc   2580
atggccggat ctctgacagg actgctgctg cttcaggccg tgtcttgggc ttctggcgct   2640
agaccttgca tccccaagag cttcggctac agcagcgtcg tgtgcgtgtg caatgccacc   2700
tactgcgaca gcttcgaccc tcctaccttt cctgctctgg gcaccttcag cagatacgag   2760
agcaccagat ccggcagacg gatggaactg agcatgggac ccatccaggc caatcacaca   2820
ggcactggcc tgctgctgac actgcagcct gagcagaaat tccagaaagt gaaaggcttc   2880
ggcggagcca tgacagatgc cgccgctctg aatatcctgg ctctgtctcc accagctcag   2940
aacctgctgc tcaagagcta cttcagcgag gaaggcatcg gctacaacat catcagagtg   3000
cccatggcca gctgcgactt cagcatcagg acctacacct acgccgacac acccgacgat   3060
ttccagctgc acaacttcag cctgcctgaa gaggacacca agctgaagat ccctctgatc   3120
cacagagccc tgcagctggc acaaagaccc gtgtcactgc tggcctctcc atggacatct   3180
cccacctggc tgaaaacaaa tggcgccgtg aatggcaagg gcagcctgaa aggccaacct   3240
ggcgacatct accaccagac ctgggccaga tacttcgtga agttcctgga cgcctatgcc   3300
gagcacaagc tgcagttttg ggccgtgaca gccgagaacg aaccttctgc tggactgctg   3360
agcggctacc cctttcagtg cctgggcttt acacccgagc accagcggga ctttatcgcc   3420
cgtgatctgg gacccacact ggccaatagc acccaccata atgtgcggct gctgatgctg   3480
gacgaccaga gactgcttct gccccactgg gctaaagtgg tgctgacaga tcctgaggcc   3540
gccaaatacg tgcacggaat cgccgtgcac tggtatctgg actttctggc ccctgccaag   3600
gccacactgg gagagacaca cagactgttc cccaacacca tgctgttcgc cagcgaagcc   3660
tgtgtgggca gcaagttttg ggaacagagc gtgcggctcg gcagctggga tagaggcatg   3720
cagtacagcc acagcatcat caccaacctg ctgtaccacg tcgtcggctg gaccgactgg   3780
aatctggccc tgaatcctga aggcggccct aactgggtcc gaaacttcgt ggacagcccc   3840
atcatcgtgg acatcaccaa ggacaccttc tacaagcagc ccatgttcta ccacctggga   3900
```

```
cacttcagca agttcatccc cgagggctct cagcgcgttg gactggtggc ttcccagaag   3960
aacgatctgg acgccgtggc tctgatgcac cctgatggat ctgctgtggt ggtggtcctg   4020
aaccgcagca gcaaagatgt gcccctgacc atcaaggatc ccgccgtggg attcctggaa   4080
acaatcagcc ctggctactc catccacacc tacctgtggc gtagacagtg acaattgtta   4140
attaagttta aaccctcgag gccgcaagcc gcatcgatac cgtcgactag agctcgctga   4200
tcagcctcga ctgtgccttc tagttgccag ccatctgttg tttgcccctc ccccgtgcct   4260
tccttgaccc tggaaggtgc cactcccact gtcctttcct aataaaatga ggaaattgca   4320
tcgcattgtc tgagtaggtg tcattctatt ctggggggtg gggtggggca ggacagcaag   4380
ggggaggatt gggaagacaa tagcaggcat gctggggaga gatccacgat aacaaacagc   4440
tttttggggg tgaacatatt gactgaattc cctgcaggtt ggccactccc tctctgcgcg   4500
ctcgctcgct cactgaggcc gcccgggcaa agcccgggcg tcgggcgacc tttggtcgcc   4560
cggcctcagt gagcgagcga gcgcgcagag agggagtggc caactccatc actaggggtt   4620
cctgcggccg ctcgtacggt ctcgaggaat tcctgcagga taacttgcca acctcattct   4680
aaaatgtata tagaagccca aaagacaata acaaaaatat tcttgtagaa caaaatggga   4740
aagaatgttc cactaaatat caagatttag agcaaagcat gagatgtgtg gggatagaca   4800
gtgaggctga taaaatagag tagagctcag aaacagaccc attgatatat gtaagtgacc   4860
tatgaaaaaa atatggcatt ttacaatggg aaaatgatgg tctttttctt ttttagaaaa   4920
acagggaaat atatttatat gtaaaaaata aaagggaacc catatgtcat accatacaca   4980
caaaaaaatt ccagtgaatt ataagtctaa atggagaagg caaaacttta aatcttttag   5040
aaaataatat agaagcatgc agaccagcct ggccaacatg atgaaaccct ctctactaat   5100
aataaaatca gtagaactac tcaggactac tttgagtggg aagtcctttt ctatgaagac   5160
ttctttggcc aaaattaggc tctaaatgca aggagatagt gcatcatgcc tggctgcact   5220
tactgataaa tgatgttatc accatcttta accaaatgca caggaacaag ttatggtact   5280
gatgtgctgg attgagaagg agctctactt ccttgacagg acacatttgt atcaacttaa   5340
aaaagcagat tttgccagc agaactattc attcagaggt aggaaactta gaatagatga   5400
tgtcactgat tagcatggct tccccatctc cacagctgct tcccacccag gttgcccaca   5460
gttgagtttg tccagtgctc agggctgccc actctcagta agaagcccca caccagcccc   5520
tctccaaata tgttggctgt tccttccatt aaagtgaccc cactttagag cagcaagtgg   5580
atttctgttt cttacagttc aggaaggagg agtcagctgt gagaacctgg agcctgagat   5640
gcttctaagt cccactgcta ctggggtcag ggaagccaga ctccagcatc agcagtcagg   5700
agcactaagc ccttgccaac atcctgtttc tcagagaaac tgcttccatt ataatggttg   5760
tcctttttta agctatcaag ccaaacaacc agtgtctacc attattctca tcacctgaag   5820
ccaagggttc tagcaaaagt caagctgtct tgtaatggtt gatgtgcctc cagcttctgt   5880
cttcagtcac tccactctta gcctgctctg aatcaactct gaccacagtt ccctggagcc   5940
cctgccacct gctgcccctg ccaccttctc catctgcagt gctgtgcagc cttctgcact   6000
cttgcagagc taataggtgg agacttgaag gaagaggagg aaagtttctc ataatagcct   6060
tgctgcaagc tcaaatggga ggtgggcact gtgcccagga gccttggagc aaaggctgtg   6120
cccaacctct gactgcatcc aggtttggtc ttgacagaga taagaagccc tggcttttgg   6180
agccaaaatc taggtcagac ttaggcagga ttctcaaagt ttatcagcag aacatgaggc   6240
```

-continued

```
agaagaccct ttctgctcca gcttcttcag gctcaacctt catcagaata gatagaaaga   6300
gaggctgtga gggttcttaa aacagaagca aatctgactc agagaataaa caacctccta   6360
gtaaactaca gcttagacag agcatctggt ggtgagtgtg ctcagtgtcc tactcaactg   6420
tctggtatca gccctcatga ggacttctct tctttccctc atagacctcc atctctgttt   6480
tccttagcct gcagaaatct ggatggctat tcacagaatg cctgtgcttt cagagttgca   6540
ttttttctct ggtattctgg ttcaagcatt tgaaggtagg aaaggttctc caagtgcaag   6600
aaagccagcc ctgagcctca actgcctggc tagtgtggtc agtaggatgc aaaggctgtt   6660
gaatgccaca aggccaaact ttaacctgtg taccacaagc ctagcagcag aggcagctct   6720
gctcactgga actctctgtc ttctttctcc tgagcctttt cttttcctga gttttctagc   6780
tctcctcaac cttacctctg ccctacccag gacaaaccca agagccactg tttctgtgat   6840
gtcctctcca gccctaatta ggcatcatga cttcagcctg accttccatg ctcagaagca   6900
gtgctaatcc acttcagatg agctgctcta tgcaacacag gcagagccta caaacctttg   6960
caccagagcc ctccacatat cagtgtttgt tcatactcac ttcaacagca aatgtgactg   7020
ctgagattaa gattttacac aagatggtct gtaatttcac agttagtttt atcccattag   7080
gtatgaaaga attagcataa ttccccttaa acatgaatga atcttagatt ttttaataaa   7140
tagttttgga agtaaagaca gagacatcag gagcacaagg aatagcctga gaggacaaac   7200
agaacaagaa agagtctgga aatacacagg atgttcttgg cctcctcaaa gcaagtgcaa   7260
gcagatagta ccagcagccc caggctatca gagcccagtg aagagaagta ccatgaaagc   7320
cacagctcta accaccctgt tccagagtga cagacagtcc ccaagacaag ccagcctgag   7380
ccagagagag aactgcaaga gaaagtttct aatttaggtt ctgttagatt cagacaagtg   7440
caggtcatcc tctctccaca gctactcacc tctccagcct aacaaagcct gcagtccaca   7500
ctccaaccct ggtgtctcac ctcctagcct ctcccaacat cctgctctct gaccatcttc   7560
tgcatctctc atctcaccat ctcccactgt ctacagccta ctcttgcaac taccatctca   7620
ttttctgaca tcctgtctac atcttctgcc atactctgcc atctaccata ccacctctta   7680
ccatctacca caccatcttt tatctccatc cctctcagaa gcctccaagc tgaatcctgc   7740
tttatgtgtt catctcagcc cctgcatgga aagctgaccc cagaggcaga actattccca   7800
gagagcttgg ccaagaaaaa caaaactacc agcctggcca ggctcaggag tagtaagctg   7860
cagtgtctgt tgtgttctag cttcaacagc tgcaggagtt ccactctcaa atgctccaca   7920
tttctcacat cctcctgatt ctggtcacta cccatcttca aagaacagaa tatctcacat   7980
cagcatactg tgaaggacta gtcatgggtg cagctgctca gagctgcaaa gtcattctgg   8040
atggtggaga gcttacaaac atttcatgat gctccccccg ctctgatggc tggagcccaa   8100
tccctacaca gactcctgct gtatgtgttt tcctttcact ctgagccaca gccagagggc   8160
aggcattcag tctcctcttc aggctggggc tggggcactg agaactcacc caacaccttg   8220
ctctcactcc ttctgcaaaa caagaaagag ctttgtgctg cagtagccat gaagaatgaa   8280
aggaaggctt taactaaaaa atgtcagaga ttattttcaa cccctactg tggatcacca    8340
gcaaggagga aacacaacac agagacattt tttcccctca aattatcaaa agaatcactg   8400
catttgttaa agagagcaac tgaatcagga agcagagttt tgaacatatc agaagttagg   8460
aatctgcatc agagacaaat gcagtcatgg ttgtttgctg cataccagcc ctaatcatta   8520
gaagcctcat ggacttcaaa catcattccc tctgacaaga tgctctagcc taactccatg   8580
agataaaata aatctgcctt tcagagccaa agaagagtcc accagcttct tctcagtgtg   8640
```

```
aacaagagct ccagtcaggt tagtcagtcc agtgcagtag aggagaccag tctgcatcct   8700
ctaattttca aaggcaagaa gatttgttta ccctggacac caggcacaag tgaggtcaca   8760
gagctcttag atatgcagtc ctcatgagtg aggagactaa agcgcatgcc atcaagactt   8820
cagtgtagag aaaacctcca aaaaagcctc ctcactactt ctggaatagc tcagaggccg   8880
aggcggcctc ggcctctgca taaataaaaa aaattagtca gccatggggc ggagaatggg   8940
cggaactggg cggagttagg ggcgggatgg gcggagttag gggcgggact atggttgctg   9000
actaattgag atgcatgctt tgcatacttc tgcctgctgg ggagcctggg gactttccac   9060
acctggttgc tgactaattg agatgcatgc tttgcatact tctgcctgct ggggagcctg   9120
gggactttcc acaccctaac tgacacacat tccacagctg cattaatgaa tcggccaacg   9180
cgcggggaga ggcggtttgc gtattgggcg ctcttccgct tcctcgctca ctgactcgct   9240
gcgctcggtc gttcggctgc ggcgagcggt atcagctcac tcaaaggcgg taatacggtt   9300
atccacagaa tcaggggata acgcaggaaa gaacatgtga gcaaaaggcc agcaaaaggc   9360
caggaaccgt aaaaaggccg cgttgctggc gtttttccat aggctccgcc cccctgacga   9420
gcatcacaaa aatcgacgct caagtcagag gtggcgaaac ccgacaggac tataaagata   9480
ccaggcgttt ccccctggaa gctccctcgt gcgctctcct gttccgaccc tgccgcttac   9540
cggatacctg tccgcctttc tcccttcggg aagcgtggcg ctttctcata gctcacgctg   9600
taggtatctc agttcggtgt aggtcgttcg ctccaagctg ggctgtgtgc acgaaccccc   9660
cgttcagccc gaccgctgcg ccttatccgg taactatcgt cttgagtcca acccggtaag   9720
acacgactta tcgccactgg cagcagccac tggtaacagg attagcagag cgaggtatgt   9780
aggcggtgct acagagttct tgaagtggtg gcctaactac ggctacacta gaagaacagt   9840
atttggtatc tgcgctctgc tgaagccagt taccttcgga aaaagagttg gtagctcttg   9900
atccggcaaa caaaccaccg ctggtagcgg tggttttttt gtttgcaagc agcagattac   9960
gcgcagaaaa aaaggatctc aagaagatcc tttgatcttt tctacggggt ctgacgctca  10020
gtggaacgaa aactcacgtt aagggatttt ggtcatgaga ttatcaaaaa ggatcttcac  10080
ctagatcctt ttaaattaaa aatgaagttt taaatcaatc taaagtatat atgagtaaac  10140
ttggtctgac agttaccaat gcttaatcag tgaggcacct atctcagcga tctgtctatt  10200
tcgttcatcc atagttgcct gactcctgca aaccacgttg tgtctcaaaa tctctgatgt  10260
tacattgcac aagataaaaa tatatcatca tgaacaataa aactgtctgc ttacataaac  10320
agtaatacaa ggggtgttat gagccatatt caacgggaaa cgtcttgctc gaggccgcga  10380
ttaaattcca acatggatgc tgatttatat gggtataaat gggctcgcga taatgtcggg  10440
caatcaggtg cgacaatcta tcgattgtat gggaagcccg atgcgccaga gttgtttctg  10500
aaacatggca aaggtagcgt tgccaatgat gttacagatg agatggtcag actaaactgg  10560
ctgacggaat ttatgcctct tccgaccatc aagcatttta tccgtactcc tgatgatgca  10620
tggttactca ccactgcgat ccccgggaaa acagcattcc aggtattaga agaatatcct  10680
gattcaggtg aaaatattgt tgatgcgctg gcagtgttcc tgcgccggtt gcattcgatt  10740
cctgtttgta attgtccttt taacagcgat cgcgtatttc gtctcgctca ggcgcaatca  10800
cgaatgaata acggtttggt tgatgcgagt gattttgatg acgagcgtaa tggctggcct  10860
gttgaacaag tctggaaaga aatgcataag cttttgccat tctcaccgga ttcagtcgtc  10920
actcatggtg atttctcact tgataacctt atttttgacg aggggaaatt aataggttgt  10980
```

```
attgatgttg gacgagtcgg aatcgcagac cgataccagg atcttgccat cctatggaac  11040

tgcctcggtg agttttctcc ttcattacag aaacggcttt ttcaaaaata tggtattgat  11100

aatcctgata tgaataaatt gcagtttcat ttgatgctcg atgagttttt ctaagggcgg  11160

cctgccacca tacccacgcc gaaacaagcg ctcatgagcc cgaagtggcg agcccgatct  11220

tccccatcgg tgatgtcggc gatataggcg ccagcaaccg cacctgtggc gccggtgatg  11280

agggcgcgcc aagtcgacgt ccggcagtc                                  11309
```

<210> SEQ ID NO 6
<211> LENGTH: 11293
<212> TYPE: DNA
<213> ORGANISM: Artificial sequence
<220> FEATURE:
<223> OTHER INFORMATION: Synthetic polynucleotide

<400> SEQUENCE: 6

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg agggcggagt    300

tagggcggag ccaatcagcg tgcgccgttc cgaaagttgc cttttatggc tgggcggaga    360

atgggcggtg aacgccgatg attatataag gacgcgccgg gtgtggcaca gctagttccg    420

tcgcagccgg gatttgggtc gcggttcttg tttgtggatc cctgtgatcg tcacttggta    480

agtcactgac tgtctatgcc tgggaaaggg tgggcaggag atggggcagt gcaggaaaag    540

tggcactatg aaccctgcag ccctaggaat gcatctagac aattgtacta accttcttct    600

ctttcctctc ctgacagtcc ggaaagccac catgtacgcc ctgttcctgc tggccagcct    660

gctgggcgcc gccctggccg gccccgtgct gggcctgaag gagtgcaccc gcggcagcgc    720

cgtgtggtgc cagaacgtga agaccgccag cgactgcggc gccgtgaagc actgcctgca    780

gaccgtgtgg aacaagccca ccgtgaagag cctgccctgc gacatctgca aggacgtggt    840

gaccgccgcc ggcgacatgc tgaaggacaa cgccaccgag gaggagatcc tggtgtacct    900

ggagaagacc tgcgactggc tgcccaagcc caacatgagc gccagctgca aggagatcgt    960

ggacagctac ctgcccgtga tcctggacat catcaagggc gagatgagcc gccccggcga   1020

ggtgtgcagc gccctgaacc tgtgcgagag cctgcagaag cacctggccg agctgaacca   1080

ccagaagcag ctggagagca acaagatccc cgagctggac atgaccgagg tggtggcccc   1140

cttcatggcc aacatccccc tgctgctgta cccccaggac ggcccccgca gcaagcccca   1200

gcccaaggac aacggcgacg tgtgccagga ctgcatccag atggtgaccg acatccagac   1260

cgccgtgcgc accaacagca ccttcgtgca ggccctggtg gagcacgtga aggaggagtg   1320

cgaccgcctg ggccccggca tggccgacat ctgcaagaac tacatcagcc agtacagcga   1380

gatcgccatc cagatgatga tgcacatgca gcccaaggag atctgcgccc tggtgggctt   1440

ctgcgacgag gtgaaggaga tgcccatgca gaccctggtg cccgccaagg tggccagcaa   1500

gaacgtgatc cccgccctgg agctggtgga gcccatcaag aagcacgagg tgcccgccaa   1560

gagcgacgtg tactgcgagg tgtgcgagtt cctggtgaag gaggtgacca agctgatcga   1620

caacaacaag accgagaagg agatcctgga cgccttcgac aagatgtgca gcaagctgcc   1680

caagagcctg agcgaggagt gccaggaggt ggtggacacc tacggcagca gcatcctgag   1740
```

```
catcctgctg gaggaggtga gccccgagct ggtgtgcagc atgctgcacc tgtgcagcgg   1800
cacccgcctg cccgccctga ccgtgcacgt gacccagccc aaggacggcg gcttctgcga   1860
ggtgtgcaag aagctggtgg gctacctgga ccgcaacctg gagaagaaca gcaccaagca   1920
ggagatcctg gccgccctgg agaagggctg cagcttcctg cccgacccct accagaagca   1980
gtgcgaccag ttcgtggccg agtacgagcc cgtgctgatc gagatcctgg tggaggtgat   2040
ggaccccagc ttcgtgtgcc tgaagatcgg cgcctgcccc agcgcccaca agcccctgct   2100
gggcaccgag aagtgcatct ggggccccag ctactggtgc cagaacaccg agaccgccgc   2160
ccagtgcaac gccgtggagc actgcaagcg ccacgtgtgg aactgattgt ggccgaaccg   2220
ccgaactcag aggccggccc cagaaaaccc gagcgagtag gggcggcgc gcaggaggga   2280
ggagaactgg gggcgcggga ggctggtggg tgtgggggt ggagatgtag aagatgtgac   2340
gccgcggccc ggcgggtgcc agattagcgg acgcggtgcc cgcggttgca acgggatccc   2400
gggcgctgca gcttgggagg cggctctccc caggcggcgt ccgcggagac acccatccgt   2460
gaaccccagg tcccgggccg ccggctcgcc gcgcaccagg ggccggcgga cagaagagcg   2520
gccgagcggc tcgaggctgg gggaccgcgg gcgcggccgc gcgctgccgg gcgggaggct   2580
ggggggccgg ggccggggcc gtgccccgga gcgggtcgga ggccggggcc ggggccgggg   2640
gacggcggct ccccgcgcgg ctccagcggc tcggggatcc cggccgggcc ccgcagggac   2700
catgatggaa ttcagcagcc ccagcagaga ggaatgcccc aagcctctga gccgggtgtc   2760
aatcatggcc ggatctctga caggactgct gctgcttcag gccgtgtctt gggcttctgg   2820
cgctagacct tgcatcccca agagcttcgg ctacagcagc gtcgtgtgcg tgtgcaatgc   2880
cacctactgc gacagcttcg accctcctac ctttcctgct ctgggcacct tcagcagata   2940
cgagagcacc agatccggca gacggatgga actgagcatg ggacccatcc aggccaatca   3000
cacaggcact ggcctgctgc tgacactgca gcctgagcag aaattccaga aagtgaaagg   3060
cttcggcgga gccatgacag atgccgccgc tctgaatatc ctggctctgt ctccaccagc   3120
tcagaacctg ctgctcaaga gctacttcag cgaggaaggc atcggctaca acatcatcag   3180
agtgcccatg gccagctgcg acttcagcat caggacctac acctacgccg acacacccga   3240
cgatttccag ctgcacaact tcagcctgcc tgaagaggac accaagctga agatccctct   3300
gatccacaga gccctgcagc tggcacaaag acccgtgtca ctgctggcct ctccatggac   3360
atctcccacc tggctgaaaa caaatggcgc cgtgaatggc aagggcagcc tgaaaggcca   3420
acctggcgac atctaccacc agacctgggc cagatacttc gtgaagttcc tggacgccta   3480
tgccgagcac aagctgcagt tttgggccgt gacagccgag aacgaacctt ctgctggact   3540
gctgagcggc taccccttc agtgcctggg ctttacaccc gagcaccagc gggactttat   3600
cgcccgtgat ctgggaccca cactggccaa tagcacccac cataatgtgc ggctgctgat   3660
gctggacgac cagagactgc ttctgcccca ctgggctaaa gtggtgctga cagatcctga   3720
ggccgccaaa tacgtgcacg gaatcgccgt gcactggtat ctggactttc tggcccctgc   3780
caaggccaca ctgggagaga cacacagact gttccccaac accatgctgt tcgccagcga   3840
agcctgtgtg ggcagcaagt tttgggaaca gagcgtgcgg ctcggcagct gggatagagg   3900
catgcagtac agccacagca tcatcaccaa cctgctgtac cacgtcgtcg gctggaccga   3960
ctggaatctg gccctgaatc ctgaaggcgg ccctaactgg gtccgaaact tcgtggacag   4020
ccccatcatc gtggacatca ccaaggacac cttctacaag cagcccatgt tctaccacct   4080
```

```
gggacacttc agcaagttca tccccgaggg ctctcagcgc gttggactgg tggcttccca   4140
gaagaacgat ctggacgccg tggctctgat gcaccctgat ggatctgctg tggtggtggt   4200
cctgaaccgc agcagcaaag atgtgcccct gaccatcaag gatcccgccg tgggattcct   4260
ggaaacaatc agccctggct actccatcca cacctacctg tggcgtagac agtgacaatt   4320
gttaattaag tttaaaccct cgaggccgca agcaataaaa tatctttatt ttcattacat   4380
ctgtgtgttg gttttttgtg tggagatcca cgataacaaa cagctttttt ggggtgaaca   4440
tattgactga attccctgca ggttggccac tccctctctg cgcgctcgct cgctcactga   4500
ggccgcccgg gcaaagcccg ggcgtcgggc gacctttggt cgcccggcct cagtgagcga   4560
gcgagcgcgc agagagggag tggccaactc catcactagg ggttcctgcg gccgctcgta   4620
cggtctcgag gaattcctgc aggataactt gccaacctca ttctaaaatg tatatagaag   4680
cccaaaagac aataacaaaa atattcttgt agaacaaaat gggaaagaat gttccactaa   4740
atatcaagat ttagagcaaa gcatgagatg tgtggggata gacagtgagg ctgataaaat   4800
agagtagagc tcagaaacag acccattgat atatgtaagt gacctatgaa aaaaatatgg   4860
cattttacaa tgggaaaatg atggtctttt tctttttttag aaaaacaggg aaatatattt   4920
atatgtaaaa aataaaaggg aacccatatg tcataccata cacacaaaaa aattccagtg   4980
aattataagt ctaaatggag aaggcaaaac tttaaatctt ttagaaaata atatagaagc   5040
atgcagacca gcctggccaa catgatgaaa ccctctctac taataataaa atcagtagaa   5100
ctactcagga ctactttgag tgggaagtcc ttttctatga agacttcttt ggccaaaatt   5160
aggctctaaa tgcaaggaga tagtgcatca tgcctggctg cacttactga taaatgatgt   5220
tatcaccatc tttaaccaaa tgcacaggaa caagttatgg tactgatgtg ctggattgag   5280
aaggagctct acttccttga caggacacat ttgtatcaac ttaaaaaagc agatttttgc   5340
cagcagaact attcattcag aggtaggaaa cttagaatag atgatgtcac tgattagcat   5400
ggcttcccca tctccacagc tgcttcccac ccaggttgcc cacagttgag tttgtccagt   5460
gctcagggct gcccactctc agtaagaagc ccccacaccag cccctctcca aatatgttgg   5520
ctgttccttc cattaaagtg accccacttt agagcagcaa gtggatttct gtttcttaca   5580
gttcaggaag gaggagtcag ctgtgagaac ctggagcctg agatgcttct aagtcccact   5640
gctactgggg tcagggaagc cagactccag catcagcagt caggagcact aagcccttgc   5700
caacatcctg tttctcagag aaactgcttc cattataatg gttgtccttt tttaagctat   5760
caagccaaac aaccagtgtc taccattatt ctcatcacct gaagccaagg gttctagcaa   5820
aagtcaagct gtcttgtaat ggttgatgtg cctccagctt ctgtcttcag tcactccact   5880
cttagcctgc tctgaatcaa ctctgaccac agttccctgg agcccctgcc acctgctgcc   5940
cctgccacct tctccatctg cagtgctgtg cagccttctg cactcttgca gagctaatag   6000
gtggagactt gaaggaagag gaggaaagtt tctcataata gccttgctgc aagctcaaat   6060
gggaggtggg cactgtgccc aggagccttg gagcaaaggc tgtgcccaac ctctgactgc   6120
atccaggttt ggtcttgaca gagataagaa gccctggctt ttggagccaa aatctaggtc   6180
agacttaggc aggattctca aagtttatca gcagaacatg aggcagaaga ccctttctgc   6240
tccagcttct tcaggctcaa ccttcatcag aatagataga aagagaggct gtgagggttc   6300
ttaaaacaga agcaaatctg actcagagaa taaacaacct cctagtaaac tacagcttag   6360
acagagcatc tggtggtgag tgtgctcagt gtcctactca actgtctggt atcagccctc   6420
atgaggactt ctcttctttc cctcatagac ctccatctct gttttcctta gcctgcagaa   6480
```

```
atctggatgg ctattcacag aatgcctgtg ctttcagagt tgcatttttt ctctggtatt   6540
ctggttcaag catttgaagg taggaaaggt tctccaagtg caagaaagcc agccctgagc   6600
ctcaactgcc tggctagtgt ggtcagtagg atgcaaaggc tgttgaatgc cacaaggcca   6660
aactttaacc tgtgtaccac aagcctagca gcagaggcag ctctgctcac tggaactctc   6720
tgtcttcttt ctcctgagcc ttttcttttc ctgagttttc tagctctcct caaccttacc   6780
tctgccctac ccaggacaaa cccaagagcc actgtttctg tgatgtcctc tccagcccta   6840
attaggcatc atgacttcag cctgaccttc catgctcaga agcagtgcta atccacttca   6900
gatgagctgc tctatgcaac acaggcagag cctacaaacc tttgcaccag agccctccac   6960
atatcagtgt ttgttcatac tcacttcaac agcaaatgtg actgctgaga ttaagatttt   7020
acacaagatg gtctgtaatt tcacagttag ttttatccca ttaggtatga aagaattagc   7080
ataattcccc ttaaacatga atgaatctta gatttttttaa taaatagttt tggaagtaaa   7140
gacagagaca tcaggagcac aaggaatagc ctgagaggac aaacagaaca agaaagagtc   7200
tggaaataca caggatgttc ttggcctcct caaagcaagt gcaagcagat agtaccagca   7260
gccccaggct atcagagccc agtgaagaga agtaccatga aagccacagc tctaaccacc   7320
ctgttccaga gtgacagaca gtccccaaga caagccagcc tgagccagag agagaactgc   7380
aagagaaagt ttctaattta ggttctgtta gattcagaca agtgcaggtc atcctctctc   7440
cacagctact cacctctcca gcctaacaaa gcctgcagtc cacactccaa ccctggtgtc   7500
tcacctccta gcctctccca acatcctgct ctctgaccat cttctgcatc tctcatctca   7560
ccatctccca ctgtctacag cctactcttg caactaccat ctcattttct gacatcctgt   7620
ctacatcttc tgccatactc tgccatctac cataccacct cttaccatct accacaccat   7680
cttttatctc catccctctc agaagcctcc aagctgaatc ctgctttatg tgttcatctc   7740
agcccctgca tggaaagctg accccagagg cagaactatt cccagagagc ttggccaaga   7800
aaaacaaaac taccagcctg gccaggctca ggagtagtaa gctgcagtgt ctgttgtgtt   7860
ctagcttcaa cagctgcagg agttccactc tcaaatgctc cacatttctc acatcctcct   7920
gattctggtc actacccatc ttcaaagaac agaatatctc acatcagcat actgtgaagg   7980
actagtcatg ggtgcagctg ctcagagctg caaagtcatt ctggatggtg gagagcttac   8040
aaacatttca tgatgctccc cccgctctga tggctggagc ccaatcccta cacagactcc   8100
tgctgtatgt gttttccttt cactctgagc cacagccaga gggcaggcat tcagtctcct   8160
cttcaggctg gggctggggc actgagaact cacccaacac cttgctctca ctccttctgc   8220
aaaacaagaa agagctttgt gctgcagtag ccatgaagaa tgaaaggaag gctttaacta   8280
aaaaatgtca gagattattt tcaacccctt actgtggatc accagcaagg aggaaacaca   8340
acacagagac attttttccc ctcaaattat caaaagaatc actgcatttg ttaaagagag   8400
caactgaatc aggaagcaga gttttgaaca tatcagaagt taggaatctg catcagagac   8460
aaatgcagtc atggttgttt gctgcatacc agccctaatc attagaagcc tcatggactt   8520
caaacatcat tccctctgac aagatgctct agcctaactc catgagataa aataaatctg   8580
cctttcagag ccaaagaaga gtccaccagc ttcttctcag tgtgaacaag agctccagtc   8640
aggttagtca gtccagtgca gtagaggaga ccagtctgca tcctctaatt ttcaaaggca   8700
agaagatttg tttaccctgg acaccaggca caagtgaggt cacagagctc ttagatatgc   8760
agtcctcatg agtgaggaga ctaaagcgca tgccatcaag acttcagtgt agagaaaacc   8820
```

```
tccaaaaaag cctcctcact acttctggaa tagctcagag gccgaggcgg cctcggcctc   8880
tgcataaata aaaaaaatta gtcagccatg gggcggagaa tgggcggaac tgggcggagt   8940
taggggcggg atgggcggag ttaggggcgg gactatggtt gctgactaat tgagatgcat   9000
gctttgcata cttctgcctg ctggggagcc tggggacttt ccacacctgg ttgctgacta   9060
attgagatgc atgctttgca tacttctgcc tgctggggag cctggggact ttccacaccc   9120
taactgacac acattccaca gctgcattaa tgaatcggcc aacgcgcggg gagaggcggt   9180
ttgcgtattg ggcgctcttc cgcttcctcg ctcactgact cgctgcgctc ggtcgttcgg   9240
ctgcggcgag cggtatcagc tcactcaaag gcggtaatac ggttatccac agaatcaggg   9300
gataacgcag gaaagaacat gtgagcaaaa ggccagcaaa aggccaggaa ccgtaaaaag   9360
gccgcgttgc tggcgttttt ccataggctc cgcccccctg acgagcatca caaaaatcga   9420
cgctcaagtc agaggtggcg aaacccgaca ggactataaa gataccaggc gtttccccct   9480
ggaagctccc tcgtgcgctc tcctgttccg accctgccgc ttaccggata cctgtccgcc   9540
tttctccctt cgggaagcgt ggcgctttct catagctcac gctgtaggta tctcagttcg   9600
gtgtaggtcg ttcgctccaa gctgggctgt gtgcacgaac cccccgttca gcccgaccgc   9660
tgcgccttat ccggtaacta tcgtcttgag tccaacccgg taagacacga cttatcgcca   9720
ctggcagcag ccactggtaa caggattagc agagcgaggt atgtaggcgg tgctacagag   9780
ttcttgaagt ggtggcctaa ctacggctac actagaagaa cagtatttgg tatctgcgct   9840
ctgctgaagc cagttacctt cggaaaaaga gttggtagct cttgatccgg caaacaaacc   9900
accgctggta gcggtggttt ttttgtttgc aagcagcaga ttacgcgcag aaaaaaagga   9960
tctcaagaag atcctttgat cttttctacg gggtctgacg ctcagtggaa cgaaaactca  10020
cgttaaggga ttttggtcat gagattatca aaaaggatct tcacctagat ccttttaaat  10080
taaaaatgaa gttttaaatc aatctaaagt atatatgagt aaacttggtc tgacagttac  10140
caatgcttaa tcagtgaggc acctatctca gcgatctgtc tatttcgttc atccatagtt  10200
gcctgactcc tgcaaaccac gttgtgtctc aaaatctctg atgttacatt gcacaagata  10260
aaaatatatc atcatgaaca ataaaactgt ctgcttacat aaacagtaat acaaggggtg  10320
ttatgagcca tattcaacgg gaaacgtctt gctcgaggcc gcgattaaat tccaacatgg  10380
atgctgattt atatgggtat aaatgggctc gcgataatgt cgggcaatca ggtgcgacaa  10440
tctatcgatt gtatgggaag cccgatgcgc cagagttgtt tctgaaacat ggcaaaggta  10500
gcgttgccaa tgatgttaca gatgagatgg tcagactaaa ctggctgacg gaatttatgc  10560
ctcttccgac catcaagcat tttatccgta ctcctgatga tgcatggtta ctcaccactg  10620
cgatccccgg gaaaacagca ttccaggtat tagaagaata tcctgattca ggtgaaaata  10680
ttgttgatgc gctggcagtg ttcctgcgcc ggttgcattc gattcctgtt tgtaattgtc  10740
cttttaacag cgatcgcgta tttcgtctcg ctcaggcgca atcacgaatg aataacggtt  10800
tggttgatgc gagtgatttt gatgacgagc gtaatggctg gcctgttgaa caagtctgga  10860
aagaaatgca taagcttttg ccattctcac cggattcagt cgtcactcat ggtgatttct  10920
cacttgataa ccttattttt gacgagggga aattaatagg ttgtattgat gttggacgag  10980
tcggaatcgc agaccgatac caggatcttg ccatcctatg gaactgcctc ggtgagtttt  11040
ctccttcatt acagaaacgg ctttttcaaa aatatggtat tgataatcct gatatgaata  11100
aattgcagtt tcatttgatg ctcgatgagt ttttctaagg gcggcctgcc accataccca  11160
cgccgaaaca agcgctcatg agcccgaagt ggcgagcccg atcttcccca tcggtgatgt  11220
```

cggcgatata ggcgccagca accgcacctg tggcgccggt gatgagggcg cgccaagtcg 11280
acgtccggca gtc 11293

<210> SEQ ID NO 7
<211> LENGTH: 10700
<212> TYPE: DNA
<213> ORGANISM: Artificial sequence
<220> FEATURE:
<223> OTHER INFORMATION: Synthetic polynucleotide

<400> SEQUENCE: 7
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
ctagttatta atagtaatca attacggggt cattagttca tagcccatat atggagttcc 360
gcgttacata acttacggta aatggcccgc ctggctgacc gcccaacgac ccccgcccat 420
tgacgtcaat aatgacgtat gttcccatag taacgccaat agggactttc cattgacgtc 480
aatgggtgga gtatttacgg taaactgccc acttggcagt acatcaagtg tatcatatgc 540
caagtacgcc ccctattgac gtcaatgacg gtaaatggcc cgcctggcat tatgcccagt 600
acatgacctt atgggacttt cctacttggc agtacatcta cgtattagtc atcgctatta 660
ccatggtcga ggtgagcccc acgttctgct tcactctccc catctccccc ccctccccac 720
ccccaatttt gtatttattt atttttaat tattttgtgc agcgatgggg gcgggggggg 780
ggggggggcg cgcgccaggc ggggcggggc ggggcgaggg gcggggcggg gcgaggcgga 840
gaggtgcggc ggcagccaat cagagcggcg cgctccgaaa gtttcctttt atggcgaggc 900
ggcggcggcg gcggccctat aaaaagcgaa gcgcgcggcg ggcgggagtc gctgcgacgc 960
tgccttcgcc ccgtgccccg ctccgccgcc gcctcgcgcc gcccgccccg gctctgactg 1020
accgcgttac tcccacaggt gagcgggcgg gacggccctt ctcctccggg ctgtaattag 1080
cgcttggttt aatgacggct tgtttctttt ctgtggctgc gtgaaagcct tgaggggctc 1140
cgggagctag agcctctgct aaccatgttc atgccttctt ctttttccta cagctcctgg 1200
gcaacgtgct ggttattgtg ctgtctcatc attttggcaa agaattcctc gaagatccga 1260
agggaaagtc ttccacgact gtgggatccg ttcgaagata tcaccggttg agccaccatg 1320
gaattcagca gccccagcag agaggaatgc cccaagcctc tgagccgggt gtcaatcatg 1380
gccggatctc tgacaggact gctgctgctt caggccgtgt cttgggcttc tggcgctaga 1440
ccttgcatcc ccaagagctt cggctacagc agcgtcgtgt gcgtgtgcaa tgccacctac 1500
tgcgacagct tcgaccctcc tacctttcct gctctgggca ccttcagcag atacgagagc 1560
accagatccg gcagacggat ggaactgagc atgggaccca tccaggccaa tcacacaggc 1620
actggcctgc tgctgacact gcagcctgag cagaaattcc agaaagtgaa aggcttcggc 1680
ggagccatga cagatgccgc cgctctgaat atcctggctc tgtctccacc agctcagaac 1740
ctgctgctca agagctactt cagcgaggaa ggcatcggct acaacatcat cagagtgccc 1800
atggccagct gcgacttcag catcaggacc tacacctacg ccgacacacc cgacgatttc 1860
cagctgcaca acttcagcct gcctgaagag gacaccaagc tgaagatccc tctgatccac 1920

-continued

```
agagccctgc agctggcaca aagacccgtg tcactgctgg cctctccatg gacatctccc   1980
acctggctga aaacaaatgg cgccgtgaat ggcaagggca gcctgaaagg ccaacctggc   2040
gacatctacc accagacctg ggccagatac ttcgtgaagt tcctggacgc ctatgccgag   2100
cacaagctgc agttttgggc cgtgacagcc gagaacgaac cttctgctgg actgctgagc   2160
ggctacccct ttcagtgcct gggctttaca cccgagcacc agcgggactt tatcgcccgt   2220
gatctgggac ccacactggc caatagcacc caccataatg tgcggctgct gatgctggac   2280
gaccagagac tgcttctgcc ccactgggct aaagtggtgc tgacagatcc tgaggccgcc   2340
aaatacgtgc acggaatcgc cgtgcactgg tatctggact ttctggcccc tgccaaggcc   2400
acactgggag agacacacag actgttcccc aacaccatgc tgttcgccag cgaagcctgt   2460
gtgggcagca agttttggga acagagcgtg cggctcggca gctgggatag aggcatgcag   2520
tacagccaca gcatcatcac caacctgctg taccacgtcg tcggctggac cgactggaat   2580
ctggccctga atcctgaagg cggccctaac tgggtccgaa acttcgtgga cagccccatc   2640
atcgtggaca tcaccaagga caccttctac aagcagccca tgttctacca cctgggacac   2700
ttcagcaagt tcatccccga gggctctcag cgcgttggac tggtggcttc ccagaagaac   2760
gatctggacg ccgtggctct gatgcaccct gatggatctg ctgtggtggt ggtcctgaac   2820
cgcagcagca aagatgtgcc cctgaccatc aaggatcccg ccgtgggatt cctggaaaca   2880
atcagccctg gctactccat ccacacctac ctgtggcgta gacagtgaca attgttaatt   2940
aagtttaaac cctcgaggcc gcaagcttat cgataatcaa cctctggatt acaaaatttg   3000
tgaaagattg actggtattc ttaactatgt tgctcctttt acgctatgtg gatacgctgc   3060
tttaatgcct ttgtatcatg ctattgcttc ccgtatggct ttcattttct cctccttgta   3120
taaatcctgg ttgctgtctc tttatgagga gttgtggccc gttgtcaggc aacgtggcgt   3180
ggtgtgcact gtgtttgctg acgcaacccc cactggttgg ggcattgcca ccacctgtca   3240
gctcctttcc gggactttcg ctttccccct ccctattgcc acggcggaac tcatcgccgc   3300
ctgccttgcc cgctgctgga caggggctcg gctgttgggc actgacaatt ccgtggtgtt   3360
gtcggggaaa tcatcgtcct ttccttggct gctcgcctgt gttgccacct ggattctgcg   3420
cgggacgtcc ttctgctacg tcccttcggc cctcaatcca gcggaccttc cttcccgcgg   3480
cctgctgccg gctctgcggc ctcttccgcg tcttcgcctt cgccctcaga cgagtcggat   3540
ctccctttgg gccgcctccc cgcatcgata ccgtcgacta gagctcgctg atcagcctcg   3600
actgtgcctt ctagttgcca gccatctgtt gtttgcccct cccccgtgcc ttccttgacc   3660
ctggaaggtg ccactcccac tgtcctttcc taataaaatg aggaaattgc atcgcattgt   3720
ctgagtaggt gtcattctat tctggggggt ggggtggggc aggacagcaa gggggaggat   3780
tgggaagaca atagcaggca tgctggggag agatccacga taacaaacag ctttttttggg   3840
gtgaacatat tgactgaatt ccctgcaggt tggccactcc ctctctgcgc gctcgctcgc   3900
tcactgaggc cgcccgggca aagcccgggc gtcgggcgac ctttggtcgc ccggcctcag   3960
tgagcgagcg agcgcgcaga gagggagtgg ccaactccat cactaggggt tcctgcggcc   4020
gctcgtacgg tctcgaggaa ttcctgcagg ataacttgcc aacctcattc taaaatgtat   4080
atagaagccc aaaagacaat aacaaaaata ttcttgtaga acaaaatggg aaagaatgtt   4140
ccactaaata tcaagattta gagcaaagca tgagatgtgt ggggatagac agtgaggctg   4200
ataaaataga gtagagctca gaaacagacc cattgatata tgtaagtgac ctatgaaaaa   4260
aatatggcat tttacaatgg gaaaatgatg gtctttttct tttttagaaa aacagggaaa   4320
```

```
tatatttata tgtaaaaaat aaaagggaac ccatatgtca taccatacac acaaaaaaat   4380
tccagtgaat tataagtcta aatggagaag gcaaaacttt aaatctttta gaaaataata   4440
tagaagcatg cagaccagcc tggccaacat gatgaaaccc tctctactaa taataaaatc   4500
agtagaacta ctcaggacta ctttgagtgg gaagtccttt tctatgaaga cttctttggc   4560
caaaattagg ctctaaatgc aaggagatag tgcatcatgc ctggctgcac ttactgataa   4620
atgatgttat caccatcttt aaccaaatgc acaggaacaa gttatggtac tgatgtgctg   4680
gattgagaag gagctctact tccttgacag gacacatttg tatcaactta aaaaagcaga   4740
tttttgccag cagaactatt cattcagagg taggaaactt agaatagatg atgtcactga   4800
ttagcatggc ttccccatct ccacagctgc ttcccaccca ggttgcccac agttgagttt   4860
gtccagtgct cagggctgcc cactctcagt aagaagcccc acaccagccc ctctccaaat   4920
atgttggctg ttccttccat taaagtgacc ccactttaga gcagcaagtg gatttctgtt   4980
tcttacagtt caggaaggag gagtcagctg tgagaacctg gagcctgaga tgcttctaag   5040
tcccactgct actggggtca gggaagccag actccagcat cagcagtcag gagcactaag   5100
cccttgccaa catcctgttt ctcagagaaa ctgcttccat tataatggtt gtcctttttt   5160
aagctatcaa gccaaacaac cagtgtctac cattattctc atcacctgaa gccaagggtt   5220
ctagcaaaag tcaagctgtc ttgtaatggt tgatgtgcct ccagcttctg tcttcagtca   5280
ctccactctt agcctgctct gaatcaactc tgaccacagt tccctggagc ccctgccacc   5340
tgctgcccct gccaccttct ccatctgcag tgctgtgcag ccttctgcac tcttgcagag   5400
ctaataggtg gagacttgaa ggaagaggag gaaagtttct cataatagcc ttgctgcaag   5460
ctcaaatggg aggtgggcac tgtgcccagg agccttggag caaaggctgt gcccaacctc   5520
tgactgcatc caggtttggt cttgacagag ataagaagcc ctggcttttg gagccaaaat   5580
ctaggtcaga cttaggcagg attctcaaag tttatcagca gaacatgagg cagaagaccc   5640
tttctgctcc agcttcttca ggctcaacct tcatcagaat agatagaaag agaggctgtg   5700
agggttctta aaacagaagc aaatctgact cagagaataa acaacctcct agtaaactac   5760
agcttagaca gagcatctgg tggtgagtgt gctcagtgtc ctactcaact gtctggtatc   5820
agccctcatg aggacttctc ttctttccct catagacctc catctctgtt ttccttagcc   5880
tgcagaaatc tggatggcta ttcacagaat gcctgtgctt tcagagttgc atttttttctc   5940
tggtattctg gttcaagcat ttgaaggtag gaaaggttct ccaagtgcaa gaaagccagc   6000
cctgagcctc aactgcctgg ctagtgtggt cagtaggatg caaaggctgt tgaatgccac   6060
aaggccaaac tttaacctgt gtaccacaag cctagcagca gaggcagctc tgctcactgg   6120
aactctctgt cttctttctc ctgagccttt tcttttcctg agttttctag ctctcctcaa   6180
ccttacctct gccctaccca ggacaaaccc aagagccact gtttctgtga tgtcctctcc   6240
agccctaatt aggcatcatg acttcagcct gaccttccat gctcagaagc agtgctaatc   6300
cacttcagat gagctgctct atgcaacaca ggcagagcct acaaaccttt gcaccagagc   6360
cctccacata tcagtgtttg ttcatactca cttcaacagc aaatgtgact gctgagatta   6420
agattttaca caagatggtc tgtaatttca cagttagttt tatcccatta ggtatgaaag   6480
aattagcata attcccctta aacatgaatg aatcttagat tttttaataa atagttttgg   6540
aagtaaagac agagacatca ggagcacaag gaatagcctg agaggacaaa cagaacaaga   6600
aagagtctgg aaatacacag gatgttcttg gcctcctcaa agcaagtgca agcagatagt   6660
```

-continued

```
accagcagcc ccaggctatc agagcccagt gaagagaagt accatgaaag ccacagctct   6720
aaccaccctg ttccagagtg acagacagtc cccaagacaa gccagcctga gccagagaga   6780
gaactgcaag agaaagtttc taatttaggt tctgttagat tcagacaagt gcaggtcatc   6840
ctctctccac agctactcac ctctccagcc taacaaagcc tgcagtccac actccaaccc   6900
tggtgtctca cctcctagcc tctcccaaca tcctgctctc tgaccatctt ctgcatctct   6960
catctcacca tctcccactg tctacagcct actcttgcaa ctaccatctc attttctgac   7020
atcctgtcta catcttctgc catactctgc catctaccat accacctctt accatctacc   7080
acaccatctt ttatctccat ccctctcaga agcctccaag ctgaatcctg ctttatgtgt   7140
tcatctcagc ccctgcatgg aaagctgacc ccagaggcag aactattccc agagagcttg   7200
gccaagaaaa acaaaactac cagcctggcc aggctcagga gtagtaagct gcagtgtctg   7260
ttgtgttcta gcttcaacag ctgcaggagt tccactctca aatgctccac atttctcaca   7320
tcctcctgat tctggtcact acccatcttc aaagaacaga atatctcaca tcagcatact   7380
gtgaaggact agtcatgggt gcagctgctc agagctgcaa agtcattctg gatggtggag   7440
agcttacaaa catttcatga tgctcccccc gctctgatgg ctggagccca atccctacac   7500
agactcctgc tgtatgtgtt ttcctttcac tctgagccac agccagaggg caggcattca   7560
gtctcctctt caggctgggg ctggggcact gagaactcac ccaacacctt gctctcactc   7620
cttctgcaaa acaagaaaga gctttgtgct gcagtagcca tgaagaatga aaggaaggct   7680
ttaactaaaa aatgtcagag attattttca accccttact gtggatcacc agcaaggagg   7740
aaacacaaca cagagacatt ttttcccctc aaattatcaa aagaatcact gcatttgtta   7800
aagagagcaa ctgaatcagg aagcagagtt ttgaacatat cagaagttag gaatctgcat   7860
cagagacaaa tgcagtcatg gttgtttgct gcataccagc cctaatcatt agaagcctca   7920
tggacttcaa acatcattcc ctctgacaag atgctctagc ctaactccat gagataaaat   7980
aaatctgcct ttcagagcca aagaagagtc caccagcttc ttctcagtgt gaacaagagc   8040
tccagtcagg ttagtcagtc cagtgcagta gaggagacca gtctgcatcc tctaattttc   8100
aaaggcaaga agatttgttt accctggaca ccaggcacaa gtgaggtcac agagctctta   8160
gatatgcagt cctcatgagt gaggagacta aagcgcatgc catcaagact tcagtgtaga   8220
gaaaacctcc aaaaaagcct cctcactact tctggaatag ctcagaggcc gaggcggcct   8280
cggcctctgc ataaataaaa aaaattagtc agccatgggg cggagaatgg gcggaactgg   8340
gcggagttag gggcgggatg ggcggagtta ggggcgggac tatggttgct gactaattga   8400
gatgcatgct ttgcatactt ctgcctgctg gggagcctgg ggactttcca cacctggttg   8460
ctgactaatt gagatgcatg ctttgcatac ttctgcctgc tggggagcct ggggactttc   8520
cacaccctaa ctgacacaca ttccacagct gcattaatga atcggccaac gcgcggggag   8580
aggcggtttg cgtattgggc gctcttccgc ttcctcgctc actgactcgc tgcgctcggt   8640
cgttcggctg cggcgagcgg tatcagctca ctcaaaggcg gtaatacggt tatccacaga   8700
atcaggggat aacgcaggaa agaacatgtg agcaaaaggc cagcaaaagg ccaggaaccg   8760
taaaaaggcc gcgttgctgg cgtttttcca taggctccgc ccccctgacg agcatcacaa   8820
aaatcgacgc tcaagtcaga ggtggcgaaa cccgacagga ctataaagat accaggcgtt   8880
tccccctgga agctccctcg tgcgctctcc tgttccgacc ctgccgctta ccggatacct   8940
gtccgccttt ctcccttcgg gaagcgtggc gctttctcat agctcacgct gtaggtatct   9000
cagttcggtg taggtcgttc gctccaagct gggctgtgtg cacgaacccc ccgttcagcc   9060
```

```
cgaccgctgc gccttatccg gtaactatcg tcttgagtcc aacccggtaa gacacgactt   9120

atcgccactg gcagcagcca ctggtaacag gattagcaga gcgaggtatg taggcggtgc   9180

tacagagttc ttgaagtggt ggcctaacta cggctacact agaagaacag tatttggtat   9240

ctgcgctctg ctgaagccag ttaccttcgg aaaaagagtt ggtagctctt gatccggcaa   9300

acaaaccacc gctggtagcg gtggtttttt tgtttgcaag cagcagatta cgcgcagaaa   9360

aaaaggatct caagaagatc ctttgatctt ttctacgggg tctgacgctc agtggaacga   9420

aaactcacgt taagggattt tggtcatgag attatcaaaa aggatcttca cctagatcct   9480

tttaaattaa aaatgaagtt ttaaatcaat ctaaagtata tatgagtaaa cttggtctga   9540

cagttaccaa tgcttaatca gtgaggcacc tatctcagcg atctgtctat ttcgttcatc   9600

catagttgcc tgactcctgc aaaccacgtt gtgtctcaaa atctctgatg ttacattgca   9660

caagataaaa atatatcatc atgaacaata aaactgtctg cttacataaa cagtaataca   9720

aggggtgtta tgagccatat tcaacgggaa acgtcttgct cgaggccgcg attaaattcc   9780

aacatggatg ctgatttata tgggtataaa tgggctcgcg ataatgtcgg gcaatcaggt   9840

gcgacaatct atcgattgta tgggaagccc gatgcgccag agttgtttct gaaacatggc   9900

aaaggtagcg ttgccaatga tgttacagat gagatggtca gactaaactg gctgacggaa   9960

tttatgcctc ttccgaccat caagcatttt atccgtactc ctgatgatgc atggttactc  10020

accactgcga tccccgggaa aacagcattc caggtattag aagaatatcc tgattcaggt  10080

gaaaatattg ttgatgcgct ggcagtgttc ctgcgccggt tgcattcgat tcctgtttgt  10140

aattgtcctt ttaacagcga tcgcgtattt cgtctcgctc aggcgcaatc acgaatgaat  10200

aacggtttgg ttgatgcgag tgattttgat gacgagcgta atggctggcc tgttgaacaa  10260

gtctggaaag aaatgcataa gcttttgcca ttctcaccgg attcagtcgt cactcatggt  10320

gatttctcac ttgataacct tatttttgac gaggggaaat taataggttg tattgatgtt  10380

ggacgagtcg gaatcgcaga ccgataccag gatcttgcca tcctatggaa ctgcctcggt  10440

gagttttctc cttcattaca gaaacggctt tttcaaaaat atggtattga taatcctgat  10500

atgaataaat tgcagtttca tttgatgctc gatgagtttt tctaagggcg gcctgccacc  10560

atacccacgc cgaaacaagc gctcatgagc ccgaagtggc gagcccgatc ttccccatcg  10620

gtgatgtcgg cgatataggc gccagcaacc gcacctgtgg cgccggtgat gagggcgcgc  10680

caagtcgacg tccggcagtc                                               10700
```

```
<210> SEQ ID NO 8
<211> LENGTH: 10700
<212> TYPE: DNA
<213> ORGANISM: Artificial sequence
<220> FEATURE:
<223> OTHER INFORMATION: Synthetic polynucleotide

<400> SEQUENCE: 8
```

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactatt agatctgatg gccgcgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg aattcggtac    300

ctagttatta atagtaatca attacggggt cattagttca tagcccatat atggagttcc    360
```

```
gcgttacata acttacggta aatggcccgc ctggctgacc gcccaacgac ccccgcccat    420
tgacgtcaat aatgacgtat gttcccatag taacgccaat agggactttc cattgacgtc    480
aatgggtgga gtatttacgg taaactgccc acttggcagt acatcaagtg tatcatatgc    540
caagtacgcc ccctattgac gtcaatgacg gtaaatggcc cgcctggcat tatgcccagt    600
acatgacctt atgggacttt cctacttggc agtacatcta cgtattagtc atcgctatta    660
ccatggtcga ggtgagcccc acgttctgct tcactctccc catctccccc ccctccccac    720
ccccaatttt gtatttattt atttttaat tattttgtgc agcgatgggg gcgggggggg    780
gggggggcg cgcgccaggc ggggcggggc ggggcgaggg gcggggcggg gcgaggcgga    840
gaggtgcggc ggcagccaat cagagcggcg cgctccgaaa gtttcctttt atggcgaggc    900
ggcggcggcg gcggccctat aaaaagcgaa gcgcgcggcg ggcgggagtc gctgcgacgc    960
tgccttcgcc ccgtgccccg ctccgccgcc gcctcgcgcc gcccgccccg gctctgactg   1020
accgcgttac tcccacaggt gagcgggcgg gacggccctt ctcctccggg ctgtaattag   1080
cgcttggttt aatgacggct tgtttctttt ctgtggctgc gtgaaagcct tgaggggctc   1140
cgggagctag agcctctgct aaccatgttc atgccttctt ctttttccta cagctcctgg   1200
gcaacgtgct ggttattgtg ctgtctcatc attttggcaa agaattcctc gaagatccga   1260
agggaaagtc ttccacgact gtgggatccg ttcgaagata tcaccggttg agccaccatg   1320
gaattcagca gccccagcag agaggaatgc cccaagcctc tgagccgggt gtcaatcatg   1380
gccggatctc tgacaggact gctgctgctt caggccgtgt cttgggcttc tggcgctaga   1440
ccttgcatcc ccaagagctt cggctacagc agcgtcgtgt gcgtgtgcaa tgccacctac   1500
tgcgacagct tcgaccctcc tacctttcct gctctgggca ccttcagcag atacgagagc   1560
accagatccg gcagacggat ggaactgagc atgggaccca tccaggccaa tcacacaggc   1620
actggcctgc tgctgacact gcagcctgag cagaaattcc agaaagtgaa aggcttcggc   1680
ggagccatga cagatgccgc cgctctgaat atcctggctc tgtctccacc agctcagaac   1740
ctgctgctca agagctactt cagcgaggaa ggcatcggct acaacatcat cagagtgccc   1800
atggccagct gcgacttcag catcaggacc tacacctacg ccgacacacc cgacgatttc   1860
cagctgcaca acttcagcct gcctgaagag gacaccaagc tgaagatccc tctgatccac   1920
agagccctgc agctggcaca aagacccgtg tcactgctgg cctctccatg gacatctccc   1980
acctggctga aaacaaatgg cgccgtgaat ggcaagggca gcctgaaagg ccaacctggc   2040
gacatctacc accagacctg ggccagatac ttcgtgaagt tcctggacgc ctatgccgag   2100
cacaagctgc agttttgggc cgtgacagcc gagaacgaac cttctgctgg actgctgagc   2160
ggctacccct ttcagtgcct gggctttaca cccgagcacc agcgggactt tatcgcccgt   2220
gatctgggac ccacactggc caatagcacc caccataatg tgcggctgct gatgctggac   2280
gaccagagac tgcttctgcc ccactgggct aaagtggtgc tgacagatcc tgaggccgcc   2340
aaatacgtgc acggaatcgc cgtgcactgg tatctggact ttctggcccc tgccaaggcc   2400
acactgggag agacacacag actgttcccc aacaccatgc tgttcgccag cgaagcctgt   2460
gtgggcagca agttttggga acagagcgtg cggctcggca gctgggatag aggcatgcag   2520
tacagccaca gcatcatcac caacctgctg taccacgtcg tcggctggac cgactggaat   2580
ctggccctga atcctgaagg cggccctaac tgggtccgaa acttcgtgga cagccccatc   2640
atcgtggaca tcaccaagga caccttctac aagcagccca tgttctacca cctgggacac   2700
ttcagcaagt tcatccccga gggctctcag cgcgttggac tggtggcttc ccagaagaac   2760
```

```
gatctggacg ccgtggctct gatgcaccct gatggatctg ctgtggtggt ggtcctgaac   2820
cgcagcagca aagatgtgcc cctgaccatc aaggatcccg ccgtgggatt cctggaaaca   2880
atcagccctg gctactccat ccacacctac ctgtggcgta gacagtgaca attgttaatt   2940
aagtttaaac cctcgaggcc gcaagcttat cgataatcaa cctctggatt acaaaatttg   3000
tgaaagattg actggtattc ttaactatgt tgctcctttt acgctatgtg gatacgctgc   3060
tttaatgcct ttgtatcatg ctattgcttc ccgtatggct ttcattttct cctccttgta   3120
taaatcctgg ttgctgtctc tttatgagga gttgtggccc gttgtcaggc aacgtggcgt   3180
ggtgtgcact gtgtttgctg acgcaacccc cactggttgg ggcattgcca ccacctgtca   3240
gctcctttcc gggactttcg ctttccccct ccctattgcc acggcggaac tcatcgccgc   3300
ctgccttgcc cgctgctgga caggggctcg gctgttgggc actgacaatt ccgtggtgtt   3360
gtcggggaaa tcatcgtcct ttccttggct gctcgcctgt gttgccacct ggattctgcg   3420
cgggacgtcc ttctgctacg tcccttcggc cctcaatcca gcggaccttc cttcccgcgg   3480
cctgctgccg gctctgcggc ctcttccgcg tcttcgcctt cgccctcaga cgagtcggat   3540
ctccctttgg gccgcctccc cgcatcgata ccgtcgacta gagctcgctg atcagcctcg   3600
actgtgcctt ctagttgcca gccatctgtt gtttgcccct cccccgtgcc ttccttgacc   3660
ctggaaggtg ccactcccac tgtcctttcc taataaaatg aggaaattgc atcgcattgt   3720
ctgagtaggt gtcattctat tctggggggt ggggtggggc aggacagcaa gggggaggat   3780
tgggaagaca atagcaggca tgctggggag agatccacga taacaaacag ctttttttggg   3840
gtgaacatat tgactgaatt ccctgcaggt tggccactcc ctctctgcgc gctcgctcgc   3900
tcactgaggc cgcccgggca aagcccgggc gtcgggcgac ctttggtcgc ccggcctcag   3960
tgagcgagcg agcgcgcaga gagggagtgg ccaactccat cactaggggt tcctgcggcc   4020
gctcgtacgg tctcgaggaa ttcctgcagg ataacttgcc aacctcattc taaaatgtat   4080
atagaagccc aaaagacaat aacaaaaata ttcttgtaga acaaaatggg aaagaatgtt   4140
ccactaaata tcaagattta gagcaaagca tgagatgtgt ggggatagac agtgaggctg   4200
ataaaataga gtagagctca gaaacagacc cattgatata tgtaagtgac ctatgaaaaa   4260
aatatggcat tttacaatgg gaaaatgatg gtctttttct tttttagaaa aacagggaaa   4320
tatatttata tgtaaaaaat aaaagggaac ccatatgtca taccatacac acaaaaaaat   4380
tccagtgaat tataagtcta aatggagaag gcaaaacttt aaatctttta gaaaataata   4440
tagaagcatg cagaccagcc tggccaacat gatgaaaccc tctctactaa taataaaatc   4500
agtagaacta ctcaggacta ctttgagtgg gaagtccttt tctatgaaga cttctttggc   4560
caaaattagg ctctaaatgc aaggagatag tgcatcatgc ctggctgcac ttactgataa   4620
atgatgttat caccatcttt aaccaaatgc acaggaacaa gttatggtac tgatgtgctg   4680
gattgagaag gagctctact tccttgacag gacacattgg tatcaactta aaaaagcaga   4740
tttttgccag cagaactatt cattcagagg taggaaactt agaatagatg atgtcactga   4800
ttagcatggc ttccccatct ccacagctgc ttcccaccca ggttgcccac agttgagttt   4860
gtccagtgct cagggctgcc cactctcagt aagaagcccc acaccagccc ctctccaaat   4920
atgttggctg ttccttccat taaagtgacc ccactttaga gcagcaagtg gatttctgtt   4980
tcttacagtt caggaaggag gagtcagctg tgagaacctg gagcctgaga tgcttctaag   5040
tcccactgct actggggtca gggaagccag actccagcat cagcagtcag gagcactaag   5100
```

```
cccttgccaa catcctgttt ctcagagaaa ctgcttccat tataatggtt gtcctttttt   5160
aagctatcaa gccaaacaac cagtgtctac cattattctc atcacctgaa gccaagggtt   5220
ctagcaaaag tcaagctgtc ttgtaatggt tgatgtgcct ccagcttctg tcttcagtca   5280
ctccactctt agcctgctct gaatcaactc tgaccacagt tccctggagc ccctgccacc   5340
tgctgcccct gccaccttct ccatctgcag tgctgtgcag ccttctgcac tcttgcagag   5400
ctaataggtg gagacttgaa ggaagaggag gaaagtttct cataatagcc ttgctgcaag   5460
ctcaaatggg aggtgggcac tgtgcccagg agccttggag caaaggctgt gcccaacctc   5520
tgactgcatc caggtttggt cttgacagag ataagaagcc ctggcttttg gagccaaaat   5580
ctaggtcaga cttaggcagg attctcaaag tttatcagca gaacatgagg cagaagaccc   5640
tttctgctcc agcttcttca ggctcaacct tcatcagaat agatagaaag agaggctgtg   5700
agggttctta aaacagaagc aaatctgact cagagaataa acaacctcct agtaaactac   5760
agcttagaca gagcatctgg tggtgagtgt gctcagtgtc ctactcaact gtctggtatc   5820
agccctcatg aggacttctc ttctttccct catagacctc catctctgtt ttccttagcc   5880
tgcagaaatc tggatggcta ttcacagaat gcctgtgctt tcagagttgc atttttttctc   5940
tggtattctg gttcaagcat ttgaaggtag gaaaggttct ccaagtgcaa gaaagccagc   6000
cctgagcctc aactgcctgg ctagtgtggt cagtaggatg caaaggctgt tgaatgccac   6060
aaggccaaac tttaacctgt gtaccacaag cctagcagca gaggcagctc tgctcactgg   6120
aactctctgt cttctttctc ctgagccttt tcttttcctg agttttctag ctctcctcaa   6180
ccttacctct gccctaccca ggacaaaccc aagagccact gtttctgtga tgtcctctcc   6240
agccctaatt aggcatcatg acttcagcct gaccttccat gctcagaagc agtgctaatc   6300
cacttcagat gagctgctct atgcaacaca ggcagagcct acaaaccttt gcaccagagc   6360
cctccacata tcagtgtttg ttcatactca cttcaacagc aaatgtgact gctgagatta   6420
agattttaca caagatggtc tgtaatttca cagttagttt tatcccatta ggtatgaaag   6480
aattagcata attcccctta aacatgaatg aatcttagat tttttaataa atagttttgg   6540
aagtaaagac agagacatca ggagcacaag gaatagcctg agaggacaaa cagaacaaga   6600
aagagtctgg aaatacacag gatgttcttg gcctcctcaa agcaagtgca agcagatagt   6660
accagcagcc ccaggctatc agagcccagt gaagagaagt accatgaaag ccacagctct   6720
aaccaccctg ttccagagtg acagacagtc cccaagacaa gccagcctga gccagagaga   6780
gaactgcaag agaaagtttc taatttaggt tctgttagat tcagacaagt gcaggtcatc   6840
ctctctccac agctactcac ctctccagcc taacaaagcc tgcagtccac actccaaccc   6900
tggtgtctca cctcctagcc tctcccaaca tcctgctctc tgaccatctt ctgcatctct   6960
catctcacca tctcccactg tctacagcct actcttgcaa ctaccatctc attttctgac   7020
atcctgtcta catcttctgc catactctgc catctaccat accacctctt accatctacc   7080
acaccatctt ttatctccat ccctctcaga agcctccaag ctgaatcctg ctttatgtgt   7140
tcatctcagc ccctgcatgg aaagctgacc ccagaggcag aactattccc agagagcttg   7200
gccaagaaaa acaaaactac cagcctggcc aggctcagga gtagtaagct gcagtgtctg   7260
ttgtgttcta gcttcaacag ctgcaggagt tccactctca aatgctccac atttctcaca   7320
tcctcctgat tctggtcact acccatcttc aaagaacaga atatctcaca tcagcatact   7380
gtgaaggact agtcatgggt gcagctgctc agagctgcaa agtcattctg gatggtggag   7440
agcttacaaa catttcatga tgctccccccc gctctgatgg ctggagccca atccctacac   7500
```

```
agactcctgc tgtatgtgtt ttcctttcac tctgagccac agccagaggg caggcattca   7560
gtctcctctt caggctgggg ctggggcact gagaactcac ccaacacctt gctctcactc   7620
cttctgcaaa acaagaaaga gctttgtgct gcagtagcca tgaagaatga aaggaaggct   7680
ttaactaaaa aatgtcagag attattttca accccttact gtggatcacc agcaaggagg   7740
aaacacaaca cagagacatt ttttcccctc aaattatcaa aagaatcact gcatttgtta   7800
aagagagcaa ctgaatcagg aagcagagtt ttgaacatat cagaagttag gaatctgcat   7860
cagagacaaa tgcagtcatg gttgtttgct gcataccagc cctaatcatt agaagcctca   7920
tggacttcaa acatcattcc ctctgacaag atgctctagc ctaactccat gagataaaat   7980
aaatctgcct ttcagagcca aagaagagtc caccagcttc ttctcagtgt gaacaagagc   8040
tccagtcagg ttagtcagtc cagtgcagta gaggagacca gtctgcatcc tctaattttc   8100
aaaggcaaga agatttgttt accctggaca ccaggcacaa gtgaggtcac agagctctta   8160
gatatgcagt cctcatgagt gaggagacta aagcgcatgc catcaagact tcagtgtaga   8220
gaaaacctcc aaaaaagcct cctcactact tctggaatag ctcagaggcc gaggcggcct   8280
cggcctctgc ataaataaaa aaaattagtc agccatgggg cggagaatgg gcggaactgg   8340
gcggagttag gggcgggatg ggcggagtta ggggcgggac tatggttgct gactaattga   8400
gatgcatgct ttgcatactt ctgcctgctg gggagcctgg ggactttcca cacctggttg   8460
ctgactaatt gagatgcatg ctttgcatac ttctgcctgc tggggagcct ggggactttc   8520
cacaccctaa ctgacacaca ttccacagct gcattaatga atcggccaac gcgcggggag   8580
aggcggtttg cgtattgggc gctcttccgc ttcctcgctc actgactcgc tgcgctcggt   8640
cgttcggctg cggcgagcgg tatcagctca ctcaaaggcg gtaatacggt tatccacaga   8700
atcaggggat aacgcaggaa agaacatgtg agcaaaaggc cagcaaaagg ccaggaaccg   8760
taaaaaggcc gcgttgctgg cgtttttcca taggctccgc ccccctgacg agcatcacaa   8820
aaatcgacgc tcaagtcaga ggtggcgaaa cccgacagga ctataaagat accaggcgtt   8880
tccccctgga agctccctcg tgcgctctcc tgttccgacc ctgccgctta ccggatacct   8940
gtccgccttt ctcccttcgg gaagcgtggc gctttctcat agctcacgct gtaggtatct   9000
cagttcggtg taggtcgttc gctccaagct gggctgtgtg cacgaacccc ccgttcagcc   9060
cgaccgctgc gccttatccg gtaactatcg tcttgagtcc aacccggtaa gacacgactt   9120
atcgccactg gcagcagcca ctggtaacag gattagcaga gcgaggtatg taggcggtgc   9180
tacagagttc ttgaagtggt ggcctaacta cggctacact agaagaacag tatttggtat   9240
ctgcgctctg ctgaagccag ttaccttcgg aaaaagagtt ggtagctctt gatccggcaa   9300
acaaaccacc gctggtagcg gtggtttttt tgtttgcaag cagcagatta cgcgcagaaa   9360
aaaaggatct caagaagatc ctttgatctt ttctacgggg tctgacgctc agtggaacga   9420
aaactcacgt taagggattt tggtcatgag attatcaaaa aggatcttca cctagatcct   9480
tttaaattaa aaatgaagtt ttaaatcaat ctaaagtata tatgagtaaa cttggtctga   9540
cagttaccaa tgcttaatca gtgaggcacc tatctcagcg atctgtctat ttcgttcatc   9600
catagttgcc tgactcctgc aaaccacgtt gtgtctcaaa atctctgatg ttacattgca   9660
caagataaaa atatatcatc atgaacaata aaactgtctg cttacataaa cagtaataca   9720
aggggtgtta tgagccatat tcaacgggaa acgtcttgct cgaggccgcg attaaattcc   9780
aacatggatg ctgatttata tgggtataaa tgggctcgcg ataatgtcgg gcaatcaggt   9840
```

```
gcgacaatct atcgattgta tgggaagccc gatgcgccag agttgtttct gaaacatggc   9900

aaaggtagcg ttgccaatga tgttacagat gagatggtca gactaaactg gctgacggaa   9960

tttatgcctc ttccgaccat caagcatttt atccgtactc ctgatgatgc atggttactc  10020

accactgcga tccccgggaa aacagcattc caggtattag aagaatatcc tgattcaggt  10080

gaaaatattg ttgatgcgct ggcagtgttc ctgcgccggt tgcattcgat tcctgtttgt  10140

aattgtcctt ttaacagcga tcgcgtattt cgtctcgctc aggcgcaatc acgaatgaat  10200

aacggtttgg ttgatgcgag tgattttgat gacgagcgta atggctggcc tgttgaacaa  10260

gtctggaaag aaatgcataa gcttttgcca ttctcaccgg attcagtcgt cactcatggt  10320

gatttctcac ttgataacct tatttttgac gaggggaaat taataggttg tattgatgtt  10380

ggacgagtcg gaatcgcaga ccgataccag gatcttgcca tcctatggaa ctgcctcggt  10440

gagttttctc cttcattaca gaaacggctt tttcaaaaat atggtattga taatcctgat  10500

atgaataaat tgcagtttca tttgatgctc gatgagtttt tctaagggcg gcctgccacc  10560

atacccacgc cgaaacaagc gctcatgagc ccgaagtggc gagcccgatc ttccccatcg  10620

gtgatgtcgg cgatataggc gccagcaacc gcacctgtgg cgccggtgat gagggcgcgc  10680

caagtcgacg tccggcagtc                                              10700
```

```
<210> SEQ ID NO 9
<211> LENGTH: 10700
<212> TYPE: DNA
<213> ORGANISM: Artificial sequence
<220> FEATURE:
<223> OTHER INFORMATION: Synthetic polynucleotide

<400> SEQUENCE: 9

ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg aattcggtac    300

ctagttatta atagtaatca attacggggt cattagttca tagcccatat atggagttcc    360

gcgttacata acttacggta aatggcccgc ctggctgacc gcccaacgac ccccgcccat    420

tgacgtcaat aatgacgtat gttcccatag taacgccaat agggactttc cattgacgtc    480

aatgggtgga gtatttacgg taaactgccc acttggcagt acatcaagtg tatcatatgc    540

caagtacgcc ccctattgac gtcaatgacg gtaaatggcc cgcctggcat tatgcccagt    600

acatgacctt atgggacttt cctacttggc agtacatcta cgtattagtc atcgctatta    660

ccatggtcga ggtgagcccc acgttctgct tcactctccc catctccccc ccctccccac    720

ccccaatttt gtatttattt atttttaat tattttgtgc agcgatgggg gcgggggggg    780

gggggggcg cgcgccaggc ggggcggggc ggggcgaggg gcggggcggg gcgaggcgga    840

gaggtgcggc ggcagccaat cagagcggcg cgctccgaaa gtttcctttt atggcgaggc    900

ggcggcggcg gcggccctat aaaaagcgaa gcgcgcggcg ggcgggagtc gctgcgacgc    960

tgccttcgcc ccgtgccccg ctccgccgcc gcctcgcgcc gcccgccccg gctctgactg   1020

accgcgttac tcccacaggt gagcgggcgg gacggccctt ctcctccggg ctgtaattag   1080

cgcttggttt aatgacggct tgtttctttt ctgtggctgc gtgaaagcct tgaggggctc   1140

cgggagctag agcctctgct aaccatgttc atgccttctt ctttttccta cagctcctgg   1200
```

```
gcaacgtgct ggttattgtg ctgtctcatc attttggcaa agaattcctc gaagatccga   1260
agggaaagtc ttccacgact gtgggatccg ttcgaagata tcaccggttg agccaccatg   1320
gaattcagca gccccagcag agaggaatgc cccaagcctc tgagccgggt gtcaatcatg   1380
gccggatctc tgacaggact gctgctgctt caggccgtgt cttgggcttc tggcgctaga   1440
ccttgcatcc ccaagagctt cggctacagc agcgtcgtgt gcgtgtgcaa tgccacctac   1500
tgcgacagct tcgaccctcc tacctttcct gctctgggca ccttcagcag atacgagagc   1560
accagatccg gcagacggat ggaactgagc atgggaccca tccaggccaa tcacacaggc   1620
actggcctgc tgctgacact gcagcctgag cagaaattcc agaaagtgaa aggcttcggc   1680
ggagccatga cagatgccgc cgctctgaat atcctggctc tgtctccacc agctcagaac   1740
ctgctgctca agagctactt cagcgaggaa ggcatcggct acaacatcat cagagtgccc   1800
atggccagct gcgacttcag catcaggacc tacacctacg ccgacacacc cgacgatttc   1860
cagctgcaca acttcagcct gcctgaagag gacaccaagc tgaagatccc tctgatccac   1920
agagccctgc agctggcaca aagacccgtg tcactgctgg cctctccatg gacatctccc   1980
acctggctga aaacaaatgg cgccgtgaat ggcaagggca gcctgaaagg ccaacctggc   2040
gacatctacc accagacctg ggccagatac ttcgtgaagt tcctggacgc ctatgccgag   2100
cacaagctgc agttttgggc cgtgacagcc gagaacgaac cttctgctgg actgctgagc   2160
ggctacccct ttcagtgcct gggctttaca cccgagcacc agcgggactt tatcgcccgt   2220
gatctgggac ccacactggc caatagcacc caccataatg tgcggctgct gatgctggac   2280
gaccagagac tgcttctgcc ccactgggct aaagtggtgc tgacagatcc tgaggccgcc   2340
aaatacgtgc acggaatcgc cgtgcactgg tatctggact ttctggcccc tgccaaggcc   2400
acactgggag agacacacag actgttcccc aacaccatgc tgttcgccag cgaagcctgt   2460
gtgggcagca agttttggga acagagcgtg cggctcggca gctgggatag aggcatgcag   2520
tacagccaca gcatcatcac caacctgctg taccacgtcg tcggctggac cgactggaat   2580
ctggccctga atcctgaagg cggccctaac tgggtccgaa acttcgtgga cagccccatc   2640
atcgtggaca tcaccaagga caccttctac aagcagccca tgttctacca cctgggacac   2700
ttcagcaagt tcatccccga gggctctcag cgcgttggac tggtggcttc ccagaagaac   2760
gatctggacg ccgtggctct gatgcaccct gatggatctg ctgtggtggt ggtcctgaac   2820
cgcagcagca aagatgtgcc cctgaccatc aaggatcccg ccgtgggatt cctggaaaca   2880
atcagccctg gctactccat ccacacctac ctgtggcgta gacagtgaca attgttaatt   2940
aagtttaaac cctcgaggcc gcaagcttat cgataatcaa cctctggatt acaaaatttg   3000
tgaaagattg actggtattc ttaactatgt tgctcctttt acgctatgtg gatacgctgc   3060
tttaatgcct ttgtatcatg ctattgcttc ccgtatggct ttcattttct cctccttgta   3120
taaatcctgg ttgctgtctc tttatgagga gttgtggccc gttgtcaggc aacgtggcgt   3180
ggtgtgcact gtgtttgctg acgcaacccc cactggttgg ggcattgcca ccacctgtca   3240
gctcctttcc gggactttcg ctttccccct ccctattgcc acggcggaac tcatcgccgc   3300
ctgccttgcc cgctgctgga caggggctcg gctgttgggc actgacaatt ccgtggtgtt   3360
gtcggggaaa tcatcgtcct ttccttggct gctcgcctgt gttgccacct ggattctgcg   3420
cgggacgtcc ttctgctacg tcccttcggc cctcaatcca gcggaccttc cttcccgcgg   3480
cctgctgccg gctctgcggc ctcttccgcg tcttcgcctt cgccctcaga cgagtcggat   3540
```

```
ctccctttgg gccgcctccc cgcatcgata ccgtcgacta gagctcgctg atcagcctcg   3600
actgtgcctt ctagttgcca gccatctgtt gtttgcccct cccccgtgcc ttccttgacc   3660
ctggaaggtg ccactcccac tgtcctttcc taataaaatg aggaaattgc atcgcattgt   3720
ctgagtaggt gtcattctat tctggggggt ggggtggggc aggacagcaa gggggaggat   3780
tgggaagaca atagcaggca tgctggggag agatccacga taacaaacag ctttttttggg   3840
gtgaacatat tgactgaatt ccctgcaggt tggccactcc ctctctgcgc gctcgctcgc   3900
tcactgaggc cgcccgggca aagcccgggc gtcgggcgac ctttggtcgc ccggcctcag   3960
tgagcgagcg agcgcgcaga gagggagtgg ccaactccat cactaggggt tcctgcggcc   4020
gctcgtacgg tctcgaggaa ttcctgcagg ataacttgcc aacctcattc taaaatgtat   4080
atagaagccc aaaagacaat aacaaaaata ttcttgtaga acaaaatggg aaagaatgtt   4140
ccactaaata tcaagattta gagcaaagca tgagatgtgt ggggatagac agtgaggctg   4200
ataaaataga gtagagctca gaaacagacc cattgatata tgtaagtgac ctatgaaaaa   4260
aatatggcat tttacaatgg gaaaatgatg gtctttttct tttttagaaa aacagggaaa   4320
tatatttata tgtaaaaaat aaaagggaac ccatatgtca taccatacac acaaaaaaat   4380
tccagtgaat tataagtcta aatggagaag gcaaaacttt aaatctttta gaaaataata   4440
tagaagcatg cagaccagcc tggccaacat gatgaaaccc tctctactaa taataaaatc   4500
agtagaacta ctcaggacta ctttgagtgg gaagtccttt tctatgaaga cttctttggc   4560
caaaattagg ctctaaatgc aaggagatag tgcatcatgc ctggctgcac ttactgataa   4620
atgatgttat caccatcttt aaccaaatgc acaggaacaa gttatggtac tgatgtgctg   4680
gattgagaag gagctctact tccttgacag gacacatttg tatcaactta aaaaagcaga   4740
tttttgccag cagaactatt cattcagagg taggaaactt agaatagatg atgtcactga   4800
ttagcatggc ttccccatct ccacagctgc ttcccaccca ggttgcccac agttgagttt   4860
gtccagtgct cagggctgcc cactctcagt aagaagcccc acaccagccc ctctccaaat   4920
atgttggctg ttccttccat taaagtgacc ccactttaga gcagcaagtg gatttctgtt   4980
tcttacagtt caggaaggag gagtcagctg tgagaacctg gagcctgaga tgcttctaag   5040
tcccactgct actggggtca gggaagccag actccagcat cagcagtcag gagcactaag   5100
cccttgccaa catcctgttt ctcagagaaa ctgcttccat tataatggtt gtcctttttt   5160
aagctatcaa gccaaacaac cagtgtctac cattattctc atcacctgaa gccaagggtt   5220
ctagcaaaag tcaagctgtc ttgtaatggt tgatgtgcct ccagcttctg tcttcagtca   5280
ctccactctt agcctgctct gaatcaactc tgaccacagt tccctggagc ccctgccacc   5340
tgctgcccct gccaccttct ccatctgcag tgctgtgcag ccttctgcac tcttgcagag   5400
ctaataggtg gagacttgaa ggaagaggag gaaagtttct cataatagcc ttgctgcaag   5460
ctcaaatggg aggtgggcac tgtgcccagg agccttggag caaaggctgt gcccaacctc   5520
tgactgcatc caggtttggt cttgacagag ataagaagcc ctggcttttg gagccaaaat   5580
ctaggtcaga cttaggcagg attctcaaag tttatcagca gaacatgagg cagaagaccc   5640
tttctgctcc agcttcttca ggctcaacct tcatcagaat agatagaaag agaggctgtg   5700
agggttctta aaacagaagc aaatctgact cagagaataa acaacctcct agtaaactac   5760
agcttagaca gagcatctgg tggtgagtgt gctcagtgtc ctactcaact gtctggtatc   5820
agccctcatg aggacttctc ttctttccct catagacctc catctctgtt ttccttagcc   5880
tgcagaaatc tggatggcta ttcacagaat gcctgtgctt tcagagttgc atttttctc   5940
```

```
tggtattctg gttcaagcat ttgaaggtag gaaaggttct ccaagtgcaa gaaagccagc   6000
cctgagcctc aactgcctgg ctagtgtggt cagtaggatg caaaggctgt tgaatgccac   6060
aaggccaaac tttaacctgt gtaccacaag cctagcagca gaggcagctc tgctcactgg   6120
aactctctgt cttctttctc ctgagccttt tcttttcctg agttttctag ctctcctcaa   6180
ccttacctct gccctaccca ggacaaaccc aagagccact gtttctgtga tgtcctctcc   6240
agccctaatt aggcatcatg acttcagcct gaccttccat gctcagaagc agtgctaatc   6300
cacttcagat gagctgctct atgcaacaca ggcagagcct acaaaccttt gcaccagagc   6360
cctccacata tcagtgtttg ttcatactca cttcaacagc aaatgtgact gctgagatta   6420
agattttaca caagatggtc tgtaatttca cagttagttt tatcccatta ggtatgaaag   6480
aattagcata attcccctta aacatgaatg aatcttagat tttttaataa atagttttgg   6540
aagtaaagac agagacatca ggagcacaag gaatagcctg agaggacaaa cagaacaaga   6600
aagagtctgg aaatacacag gatgttcttg gcctcctcaa agcaagtgca agcagatagt   6660
accagcagcc ccaggctatc agagcccagt gaagagaagt accatgaaag ccacagctct   6720
aaccaccctg ttccagagtg acagacagtc cccaagacaa gccagcctga gccagagaga   6780
gaactgcaag agaaagtttc taatttaggt tctgttagat tcagacaagt gcaggtcatc   6840
ctctctccac agctactcac ctctccagcc taacaaagcc tgcagtccac actccaaccc   6900
tggtgtctca cctcctagcc tctcccaaca tcctgctctc tgaccatctt ctgcatctct   6960
catctcacca tctcccactg tctacagcct actcttgcaa ctaccatctc attttctgac   7020
atcctgtcta catcttctgc catactctgc catctaccat accacctctt accatctacc   7080
acaccatctt ttatctccat ccctctcaga agcctccaag ctgaatcctg ctttatgtgt   7140
tcatctcagc ccctgcatgg aaagctgacc ccagaggcag aactattccc agagagcttg   7200
gccaagaaaa acaaaactac cagcctggcc aggctcagga gtagtaagct gcagtgtctg   7260
ttgtgttcta gcttcaacag ctgcaggagt tccactctca aatgctccac atttctcaca   7320
tcctcctgat tctggtcact acccatcttc aaagaacaga atatctcaca tcagcatact   7380
gtgaaggact agtcatgggt gcagctgctc agagctgcaa agtcattctg gatggtggag   7440
agcttacaaa catttcatga tgctcccccc gctctgatgg ctggagccca atccctacac   7500
agactcctgc tgtatgtgtt ttcctttcac tctgagccac agccagaggg caggcattca   7560
gtctcctctt caggctgggg ctggggcact gagaactcac ccaacacctt gctctcactc   7620
cttctgcaaa acaagaaaga gctttgtgct gcagtagcca tgaagaatga aaggaaggct   7680
ttaactaaaa aatgtcagag attattttca accccttact gtggatcacc agcaaggagg   7740
aaacacaaca cagagacatt ttttcccctc aaattatcaa aagaatcact gcatttgtta   7800
aagagagcaa ctgaatcagg aagcagagtt ttgaacatat cagaagttag gaatctgcat   7860
cagagacaaa tgcagtcatg gttgtttgct gcataccagc cctaatcatt agaagcctca   7920
tggacttcaa acatcattcc ctctgacaag atgctctagc ctaactccat gagataaaat   7980
aaatctgcct ttcagagcca aagaagagtc caccagcttc ttctcagtgt gaacaagagc   8040
tccagtcagg ttagtcagtc cagtgcagta gaggagacca gtctgcatcc tctaattttc   8100
aaaggcaaga agatttgttt accctggaca ccaggcacaa gtgaggtcac agagctctta   8160
gatatgcagt cctcatgagt gaggagacta aagcgcatgc catcaagact tcagtgtaga   8220
gaaaacctcc aaaaaagcct cctcactact tctggaatag ctcagaggcc gaggcggcct   8280
```

```
cggcctctgc ataaataaaa aaaattagtc agccatgggg cggagaatgg gcggaactgg   8340
gcggagttag gggcgggatg ggcggagtta ggggcgggac tatggttgct gactaattga   8400
gatgcatgct ttgcatactt ctgcctgctg gggagcctgg ggactttcca cacctggttg   8460
ctgactaatt gagatgcatg ctttgcatac ttctgcctgc tggggagcct ggggactttc   8520
cacaccctaa ctgacacaca ttccacagct gcattaatga atcggccaac gcgcggggag   8580
aggcggtttg cgtattgggc gctcttccgc ttcctcgctc actgactcgc tgcgctcggt   8640
cgttcggctg cggcgagcgg tatcagctca ctcaaaggcg gtaatacggt tatccacaga   8700
atcaggggat aacgcaggaa agaacatgtg agcaaaaggc cagcaaaagg ccaggaaccg   8760
taaaaaggcc gcgttgctgg cgtttttcca taggctccgc ccccctgacg agcatcacaa   8820
aaatcgacgc tcaagtcaga ggtggcgaaa cccgacagga ctataaagat accaggcgtt   8880
tccccctgga agctccctcg tgcgctctcc tgttccgacc ctgccgctta ccggatacct   8940
gtccgccttt ctcccttcgg gaagcgtggc gctttctcat agctcacgct gtaggtatct   9000
cagttcggtg taggtcgttc gctccaagct gggctgtgtg cacgaacccc ccgttcagcc   9060
cgaccgctgc gccttatccg gtaactatcg tcttgagtcc aacccggtaa gacacgactt   9120
atcgccactg gcagcagcca ctggtaacag gattagcaga gcgaggtatg taggcggtgc   9180
tacagagttc ttgaagtggt ggcctaacta cggctacact agaagaacag tatttggtat   9240
ctgcgctctg ctgaagccag ttaccttcgg aaaaagagtt ggtagctctt gatccggcaa   9300
acaaaccacc gctggtagcg gtggtttttt tgtttgcaag cagcagatta cgcgcagaaa   9360
aaaaggatct caagaagatc ctttgatctt ttctacgggg tctgacgctc agtggaacga   9420
aaactcacgt taagggattt tggtcatgag attatcaaaa aggatcttca cctagatcct   9480
tttaaattaa aaatgaagtt ttaaatcaat ctaaagtata tatgagtaaa cttggtctga   9540
cagttaccaa tgcttaatca gtgaggcacc tatctcagcg atctgtctat ttcgttcatc   9600
catagttgcc tgactcctgc aaaccacgtt gtgtctcaaa atctctgatg ttacattgca   9660
caagataaaa atatatcatc atgaacaata aaactgtctg cttacataaa cagtaataca   9720
aggggtgtta tgagccatat tcaacgggaa acgtcttgct cgaggccgcg attaaattcc   9780
aacatggatg ctgatttata tgggtataaa tgggctcgcg ataatgtcgg gcaatcaggt   9840
gcgacaatct atcgattgta tgggaagccc gatgcgccag agttgtttct gaaacatggc   9900
aaaggtagcg ttgccaatga tgttacagat gagatggtca gactaaactg gctgacggaa   9960
tttatgcctc ttccgaccat caagcatttt atccgtactc ctgatgatgc atggttactc  10020
accactgcga tccccgggaa aacagcattc caggtattag aagaatatcc tgattcaggt  10080
gaaaatattg ttgatgcgct ggcagtgttc ctgcgccggt tgcattcgat tcctgtttgt  10140
aattgtcctt ttaacagcga tcgcgtattt cgtctcgctc aggcgcaatc acgaatgaat  10200
aacggtttgg ttgatgcgag tgattttgat gacgagcgta atggctggcc tgttgaacaa  10260
gtctggaaag aaatgcataa gcttttgcca ttctcaccgg attcagtcgt cactcatggt  10320
gatttctcac ttgataacct tatttttgac gaggggaaat taataggttg tattgatgtt  10380
ggacgagtcg gaatcgcaga ccgataccag gatcttgcca tcctatggaa ctgcctcggt  10440
gagttttctc cttcattaca gaaacggctt tttcaaaaat atggtattga taatcctgat  10500
atgaataaat tgcagtttca tttgatgctc gatgagtttt tctaagggcg gcctgccacc  10560
atacccacgc cgaaacaagc gctcatgagc ccgaagtggc gagcccgatc ttccccatcg  10620
gtgatgtcgg cgatataggc gccagcaacc gcacctgtgg cgccggtgat gagggcgcgc  10680
```

caagtcgacg tccggcagtc 10700

<210> SEQ ID NO 10
<211> LENGTH: 10700
<212> TYPE: DNA
<213> ORGANISM: Artificial sequence
<220> FEATURE:
<223> OTHER INFORMATION: Synthetic polynucleotide

<400> SEQUENCE: 10
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
ctagttatta atagtaatca attacggggt cattagttca tagcccatat atggagttcc 360
gcgttacata acttacggta aatggcccgc ctggctgacc gcccaacgac ccccgcccat 420
tgacgtcaat aatgacgtat gttcccatag taacgccaat agggactttc cattgacgtc 480
aatgggtgga gtatttacgg taaactgccc acttggcagt acatcaagtg tatcatatgc 540
caagtacgcc ccctattgac gtcaatgacg gtaaatggcc cgcctggcat tatgcccagt 600
acatgacctt atgggacttt cctacttggc agtacatcta cgtattagtc atcgctatta 660
ccatggtcga ggtgagcccc acgttctgct tcactctccc catctccccc ccctccccac 720
ccccaatttt gtatttattt atttttaat tattttgtgc agcgatgggg gcgggggggg 780 gggggggcg cgcgccaggc ggggcggggc ggggcgaggg gcggggcggg gcgaggcgga 840
gaggtgcggc ggcagccaat cagagcggcg cgctccgaaa gtttcctttt atggcgaggc 900
ggcggcggcg gcggccctat aaaaagcgaa gcgcgcggcg ggcgggagtc gctgcgacgc 960
tgccttcgcc ccgtgccccg ctccgccgcc gcctcgcgcc gcccgccccg gctctgactg 1020
accgcgttac tcccacaggt gagcgggcgg gacggccctt ctcctccggg ctgtaattag 1080
cgcttggttt aatgacggct tgtttctttt ctgtggctgc gtgaaagcct tgaggggctc 1140
cgggagctag agcctctgct aaccatgttc atgccttctt ctttttccta cagctcctgg 1200
gcaacgtgct ggttattgtg ctgtctcatc attttggcaa agaattcctc gaagatccga 1260
agggaaagtc ttccacgact gtgggatccg ttcgaagata tcaccggttg agccaccatg 1320
gaattcagca gccccagcag agaggaatgc cccaagcctc tgagccgggt gtcaatcatg 1380
gccggatctc tgacaggact gctgctgctt caggccgtgt cttgggcttc tggcgctaga 1440
ccttgcatcc ccaagagctt cggctacagc agcgtcgtgt gcgtgtgcaa tgccacctac 1500
tgcgacagct tcgaccctcc tacctttcct gctctgggca ccttcagcag atacgagagc 1560
accagatccg gcagacggat ggaactgagc atgggaccca tccaggccaa tcacacaggc 1620
actggcctgc tgctgacact gcagcctgag cagaaattcc agaaagtgaa aggcttcggc 1680
ggagccatga cagatgccgc cgctctgaat atcctggctc tgtctccacc agctcagaac 1740
ctgctgctca agagctactt cagcgaggaa ggcatcggct acaacatcat cagagtgccc 1800
atggccagct gcgacttcag catcaggacc tacacctacg ccgacacacc cgacgatttc 1860
cagctgcaca acttcagcct gcctgaagag gacaccaagc tgaagatccc tctgatccac 1920
agagccctgc agctggcaca aagacccgtg tcactgctgg cctctccatg gacatctccc 1980

-continued

```
acctggctga aaacaaatgg cgccgtgaat ggcaagggca gcctgaaagg ccaacctggc   2040
gacatctacc accagacctg ggccagatac ttcgtgaagt tcctggacgc ctatgccgag   2100
cacaagctgc agttttgggc cgtgacagcc gagaacgaac cttctgctgg actgctgagc   2160
ggctacccct ttcagtgcct gggctttaca cccgagcacc agcgggactt tatcgcccgt   2220
gatctgggac ccacactggc caatagcacc caccataatg tgcggctgct gatgctggac   2280
gaccagagac tgcttctgcc ccactgggct aaagtggtgc tgacagatcc tgaggccgcc   2340
aaatacgtgc acggaatcgc cgtgcactgg tatctggact ttctggcccc tgccaaggcc   2400
acactgggag agacacacag actgttcccc aacaccatgc tgttcgccag cgaagcctgt   2460
gtgggcagca agttttggga acagagcgtg cggctcggca gctgggatag aggcatgcag   2520
tacagccaca gcatcatcac caacctgctg taccacgtcg tcggctggac cgactggaat   2580
ctggccctga atcctgaagg cggccctaac tgggtccgaa acttcgtgga cagccccatc   2640
atcgtggaca tcaccaagga caccttctac aagcagccca tgttctacca cctgggacac   2700
ttcagcaagt tcatccccga gggctctcag cgcgttggac tggtggcttc ccagaagaac   2760
gatctggacg ccgtggctct gatgcaccct gatggatctg ctgtggtggt ggtcctgaac   2820
cgcagcagca aagatgtgcc cctgaccatc aaggatcccg ccgtgggatt cctggaaaca   2880
atcagccctg gctactccat ccacacctac ctgtggcgta gacagtgaca attgttaatt   2940
aagtttaaac cctcgaggcc gcaagcttat cgataatcaa cctctggatt acaaaatttg   3000
tgaaagattg actggtattc ttaactatgt tgctcctttt acgctatgtg gatacgctgc   3060
tttaatgcct ttgtatcatg ctattgcttc ccgtatggct ttcattttct cctccttgta   3120
taaatcctgg ttgctgtctc tttatgagga gttgtggccc gttgtcaggc aacgtggcgt   3180
ggtgtgcact gtgtttgctg acgcaacccc cactggttgg ggcattgcca ccacctgtca   3240
gctcctttcc gggactttcg ctttccccct ccctattgcc acggcggaac tcatcgccgc   3300
ctgccttgcc cgctgctgga caggggctcg gctgttgggc actgacaatt ccgtggtgtt   3360
gtcggggaaa tcatcgtcct ttccttggct gctcgcctgt gttgccacct ggattctgcg   3420
cgggacgtcc ttctgctacg tcccttcggc cctcaatcca gcggaccttc cttcccgcgg   3480
cctgctgccg gctctgcggc ctcttccgcg tcttcgcctt cgccctcaga cgagtcggat   3540
ctccctttgg gccgcctccc cgcatcgata ccgtcgacta gagctcgctg atcagcctcg   3600
actgtgcctt ctagttgcca gccatctgtt gtttgcccct cccccgtgcc ttccttgacc   3660
ctggaaggtg ccactcccac tgtcctttcc taataaaatg aggaaattgc atcgcattgt   3720
ctgagtaggt gtcattctat tctggggggt ggggtggggc aggacagcaa gggggaggat   3780
tgggaagaca atagcaggca tgctggggag agatccacga taacaaacag ctttttttggg   3840
gtgaacatat tgactgaatt ccctgcagga ggaaccccta gtgatggagt tggccactcc   3900
ctctctgcgc gctcgctcgc tcactgaggc cgcccgggca aagcccgggc gtcgggcgac   3960
ctttggtcgc ccggcctcag tgagcgagcg agcgcgcaga gagggagtgg ccaagcggcc   4020
gctcgtacgg tctcgaggaa ttcctgcagg ataacttgcc aacctcattc taaaatgtat   4080
atagaagccc aaaagacaat aacaaaaata ttcttgtaga acaaaatggg aaagaatgtt   4140
ccactaaata tcaagattta gagcaaagca tgagatgtgt ggggatagac agtgaggctg   4200
ataaaataga gtagagctca gaaacagacc cattgatata tgtaagtgac ctatgaaaaa   4260
aatatggcat tttacaatgg gaaaatgatg gtctttttct tttttagaaa aacagggaaa   4320
tatatttata tgtaaaaaat aaaagggaac ccatatgtca taccatacac acaaaaaaat   4380
```

```
tccagtgaat tataagtcta aatggagaag gcaaaacttt aaatctttta gaaaataata   4440
tagaagcatg cagaccagcc tggccaacat gatgaaaccc tctctactaa taataaaatc   4500
agtagaacta ctcaggacta ctttgagtgg gaagtccttt tctatgaaga cttctttggc   4560
caaaattagg ctctaaatgc aaggagatag tgcatcatgc ctggctgcac ttactgataa   4620
atgatgttat caccatcttt aaccaaatgc acaggaacaa gttatggtac tgatgtgctg   4680
gattgagaag gagctctact tccttgacag gacacatttg tatcaactta aaaaagcaga   4740
tttttgccag cagaactatt cattcagagg taggaaactt agaatagatg atgtcactga   4800
ttagcatggc ttccccatct ccacagctgc ttcccaccca ggttgcccac agttgagttt   4860
gtccagtgct cagggctgcc cactctcagt aagaagcccc acaccagccc ctctccaaat   4920
atgttggctg ttccttccat taaagtgacc ccactttaga gcagcaagtg gatttctgtt   4980
tcttacagtt caggaaggag gagtcagctg tgagaacctg gagcctgaga tgcttctaag   5040
tcccactgct actggggtca gggaagccag actccagcat cagcagtcag gagcactaag   5100
cccttgccaa catcctgttt ctcagagaaa ctgcttccat tataatggtt gtcctttttt   5160
aagctatcaa gccaaacaac cagtgtctac cattattctc atcacctgaa gccaagggtt   5220
ctagcaaaag tcaagctgtc ttgtaatggt tgatgtgcct ccagcttctg tcttcagtca   5280
ctccactctt agcctgctct gaatcaactc tgaccacagt tccctggagc ccctgccacc   5340
tgctgcccct gccaccttct ccatctgcag tgctgtgcag ccttctgcac tcttgcagag   5400
ctaataggtg gagacttgaa ggaagaggag gaaagtttct cataatagcc ttgctgcaag   5460
ctcaaatggg aggtgggcac tgtgcccagg agccttggag caaaggctgt gcccaacctc   5520
tgactgcatc caggtttggt cttgacagag ataagaagcc ctggcttttg gagccaaaat   5580
ctaggtcaga cttaggcagg attctcaaag tttatcagca gaacatgagg cagaagaccc   5640
tttctgctcc agcttcttca ggctcaacct tcatcagaat agatagaaag agaggctgtg   5700
agggttctta aaacagaagc aaatctgact cagagaataa acaacctcct agtaaactac   5760
agcttagaca gagcatctgg tggtgagtgt gctcagtgtc ctactcaact gtctggtatc   5820
agccctcatg aggacttctc ttctttccct catagacctc catctctgtt ttccttagcc   5880
tgcagaaatc tggatggcta ttcacagaat gcctgtgctt tcagagttgc atttttttctc  5940
tggtattctg gttcaagcat ttgaaggtag gaaaggttct ccaagtgcaa gaaagccagc   6000
cctgagcctc aactgcctgg ctagtgtggt cagtaggatg caaaggctgt tgaatgccac   6060
aaggccaaac tttaacctgt gtaccacaag cctagcagca gaggcagctc tgctcactgg   6120
aactctctgt cttctttctc ctgagccttt tcttttcctg agttttctag ctctcctcaa   6180
ccttacctct gccctaccca ggacaaaccc aagagccact gtttctgtga tgtcctctcc   6240
agccctaatt aggcatcatg acttcagcct gaccttccat gctcagaagc agtgctaatc   6300
cacttcagat gagctgctct atgcaacaca ggcagagcct acaaaccttt gcaccagagc   6360
cctccacata tcagtgtttg ttcatactca cttcaacagc aaatgtgact gctgagatta   6420
agattttaca caagatggtc tgtaatttca cagttagttt tatcccatta ggtatgaaag   6480
aattagcata attcccctta aacatgaatg aatcttagat tttttaataa atagttttgg   6540
aagtaaagac agagacatca ggagcacaag gaatagcctg agaggacaaa cagaacaaga   6600
aagagtctgg aaatacacag gatgttcttg gcctcctcaa agcaagtgca agcagatagt   6660
accagcagcc ccaggctatc agagcccagt gaagagaagt accatgaaag ccacagctct   6720
```

-continued

```
aaccaccctg ttccagagtg acagacagtc cccaagacaa gccagcctga gccagagaga   6780
gaactgcaag agaaagtttc taatttaggt tctgttagat tcagacaagt gcaggtcatc   6840
ctctctccac agctactcac ctctccagcc taacaaagcc tgcagtccac actccaaccc   6900
tggtgtctca cctcctagcc tctcccaaca tcctgctctc tgaccatctt ctgcatctct   6960
catctcacca tctcccactg tctacagcct actcttgcaa ctaccatctc attttctgac   7020
atcctgtcta catcttctgc catactctgc catctaccat accacctctt accatctacc   7080
acaccatctt ttatctccat ccctctcaga agcctccaag ctgaatcctg ctttatgtgt   7140
tcatctcagc cctgcatgg aaagctgacc ccagaggcag aactattccc agagagcttg   7200
gccaagaaaa acaaaactac cagcctggcc aggctcagga gtagtaagct gcagtgtctg   7260
ttgtgttcta gcttcaacag ctgcaggagt tccactctca aatgctccac atttctcaca   7320
tcctcctgat tctggtcact acccatcttc aaagaacaga atatctcaca tcagcatact   7380
gtgaaggact agtcatgggt gcagctgctc agagctgcaa agtcattctg gatggtggag   7440
agcttacaaa catttcatga tgctccccc gctctgatgg ctggagccca atccctacac   7500
agactcctgc tgtatgtgtt ttcctttcac tctgagccac agccagaggg caggcattca   7560
gtctcctctt caggctgggg ctggggcact gagaactcac ccaacacctt gctctcactc   7620
cttctgcaaa acaagaaaga gctttgtgct gcagtagcca tgaagaatga aaggaaggct   7680
ttaactaaaa aatgtcagag attattttca accccttact gtggatcacc agcaaggagg   7740
aaacacaaca cagagacatt ttttcccctc aaattatcaa aagaatcact gcatttgtta   7800
aagagagcaa ctgaatcagg aagcagagtt ttgaacatat cagaagttag gaatctgcat   7860
cagagacaaa tgcagtcatg gttgtttgct gcataccagc cctaatcatt agaagcctca   7920
tggacttcaa acatcattcc ctctgacaag atgctctagc ctaactccat gagataaaat   7980
aaatctgcct ttcagagcca aagaagagtc caccagcttc ttctcagtgt gaacaagagc   8040
tccagtcagg ttagtcagtc cagtgcagta gaggagacca gtctgcatcc tctaattttc   8100
aaaggcaaga agatttgttt accctggaca ccaggcacaa gtgaggtcac agagctctta   8160
gatatgcagt cctcatgagt gaggagacta aagcgcatgc catcaagact tcagtgtaga   8220
gaaaacctcc aaaaaagcct cctcactact tctggaatag ctcagaggcc gaggcggcct   8280
cggcctctgc ataaataaaa aaaattagtc agccatgggg cggagaatgg gcggaactgg   8340
gcggagttag gggcgggatg ggcggagtta ggggcgggac tatggttgct gactaattga   8400
gatgcatgct ttgcatactt ctgcctgctg gggagcctgg ggactttcca cacctggttg   8460
ctgactaatt gagatgcatg ctttgcatac ttctgcctgc tggggagcct ggggactttc   8520
cacaccctaa ctgacacaca ttccacagct gcattaatga atcggccaac gcgcggggag   8580
aggcggtttg cgtattgggc gctcttccgc ttcctcgctc actgactcgc tgcgctcggt   8640
cgttcggctg cggcgagcgg tatcagctca ctcaaaggcg gtaatacggt tatccacaga   8700
atcaggggat aacgcaggaa agaacatgtg agcaaaaggc cagcaaaagg ccaggaaccg   8760
taaaaaggcc gcgttgctgg cgtttttcca taggctccgc ccccctgacg agcatcacaa   8820
aaatcgacgc tcaagtcaga ggtggcgaaa cccgacagga ctataaagat accaggcgtt   8880
tccccctgga agctccctcg tgcgctctcc tgttccgacc ctgccgctta ccggatacct   8940
gtccgccttt ctcccttcgg gaagcgtggc gctttctcat agctcacgct gtaggtatct   9000
cagttcggtg taggtcgttc gctccaagct gggctgtgtg cacgaacccc ccgttcagcc   9060
cgaccgctgc gccttatccg gtaactatcg tcttgagtcc aacccggtaa gacacgactt   9120
```

atcgccactg gcagcagcca ctggtaacag gattagcaga gcgaggtatg taggcggtgc 9180
tacagagttc ttgaagtggt ggcctaacta cggctacact agaagaacag tatttggtat 9240
ctgcgctctg ctgaagccag ttaccttcgg aaaaagagtt ggtagctctt gatccggcaa 9300
acaaaccacc gctggtagcg gtggtttttt tgtttgcaag cagcagatta cgcgcagaaa 9360
aaaaggatct caagaagatc ctttgatctt ttctacgggg tctgacgctc agtggaacga 9420
aaactcacgt taagggattt tggtcatgag attatcaaaa aggatcttca cctagatcct 9480
tttaaattaa aaatgaagtt ttaaatcaat ctaaagtata tatgagtaaa cttggtctga 9540
cagttaccaa tgcttaatca gtgaggcacc tatctcagcg atctgtctat ttcgttcatc 9600
catagttgcc tgactcctgc aaaccacgtt gtgtctcaaa atctctgatg ttacattgca 9660
caagataaaa atatatcatc atgaacaata aaactgtctg cttacataaa cagtaataca 9720
aggggtgtta tgagccatat tcaacgggaa acgtcttgct cgaggccgcg attaaattcc 9780
aacatggatg ctgatttata tgggtataaa tgggctcgcg ataatgtcgg gcaatcaggt 9840
gcgacaatct atcgattgta tgggaagccc gatgcgccag agttgtttct gaaacatggc 9900
aaaggtagcg ttgccaatga tgttacagat gagatggtca gactaaactg gctgacggaa 9960
tttatgcctc ttccgaccat caagcatttt atccgtactc ctgatgatgc atggttactc 10020
accactgcga tccccgggaa aacagcattc caggtattag aagaatatcc tgattcaggt 10080
gaaaatattg ttgatgcgct ggcagtgttc ctgcgccggt tgcattcgat tcctgtttgt 10140
aattgtcctt ttaacagcga tcgcgtattt cgtctcgctc aggcgcaatc acgaatgaat 10200
aacggtttgg ttgatgcgag tgattttgat gacgagcgta atggctggcc tgttgaacaa 10260
gtctggaaag aaatgcataa gcttttgcca ttctcaccgg attcagtcgt cactcatggt 10320
gatttctcac ttgataacct tatttttgac gaggggaaat taataggttg tattgatgtt 10380
ggacgagtcg gaatcgcaga ccgataccag gatcttgcca tcctatggaa ctgcctcggt 10440
gagttttctc cttcattaca gaaacggctt tttcaaaaat atggtattga taatcctgat 10500
atgaataaat tgcagtttca tttgatgctc gatgagtttt tctaagggcg gcctgccacc 10560
atacccacgc cgaaacaagc gctcatgagc ccgaagtggc gagcccgatc ttccccatcg 10620
gtgatgtcgg cgatataggc gccagcaacc gcacctgtgg cgccggtgat gagggcgcgc 10680
caagtcgacg tccggcagtc 10700

<210> SEQ ID NO 11
<211> LENGTH: 11188
<212> TYPE: DNA
<213> ORGANISM: Artificial sequence
<220> FEATURE:
<223> OTHER INFORMATION: Synthetic polynucleotide

<400> SEQUENCE: 11
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactatt agatctgatg gccgcgctag ctctgggtat ttaagcccga gtgagcacgc 180
agggtctcca ttttgaagcg ggaggttacg cgttcgtcga ctactagtgg gtaccagagc 240
gtggtgactg agatgttttc taggaaacac aaaagataca aaaaagaaca cgtggaagga 300
tagccaaaaa ggggggctgc ccccatttcc tgcacccgc tgcgatggct ggcaccattt 360
ggaagacttc gagatacact gttgagcgca gtaagacaac agtgtatctc gaagtcttcc 420

```
agatggggcc agccggtcca ctctgtatcc aggccagttc tgcaaggcgt tcgaggacca    480
ccccccctccc ctcgccacca gggtggtctc atacagaact tataagattc ccaaatccaa   540
agacatttca cgtttatggt gatttcccag aacacatagc gacatgcaaa tattgcaggg    600
cgccactccc ctgtccctca cagccatctt cctgccaggg cgcacgcgcg ctgggtgttc    660
ccgcctagtg acactgggcc cgcgattcct tggagcgggt tgatgacgtc agcgtttccc    720
atggtgaatc cctaggttct agaaccggtg acgtctccca tggtgaagct tggatctgaa    780
ttcggtacct agttattaat agtaatcaat tacggggtca ttagttcata gcccatatat    840
ggagttccgc gttacataac ttacggtaaa tggcccgcct ggctgaccgc ccaacgaccc    900
ccgcccattg acgtcaataa tgacgtatgt tcccatagta acgccaatag ggactttcca    960
ttgacgtcaa tgggtggagt atttacggta aactgcccac ttggcagtac atcaagtgta   1020
tcatatgcca agtacgcccc ctattgacgt caatgacggt aaatggcccg cctggcatta   1080
tgcccagtac atgaccttat gggactttcc tacttggcag tacatctacg tattagtcat   1140
cgctattacc atggtcgagg tgagccccac gttctgcttc actctcccca tctccccccc   1200
ctccccaccc ccaattttgt atttatttat tttttaatta ttttgtgcag cgatgggggc   1260
gggggggggg ggggggcgcg cgccaggcgg ggcggggcgg ggcgaggggc ggggcggggc   1320
gaggcggaga ggtgcggcgg cagccaatca gagcggcgcg ctccgaaagt ttccttttat   1380
ggcgaggcgg cggcggcggc ggccctataa aaagcgaagc gcgcggcggg cgggagtcgc   1440
tgcgacgctg ccttcgcccc gtgccccgct ccgccgccgc ctcgcgccgc ccgccccggc   1500
tctgactgac cgcgttactc ccacaggtga gcgggcggga cggcccttct cctccgggct   1560
gtaattagcg cttggtttaa tgacggcttg tttcttttct gtggctgcgt gaaagccttg   1620
aggggctccg ggagctagag cctctgctaa ccatgttcat gccttcttct ttttcctaca   1680
gctcctgggc aacgtgctgg ttattgtgct gtctcatcat tttggcaaag aattcctcga   1740
agatccgaag ggaaagtctt ccacgactgt gggatccgtt cgaagatatc accggttgag   1800
ccaccatgga attcagcagc cccagcagag aggaatgccc caagcctctg agccgggtgt   1860
caatcatggc cggatctctg acaggactgc tgctgcttca ggccgtgtct tgggcttctg   1920
gcgctagacc ttgcatcccc aagagcttcg gctacagcag cgtcgtgtgc gtgtgcaatg   1980
ccacctactg cgacagcttc gaccctccta cctttcctgc tctgggcacc ttcagcagat   2040
acgagagcac cagatccggc agacggatgg aactgagcat gggacccatc caggccaatc   2100
acacaggcac tggcctgctg ctgacactgc agcctgagca gaaattccag aaagtgaaag   2160
gcttcggcgg agccatgaca gatgccgccg ctctgaatat cctggctctg tctccaccag   2220
ctcagaacct gctgctcaag agctacttca gcgaggaagg catcggctac aacatcatca   2280
gagtgcccat ggccagctgc gacttcagca tcaggaccta cacctacgcc gacacacccg   2340
acgatttcca gctgcacaac ttcagcctgc ctgaagagga caccaagctg aagatccctc   2400
tgatccacag agccctgcag ctggcacaaa gacccgtgtc actgctggcc tctccatgga   2460
catctcccac ctggctgaaa acaaatggcg ccgtgaatgg caagggcagc ctgaaaggcc   2520
aacctggcga catctaccac cagacctggg ccagatactt cgtgaagttc ctggacgcct   2580
atgccgagca caagctgcag ttttgggccg tgacagccga gaacgaacct tctgctggac   2640
tgctgagcgg ctaccccttt cagtgcctgg gctttacacc cgagcaccag cgggacttta   2700
tcgcccgtga tctgggaccc acactggcca atagcaccca ccataatgtg cggctgctga   2760
tgctggacga ccagagactg cttctgcccc actgggctaa agtggtgctg acagatcctg   2820
```

```
aggccgccaa atacgtgcac ggaatcgccg tgcactggta tctggacttt ctggcccctg   2880
ccaaggccac actgggagag acacacagac tgttccccaa caccatgctg ttcgccagcg   2940
aagcctgtgt gggcagcaag ttttgggaac agagcgtgcg gctcggcagc tgggatagag   3000
gcatgcagta cagccacagc atcatcacca acctgctgta ccacgtcgtc ggctggaccg   3060
actggaatct ggccctgaat cctgaaggcg gccctaactg ggtccgaaac ttcgtggaca   3120
gccccatcat cgtggacatc accaaggaca ccttctacaa gcagcccatg ttctaccacc   3180
tgggacactt cagcaagttc atccccgagg gctctcagcg cgttggactg gtggcttccc   3240
agaagaacga tctggacgcc gtggctctga tgcaccctga tggatctgct gtggtggtgg   3300
tcctgaaccg cagcagcaaa gatgtgcccc tgaccatcaa ggatcccgcc gtgggattcc   3360
tggaaacaat cagccctggc tactccatcc acacctacct gtggcgtaga cagtgacaat   3420
tgttaattaa gtttaaaccc tcgaggccgc aagcttatcg ataatcaacc tctggattac   3480
aaaatttgtg aaagattgac tggtattctt aactatgttg ctccttttac gctatgtgga   3540
tacgctgctt taatgccttt gtatcatgct attgcttccc gtatggcttt cattttctcc   3600
tccttgtata aatcctggtt gctgtctctt tatgaggagt tgtggcccgt tgtcaggcaa   3660
cgtggcgtgg tgtgcactgt gtttgctgac gcaaccccca ctggttgggg cattgccacc   3720
acctgtcagc tcctttccgg gactttcgct ttccccctcc ctattgccac ggcggaactc   3780
atcgccgcct gccttgcccg ctgctggaca ggggctcggc tgttgggcac tgacaattcc   3840
gtggtgttgt cggggaaatc atcgtccttt ccttggctgc tcgcctgtgt tgccacctgg   3900
attctgcgcg ggacgtcctt ctgctacgtc ccttcggccc tcaatccagc ggaccttcct   3960
tcccgcggcc tgctgccggc tctgcggcct cttccgcgtc ttcgccttcg ccctcagacg   4020
agtcggatct ccctttgggc cgcctccccg catcgatacc gtcgactaga gctcgctgat   4080
cagcctcgac tgtgccttct agttgccagc catctgttgt ttgcccctcc cccgtgcctt   4140
ccttgaccct ggaaggtgcc actcccactg tcctttccta ataaaatgag gaaattgcat   4200
cgcattgtct gagtaggtgt cattctattc tggggggtgg ggtggggcag gacagcaagg   4260
gggaggattg ggaagacaat agcaggcatg ctggggagag atccacgata acaaacagct   4320
tttttggggt gaacatattg actgaattcc ctgcaggttg gccactccct ctctgcgcgc   4380
tcgctcgctc actgaggccg cccgggcaaa gcccgggcgt cgggcgacct ttggtcgccc   4440
ggcctcagtg agcgagcgag cgcgcagaga gggagtggcc aactccatca ctaggggttc   4500
ctgcggccgc tcgtacggtc tcgaggaatt cctgcaggat aacttgccaa cctcattcta   4560
aaatgtatat agaagcccaa aagacaataa caaaaatatt cttgtagaac aaaatgggaa   4620
agaatgttcc actaaatatc aagatttaga gcaaagcatg agatgtgtgg ggatagacag   4680
tgaggctgat aaaatagagt agagctcaga aacagaccca ttgatatatg taagtgacct   4740
atgaaaaaaa tatggcattt tacaatggga aaatgatggt ctttttcttt tttagaaaaa   4800
cagggaaata tatttatatg taaaaaataa aagggaaccc atatgtcata ccatacacac   4860
aaaaaaattc cagtgaatta taagtctaaa tggagaaggc aaaactttaa atcttttaga   4920
aaataatata gaagcatgca gaccagcctg gccaacatga tgaaaccctc tctactaata   4980
ataaaatcag tagaactact caggactact ttgagtggga agtccttttc tatgaagact   5040
tctttggcca aaattaggct ctaaatgcaa ggagatagtg catcatgcct ggctgcactt   5100
actgataaat gatgttatca ccatctttaa ccaaatgcac aggaacaagt tatggtactg   5160
```

-continued

```
atgtgctgga ttgagaagga gctctacttc cttgacagga cacatttgta tcaacttaaa   5220
aaagcagatt tttgccagca gaactattca ttcagaggta ggaaacttag aatagatgat   5280
gtcactgatt agcatggctt ccccatctcc acagctgctt cccacccagg ttgcccacag   5340
ttgagtttgt ccagtgctca gggctgccca ctctcagtaa gaagccccac accagcccct   5400
ctccaaatat gttggctgtt ccttccatta aagtgacccc actttagagc agcaagtgga   5460
tttctgtttc ttacagttca ggaaggagga gtcagctgtg agaacctgga gcctgagatg   5520
cttctaagtc ccactgctac tggggtcagg gaagccagac tccagcatca gcagtcagga   5580
gcactaagcc cttgccaaca tcctgtttct cagagaaact gcttccatta taatggttgt   5640
cctttttaa gctatcaagc caaacaacca gtgtctacca ttattctcat cacctgaagc    5700
caagggttct agcaaaagtc aagctgtctt gtaatggttg atgtgcctcc agcttctgtc   5760
ttcagtcact ccactcttag cctgctctga atcaactctg accacagttc cctggagccc   5820
ctgccacctg ctgcccctgc caccttctcc atctgcagtg ctgtgcagcc ttctgcactc   5880
ttgcagagct aataggtgga gacttgaagg aagaggagga aagtttctca taatagcctt   5940
gctgcaagct caaatgggag gtgggcactg tgcccaggag ccttggagca aaggctgtgc   6000
ccaacctctg actgcatcca ggtttggtct tgacagagat aagaagccct ggcttttgga   6060
gccaaaatct aggtcagact taggcaggat tctcaaagtt tatcagcaga acatgaggca   6120
gaagaccctt tctgctccag cttcttcagg ctcaaccttc atcagaatag atagaaagag   6180
aggctgtgag ggttcttaaa acagaagcaa atctgactca gagaataaac aacctcctag   6240
taaactacag cttagacaga gcatctggtg gtgagtgtgc tcagtgtcct actcaactgt   6300
ctggtatcag ccctcatgag gacttctctt ctttccctca tagacctcca tctctgtttt   6360
ccttagcctg cagaaatctg gatggctatt cacagaatgc ctgtgctttc agagttgcat   6420
tttttctctg gtattctggt tcaagcattt gaaggtagga aaggttctcc aagtgcaaga   6480
aagccagccc tgagcctcaa ctgcctggct agtgtggtca gtaggatgca aaggctgttg   6540
aatgccacaa ggccaaactt taacctgtgt accacaagcc tagcagcaga ggcagctctg   6600
ctcactggaa ctctctgtct tctttctcct gagccttttc ttttcctgag ttttctagct   6660
ctcctcaacc ttacctctgc cctacccagg acaaacccaa gagccactgt ttctgtgatg   6720
tcctctccag ccctaattag gcatcatgac ttcagcctga ccttccatgc tcagaagcag   6780
tgctaatcca cttcagatga gctgctctat gcaacacagg cagagcctac aaacctttgc   6840
accagagccc tccacatatc agtgtttgtt catactcact tcaacagcaa atgtgactgc   6900
tgagattaag attttacaca agatggtctg taatttcaca gttagtttta tcccattagg   6960
tatgaaagaa ttagcataat tccccttaaa catgaatgaa tcttagattt tttaataaat   7020
agttttggaa gtaaagacag agacatcagg agcacaagga atagcctgag aggacaaaca   7080
gaacaagaaa gagtctggaa atacacagga tgttcttggc ctcctcaaag caagtgcaag   7140
cagatagtac cagcagcccc aggctatcag agcccagtga agagaagtac catgaaagcc   7200
acagctctaa ccaccctgtt ccagagtgac agacagtccc caagacaagc cagcctgagc   7260
cagagagaga actgcaagag aaagtttcta atttaggttc tgttagattc agacaagtgc   7320
aggtcatcct ctctccacag ctactcacct ctccagccta acaaagcctg cagtccacac   7380
tccaaccctg gtgtctcacc tcctagcctc tcccaacatc ctgctctctg accatcttct   7440
gcatctctca tctcaccatc tcccactgtc tacagcctac tcttgcaact accatctcat   7500
tttctgacat cctgtctaca tcttctgcca tactctgcca tctaccatac cacctcttac   7560
```

```
catctaccac accatctttt atctccatcc ctctcagaag cctccaagct gaatcctgct   7620
ttatgtgttc atctcagccc ctgcatggaa agctgacccc agaggcagaa ctattcccag   7680
agagcttggc caagaaaaac aaaactacca gcctggccag gctcaggagt agtaagctgc   7740
agtgtctgtt gtgttctagc ttcaacagct gcaggagttc cactctcaaa tgctccacat   7800
ttctcacatc ctcctgattc tggtcactac ccatcttcaa agaacagaat atctcacatc   7860
agcatactgt gaaggactag tcatgggtgc agctgctcag agctgcaaag tcattctgga   7920
tggtggagag cttacaaaca tttcatgatg ctccccccgc tctgatggct ggagcccaat   7980
ccctacacag actcctgctg tatgtgtttt cctttcactc tgagccacag ccagagggca   8040
ggcattcagt ctcctcttca ggctggggct ggggcactga gaactcaccc aacaccttgc   8100
tctcactcct tctgcaaaac aagaaagagc tttgtgctgc agtagccatg aagaatgaaa   8160
ggaaggcttt aactaaaaaa tgtcagagat tattttcaac cccttactgt ggatcaccag   8220
caaggaggaa acacaacaca gagacatttt ttcccctcaa attatcaaaa gaatcactgc   8280
atttgttaaa gagagcaact gaatcaggaa gcagagtttt gaacatatca gaagttagga   8340
atctgcatca gagacaaatg cagtcatggt tgtttgctgc ataccagccc taatcattag   8400
aagcctcatg gacttcaaac atcattccct ctgacaagat gctctagcct aactccatga   8460
gataaaataa atctgccttt cagagccaaa gaagagtcca ccagcttctt ctcagtgtga   8520
acaagagctc cagtcaggtt agtcagtcca gtgcagtaga ggagaccagt ctgcatcctc   8580
taattttcaa aggcaagaag atttgtttac cctggacacc aggcacaagt gaggtcacag   8640
agctcttaga tatgcagtcc tcatgagtga ggagactaaa gcgcatgcca tcaagacttc   8700
agtgtagaga aaacctccaa aaaagcctcc tcactacttc tggaatagct cagaggccga   8760
ggcggcctcg gcctctgcat aaataaaaaa aattagtcag ccatggggcg gagaatgggc   8820
ggaactgggc ggagttaggg gcgggatggg cggagttagg ggcgggacta tggttgctga   8880
ctaattgaga tgcatgcttt gcatacttct gcctgctggg gagcctgggg actttccaca   8940
cctggttgct gactaattga gatgcatgct ttgcatactt ctgcctgctg gggagcctgg   9000
ggactttcca caccctaact gacacacatt ccacagctgc attaatgaat cggccaacgc   9060
gcggggagag gcggtttgcg tattgggcgc tcttccgctt cctcgctcac tgactcgctg   9120
cgctcggtcg ttcggctgcg gcgagcggta tcagctcact caaaggcggt aatacggtta   9180
tccacagaat caggggataa cgcaggaaag aacatgtgag caaaaggcca gcaaaaggcc   9240
aggaaccgta aaaaggccgc gttgctggcg tttttccata ggctccgccc ccctgacgag   9300
catcacaaaa atcgacgctc aagtcagagg tggcgaaacc cgacaggact ataaagatac   9360
caggcgtttc cccctggaag ctccctcgtg cgctctcctg ttccgaccct gccgcttacc   9420
ggatacctgt ccgcctttct cccttcggga agcgtggcgc tttctcatag ctcacgctgt   9480
aggtatctca gttcggtgta ggtcgttcgc tccaagctgg gctgtgtgca cgaacccccc   9540
gttcagcccg accgctgcgc cttatccggt aactatcgtc ttgagtccaa cccggtaaga   9600
cacgacttat cgccactggc agcagccact ggtaacagga ttagcagagc gaggtatgta   9660
ggcggtgcta cagagttctt gaagtggtgg cctaactacg gctacactag aagaacagta   9720
tttggtatct gcgctctgct gaagccagtt accttcggaa aaagagttgg tagctcttga   9780
tccggcaaac aaaccaccgc tggtagcggt ggtttttttg tttgcaagca gcagattacg   9840
cgcagaaaaa aaggatctca agaagatcct ttgatctttt ctacggggtc tgacgctcag   9900
```

```
tggaacgaaa actcacgtta agggattttg gtcatgagat tatcaaaaag gatcttcacc   9960
tagatccttt taaattaaaa atgaagtttt aaatcaatct aaagtatata tgagtaaact  10020
tggtctgaca gttaccaatg cttaatcagt gaggcaccta tctcagcgat ctgtctattt  10080
cgttcatcca tagttgcctg actcctgcaa accacgttgt gtctcaaaat ctctgatgtt  10140
acattgcaca agataaaaat atatcatcat gaacaataaa actgtctgct tacataaaca  10200
gtaatacaag gggtgttatg agccatattc aacgggaaac gtcttgctcg aggccgcgat  10260
taaattccaa catggatgct gatttatatg ggtataaatg ggctcgcgat aatgtcgggc  10320
aatcaggtgc gacaatctat cgattgtatg ggaagcccga tgcgccagag ttgtttctga  10380
aacatggcaa aggtagcgtt gccaatgatg ttacagatga gatggtcaga ctaaactggc  10440
tgacggaatt tatgcctctt ccgaccatca agcattttat ccgtactcct gatgatgcat  10500
ggttactcac cactgcgatc cccgggaaaa cagcattcca ggtattagaa gaatatcctg  10560
attcaggtga aaatattgtt gatgcgctgg cagtgttcct gcgccggttg cattcgattc  10620
ctgtttgtaa ttgtcctttt aacagcgatc gcgtatttcg tctcgctcag gcgcaatcac  10680
gaatgaataa cggtttggtt gatgcgagtg attttgatga cgagcgtaat ggctggcctg  10740
ttgaacaagt ctggaaagaa atgcataagc ttttgccatt ctcaccggat tcagtcgtca  10800
ctcatggtga tttctcactt gataacctta tttttgacga ggggaaatta ataggttgta  10860
ttgatgttgg acgagtcgga atcgcagacc gataccagga tcttgccatc ctatggaact  10920
gcctcggtga gttttctcct tcattacaga aacggctttt tcaaaaatat ggtattgata  10980
atcctgatat gaataaattg cagtttcatt tgatgctcga tgagtttttc taagggcggc  11040
ctgccaccat acccacgccg aaacaagcgc tcatgagccc gaagtggcga gcccgatctt  11100
ccccatcggt gatgtcggcg atataggcgc cagcaaccgc acctgtggcg ccggtgatga  11160
gggcgcgcca agtcgacgtc cggcagtc                                     11188
```

<210> SEQ ID NO 12
<211> LENGTH: 11187
<212> TYPE: DNA
<213> ORGANISM: Artificial sequence
<220> FEATURE:
<223> OTHER INFORMATION: Synthetic polynucleotide

<400> SEQUENCE: 12

```
ctagaaccgg tgacgtctcc catggtgaag cttggatctg aattcggtac ctagttataa     60
tagtaatcaa ttacggggtc attagttcat agcccatata tggagttccg cgttacataa    120
cttacggtaa atggcccgcc tggctgaccg cccaacgacc cccgcccatt gacgtcaata    180
atgacgtatg ttcccatagt aacgccaata gggactttcc attgacgtca atgggtggag    240
tatttacggt aaactgccca cttggcagta catcaagtgt atcatatgcc aagtacgccc    300
cctattgacg tcaatgacgg taaatggccc gcctggcatt atgcccagta catgacctta    360
tgggactttc ctacttggca gtacatctac gtattagtca tcgctattac catggtcgag    420
gtgagcccca cgttctgctt cactctcccc atctcccccc cctccccacc cccaattttg    480
tatttattta tttttaatt attttgtgca gcgatggggg cggggggggg ggggggcgc    540
gcgccaggcg gggcggggcg gggcgagggg cggggcgggg cgaggcggag aggtgcggcg    600
gcagccaatc agagcggcgc gctccgaaag tttcctttta tggcgaggcg gcggcggcgg    660
cggccctata aaaagcgaag cgcgcggcgg gcgggagtcg ctgcgacgct gccttcgccc    720
cgtgccccgc tccgccgccg cctcgcgccg cccgccccgg ctctgactga ccgcgttact    780
```

```
cccacaggtg agcgggcggg acggcccttc tcctccgggc tgtaattagc gcttggttta    840
atgacggctt gtttcttttc tgtggctgcg tgaaagcctt gaggggctcc gggagctaga    900
gcctctgcta accatgttca tgccttcttc tttttcctac agctcctggg caacgtgctg    960
gttattgtgc tgtctcatca ttttggcaaa gaattcctcg aagatccgaa gggaaagtct   1020
tccacgactg tgggatccgt tcgaagatat caccggttga gccaccatgg aattcagcag   1080
ccccagcaga gaggaatgcc ccaagcctct gagccgggtg tcaatcatgg ccggatctct   1140
gacaggactg ctgctgcttc aggccgtgtc ttgggcttct ggcgctagac cttgcatccc   1200
caagagcttc ggctacagca gcgtcgtgtg cgtgtgcaat gccacctact gcgacagctt   1260
cgaccctcct acctttcctg ctctgggcac cttcagcaga tacgagagca ccagatccgg   1320
cagacggatg gaactgagca tgggacccat ccaggccaat cacacaggca ctggcctgct   1380
gctgacactg cagcctgagc agaaattcca gaaagtgaaa ggcttcggcg gagccatgac   1440
agatgccgcc gctctgaata tcctggctct gtctccacca gctcagaacc tgctgctcaa   1500
gagctacttc agcgaggaag gcatcggcta caacatcatc agagtgccca tggccagctg   1560
cgacttcagc atcaggacct acacctacgc cgacacaccc gacgatttcc agctgcacaa   1620
cttcagcctg cctgaagagg acaccaagct gaagatccct ctgatccaca gagccctgca   1680
gctggcacaa agacccgtgt cactgctggc ctctccatgg acatctccca cctggctgaa   1740
aacaaatggc gccgtgaatg gcaagggcag cctgaaaggc caacctggcg acatctacca   1800
ccagacctgg gccagatact tcgtgaagtt cctggacgcc tatgccgagc acaagctgca   1860
gttttgggcc gtgacagccg agaacgaacc ttctgctgga ctgctgagcg gctacccctt   1920
tcagtgcctg ggctttacac ccgagcacca gcgggacttt atcgcccgtg atctgggacc   1980
cacactggcc aatagcaccc accataatgt gcggctgctg atgctggacg accagagact   2040
gcttctgccc cactgggcta aagtggtgct gacagatcct gaggccgcca aatacgtgca   2100
cggaatcgcc gtgcactggt atctggactt tctggcccct gccaaggcca cactgggaga   2160
gacacacaga ctgttcccca acaccatgct gttcgccagc gaagcctgtg tgggcagcaa   2220
gttttgggaa cagagcgtgc ggctcggcag ctgggataga ggcatgcagt acagccacag   2280
catcatcacc aacctgctgt accacgtcgt cggctggacc gactggaatc tggccctgaa   2340
tcctgaaggc ggccctaact gggtccgaaa cttcgtggac agccccatca tcgtggacat   2400
caccaaggac accttctaca agcagcccat gttctaccac ctgggacact tcagcaagtt   2460
catccccgag ggctctcagc gcgttggact ggtggcttcc cagaagaacg atctggacgc   2520
cgtggctctg atgcaccctg atggatctgc tgtggtggtg gtcctgaacc gcagcagcaa   2580
agatgtgccc ctgaccatca aggatcccgc cgtgggattc ctggaaacaa tcagccctgg   2640
ctactccatc cacacctacc tgtggcgtag acagtgacaa ttgttaatta agtttaaacc   2700
ctcgaggccg caagcttatc gataatcaac ctctggatta caaaatttgt gaaagattga   2760
ctggtattct taactatgtt gctcctttta cgctatgtgg atacgctgct ttaatgcctt   2820
tgtatcatgc tattgcttcc cgtatggctt tcattttctc ctccttgtat aaatcctggt   2880
tgctgtctct ttatgaggag ttgtggcccg ttgtcaggca acgtggcgtg gtgtgcactg   2940
tgtttgctga cgcaaccccc actggttggg gcattgccac cacctgtcag ctcctttccg   3000
ggactttcgc tttccccctc cctattgcca cggcggaact catcgccgcc tgccttgccc   3060
gctgctggac aggggctcgg ctgttgggca ctgacaattc cgtggtgttg tcggggaaat   3120
```

```
catcgtcctt tccttggctg ctcgcctgtg ttgccacctg gattctgcgc gggacgtcct   3180
tctgctacgt cccttcggcc ctcaatccag cggaccttcc ttcccgcggc ctgctgccgg   3240
ctctgcggcc tcttccgcgt cttcgccttc gccctcagac gagtcggatc tccctttggg   3300
ccgcctcccc gcatcgatac cgtcgactag agctcgctga tcagcctcga ctgtgccttc   3360
tagttgccag ccatctgttg tttgcccctc ccccgtgcct tccttgaccc tggaaggtgc   3420
cactcccact gtcctttcct aataaaatga ggaaattgca tcgcattgtc tgagtaggtg   3480
tcattctatt ctggggggtg gggtggggca ggacagcaag ggggaggatt gggaagacaa   3540
tagcaggcat gctggggaga gatccacgat aacaaacagc tttttggggg tgaacatatt   3600
gactgaattc cctgcaggtt ggccactccc tctctgcgcg ctcgctcgct cactgaggcc   3660
gcccgggcaa agcccgggcg tcgggcgacc tttggtcgcc cggcctcagt gagcgagcga   3720
gcgcgcagag agggagtggc caactccatc actaggggtt cctgcggccg ctcgtacggt   3780
ctcgaggaat tcctgcagga taacttgcca acctcattct aaaatgtata tagaagccca   3840
aaagacaata acaaaaatat tcttgtagaa caaaatggga aagaatgttc cactaaatat   3900
caagatttag agcaaagcat gagatgtgtg gggatagaca gtgaggctga taaaatagag   3960
tagagctcag aaacagaccc attgatatat gtaagtgacc tatgaaaaaa atatggcatt   4020
ttacaatggg aaaatgatgg tctttttctt ttttagaaaa acagggaaat atatttatat   4080
gtaaaaaata aaagggaacc catatgtcat accatacaca caaaaaaatt ccagtgaatt   4140
ataagtctaa atggagaagg caaaacttta aatcttttag aaaataatat agaagcatgc   4200
agaccagcct ggccaacatg atgaaaccct ctctactaat aataaaatca gtagaactac   4260
tcaggactac tttgagtggg aagtcctttt ctatgaagac ttctttggcc aaaattaggc   4320
tctaaatgca aggagatagt gcatcatgcc tggctgcact tactgataaa tgatgttatc   4380
accatcttta accaaatgca caggaacaag ttatggtact gatgtgctgg attgagaagg   4440
agctctactt ccttgacagg acacatttgt atcaacttaa aaaagcagat ttttgccagc   4500
agaactattc attcagaggt aggaaactta gaatagatga tgtcactgat tagcatggct   4560
tccccatctc cacagctgct tcccacccag gttgcccaca gttgagtttg tccagtgctc   4620
agggctgccc actctcagta agaagcccca caccagcccc tctccaaata tgttggctgt   4680
tccttccatt aaagtgaccc cactttagag cagcaagtgg atttctgttt cttacagttc   4740
aggaaggagg agtcagctgt gagaacctgg agcctgagat gcttctaagt cccactgcta   4800
ctggggtcag ggaagccaga ctccagcatc agcagtcagg agcactaagc ccttgccaac   4860
atcctgtttc tcagagaaac tgcttccatt ataatggttg tcctttttta agctatcaag   4920
ccaaacaacc agtgtctacc attattctca tcacctgaag ccaagggttc tagcaaaagt   4980
caagctgtct tgtaatggtt gatgtgcctc cagcttctgt cttcagtcac tccactctta   5040
gcctgctctg aatcaactct gaccacagtt ccctggagcc cctgccacct gctgcccctg   5100
ccaccttctc catctgcagt gctgtgcagc cttctgcact cttgcagagc taataggtgg   5160
agacttgaag gaagaggagg aaagtttctc ataatagcct tgctgcaagc tcaaatggga   5220
ggtgggcact gtgcccagga gccttggagc aaaggctgtg cccaacctct gactgcatcc   5280
aggtttggtc ttgacagaga taagaagccc tggcttttgg agccaaaatc taggtcagac   5340
ttaggcagga ttctcaaagt ttatcagcag aacatgaggc agaagaccct ttctgctcca   5400
gcttcttcag gctcaacctt catcagaata gatagaaaga gaggctgtga gggttcttaa   5460
aacagaagca aatctgactc agagaataaa caacctccta gtaaactaca gcttagacag   5520
```

```
agcatctggt ggtgagtgtg ctcagtgtcc tactcaactg tctggtatca gccctcatga   5580
ggacttctct tctttccctc atagacctcc atctctgttt tccttagcct gcagaaatct   5640
ggatggctat tcacagaatg cctgtgcttt cagagttgca ttttttctct ggtattctgg   5700
ttcaagcatt tgaaggtagg aaaggttctc caagtgcaag aaagccagcc ctgagcctca   5760
actgcctggc tagtgtggtc agtaggatgc aaaggctgtt gaatgccaca aggccaaact   5820
ttaacctgtg taccacaagc ctagcagcag aggcagctct gctcactgga actctctgtc   5880
ttctttctcc tgagcctttt cttttcctga gttttctagc tctcctcaac cttacctctg   5940
ccctacccag gacaaaccca agagccactg tttctgtgat gtcctctcca gccctaatta   6000
ggcatcatga cttcagcctg accttccatg ctcagaagca gtgctaatcc acttcagatg   6060
agctgctcta tgcaacacag gcagagccta caaacctttg caccagagcc ctccacatat   6120
cagtgtttgt tcatactcac ttcaacagca aatgtgactg ctgagattaa gattttacac   6180
aagatggtct gtaatttcac agttagtttt atcccattag gtatgaaaga attagcataa   6240
ttccccttaa acatgaatga atcttagatt ttttaataaa tagttttgga agtaaagaca   6300
gagacatcag gagcacaagg aatagcctga gaggacaaac agaacaagaa agagtctgga   6360
aatacacagg atgttcttgg cctcctcaaa gcaagtgcaa gcagatagta ccagcagccc   6420
caggctatca gagcccagtg aagagaagta ccatgaaagc cacagctcta accaccctgt   6480
tccagagtga cagacagtcc ccaagacaag ccagcctgag ccagagagag aactgcaaga   6540
gaaagtttct aatttaggtt ctgttagatt cagacaagtg caggtcatcc tctctccaca   6600
gctactcacc tctccagcct aacaaagcct gcagtccaca ctccaaccct ggtgtctcac   6660
ctcctagcct ctcccaacat cctgctctct gaccatcttc tgcatctctc atctcaccat   6720
ctcccactgt ctacagccta ctcttgcaac taccatctca ttttctgaca tcctgtctac   6780
atcttctgcc atactctgcc atctaccata ccacctctta ccatctacca caccatcttt   6840
tatctccatc cctctcagaa gcctccaagc tgaatcctgc tttatgtgtt catctcagcc   6900
cctgcatgga aagctgaccc cagaggcaga actattccca gagagcttgg ccaagaaaaa   6960
caaaactacc agcctggcca ggctcaggag tagtaagctg cagtgtctgt tgtgttctag   7020
cttcaacagc tgcaggagtt ccactctcaa atgctccaca tttctcacat cctcctgatt   7080
ctggtcacta cccatcttca aagaacagaa tatctcacat cagcatactg tgaaggacta   7140
gtcatgggtg cagctgctca gagctgcaaa gtcattctgg atggtggaga gcttacaaac   7200
atttcatgat gctccccccg ctctgatggc tggagcccaa tccctacaca gactcctgct   7260
gtatgtgttt tcctttcact ctgagccaca gccagagggc aggcattcag tctcctcttc   7320
aggctggggc tggggcactg agaactcacc caacaccttg ctctcactcc ttctgcaaaa   7380
caagaaagag ctttgtgctg cagtagccat gaagaatgaa aggaaggctt taactaaaaa   7440
atgtcagaga ttattttcaa ccccttactg tggatcacca gcaaggagga aacacaacac   7500
agagacattt tttccccctca aattatcaaa agaatcactg catttgttaa agagagcaac   7560
tgaatcagga agcagagttt tgaacatatc agaagttagg aatctgcatc agagacaaat   7620
gcagtcatgg ttgtttgctg cataccagcc ctaatcatta gaagcctcat ggacttcaaa   7680
catcattccc tctgacaaga tgctctagcc taactccatg agataaaata aatctgcctt   7740
tcagagccaa agaagagtcc accagcttct tctcagtgtg aacaagagct ccagtcaggt   7800
tagtcagtcc agtgcagtag aggagaccag tctgcatcct ctaattttca aaggcaagaa   7860
```

-continued

```
gatttgttta ccctggacac caggcacaag tgaggtcaca gagctcttag atatgcagtc   7920
ctcatgagtg aggagactaa agcgcatgcc atcaagactt cagtgtagag aaaacctcca   7980
aaaaagcctc ctcactactt ctggaatagc tcagaggccg aggcggcctc ggcctctgca   8040
taaataaaaa aaattagtca gccatggggc ggagaatggg cggaactggg cggagttagg   8100
ggcgggatgg gcggagttag gggcgggact atggttgctg actaattgag atgcatgctt   8160
tgcatacttc tgcctgctgg ggagcctggg gactttccac acctggttgc tgactaattg   8220
agatgcatgc tttgcatact tctgcctgct ggggagcctg gggactttcc acaccctaac   8280
tgacacacat tccacagctg cattaatgaa tcggccaacg cgcggggaga ggcggtttgc   8340
gtattgggcg ctcttccgct tcctcgctca ctgactcgct gcgctcggtc gttcggctgc   8400
ggcgagcggt atcagctcac tcaaaggcgg taatacggtt atccacagaa tcaggggata   8460
acgcaggaaa gaacatgtga gcaaaaggcc agcaaaaggc caggaaccgt aaaaaggccg   8520
cgttgctggc gtttttccat aggctccgcc cccctgacga gcatcacaaa aatcgacgct   8580
caagtcagag gtggcgaaac ccgacaggac tataaagata ccaggcgttt ccccctggaa   8640
gctccctcgt gcgctctcct gttccgaccc tgccgcttac cggatacctg tccgcctttc   8700
tcccttcggg aagcgtggcg ctttctcata gctcacgctg taggtatctc agttcggtgt   8760
aggtcgttcg ctccaagctg ggctgtgtgc acgaaccccc cgttcagccc gaccgctgcg   8820
ccttatccgg taactatcgt cttgagtcca acccggtaag acacgactta tcgccactgg   8880
cagcagccac tggtaacagg attagcagag cgaggtatgt aggcggtgct acagagttct   8940
tgaagtggtg gcctaactac ggctacacta gaagaacagt atttggtatc tgcgctctgc   9000
tgaagccagt taccttcgga aaaagagttg gtagctcttg atccggcaaa caaaccaccg   9060
ctggtagcgg tggttttttt gtttgcaagc agcagattac gcgcagaaaa aaaggatctc   9120
aagaagatcc tttgatcttt tctacggggt ctgacgctca gtggaacgaa aactcacgtt   9180
aagggatttt ggtcatgaga ttatcaaaaa ggatcttcac ctagatcctt ttaaattaaa   9240
aatgaagttt taaatcaatc taaagtatat atgagtaaac ttggtctgac agttaccaat   9300
gcttaatcag tgaggcacct atctcagcga tctgtctatt tcgttcatcc atagttgcct   9360
gactcctgca aaccacgttg tgtctcaaaa tctctgatgt tacattgcac aagataaaaa   9420
tatatcatca tgaacaataa aactgtctgc ttacataaac agtaatacaa ggggtgttat   9480
gagccatatt caacgggaaa cgtcttgctc gaggccgcga ttaaattcca acatggatgc   9540
tgatttatat gggtataaat gggctcgcga taatgtcggg caatcaggtg cgacaatcta   9600
tcgattgtat gggaagcccg atgcgccaga gttgtttctg aaacatggca aaggtagcgt   9660
tgccaatgat gttacagatg agatggtcag actaaactgg ctgacggaat ttatgcctct   9720
tccgaccatc aagcatttta tccgtactcc tgatgatgca tggttactca ccactgcgat   9780
ccccgggaaa acagcattcc aggtattaga agaatatcct gattcaggtg aaaatattgt   9840
tgatgcgctg gcagtgttcc tgcgccggtt gcattcgatt cctgtttgta attgtccttt   9900
taacagcgat cgcgtatttc gtctcgctca ggcgcaatca cgaatgaata acggtttggt   9960
tgatgcgagt gattttgatg acgagcgtaa tggctggcct gttgaacaag tctggaaaga  10020
aatgcataag cttttgccat tctcaccgga ttcagtcgtc actcatggtg atttctcact  10080
tgataacctt atttttgacg aggggaaatt aataggttgt attgatgttg gacgagtcgg  10140
aatcgcagac cgataccagg atcttgccat cctatggaac tgcctcggtg agttttctcc  10200
ttcattacag aaacggcttt ttcaaaaata tggtattgat aatcctgata tgaataaatt  10260
```

```
gcagtttcat ttgatgctcg atgagttttt ctaagggcgg cctgccacca tacccacgcc  10320
gaaacaagcg ctcatgagcc cgaagtggcg agcccgatct tccccatcgg tgatgtcggc  10380
gatataggcg ccagcaaccg cacctgtggc gccggtgatg agggcgcgcc aagtcgacgt  10440
ccggcagtct tggccactcc ctctctgcgc gctcgctcgc tcactgaggc cgggcgacca  10500
aaggtcgccc gacgcccggg ctttgcccgg gcggcctcag tgagcgagcg agcgcgcaga  10560
gagggagtgg ccaactccat cactaggggt tcctgctagc tctgggtatt taagcccgag  10620
tgagcacgca gggtctccat tttgaagcgg gaggttacgc gttcgtcgac tactagtggg  10680
taccagagcg tggtgactga gatgttttct aggaaacaca aaagatacaa aaaagaacac  10740
gtggaaggat agccaaaaag gggggctgcc cccatttcct gcaccccgct gcgatggctg  10800
gcaccatttg gaagacttcg agatacactg ttgagcgcag taagacaaca gtgtatctcg  10860
aagtcttcca gatggggcca gccggtccac tctgtatcca ggccagttct gcaaggcgtt  10920
cgaggaccac ccccctcccc tcgccaccag ggtggtctca tacagaactt ataagattcc  10980
caaatccaaa gacatttcac gtttatggtg atttcccaga acacatagcg acatgcaaat  11040
attgcagggc gccactcccc tgtccctcac agccatcttc ctgccagggc gcacgcgcgc  11100
tgggtgttcc cgcctagtga cactgggccc gcgattcctt ggagcgggtt gatgacgtca  11160
gcgtttccca tggtgaatcc ctaggtt                                      11187
```

<210> SEQ ID NO 13
<211> LENGTH: 10960
<212> TYPE: DNA
<213> ORGANISM: Artificial sequence
<220> FEATURE:
<223> OTHER INFORMATION: Synthetic polynucleotide

<400> SEQUENCE: 13

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg aattcggtac    300
cctagttatt aatagtaatc aattacgggg tcattagttc atagcccata tatggagttc    360
cgcgttacat aacttacggt aaatggcccg cctggctgac cgcccaacga cccccgccca    420
ttgacgtcaa taatgacgta tgttcccata gtaacgccaa tagggacttt ccattgacgt    480
caatgggtgg actatttacg gtaaactgcc cacttggcag tacatcaagt gtatcatatg    540
ccaagtacgc cccctattga cgtcaatgac ggtaaatggc ccgcctggca ttatgcccag    600
tacatgacct tatgggactt tcctacttgg cagtacatct acgtattagt catcgctatt    660
accatggtcg aggtgagccc cacgttctgc ttcactctcc ccatctcccc cccctcccca    720
cccccaattt tgtatttatt tatttttaa ttattttgtg cagcgatggg ggcggggggg    780
gggggggggc gcgcgccagg cggggcgggg cggggcgagg ggcggggcgg ggcgaggcgg    840
agaggtgcgg cggcagccaa tcagagcggc gcgctccgaa agtttccttt tatggcgagg    900
cggcggcggc ggcggcccta taaaaagcga agcgcgcggc gggcgggagt cgctgcgacg    960
ctgccttcgc cccgtgcccc gctccgccgc cgcctcgcgc cgcccgcccc ggctctgact   1020
gaccgcgtta ctcccacagg tgagcgggcg ggacggccct tctcctccgg gctgtaatta   1080
```

```
gcgcttggtt taatgacggc ttgtcctggt ggcgagggga ggggggtggt cctcgaacgc   1140
cttgcagaac tggcctggat acagagtgga ccggctggcc ccatctggaa gacttcgaga   1200
tacactgttg tcttactgcg ctcaacagtg tatctcgaag tcttccaaat ggtgccagcc   1260
atcgcagcgg ggtgcaggaa atgggggcag ccccccttt tggctatcct tccacgtgtt   1320
ctttttgta tcttttgtgt ttcctagaaa acatctcagt caccaccttt ctgtggctgc   1380
gtgaaagcct tgaggggctc cgggagctag agcctctgct aaccatgttc atgccttctt   1440
ctttttccta cagctcctgg gcaacgtgct ggttattgtg ctgtctcatc attttggcaa   1500
agaattcctc gaagatccga agggaaagtc ttccacgact gtgggatccg ttcgaagata   1560
tcaccggttg agccaccatg gaattcagca gccccagcag agaggaatgc cccaagcctc   1620
tgagccgggt gtcaatcatg gccggatctc tgacaggact gctgctgctt caggccgtgt   1680
cttgggcttc tggcgctaga ccttgcatcc ccaagagctt cggctacagc agcgtcgtgt   1740
gcgtgtgcaa tgccacctac tgcgacagct tcgaccctcc tacctttcct gctctgggca   1800
ccttcagcag atacgagagc accagatccg gcagacggat ggaactgagc atgggaccca   1860
tccaggccaa tcacacaggc actggcctgc tgctgacact gcagcctgag cagaaattcc   1920
agaaagtgaa aggcttcggc ggagccatga cagatgccgc cgctctgaat atcctggctc   1980
tgtctccacc agctcagaac ctgctgctca agagctactt cagcgaggaa ggcatcggct   2040
acaacatcat cagagtgccc atggccagct gcgacttcag catcaggacc tacacctacg   2100
ccgacacacc cgacgatttc cagctgcaca acttcagcct gcctgaagag gacaccaagc   2160
tgaagatccc tctgatccac agagccctgc agctggcaca aagacccgtg tcactgctgg   2220
cctctccatg gacatctccc acctggctga aaacaaatgg cgccgtgaat ggcaagggca   2280
gcctgaaagg ccaacctggc gacatctacc accagacctg ggccagatac ttcgtgaagt   2340
tcctggacgc ctatgccgag cacaagctgc agttttgggc cgtgacagcc gagaacgaac   2400
cttctgctgg actgctgagc ggctacccct ttcagtgcct gggctttaca cccgagcacc   2460
agcgggactt tatcgcccgt gatctgggac ccacactggc caatagcacc caccataatg   2520
tgcggctgct gatgctggac gaccagagac tgcttctgcc ccactgggct aaagtggtgc   2580
tgacagatcc tgaggccgcc aaatacgtgc acggaatcgc cgtgcactgg tatctggact   2640
ttctggcccc tgccaaggcc acactgggag agacacacag actgttcccc aacaccatgc   2700
tgttcgccag cgaagcctgt gtgggcagca agttttggga acagagcgtg cggctcggca   2760
gctgggatag aggcatgcag tacagccaca gcatcatcac caacctgctg taccacgtcg   2820
tcggctggac cgactggaat ctggccctga atcctgaagg cggccctaac tgggtccgaa   2880
acttcgtgga cagccccatc atcgtggaca tcaccaagga caccttctac aagcagccca   2940
tgttctacca cctgggacac ttcagcaagt tcatccccga gggctctcag cgcgttggac   3000
tggtggcttc ccagaagaac gatctggacg ccgtggctct gatgcaccct gatggatctg   3060
ctgtggtggt ggtcctgaac cgcagcagca aagatgtgcc cctgaccatc aaggatcccg   3120
ccgtgggatt cctggaaaca atcagccctg gctactccat ccacacctac ctgtggcgta   3180
gacagtgaca attgttaatt aagtttaaac cctcgaggcc gcaagcttat cgataatcaa   3240
cctctggatt acaaaatttg tgaaagattg actggtattc ttaactatgt tgctcctttt   3300
acgctatgtg gatacgctgc tttaatgcct ttgtatcatg ctattgcttc ccgtatggct   3360
ttcattttct cctccttgta taaatcctgg ttgctgtctc tttatgagga gttgtggccc   3420
gttgtcaggc aacgtggcgt ggtgtgcact gtgtttgctg acgcaacccc cactggttgg   3480
```

```
ggcattgcca ccacctgtca gctcctttcc gggactttcg ctttccccct ccctattgcc   3540
acggcggaac tcatcgccgc ctgccttgcc cgctgctgga caggggctcg gctgttgggc   3600
actgacaatt ccgtggtgtt gtcggggaaa tcatcgtcct ttccttggct gctcgcctgt   3660
gttgccacct ggattctgcg cgggacgtcc ttctgctacg tcccttcggc cctcaatcca   3720
gcggaccttc cttcccgcgg cctgctgccg gctctgcggc ctcttccgcg tcttcgcctt   3780
cgccctcaga cgagtcggat ctccctttgg gccgcctccc cgcatcgata ccgtcgacta   3840
gagctcgctg atcagcctcg actgtgcctt ctagttgcca gccatctgtt gtttgcccct   3900
cccccgtgcc ttccttgacc ctggaaggtg ccactcccac tgtcctttcc taataaaatg   3960
aggaaattgc atcgcattgt ctgagtaggt gtcattctat tctggggggt ggggtggggc   4020
aggacagcaa gggggaggat tgggaagaca atagcaggca tgctggggag agatccacga   4080
taacaaacag ctttttttggg gtgaacatat tgactgaatt ccctgcaggt tggccactcc   4140
ctctctgcgc gctcgctcgc tcactgaggc cgcccgggca aagcccgggc gtcgggcgac   4200
ctttggtcgc ccggcctcag tgagcgagcg agcgcgcaga gagggagtgg ccaactccat   4260
cactaggggt tcctgcggcc gctcgtacgg tctcgaggaa ttcctgcagg ataacttgcc   4320
aacctcattc taaaatgtat atagaagccc aaaagacaat aacaaaaata ttcttgtaga   4380
acaaaatggg aaagaatgtt ccactaaata tcaagattta gagcaaagca tgagatgtgt   4440
ggggatagac agtgaggctg ataaaataga gtagagctca gaaacagacc cattgatata   4500
tgtaagtgac ctatgaaaaa aatatggcat tttacaatgg gaaaatgatg gtctttttct   4560
tttttagaaa aacagggaaa tatatttata tgtaaaaaat aaaagggaac ccatatgtca   4620
taccatacac acaaaaaaat tccagtgaat tataagtcta aatggagaag gcaaaacttt   4680
aaatctttta gaaaataata tagaagcatg cagaccagcc tggccaacat gatgaaaccc   4740
tctctactaa taataaaatc agtagaacta ctcaggacta ctttgagtgg gaagtccttt   4800
tctatgaaga cttctttggc caaaattagg ctctaaatgc aaggagatag tgcatcatgc   4860
ctggctgcac ttactgataa atgatgttat caccatcttt aaccaaatgc acaggaacaa   4920
gttatggtac tgatgtgctg gattgagaag gagctctact tccttgacag gacacatttg   4980
tatcaactta aaaaagcaga tttttgccag cagaactatt cattcagagg taggaaactt   5040
agaatagatg atgtcactga ttagcatggc ttccccatct ccacagctgc ttcccaccca   5100
ggttgcccac agttgagttt gtccagtgct cagggctgcc cactctcagt aagaagcccc   5160
acaccagccc ctctccaaat atgttggctg ttccttccat taaagtgacc ccactttaga   5220
gcagcaagtg gatttctgtt tcttacagtt caggaaggag gagtcagctg tgagaacctg   5280
gagcctgaga tgcttctaag tcccactgct actggggtca gggaagccag actccagcat   5340
cagcagtcag gagcactaag ccccttgccaa catcctgttt ctcagagaaa ctgcttccat   5400
tataatggtt gtcctttttt aagctatcaa gccaaacaac cagtgtctac cattattctc   5460
atcacctgaa gccaagggtt ctagcaaaag tcaagctgtc ttgtaatggt tgatgtgcct   5520
ccagcttctg tcttcagtca ctccactctt agcctgctct gaatcaactc tgaccacagt   5580
tccctggagc ccctgccacc tgctgcccct gccaccttct ccatctgcag tgctgtgcag   5640
ccttctgcac tcttgcagag ctaataggtg gagacttgaa ggaagaggag gaaagtttct   5700
cataatagcc ttgctgcaag ctcaaatggg aggtgggcac tgtgcccagg agccttggag   5760
caaaggctgt gcccaacctc tgactgcatc caggtttggt cttgacagag ataagaagcc   5820
```

ctggcttttg gagccaaaat ctaggtcaga cttaggcagg attctcaaag tttatcagca 5880
gaacatgagg cagaagaccc tttctgctcc agcttcttca ggctcaacct tcatcagaat 5940
agatagaaag agaggctgtg agggttctta aaacagaagc aaatctgact cagagaataa 6000
acaacctcct agtaaactac agcttagaca gagcatctgg tggtgagtgt gctcagtgtc 6060
ctactcaact gtctggtatc agccctcatg aggacttctc ttctttccct catagacctc 6120
catctctgtt ttccttagcc tgcagaaatc tggatggcta ttcacagaat gcctgtgctt 6180
tcagagttgc attttttctc tggtattctg gttcaagcat ttgaaggtag gaaaggttct 6240
ccaagtgcaa gaaagccagc cctgagcctc aactgcctgg ctagtgtggt cagtaggatg 6300
caaaggctgt tgaatgccac aaggccaaac tttaacctgt gtaccacaag cctagcagca 6360
gaggcagctc tgctcactgg aactctctgt cttctttctc ctgagccttt tcttttcctg 6420
agttttctag ctctcctcaa ccttacctct gccctaccca ggacaaaccc aagagccact 6480
gtttctgtga tgtcctctcc agccctaatt aggcatcatg acttcagcct gaccttccat 6540
gctcagaagc agtgctaatc cacttcagat gagctgctct atgcaacaca ggcagagcct 6600
acaaaccttt gcaccagagc cctccacata tcagtgtttg ttcatactca cttcaacagc 6660
aaatgtgact gctgagatta agattttaca caagatggtc tgtaatttca cagttagttt 6720
tatcccatta ggtatgaaag aattagcata attcccctta aacatgaatg aatcttagat 6780
tttttaataa atagttttgg aagtaaagac agagacatca ggagcacaag gaatagcctg 6840
agaggacaaa cagaacaaga aagagtctgg aaatacacag gatgttcttg gcctcctcaa 6900
agcaagtgca agcagatagt accagcagcc ccaggctatc agagcccagt gaagagaagt 6960
accatgaaag ccacagctct aaccaccctg ttccagagtg acagacagtc cccaagacaa 7020
gccagcctga gccagagaga gaactgcaag agaaagtttc taatttaggt tctgttagat 7080
tcagacaagt gcaggtcatc ctctctccac agctactcac ctctccagcc taacaaagcc 7140
tgcagtccac actccaaccc tggtgtctca cctcctagcc tctcccaaca tcctgctctc 7200
tgaccatctt ctgcatctct catctcacca tctcccactg tctacagcct actcttgcaa 7260
ctaccatctc attttctgac atcctgtcta catcttctgc catactctgc catctaccat 7320
accacctctt accatctacc acaccatctt ttatctccat ccctctcaga agcctccaag 7380
ctgaatcctg ctttatgtgt tcatctcagc ccctgcatgg aaagctgacc ccagaggcag 7440
aactattccc agagagcttg gccaagaaaa acaaaactac cagcctggcc aggctcagga 7500
gtagtaagct gcagtgtctg ttgtgttcta gcttcaacag ctgcaggagt tccactctca 7560
aatgctccac atttctcaca tcctcctgat tctggtcact acccatcttc aaagaacaga 7620
atatctcaca tcagcatact gtgaaggact agtcatgggt gcagctgctc agagctgcaa 7680
agtcattctg gatggtggag agcttacaaa catttcatga tgctcccccc gctctgatgg 7740
ctggagccca atccctacac agactcctgc tgtatgtgtt ttcctttcac tctgagccac 7800
agccagaggg caggcattca gtctcctctt caggctgggg ctggggcact gagaactcac 7860
ccaacacctt gctctcactc cttctgcaaa acaagaaaga gctttgtgct gcagtagcca 7920
tgaagaatga aaggaaggct ttaactaaaa aatgtcagag attattttca accccttact 7980
gtggatcacc agcaaggagg aaacacaaca cagagacatt ttttcccctc aaattatcaa 8040
aagaatcact gcatttgtta aagagagcaa ctgaatcagg aagcagagtt ttgaacatat 8100
cagaagttag gaatctgcat cagagacaaa tgcagtcatg gttgtttgct gcataccagc 8160
cctaatcatt agaagcctca tggacttcaa acatcattcc ctctgacaag atgctctagc 8220

```
ctaactccat gagataaaat aaatctgcct ttcagagcca aagaagagtc caccagcttc   8280
ttctcagtgt gaacaagagc tccagtcagg ttagtcagtc cagtgcagta gaggagacca   8340
gtctgcatcc tctaattttc aaaggcaaga agatttgttt accctggaca ccaggcacaa   8400
gtgaggtcac agagctctta gatatgcagt cctcatgagt gaggagacta aagcgcatgc   8460
catcaagact tcagtgtaga gaaaacctcc aaaaaagcct cctcactact tctggaatag   8520
ctcagaggcc gaggcggcct cggcctctgc ataaataaaa aaaattagtc agccatgggg   8580
cggagaatgg gcggaactgg gcggagttag gggcgggatg ggcggagtta ggggcgggac   8640
tatggttgct gactaattga gatgcatgct ttgcatactt ctgcctgctg gggagcctgg   8700
ggactttcca cacctggttg ctgactaatt gagatgcatg ctttgcatac ttctgcctgc   8760
tggggagcct ggggactttc cacaccctaa ctgacacaca ttccacagct gcattaatga   8820
atcggccaac gcgcggggag aggcggtttg cgtattgggc gctcttccgc ttcctcgctc   8880
actgactcgc tgcgctcggt cgttcggctg cggcgagcgg tatcagctca ctcaaaggcg   8940
gtaatacggt tatccacaga atcaggggat aacgcaggaa agaacatgtg agcaaaaggc   9000
cagcaaaagg ccaggaaccg taaaaaggcc gcgttgctgg cgtttttcca taggctccgc   9060
ccccctgacg agcatcacaa aaatcgacgc tcaagtcaga ggtggcgaaa cccgacagga   9120
ctataaagat accaggcgtt tccccctgga agctccctcg tgcgctctcc tgttccgacc   9180
ctgccgctta ccggatacct gtccgccttt ctcccttcgg gaagcgtggc gctttctcat   9240
agctcacgct gtaggtatct cagttcggtg taggtcgttc gctccaagct gggctgtgtg   9300
cacgaacccc ccgttcagcc cgaccgctgc gccttatccg gtaactatcg tcttgagtcc   9360
aacccggtaa gacacgactt atcgccactg gcagcagcca ctggtaacag gattagcaga   9420
gcgaggtatg taggcggtgc tacagagttc ttgaagtggt ggcctaacta cggctacact   9480
agaagaacag tatttggtat ctgcgctctg ctgaagccag ttaccttcgg aaaaagagtt   9540
ggtagctctt gatccggcaa acaaaccacc gctggtagcg gtggtttttt tgtttgcaag   9600
cagcagatta cgcgcagaaa aaaaggatct caagaagatc ctttgatctt ttctacgggg   9660
tctgacgctc agtggaacga aaactcacgt taagggattt tggtcatgag attatcaaaa   9720
aggatcttca cctagatcct tttaaattaa aaatgaagtt ttaaatcaat ctaaagtata   9780
tatgagtaaa cttggtctga cagttaccaa tgcttaatca gtgaggcacc tatctcagcg   9840
atctgtctat ttcgttcatc catagttgcc tgactcctgc aaaccacgtt gtgtctcaaa   9900
atctctgatg ttacattgca caagataaaa atatatcatc atgaacaata aaactgtctg   9960
cttacataaa cagtaataca aggggtgtta tgagccatat tcaacgggaa acgtcttgct  10020
cgaggccgcg attaaattcc aacatggatg ctgatttata tgggtataaa tgggctcgcg  10080
ataatgtcgg gcaatcaggt gcgacaatct atcgattgta tgggaagccc gatgcgccag  10140
agttgtttct gaaacatggc aaaggtagcg ttgccaatga tgttacagat gagatggtca  10200
gactaaactg gctgacggaa tttatgcctc ttccgaccat caagcatttt atccgtactc  10260
ctgatgatgc atggttactc accactgcga tccccgggaa aacagcattc caggtattag  10320
aagaatatcc tgattcaggt gaaaatattg ttgatgcgct ggcagtgttc ctgcgccggt  10380
tgcattcgat tcctgtttgt aattgtcctt ttaacagcga tcgcgtattt cgtctcgctc  10440
aggcgcaatc acgaatgaat aacggtttgg ttgatgcgag tgattttgat gacgagcgta  10500
atggctggcc tgttgaacaa gtctggaaag aaatgcataa gcttttgcca ttctcaccgg  10560
```

```
attcagtcgt cactcatggt gatttctcac ttgataacct tatttttgac gaggggaaat  10620

taataggttg tattgatgtt ggacgagtcg gaatcgcaga ccgataccag gatcttgcca  10680

tcctatggaa ctgcctcggt gagttttctc cttcattaca gaaacggctt tttcaaaaat  10740

atggtattga taatcctgat atgaataaat tgcagtttca tttgatgctc gatgagtttt  10800

tctaagggcg gcctgccacc atacccacgc cgaaacaagc gctcatgagc ccgaagtggc  10860

gagcccgatc ttccccatcg gtgatgtcgg cgatataggc gccagcaacc gcacctgtgg  10920

cgccggtgat gagggcgcgc caagtcgacg tccggcagtc                        10960
```

<210> SEQ ID NO 14
<211> LENGTH: 536
<212> TYPE: PRT
<213> ORGANISM: Homo sapiens

<400> SEQUENCE: 14

```
Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
    290                 295                 300
```

```
Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
        355                 360                 365

Leu Phe Pro Asn Thr Met Leu Phe Ala Ser Glu Ala Cys Val Gly Ser
    370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
        435                 440                 445

Thr Phe Tyr Lys Gln Pro Met Phe Tyr His Leu Gly His Phe Ser Lys
    450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
        515                 520                 525

His Thr Tyr Leu Trp Arg Arg Gln
    530                 535


<210> SEQ ID NO 15
<211> LENGTH: 1608
<212> TYPE: DNA
<213> ORGANISM: Homo sapiens

<400> SEQUENCE: 15

atggaattca gcagccccag cagagaggaa tgccccaagc ctctgagccg ggtgtcaatc      60

atggccggat ctctgacagg actgctgctg cttcaggccg tgtcttgggc ttctggcgct     120

agaccttgca tccccaagag cttcggctac agcagcgtcg tgtgcgtgtg caatgccacc     180

tactgcgaca gcttcgaccc tcctaccttt cctgctctgg gcaccttcag cagatacgag     240

agcaccagat ccggcagacg gatggaactg agcatgggac ccatccaggc caatcacaca     300

ggcactggcc tgctgctgac actgcagcct gagcagaaat tccagaaagt gaaaggcttc     360

ggcggagcca tgacagatgc cgccgctctg aatatcctgg ctctgtctcc accagctcag     420

aacctgctgc tcaagagcta cttcagcgag gaaggcatcg gctacaacat catcagagtg     480

cccatggcca gctgcgactt cagcatcagg acctacacct acgccgacac acccgacgat     540

ttccagctgc acaacttcag cctgcctgaa gaggacacca agctgaagat ccctctgatc     600

cacagagccc tgcagctggc acaaagaccc gtgtcactgc tggcctctcc atggacatct     660

cccacctggc tgaaaacaaa tggcgccgtg aatggcaagg gcagcctgaa aggccaacct     720

ggcgacatct accaccagac ctgggccaga tacttcgtga agttcctgga cgcctatgcc     780
```

```
gagcacaagc tgcagttttg ggccgtgaca gccgagaacg aaccttctgc tggactgctg    840

agcggctacc cctttcagtg cctgggcttt acacccgagc accagcggga ctttatcgcc    900

cgtgatctgg gacccacact ggccaatagc acccaccata atgtgcggct gctgatgctg    960

gacgaccaga gactgcttct gccccactgg gctaaagtgg tgctgacaga tcctgaggcc   1020

gccaaatacg tgcacggaat cgccgtgcac tggtatctgg actttctggc cctgccaag    1080

gccacactgg gagagacaca cagactgttc cccaacacca tgctgttcgc cagcgaagcc   1140

tgtgtgggca gcaagttttg ggaacagagc gtgcggctcg gcagctggga tagaggcatg   1200

cagtacagcc acagcatcat caccaacctg ctgtaccacg tcgtcggctg gaccgactgg   1260

aatctggccc tgaatcctga aggcggccct aactgggtcc gaaacttcgt ggacagcccc   1320

atcatcgtgg acatcaccaa ggacaccttc tacaagcagc ccatgttcta ccacctggga   1380

cacttcagca agttcatccc cgagggctct cagcgcgttg gactggtggc ttcccagaag   1440

aacgatctgg acgccgtggc tctgatgcac cctgatggat ctgctgtggt ggtggtcctg   1500

aaccgcagca gcaaagatgt gcccctgacc atcaaggatc ccgccgtggg attcctggaa   1560

acaatcagcc ctggctactc catccacacc tacctgtggc gtagacag                1608
```

<210> SEQ ID NO 16
<211> LENGTH: 524
<212> TYPE: PRT
<213> ORGANISM: Homo sapiens

<400> SEQUENCE: 16

```
Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Glu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
        115                 120                 125

Gly Glu Val Cys Ser Ala Leu Asn Leu Cys Glu Ser Leu Gln Lys His
    130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

Asp Asn Gly Asp Val Cys Gln Asp Cys Ile Gln Met Val Thr Asp Ile
        195                 200                 205

Gln Thr Ala Val Arg Thr Asn Ser Thr Phe Val Gln Ala Leu Val Glu
    210                 215                 220

His Val Lys Glu Glu Cys Asp Arg Leu Gly Pro Gly Met Ala Asp Ile
```

```
225                 230                 235                 240

Cys Lys Asn Tyr Ile Ser Gln Tyr Ser Glu Ile Ala Ile Gln Met Met
                245                 250                 255

Met His Met Gln Pro Lys Glu Ile Cys Ala Leu Val Gly Phe Cys Asp
            260                 265                 270

Glu Val Lys Glu Met Pro Met Gln Thr Leu Val Pro Ala Lys Val Ala
        275                 280                 285

Ser Lys Asn Val Ile Pro Ala Leu Glu Leu Val Glu Pro Ile Lys Lys
    290                 295                 300

His Glu Val Pro Ala Lys Ser Asp Val Tyr Cys Glu Val Cys Glu Phe
305                 310                 315                 320

Leu Val Lys Glu Val Thr Lys Leu Ile Asp Asn Asn Lys Thr Glu Lys
                325                 330                 335

Glu Ile Leu Asp Ala Phe Asp Lys Met Cys Ser Lys Leu Pro Lys Ser
            340                 345                 350

Leu Ser Glu Glu Cys Gln Glu Val Val Asp Thr Tyr Gly Ser Ser Ile
        355                 360                 365

Leu Ser Ile Leu Leu Glu Glu Val Ser Pro Glu Leu Val Cys Ser Met
    370                 375                 380

Leu His Leu Cys Ser Gly Thr Arg Leu Pro Ala Leu Thr Val His Val
385                 390                 395                 400

Thr Gln Pro Lys Asp Gly Gly Phe Cys Glu Val Cys Lys Lys Leu Val
                405                 410                 415

Gly Tyr Leu Asp Arg Asn Leu Glu Lys Asn Ser Thr Lys Gln Glu Ile
            420                 425                 430

Leu Ala Ala Leu Glu Lys Gly Cys Ser Phe Leu Pro Asp Pro Tyr Gln
        435                 440                 445

Lys Gln Cys Asp Gln Phe Val Ala Glu Tyr Glu Pro Val Leu Ile Glu
    450                 455                 460

Ile Leu Val Glu Val Met Asp Pro Ser Phe Val Cys Leu Lys Ile Gly
465                 470                 475                 480

Ala Cys Pro Ser Ala His Lys Pro Leu Leu Gly Thr Glu Lys Cys Ile
                485                 490                 495

Trp Gly Pro Ser Tyr Trp Cys Gln Asn Thr Glu Thr Ala Ala Gln Cys
            500                 505                 510

Asn Ala Val Glu His Cys Lys Arg His Val Trp Asn
        515                 520


<210> SEQ ID NO 17
<211> LENGTH: 1572
<212> TYPE: DNA
<213> ORGANISM: Homo sapiens

<400> SEQUENCE: 17

atgtacgccc tgttcctgct ggccagcctg ctgggcgccg ccctggccgg ccccgtgctg      60

ggcctgaagg agtgcacccg cggcagcgcc gtgtggtgcc agaacgtgaa gaccgccagc     120

gactgcggcg ccgtgaagca ctgcctgcag accgtgtgga acaagcccac cgtgaagagc     180

ctgccctgcg acatctgcaa ggacgtggtg accgccgccg gcgacatgct gaaggacaac     240

gccaccgagg aggagatcct ggtgtacctg gagaagacct gcgactggct gcccaagccc     300

aacatgagcg ccagctgcaa ggagatcgtg gacagctacc tgcccgtgat cctggacatc     360

atcaagggcg agatgagccg ccccggcgag gtgtgcagcg ccctgaacct gtgcgagagc     420

ctgcagaagc acctggccga gctgaaccac cagaagcagc tggagagcaa caagatcccc     480
```

```
gagctggaca tgaccgaggt ggtggccccc ttcatggcca acatccccct gctgctgtac    540

ccccaggacg gcccccgcag caagccccag cccaaggaca acggcgacgt gtgccaggac    600

tgcatccaga tggtgaccga catccagacc gccgtgcgca ccaacagcac cttcgtgcag    660

gccctggtgg agcacgtgaa ggaggagtgc gaccgcctgg gccccggcat ggccgacatc    720

tgcaagaact acatcagcca gtacagcgag atcgccatcc agatgatgat gcacatgcag    780

cccaaggaga tctgcgccct ggtgggcttc tgcgacgagg tgaaggagat gcccatgcag    840

accctggtgc ccgccaaggt ggccagcaag aacgtgatcc ccgccctgga gctggtggag    900

cccatcaaga agcacgaggt gcccgccaag agcgacgtgt actgcgaggt gtgcgagttc    960

ctggtgaagg aggtgaccaa gctgatcgac aacaacaaga ccgagaagga gatcctggac   1020

gccttcgaca agatgtgcag caagctgccc aagagcctga gcgaggagtg ccaggaggtg   1080

gtggacacct acggcagcag catcctgagc atcctgctgg aggaggtgag ccccgagctg   1140

gtgtgcagca tgctgcacct gtgcagcggc acccgcctgc ccgccctgac cgtgcacgtg   1200

acccagccca aggacggcgg cttctgcgag gtgtgcaaga agctggtggg ctacctggac   1260

cgcaacctgg agaagaacag caccaagcag gagatcctgg ccgccctgga gaagggctgc   1320

agcttcctgc ccgaccccta ccagaagcag tgcgaccagt tcgtggccga gtacgagccc   1380

gtgctgatcg agatcctggt ggaggtgatg gaccccagct tcgtgtgcct gaagatcggc   1440

gcctgcccca gcgcccacaa gcccctgctg ggcaccgaga agtgcatctg gggccccagc   1500

tactggtgcc agaacaccga gaccgccgcc cagtgcaacg ccgtggagca ctgcaagcgc   1560

cacgtgtgga ac                                                       1572
```

<210> SEQ ID NO 18
<211> LENGTH: 478
<212> TYPE: PRT
<213> ORGANISM: Homo sapiens

<400> SEQUENCE: 18

```
Met Gly Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gln Lys Ala
            20                  25                  30

Val Asp Gln Ser Ile Glu Lys Lys Ile Val Leu Arg Asn Gly Thr Glu
        35                  40                  45

Ala Phe Asp Ser Trp Glu Lys Pro Pro Leu Pro Val Tyr Thr Gln Phe
    50                  55                  60

Tyr Phe Phe Asn Val Thr Asn Pro Glu Glu Ile Leu Arg Gly Glu Thr
65                  70                  75                  80

Pro Arg Val Glu Glu Val Gly Pro Tyr Thr Tyr Arg Glu Leu Arg Asn
                85                  90                  95

Lys Ala Asn Ile Gln Phe Gly Asp Asn Gly Thr Thr Ile Ser Ala Val
            100                 105                 110

Ser Asn Lys Ala Tyr Val Phe Glu Arg Asp Gln Ser Val Gly Asp Pro
        115                 120                 125

Lys Ile Asp Leu Ile Arg Thr Leu Asn Ile Pro Val Leu Thr Val Ile
    130                 135                 140

Glu Trp Ser Gln Val His Phe Leu Arg Glu Ile Ile Glu Ala Met Leu
145                 150                 155                 160

Lys Ala Tyr Gln Gln Lys Leu Phe Val Thr His Thr Val Asp Glu Leu
                165                 170                 175
```

```
Leu Trp Gly Tyr Lys Asp Glu Ile Leu Ser Leu Ile His Val Phe Arg
            180                 185                 190

Pro Asp Ile Ser Pro Tyr Phe Gly Leu Phe Tyr Glu Lys Asn Gly Thr
        195                 200                 205

Asn Asp Gly Asp Tyr Val Phe Leu Thr Gly Glu Asp Ser Tyr Leu Asn
    210                 215                 220

Phe Thr Lys Ile Val Glu Trp Asn Gly Lys Thr Ser Leu Asp Trp Trp
225                 230                 235                 240

Ile Thr Asp Lys Cys Asn Met Ile Asn Gly Thr Asp Gly Asp Ser Phe
                245                 250                 255

His Pro Leu Ile Thr Lys Asp Glu Val Leu Tyr Val Phe Pro Ser Asp
            260                 265                 270

Phe Cys Arg Ser Val Tyr Ile Thr Phe Ser Asp Tyr Glu Ser Val Gln
        275                 280                 285

Gly Leu Pro Ala Phe Arg Tyr Lys Val Pro Ala Glu Ile Leu Ala Asn
    290                 295                 300

Thr Ser Asp Asn Ala Gly Phe Cys Ile Pro Glu Gly Asn Cys Leu Gly
305                 310                 315                 320

Ser Gly Val Leu Asn Val Ser Ile Cys Lys Asn Gly Ala Pro Ile Ile
                325                 330                 335

Met Ser Phe Pro His Phe Tyr Gln Ala Asp Glu Arg Phe Val Ser Ala
            340                 345                 350

Ile Glu Gly Met His Pro Asn Gln Glu Asp His Glu Thr Phe Val Asp
        355                 360                 365

Ile Asn Pro Leu Thr Gly Ile Ile Leu Lys Ala Ala Lys Arg Phe Gln
    370                 375                 380

Ile Asn Ile Tyr Val Lys Lys Leu Asp Asp Phe Val Glu Thr Gly Asp
385                 390                 395                 400

Ile Arg Thr Met Val Phe Pro Val Met Tyr Leu Asn Glu Ser Val His
                405                 410                 415

Ile Asp Lys Glu Thr Ala Ser Arg Leu Lys Ser Met Ile Asn Thr Thr
            420                 425                 430

Leu Ile Ile Thr Asn Ile Pro Tyr Ile Ile Met Ala Leu Gly Val Phe
        435                 440                 445

Phe Gly Leu Val Phe Thr Trp Leu Ala Cys Lys Gly Gln Gly Ser Met
    450                 455                 460

Asp Glu Gly Thr Ala Asp Glu Arg Ala Pro Leu Ile Arg Thr
465                 470                 475
```

<210> SEQ ID NO 19
<211> LENGTH: 1434
<212> TYPE: DNA
<213> ORGANISM: Homo sapiens

<400> SEQUENCE: 19

```
atgggccgct gctgcttcta caccgccggc accctgagcc tgctgctgct ggtgaccagc      60

gtgaccctgc tggtggcccg cgtgttccag aaggccgtgg accagagcat cgagaagaag     120

atcgtgctgc gcaacggcac cgaggccttc gacagctggg agaagccccc cctgcccgtg     180

tacacccagt tctacttctt caacgtgacc aaccccgagg agatcctgcg cggcgagacc     240

ccccgcgtgg aggaggtggg cccctacacc taccgcgagc tgcgcaacaa ggccaacatc     300

cagttcggcg acaacggcac caccatcagc gccgtgagca acaaggccta cgtgttcgag     360

cgcgaccaga gcgtgggcga ccccaagatc gacctgatcc gcaccctgaa catccccgtg     420
```

ctgaccgtga tcgagtggag ccaggtgcac ttcctgcgcg agatcatcga ggccatgctg 480
aaggcctacc agcagaagct gttcgtgacc cacaccgtgg acgagctgct gtggggctac 540
aaggacgaga tcctgagcct gatccacgtg ttccgccccg acatcagccc ctacttcggc 600
ctgttctacg agaagaacgg caccaacgac ggcgactacg tgttcctgac cggcgaggac 660
agctacctga acttcaccaa gatcgtggag tggaacggca agaccagcct ggactggtgg 720
atcaccgaca agtgcaacat gatcaacggc accgacggcg acagcttcca ccccctgatc 780
accaaggacg aggtgctgta cgtgttcccc agcgacttct gccgcagcgt gtacatcacc 840
ttcagcgact acgagagcgt gcagggcctg cccgccttcc gctacaaggt gcccgccgag 900
atcctggcca acaccagcga caacgccggc ttctgcatcc ccgagggcaa ctgcctgggc 960
agcggcgtgc tgaacgtgag catctgcaag aacggcgccc ccatcatcat gagcttcccc 1020
cacttctacc aggccgacga gcgcttcgtg agcgccatcg agggcatgca ccccaaccag 1080
gaggaccacg agaccttcgt ggacatcaac cccctgaccg gcatcatcct gaaggccgcc 1140
aagcgcttcc agatcaacat ctacgtgaag aagctggacg acttcgtgga gaccggcgac 1200
atccgcacca tggtgttccc cgtgatgtac ctgaacgaga gcgtgcacat cgacaaggag 1260
accgccagcc gcctgaagag catgatcaac accaccctga tcatcaccaa catcccctac 1320
atcatcatgg ccctgggcgt gttcttcggc ctggtgttca cctggctggc ctgcaagggc 1380
cagggcagca tggacgaggg caccgccgac gagcgcgccc ccctgatccg cacc 1434

<210> SEQ ID NO 20
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 20
tggaagactt cgagatacac tgt 23

<210> SEQ ID NO 21
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 21
acagtgtatc tcgaagtctt cca 23

<210> SEQ ID NO 22
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 22
tttagaaata agtggtagtc a 21

<210> SEQ ID NO 23
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 23
tgactaccac ttatttctaa a 21

<210> SEQ ID NO 24
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 24
agggtatcaa gactacgaa 19

<210> SEQ ID NO 25
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 25
ttcgtagtct tgataccct 19

<210> SEQ ID NO 26
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 26
tattagatct gatggccgc 19

<210> SEQ ID NO 27
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 27
ctccatcact aggggttcct 20

<210> SEQ ID NO 28
<211> LENGTH: 60
<212> TYPE: DNA
<213> ORGANISM: Artificial sequence
<220> FEATURE:
<223> OTHER INFORMATION: Synthetic polynucleotide

<400> SEQUENCE: 28
agctctgggt atttaagccc gagtgagcac gcagggtctc cattttgaag cgggaggtta 60

<210> SEQ ID NO 29
<211> LENGTH: 145
<212> TYPE: DNA
<213> ORGANISM: Unknown
<220> FEATURE:
<223> OTHER INFORMATION: AAV2 ITR

<400> SEQUENCE: 29
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcag agagggagtg gccaa 145

<210> SEQ ID NO 30
<211> LENGTH: 927
<212> TYPE: PRT
<213> ORGANISM: Homo sapiens

<400> SEQUENCE: 30

```
Met Gly Thr Gln Asp Pro Gly Asn Met Gly Thr Gly Val Pro Ala Ser
1               5                   10                  15

Glu Gln Ile Ser Cys Ala Lys Glu Asp Pro Gln Val Tyr Cys Pro Glu
            20                  25                  30

Glu Thr Gly Gly Thr Lys Asp Val Gln Val Thr Asp Cys Lys Ser Pro
        35                  40                  45

Glu Asp Ser Arg Pro Pro Lys Glu Thr Asp Cys Cys Asn Pro Glu Asp
    50                  55                  60

Ser Gly Gln Leu Met Val Ser Tyr Glu Gly Lys Ala Met Gly Tyr Gln
65                  70                  75                  80

Val Pro Pro Phe Gly Trp Arg Ile Cys Leu Ala His Glu Phe Thr Glu
                85                  90                  95

Lys Arg Lys Pro Phe Gln Ala Asn Asn Val Ser Leu Ser Asn Met Ile
            100                 105                 110

Lys His Ile Gly Met Gly Leu Arg Tyr Leu Gln Trp Trp Tyr Arg Lys
        115                 120                 125

Thr His Val Glu Lys Lys Thr Pro Phe Ile Asp Met Ile Asn Ser Val
    130                 135                 140

Pro Leu Arg Gln Ile Tyr Gly Cys Pro Leu Gly Gly Ile Gly Gly Gly
145                 150                 155                 160

Thr Ile Thr Arg Gly Trp Arg Gly Gln Phe Cys Arg Trp Gln Leu Asn
                165                 170                 175

Pro Gly Met Tyr Gln His Arg Thr Val Ile Ala Asp Gln Phe Thr Val
            180                 185                 190

Cys Leu Arg Arg Glu Gly Gln Thr Val Tyr Gln Gln Val Leu Ser Leu
        195                 200                 205

Glu Arg Pro Ser Val Leu Arg Ser Trp Asn Trp Gly Leu Cys Gly Tyr
    210                 215                 220

Phe Ala Phe Tyr His Ala Leu Tyr Pro Arg Ala Trp Thr Val Tyr Gln
225                 230                 235                 240

Leu Pro Gly Gln Asn Val Thr Leu Thr Cys Arg Gln Ile Thr Pro Ile
                245                 250                 255

Leu Pro His Asp Tyr Gln Asp Ser Ser Leu Pro Val Gly Val Phe Val
            260                 265                 270

Trp Asp Val Glu Asn Glu Gly Asp Glu Ala Leu Asp Val Ser Ile Met
        275                 280                 285

Phe Ser Met Arg Asn Gly Leu Gly Gly Gly Asp Asp Ala Pro Gly Gly
    290                 295                 300

Leu Trp Asn Glu Pro Phe Cys Leu Glu Arg Ser Gly Glu Thr Val Arg
305                 310                 315                 320

Gly Leu Leu Leu His His Pro Thr Leu Pro Asn Pro Tyr Thr Met Ala
                325                 330                 335

Val Ala Ala Arg Val Thr Ala Ala Thr Thr Val Thr His Ile Thr Ala
            340                 345                 350

Phe Asp Pro Asp Ser Thr Gly Gln Gln Val Trp Gln Asp Leu Leu Gln
        355                 360                 365

Asp Gly Gln Leu Asp Ser Pro Thr Gly Gln Ser Thr Pro Thr Gln Lys
```

```
    370                 375                 380

Gly Val Gly Ile Ala Gly Ala Val Cys Val Ser Ser Lys Leu Arg Pro
385                 390                 395                 400

Arg Gly Gln Cys Arg Leu Glu Phe Ser Leu Ala Trp Asp Met Pro Arg
                405                 410                 415

Ile Met Phe Gly Ala Lys Gly Gln Val His Tyr Arg Arg Tyr Thr Arg
            420                 425                 430

Phe Phe Gly Gln Asp Gly Asp Ala Ala Pro Ala Leu Ser His Tyr Ala
        435                 440                 445

Leu Cys Arg Tyr Ala Glu Trp Glu Glu Arg Ile Ser Ala Trp Gln Ser
    450                 455                 460

Pro Val Leu Asp Asp Arg Ser Leu Pro Ala Trp Tyr Lys Ser Ala Leu
465                 470                 475                 480

Phe Asn Glu Leu Tyr Phe Leu Ala Asp Gly Gly Thr Val Trp Leu Glu
                485                 490                 495

Val Leu Glu Asp Ser Leu Pro Glu Glu Leu Gly Arg Asn Met Cys His
            500                 505                 510

Leu Arg Pro Thr Leu Arg Asp Tyr Gly Arg Phe Gly Tyr Leu Glu Gly
        515                 520                 525

Gln Glu Tyr Arg Met Tyr Asn Thr Tyr Asp Val His Phe Tyr Ala Ser
    530                 535                 540

Phe Ala Leu Ile Met Leu Trp Pro Lys Leu Glu Leu Ser Leu Gln Tyr
545                 550                 555                 560

Asp Met Ala Leu Ala Thr Leu Arg Glu Asp Leu Thr Arg Arg Arg Tyr
                565                 570                 575

Leu Met Ser Gly Val Met Ala Pro Val Lys Arg Arg Asn Val Ile Pro
            580                 585                 590

His Asp Ile Gly Asp Pro Asp Asp Glu Pro Trp Leu Arg Val Asn Ala
        595                 600                 605

Tyr Leu Ile His Asp Thr Ala Asp Trp Lys Asp Leu Asn Leu Lys Phe
    610                 615                 620

Val Leu Gln Val Tyr Arg Asp Tyr Tyr Leu Thr Gly Asp Gln Asn Phe
625                 630                 635                 640

Leu Lys Asp Met Trp Pro Val Cys Leu Ala Val Met Glu Ser Glu Met
                645                 650                 655

Lys Phe Asp Lys Asp His Asp Gly Leu Ile Glu Asn Gly Gly Tyr Ala
            660                 665                 670

Asp Gln Thr Tyr Asp Gly Trp Val Thr Thr Gly Pro Ser Ala Tyr Cys
        675                 680                 685

Gly Gly Leu Trp Leu Ala Ala Val Ala Val Met Val Gln Met Ala Ala
    690                 695                 700

Leu Cys Gly Ala Gln Asp Ile Gln Asp Lys Phe Ser Ser Ile Leu Ser
705                 710                 715                 720

Arg Gly Gln Glu Ala Tyr Glu Arg Leu Leu Trp Asn Gly Arg Tyr Tyr
                725                 730                 735

Asn Tyr Asp Ser Ser Ser Arg Pro Gln Ser Arg Ser Val Met Ser Asp
            740                 745                 750

Gln Cys Ala Gly Gln Trp Phe Leu Lys Ala Cys Gly Leu Gly Glu Gly
        755                 760                 765

Asp Thr Glu Val Phe Pro Thr Gln His Val Val Arg Ala Leu Gln Thr
    770                 775                 780

Ile Phe Glu Leu Asn Val Gln Ala Phe Ala Gly Gly Ala Met Gly Ala
785                 790                 795                 800
```

```
Val Asn Gly Met Gln Pro His Gly Val Pro Asp Lys Ser Ser Val Gln
                805                 810                 815

Ser Asp Glu Val Trp Val Gly Val Val Tyr Gly Leu Ala Ala Thr Met
            820                 825                 830

Ile Gln Glu Gly Leu Thr Trp Glu Gly Phe Gln Thr Ala Glu Gly Cys
        835                 840                 845

Tyr Arg Thr Val Trp Glu Arg Leu Gly Leu Ala Phe Gln Thr Pro Glu
    850                 855                 860

Ala Tyr Cys Gln Gln Arg Val Phe Arg Ser Leu Ala Tyr Met Arg Pro
865                 870                 875                 880

Leu Ser Ile Trp Ala Met Gln Leu Ala Leu Gln Gln Gln Gln His Lys
                885                 890                 895

Lys Ala Ser Trp Pro Lys Val Lys Gln Gly Thr Gly Leu Arg Thr Gly
            900                 905                 910

Pro Met Phe Gly Pro Lys Glu Ala Met Ala Asn Leu Ser Pro Glu
        915                 920                 925


<210> SEQ ID NO 31
<211> LENGTH: 2781
<212> TYPE: DNA
<213> ORGANISM: Homo sapiens

<400> SEQUENCE: 31

atgggcaccc aggaccccgg caacatgggc accggcgtgc ccgccagcga gcagatcagc     60

tgcgccaagg aggaccccca ggtgtactgc cccgaggaga ccggcggcac caaggacgtg    120

caggtgaccg actgcaagag ccccgaggac agccgccccc ccaaggagac cgactgctgc    180

aaccccgagg acagcggcca gctgatggtg agctacgagg gcaaggccat gggctaccag    240

gtgcccccct tcggctggcg catctgcctg gcccacgagt tcaccgagaa gcgcaagccc    300

ttccaggcca acaacgtgag cctgagcaac atgatcaagc acatcggcat gggcctgcgc    360

tacctgcagt ggtggtaccg caagacccac gtggagaaga agaccccctt catcgacatg    420

atcaacagcg tgcccctgcg ccagatctac ggctgccccc tgggcggcat cggcggcggc    480

accatcaccc gcggctggcg cggccagttc tgccgctggc agctgaaccc cggcatgtac    540

cagcaccgca ccgtgatcgc cgaccagttc accgtgtgcc tgcgccgcga gggccagacc    600

gtgtaccagc aggtgctgag cctggagcgc cccagcgtgc tgcgcagctg gaactggggc    660

ctgtgcggct acttcgcctt ctaccacgcc ctgtaccccc gcgcctggac cgtgtaccag    720

ctgcccggcc agaacgtgac cctgacctgc cgccagatca cccccatcct gccccacgac    780

taccaggaca gcagcctgcc cgtgggcgtg ttcgtgtggg acgtggagaa cgagggcgac    840

gaggccctgg acgtgagcat catgttcagc atgcgcaacg gcctgggcgg cggcgacgac    900

gcccccggcg gcctgtggaa cgagcccttc tgcctggagc gcagcggcga gaccgtgcgc    960

ggcctgctgc tgcaccaccc caccctgccc aacccctaca ccatggccgt ggccgcccgc   1020

gtgaccgccg ccaccaccgt gacccacatc accgccttcg accccgacag caccggccag   1080

caggtgtggc aggacctgct gcaggacggc cagctggaca gccccaccgg ccagagcacc   1140

cccacccaga agggcgtggg catcgccggc gccgtgtgcg tgagcagcaa gctgcgcccc   1200

cgcggccagt gccgcctgga gttcagcctg gcctgggaca tgccccgcat catgttcggc   1260

gccaagggcc aggtgcacta ccgccgctac acccgcttct tcggccagga cggcgacgcc   1320

gcccccgccc tgagccacta cgccctgtgc cgctacgccg agtgggagga gcgcatcagc   1380
```

```
gcctggcaga gccccgtgct ggacgaccgc agcctgcccg cctggtacaa gagcgccctg   1440
ttcaacgagc tgtacttcct ggccgacggc ggcaccgtgt ggctggaggt gctggaggac   1500
agcctgcccg aggagctggg ccgcaacatg tgccacctgc gccccaccct gcgcgactac   1560
ggccgcttcg gctacctgga gggccaggag taccgcatgt acaacaccta cgacgtgcac   1620
ttctacgcca gcttcgccct gatcatgctg tggcccaagc tggagctgag cctgcagtac   1680
gacatggccc tggccaccct gcgcgaggac ctgacccgcc gccgctacct gatgagcggc   1740
gtgatggccc ccgtgaagcg ccgcaacgtg atcccccacg acatcggcga ccccgacgac   1800
gagccctggc tgcgcgtgaa cgcctacctg atccacgaca ccgccgactg gaaggacctg   1860
aacctgaagt tcgtgctgca ggtgtaccgc gactactacc tgaccggcga ccagaacttc   1920
ctgaaggaca tgtggcccgt gtgcctggcc gtgatggaga gcgagatgaa gttcgacaag   1980
gaccacgacg gcctgatcga gaacggcggc tacgccgacc agacctacga cggctgggtg   2040
accaccggcc ccagcgccta ctgcggcggc ctgtggctgg ccgccgtggc cgtgatggtg   2100
cagatggccg ccctgtgcgg cgcccaggac atccaggaca agttcagcag catcctgagc   2160
cgcggccagg aggcctacga gcgcctgctg tggaacggcc gctactacaa ctacgacagc   2220
agcagccgcc cccagagccg cagcgtgatg agcgaccagt gcgccggcca gtggttcctg   2280
aaggcctgcg gcctgggcga gggcgacacc gaggtgttcc ccacccagca cgtggtgcgc   2340
gccctgcaga ccatcttcga gctgaacgtg caggccttcg ccggcggcgc catgggcgcc   2400
gtgaacggca tgcagcccca cggcgtgccc gacaagagca gcgtgcagag cgacgaggtg   2460
tgggtgggcg tggtgtacgg cctggccgcc accatgatcc aggagggcct gacctgggag   2520
ggcttccaga ccgccgaggg ctgctaccgc accgtgtggg agcgcctggg cctggccttc   2580
cagacccccg aggcctactg ccagcagcgc gtgttccgca gcctggccta catgcgcccc   2640
ctgagcatct gggccatgca gctggccctg cagcagcagc agcacaagaa ggccagctgg   2700
cccaaggtga agcagggcac cggcctgcgc accggcccca tgttcggccc caaggaggcc   2760
atggccaacc tgagccccga g                                              2781
```

<210> SEQ ID NO 32
<211> LENGTH: 11264
<212> TYPE: DNA
<213> ORGANISM: Artificial sequence
<220> FEATURE:
<223> OTHER INFORMATION: Synthetic polynucleotide

<400> SEQUENCE: 32

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg agtaagtcac    300
tgactgtcta tgcctgggaa agggtgggca ggagatgggg cagtgcagga aaagtggcac    360
tatgaaccct cctggtggcg aggggagggg ggtggtcctc gaacgccttg cagaactggc    420
ctggatacag agtggaccgg ctggccccat ctggaagact tcgagataca ctgttgtctt    480
actgcgctca acagtgtatc tcgaagtctt ccaaatggtg ccagccatcg cagcggggtg    540
caggaaatgg gggcagcccc ccttttttggc tatccttcca cgtgttcttt tttgtatctt    600
ttgtgtttcc tagaaaacat ctcagtcacc accgcagccc taggaatgca tctagacaat    660
```

```
tgtactaacc ttcttctctt tcctctcctg acagtccgga aagccaccat gggcacccag    720
gaccccggca acatgggcac cggcgtgccc gccagcgagc agatcagctg cgccaaggag    780
gacccccagg tgtactgccc cgaggagacc ggcggcacca aggacgtgca ggtgaccgac    840
tgcaagagcc ccgaggacag ccgccccccc aaggagaccg actgctgcaa ccccgaggac    900
agcggccagc tgatggtgag ctacgagggc aaggccatgg gctaccaggt gccccccttc    960
ggctggcgca tctgcctggc ccacgagttc accgagaagc gcaagccctt ccaggccaac   1020
aacgtgagcc tgagcaacat gatcaagcac atcggcatgg gcctgcgcta cctgcagtgg   1080
tggtaccgca agacccacgt ggagaagaag accccctca tcgacatgat caacagcgtg    1140
cccctgcgcc agatctacgg ctgcccctg ggcggcatcg gcggcggcac catcacccgc    1200
ggctggcgcg gccagttctg ccgctggcag ctgaaccccg gcatgtacca gcaccgcacc   1260
gtgatcgccg accagttcac cgtgtgcctg cgccgcgagg gccagaccgt gtaccagcag   1320
gtgctgagcc tggagcgccc cagcgtgctg cgcagctgga actggggcct gtgcggctac   1380
ttcgccttct accacgccct gtaccccgc gcctggaccg tgtaccagct gcccggccag    1440
aacgtgaccc tgacctgccg ccagatcacc cccatcctgc cccacgacta ccaggacagc   1500
agcctgcccg tgggcgtgtt cgtgtgggac gtggagaacg agggcgacga ggccctggac   1560
gtgagcatca tgttcagcat gcgcaacggc ctgggcggcg gcgacgacgc ccccggcggc   1620
ctgtggaacg agcccttctg cctggagcgc agcggcgaga ccgtgcgcgg cctgctgctg   1680
caccaccca ccctgcccaa cccctacacc atggccgtgg ccgcccgcgt gaccgccgcc    1740
accaccgtga cccacatcac cgccttcgac cccgacagca ccggccagca ggtgtggcag   1800
gacctgctgc aggacggcca gctggacagc cccaccggcc agagcacccc cacccagaag   1860
ggcgtgggca tcgccggcgc cgtgtgcgtg agcagcaagc tgcgcccccg cggccagtgc   1920
cgcctggagt tcagcctggc ctgggacatg ccccgcatca tgttcggcgc caagggccag   1980
gtgcactacc gccgctacac ccgcttcttc ggccaggacg gcgacgccgc ccccgccctg   2040
agccactacg ccctgtgccg ctacgccgag tgggaggagc gcatcagcgc ctggcagagc   2100
cccgtgctgg acgaccgcag cctgcccgcc tggtacaaga gcgccctgtt caacgagctg   2160
tacttcctgg ccgacggcgg caccgtgtgg ctggaggtgc tggaggacag cctgcccgag   2220
gagctgggcc gcaacatgtg ccacctgcgc cccaccctgc gcgactacgg ccgcttcggc   2280
tacctggagg gccaggagta ccgcatgtac aacacctacg acgtgcactt ctacgccagc   2340
ttcgccctga tcatgctgtg gcccaagctg gagctgagcc tgcagtacga catggccctg   2400
gccaccctgc gcgaggacct gacccgccgc cgctacctga tgagcggcgt gatggccccc   2460
gtgaagcgcc gcaacgtgat cccccacgac atcggcgacc ccgacgacga gccctggctg   2520
cgcgtgaacg cctacctgat ccacgacacc gccgactgga aggacctgaa cctgaagttc   2580
gtgctgcagg tgtaccgcga ctactacctg accggcgacc agaacttcct gaaggacatg   2640
tggcccgtgt gcctggccgt gatggagagc gagatgaagt tcgacaagga ccacgacggc   2700
ctgatcgaga acggcggcta cgccgaccag acctacgacg gctgggtgac caccggcccc   2760
agcgcctact gcggcggcct gtggctggcc gccgtggccg tgatggtgca gatggccgcc   2820
ctgtgcggcg cccaggacat ccaggacaag ttcagcagca tcctgagccg cggccaggag   2880
gcctacgagc gcctgctgtg gaacggccgc tactacaact acgacagcag cagccgcccc   2940
cagagccgca gcgtgatgag cgaccagtgc gccggccagt ggttcctgaa ggcctgcggc   3000
```

-continued

```
ctgggcgagg gcgacaccga ggtgttcccc acccagcacg tggtgcgcgc cctgcagacc   3060
atcttcgagc tgaacgtgca ggccttcgcc ggcggcgcca tgggcgccgt gaacggcatg   3120
cagccccacg gcgtgcccga caagagcagc gtgcagagcg acgaggtgtg ggtgggcgtg   3180
gtgtacggcc tggccgccac catgatccag gagggcctga cctgggaggg cttccagacc   3240
gccgagggct gctaccgcac cgtgtgggag cgcctgggcc tggccttcca gacccccgag   3300
gcctactgcc agcagcgcgt gttccgcagc ctggcctaca tgcgcccct gagcatctgg    3360
gccatgcagc tggccctgca gcagcagcag cacaagaagg ccagctggcc caaggtgaag   3420
cagggcaccg gcctgcgcac cggccccatg ttcggcccca aggaggccat ggccaacctg   3480
agccccgagt gacaattgtt aattaagttt aaaccctcga ggccgcaagc ttatcgataa   3540
tcaacctctg gattacaaaa tttgtgaaag attgactggt attcttaact atgttgctcc   3600
ttttacgcta tgtggatacg ctgctttaat gcctttgtat catgctattg cttcccgtat   3660
ggctttcatt ttctcctcct tgtataaatc ctggttgctg tctctttatg aggagttgtg   3720
gcccgttgtc aggcaacgtg gcgtggtgtg cactgtgttt gctgacgcaa cccccactgg   3780
ttggggcatt gccaccacct gtcagctcct ttccgggact ttcgctttcc ccctccctat   3840
tgccacggcg gaactcatcg ccgcctgcct tgcccgctgc tggacagggg ctcggctgtt   3900
gggcactgac aattccgtgg tgttgtcggg gaaatcatcg tcctttcctt ggctgctcgc   3960
ctgtgttgcc acctggattc tgcgcgggac gtccttctgc tacgtccctt cggccctcaa   4020
tccagcggac cttccttccc gcggcctgct gccggctctg cggcctcttc cgcgtcttcg   4080
ccttcgccct cagacgagtc ggatctccct ttgggccgcc tccccgcatc gataccgtcg   4140
actagagctc gctgatcagc ctcgactgtg ccttctagtt gccagccatc tgttgtttgc   4200
ccctcccccg tgccttcctt gaccctggaa ggtgccactc ccactgtcct ttcctaataa   4260
aatgaggaaa ttgcatcgca ttgtctgagt aggtgtcatt ctattctggg gggtggggtg   4320
gggcaggaca gcaaggggga ggattgggaa gacaatagca ggcatgctgg ggagagatcc   4380
acgataacaa acagcttttt tggggtgaac atattgactg aattccctgc aggttggcca   4440
ctccctctct gcgcgctcgc tcgctcactg aggccgcccg ggcaaagccc gggcgtcggg   4500
cgacctttgg tcgcccggcc tcagtgagcg agcgagcgcg cagagaggga gtggccaact   4560
ccatcactag gggttcctgc ggccgctcgt acggtctcga ggaattcctg caggataact   4620
tgccaacctc attctaaaat gtatatagaa gcccaaaaga caataacaaa aatattcttg   4680
tagaacaaaa tgggaaagaa tgttccacta aatatcaaga tttagagcaa agcatgagat   4740
gtgtggggat agacagtgag gctgataaaa tagagtagag ctcagaaaca gacccattga   4800
tatatgtaag tgacctatga aaaaaatatg gcattttaca atgggaaaat gatggtcttt   4860
ttcttttta gaaaaacagg gaaatatatt tatatgtaaa aaataaaagg gaacccatat    4920
gtcataccat acacacaaaa aaattccagt gaattataag tctaaatgga gaaggcaaaa   4980
ctttaaatct tttagaaaat aatatagaag catgcagacc agcctggcca acatgatgaa   5040
accctctcta ctaataataa aatcagtaga actactcagg actactttga gtgggaagtc   5100
cttttctatg aagacttctt tggccaaaat taggctctaa atgcaaggag atagtgcatc   5160
atgcctggct gcacttactg ataaatgatg ttatcaccat ctttaaccaa atgcacagga   5220
acaagttatg gtactgatgt gctggattga gaaggagctc tacttccttg acaggacaca   5280
tttgtatcaa cttaaaaaag cagatttttg ccagcagaac tattcattca gaggtaggaa   5340
acttagaata gatgatgtca ctgattagca tggcttcccc atctccacag ctgcttccca   5400
```

```
cccaggttgc ccacagttga gtttgtccag tgctcagggc tgcccactct cagtaagaag   5460
ccccacacca gcccctctcc aaatatgttg gctgttcctt ccattaaagt gaccccactt   5520
tagagcagca agtggatttc tgtttcttac agttcaggaa ggaggagtca gctgtgagaa   5580
cctggagcct gagatgcttc taagtcccac tgctactggg gtcagggaag ccagactcca   5640
gcatcagcag tcaggagcac taagcccttg ccaacatcct gtttctcaga gaaactgctt   5700
ccattataat ggttgtcctt ttttaagcta tcaagccaaa caaccagtgt ctaccattat   5760
tctcatcacc tgaagccaag ggttctagca aaagtcaagc tgtcttgtaa tggttgatgt   5820
gcctccagct tctgtcttca gtcactccac tcttagcctg ctctgaatca actctgacca   5880
cagttccctg gagcccctgc cacctgctgc ccctgccacc ttctccatct gcagtgctgt   5940
gcagccttct gcactcttgc agagctaata ggtggagact tgaaggaaga ggaggaaagt   6000
ttctcataat agccttgctg caagctcaaa tgggaggtgg gcactgtgcc caggagcctt   6060
ggagcaaagg ctgtgcccaa cctctgactg catccaggtt tggtcttgac agagataaga   6120
agccctggct tttggagcca aaatctaggt cagacttagg caggattctc aaagtttatc   6180
agcagaacat gaggcagaag accctttctg ctccagcttc ttcaggctca accttcatca   6240
gaatagatag aaagagaggc tgtgagggtt cttaaaacag aagcaaatct gactcagaga   6300
ataaacaacc tcctagtaaa ctacagctta gacagagcat ctggtggtga gtgtgctcag   6360
tgtcctactc aactgtctgg tatcagccct catgaggact tctcttcttt ccctcataga   6420
cctccatctc tgttttcctt agcctgcaga aatctggatg gctattcaca gaatgcctgt   6480
gctttcagag ttgcattttt tctctggtat tctggttcaa gcatttgaag gtaggaaagg   6540
ttctccaagt gcaagaaagc cagccctgag cctcaactgc ctggctagtg tggtcagtag   6600
gatgcaaagg ctgttgaatg ccacaaggcc aaactttaac ctgtgtacca caagcctagc   6660
agcagaggca gctctgctca ctggaactct ctgtcttctt tctcctgagc cttttctttt   6720
cctgagtttt ctagctctcc tcaaccttac ctctgcccta cccaggacaa acccaagagc   6780
cactgtttct gtgatgtcct ctccagccct aattaggcat catgacttca gcctgacctt   6840
ccatgctcag aagcagtgct aatccacttc agatgagctg ctctatgcaa cacaggcaga   6900
gcctacaaac ctttgcacca gagccctcca catatcagtg tttgttcata ctcacttcaa   6960
cagcaaatgt gactgctgag attaagattt tacacaagat ggtctgtaat ttcacagtta   7020
gttttatccc attaggtatg aaagaattag cataattccc cttaaacatg aatgaatctt   7080
agatttttta ataaatagtt ttggaagtaa agacagagac atcaggagca caaggaatag   7140
cctgagagga caaacagaac aagaaagagt ctggaaatac acaggatgtt cttggcctcc   7200
tcaaagcaag tgcaagcaga tagtaccagc agccccaggc tatcagagcc cagtgaagag   7260
aagtaccatg aaagccacag ctctaaccac cctgttccag agtgacagac agtccccaag   7320
acaagccagc ctgagccaga gagagaactg caagagaaag tttctaattt aggttctgtt   7380
agattcagac aagtgcaggt catcctctct ccacagctac tcacctctcc agcctaacaa   7440
agcctgcagt ccacactcca accctggtgt ctcacctcct agcctctccc aacatcctgc   7500
tctctgacca tcttctgcat ctctcatctc accatctccc actgtctaca gcctactctt   7560
gcaactacca tctcattttc tgacatcctg tctacatctt ctgccatact ctgccatcta   7620
ccataccacc tcttaccatc taccacacca tcttttatct ccatccctct cagaagcctc   7680
caagctgaat cctgctttat gtgttcatct cagcccctgc atggaaagct gaccccagag   7740
```

```
gcagaactat tcccagagag cttggccaag aaaaacaaaa ctaccagcct ggccaggctc   7800
aggagtagta agctgcagtg tctgttgtgt tctagcttca acagctgcag gagttccact   7860
ctcaaatgct ccacatttct cacatcctcc tgattctggt cactacccat cttcaaagaa   7920
cagaatatct cacatcagca tactgtgaag gactagtcat gggtgcagct gctcagagct   7980
gcaaagtcat tctggatggt ggagagctta caaacatttc atgatgctcc ccccgctctg   8040
atggctggag cccaatccct acacagactc ctgctgtatg tgttttcctt tcactctgag   8100
ccacagccag agggcaggca ttcagtctcc tcttcaggct ggggctgggg cactgagaac   8160
tcacccaaca ccttgctctc actccttctg caaaacaaga aagagctttg tgctgcagta   8220
gccatgaaga atgaaaggaa ggctttaact aaaaaatgtc agagattatt ttcaacccct   8280
tactgtggat caccagcaag gaggaaacac aacacagaga catttttttcc cctcaaatta   8340
tcaaaagaat cactgcattt gttaaagaga gcaactgaat caggaagcag agttttgaac   8400
atatcagaag ttaggaatct gcatcagaga caaatgcagt catggttgtt tgctgcatac   8460
cagccctaat cattagaagc ctcatggact tcaaacatca ttccctctga caagatgctc   8520
tagcctaact ccatgagata aaataaatct gcctttcaga gccaaagaag agtccaccag   8580
cttcttctca gtgtgaacaa gagctccagt caggttagtc agtccagtgc agtagaggag   8640
accagtctgc atcctctaat tttcaaaggc aagaagattt gtttaccctg gacaccaggc   8700
acaagtgagg tcacagagct cttagatatg cagtcctcat gagtgaggag actaaagcgc   8760
atgccatcaa gacttcagtg tagagaaaac ctccaaaaaa gcctcctcac tacttctgga   8820
atagctcaga ggccgaggcg gcctcggcct ctgcataaat aaaaaaaatt agtcagccat   8880
ggggcggaga atgggcggaa ctgggcggag ttaggggcgg gatgggcgga gttaggggcg   8940
ggactatggt tgctgactaa ttgagatgca tgctttgcat acttctgcct gctggggagc   9000
ctggggactt tccacacctg gttgctgact aattgagatg catgctttgc atacttctgc   9060
ctgctgggga gcctggggac tttccacacc ctaactgaca cacattccac agctgcatta   9120
atgaatcggc caacgcgcgg ggagaggcgg tttgcgtatt gggcgctctt ccgcttcctc   9180
gctcactgac tcgctgcgct cggtcgttcg gctgcggcga gcggtatcag ctcactcaaa   9240
ggcggtaata cggttatcca cagaatcagg ggataacgca ggaaagaaca tgtgagcaaa   9300
aggccagcaa aaggccagga accgtaaaaa ggccgcgttg ctggcgtttt tccataggct   9360
ccgcccccct gacgagcatc acaaaaatcg acgctcaagt cagaggtggc gaaacccgac   9420
aggactataa agataccagg cgtttccccc tggaagctcc ctcgtgcgct ctcctgttcc   9480
gaccctgccg cttaccggat acctgtccgc ctttctccct tcgggaagcg tggcgctttc   9540
tcatagctca cgctgtaggt atctcagttc ggtgtaggtc gttcgctcca agctgggctg   9600
tgtgcacgaa ccccccgttc agcccgaccg ctgcgcctta tccggtaact atcgtcttga   9660
gtccaacccg gtaagacacg acttatcgcc actggcagca gccactggta acaggattag   9720
cagagcgagg tatgtaggcg gtgctacaga gttcttgaag tggtggccta actacggcta   9780
cactagaaga acagtatttg gtatctgcgc tctgctgaag ccagttacct tcggaaaaag   9840
agttggtagc tcttgatccg gcaaacaaac caccgctggt agcggtggtt tttttgtttg   9900
caagcagcag attacgcgca gaaaaaaagg atctcaagaa gatcctttga tcttttctac   9960
ggggtctgac gctcagtgga acgaaaactc acgttaaggg attttggtca tgagattatc  10020
aaaaaggatc ttcacctaga tccttttaaa ttaaaaatga agttttaaat caatctaaag  10080
tatatatgag taaacttggt ctgacagtta ccaatgctta atcagtgagg cacctatctc  10140
```

```
agcgatctgt ctatttcgtt catccatagt tgcctgactc ctgcaaacca cgttgtgtct  10200

caaaatctct gatgttacat tgcacaagat aaaaatatat catcatgaac aataaaactg  10260

tctgcttaca taaacagtaa tacaaggggt gttatgagcc atattcaacg ggaaacgtct  10320

tgctcgaggc cgcgattaaa ttccaacatg gatgctgatt tatatgggta taaatgggct  10380

cgcgataatg tcgggcaatc aggtgcgaca atctatcgat tgtatgggaa gcccgatgcg  10440

ccagagttgt ttctgaaaca tggcaaaggt agcgttgcca atgatgttac agatgagatg  10500

gtcagactaa actggctgac ggaatttatg cctcttccga ccatcaagca ttttatccgt  10560

actcctgatg atgcatggtt actcaccact gcgatccccg ggaaaacagc attccaggta  10620

ttagaagaat atcctgattc aggtgaaaat attgttgatg cgctggcagt gttcctgcgc  10680

cggttgcatt cgattcctgt ttgtaattgt ccttttaaca gcgatcgcgt atttcgtctc  10740

gctcaggcgc aatcacgaat gaataacggt ttggttgatg cgagtgattt tgatgacgag  10800

cgtaatggct ggcctgttga acaagtctgg aaagaaatgc ataagctttt gccattctca  10860

ccggattcag tcgtcactca tggtgatttc tcacttgata accttatttt tgacgagggg  10920

aaattaatag gttgtattga tgttggacga gtcggaatcg cagaccgata ccaggatctt  10980

gccatcctat ggaactgcct cggtgagttt tctccttcat tacagaaacg gctttttcaa  11040

aaatatggta ttgataatcc tgatatgaat aaattgcagt ttcatttgat gctcgatgag  11100

tttttctaag ggcggcctgc caccataccc acgccgaaac aagcgctcat gagcccgaag  11160

tggcgagccc gatcttcccc atcggtgatg tcggcgatat aggcgccagc aaccgcacct  11220

gtggcgccgg tgatgagggc gcgccaagtc gacgtccggc agtc                  11264
```

<210> SEQ ID NO 33
<211> LENGTH: 685
<212> TYPE: PRT
<213> ORGANISM: Artificial sequence
<220> FEATURE:
<223> OTHER INFORMATION: Synthetic polypeptide

<400> SEQUENCE: 33

```
Met Ala Glu Trp Leu Leu Ser Ala Ser Trp Gln Arg Arg Ala Lys Ala
1               5                   10                  15

Met Thr Ala Ala Ala Gly Ser Ala Gly Arg Ala Ala Val Pro Leu Leu
            20                  25                  30

Leu Cys Ala Leu Leu Ala Pro Gly Gly Ala Tyr Val Leu Asp Asp Ser
        35                  40                  45

Asp Gly Leu Gly Arg Glu Phe Asp Gly Ile Gly Ala Val Ser Gly Gly
    50                  55                  60

Gly Ala Thr Ser Arg Leu Leu Val Asn Tyr Pro Glu Pro Tyr Arg Ser
65                  70                  75                  80

Gln Ile Leu Asp Tyr Leu Phe Lys Pro Asn Phe Gly Ala Ser Leu His
                85                  90                  95

Ile Leu Lys Val Glu Ile Gly Gly Asp Gly Gln Thr Thr Asp Gly Thr
            100                 105                 110

Glu Pro Ser His Met His Tyr Ala Leu Asp Glu Asn Tyr Phe Arg Gly
        115                 120                 125

Tyr Glu Trp Trp Leu Met Lys Glu Ala Lys Lys Arg Asn Pro Asn Ile
    130                 135                 140

Thr Leu Ile Gly Leu Pro Trp Ser Phe Pro Gly Trp Leu Gly Lys Gly
145                 150                 155                 160
```

```
Phe Asp Trp Pro Tyr Val Asn Leu Gln Leu Thr Ala Tyr Tyr Val Val
                165                 170                 175

Thr Trp Ile Val Gly Ala Lys Arg Tyr His Asp Leu Asp Ile Asp Tyr
            180                 185                 190

Ile Gly Ile Trp Asn Glu Arg Ser Tyr Asn Ala Asn Tyr Ile Lys Ile
        195                 200                 205

Leu Arg Lys Met Leu Asn Tyr Gln Gly Leu Gln Arg Val Lys Ile Ile
    210                 215                 220

Ala Ser Asp Asn Leu Trp Glu Ser Ile Ser Ala Ser Met Leu Leu Asp
225                 230                 235                 240

Ala Glu Leu Phe Lys Val Val Asp Val Ile Gly Ala His Tyr Pro Gly
                245                 250                 255

Thr His Ser Ala Lys Asp Ala Lys Leu Thr Gly Lys Lys Leu Trp Ser
            260                 265                 270

Ser Glu Asp Phe Ser Thr Leu Asn Ser Asp Met Gly Ala Gly Cys Trp
        275                 280                 285

Gly Arg Ile Leu Asn Gln Asn Tyr Ile Asn Gly Tyr Met Thr Ser Thr
    290                 295                 300

Ile Ala Trp Asn Leu Val Ala Ser Tyr Tyr Glu Gln Leu Pro Tyr Gly
305                 310                 315                 320

Arg Cys Gly Leu Met Thr Ala Gln Glu Pro Trp Ser Gly His Tyr Val
                325                 330                 335

Val Glu Ser Pro Val Trp Val Ser Ala His Thr Thr Gln Phe Thr Gln
            340                 345                 350

Pro Gly Trp Tyr Tyr Leu Lys Thr Val Gly His Leu Glu Lys Gly Gly
        355                 360                 365

Ser Tyr Val Ala Leu Thr Asp Gly Leu Gly Asn Leu Thr Ile Ile Ile
    370                 375                 380

Glu Thr Met Ser His Lys His Ser Lys Cys Ile Arg Pro Phe Leu Pro
385                 390                 395                 400

Tyr Phe Asn Val Ser Gln Gln Phe Ala Thr Phe Val Leu Lys Gly Ser
                405                 410                 415

Phe Ser Glu Ile Pro Glu Leu Gln Val Trp Tyr Thr Lys Leu Gly Lys
            420                 425                 430

Thr Ser Glu Arg Phe Leu Phe Lys Gln Leu Asp Ser Leu Trp Leu Leu
        435                 440                 445

Asp Ser Asp Gly Ser Phe Thr Leu Ser Leu His Glu Asp Glu Leu Phe
    450                 455                 460

Thr Leu Thr Thr Leu Thr Thr Gly Arg Lys Gly Ser Tyr Pro Leu Pro
465                 470                 475                 480

Pro Lys Ser Gln Pro Phe Pro Ser Thr Tyr Lys Asp Asp Phe Asn Val
                485                 490                 495

Asp Tyr Pro Phe Phe Ser Glu Ala Pro Asn Phe Ala Asp Gln Thr Gly
            500                 505                 510

Val Phe Glu Tyr Phe Thr Asn Ile Glu Asp Pro Gly Glu His His Phe
        515                 520                 525

Thr Leu Arg Gln Val Leu Asn Gln Arg Pro Ile Thr Trp Ala Ala Asp
    530                 535                 540

Ala Ser Asn Thr Ile Ser Ile Ile Gly Asp Tyr Asn Trp Thr Asn Leu
545                 550                 555                 560

Thr Ile Lys Cys Asp Val Tyr Ile Glu Thr Pro Asp Thr Gly Gly Val
                565                 570                 575

Phe Ile Ala Gly Arg Val Asn Lys Gly Gly Ile Leu Ile Arg Ser Ala
```

```
            580                 585                 590

Arg Gly Ile Phe Phe Trp Ile Phe Ala Asn Gly Ser Tyr Arg Val Thr
        595                 600                 605

Gly Asp Leu Ala Gly Trp Ile Ile Tyr Ala Leu Gly Arg Val Glu Val
    610                 615                 620

Thr Ala Lys Lys Trp Tyr Thr Leu Thr Leu Thr Ile Lys Gly His Phe
625                 630                 635                 640

Thr Ser Gly Met Leu Asn Asp Lys Ser Leu Trp Thr Asp Ile Pro Val
                645                 650                 655

Asn Phe Pro Lys Asn Gly Trp Ala Ala Ile Gly Thr His Ser Phe Glu
            660                 665                 670

Phe Ala Gln Phe Asp Asn Phe Leu Val Glu Ala Thr Arg
        675                 680                 685


<210> SEQ ID NO 34
<211> LENGTH: 2055
<212> TYPE: DNA
<213> ORGANISM: Artificial sequence
<220> FEATURE:
<223> OTHER INFORMATION: Synthetic polynucleotide

<400> SEQUENCE: 34

atggccgagt ggctgctgag cgccagctgg cagcgccgcg ccaaggccat gaccgccgcc     60

gccggcagcg ccggccgcgc cgccgtgccc ctgctgctgt gcgccctgct ggcccccggc    120

ggcgcctacg tgctggacga cagcgacggc ctgggccgcg agttcgacgg catcggcgcc    180

gtgagcggcg gcggcgccac cagccgcctg ctggtgaact accccgagcc ctaccgcagc    240

cagatcctgg actacctgtt caagcccaac ttcggcgcca gcctgcacat cctgaaggtg    300

gagatcggcg gcgacggcca gaccaccgac ggcaccgagc ccagccacat gcactacgcc    360

ctggacgaga actacttccg cggctacgag tggtggctga tgaaggaggc caagaagcgc    420

aaccccaaca tcaccctgat cggcctgccc tggagcttcc ccggctggct gggcaagggc    480

ttcgactggc cctacgtgaa cctgcagctg accgcctact acgtggtgac ctggatcgtg    540

ggcgccaagc gctaccacga cctggacatc gactacatcg gcatctggaa cgagcgcagc    600

tacaacgcca actacatcaa gatcctgcgc aagatgctga actaccaggg cctgcagcgc    660

gtgaagatca tcgccagcga caacctgtgg gagagcatca gcgccagcat gctgctggac    720

gccgagctgt tcaaggtggt ggacgtgatc ggcgcccact accccggcac ccacagcgcc    780

aaggacgcca agctgaccgg caagaagctg tggagcagcg aggacttcag caccctgaac    840

agcgacatgg gcgccggctg ctggggccgc atcctgaacc agaactacat caacggctac    900

atgaccagca ccatcgcctg gaacctggtg gccagctact acgagcagct gccctacggc    960

cgctgcggcc tgatgaccgc ccaggagccc tggagcggcc actacgtggt ggagagcccc   1020

gtgtgggtga gcgcccacac cacccagttc acccagcccg gctggtacta cctgaagacc   1080

gtgggccacc tggagaaggg cggcagctac gtggccctga ccgacggcct gggcaacctg   1140

accatcatca tcgagaccat gagccacaag cacagcaagt gcatccgccc cttcctgccc   1200

tacttcaacg tgagccagca gttcgccacc ttcgtgctga agggcagctt cagcgagatc   1260

cccgagctgc aggtgtggta caccaagctg ggcaagacca gcgagcgctt cctgttcaag   1320

cagctggaca gcctgtggct gctggacagc gacggcagct tcaccctgag cctgcacgag   1380

gacgagctgt tcaccctgac caccctgacc accggccgca agggcagcta cccccctgcc   1440

cccaagagcc agcccttccc cagcacctac aaggacgact tcaacgtgga ctaccccttc   1500
```

```
ttcagcgagg cccccaactt cgccgaccag accggcgtgt tcgagtactt caccaacatc   1560

gaggaccccg gcgagcacca cttcaccctg cgccaggtgc tgaaccagcg ccccatcacc   1620

tgggccgccg acgccagcaa caccatcagc atcatcggcg actacaactg gaccaacctg   1680

accatcaagt gcgacgtgta catcgagacc cccgacaccg gcggcgtgtt catcgccggc   1740

cgcgtgaaca agggcggcat cctgatccgc agcgcccgcg gcatcttctt ctggatcttc   1800

gccaacggca gctaccgcgt gaccggcgac ctggccggct ggatcatcta cgccctgggc   1860

cgcgtggagg tgaccgccaa gaagtggtac accctgaccc tgaccatcaa gggccacttc   1920

accagcggca tgctgaacga caagagcctg tggaccgaca tccccgtgaa cttccccaag   1980

aacggctggg ccgccatcgg cacccacagc ttcgagttcg cccagttcga caacttcctg   2040

gtggaggcca cccgc                                                    2055
```

<210> SEQ ID NO 35
<211> LENGTH: 339
<212> TYPE: PRT
<213> ORGANISM: Artificial sequence
<220> FEATURE:
<223> OTHER INFORMATION: Synthetic polypeptide

<400> SEQUENCE: 35

```
Met Trp Gln Leu Trp Ala Ser Leu Cys Cys Leu Leu Val Leu Ala Asn
1               5                   10                  15

Ala Arg Ser Arg Pro Ser Phe His Pro Leu Ser Asp Glu Leu Val Asn
            20                  25                  30

Tyr Val Asn Lys Arg Asn Thr Thr Trp Gln Ala Gly His Asn Phe Tyr
        35                  40                  45

Asn Val Asp Met Ser Tyr Leu Lys Arg Leu Cys Gly Thr Phe Leu Gly
    50                  55                  60

Gly Pro Lys Pro Pro Gln Arg Val Met Phe Thr Glu Asp Leu Lys Leu
65                  70                  75                  80

Pro Ala Ser Phe Asp Ala Arg Glu Gln Trp Pro Gln Cys Pro Thr Ile
                85                  90                  95

Lys Glu Ile Arg Asp Gln Gly Ser Cys Gly Ser Cys Trp Ala Phe Gly
            100                 105                 110

Ala Val Glu Ala Ile Ser Asp Arg Ile Cys Ile His Thr Asn Ala His
        115                 120                 125

Val Ser Val Glu Val Ser Ala Glu Asp Leu Leu Thr Cys Cys Gly Ser
    130                 135                 140

Met Cys Gly Asp Gly Cys Asn Gly Gly Tyr Pro Ala Glu Ala Trp Asn
145                 150                 155                 160

Phe Trp Thr Arg Lys Gly Leu Val Ser Gly Gly Leu Tyr Glu Ser His
                165                 170                 175

Val Gly Cys Arg Pro Tyr Ser Ile Pro Pro Cys Glu His His Val Asn
            180                 185                 190

Gly Ser Arg Pro Pro Cys Thr Gly Glu Gly Asp Thr Pro Lys Cys Ser
        195                 200                 205

Lys Ile Cys Glu Pro Gly Tyr Ser Pro Thr Tyr Lys Gln Asp Lys His
    210                 215                 220

Tyr Gly Tyr Asn Ser Tyr Ser Val Ser Asn Ser Glu Lys Asp Ile Met
225                 230                 235                 240

Ala Glu Ile Tyr Lys Asn Gly Pro Val Glu Gly Ala Phe Ser Val Tyr
                245                 250                 255
```

```
Ser Asp Phe Leu Leu Tyr Lys Ser Gly Val Tyr Gln His Val Thr Gly
            260                 265                 270

Glu Met Met Gly Gly His Ala Ile Arg Ile Leu Gly Trp Gly Val Glu
        275                 280                 285

Asn Gly Thr Pro Tyr Trp Leu Val Ala Asn Ser Trp Asn Thr Asp Trp
    290                 295                 300

Gly Asp Asn Gly Phe Phe Lys Ile Leu Arg Gly Gln Asp His Cys Gly
305                 310                 315                 320

Ile Glu Ser Glu Val Val Ala Gly Ile Pro Arg Thr Asp Gln Tyr Trp
                325                 330                 335

Glu Lys Ile
```

<210> SEQ ID NO 36
<211> LENGTH: 1017
<212> TYPE: DNA
<213> ORGANISM: Artificial sequence
<220> FEATURE:
<223> OTHER INFORMATION: Synthetic polynucleotide

<400> SEQUENCE: 36

```
atgtggcagc tgtgggccag cctgtgctgc ctgctggtgc tggccaacgc ccgcagccgc      60

cccagcttcc accccctgag cgacgagctg gtgaactacg tgaacaagcg caacaccacc     120

tggcaggccg gccacaactt ctacaacgtg gacatgagct acctgaagcg cctgtgcggc     180

accttcctgg gcggccccaa gcccccccag cgcgtgatgt tcaccgagga cctgaagctg     240

cccgccagct tcgacgcccg cgagcagtgg ccccagtgcc ccaccatcaa ggagatccgc     300

gaccagggca gctgcggcag ctgctgggcc ttcggcgccg tggaggccat cagcgaccgc     360

atctgcatcc acaccaacgc ccacgtgagc gtggaggtga gcgccgagga cctgctgacc     420

tgctgcggca gcatgtgcgg cgacggctgc aacggcggct accccgccga ggcctggaac     480

ttctggaccc gcaagggcct ggtgagcggc ggcctgtacg agagccacgt gggctgccgc     540

ccctacagca tccccccctg cgagcaccac gtgaacggca gccgcccccc ctgcaccggc     600

gagggcgaca cccccaagtg cagcaagatc tgcgagcccg gctacagccc cacctacaag     660

caggacaagc actacggcta caacagctac agcgtgagca acagcgagaa ggacatcatg     720

gccgagatct acaagaacgg ccccgtggag ggcgccttca gcgtgtacag cgacttcctg     780

ctgtacaaga gcggcgtgta ccagcacgtg accggcgaga tgatgggcgg ccacgccatc     840

cgcatcctgg gctggggcgt ggagaacggc accccctact ggctggtggc caacagctgg     900

aacaccgact ggggcgacaa cggcttcttc aagatcctgc gcggccagga ccactgcggc     960

atcgagagcg aggtggtggc cggcatcccc cgcaccgacc agtactggga gaagatc       1017
```

<210> SEQ ID NO 37
<211> LENGTH: 631
<212> TYPE: PRT
<213> ORGANISM: Artificial sequence
<220> FEATURE:
<223> OTHER INFORMATION: Synthetic polypeptide

<400> SEQUENCE: 37

```
Met Pro Arg Tyr Gly Ala Ser Leu Arg Gln Ser Cys Pro Arg Ser Gly
1               5                   10                  15

Arg Glu Gln Gly Gln Asp Gly Thr Ala Gly Ala Pro Gly Leu Leu Trp
            20                  25                  30

Met Gly Leu Val Leu Ala Leu Ala Leu Ala Leu Ala Leu Ala Leu Ala
        35                  40                  45
```

```
Leu Ser Asp Ser Arg Val Leu Trp Ala Pro Ala Glu Ala His Pro Leu
    50                  55                  60

Ser Pro Gln Gly His Pro Ala Arg Leu His Arg Ile Val Pro Arg Leu
65                  70                  75                  80

Arg Asp Val Phe Gly Trp Gly Asn Leu Thr Cys Pro Ile Cys Lys Gly
                85                  90                  95

Leu Phe Thr Ala Ile Asn Leu Gly Leu Lys Lys Glu Pro Asn Val Ala
            100                 105                 110

Arg Val Gly Ser Val Ala Ile Lys Leu Cys Asn Leu Leu Lys Ile Ala
        115                 120                 125

Pro Pro Ala Val Cys Gln Ser Ile Val His Leu Phe Glu Asp Asp Met
    130                 135                 140

Val Glu Val Trp Arg Arg Ser Val Leu Ser Pro Ser Glu Ala Cys Gly
145                 150                 155                 160

Leu Leu Leu Gly Ser Thr Cys Gly His Trp Asp Ile Phe Ser Ser Trp
                165                 170                 175

Asn Ile Ser Leu Pro Thr Val Pro Lys Pro Pro Pro Lys Pro Pro Ser
            180                 185                 190

Pro Pro Ala Pro Gly Ala Pro Val Ser Arg Ile Leu Phe Leu Thr Asp
        195                 200                 205

Leu His Trp Asp His Asp Tyr Leu Glu Gly Thr Asp Pro Asp Cys Ala
    210                 215                 220

Asp Pro Leu Cys Cys Arg Arg Gly Ser Gly Leu Pro Pro Ala Ser Arg
225                 230                 235                 240

Pro Gly Ala Gly Tyr Trp Gly Glu Tyr Ser Lys Cys Asp Leu Pro Leu
                245                 250                 255

Arg Thr Leu Glu Ser Leu Leu Ser Gly Leu Gly Pro Ala Gly Pro Phe
            260                 265                 270

Asp Met Val Tyr Trp Thr Gly Asp Ile Pro Ala His Asp Val Trp His
        275                 280                 285

Gln Thr Arg Gln Asp Gln Leu Arg Ala Leu Thr Thr Val Thr Ala Leu
    290                 295                 300

Val Arg Lys Phe Leu Gly Pro Val Pro Val Tyr Pro Ala Val Gly Asn
305                 310                 315                 320

His Glu Ser Thr Pro Val Asn Ser Phe Pro Pro Pro Phe Ile Glu Gly
                325                 330                 335

Asn His Ser Ser Arg Trp Leu Tyr Glu Ala Met Ala Lys Ala Trp Glu
            340                 345                 350

Pro Trp Leu Pro Ala Glu Ala Leu Arg Thr Leu Arg Ile Gly Gly Phe
        355                 360                 365

Tyr Ala Leu Ser Pro Tyr Pro Gly Leu Arg Leu Ile Ser Leu Asn Met
    370                 375                 380

Asn Phe Cys Ser Arg Glu Asn Phe Trp Leu Leu Ile Asn Ser Thr Asp
385                 390                 395                 400

Pro Ala Gly Gln Leu Gln Trp Leu Val Gly Glu Leu Gln Ala Ala Glu
                405                 410                 415

Asp Arg Gly Asp Lys Val His Ile Ile Gly His Ile Pro Pro Gly His
            420                 425                 430

Cys Leu Lys Ser Trp Ser Trp Asn Tyr Tyr Arg Ile Val Ala Arg Tyr
        435                 440                 445

Glu Asn Thr Leu Ala Ala Gln Phe Phe Gly His Thr His Val Asp Glu
    450                 455                 460
```

```
Phe Glu Val Phe Tyr Asp Glu Glu Thr Leu Ser Arg Pro Leu Ala Val
465                 470                 475                 480

Ala Phe Leu Ala Pro Ser Ala Thr Thr Tyr Ile Gly Leu Asn Pro Gly
                485                 490                 495

Tyr Arg Val Tyr Gln Ile Asp Gly Asn Tyr Ser Gly Ser Ser His Val
            500                 505                 510

Val Leu Asp His Glu Thr Tyr Ile Leu Asn Leu Thr Gln Ala Asn Ile
        515                 520                 525

Pro Gly Ala Ile Pro His Trp Gln Leu Leu Tyr Arg Ala Arg Glu Thr
    530                 535                 540

Tyr Gly Leu Pro Asn Thr Leu Pro Thr Ala Trp His Asn Leu Val Tyr
545                 550                 555                 560

Arg Met Arg Gly Asp Met Gln Leu Phe Gln Thr Phe Trp Phe Leu Tyr
                565                 570                 575

His Lys Gly His Pro Pro Ser Glu Pro Cys Gly Thr Pro Cys Arg Leu
            580                 585                 590

Ala Thr Leu Cys Ala Gln Leu Ser Ala Arg Ala Asp Ser Pro Ala Leu
        595                 600                 605

Cys Arg His Leu Met Pro Asp Gly Ser Leu Pro Glu Ala Gln Ser Leu
    610                 615                 620

Trp Pro Arg Pro Leu Phe Cys
625                 630


<210> SEQ ID NO 38
<211> LENGTH: 1896
<212> TYPE: DNA
<213> ORGANISM: Artificial sequence
<220> FEATURE:
<223> OTHER INFORMATION: Synthetic polynucleotide

<400> SEQUENCE: 38

atgccccgct acggcgccag cctgcgccag agctgccccc gcagcggccg cgagcagggc      60

caggacggca ccgccggcgc ccccggcctg ctgtggatgg gcctggtgct ggccctggcc     120

ctggccctgg ccctggccct ggccctgagc gacagccgcg tgctgtgggc ccccgccgag     180

gcccaccccc tgagccccca gggccacccc gcccgcctgc accgcatcgt gccccgcctg     240

cgcgacgtgt tcggctgggg caacctgacc tgccccatct gcaagggcct gttcaccgcc     300

atcaacctgg gcctgaagaa ggagcccaac gtggcccgcg tgggcagcgt ggccatcaag     360

ctgtgcaacc tgctgaagat cgcccccccc gccgtgtgcc agagcatcgt gcacctgttc     420

gaggacgaca tggtggaggt gtggcgccgc agcgtgctga gccccagcga ggcctgcggc     480

ctgctgctgg gcagcacctg cggccactgg gacatcttca gcagctggaa catcagcctg     540

cccaccgtgc ccaagccccc ccccaagccc cccagccccc ccgcccccgg cgcccccgtg     600

agccgcatcc tgttcctgac cgacctgcac tgggaccacg actacctgga gggcaccgac     660

cccgactgcg ccgaccccct gtgctgccgc cgcggcagcg gcctgccccc cgccagccgc     720

cccggcgccg gctactgggg cgagtacagc aagtgcgacc tgcccctgcg caccctggag     780

agcctgctga gcggcctggg ccccgccggc cccttcgaca tggtgtactg gaccggcgac     840

atccccgccc acgacgtgtg gcaccagacc cgccaggacc agctgcgcgc cctgaccacc     900

gtgaccgccc tggtgcgcaa gttcctgggc cccgtgcccg tgtaccccgc cgtgggcaac     960

cacgagagca cccccgtgaa cagcttcccc ccccccttca tcgagggcaa ccacagcagc    1020

cgctggctgt acgaggccat ggccaaggcc tgggagccct ggctgcccgc cgaggccctg    1080
```

```
cgcaccctgc gcatcggcgg cttctacgcc ctgagcccct accccggcct gcgcctgatc   1140

agcctgaaca tgaacttctg cagccgcgag aacttctggc tgctgatcaa cagcaccgac   1200

cccgccggcc agctgcagtg gctggtgggc gagctgcagg ccgccgagga ccgcggcgac   1260

aaggtgcaca tcatcggcca catccccccc ggccactgcc tgaagagctg gagctggaac   1320

tactaccgca tcgtggcccg ctacgagaac accctggccg cccagttctt cggccacacc   1380

cacgtggacg agttcgaggt gttctacgac gaggagaccc tgagccgccc cctggccgtg   1440

gccttcctgg cccccagcgc caccacctac atcggcctga accccggcta ccgcgtgtac   1500

cagatcgacg gcaactacag cggcagcagc cacgtggtgc tggaccacga gacctacatc   1560

ctgaacctga cccaggccaa catccccggc gccatccccc actggcagct gctgtaccgc   1620

gcccgcgaga cctacggcct gcccaacacc ctgcccaccg cctggcacaa cctggtgtac   1680

cgcatgcgcg gcgacatgca gctgttccag accttctggt tcctgtacca caagggccac   1740

ccccccagcg agccctgcgg caccccctgc cgcctggcca ccctgtgcgc ccagctgagc   1800

gcccgcgccg acagccccgc cctgtgccgc cacctgatgc ccgacggcag cctgcccgag   1860

gcccagagcc tgtggccccg cccccctgttc tgctaa                            1896
```

<210> SEQ ID NO 39
<211> LENGTH: 11329
<212> TYPE: DNA
<213> ORGANISM: Artificial sequence
<220> FEATURE:
<223> OTHER INFORMATION: Synthetic polynucleotide

<400> SEQUENCE: 39

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg agggcggagt    300

tagggcggag ccaatcagcg tgcgccgttc cgaaagttgc cttttatggc tgggcggaga    360

atgggcggtg aacgccgatg attatataag gacgcgccgg gtgtggcaca gctagttccg    420

tcgcagccgg gatttgggtc gcggttcttg tttgtggatc cctgtgatcg tcacttggta    480

agtcactgac tgtctatgcc tgggaaaggg tgggcaggag atggggcagt gcaggaaaag    540

tggcactatg aaccctgcag ccctaggaat gcatctagac aattgtacta accttcttct    600

ctttcctctc ctgacagtcc ggaaagccac catggaattc agcagcccca gcagagagga    660

atgccccaag cctctgagcc gggtgtcaat catggccgga tctctgacag gactgctgct    720

gcttcaggcc gtgtcttggg cttctggcgc tagaccttgc atccccaaga gcttcggcta    780

cagcagcgtc gtgtgcgtgt gcaatgccac ctactgcgac agcttcgacc ctcctacctt    840

tcctgctctg ggcaccttca gcagatacga gagcaccaga tccggcagac ggatggaact    900

gagcatggga cccatccagg ccaatcacac aggcactggc ctgctgctga cactgcagcc    960

tgagcagaaa ttccagaaag tgaaaggctt cggcggagcc atgacagatg ccgccgctct   1020

gaatatcctg gctctgtctc caccagctca gaacctgctg ctcaagagct acttcagcga   1080

ggaaggcatc ggctacaaca tcatcagagt gcccatggcc agctgcgact tcagcatcag   1140

gacctacacc tacgccgaca cacccgacga tttccagctg cacaacttca gcctgcctga   1200

agaggacacc aagctgaaga tccctctgat ccacagagcc ctgcagctgg cacaaagacc   1260
```

```
cgtgtcactg ctggcctctc catggacatc tcccacctgg ctgaaaacaa atggcgccgt   1320
gaatggcaag ggcagcctga aaggccaacc tggcgacatc taccaccaga cctgggccag   1380
atacttcgtg aagttcctgg acgcctatgc cgagcacaag ctgcagtttt gggccgtgac   1440
agccgagaac gaaccttctg ctggactgct gagcggctac ccctttcagt gcctgggctt   1500
tacacccgag caccagcggg actttatcgc ccgtgatctg ggacccacac tggccaatag   1560
cacccaccat aatgtgcggc tgctgatgct ggacgaccag agactgcttc tgccccactg   1620
ggctaaagtg gtgctgacag atcctgaggc cgccaaatac gtgcacggaa tcgccgtgca   1680
ctggtatctg gactttctgg cccctgccaa ggccacactg ggagagacac acagactgtt   1740
ccccaacacc atgctgttcg ccagcgaagc ctgtgtgggc agcaagtttt gggaacagag   1800
cgtgcggctc ggcagctggg atagaggcat gcagtacagc cacagcatca tcaccaacct   1860
gctgtaccac gtcgtcggct ggaccgactg gaatctggcc ctgaatcctg aaggcggccc   1920
taactgggtc cgaaacttcg tggacagccc catcatcgtg gacatcacca aggacacctt   1980
ctacaagcag cccatgttct accacctggg acacttcagc aagttcatcc ccgagggctc   2040
tcagcgcgtt ggactggtgg cttcccagaa gaacgatctg gacgccgtgg ctctgatgca   2100
ccctgatgga tctgctgtgg tggtggtcct gaaccgcagc agcaaagatg tgcccctgac   2160
catcaaggat cccgccgtgg gattcctgga aacaatcagc cctggctact ccatccacac   2220
ctacctgtgg cgtagacagg agggcagagg aagtcttctg acatgcggag acgtggaaga   2280
gaatcccggc cctatggccg agtggctgct gagcgccagc tggcagcgcc gcgccaaggc   2340
catgaccgcc gccgccggca gcgccggccg cgccgccgtg cccctgctgc tgtgcgccct   2400
gctggccccc ggcggcgcct acgtgctgga cgacagcgac ggcctgggcc gcgagttcga   2460
cggcatcggc gccgtgagcg gcggcggcgc caccagccgc ctgctggtga actacccccga   2520
gccctaccgc agccagatcc tggactacct gttcaagccc aacttcggcg ccagcctgca   2580
catcctgaag gtggagatcg gcggcgacgg ccagaccacc gacggcaccg agcccagcca   2640
catgcactac gccctggacg agaactactt ccgcggctac gagtggtggc tgatgaagga   2700
ggccaagaag cgcaacccca acatcaccct gatcggcctg ccctggagct tccccggctg   2760
gctgggcaag ggcttcgact ggccctacgt gaacctgcag ctgaccgcct actacgtggt   2820
gacctggatc gtgggcgcca agcgctacca cgacctggac atcgactaca tcggcatctg   2880
gaacgagcgc agctacaacg ccaactacat caagatcctg cgcaagatgc tgaactacca   2940
gggcctgcag cgcgtgaaga tcatcgccag cgacaacctg tgggagagca tcagcgccag   3000
catgctgctg gacgccgagc tgttcaaggt ggtggacgtg atcggcgccc actacccccgg   3060
cacccacagc gccaaggacg ccaagctgac cggcaagaag ctgtggagca gcgaggactt   3120
cagcaccctg aacagcgaca tgggcgccgg ctgctggggc cgcatcctga accagaacta   3180
catcaacggc tacatgacca gcaccatcgc ctggaacctg gtggccagct actacgagca   3240
gctgccctac ggccgctgcg gcctgatgac cgcccaggag ccctggagcg gccactacgt   3300
ggtggagagc cccgtgtggg tgagcgccca caccacccag ttcacccagc ccggctggta   3360
ctacctgaag accgtgggcc acctggagaa gggcggcagc tacgtggccc tgaccgacgg   3420
cctgggcaac ctgaccatca tcatcgagac catgagccac aagcacagca agtgcatccg   3480
ccccttcctg ccctacttca acgtgagcca gcagttcgcc accttcgtgc tgaagggcag   3540
cttcagcgag atccccgagc tgcaggtgtg gtacaccaag ctgggcaaga ccagcgagcg   3600
```

```
cttcctgttc aagcagctgg acagcctgtg gctgctggac agcgacggca gcttcaccct   3660
gagcctgcac gaggacgagc tgttcaccct gaccaccctg accaccggcc gcaagggcag   3720
ctaccccctg ccccccaaga gccagccctt ccccagcacc tacaaggacg acttcaacgt   3780
ggactacccc ttcttcagcg aggcccccaa cttcgccgac cagaccggcg tgttcgagta   3840
cttcaccaac atcgaggacc ccggcgagca ccacttcacc ctgcgccagg tgctgaacca   3900
gcgccccatc acctgggccg ccgacgccag caacaccatc agcatcatcg gcgactacaa   3960
ctggaccaac ctgaccatca agtgcgacgt gtacatcgag acccccgaca ccggcggcgt   4020
gttcatcgcc ggccgcgtga acaagggcgg catcctgatc cgcagcgccc gcggcatctt   4080
cttctggatc ttcgccaacg gcagctaccg cgtgaccggc gacctggccg gctggatcat   4140
ctacgccctg ggccgcgtgg aggtgaccgc caagaagtgg tacaccctga ccctgaccat   4200
caagggccac ttcaccagcg gcatgctgaa cgacaagagc ctgtggaccg acatccccgt   4260
gaacttcccc aagaacggct gggccgccat cggcacccac agcttcgagt tcgcccagtt   4320
cgacaacttc ctggtggagg ccacccgctg acaattgtta attaagttta aaccctcgag   4380
gccgcaagca ataaaatatc tttattttca ttacatctgt gtgttggttt tttgtgtgga   4440
gatccacgat aacaaacagc tttttggggg tgaacatatt gactgaattc cctgcaggtt   4500
ggccactccc tctctgcgcg ctcgctcgct cactgaggcc gcccgggcaa agcccgggcg   4560
tcgggcgacc tttggtcgcc cggcctcagt gagcgagcga gcgcgcagag agggagtggc   4620
caactccatc actaggggtt cctgcggccg ctcgtacggt ctcgaggaat tcctgcagga   4680
taacttgcca acctcattct aaaatgtata tagaagccca aaagacaata acaaaaatat   4740
tcttgtagaa caaaatggga aagaatgttc cactaaatat caagatttag agcaaagcat   4800
gagatgtgtg ggatagacag gtgaggctga taaaatagag tagagctcag aaacagaccc   4860
attgatatat gtaagtgacc tatgaaaaaa atatggcatt ttacaatggg aaaatgatgg   4920
tctttttctt ttttagaaaa acagggaaat atatttatat gtaaaaaata aaagggaacc   4980
catatgtcat accatacaca caaaaaaatt ccagtgaatt ataagtctaa atggagaagg   5040
caaaacttta aatcttttag aaaataatat agaagcatgc agaccagcct ggccaacatg   5100
atgaaaccct ctctactaat aataaaatca gtagaactac tcaggactac tttgagtggg   5160
aagtcctttt ctatgaagac ttctttggcc aaaattaggc tctaaatgca aggagatagt   5220
gcatcatgcc tggctgcact tactgataaa tgatgttatc accatcttta accaaatgca   5280
caggaacaag ttatggtact gatgtgctgg attgagaagg agctctactt ccttgacagg   5340
acacatttgt atcaacttaa aaaagcagat ttttgccagc agaactattc attcagaggt   5400
aggaaactta gaatagatga tgtcactgat tagcatggct tccccatctc cacagctgct   5460
tcccacccag gttgcccaca gttgagtttg tccagtgctc agggctgccc actctcagta   5520
agaagcccca caccagcccc tctccaaata tgttggctgt tccttccatt aaagtgaccc   5580
cactttagag cagcaagtgg atttctgttt cttacagttc aggaaggagg agtcagctgt   5640
gagaacctgg agcctgagat gcttctaagt cccactgcta ctggggtcag ggaagccaga   5700
ctccagcatc agcagtcagg agcactaagc ccttgccaac atcctgtttc tcagagaaac   5760
tgcttccatt ataatggttg tcctttttta agctatcaag ccaaacaacc agtgtctacc   5820
attattctca tcacctgaag ccaagggttc tagcaaaagt caagctgtct tgtaatggtt   5880
gatgtgcctc cagcttctgt cttcagtcac tccactctta gcctgctctg aatcaactct   5940
gaccacagtt ccctggagcc cctgccacct gctgcccctg ccaccttctc catctgcagt   6000
```

```
gctgtgcagc cttctgcact cttgcagagc taataggtgg agacttgaag gaagaggagg   6060
aaagtttctc ataatagcct tgctgcaagc tcaaatggga ggtgggcact gtgcccagga   6120
gccttggagc aaaggctgtg cccaacctct gactgcatcc aggtttggtc ttgacagaga   6180
taagaagccc tggcttttgg agccaaaatc taggtcagac ttaggcagga ttctcaaagt   6240
ttatcagcag aacatgaggc agaagaccct ttctgctcca gcttcttcag gctcaacctt   6300
catcagaata gatagaaaga gaggctgtga gggttcttaa aacagaagca aatctgactc   6360
agagaataaa caacctccta gtaaactaca gcttagacag agcatctggt ggtgagtgtg   6420
ctcagtgtcc tactcaactg tctggtatca gccctcatga ggacttctct tctttccctc   6480
atagacctcc atctctgttt tccttagcct gcagaaatct ggatggctat tcacagaatg   6540
cctgtgcttt cagagttgca ttttttctct ggtattctgg ttcaagcatt tgaaggtagg   6600
aaaggttctc caagtgcaag aaagccagcc ctgagcctca actgcctggc tagtgtggtc   6660
agtaggatgc aaaggctgtt gaatgccaca aggccaaact ttaacctgtg taccacaagc   6720
ctagcagcag aggcagctct gctcactgga actctctgtc ttctttctcc tgagcctttt   6780
cttttcctga gttttctagc tctcctcaac cttacctctg ccctacccag gacaaaccca   6840
agagccactg tttctgtgat gtcctctcca gccctaatta ggcatcatga cttcagcctg   6900
accttccatg ctcagaagca gtgctaatcc acttcagatg agctgctcta tgcaacacag   6960
gcagagccta caaacctttg caccagagcc ctccacatat cagtgtttgt tcatactcac   7020
ttcaacagca aatgtgactg ctgagattaa gattttacac aagatggtct gtaatttcac   7080
agttagtttt atcccattag gtatgaaaga attagcataa ttccccttaa acatgaatga   7140
atcttagatt ttttaataaa tagttttgga agtaaagaca gagacatcag gagcacaagg   7200
aatagcctga gaggacaaac agaacaagaa agagtctgga aatacacagg atgttcttgg   7260
cctcctcaaa gcaagtgcaa gcagatagta ccagcagccc caggctatca gagcccagtg   7320
aagagaagta ccatgaaagc cacagctcta accaccctgt tccagagtga cagacagtcc   7380
ccaagacaag ccagcctgag ccagagagag aactgcaaga gaaagtttct aatttaggtt   7440
ctgttagatt cagacaagtg caggtcatcc tctctccaca gctactcacc tctccagcct   7500
aacaaagcct gcagtccaca ctccaaccct ggtgtctcac ctcctagcct ctcccaacat   7560
cctgctctct gaccatcttc tgcatctctc atctcaccat ctcccactgt ctacagccta   7620
ctcttgcaac taccatctca ttttctgaca tcctgtctac atcttctgcc atactctgcc   7680
atctaccata ccacctctta ccatctacca caccatcttt tatctccatc cctctcagaa   7740
gcctccaagc tgaatcctgc tttatgtgtt catctcagcc cctgcatgga aagctgaccc   7800
cagaggcaga actattccca gagagcttgg ccaagaaaaa caaaactacc agcctggcca   7860
ggctcaggag tagtaagctg cagtgtctgt tgtgttctag cttcaacagc tgcaggagtt   7920
ccactctcaa atgctccaca tttctcacat cctcctgatt ctggtcacta cccatcttca   7980
aagaacagaa tatctcacat cagcatactg tgaaggacta gtcatgggtg cagctgctca   8040
gagctgcaaa gtcattctgg atggtggaga gcttacaaac atttcatgat gctccccccg   8100
ctctgatggc tggagcccaa tccctacaca gactcctgct gtatgtgttt tcctttcact   8160
ctgagccaca gccagagggc aggcattcag tctcctcttc aggctggggc tggggcactg   8220
agaactcacc caacaccttg ctctcactcc ttctgcaaaa caagaaagag ctttgtgctg   8280
cagtagccat gaagaatgaa aggaaggctt taactaaaaa atgtcagaga ttattttcaa   8340
```

```
ccccttactg tggatcacca gcaaggagga aacacaacac agagacattt tttcccctca   8400
aattatcaaa agaatcactg catttgttaa agagagcaac tgaatcagga agcagagttt   8460
tgaacatatc agaagttagg aatctgcatc agagacaaat gcagtcatgg ttgtttgctg   8520
cataccagcc ctaatcatta gaagcctcat ggacttcaaa catcattccc tctgacaaga   8580
tgctctagcc taactccatg agataaaata aatctgcctt tcagagccaa agaagagtcc   8640
accagcttct tctcagtgtg aacaagagct ccagtcaggt tagtcagtcc agtgcagtag   8700
aggagaccag tctgcatcct ctaattttca aaggcaagaa gatttgttta ccctggacac   8760
caggcacaag tgaggtcaca gagctcttag atatgcagtc ctcatgagtg aggagactaa   8820
agcgcatgcc atcaagactt cagtgtagag aaaacctcca aaaaagcctc ctcactactt   8880
ctggaatagc tcagaggccg aggcggcctc ggcctctgca taaataaaaa aaattagtca   8940
gccatggggc ggagaatggg cggaactggg cggagttagg ggcgggatgg gcggagttag   9000
gggcgggact atggttgctg actaattgag atgcatgctt tgcatacttc tgcctgctgg   9060
ggagcctggg gactttccac acctggttgc tgactaattg agatgcatgc tttgcatact   9120
tctgcctgct ggggagcctg gggactttcc acaccctaac tgacacacat tccacagctg   9180
cattaatgaa tcggccaacg cgcggggaga ggcggtttgc gtattgggcg ctcttccgct   9240
tcctcgctca ctgactcgct gcgctcggtc gttcggctgc ggcgagcggt atcagctcac   9300
tcaaaggcgg taatacggtt atccacagaa tcaggggata acgcaggaaa gaacatgtga   9360
gcaaaaggcc agcaaaaggc caggaaccgt aaaaaggccg cgttgctggc gtttttccat   9420
aggctccgcc cccctgacga gcatcacaaa aatcgacgct caagtcagag gtggcgaaac   9480
ccgacaggac tataaagata ccaggcgttt ccccctggaa gctccctcgt gcgctctcct   9540
gttccgaccc tgccgcttac cggatacctg tccgcctttc tcccttcggg aagcgtggcg   9600
ctttctcata gctcacgctg taggtatctc agttcggtgt aggtcgttcg ctccaagctg   9660
ggctgtgtgc acgaaccccc cgttcagccc gaccgctgcg ccttatccgg taactatcgt   9720
cttgagtcca acccggtaag acacgactta tcgccactgg cagcagccac tggtaacagg   9780
attagcagag cgaggtatgt aggcggtgct acagagttct tgaagtggtg gcctaactac   9840
ggctacacta gaagaacagt atttggtatc tgcgctctgc tgaagccagt taccttcgga   9900
aaaagagttg gtagctcttg atccggcaaa caaaccaccg ctggtagcgg tggttttttt   9960
gtttgcaagc agcagattac gcgcagaaaa aaaggatctc aagaagatcc tttgatcttt  10020
tctacggggt ctgacgctca gtggaacgaa aactcacgtt aagggatttt ggtcatgaga  10080
ttatcaaaaa ggatcttcac ctagatcctt ttaaattaaa aatgaagttt taaatcaatc  10140
taaagtatat atgagtaaac ttggtctgac agttaccaat gcttaatcag tgaggcacct  10200
atctcagcga tctgtctatt tcgttcatcc atagttgcct gactcctgca aaccacgttg  10260
tgtctcaaaa tctctgatgt tacattgcac aagataaaaa tatatcatca tgaacaataa  10320
aactgtctgc ttacataaac agtaatacaa ggggtgttat gagccatatt caacgggaaa  10380
cgtcttgctc gaggccgcga ttaaattcca acatggatgc tgatttatat gggtataaat  10440
gggctcgcga taatgtcggg caatcaggtg cgacaatcta tcgattgtat gggaagcccg  10500
atgcgccaga gttgtttctg aaacatggca aaggtagcgt tgccaatgat gttacagatg  10560
agatggtcag actaaactgg ctgacggaat ttatgcctct tccgaccatc aagcatttta  10620
tccgtactcc tgatgatgca tggttactca ccactgcgat ccccgggaaa acagcattcc  10680
aggtattaga agaatatcct gattcaggtg aaaatattgt tgatgcgctg gcagtgttcc  10740
```

tgcgccggtt gcattcgatt cctgtttgta attgtccttt taacagcgat cgcgtatttc 10800
gtctcgctca ggcgcaatca cgaatgaata acggtttggt tgatgcgagt gattttgatg 10860
acgagcgtaa tggctggcct gttgaacaag tctggaaaga aatgcataag cttttgccat 10920
tctcaccgga ttcagtcgtc actcatggtg atttctcact tgataacctt atttttgacg 10980
aggggaaatt aataggttgt attgatgttg gacgagtcgg aatcgcagac cgataccagg 11040
atcttgccat cctatggaac tgcctcggtg agttttctcc ttcattacag aaacggcttt 11100
ttcaaaaata tggtattgat aatcctgata tgaataaatt gcagtttcat ttgatgctcg 11160
atgagttttt ctaagggcgg cctgccacca tacccacgcc gaaacaagcg ctcatgagcc 11220
cgaagtggcg agcccgatct tccccatcgg tgatgtcggc gatataggcg ccagcaaccg 11280
cacctgtggc gccggtgatg agggcgcgcc aagtcgacgt ccggcagtc 11329

<210> SEQ ID NO 40
<211> LENGTH: 11776
<212> TYPE: DNA
<213> ORGANISM: Artificial sequence
<220> FEATURE:
<223> OTHER INFORMATION: Synthetic polynucleotide

<400> SEQUENCE: 40
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg agggcggagt 300
tagggcggag ccaatcagcg tgcgccgttc cgaaagttgc cttttatggc tgggcggaga 360
atgggcggtg aacgccgatg attatataag gacgcgccgg gtgtggcaca gctagttccg 420
tcgcagccgg gatttgggtc gcggttcttg tttgtggatc cctgtgatcg tcacttggta 480
agtcactgac tgtctatgcc tgggaaaggg tgggcaggag atggggcagt gcaggaaaag 540
tggcactatg aaccctgcag ccctaggaat gcatctagac aattgtacta accttcttct 600
ctttcctctc ctgacagtcc ggaaagccac catggccgag tggctgctga gcgccagctg 660
gcagcgccgc gccaaggcca tgaccgccgc cgccggcagc gccggccgcg ccgccgtgcc 720
cctgctgctg tgcgccctgc tggcccccgg cggcgcctac gtgctggacg acagcgacgg 780
cctgggccgc gagttcgacg gcatcggcgc cgtgagcggc ggcggcgcca ccagccgcct 840
gctggtgaac taccccgagc cctaccgcag ccagatcctg gactacctgt tcaagcccaa 900
cttcggcgcc agcctgcaca tcctgaaggt ggagatcggc ggcgacggcc agaccaccga 960
cggcaccgag cccagccaca tgcactacgc cctggacgag aactacttcc gcggctacga 1020
gtggtggctg atgaaggagg ccaagaagcg caaccccaac atcaccctga tcggcctgcc 1080
ctggagcttc cccggctggc tgggcaaggg cttcgactgg ccctacgtga acctgcagct 1140
gaccgcctac tacgtggtga cctggatcgt gggcgccaag cgctaccacg acctggacat 1200
cgactacatc ggcatctgga acgagcgcag ctacaacgcc aactacatca agatcctgcg 1260
caagatgctg aactaccagg gcctgcagcg cgtgaagatc atcgccagcg acaacctgtg 1320
ggagagcatc agcgccagca tgctgctgga cgccgagctg ttcaaggtgg tggacgtgat 1380
cggcgcccac taccccggca cccacagcgc caaggacgcc aagctgaccg gcaagaagct 1440

```
gtggagcagc gaggacttca gcaccctgaa cagcgacatg ggcgccggct gctggggccg   1500
catcctgaac cagaactaca tcaacggcta catgaccagc accatcgcct ggaacctggt   1560
ggccagctac tacgagcagc tgccctacgg ccgctgcggc ctgatgaccg cccaggagcc   1620
ctggagcggc cactacgtgg tggagagccc cgtgtgggtg agcgcccaca ccacccagtt   1680
cacccagccc ggctggtact acctgaagac cgtgggccac ctggagaagg gcggcagcta   1740
cgtggccctg accgacggcc tgggcaacct gaccatcatc atcgagacca tgagccacaa   1800
gcacagcaag tgcatccgcc ccttcctgcc ctacttcaac gtgagccagc agttcgccac   1860
cttcgtgctg aagggcagct tcagcgagat ccccgagctg caggtgtggt acaccaagct   1920
gggcaagacc agcgagcgct tcctgttcaa gcagctggac agcctgtggc tgctggacag   1980
cgacggcagc ttcaccctga gcctgcacga ggacgagctg ttcaccctga ccaccctgac   2040
caccggccgc aagggcagct acccccctgcc ccccaagagc cagcccttcc ccagcaccta   2100
caaggacgac ttcaacgtgg actacccctt cttcagcgag gcccccaact tcgccgacca   2160
gaccggcgtg ttcgagtact tcaccaacat cgaggacccc ggcgagcacc acttcaccct   2220
gcgccaggtg ctgaaccagc gccccatcac ctgggccgcc gacgccagca acaccatcag   2280
catcatcggc gactacaact ggaccaacct gaccatcaag tgcgacgtgt acatcgagac   2340
ccccgacacc ggcggcgtgt tcatcgccgg ccgcgtgaac aagggcggca tcctgatccg   2400
cagcgcccgc ggcatcttct tctggatctt cgccaacggc agctaccgcg tgaccggcga   2460
cctggccggc tggatcatct acgccctggg ccgcgtggag gtgaccgcca agaagtggta   2520
caccctgacc ctgaccatca agggccactt caccagcggc atgctgaacg acaagagcct   2580
gtggaccgac atccccgtga acttccccaa gaacggctgg gccgccatcg gcacccacag   2640
cttcgagttc gcccagttcg acaacttcct ggtggaggcc acccgctgat tgtggccgaa   2700
ccgccgaact cagaggccgg ccccagaaaa cccgagcgag tagggggcgg cgcgcaggag   2760
ggaggagaac tgggggcgcg ggaggctggt gggtgtgggg ggtggagatg tagaagatgt   2820
gacgccgcgg cccggcgggt gccagattag cggacgcggt gcccgcggtt gcaacgggat   2880
cccgggcgct gcagcttggg aggcggctct ccccaggcgg cgtccgcgga gacacccatc   2940
cgtgaacccc aggtcccggg ccgccggctc gccgcgcacc aggggccggc ggacagaaga   3000
gcggccgagc ggctcgaggc tgggggaccg cgggcgcggc cgcgcgctgc cgggcgggag   3060
gctgggggc cggggccggg gccgtgcccc ggagcgggtc ggaggccggg gccggggccg   3120
ggggacggcg gctccccgcg cggctccagc ggctcgggga tcccggccgg gccccgcagg   3180
gaccatgatg gaattcagca gccccagcag agaggaatgc cccaagcctc tgagccgggt   3240
gtcaatcatg gccggatctc tgacaggact gctgctgctt caggccgtgt cttgggcttc   3300
tggcgctaga ccttgcatcc ccaagagctt cggctacagc agcgtcgtgt gcgtgtgcaa   3360
tgccacctac tgcgacagct tcgaccctcc tacctttcct gctctgggca ccttcagcag   3420
atacgagagc accagatccg gcagacggat ggaactgagc atgggaccca tccaggccaa   3480
tcacacaggc actggcctgc tgctgacact gcagcctgag cagaaattcc agaaagtgaa   3540
aggcttcggc ggagccatga cagatgccgc cgctctgaat atcctggctc tgtctccacc   3600
agctcagaac ctgctgctca agagctactt cagcgaggaa ggcatcggct acaacatcat   3660
cagagtgccc atggccagct gcgacttcag catcaggacc tacacctacg ccgacacacc   3720
cgacgatttc cagctgcaca acttcagcct gcctgaagag gacaccaagc tgaagatccc   3780
tctgatccac agagccctgc agctggcaca aagacccgtg tcactgctgg cctctccatg   3840
```

```
gacatctccc acctggctga aaacaaatgg cgccgtgaat ggcaagggca gcctgaaagg   3900
ccaacctggc gacatctacc accagacctg ggccagatac ttcgtgaagt tcctggacgc   3960
ctatgccgag cacaagctgc agttttgggc cgtgacagcc gagaacgaac cttctgctgg   4020
actgctgagc ggctacccct ttcagtgcct gggctttaca cccgagcacc agcgggactt   4080
tatcgcccgt gatctgggac ccacactggc caatagcacc caccataatg tgcggctgct   4140
gatgctggac gaccagagac tgcttctgcc ccactgggct aaagtggtgc tgacagatcc   4200
tgaggccgcc aaatacgtgc acggaatcgc cgtgcactgg tatctggact ttctggcccc   4260
tgccaaggcc acactgggag agacacacag actgttcccc aacaccatgc tgttcgccag   4320
cgaagcctgt gtgggcagca agttttggga acagagcgtg cggctcggca gctgggatag   4380
aggcatgcag tacagccaca gcatcatcac caacctgctg taccacgtcg tcggctggac   4440
cgactggaat ctggccctga atcctgaagg cggccctaac tgggtccgaa acttcgtgga   4500
cagccccatc atcgtggaca tcaccaagga caccttctac aagcagccca tgttctacca   4560
cctgggacac ttcagcaagt tcatccccga gggctctcag cgcgttggac tggtggcttc   4620
ccagaagaac gatctggacg ccgtggctct gatgcaccct gatggatctg ctgtggtggt   4680
ggtcctgaac cgcagcagca aagatgtgcc cctgaccatc aaggatcccg ccgtgggatt   4740
cctggaaaca atcagccctg gctactccat ccacacctac ctgtggcgta gacagtgaca   4800
attgttaatt aagtttaaac cctcgaggcc gcaagcaata aaatatcttt attttcatta   4860
catctgtgtg ttggtttttt gtgtggagat ccacgataac aaacagcttt tttggggtga   4920
acatattgac tgaattccct gcaggttggc cactccctct ctgcgcgctc gctcgctcac   4980
tgaggccgcc cgggcaaagc ccgggcgtcg ggcgaccttt ggtcgcccgg cctcagtgag   5040
cgagcgagcg cgcagagagg gagtggccaa ctccatcact aggggttcct gcggccgctc   5100
gtacggtctc gaggaattcc tgcaggataa cttgccaacc tcattctaaa atgtatatag   5160
aagcccaaaa gacaataaca aaaatattct tgtagaacaa aatgggaaag aatgttccac   5220
taaatatcaa gatttagagc aaagcatgag atgtgtgggg atagacagtg aggctgataa   5280
aatagagtag agctcagaaa cagacccatt gatatatgta agtgacctat gaaaaaaata   5340
tggcatttta caatgggaaa atgatggtct ttttcttttt tagaaaaaca gggaaatata   5400
tttatatgta aaaaataaaa gggaacccat atgtcatacc atacacacaa aaaaattcca   5460
gtgaattata agtctaaatg gagaaggcaa aactttaaat cttttagaaa ataatataga   5520
agcatgcaga ccagcctggc caacatgatg aaaccctctc tactaataat aaaatcagta   5580
gaactactca ggactacttt gagtgggaag tccttttcta tgaagacttc tttggccaaa   5640
attaggctct aaatgcaagg agatagtgca tcatgcctgg ctgcacttac tgataaatga   5700
tgttatcacc atctttaacc aaatgcacag gaacaagtta tggtactgat gtgctggatt   5760
gagaaggagc tctacttcct tgacaggaca catttgtatc aacttaaaaa agcagatttt   5820
tgccagcaga actattcatt cagaggtagg aaacttagaa tagatgatgt cactgattag   5880
catggcttcc ccatctccac agctgcttcc cacccaggtt gcccacagtt gagtttgtcc   5940
agtgctcagg gctgcccact ctcagtaaga agccccacac cagcccctct ccaaatatgt   6000
tggctgttcc ttccattaaa gtgaccccac tttagagcag caagtggatt tctgtttctt   6060
acagttcagg aaggaggagt cagctgtgag aacctggagc ctgagatgct tctaagtccc   6120
actgctactg gggtcaggga agccagactc cagcatcagc agtcaggagc actaagccct   6180
```

```
tgccaacatc ctgtttctca gagaaactgc ttccattata atggttgtcc ttttttaagc   6240
tatcaagcca aacaaccagt gtctaccatt attctcatca cctgaagcca agggttctag   6300
caaaagtcaa gctgtcttgt aatggttgat gtgcctccag cttctgtctt cagtcactcc   6360
actcttagcc tgctctgaat caactctgac cacagttccc tggagcccct gccacctgct   6420
gcccctgcca ccttctccat ctgcagtgct gtgcagcctt ctgcactctt gcagagctaa   6480
taggtggaga cttgaaggaa gaggaggaaa gtttctcata atagccttgc tgcaagctca   6540
aatgggaggt gggcactgtg cccaggagcc ttggagcaaa ggctgtgccc aacctctgac   6600
tgcatccagg tttggtcttg acagagataa gaagccctgg cttttggagc caaaatctag   6660
gtcagactta ggcaggattc tcaaagttta tcagcagaac atgaggcaga agaccctttc   6720
tgctccagct tcttcaggct caaccttcat cagaatagat agaaagagag gctgtgaggg   6780
ttcttaaaac agaagcaaat ctgactcaga gaataaacaa cctcctagta aactacagct   6840
tagacagagc atctggtggt gagtgtgctc agtgtcctac tcaactgtct ggtatcagcc   6900
ctcatgagga cttctcttct ttccctcata gacctccatc tctgttttcc ttagcctgca   6960
gaaatctgga tggctattca cagaatgcct gtgctttcag agttgcattt ttttctctggt   7020
attctggttc aagcatttga aggtaggaaa ggttctccaa gtgcaagaaa gccagccctg   7080
agcctcaact gcctggctag tgtggtcagt aggatgcaaa ggctgttgaa tgccacaagg   7140
ccaaacttta acctgtgtac cacaagccta gcagcagagg cagctctgct cactggaact   7200
ctctgtcttc tttctcctga gccttttctt ttcctgagtt ttctagctct cctcaacctt   7260
acctctgccc tacccaggac aaacccaaga gccactgttt ctgtgatgtc ctctccagcc   7320
ctaattaggc atcatgactt cagcctgacc ttccatgctc agaagcagtg ctaatccact   7380
tcagatgagc tgctctatgc aacacaggca gagcctacaa acctttgcac cagagccctc   7440
cacatatcag tgtttgttca tactcacttc aacagcaaat gtgactgctg agattaagat   7500
tttacacaag atggtctgta atttcacagt tagttttatc ccattaggta tgaaagaatt   7560
agcataattc cccttaaaca tgaatgaatc ttagattttt taataaatag ttttggaagt   7620
aaagacagag acatcaggag cacaaggaat agcctgagag gacaaacaga acaagaaaga   7680
gtctggaaat acacaggatg ttcttggcct cctcaaagca agtgcaagca gatagtacca   7740
gcagccccag gctatcagag cccagtgaag agaagtacca tgaaagccac agctctaacc   7800
accctgttcc agagtgacag acagtcccca agacaagcca gcctgagcca gagagagaac   7860
tgcaagagaa agtttctaat ttaggttctg ttagattcag acaagtgcag gtcatcctct   7920
ctccacagct actcacctct ccagcctaac aaagcctgca gtccacactc caaccctggt   7980
gtctcacctc ctagcctctc ccaacatcct gctctctgac catcttctgc atctctcatc   8040
tcaccatctc ccactgtcta cagcctactc ttgcaactac catctcattt tctgacatcc   8100
tgtctacatc ttctgccata ctctgccatc taccatacca cctcttacca tctaccacac   8160
catcttttat ctccatccct ctcagaagcc tccaagctga atcctgcttt atgtgttcat   8220
ctcagcccct gcatggaaag ctgaccccag aggcagaact attcccagag agcttggcca   8280
agaaaaacaa aactaccagc ctggccaggc tcaggagtag taagctgcag tgtctgttgt   8340
gttctagctt caacagctgc aggagttcca ctctcaaatg ctccacattt ctcacatcct   8400
cctgattctg gtcactaccc atcttcaaag aacagaatat ctcacatcag catactgtga   8460
aggactagtc atgggtgcag ctgctcagag ctgcaaagtc attctggatg gtggagagct   8520
tacaaacatt tcatgatgct ccccccgctc tgatggctgg agcccaatcc ctacacagac   8580
```

```
tcctgctgta tgtgttttcc tttcactctg agccacagcc agagggcagg cattcagtct   8640
cctcttcagg ctggggctgg ggcactgaga actcacccaa caccttgctc tcactccttc   8700
tgcaaaacaa gaaagagctt tgtgctgcag tagccatgaa gaatgaaagg aaggctttaa   8760
ctaaaaaatg tcagagatta ttttcaaccc cttactgtgg atcaccagca aggaggaaac   8820
acaacacaga gacatttttt cccctcaaat tatcaaaaga atcactgcat ttgttaaaga   8880
gagcaactga atcaggaagc agagttttga acatatcaga agttaggaat ctgcatcaga   8940
gacaaatgca gtcatggttg tttgctgcat accagcccta atcattagaa gcctcatgga   9000
cttcaaacat cattccctct gacaagatgc tctagcctaa ctccatgaga taaaataaat   9060
ctgcctttca gagccaaaga agagtccacc agcttcttct cagtgtgaac aagagctcca   9120
gtcaggttag tcagtccagt gcagtagagg agaccagtct gcatcctcta attttcaaag   9180
gcaagaagat ttgtttaccc tggacaccag gcacaagtga ggtcacagag ctcttagata   9240
tgcagtcctc atgagtgagg agactaaagc gcatgccatc aagacttcag tgtagagaaa   9300
acctccaaaa aagcctcctc actacttctg gaatagctca gaggccgagg cggcctcggc   9360
ctctgcataa ataaaaaaaa ttagtcagcc atggggcgga gaatgggcgg aactgggcgg   9420
agttaggggc gggatgggcg gagttagggg cgggactatg gttgctgact aattgagatg   9480
catgctttgc atacttctgc ctgctgggga gcctggggac tttccacacc tggttgctga   9540
ctaattgaga tgcatgcttt gcatacttct gcctgctggg gagcctgggg actttccaca   9600
ccctaactga cacacattcc acagctgcat taatgaatcg gccaacgcgc ggggagaggc   9660
ggtttgcgta ttgggcgctc ttccgcttcc tcgctcactg actcgctgcg ctcggtcgtt   9720
cggctgcggc gagcggtatc agctcactca aaggcggtaa tacggttatc cacagaatca   9780
ggggataacg caggaaagaa catgtgagca aaaggccagc aaaaggccag gaaccgtaaa   9840
aaggccgcgt tgctggcgtt tttccatagg ctccgccccc ctgacgagca tcacaaaaat   9900
cgacgctcaa gtcagaggtg gcgaaacccg acaggactat aaagatacca ggcgtttccc   9960
cctggaagct ccctcgtgcg ctctcctgtt ccgaccctgc cgcttaccgg atacctgtcc  10020
gcctttctcc cttcgggaag cgtggcgctt tctcatagct cacgctgtag gtatctcagt  10080
tcggtgtagg tcgttcgctc caagctgggc tgtgtgcacg aaccccccgt tcagcccgac  10140
cgctgcgcct tatccggtaa ctatcgtctt gagtccaacc cggtaagaca cgacttatcg  10200
ccactggcag cagccactgg taacaggatt agcagagcga ggtatgtagg cggtgctaca  10260
gagttcttga agtggtggcc taactacggc tacactagaa gaacagtatt tggtatctgc  10320
gctctgctga agccagttac cttcggaaaa agagttggta gctcttgatc cggcaaacaa  10380
accaccgctg gtagcggtgg tttttttgtt tgcaagcagc agattacgcg cagaaaaaaa  10440
ggatctcaag aagatccttt gatcttttct acggggtctg acgctcagtg gaacgaaaac  10500
tcacgttaag ggattttggt catgagatta tcaaaaagga tcttcaccta gatcctttta  10560
aattaaaaat gaagttttaa atcaatctaa agtatatatg agtaaacttg gtctgacagt  10620
taccaatgct taatcagtga ggcacctatc tcagcgatct gtctatttcg ttcatccata  10680
gttgcctgac tcctgcaaac cacgttgtgt ctcaaaatct ctgatgttac attgcacaag  10740
ataaaaatat atcatcatga acaataaaac tgtctgctta cataaacagt aatacaaggg  10800
gtgttatgag ccatattcaa cgggaaacgt cttgctcgag gccgcgatta aattccaaca  10860
tggatgctga tttatatggg tataaatggg ctcgcgataa tgtcgggcaa tcaggtgcga  10920
```

```
caatctatcg attgtatggg aagcccgatg cgccagagtt gtttctgaaa catggcaaag  10980

gtagcgttgc caatgatgtt acagatgaga tggtcagact aaactggctg acggaattta  11040

tgcctcttcc gaccatcaag cattttatcc gtactcctga tgatgcatgg ttactcacca  11100

ctgcgatccc cgggaaaaca gcattccagg tattagaaga atatcctgat tcaggtgaaa  11160

atattgttga tgcgctggca gtgttcctgc gccggttgca ttcgattcct gtttgtaatt  11220

gtccttttaa cagcgatcgc gtatttcgtc tcgctcaggc gcaatcacga atgaataacg  11280

gtttggttga tgcgagtgat tttgatgacg agcgtaatgg ctggcctgtt gaacaagtct  11340

ggaaagaaat gcataagctt ttgccattct caccggattc agtcgtcact catggtgatt  11400

tctcacttga taaccttatt tttgacgagg ggaaattaat aggttgtatt gatgttggac  11460

gagtcggaat cgcagaccga taccaggatc ttgccatcct atggaactgc ctcggtgagt  11520

tttctccttc attacagaaa cggctttttc aaaaatatgg tattgataat cctgatatga  11580

ataaattgca gtttcatttg atgctcgatg agtttttcta agggcggcct gccaccatac  11640

ccacgccgaa acaagcgctc atgagcccga agtggcgagc ccgatcttcc ccatcggtga  11700

tgtcggcgat ataggcgcca gcaaccgcac ctgtggcgcc ggtgatgagg gcgcgccaag  11760

tcgacgtccg gcagtc                                                  11776
```

<210> SEQ ID NO 41
<211> LENGTH: 11348
<212> TYPE: DNA
<213> ORGANISM: Artificial sequence
<220> FEATURE:
<223> OTHER INFORMATION: Synthetic polynucleotide

<400> SEQUENCE: 41

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg agggcggagt    300

tagggcggag ccaatcagcg tgcgccgttc cgaaagttgc cttttatggc tgggcggaga    360

atgggcggtg aacgccgatg attatataag gacgcgccgg gtgtggcaca gctagttccg    420

tcgcagccgg gatttgggtc gcggttcttg tttgtggatc cctgtgatcg tcacttggta    480

agtcactgac tgtctatgcc tgggaaaggg tgggcaggag atggggcagt gcaggaaaag    540

tggcactatg aaccctcctg gtggcgaggg gaggggggtg gtcctcgaac gccttgcaga    600

actggcctgg atacagagtg gaccggctgg ccccatctgg aagacttcga gatacactgt    660

tgtcttactg cgctcaacag tgtatctcga agtcttccaa atggtgccag ccatcgcagc    720

ggggtgcagg aaatgggggc agcccccctt tttggctatc cttccacgtg ttcttttttg    780

tatcttttgt gtttcctaga aacatctcta gtcaccaccg cagccctagg aatgcatcta    840

gacaattgta ctaaccttct tctctttcct ctcctgacag tccggaaagc caccatgtgg    900

cagctgtggg ccagcctgtg ctgcctgctg gtgctggcca acgcccgcag ccgccccagc    960

ttccaccccc tgagcgacga gctggtgaac tacgtgaaca agcgcaacac cacctggcag   1020

gccggccaca acttctacaa cgtggacatg agctacctga agcgcctgtg cggcaccttc   1080

ctgggcggcc ccaagccccc ccagcgcgtg atgttcaccg aggacctgaa gctgcccgcc   1140

agcttcgacg cccgcgagca gtggccccag tgccccacca tcaaggagat ccgcgaccag   1200
```

```
ggcagctgcg gcagctgctg ggccttcggc gccgtggagg ccatcagcga ccgcatctgc   1260
atccacacca acgcccacgt gagcgtggag gtgagcgccg aggacctgct gacctgctgc   1320
ggcagcatgt gcggcgacgg ctgcaacggc ggctaccccg ccgaggcctg gaacttctgg   1380
acccgcaagg gcctggtgag cggcggcctg tacgagagcc acgtgggctg ccgcccctac   1440
agcatccccc cctgcgagca ccacgtgaac ggcagccgcc cccctgcac cggcgagggc    1500
gacaccccca agtgcagcaa gatctgcgag cccggctaca gccccaccta caagcaggac   1560
aagcactacg gctacaacag ctacagcgtg agcaacagcg agaaggacat catggccgag   1620
atctacaaga acggccccgt ggagggcgcc ttcagcgtgt acagcgactt cctgctgtac   1680
aagagcggcg tgtaccagca cgtgaccggc gagatgatgg gcggccacgc catccgcatc   1740
ctgggctggg gcgtggagaa cggcaccccc tactggctgg tggccaacag ctggaacacc   1800
gactggggcg acaacggctt cttcaagatc ctgcgcggcc aggaccactg cggcatcgag   1860
agcgaggtgg tggccggcat cccccgcacc gaccagtact gggagaagat cgagggcaga   1920
ggaagtcttc tgacatgcgg agacgtggaa gagaatcccg gccctatgga attcagcagc   1980
cccagcagag aggaatgccc caagcctctg agccgggtgt caatcatggc cggatctctg   2040
acaggactgc tgctgcttca ggccgtgtct tgggcttctg gcgctagacc ttgcatcccc   2100
aagagcttcg gctacagcag cgtcgtgtgc gtgtgcaatg ccacctactg cgacagcttc   2160
gaccctccta cctttcctgc tctgggcacc ttcagcagat acgagagcac cagatccggc   2220
agacggatgg aactgagcat gggacccatc caggccaatc acacaggcac tggcctgctg   2280
ctgacactgc agcctgagca gaaattccag aaagtgaaag gcttcggcgg agccatgaca   2340
gatgccgccg ctctgaatat cctggctctg tctccaccag ctcagaacct gctgctcaag   2400
agctacttca gcgaggaagg catcggctac aacatcatca gagtgcccat ggccagctgc   2460
gacttcagca tcaggaccta cacctacgcc gacacacccg acgatttcca gctgcacaac   2520
ttcagcctgc ctgaagagga caccaagctg aagatccctc tgatccacag agccctgcag   2580
ctggcacaaa gacccgtgtc actgctggcc tctccatgga catctcccac ctggctgaaa   2640
acaaatggcg ccgtgaatgg caagggcagc ctgaaaggcc aacctggcga catctaccac   2700
cagacctggg ccagatactt cgtgaagttc ctggacgcct atgccgagca caagctgcag   2760
ttttgggccg tgacagccga gaacgaacct tctgctggac tgctgagcgg ctaccccttt   2820
cagtgcctgg gctttacacc cgagcaccag cgggacttta tcgcccgtga tctgggaccc   2880
acactggcca atagcaccca ccataatgtg cggctgctga tgctggacga ccagagactg   2940
cttctgcccc actgggctaa agtggtgctg acagatcctg aggccgccaa atacgtgcac   3000
ggaatcgccg tgcactggta tctggacttt ctggcccctg ccaaggccac actgggagag   3060
acacacagac tgttccccaa caccatgctg ttcgccagcg aagcctgtgt gggcagcaag   3120
ttttgggaac agagcgtgcg gctcggcagc tgggatagag gcatgcagta cagccacagc   3180
atcatcacca acctgctgta ccacgtcgtc ggctggaccg actggaatct ggccctgaat   3240
cctgaaggcg gccctaactg ggtccgaaac ttcgtggaca gccccatcat cgtggacatc   3300
accaaggaca ccttctacaa gcagcccatg ttctaccacc tgggacactt cagcaagttc   3360
atccccgagg gctctcagcg cgttggactg gtggcttccc agaagaacga tctggacgcc   3420
gtggctctga tgcaccctga tggatctgct gtggtggtgg tcctgaaccg cagcagcaaa   3480
gatgtgcccc tgaccatcaa ggatcccgcc gtgggattcc tggaaacaat cagccctggc   3540
```

```
tactccatcc acacctacct gtggcgtaga cagtgacaat tgttaattaa gtttaaaccc   3600
tcgaggccgc aagcttatcg ataatcaacc tctggattac aaaatttgtg aaagattgac   3660
tggtattctt aactatgttg ctccttttac gctatgtgga tacgctgctt taatgccttt   3720
gtatcatgct attgcttccc gtatggcttt cattttctcc tccttgtata aatcctggtt   3780
gctgtctctt tatgaggagt tgtggcccgt tgtcaggcaa cgtggcgtgg tgtgcactgt   3840
gtttgctgac gcaaccccca ctggttgggg cattgccacc acctgtcagc tcctttccgg   3900
gactttcgct ttccccctcc ctattgccac ggcggaactc atcgccgcct gccttgcccg   3960
ctgctggaca ggggctcggc tgttgggcac tgacaattcc gtggtgttgt cggggaaatc   4020
atcgtccttt ccttggctgc tcgcctgtgt tgccacctgg attctgcgcg ggacgtcctt   4080
ctgctacgtc ccttcggccc tcaatccagc ggaccttcct tcccgcggcc tgctgccggc   4140
tctgcggcct cttccgcgtc ttcgccttcg ccctcagacg agtcggatct ccctttgggc   4200
cgcctccccg catcgatacc gtcgactaga gctcgctgat cagcctcgac tgtgccttct   4260
agttgccagc catctgttgt ttgcccctcc cccgtgcctt ccttgaccct ggaaggtgcc   4320
actcccactg tcctttccta ataaaatgag gaaattgcat cgcattgtct gagtaggtgt   4380
cattctattc tggggggtgg ggtggggcag gacagcaagg gggaggattg ggaagacaat   4440
agcaggcatg ctggggagag atccacgata acaaacagct tttttggggt gaacatattg   4500
actgaattcc ctgcaggttg gccactccct ctctgcgcgc tcgctcgctc actgaggccg   4560
cccgggcaaa gcccgggcgt cgggcgacct ttggtcgccc ggcctcagtg agcgagcgag   4620
cgcgcagaga gggagtggcc aactccatca ctaggggttc ctgcggccgc tcgtacggtc   4680
tcgaggaatt cctgcaggat aacttgccaa cctcattcta aaatgtatat agaagcccaa   4740
aagacaataa caaaaatatt cttgtagaac aaaatgggaa agaatgttcc actaaatatc   4800
aagatttaga gcaaagcatg agatgtgtgg ggatagacag tgaggctgat aaaatagagt   4860
agagctcaga aacagaccca ttgatatatg taagtgacct atgaaaaaaa tatggcattt   4920
tacaatggga aatgatggtc ctttttcttt tttagaaaaa cagggaaata tatttatatg   4980
taaaaaataa aagggaaccc atatgtcata ccatacacac aaaaaaattc cagtgaatta   5040
taagtctaaa tggagaaggc aaaactttaa atcttttaga aaataatata gaagcatgca   5100
gaccagcctg gccaacatga tgaaaccctc tctactaata ataaaatcag tagaactact   5160
caggactact ttgagtggga agtccttttc tatgaagact tctttggcca aaattaggct   5220
ctaaatgcaa ggagatagtg catcatgcct ggctgcactt actgataaat gatgttatca   5280
ccatctttaa ccaaatgcac aggaacaagt tatggtactg atgtgctgga ttgagaagga   5340
gctctacttc cttgacagga cacatttgta tcaacttaaa aaagcagatt tttgccagca   5400
gaactattca ttcagaggta ggaaacttag aatagatgat gtcactgatt agcatggctt   5460
ccccatctcc acagctgctt cccacccagg ttgcccacag ttgagtttgt ccagtgctca   5520
gggctgccca ctctcagtaa gaagccccac accagcccct ctccaaatat gttggctgtt   5580
ccttccatta aagtgacccc actttagagc agcaagtgga tttctgtttc ttacagttca   5640
ggaaggagga gtcagctgtg agaacctgga gcctgagatg cttctaagtc ccactgctac   5700
tggggtcagg gaagccagac tccagcatca gcagtcagga gcactaagcc cttgccaaca   5760
tcctgtttct cagagaaact gcttccatta taatggttgt cctttttttaa gctatcaagc   5820
caaacaacca gtgtctacca ttattctcat cacctgaagc caagggttct agcaaaagtc   5880
aagctgtctt gtaatggttg atgtgcctcc agcttctgtc ttcagtcact ccactcttag   5940
```

```
cctgctctga atcaactctg accacagttc cctggagccc ctgccacctg ctgcccctgc   6000
caccttctcc atctgcagtg ctgtgcagcc ttctgcactc ttgcagagct aataggtgga   6060
gacttgaagg aagaggagga aagtttctca taatagcctt gctgcaagct caaatgggag   6120
gtgggcactg tgcccaggag ccttggagca aaggctgtgc ccaacctctg actgcatcca   6180
ggtttggtct tgacagagat aagaagccct ggcttttgga gccaaaatct aggtcagact   6240
taggcaggat tctcaaagtt tatcagcaga acatgaggca gaagaccctt tctgctccag   6300
cttcttcagg ctcaaccttc atcagaatag atagaaagag aggctgtgag ggttcttaaa   6360
acagaagcaa atctgactca gagaataaac aacctcctag taaactacag cttagacaga   6420
gcatctggtg gtgagtgtgc tcagtgtcct actcaactgt ctggtatcag ccctcatgag   6480
gacttctctt ctttccctca tagacctcca tctctgtttt ccttagcctg cagaaatctg   6540
gatggctatt cacagaatgc ctgtgctttc agagttgcat tttttctctg gtattctggt   6600
tcaagcattt gaaggtagga aaggttctcc aagtgcaaga aagccagccc tgagcctcaa   6660
ctgcctggct agtgtggtca gtaggatgca aaggctgttg aatgccacaa ggccaaactt   6720
taacctgtgt accacaagcc tagcagcaga ggcagctctg ctcactggaa ctctctgtct   6780
tctttctcct gagccttttc ttttcctgag ttttctagct ctcctcaacc ttacctctgc   6840
cctacccagg acaaacccaa gagccactgt ttctgtgatg tcctctccag ccctaattag   6900
gcatcatgac ttcagcctga ccttccatgc tcagaagcag tgctaatcca cttcagatga   6960
gctgctctat gcaacacagg cagagcctac aaacctttgc accagagccc tccacatatc   7020
agtgtttgtt catactcact tcaacagcaa atgtgactgc tgagattaag attttacaca   7080
agatggtctg taatttcaca gttagtttta tcccattagg tatgaaagaa ttagcataat   7140
tccccttaaa catgaatgaa tcttagattt tttaataaat agttttggaa gtaaagacag   7200
agacatcagg agcacaagga atagcctgag aggacaaaca gaacaagaaa gagtctggaa   7260
atacacagga tgttcttggc ctcctcaaag caagtgcaag cagatagtac cagcagcccc   7320
aggctatcag agcccagtga agagaagtac catgaaagcc acagctctaa ccaccctgtt   7380
ccagagtgac agacagtccc caagacaagc cagcctgagc cagagagaga actgcaagag   7440
aaagtttcta atttaggttc tgttagattc agacaagtgc aggtcatcct ctctccacag   7500
ctactcacct ctccagccta acaaagcctg cagtccacac tccaaccctg gtgtctcacc   7560
tcctagcctc tcccaacatc ctgctctctg accatcttct gcatctctca tctcaccatc   7620
tcccactgtc tacagcctac tcttgcaact accatctcat tttctgacat cctgtctaca   7680
tcttctgcca tactctgcca tctaccatac cacctcttac catctaccac accatctttt   7740
atctccatcc ctctcagaag cctccaagct gaatcctgct ttatgtgttc atctcagccc   7800
ctgcatggaa agctgacccc agaggcagaa ctattcccag agagcttggc caagaaaaac   7860
aaaactacca gcctggccag gctcaggagt agtaagctgc agtgtctgtt gtgttctagc   7920
ttcaacagct gcaggagttc cactctcaaa tgctccacat ttctcacatc ctcctgattc   7980
tggtcactac ccatcttcaa agaacagaat atctcacatc agcatactgt gaaggactag   8040
tcatgggtgc agctgctcag agctgcaaag tcattctgga tggtggagag cttacaaaca   8100
tttcatgatg ctccccccgc tctgatggct ggagcccaat ccctacacag actcctgctg   8160
tatgtgtttt cctttcactc tgagccacag ccagagggca ggcattcagt ctcctcttca   8220
ggctggggct ggggcactga gaactcaccc aacaccttgc tctcactcct tctgcaaaac   8280
```

-continued

```
aagaaagagc tttgtgctgc agtagccatg aagaatgaaa ggaaggcttt aactaaaaaa   8340
tgtcagagat tattttcaac cccttactgt ggatcaccag caaggaggaa acacaacaca   8400
gagacatttt ttcccctcaa attatcaaaa gaatcactgc atttgttaaa gagagcaact   8460
gaatcaggaa gcagagtttt gaacatatca gaagttagga atctgcatca gagacaaatg   8520
cagtcatggt tgtttgctgc ataccagccc taatcattag aagcctcatg gacttcaaac   8580
atcattccct ctgacaagat gctctagcct aactccatga gataaaataa atctgccttt   8640
cagagccaaa gaagagtcca ccagcttctt ctcagtgtga acaagagctc cagtcaggtt   8700
agtcagtcca gtgcagtaga ggagaccagt ctgcatcctc taattttcaa aggcaagaag   8760
atttgtttac cctggacacc aggcacaagt gaggtcacag agctcttaga tatgcagtcc   8820
tcatgagtga ggagactaaa gcgcatgcca tcaagacttc agtgtagaga aaacctccaa   8880
aaaagcctcc tcactacttc tggaatagct cagaggccga ggcggcctcg gcctctgcat   8940
aaataaaaaa aattagtcag ccatggggcg gagaatgggc ggaactgggc ggagttaggg   9000
gcgggatggg cggagttagg ggcgggacta tggttgctga ctaattgaga tgcatgcttt   9060
gcatacttct gcctgctggg gagcctgggg actttccaca cctggttgct gactaattga   9120
gatgcatgct ttgcatactt ctgcctgctg gggagcctgg ggactttcca caccctaact   9180
gacacacatt ccacagctgc attaatgaat cggccaacgc gcggggagag gcggtttgcg   9240
tattgggcgc tcttccgctt cctcgctcac tgactcgctg cgctcggtcg ttcggctgcg   9300
gcgagcggta tcagctcact caaaggcggt aatacggtta tccacagaat caggggataa   9360
cgcaggaaag aacatgtgag caaaaggcca gcaaaaggcc aggaaccgta aaaaggccgc   9420
gttgctggcg tttttccata ggctccgccc ccctgacgag catcacaaaa atcgacgctc   9480
aagtcagagg tggcgaaacc cgacaggact ataaagatac caggcgtttc cccctggaag   9540
ctccctcgtg cgctctcctg ttccgaccct gccgcttacc ggatacctgt ccgcctttct   9600
cccttcggga agcgtggcgc tttctcatag ctcacgctgt aggtatctca gttcggtgta   9660
ggtcgttcgc tccaagctgg gctgtgtgca cgaacccccc gttcagcccg accgctgcgc   9720
cttatccggt aactatcgtc ttgagtccaa cccggtaaga cacgacttat cgccactggc   9780
agcagccact ggtaacagga ttagcagagc gaggtatgta ggcggtgcta cagagttctt   9840
gaagtggtgg cctaactacg gctacactag aagaacagta tttggtatct gcgctctgct   9900
gaagccagtt accttcggaa aaagagttgg tagctcttga tccggcaaac aaaccaccgc   9960
tggtagcggt ggtttttttg tttgcaagca gcagattacg cgcagaaaaa aaggatctca  10020
agaagatcct ttgatctttt ctacggggtc tgacgctcag tggaacgaaa actcacgtta  10080
agggattttg gtcatgagat tatcaaaaag gatcttcacc tagatccttt taaattaaaa  10140
atgaagtttt aaatcaatct aaagtatata tgagtaaact tggtctgaca gttaccaatg  10200
cttaatcagt gaggcaccta tctcagcgat ctgtctattt cgttcatcca tagttgcctg  10260
actcctgcaa accacgttgt gtctcaaaat ctctgatgtt acattgcaca agataaaaat  10320
atatcatcat gaacaataaa actgtctgct tacataaaca gtaatacaag gggtgttatg  10380
agccatattc aacgggaaac gtcttgctcg aggccgcgat taaattccaa catggatgct  10440
gatttatatg ggtataaatg ggctcgcgat aatgtcgggc aatcaggtgc gacaatctat  10500
cgattgtatg ggaagcccga tgcgccagag ttgtttctga aacatggcaa aggtagcgtt  10560
gccaatgatg ttacagatga gatggtcaga ctaaactggc tgacggaatt tatgcctctt  10620
ccgaccatca agcattttat ccgtactcct gatgatgcat ggttactcac cactgcgatc  10680
```

```
cccgggaaaa cagcattcca ggtattagaa gaatatcctg attcaggtga aaatattgtt  10740

gatgcgctgg cagtgttcct gcgccggttg cattcgattc ctgtttgtaa ttgtcctttt  10800

aacagcgatc gcgtatttcg tctcgctcag gcgcaatcac gaatgaataa cggtttggtt  10860

gatgcgagtg attttgatga cgagcgtaat ggctggcctg ttgaacaagt ctggaaagaa  10920

atgcataagc ttttgccatt ctcaccggat tcagtcgtca ctcatggtga tttctcactt  10980

gataacctta tttttgacga ggggaaatta ataggttgta ttgatgttgg acgagtcgga  11040

atcgcagacc gataccagga tcttgccatc ctatggaact gcctcggtga gttttctcct  11100

tcattacaga aacggctttt tcaaaaatat ggtattgata atcctgatat gaataaattg  11160

cagtttcatt tgatgctcga tgagtttttc taagggcggc ctgccaccat acccacgccg  11220

aaacaagcgc tcatgagccc gaagtggcga gcccgatctt ccccatcggt gatgtcggcg  11280

atataggcgc cagcaaccgc acctgtggcg ccggtgatga gggcgcgcca agtcgacgtc  11340

cggcagtc                                                            11348
```

```
<210> SEQ ID NO 42
<211> LENGTH: 11433
<212> TYPE: DNA
<213> ORGANISM: Artificial sequence
<220> FEATURE:
<223> OTHER INFORMATION: Synthetic polynucleotide

<400> SEQUENCE: 42

ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg agggcggagt    300

tagggcggag ccaatcagcg tgcgccgttc cgaaagttgc cttttatggc tgggcggaga    360

atgggcggtg aacgccgatg attatataag gacgcgccgg gtgtggcaca gctagttccg    420

tcgcagccgg gatttgggtc gcggttcttg tttgtggatc cctgtgatcg tcacttggta    480

agtcactgac tgtctatgcc tgggaaaggg tgggcaggag atggggcagt gcaggaaaag    540

tggcactatg aaccctcctg gtggcgaggg gaggggggtg gtcctcgaac gccttgcaga    600

actggcctgg atacagagtg gaccggctgg ccccatctgg aagacttcga gatacactgt    660

tgtcttactg cgctcaacag tgtatctcga agtcttccaa atggtgccag ccatcgcagc    720

ggggtgcagg aaatgggggc agcccccctt tttggctatc cttccacgtg ttcttttttg    780

tatcttttgt gtttcctaga aaacatctca gtcaccaccg cagccctagg aatgcatcta    840

gacaattgta ctaaccttct tctctttcct ctcctgacag tccggaaagc caccatggaa    900

ttcagcagcc ccagcagaga ggaatgcccc aagcctctga gccgggtgtc aatcatggcc    960

ggatctctga caggactgct gctgcttcag gccgtgtctt gggcttctgg cgctagacct   1020

tgcatcccca agagcttcgg ctacagcagc gtcgtgtgcg tgtgcaatgc cacctactgc   1080

gacagcttcg accctcctac ctttcctgct ctgggcacct tcagcagata cgagagcacc   1140

agatccggca gacggatgga actgagcatg ggacccatcc aggccaatca cacaggcact   1200

ggcctgctgc tgacactgca gcctgagcag aaattccaga aagtgaaagg cttcggcgga   1260

gccatgacag atgccgccgc tctgaatatc ctggctctgt ctccaccagc tcagaacctg   1320
```

```
ctgctcaaga gctacttcag cgaggaaggc atcggctaca acatcatcag agtgcccatg   1380
gccagctgcg acttcagcat caggacctac acctacgccg acacacccga cgatttccag   1440
ctgcacaact tcagcctgcc tgaagaggac accaagctga agatccctct gatccacaga   1500
gccctgcagc tggcacaaag acccgtgtca ctgctggcct ctccatggac atctcccacc   1560
tggctgaaaa caaatggcgc cgtgaatggc aagggcagcc tgaaaggcca acctggcgac   1620
atctaccacc agacctgggc cagatacttc gtgaagttcc tggacgccta tgccgagcac   1680
aagctgcagt tttgggccgt gacagccgag aacgaacctt ctgctggact gctgagcggc   1740
taccccttc agtgcctggg ctttacaccc gagcaccagc gggactttat cgcccgtgat   1800
ctgggaccca cactggccaa tagcacccac cataatgtgc ggctgctgat gctggacgac   1860
cagagactgc ttctgcccca ctgggctaaa gtggtgctga cagatcctga ggccgccaaa   1920
tacgtgcacg gaatcgccgt gcactggtat ctggactttc tggcccctgc caaggccaca   1980
ctgggagaga cacacagact gttccccaac accatgctgt tcgccagcga agcctgtgtg   2040
ggcagcaagt tttgggaaca gagcgtgcgg ctcggcagct gggatagagg catgcagtac   2100
agccacagca tcatcaccaa cctgctgtac cacgtcgtcg gctggaccga ctggaatctg   2160
gccctgaatc ctgaaggcgg ccctaactgg gtccgaaact tcgtggacag ccccatcatc   2220
gtggacatca ccaaggacac cttctacaag cagcccatgt tctaccacct gggacacttc   2280
agcaagttca tccccgaggg ctctcagcgc gttggactgg tggcttccca gaagaacgat   2340
ctggacgccg tggctctgat gcaccctgat ggatctgctg tggtggtggt cctgaaccgc   2400
agcagcaaag atgtgcccct gaccatcaag gatcccgccg tgggattcct ggaaacaatc   2460
agccctggct actccatcca cacctacctg tggcgtagac aggagggcag aggaagtctt   2520
ctgacatgcg gagacgtgga agagaatccc ggccctatgc cccgctacgg cgccagcctg   2580
cgccagagct gcccccgcag cggccgcgag cagggccagg acggcaccgc cggcgccccc   2640
ggcctgctgt ggatgggcct ggtgctggcc ctggccctgg ccctggccct ggccctggcc   2700
ctgagcgaca gccgcgtgct gtgggccccc gccgaggccc acccccctgag cccccagggc   2760
caccccgccc gcctgcaccg catcgtgccc cgcctgcgcg acgtgttcgg ctggggcaac   2820
ctgacctgcc ccatctgcaa gggcctgttc accgccatca acctgggcct gaagaaggag   2880
cccaacgtgg cccgcgtggg cagcgtggcc atcaagctgt gcaacctgct gaagatcgcc   2940
ccccccgccg tgtgccagag catcgtgcac ctgttcgagg acgacatggt ggaggtgtgg   3000
cgccgcagcg tgctgagccc cagcgaggcc tgcggcctgc tgctgggcag cacctgcggc   3060
cactgggaca tcttcagcag ctggaacatc agcctgccca ccgtgcccaa gccccccccc   3120
aagcccccca gcccccccgc ccccggcgcc cccgtgagcc gcatcctgtt cctgaccgac   3180
ctgcactggg accacgacta cctggagggc accgaccccg actgcgccga ccccctgtgc   3240
tgccgccgcg gcagcggcct gccccccgcc agccgccccg gcgccggcta ctggggcgag   3300
tacagcaagt gcgacctgcc cctgcgcacc ctggagagcc tgctgagcgg cctgggcccc   3360
gccggcccct tcgacatggt gtactggacc ggcgacatcc ccgcccacga cgtgtggcac   3420
cagacccgcc aggaccagct gcgcgccctg accaccgtga ccgccctggt gcgcaagttc   3480
ctgggccccg tgcccgtgta ccccgccgtg ggcaaccacg agagcacccc cgtgaacagc   3540
ttcccccccc ccttcatcga gggcaaccac agcagccgct ggctgtacga ggccatggcc   3600
aaggcctggg agccctggct gcccgccgag gccctgcgca ccctgcgcat cggcggcttc   3660
tacgccctga gcccctaccc cggcctgcgc ctgatcagcc tgaacatgaa cttctgcagc   3720
```

```
cgcgagaact tctggctgct gatcaacagc accgaccccg ccggccagct gcagtggctg   3780
gtgggcgagc tgcaggccgc cgaggaccgc ggcgacaagg tgcacatcat cggccacatc   3840
ccccccggcc actgcctgaa gagctggagc tggaactact accgcatcgt ggcccgctac   3900
gagaacaccc tggccgccca gttcttcggc cacacccacg tggacgagtt cgaggtgttc   3960
tacgacgagg agaccctgag ccgcccccctg gccgtggcct tcctggcccc cagcgccacc   4020
acctacatcg gcctgaaccc cggctaccgc gtgtaccaga tcgacggcaa ctacagcggc   4080
agcagccacg tggtgctgga ccacgagacc tacatcctga acctgaccca ggccaacatc   4140
cccggcgcca tcccccactg gcagctgctg taccgcgccc gcgagaccta cggcctgccc   4200
aacaccctgc ccaccgcctg gcacaacctg gtgtaccgca tgcgcggcga catgcagctg   4260
ttccagacct tctggttcct gtaccacaag ggccaccccc ccagcgagcc ctgcggcacc   4320
ccctgccgcc tggccaccct gtgcgcccag ctgagcgccc gcgccgacag ccccgccctg   4380
tgccgccacc tgatgcccga cggcagcctg cccgaggccc agagcctgtg gccccgcccc   4440
ctgttctgct aatgacaatt gttaattaag tttaaaccct cgaggccgca agcaataaaa   4500
tatctttatt ttcattacat ctgtgtgttg gttttttgtg tggagatcca cgataacaaa   4560
cagctttttt ggggtgaaca tattgactga attccctgca ggttggccac tccctctctg   4620
cgcgctcgct cgctcactga ggccgcccgg gcaaagcccg ggcgtcgggc gacctttggt   4680
cgcccggcct cagtgagcga gcgagcgcgc agagagggag tggccaactc catcactagg   4740
ggttcctgcg gccgctcgta cggtctcgag gaattcctgc aggataactt gccaacctca   4800
ttctaaaatg tatatagaag cccaaaagac aataacaaaa atattcttgt agaacaaaat   4860
gggaaagaat gttccactaa atatcaagat ttagagcaaa gcatgagatg tgtggggata   4920
gacagtgagg ctgataaaat agagtagagc tcagaaacag acccattgat atatgtaagt   4980
gacctatgaa aaaaatatgg cattttacaa tgggaaaatg atggtctttt tctttttttag   5040
aaaaacaggg aaatatattt atatgtaaaa aataaaaggg aacccatatg tcataccata   5100
cacacaaaaa aattccagtg aattataagt ctaaatggag aaggcaaaac tttaaatctt   5160
ttagaaaata atatagaagc atgcagacca gcctggccaa catgatgaaa ccctctctac   5220
taataataaa atcagtagaa ctactcagga ctactttgag tgggaagtcc ttttctatga   5280
agacttcttt ggccaaaatt aggctctaaa tgcaaggaga tagtgcatca tgcctggctg   5340
cacttactga taaatgatgt tatcaccatc tttaaccaaa tgcacaggaa caagttatgg   5400
tactgatgtg ctggattgag aaggagctct acttccttga caggacacat ttgtatcaac   5460
ttaaaaaagc agatttttgc cagcagaact attcattcag aggtaggaaa cttagaatag   5520
atgatgtcac tgattagcat ggcttcccca tctccacagc tgcttcccac ccaggttgcc   5580
cacagttgag tttgtccagt gctcagggct gcccactctc agtaagaagc cccacaccag   5640
cccctctcca aatatgttgg ctgttccttc cattaaagtg accccacttt agagcagcaa   5700
gtggatttct gtttcttaca gttcaggaag gaggagtcag ctgtgagaac ctggagcctg   5760
agatgcttct aagtcccact gctactgggg tcagggaagc cagactccag catcagcagt   5820
caggagcact aagcccttgc caacatcctg tttctcagag aaactgcttc cattataatg   5880
gttgtccttt tttaagctat caagccaaac aaccagtgtc taccattatt ctcatcacct   5940
gaagccaagg gttctagcaa aagtcaagct gtcttgtaat ggttgatgtg cctccagctt   6000
ctgtcttcag tcactccact cttagcctgc tctgaatcaa ctctgaccac agttccctgg   6060
```

```
agcccctgcc acctgctgcc cctgccacct tctccatctg cagtgctgtg cagccttctg   6120
cactcttgca gagctaatag gtggagactt gaaggaagag gaggaaagtt tctcataata   6180
gccttgctgc aagctcaaat gggaggtggg cactgtgccc aggagccttg gagcaaaggc   6240
tgtgcccaac ctctgactgc atccaggttt ggtcttgaca gagataagaa gccctggctt   6300
ttggagccaa aatctaggtc agacttaggc aggattctca aagtttatca gcagaacatg   6360
aggcagaaga ccctttctgc tccagcttct tcaggctcaa ccttcatcag aatagataga   6420
aagagaggct gtgagggttc ttaaaacaga agcaaatctg actcagagaa taaacaacct   6480
cctagtaaac tacagcttag acagagcatc tggtggtgag tgtgctcagt gtcctactca   6540
actgtctggt atcagccctc atgaggactt ctcttctttc cctcatagac ctccatctct   6600
gttttcctta gcctgcagaa atctggatgg ctattcacag aatgcctgtg ctttcagagt   6660
tgcatttttt ctctggtatt ctggttcaag catttgaagg taggaaaggt tctccaagtg   6720
caagaaagcc agccctgagc ctcaactgcc tggctagtgt ggtcagtagg atgcaaaggc   6780
tgttgaatgc cacaaggcca aactttaacc tgtgtaccac aagcctagca gcagaggcag   6840
ctctgctcac tggaactctc tgtcttcttt ctcctgagcc ttttcttttc ctgagttttc   6900
tagctctcct caaccttacc tctgccctac ccaggacaaa cccaagagcc actgtttctg   6960
tgatgtcctc tccagcccta attaggcatc atgacttcag cctgaccttc catgctcaga   7020
agcagtgcta atccacttca gatgagctgc tctatgcaac acaggcagag cctacaaacc   7080
tttgcaccag agccctccac atatcagtgt ttgttcatac tcacttcaac agcaaatgtg   7140
actgctgaga ttaagatttt acacaagatg gtctgtaatt tcacagttag ttttatccca   7200
ttaggtatga aagaattagc ataattcccc ttaaacatga atgaatctta gattttttaa   7260
taaatagttt tggaagtaaa gacagagaca tcaggagcac aaggaatagc ctgagaggac   7320
aaacagaaca agaaagagtc tggaaataca caggatgttc ttggcctcct caaagcaagt   7380
gcaagcagat agtaccagca gccccaggct atcagagccc agtgaagaga agtaccatga   7440
aagccacagc tctaaccacc ctgttccaga gtgacagaca gtccccaaga caagccagcc   7500
tgagccagag agagaactgc aagagaaagt ttctaattta ggttctgtta gattcagaca   7560
agtgcaggtc atcctctctc cacagctact cacctctcca gcctaacaaa gcctgcagtc   7620
cacactccaa ccctggtgtc tcacctccta gcctctccca acatcctgct ctctgaccat   7680
cttctgcatc tctcatctca ccatctccca ctgtctacag cctactcttg caactaccat   7740
ctcattttct gacatcctgt ctacatcttc tgccatactc tgccatctac cataccacct   7800
cttaccatct accacaccat cttttatctc catccctctc agaagcctcc aagctgaatc   7860
ctgctttatg tgttcatctc agcccctgca tggaaagctg accccagagg cagaactatt   7920
cccagagagc ttggccaaga aaaacaaaac taccagcctg gccaggctca ggagtagtaa   7980
gctgcagtgt ctgttgtgtt ctagcttcaa cagctgcagg agttccactc tcaaatgctc   8040
cacatttctc acatcctcct gattctggtc actacccatc ttcaaagaac agaatatctc   8100
acatcagcat actgtgaagg actagtcatg ggtgcagctg ctcagagctg caaagtcatt   8160
ctggatggtg gagagcttac aaacatttca tgatgctccc cccgctctga tggctggagc   8220
ccaatcccta cacagactcc tgctgtatgt gttttccttt cactctgagc cacagccaga   8280
gggcaggcat tcagtctcct cttcaggctg gggctggggc actgagaact cacccaacac   8340
cttgctctca ctccttctgc aaaacaagaa agagctttgt gctgcagtag ccatgaagaa   8400
tgaaaggaag gctttaacta aaaaatgtca gagattattt tcaacccctt actgtggatc   8460
```

```
accagcaagg aggaaacaca acacagagac attttttccc ctcaaattat caaaagaatc   8520
actgcatttg ttaaagagag caactgaatc aggaagcaga gttttgaaca tatcagaagt   8580
taggaatctg catcagagac aaatgcagtc atggttgttt gctgcatacc agccctaatc   8640
attagaagcc tcatggactt caaacatcat tccctctgac aagatgctct agcctaactc   8700
catgagataa aataaatctg cctttcagag ccaaagaaga gtccaccagc ttcttctcag   8760
tgtgaacaag agctccagtc aggttagtca gtccagtgca gtagaggaga ccagtctgca   8820
tcctctaatt ttcaaaggca agaagatttg tttaccctgg acaccaggca caagtgaggt   8880
cacagagctc ttagatatgc agtcctcatg agtgaggaga ctaaagcgca tgccatcaag   8940
acttcagtgt agagaaaacc tccaaaaaag cctcctcact acttctggaa tagctcagag   9000
gccgaggcgg cctcggcctc tgcataaata aaaaaaatta gtcagccatg gggcggagaa   9060
tgggcggaac tgggcggagt taggggcggg atgggcggag ttaggggcgg gactatggtt   9120
gctgactaat tgagatgcat gctttgcata cttctgcctg ctggggagcc tggggacttt   9180
ccacacctgg ttgctgacta attgagatgc atgctttgca tacttctgcc tgctggggag   9240
cctggggact ttccacaccc taactgacac acattccaca gctgcattaa tgaatcggcc   9300
aacgcgcggg gagaggcggt ttgcgtattg ggcgctcttc cgcttcctcg ctcactgact   9360
cgctgcgctc ggtcgttcgg ctgcggcgag cggtatcagc tcactcaaag gcggtaatac   9420
ggttatccac agaatcaggg gataacgcag gaaagaacat gtgagcaaaa ggccagcaaa   9480
aggccaggaa ccgtaaaaag gccgcgttgc tggcgttttt ccataggctc cgcccccctg   9540
acgagcatca caaaaatcga cgctcaagtc agaggtggcg aaacccgaca ggactataaa   9600
gataccaggc gtttccccct ggaagctccc tcgtgcgctc tcctgttccg accctgccgc   9660
ttaccggata cctgtccgcc tttctccctt cgggaagcgt ggcgctttct catagctcac   9720
gctgtaggta tctcagttcg gtgtaggtcg ttcgctccaa gctgggctgt gtgcacgaac   9780
cccccgttca gcccgaccgc tgcgccttat ccggtaacta tcgtcttgag tccaacccgg   9840
taagacacga cttatcgcca ctggcagcag ccactggtaa caggattagc agagcgaggt   9900
atgtaggcgg tgctacagag ttcttgaagt ggtggcctaa ctacggctac actagaagaa   9960
cagtatttgg tatctgcgct ctgctgaagc cagttacctt cggaaaaaga gttggtagct  10020
cttgatccgg caaacaaacc accgctggta gcggtggttt ttttgtttgc aagcagcaga  10080
ttacgcgcag aaaaaaagga tctcaagaag atcctttgat cttttctacg gggtctgacg  10140
ctcagtggaa cgaaaactca cgttaaggga ttttggtcat gagattatca aaaaggatct  10200
tcacctagat ccttttaaat taaaaatgaa gttttaaatc aatctaaagt atatatgagt  10260
aaacttggtc tgacagttac caatgcttaa tcagtgaggc acctatctca gcgatctgtc  10320
tatttcgttc atccatagtt gcctgactcc tgcaaaccac gttgtgtctc aaaatctctg  10380
atgttacatt gcacaagata aaaatatatc atcatgaaca ataaaactgt ctgcttacat  10440
aaacagtaat acaaggggtg ttatgagcca tattcaacgg gaaacgtctt gctcgaggcc  10500
gcgattaaat tccaacatgg atgctgattt atatgggtat aaatgggctc gcgataatgt  10560
cgggcaatca ggtgcgacaa tctatcgatt gtatgggaag cccgatgcgc cagagttgtt  10620
tctgaaacat ggcaaaggta gcgttgccaa tgatgttaca gatgagatgg tcagactaaa  10680
ctggctgacg gaatttatgc ctcttccgac catcaagcat tttatccgta ctcctgatga  10740
tgcatggtta ctcaccactg cgatccccgg gaaaacagca ttccaggtat tagaagaata  10800
```

tcctgattca ggtgaaaata ttgttgatgc gctggcagtg ttcctgcgcc ggttgcattc 10860
gattcctgtt tgtaattgtc cttttaacag cgatcgcgta tttcgtctcg ctcaggcgca 10920
atcacgaatg aataacggtt tggttgatgc gagtgatttt gatgacgagc gtaatggctg 10980
gcctgttgaa caagtctgga aagaaatgca taagcttttg ccattctcac cggattcagt 11040
cgtcactcat ggtgatttct cacttgataa ccttattttt gacgagggga aattaatagg 11100
ttgtattgat gttggacgag tcggaatcgc agaccgatac caggatcttg ccatcctatg 11160
gaactgcctc ggtgagtttt ctccttcatt acagaaacgg ctttttcaaa aatatggtat 11220
tgataatcct gatatgaata aattgcagtt tcatttgatg ctcgatgagt ttttctaagg 11280
gcggcctgcc accataccca cgccgaaaca agcgctcatg agcccgaagt ggcgagcccg 11340
atcttcccca tcggtgatgt cggcgatata ggcgccagca accgcacctg tggcgccggt 11400
gatgagggcg cgccaagtcg acgtccggca gtc 11433

<210> SEQ ID NO 43
<211> LENGTH: 11776
<212> TYPE: DNA
<213> ORGANISM: Artificial sequence
<220> FEATURE:
<223> OTHER INFORMATION: Synthetic polynucleotide

<400> SEQUENCE: 43
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg agggcggagt 300
tagggcggag ccaatcagcg tgcgccgttc cgaaagttgc cttttatggc tgggcggaga 360
atgggcggtg aacgccgatg attatataag gacgcgccgg gtgtggcaca gctagttccg 420
tcgcagccgg gatttgggtc gcggttcttg tttgtggatc cctgtgatcg tcacttggta 480
agtcactgac tgtctatgcc tgggaaaggg tgggcaggag atggggcagt gcaggaaaag 540
tggcactatg aaccctgcag ccctaggaat gcatctagac aattgtacta accttcttct 600
ctttcctctc ctgacagtcc ggaaagccac catggccgag tggctgctga gcgccagctg 660
gcagcgccgc gccaaggcca tgaccgccgc cgccggcagc gccggccgcg ccgccgtgcc 720
cctgctgctg tgcgccctgc tggccccccgg cggcgcctac gtgctggacg acagcgacgg 780
cctgggccgc gagttcgacg gcatcggcgc cgtgagcggc ggcggcgcca ccagccgcct 840
gctggtgaac taccccgagc cctaccgcag ccagatcctg gactacctgt tcaagcccaa 900
cttcggcgcc agcctgcaca tcctgaaggt ggagatcggc ggcgacggcc agaccaccga 960
cggcaccgag cccagccaca tgcactacgc cctggacgag aactacttcc gcggctacga 1020
gtggtggctg atgaaggagg ccaagaagcg caaccccaac atcaccctga tcggcctgcc 1080
ctggagcttc cccggctggc tgggcaaggg cttcgactgg ccctacgtga acctgcagct 1140
gaccgcctac tacgtggtga cctggatcgt gggcgccaag cgctaccacg acctggacat 1200
cgactacatc ggcatctgga acgagcgcag ctacaacgcc aactacatca agatcctgcg 1260
caagatgctg aactaccagg gcctgcagcg cgtgaagatc atcgccagcg acaacctgtg 1320
ggagagcatc agcgccagca tgctgctgga cgccgagctg ttcaaggtgg tggacgtgat 1380
cggcgcccac taccccggca cccacagcgc caaggacgcc aagctgaccg gcaagaagct 1440

```
gtggagcagc gaggacttca gcaccctgaa cagcgacatg ggcgccggct gctggggccg   1500
catcctgaac cagaactaca tcaacggcta catgaccagc accatcgcct ggaacctggt   1560
ggccagctac tacgagcagc tgccctacgg ccgctgcggc ctgatgaccg cccaggagcc   1620
ctggagcggc cactacgtgg tggagagccc cgtgtgggtg agcgcccaca ccacccagtt   1680
cacccagccc ggctggtact acctgaagac cgtgggccac ctggagaagg gcggcagcta   1740
cgtggccctg accgacggcc tgggcaacct gaccatcatc atcgagacca tgagccacaa   1800
gcacagcaag tgcatccgcc ccttcctgcc ctacttcaac gtgagccagc agttcgccac   1860
cttcgtgctg aagggcagct tcagcgagat ccccgagctg caggtgtggt acaccaagct   1920
gggcaagacc agcgagcgct tcctgttcaa gcagctggac agcctgtggc tgctggacag   1980
cgacggcagc ttcaccctga gcctgcacga ggacgagctg ttcaccctga ccaccctgac   2040
caccggccgc aagggcagct acccccctgcc ccccaagagc cagcccttcc ccagcaccta   2100
caaggacgac ttcaacgtgg actacccctt cttcagcgag gcccccaact tcgccgacca   2160
gaccggcgtg ttcgagtact tcaccaacat cgaggacccc ggcgagcacc acttcaccct   2220
gcgccaggtg ctgaaccagc gccccatcac ctgggccgcc gacgccagca acaccatcag   2280
catcatcggc gactacaact ggaccaacct gaccatcaag tgcgacgtgt acatcgagac   2340
ccccgacacc ggcggcgtgt tcatcgccgg ccgcgtgaac aagggcggca tcctgatccg   2400
cagcgcccgc ggcatcttct tctggatctt cgccaacggc agctaccgcg tgaccggcga   2460
cctggccggc tggatcatct acgccctggg ccgcgtggag gtgaccgcca agaagtggta   2520
caccctgacc ctgaccatca agggccactt caccagcggc atgctgaacg acaagagcct   2580
gtggaccgac atccccgtga acttccccaa gaacggctgg gccgccatcg gcacccacag   2640
cttcgagttc gcccagttcg acaacttcct ggtggaggcc acccgctgat tgtggccgaa   2700
ccgccgaact cagaggccgg ccccagaaaa cccgagcgag tagggggcgg cgcgcaggag   2760
ggaggagaac tgggggcgcg ggaggctggt gggtgtgggg ggtggagatg tagaagatgt   2820
gacgccgcgg cccggcgggt gccagattag cggacgcggt gcccgcggtt gcaacgggat   2880
cccgggcgct gcagcttggg aggcggctct ccccaggcgg cgtccgcgga gacacccatc   2940
cgtgaacccc aggtcccggg ccgccggctc gccgcgcacc aggggccggc ggacagaaga   3000
gcggccgagc ggctcgaggc tgggggaccg cgggcgcggc cgcgcgctgc cgggcgggag   3060
gctgggggc cggggccggg gccgtgcccc ggagcgggtc ggaggccggg gccggggccg   3120
ggggacggcg gctccccgcg cggctccagc ggctcgggga tcccggccgg gccccgcagg   3180
gaccatgatg gaattcagca gccccagcag agaggaatgc cccaagcctc tgagccgggt   3240
gtcaatcatg gccggatctc tgacaggact gctgctgctt caggccgtgt cttgggcttc   3300
tggcgctaga ccttgcatcc ccaagagctt cggctacagc agcgtcgtgt gcgtgtgcaa   3360
tgccacctac tgcgacagct tcgaccctcc tacctttcct gctctgggca ccttcagcag   3420
atacgagagc accagatccg gcagacggat ggaactgagc atgggaccca tccaggccaa   3480
tcacacaggc actggcctgc tgctgacact gcagcctgag cagaaattcc agaaagtgaa   3540
aggcttcggc ggagccatga cagatgccgc cgctctgaat atcctggctc tgtctccacc   3600
agctcagaac ctgctgctca agagctactt cagcgaggaa ggcatcggct acaacatcat   3660
cagagtgccc atggccagct gcgacttcag catcaggacc tacacctacg ccgacacacc   3720
cgacgatttc cagctgcaca acttcagcct gcctgaagag gacaccaagc tgaagatccc   3780
```

```
tctgatccac agagccctgc agctggcaca aagacccgtg tcactgctgg cctctccatg   3840
gacatctccc acctggctga aaacaaatgg cgccgtgaat ggcaagggca gcctgaaagg   3900
ccaacctggc gacatctacc accagacctg ggccagatac ttcgtgaagt tcctggacgc   3960
ctatgccgag cacaagctgc agttttgggc cgtgacagcc gagaacgaac cttctgctgg   4020
actgctgagc ggctacccct ttcagtgcct gggctttaca cccgagcacc agcgggactt   4080
tatcgcccgt gatctgggac ccacactggc caatagcacc caccataatg tgcggctgct   4140
gatgctggac gaccagagac tgcttctgcc ccactgggct aaagtggtgc tgacagatcc   4200
tgaggccgcc aaatacgtgc acggaatcgc cgtgcactgg tatctggact ttctggcccc   4260
tgccaaggcc acactgggag agacacacag actgttcccc aacaccatgc tgttcgccag   4320
cgaagcctgt gtgggcagca agttttggga acagagcgtg cggctcggca gctgggatag   4380
aggcatgcag tacagccaca gcatcatcac caacctgctg taccacgtcg tcggctggac   4440
cgactggaat ctggccctga atcctgaagg cggccctaac tgggtccgaa acttcgtgga   4500
cagccccatc atcgtggaca tcaccaagga caccttctac aagcagccca tgttctacca   4560
cctgggacac ttcagcaagt tcatccccga gggctctcag cgcgttggac tggtggcttc   4620
ccagaagaac gatctggacg ccgtggctct gatgcaccct gatggatctg ctgtggtggt   4680
ggtcctgaac cgcagcagca aagatgtgcc cctgaccatc aaggatcccg ccgtgggatt   4740
cctggaaaca atcagccctg gctactccat ccacacctac ctgtggcgta gacagtgaca   4800
attgttaatt aagtttaaac cctcgaggcc gcaagcaata aaatatcttt attttcatta   4860
catctgtgtg ttggtttttt gtgtggagat ccacgataac aaacagcttt tttggggtga   4920
acatattgac tgaattccct gcaggttggc cactccctct ctgcgcgctc gctcgctcac   4980
tgaggccgcc cgggcaaagc ccgggcgtcg ggcgaccttt ggtcgcccgg cctcagtgag   5040
cgagcgagcg cgcagagagg gagtggccaa ctccatcact aggggttcct gcggccgctc   5100
gtacggtctc gaggaattcc tgcaggataa cttgccaacc tcattctaaa atgtatatag   5160
aagcccaaaa gacaataaca aaaatattct tgtagaacaa aatgggaaag aatgttccac   5220
taaatatcaa gatttagagc aaagcatgag atgtgtgggg atagacagtg aggctgataa   5280
aatagagtag agctcagaaa cagacccatt gatatatgta agtgacctat gaaaaaaata   5340
tggcatttta caatgggaaa atgatggtct ttttcttttt tagaaaaaca gggaaatata   5400
tttatatgta aaaaataaaa gggaacccat atgtcatacc atacacacaa aaaaattcca   5460
gtgaattata agtctaaatg gagaaggcaa aactttaaat cttttagaaa ataatataga   5520
agcatgcaga ccagcctggc caacatgatg aaaccctctc tactaataat aaaatcagta   5580
gaactactca ggactacttt gagtgggaag tccttttcta tgaagacttc tttggccaaa   5640
attaggctct aaatgcaagg agatagtgca tcatgcctgg ctgcacttac tgataaatga   5700
tgttatcacc atctttaacc aaatgcacag gaacaagtta tggtactgat gtgctggatt   5760
gagaaggagc tctacttcct tgacaggaca catttgtatc aacttaaaaa agcagatttt   5820
tgccagcaga actattcatt cagaggtagg aaacttagaa tagatgatgt cactgattag   5880
catggcttcc ccatctccac agctgcttcc cacccaggtt gcccacagtt gagtttgtcc   5940
agtgctcagg gctgcccact ctcagtaaga agccccacac cagcccctct ccaaatatgt   6000
tggctgttcc ttccattaaa gtgaccccac tttagagcag caagtggatt tctgtttctt   6060
acagttcagg aaggaggagt cagctgtgag aacctggagc ctgagatgct tctaagtccc   6120
actgctactg ggtcaggga agccagactc cagcatcagc agtcaggagc actaagccct   6180
```

```
tgccaacatc ctgtttctca gagaaactgc ttccattata atggttgtcc ttttttaagc   6240
tatcaagcca aacaaccagt gtctaccatt attctcatca cctgaagcca agggttctag   6300
caaaagtcaa gctgtcttgt aatggttgat gtgcctccag cttctgtctt cagtcactcc   6360
actcttagcc tgctctgaat caactctgac cacagttccc tggagcccct gccacctgct   6420
gcccctgcca ccttctccat ctgcagtgct gtgcagcctt ctgcactctt gcagagctaa   6480
taggtggaga cttgaaggaa gaggaggaaa gtttctcata atagccttgc tgcaagctca   6540
aatgggaggt gggcactgtg cccaggagcc ttggagcaaa ggctgtgccc aacctctgac   6600
tgcatccagg tttggtcttg acagagataa gaagccctgg cttttggagc caaaatctag   6660
gtcagactta ggcaggattc tcaaagttta tcagcagaac atgaggcaga agaccctttc   6720
tgctccagct tcttcaggct caaccttcat cagaatagat agaaagagag gctgtgaggg   6780
ttcttaaaac agaagcaaat ctgactcaga gaataaacaa cctcctagta aactacagct   6840
tagacagagc atctggtggt gagtgtgctc agtgtcctac tcaactgtct ggtatcagcc   6900
ctcatgagga cttctcttct ttccctcata gacctccatc tctgttttcc ttagcctgca   6960
gaaatctgga tggctattca cagaatgcct gtgctttcag agttgcattt tttctctggt   7020
attctggttc aagcatttga aggtaggaaa ggttctccaa gtgcaagaaa gccagccctg   7080
agcctcaact gcctggctag tgtggtcagt aggatgcaaa ggctgttgaa tgccacaagg   7140
ccaaacttta acctgtgtac cacaagccta gcagcagagg cagctctgct cactggaact   7200
ctctgtcttc tttctcctga gccttttctt ttcctgagtt ttctagctct cctcaacctt   7260
acctctgccc tacccaggac aaacccaaga gccactgttt ctgtgatgtc ctctccagcc   7320
ctaattaggc atcatgactt cagcctgacc ttccatgctc agaagcagtg ctaatccact   7380
tcagatgagc tgctctatgc aacacaggca gagcctacaa acctttgcac cagagccctc   7440
cacatatcag tgtttgttca tactcacttc aacagcaaat gtgactgctg agattaagat   7500
tttacacaag atggtctgta atttcacagt tagttttatc ccattaggta tgaaagaatt   7560
agcataattc cccttaaaca tgaatgaatc ttagattttt taataaatag ttttggaagt   7620
aaagacagag acatcaggag cacaaggaat agcctgagag gacaaacaga acaagaaaga   7680
gtctggaaat acacaggatg ttcttggcct cctcaaagca agtgcaagca gatagtacca   7740
gcagccccag gctatcagag cccagtgaag agaagtacca tgaaagccac agctctaacc   7800
accctgttcc agagtgacag acagtcccca agacaagcca gcctgagcca gagagagaac   7860
tgcaagagaa agtttctaat ttaggttctg ttagattcag acaagtgcag gtcatcctct   7920
ctccacagct actcacctct ccagcctaac aaagcctgca gtccacactc caaccctggt   7980
gtctcacctc ctagcctctc ccaacatcct gctctctgac catcttctgc atctctcatc   8040
tcaccatctc ccactgtcta cagcctactc ttgcaactac catctcattt tctgacatcc   8100
tgtctacatc ttctgccata ctctgccatc taccatacca cctcttacca tctaccacac   8160
catcttttat ctccatccct ctcagaagcc tccaagctga atcctgcttt atgtgttcat   8220
ctcagcccct gcatggaaag ctgaccccag aggcagaact attcccagag agcttggcca   8280
agaaaaacaa aactaccagc ctggccaggc tcaggagtag taagctgcag tgtctgttgt   8340
gttctagctt caacagctgc aggagttcca ctctcaaatg ctccacattt ctcacatcct   8400
cctgattctg gtcactaccc atcttcaaag aacagaatat ctcacatcag catactgtga   8460
aggactagtc atgggtgcag ctgctcagag ctgcaaagtc attctggatg gtggagagct   8520
```

```
tacaaacatt tcatgatgct ccccccgctc tgatggctgg agcccaatcc ctacacagac   8580
tcctgctgta tgtgttttcc tttcactctg agccacagcc agagggcagg cattcagtct   8640
cctcttcagg ctggggctgg ggcactgaga actcacccaa caccttgctc tcactccttc   8700
tgcaaaacaa gaaagagctt tgtgctgcag tagccatgaa gaatgaaagg aaggctttaa   8760
ctaaaaaatg tcagagatta ttttcaaccc cttactgtgg atcaccagca aggaggaaac   8820
acaacacaga gacatttttt cccctcaaat tatcaaaaga atcactgcat ttgttaaaga   8880
gagcaactga atcaggaagc agagttttga acatatcaga agttaggaat ctgcatcaga   8940
gacaaatgca gtcatggttg tttgctgcat accagcccta atcattagaa gcctcatgga   9000
cttcaaacat cattccctct gacaagatgc tctagcctaa ctccatgaga taaaataaat   9060
ctgcctttca gagccaaaga agagtccacc agcttcttct cagtgtgaac aagagctcca   9120
gtcaggttag tcagtccagt gcagtagagg agaccagtct gcatcctcta attttcaaag   9180
gcaagaagat ttgtttaccc tggacaccag gcacaagtga ggtcacagag ctcttagata   9240
tgcagtcctc atgagtgagg agactaaagc gcatgccatc aagacttcag tgtagagaaa   9300
acctccaaaa aagcctcctc actacttctg gaatagctca gaggccgagg cggcctcggc   9360
ctctgcataa ataaaaaaaa ttagtcagcc atggggcgga gaatgggcgg aactgggcgg   9420
agttaggggc gggatgggcg gagttagggg cgggactatg gttgctgact aattgagatg   9480
catgctttgc atacttctgc ctgctgggga gcctggggac tttccacacc tggttgctga   9540
ctaattgaga tgcatgcttt gcatacttct gcctgctggg gagcctgggg actttccaca   9600
ccctaactga cacacattcc acagctgcat taatgaatcg gccaacgcgc ggggagaggc   9660
ggtttgcgta ttgggcgctc ttccgcttcc tcgctcactg actcgctgcg ctcggtcgtt   9720
cggctgcggc gagcggtatc agctcactca aaggcggtaa tacggttatc cacagaatca   9780
ggggataacg caggaaagaa catgtgagca aaaggccagc aaaaggccag gaaccgtaaa   9840
aaggccgcgt tgctggcgtt tttccatagg ctccgccccc ctgacgagca tcacaaaaat   9900
cgacgctcaa gtcagaggtg gcgaaacccg acaggactat aaagatacca ggcgtttccc   9960
cctggaagct ccctcgtgcg ctctcctgtt ccgaccctgc cgcttaccgg atacctgtcc  10020
gcctttctcc cttcgggaag cgtggcgctt tctcatagct cacgctgtag gtatctcagt  10080
tcggtgtagg tcgttcgctc caagctgggc tgtgtgcacg aaccccccgt tcagcccgac  10140
cgctgcgcct tatccggtaa ctatcgtctt gagtccaacc cggtaagaca cgacttatcg  10200
ccactggcag cagccactgg taacaggatt agcagagcga ggtatgtagg cggtgctaca  10260
gagttcttga agtggtggcc taactacggc tacactagaa gaacagtatt tggtatctgc  10320
gctctgctga agccagttac cttcggaaaa agagttggta gctcttgatc cggcaaacaa  10380
accaccgctg gtagcggtgg tttttttgtt tgcaagcagc agattacgcg cagaaaaaaa  10440
ggatctcaag aagatccttt gatcttttct acggggtctg acgctcagtg gaacgaaaac  10500
tcacgttaag ggattttggt catgagatta tcaaaaagga tcttcaccta gatcctttta  10560
aattaaaaat gaagttttaa atcaatctaa agtatatatg agtaaacttg gtctgacagt  10620
taccaatgct taatcagtga ggcacctatc tcagcgatct gtctatttcg ttcatccata  10680
gttgcctgac tcctgcaaac cacgttgtgt ctcaaaatct ctgatgttac attgcacaag  10740
ataaaaatat atcatcatga acaataaaac tgtctgctta cataaacagt aatacaaggg  10800
gtgttatgag ccatattcaa cgggaaacgt cttgctcgag gccgcgatta aattccaaca  10860
tggatgctga tttatatggg tataaatggg ctcgcgataa tgtcgggcaa tcaggtgcga  10920
```

```
caatctatcg attgtatggg aagcccgatg cgccagagtt gtttctgaaa catggcaaag  10980

gtagcgttgc caatgatgtt acagatgaga tggtcagact aaactggctg acggaattta  11040

tgcctcttcc gaccatcaag cattttatcc gtactcctga tgatgcatgg ttactcacca  11100

ctgcgatccc cgggaaaaca gcattccagg tattagaaga atatcctgat tcaggtgaaa  11160

atattgttga tgcgctggca gtgttcctgc gccggttgca ttcgattcct gtttgtaatt  11220

gtccttttaa cagcgatcgc gtatttcgtc tcgctcaggc gcaatcacga atgaataacg  11280

gtttggttga tgcgagtgat tttgatgacg agcgtaatgg ctggcctgtt gaacaagtct  11340

ggaaagaaat gcataagctt ttgccattct caccggattc agtcgtcact catggtgatt  11400

tctcacttga taaccttatt tttgacgagg ggaaattaat aggttgtatt gatgttggac  11460

gagtcggaat cgcagaccga taccaggatc ttgccatcct atggaactgc ctcggtgagt  11520

tttctccttc attacagaaa cggctttttc aaaaatatgg tattgataat cctgatatga  11580

ataaattgca gtttcatttg atgctcgatg agtttttcta agggcggcct gccaccatac  11640

ccacgccgaa acaagcgctc atgagcccga agtggcgagc ccgatcttcc ccatcggtga  11700

tgtcggcgat ataggcgcca gcaaccgcac ctgtggcgcc ggtgatgagg gcgcgccaag  11760

tcgacgtccg gcagtc                                                  11776
```

<210> SEQ ID NO 44
<211> LENGTH: 11064
<212> TYPE: DNA
<213> ORGANISM: Artificial sequence
<220> FEATURE:
<223> OTHER INFORMATION: Synthetic polynucleotide

<400> SEQUENCE: 44

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg agggcggagt    300

tagggcggag ccaatcagcg tgcgccgttc cgaaagttgc cttttatggc tgggcggaga    360

atgggcggtg aacgccgatg attatataag gacgcgccgg gtgtggcaca gctagttccg    420

tcgcagccgg gatttgggtc gcggttcttg tttgtggatc cctgtgatcg tcacttggta    480

agtcactgac tgtctatgcc tgggaaaggg tgggcaggag atggggcagt gcaggaaaag    540

tggcactatg aaccctgcag ccctaggaat gcatctagac aattgtacta accttcttct    600

ctttcctctc ctgacagtcc ggaaagccac catggaattc agcagcccca gcagagagga    660

atgccccaag cctctgagcc gggtgtcaat catggccgga tctctgacag gactgctgct    720

gcttcaggcc gtgtcttggg cttctggcgc tagaccttgc atccccaaga gcttcggcta    780

cagcagcgtc gtgtgcgtgt gcaatgccac ctactgcgac agcttcgacc ctcctacctt    840

tcctgctctg ggcaccttca gcagatacga gagcaccaga tccggcagac ggatggaact    900

gagcatggga cccatccagg ccaatcacac aggcactggc ctgctgctga cactgcagcc    960

tgagcagaaa ttccagaaag tgaaaggctt cggcggagcc atgacagatg ccgccgctct   1020

gaatatcctg gctctgtctc caccagctca gaacctgctg ctcaagagct acttcagcga   1080

ggaaggcatc ggctacaaca tcatcagagt gcccatggcc agctgcgact tcagcatcag   1140
```

```
gacctacacc tacgccgaca cacccgacga tttccagctg cacaacttca gcctgcctga   1200
agaggacacc aagctgaaga tccctctgat ccacagagcc ctgcagctgg cacaaagacc   1260
cgtgtcactg ctggcctctc catggacatc tcccacctgg ctgaaaacaa atggcgccgt   1320
gaatggcaag ggcagcctga aaggccaacc tggcgacatc taccaccaga cctgggccag   1380
atacttcgtg aagttcctgg acgcctatgc cgagcacaag ctgcagtttt gggccgtgac   1440
agccgagaac gaaccttctg ctggactgct gagcggctac ccctttcagt gcctgggctt   1500
tacacccgag caccagcggg actttatcgc ccgtgatctg ggacccacac tggccaatag   1560
cacccaccat aatgtgcggc tgctgatgct ggacgaccag agactgcttc tgccccactg   1620
ggctaaagtg gtgctgacag atcctgaggc cgccaaatac gtgcacggaa tcgccgtgca   1680
ctggtatctg gactttctgg cccctgccaa ggccacactg ggagagacac acagactgtt   1740
ccccaacacc atgctgttcg ccagcgaagc ctgtgtgggc agcaagtttt gggaacagag   1800
cgtgcggctc ggcagctggg atagaggcat gcagtacagc cacagcatca tcaccaacct   1860
gctgtaccac gtcgtcggct ggaccgactg gaatctggcc ctgaatcctg aaggcggccc   1920
taactgggtc cgaaacttcg tggacagccc catcatcgtg gacatcacca aggacacctt   1980
ctacaagcag cccatgttct accacctggg acacttcagc aagttcatcc ccgagggctc   2040
tcagcgcgtt ggactggtgg cttcccagaa gaacgatctg gacgccgtgg ctctgatgca   2100
ccctgatgga tctgctgtgg tggtggtcct gaaccgcagc agcaaagatg tgcccctgac   2160
catcaaggat cccgccgtgg gattcctgga aacaatcagc cctggctact ccatccacac   2220
ctacctgtgg cgtagacagt gacaattgtt aattaagttt aaaccctcga ggccgcaagc   2280
cgcatcgata ccgtcgacta gagctcgctg atcagcctcg actgtgcctt ctagttgcca   2340
gccatctgtt gtttgcccct cccccgtgcc ttccttgacc ctggaaggtg ccactcccac   2400
tgtcctttcc taataaaatg aggaaattgc atcgcattgt ctgagtaggt gtcattctat   2460
tctggggggt ggggtggggc aggacagcaa gggggaggat tgggaagaca atagcaggca   2520
tgctggggag agatccacga taacaaacag ctttttttggg ggggcggagt tagggcggag   2580
ccaatcagcg tgcgccgttc cgaaagttgc cttttatggc tgggcggaga atgggcggtg   2640
aacgccgatg attatataag gacgcgccgg gtgtggcaca gctagttccg tcgcagccgg   2700
gatttgggtc gcggttcttg tttgtggatc cctgtgatcg tcacttggta agtcactgac   2760
tgtctatgcc tgggaaaggg tgggcaggag atggggcagt gcaggaaaag tggcactatg   2820
aaccctgcag ccctaggaat gcatctagac aattgtacta accttcttct ctttcctctc   2880
ctgacagtcc ggaaagccac catgtggcag ctgtgggcca gcctgtgctg cctgctggtg   2940
ctggccaacg cccgcagccg ccccagcttc caccccctga gcgacgagct ggtgaactac   3000
gtgaacaagc gcaacaccac ctggcaggcc ggccacaact tctacaacgt ggacatgagc   3060
tacctgaagc gcctgtgcgg caccttcctg ggcggcccca agcccccccca gcgcgtgatg   3120
ttcaccgagg acctgaagct gcccgccagc ttcgacgccc gcgagcagtg gccccagtgc   3180
cccaccatca aggagatccg cgaccagggc agctgcggca gctgctgggc cttcggcgcc   3240
gtggaggcca tcagcgaccg catctgcatc cacaccaacg cccacgtgag cgtggaggtg   3300
agcgccgagg acctgctgac ctgctgcggc agcatgtgcg gcgacggctg caacggcggc   3360
taccccgccg aggcctggaa cttctggacc cgcaagggcc tggtgagcgg cggcctgtac   3420
gagagccacg tgggctgccg cccctacagc atcccccccct gcgagcacca cgtgaacggc   3480
agccgccccc cctgcaccgg cgagggcgac acccccaagt gcagcaagat ctgcgagccc   3540
```

```
ggctacagcc ccacctacaa gcaggacaag cactacggct acaacagcta cagcgtgagc   3600
aacagcgaga aggacatcat ggccgagatc tacaagaacg gccccgtgga gggcgccttc   3660
agcgtgtaca gcgacttcct gctgtacaag agcggcgtgt accagcacgt gaccggcgag   3720
atgatgggcg gccacgccat ccgcatcctg ggctggggcg tggagaacgg caccccctac   3780
tggctggtgg ccaacagctg gaacaccgac tggggcgaca acggcttctt caagatcctg   3840
cgcggccagg accactgcgg catcgagagc gaggtggtgg ccggcatccc ccgcaccgac   3900
cagtactggg agaagatctg acccagggga ctcagcggcc gctcgagtct agagggcccg   3960
tttaaacccg ctgatcagcc tcgaagacat gataagatac attgatgagt ttggacaaac   4020
cacaacaaga atgcagtgaa aaaaatgctt tatttgtgaa atttgtgatg ctattgcttt   4080
atttgtaacc attataagct gcaataaaca agttaacaac aacaattgca ttcattttat   4140
gtttcaggtt cagggggaga tgtgggaggt tttttaaagc aagtaaaacc tctacaaatg   4200
tggtatgaac atattgactg aattccctgc aggttggcca ctccctctct gcgcgctcgc   4260
tcgctcactg aggccgcccg ggcaaagccc gggcgtcggg cgacctttgg tcgcccggcc   4320
tcagtgagcg agcgagcgcg cagagaggga gtggccaact ccatcactag gggttcctgc   4380
ggccgctcgt acggtctcga ggaattcctg caggataact tgccaacctc attctaaaat   4440
gtatatagaa gcccaaaaga caataacaaa aatattcttg tagaacaaaa tgggaaagaa   4500
tgttccacta aatatcaaga tttagagcaa agcatgagat gtgtggggat agacagtgag   4560
gctgataaaa tagagtagag ctcagaaaca gacccattga tatatgtaag tgacctatga   4620
aaaaaatatg gcattttaca atgggaaaat gatggtcttt ttcttttttta gaaaaacagg   4680
gaaatatatt tatatgtaaa aaataaaagg gaacccatat gtcataccat acacacaaaa   4740
aaattccagt gaattataag tctaaatgga gaaggcaaaa ctttaaatct tttagaaaat   4800
aatatagaag catgcagacc agcctggcca acatgatgaa accctctcta ctaataataa   4860
aatcagtaga actactcagg actactttga gtgggaagtc cttttctatg aagacttctt   4920
tggccaaaat taggctctaa atgcaaggag atagtgcatc atgcctggct gcacttactg   4980
ataaatgatg ttatcaccat ctttaaccaa atgcacagga acaagttatg gtactgatgt   5040
gctggattga gaaggagctc tacttccttg acaggacaca tttgtatcaa cttaaaaaag   5100
cagatttttg ccagcagaac tattcattca gaggtaggaa acttagaata gatgatgtca   5160
ctgattagca tggcttcccc atctccacag ctgcttccca cccaggttgc ccacagttga   5220
gtttgtccag tgctcagggc tgcccactct cagtaagaag ccccacacca gcccctctcc   5280
aaatatgttg gctgttcctt ccattaaagt gaccccactt tagagcagca agtggatttc   5340
tgtttcttac agttcaggaa ggaggagtca gctgtgagaa cctggagcct gagatgcttc   5400
taagtcccac tgctactggg gtcagggaag ccagactcca gcatcagcag tcaggagcac   5460
taagcccttg ccaacatcct gtttctcaga gaaactgctt ccattataat ggttgtcctt   5520
ttttaagcta tcaagccaaa caaccagtgt ctaccattat tctcatcacc tgaagccaag   5580
ggttctagca aaagtcaagc tgtcttgtaa tggttgatgt gcctccagct tctgtcttca   5640
gtcactccac tcttagcctg ctctgaatca actctgacca cagttccctg gagcccctgc   5700
cacctgctgc ccctgccacc ttctccatct gcagtgctgt gcagccttct gcactcttgc   5760
agagctaata ggtggagact tgaaggaaga ggaggaaagt ttctcataat agccttgctg   5820
caagctcaaa tgggaggtgg gcactgtgcc caggagcctt ggagcaaagg ctgtgcccaa   5880
```

```
cctctgactg catccaggtt tggtcttgac agagataaga agccctggct tttggagcca   5940
aaatctaggt cagacttagg caggattctc aaagtttatc agcagaacat gaggcagaag   6000
accctttctg ctccagcttc ttcaggctca accttcatca gaatagatag aaagagaggc   6060
tgtgagggtt cttaaaacag aagcaaatct gactcagaga ataaacaacc tcctagtaaa   6120
ctacagctta gacagagcat ctggtggtga gtgtgctcag tgtcctactc aactgtctgg   6180
tatcagccct catgaggact tctcttcttt ccctcataga cctccatctc tgttttcctt   6240
agcctgcaga aatctggatg gctattcaca gaatgcctgt gctttcagag ttgcattttt   6300
tctctggtat tctggttcaa gcatttgaag gtaggaaagg ttctccaagt gcaagaaagc   6360
cagccctgag cctcaactgc ctggctagtg tggtcagtag gatgcaaagg ctgttgaatg   6420
ccacaaggcc aaactttaac ctgtgtacca caagcctagc agcagaggca gctctgctca   6480
ctggaactct ctgtcttctt tctcctgagc cttttctttt cctgagtttt ctagctctcc   6540
tcaaccttac ctctgcccta cccaggacaa acccaagagc cactgtttct gtgatgtcct   6600
ctccagccct aattaggcat catgacttca gcctgacctt ccatgctcag aagcagtgct   6660
aatccacttc agatgagctg ctctatgcaa cacaggcaga gcctacaaac ctttgcacca   6720
gagccctcca catatcagtg tttgttcata ctcacttcaa cagcaaatgt gactgctgag   6780
attaagattt tacacaagat ggtctgtaat ttcacagtta gttttatccc attaggtatg   6840
aaagaattag cataattccc cttaaacatg aatgaatctt agattttta ataaatagtt   6900
ttggaagtaa agacagagac atcaggagca caaggaatag cctgagagga caaacagaac   6960
aagaaagagt ctggaaatac acaggatgtt cttggcctcc tcaaagcaag tgcaagcaga   7020
tagtaccagc agccccaggc tatcagagcc cagtgaagag aagtaccatg aaagccacag   7080
ctctaaccac cctgttccag agtgacagac agtccccaag acaagccagc ctgagccaga   7140
gagagaactg caagagaaag tttctaattt aggttctgtt agattcagac aagtgcaggt   7200
catcctctct ccacagctac tcacctctcc agcctaacaa agcctgcagt ccacactcca   7260
accctggtgt ctcacctcct agcctctccc aacatcctgc tctctgacca tcttctgcat   7320
ctctcatctc accatctccc actgtctaca gcctactctt gcaactacca tctcattttc   7380
tgacatcctg tctacatctt ctgccatact ctgccatcta ccataccacc tcttaccatc   7440
taccacacca tcttttatct ccatccctct cagaagcctc caagctgaat cctgctttat   7500
gtgttcatct cagcccctgc atggaaagct gaccccagag gcagaactat tcccagagag   7560
cttggccaag aaaaacaaaa ctaccagcct ggccaggctc aggagtagta agctgcagtg   7620
tctgttgtgt tctagcttca acagctgcag gagttccact ctcaaatgct ccacatttct   7680
cacatcctcc tgattctggt cactacccat cttcaaagaa cagaatatct cacatcagca   7740
tactgtgaag gactagtcat gggtgcagct gctcagagct gcaaagtcat tctggatggt   7800
ggagagctta caaacatttc atgatgctcc ccccgctctg atggctggag cccaatccct   7860
acacagactc ctgctgtatg tgttttcctt tcactctgag ccacagccag agggcaggca   7920
ttcagtctcc tcttcaggct ggggctgggg cactgagaac tcacccaaca ccttgctctc   7980
actccttctg caaaacaaga aagagctttg tgctgcagta gccatgaaga atgaaaggaa   8040
ggctttaact aaaaaatgtc agagattatt ttcaacccct tactgtggat caccagcaag   8100
gaggaaacac aacacagaga catttttcc cctcaaatta tcaaaagaat cactgcattt   8160
gttaaagaga gcaactgaat caggaagcag agttttgaac atatcagaag ttaggaatct   8220
gcatcagaga caaatgcagt catggttgtt tgctgcatac cagccctaat cattagaagc   8280
```

```
ctcatggact tcaaacatca ttccctctga caagatgctc tagcctaact ccatgagata   8340
aaataaatct gcctttcaga gccaaagaag agtccaccag cttcttctca gtgtgaacaa   8400
gagctccagt caggttagtc agtccagtgc agtagaggag accagtctgc atcctctaat   8460
tttcaaaggc aagaagattt gtttaccctg gacaccaggc acaagtgagg tcacagagct   8520
cttagatatg cagtcctcat gagtgaggag actaaagcgc atgccatcaa gacttcagtg   8580
tagagaaaac ctccaaaaaa gcctcctcac tacttctgga atagctcaga ggccgaggcg   8640
gcctcggcct ctgcataaat aaaaaaaatt agtcagccat ggggcggaga atgggcggaa   8700
ctgggcggag ttaggggcgg gatgggcgga gttaggggcg ggactatggt tgctgactaa   8760
ttgagatgca tgctttgcat acttctgcct gctggggagc ctggggactt tccacacctg   8820
gttgctgact aattgagatg catgctttgc atacttctgc ctgctgggga gcctggggac   8880
tttccacacc ctaactgaca cacattccac agctgcatta atgaatcggc caacgcgcgg   8940
ggagaggcgg tttgcgtatt gggcgctctt ccgcttcctc gctcactgac tcgctgcgct   9000
cggtcgttcg gctgcggcga gcggtatcag ctcactcaaa ggcggtaata cggttatcca   9060
cagaatcagg ggataacgca ggaaagaaca tgtgagcaaa aggccagcaa aaggccagga   9120
accgtaaaaa ggccgcgttg ctggcgtttt tccataggct ccgcccccct gacgagcatc   9180
acaaaaatcg acgctcaagt cagaggtggc gaaacccgac aggactataa agataccagg   9240
cgtttccccc tggaagctcc ctcgtgcgct ctcctgttcc gaccctgccg cttaccggat   9300
acctgtccgc ctttctccct tcgggaagcg tggcgctttc tcatagctca cgctgtaggt   9360
atctcagttc ggtgtaggtc gttcgctcca agctgggctg tgtgcacgaa ccccccgttc   9420
agcccgaccg ctgcgcctta tccggtaact atcgtcttga gtccaacccg gtaagacacg   9480
acttatcgcc actggcagca gccactggta acaggattag cagagcgagg tatgtaggcg   9540
gtgctacaga gttcttgaag tggtggccta actacggcta cactagaaga acagtatttg   9600
gtatctgcgc tctgctgaag ccagttacct tcggaaaaag agttggtagc tcttgatccg   9660
gcaaacaaac caccgctggt agcggtggtt tttttgtttg caagcagcag attacgcgca   9720
gaaaaaaagg atctcaagaa gatcctttga tcttttctac ggggtctgac gctcagtgga   9780
acgaaaactc acgttaaggg attttggtca tgagattatc aaaaaggatc ttcacctaga   9840
tccttttaaa ttaaaaatga agttttaaat caatctaaag tatatatgag taaacttggt   9900
ctgacagtta ccaatgctta atcagtgagg cacctatctc agcgatctgt ctatttcgtt   9960
catccatagt tgcctgactc ctgcaaacca cgttgtgtct caaaatctct gatgttacat  10020
tgcacaagat aaaaatatat catcatgaac aataaaactg tctgcttaca taaacagtaa  10080
tacaaggggt gttatgagcc atattcaacg ggaaacgtct tgctcgaggc cgcgattaaa  10140
ttccaacatg gatgctgatt tatatgggta taaatgggct cgcgataatg tcgggcaatc  10200
aggtgcgaca atctatcgat tgtatgggaa gcccgatgcg ccagagttgt ttctgaaaca  10260
tggcaaaggt agcgttgcca atgatgttac agatgagatg gtcagactaa actggctgac  10320
ggaatttatg cctcttccga ccatcaagca ttttatccgt actcctgatg atgcatggtt  10380
actcaccact gcgatccccg ggaaaacagc attccaggta ttagaagaat atcctgattc  10440
aggtgaaaat attgttgatg cgctggcagt gttcctgcgc cggttgcatt cgattcctgt  10500
ttgtaattgt ccttttaaca gcgatcgcgt atttcgtctc gctcaggcgc aatcacgaat  10560
gaataacggt ttggttgatg cgagtgattt tgatgacgag cgtaatggct ggcctgttga  10620
```

```
acaagtctgg aaagaaatgc ataagctttt gccattctca ccggattcag tcgtcactca  10680

tggtgatttc tcacttgata accttatttt tgacgagggg aaattaatag gttgtattga  10740

tgttggacga gtcggaatcg cagaccgata ccaggatctt gccatcctat ggaactgcct  10800

cggtgagttt tctccttcat tacagaaacg gctttttcaa aaatatggta ttgataatcc  10860

tgatatgaat aaattgcagt ttcatttgat gctcgatgag tttttctaag ggcggcctgc  10920

caccataccc acgccgaaac aagcgctcat gagcccgaag tggcgagccc gatcttcccc  10980

atcggtgatg tcggcgatat aggcgccagc aaccgcacct gtggcgccgg tgatgagggc  11040

gcgccaagtc gacgtccggc agtc                                         11064


<210> SEQ ID NO 45
<211> LENGTH: 250
<212> TYPE: PRT
<213> ORGANISM: Artificial sequence
<220> FEATURE:
<223> OTHER INFORMATION: Synthetic polypeptide

<400> SEQUENCE: 45

Met Glu Lys Gly Pro Val Arg Ala Pro Ala Glu Lys Pro Arg Gly Ala
1               5                   10                  15

Arg Cys Ser Asn Gly Phe Pro Glu Arg Asp Pro Pro Arg Pro Gly Pro
            20                  25                  30

Ser Arg Pro Ala Glu Lys Pro Pro Arg Pro Glu Ala Lys Ser Ala Gln
        35                  40                  45

Pro Ala Asp Gly Trp Lys Gly Glu Arg Pro Arg Ser Glu Glu Asp Asn
    50                  55                  60

Glu Leu Asn Leu Pro Asn Leu Ala Ala Ala Tyr Ser Ser Ile Leu Ser
65                  70                  75                  80

Ser Leu Gly Glu Asn Pro Gln Arg Gln Gly Leu Leu Lys Thr Pro Trp
                85                  90                  95

Arg Ala Ala Ser Ala Met Gln Phe Phe Thr Lys Gly Tyr Gln Glu Thr
            100                 105                 110

Ile Ser Asp Val Leu Asn Asp Ala Ile Phe Asp Glu Asp His Asp Glu
        115                 120                 125

Met Val Ile Val Lys Asp Ile Asp Met Phe Ser Met Cys Glu His His
    130                 135                 140

Leu Val Pro Phe Val Gly Lys Val His Ile Gly Tyr Leu Pro Asn Lys
145                 150                 155                 160

Gln Val Leu Gly Leu Ser Lys Leu Ala Arg Ile Val Glu Ile Tyr Ser
                165                 170                 175

Arg Arg Leu Gln Val Gln Glu Arg Leu Thr Lys Gln Ile Ala Val Ala
            180                 185                 190

Ile Thr Glu Ala Leu Arg Pro Ala Gly Val Gly Val Val Val Glu Ala
        195                 200                 205

Thr His Met Cys Met Val Met Arg Gly Val Gln Lys Met Asn Ser Lys
    210                 215                 220

Thr Val Thr Ser Thr Met Leu Gly Val Phe Arg Glu Asp Pro Lys Thr
225                 230                 235                 240

Arg Glu Glu Phe Leu Thr Leu Ile Arg Ser
                245                 250


<210> SEQ ID NO 46
<211> LENGTH: 750
<212> TYPE: DNA
<213> ORGANISM: Artificial sequence
```

<220> FEATURE:
<223> OTHER INFORMATION: Synthetic polynucleotide

<400> SEQUENCE: 46

```
atggagaagg gccccgtgcg cgccccccgcc gagaagcccc gcggcgcccg ctgcagcaac      60
ggcttccccg agcgcgaccc cccccgcccc ggccccagcc gccccgccga gaagcccccc     120
cgccccgagg ccaagagcgc ccagcccgcc gacggctgga agggcgagcg cccccgcagc     180
gaggaggaca acgagctgaa cctgcccaac ctggccgccg cctacagcag catcctgagc     240
agcctgggcg agaaccccca gcgccagggc ctgctgaaga cccccctggcg cgccgccagc     300
gccatgcagt tcttcaccaa gggctaccag gagaccatca gcgacgtgct gaacgacgcc     360
atcttcgacg aggaccacga cgagatggtg atcgtgaagg acatcgacat gttcagcatg     420
tgcgagcacc acctggtgcc cttcgtgggc aaggtgcaca tcggctacct gcccaacaag     480
caggtgctgg gcctgagcaa gctggcccgc atcgtggaga tctacagccg ccgcctgcag     540
gtgcaggagc gcctgaccaa gcagatcgcc gtggccatca ccgaggccct gcgccccgcc     600
ggcgtgggcg tggtggtgga ggccacccac atgtgcatgg tgatgcgcgg cgtgcagaag     660
atgaacagca agaccgtgac cagcaccatg ctgggcgtgt tccgcgagga ccccaagacc     720
cgcgaggagt tcctgaccct gatccgcagc                                      750
```

<210> SEQ ID NO 47
<211> LENGTH: 203
<212> TYPE: PRT
<213> ORGANISM: Artificial sequence
<220> FEATURE:
<223> OTHER INFORMATION: Synthetic polypeptide

<400> SEQUENCE: 47

```
Met Gly Ser Arg Asp His Leu Phe Lys Val Leu Val Val Gly Asp Ala
1               5                   10                  15

Ala Val Gly Lys Thr Ser Leu Val Gln Arg Tyr Ser Gln Asp Ser Phe
            20                  25                  30

Ser Lys His Tyr Lys Ser Thr Val Gly Val Asp Phe Ala Leu Lys Val
        35                  40                  45

Leu Gln Trp Ser Asp Tyr Glu Ile Val Arg Leu Gln Leu Trp Asp Ile
    50                  55                  60

Ala Gly Gln Glu Arg Phe Thr Ser Met Thr Arg Leu Tyr Tyr Arg Asp
65                  70                  75                  80

Ala Ser Ala Cys Val Ile Met Phe Asp Val Thr Asn Ala Thr Thr Phe
                85                  90                  95

Ser Asn Ser Gln Arg Trp Lys Gln Asp Leu Asp Ser Lys Leu Thr Leu
            100                 105                 110

Pro Asn Gly Glu Pro Val Pro Cys Leu Leu Leu Ala Asn Lys Cys Asp
        115                 120                 125

Leu Ser Pro Trp Ala Val Ser Arg Asp Gln Ile Asp Arg Phe Ser Lys
    130                 135                 140

Glu Asn Gly Phe Thr Gly Trp Thr Glu Thr Ser Val Lys Glu Asn Lys
145                 150                 155                 160

Asn Ile Asn Glu Ala Met Arg Val Leu Ile Glu Lys Met Met Arg Asn
                165                 170                 175

Ser Thr Glu Asp Ile Met Ser Leu Ser Thr Gln Gly Asp Tyr Ile Asn
            180                 185                 190

Leu Gln Thr Lys Ser Ser Ser Trp Ser Cys Cys
        195                 200
```

```
<210> SEQ ID NO 48
<211> LENGTH: 609
<212> TYPE: DNA
<213> ORGANISM: Artificial sequence
<220> FEATURE:
<223> OTHER INFORMATION: Synthetic polynucleotide

<400> SEQUENCE: 48

atgggcagcc gcgaccacct gttcaaggtg ctggtggtgg gcgacgccgc cgtgggcaag      60

accagcctgg tgcagcgcta cagccaggac agcttcagca agcactacaa gagcaccgtg     120

ggcgtggact tcgccctgaa ggtgctgcag tggagcgact acgagatcgt gcgcctgcag     180

ctgtgggaca tcgccggcca ggagcgcttc accagcatga cccgcctgta ctaccgcgac     240

gccagcgcct gcgtgatcat gttcgacgtg accaacgcca ccaccttcag caacagccag     300

cgctggaagc aggacctgga cagcaagctg accctgccca acggcgagcc cgtgccctgc     360

ctgctgctgg ccaacaagtg cgacctgagc cctgggccg tgagccgcga ccagatcgac     420

cgcttcagca aggagaacgg cttcaccggc tggaccgaga ccagcgtgaa ggagaacaag     480

aacatcaacg aggccatgcg cgtgctgatc gagaagatga tgcgcaacag caccgaggac     540

atcatgagcc tgagcaccca gggcgactac atcaacctgc agaccaagag cagcagctgg     600

agctgctgc                                                              609


<210> SEQ ID NO 49
<211> LENGTH: 796
<212> TYPE: PRT
<213> ORGANISM: Artificial sequence
<220> FEATURE:
<223> OTHER INFORMATION: Synthetic polypeptide

<400> SEQUENCE: 49

Met Pro Thr Thr Gln Gln Ser Pro Gln Asp Glu Gln Glu Lys Leu Leu
1               5                   10                  15

Asp Glu Ala Ile Gln Ala Val Lys Val Gln Ser Phe Gln Met Lys Arg
            20                  25                  30

Cys Leu Asp Lys Asn Lys Leu Met Asp Ala Leu Lys His Ala Ser Asn
        35                  40                  45

Met Leu Gly Glu Leu Arg Thr Ser Met Leu Ser Pro Lys Ser Tyr Tyr
    50                  55                  60

Glu Leu Tyr Met Ala Ile Ser Asp Glu Leu His Tyr Leu Glu Val Tyr
65                  70                  75                  80

Leu Thr Asp Glu Phe Ala Lys Gly Arg Lys Val Ala Asp Leu Tyr Glu
                85                  90                  95

Leu Val Gln Tyr Ala Gly Asn Ile Ile Pro Arg Leu Tyr Leu Leu Ile
            100                 105                 110

Thr Val Gly Val Val Tyr Val Lys Ser Phe Pro Gln Ser Arg Lys Asp
        115                 120                 125

Ile Leu Lys Asp Leu Val Glu Met Cys Arg Gly Val Gln His Pro Leu
    130                 135                 140

Arg Gly Leu Phe Leu Arg Asn Tyr Leu Leu Gln Cys Thr Arg Asn Ile
145                 150                 155                 160

Leu Pro Asp Glu Gly Glu Pro Thr Asp Glu Glu Thr Thr Gly Asp Ile
                165                 170                 175

Ser Asp Ser Met Asp Phe Val Leu Leu Asn Phe Ala Glu Met Asn Lys
            180                 185                 190
```

```
Leu Trp Val Arg Met Gln His Gln Gly His Ser Arg Asp Arg Glu Lys
        195                 200                 205

Arg Glu Arg Glu Arg Gln Glu Leu Arg Ile Leu Val Gly Thr Asn Leu
    210                 215                 220

Val Arg Leu Ser Gln Leu Glu Gly Val Asn Val Glu Arg Tyr Lys Gln
225                 230                 235                 240

Ile Val Leu Thr Gly Ile Leu Glu Gln Val Val Asn Cys Arg Asp Ala
                245                 250                 255

Leu Ala Gln Glu Tyr Leu Met Glu Cys Ile Ile Gln Val Phe Pro Asp
            260                 265                 270

Glu Phe His Leu Gln Thr Leu Asn Pro Phe Leu Arg Ala Cys Ala Glu
        275                 280                 285

Leu His Gln Asn Val Asn Val Lys Asn Ile Ile Ile Ala Leu Ile Asp
    290                 295                 300

Arg Leu Ala Leu Phe Ala His Arg Glu Asp Gly Pro Gly Ile Pro Ala
305                 310                 315                 320

Asp Ile Lys Leu Phe Asp Ile Phe Ser Gln Gln Val Ala Thr Val Ile
                325                 330                 335

Gln Ser Arg Gln Asp Met Pro Ser Glu Asp Val Val Ser Leu Gln Val
            340                 345                 350

Ser Leu Ile Asn Leu Ala Met Lys Cys Tyr Pro Asp Arg Val Asp Tyr
        355                 360                 365

Val Asp Lys Val Leu Glu Thr Thr Val Glu Ile Phe Asn Lys Leu Asn
    370                 375                 380

Leu Glu His Ile Ala Thr Ser Ser Ala Val Ser Lys Glu Leu Thr Arg
385                 390                 395                 400

Leu Leu Lys Ile Pro Val Asp Thr Tyr Asn Asn Ile Leu Thr Val Leu
                405                 410                 415

Lys Leu Lys His Phe His Pro Leu Phe Glu Tyr Phe Asp Tyr Glu Ser
            420                 425                 430

Arg Lys Ser Met Ser Cys Tyr Val Leu Ser Asn Val Leu Asp Tyr Asn
        435                 440                 445

Thr Glu Ile Val Ser Gln Asp Gln Val Asp Ser Ile Met Asn Leu Val
    450                 455                 460

Ser Thr Leu Ile Gln Asp Gln Pro Asp Gln Pro Val Glu Asp Pro Asp
465                 470                 475                 480

Pro Glu Asp Phe Ala Asp Glu Gln Ser Leu Val Gly Arg Phe Ile His
                485                 490                 495

Leu Leu Arg Ser Glu Asp Pro Asp Gln Gln Tyr Leu Ile Leu Asn Thr
            500                 505                 510

Ala Arg Lys His Phe Gly Ala Gly Gly Asn Gln Arg Ile Arg Phe Thr
        515                 520                 525

Leu Pro Pro Leu Val Phe Ala Ala Tyr Gln Leu Ala Phe Arg Tyr Lys
    530                 535                 540

Glu Asn Ser Lys Val Asp Asp Lys Trp Glu Lys Lys Cys Gln Lys Ile
545                 550                 555                 560

Phe Ser Phe Ala His Gln Thr Ile Ser Ala Leu Ile Lys Ala Glu Leu
                565                 570                 575

Ala Glu Leu Pro Leu Arg Leu Phe Leu Gln Gly Ala Leu Ala Ala Gly
            580                 585                 590

Glu Ile Gly Phe Glu Asn His Glu Thr Val Ala Tyr Glu Phe Met Ser
        595                 600                 605

Gln Ala Phe Ser Leu Tyr Glu Asp Glu Ile Ser Asp Ser Lys Ala Gln
```

```
    610                 615                 620

Leu Ala Ala Ile Thr Leu Ile Ile Gly Thr Phe Glu Arg Met Lys Cys
625                 630                 635                 640

Phe Ser Glu Glu Asn His Glu Pro Leu Arg Thr Gln Cys Ala Leu Ala
                645                 650                 655

Ala Ser Lys Leu Leu Lys Lys Pro Asp Gln Gly Arg Ala Val Ser Thr
            660                 665                 670

Cys Ala His Leu Phe Trp Ser Gly Arg Asn Thr Asp Lys Asn Gly Glu
        675                 680                 685

Glu Leu His Gly Gly Lys Arg Val Met Glu Cys Leu Lys Lys Ala Leu
    690                 695                 700

Lys Ile Ala Asn Gln Cys Met Asp Pro Ser Leu Gln Val Gln Leu Phe
705                 710                 715                 720

Ile Glu Ile Leu Asn Arg Tyr Ile Tyr Phe Tyr Glu Lys Glu Asn Asp
                725                 730                 735

Ala Val Thr Ile Gln Val Leu Asn Gln Leu Ile Gln Lys Ile Arg Glu
            740                 745                 750

Asp Leu Pro Asn Leu Glu Ser Ser Glu Glu Thr Glu Gln Ile Asn Lys
        755                 760                 765

His Phe His Asn Thr Leu Glu His Leu Arg Leu Arg Arg Glu Ser Pro
    770                 775                 780

Glu Ser Glu Gly Pro Ile Tyr Glu Gly Leu Ile Leu
785                 790                 795


<210> SEQ ID NO 50
<211> LENGTH: 2388
<212> TYPE: DNA
<213> ORGANISM: Artificial sequence
<220> FEATURE:
<223> OTHER INFORMATION: Synthetic polynucleotide

<400> SEQUENCE: 50

atgcccacca cccagcagag cccccaggac gagcaggaga agctgctgga cgaggccatc     60

caggccgtga aggtgcagag cttccagatg aagcgctgcc tggacaagaa caagctgatg    120

gacgccctga agcacgccag caacatgctg ggcgagctgc gcaccagcat gctgagcccc    180

aagagctact acgagctgta catggccatc agcgacgagc tgcactacct ggaggtgtac    240

ctgaccgacg agttcgccaa gggccgcaag gtggccgacc tgtacgagct ggtgcagtac    300

gccggcaaca tcatcccccg cctgtacctg ctgatcaccg tgggcgtggt gtacgtgaag    360

agcttccccc agagccgcaa ggacatcctg aaggacctgg tggagatgtg ccgcggcgtg    420

cagcaccccc tgcgcggcct gttcctgcgc aactacctgc tgcagtgcac ccgcaacatc    480

ctgcccgacg agggcgagcc caccgacgag gagaccaccg gcgacatcag cgacagcatg    540

gacttcgtgc tgctgaactt cgccgagatg aacaagctgt gggtgcgcat gcagcaccag    600

ggccacagcc gcgaccgcga gaagcgcgag cgcgagcgcc aggagctgcg catcctggtg    660

ggcaccaacc tggtgcgcct gagccagctg gagggcgtga acgtggagcg ctacaagcag    720

atcgtgctga ccggcatcct ggagcaggtg gtgaactgcc gcgacgccct ggcccaggag    780

tacctgatgg agtgcatcat ccaggtgttc cccgacgagt tccacctgca gaccctgaac    840

cccttcctgc gcgcctgcgc cgagctgcac cagaacgtga acgtgaagaa catcatcatc    900

gccctgatcg accgcctggc cctgttcgcc caccgcgagg acggccccgg catccccgcc    960

gacatcaagc tgttcgacat cttcagccag caggtggcca ccgtgatcca gagccgccag   1020
```

```
gacatgccca gcgaggacgt ggtgagcctg caggtgagcc tgatcaacct ggccatgaag   1080
tgctaccccg accgcgtgga ctacgtggac aaggtgctgg agaccaccgt ggagatcttc   1140
aacaagctga acctggagca catcgccacc agcagcgccg tgagcaagga gctgacccgc   1200
ctgctgaaga tccccgtgga cacctacaac aacatcctga ccgtgctgaa gctgaagcac   1260
ttccaccccc tgttcgagta cttcgactac gagagccgca agagcatgag ctgctacgtg   1320
ctgagcaacg tgctggacta caacaccgag atcgtgagcc aggaccaggt ggacagcatc   1380
atgaacctgg tgagcaccct gatccaggac cagcccgacc agcccgtgga ggaccccgac   1440
cccgaggact tcgccgacga gcagagcctg gtgggccgct tcatccacct gctgcgcagc   1500
gaggaccccg accagcagta cctgatcctg aacaccgccc gcaagcactt cggcgccggc   1560
ggcaaccagc gcatccgctt caccctgccc cccctggtgt tcgccgccta ccagctggcc   1620
ttccgctaca aggagaacag caaggtggac gacaagtggg agaagaagtg ccagaagatc   1680
ttcagcttcg cccaccagac catcagcgcc ctgatcaagg ccgagctggc cgagctgccc   1740
ctgcgcctgt tcctgcaggg cgccctggcc gccggcgaga tcggcttcga gaaccacgag   1800
accgtggcct acgagttcat gagccaggcc ttcagcctgt acgaggacga gatcagcgac   1860
agcaaggccc agctggccgc catcaccctg atcatcggca ccttcgagcg catgaagtgc   1920
ttcagcgagg agaaccacga gcccctgcgc acccagtgcg ccctggccgc cagcaagctg   1980
ctgaagaagc ccgaccaggg ccgcgccgtg agcacctgcg cccacctgtt ctggagcggc   2040
cgcaacaccg acaagaacgg cgaggagctg cacggcggca agcgcgtgat ggagtgcctg   2100
aagaaggccc tgaagatcgc caaccagtgc atggacccca gcctgcaggt gcagctgttc   2160
atcgagatcc tgaaccgcta catctacttc tacgagaagg agaacgacgc cgtgaccatc   2220
caggtgctga accagctgat ccagaagatc cgcgaggacc tgcccaacct ggagagcagc   2280
gaggagaccg agcagatcaa caagcacttc cacaacaccc tggagcacct gcgcctgcgc   2340
cgcgagagcc ccgagagcga gggccccatc tacgagggcc tgatcctg                2388
```

<210> SEQ ID NO 51
<211> LENGTH: 11081
<212> TYPE: DNA
<213> ORGANISM: Artificial sequence
<220> FEATURE:
<223> OTHER INFORMATION: Synthetic polynucleotide

<400> SEQUENCE: 51

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg agggcggagt    300
tagggcggag ccaatcagcg tgcgccgttc cgaaagttgc cttttatggc tgggcggaga    360
atgggcggtg aacgccgatg attatataag gacgcgccgg gtgtggcaca gctagttccg    420
tcgcagccgg gatttgggtc gcggttcttg tttgtggatc cctgtgatcg tcacttggta    480
agtcactgac tgtctatgcc tgggaaaggg tgggcaggag atggggcagt gcaggaaaag    540
tggcactatg aaccctcctg gtggcgaggg gagggggtg gtcctcgaac gccttgcaga    600
actggcctgg atacagagtg gaccggctgg ccccatctgg aagacttcga gatacactgt    660
tgtcttactg cgctcaacag tgtatctcga agtcttccaa atggtgccag ccatcgcagc    720
```

```
ggggtgcagg aaatgggggc agccccccct tttggctatc cttccacgtg ttcttttttg    780
tatcttttgt gtttcctaga aaacatctca gtcaccaccg cagccctagg aatgcatcta    840
gacaattgta ctaaccttct tctctttcct ctcctgacag tccggaaagc caccatggaa    900
ttcagcagcc ccagcagaga ggaatgcccc aagcctctga gccgggtgtc aatcatggcc    960
ggatctctga caggactgct gctgcttcag gccgtgtctt gggcttctgg cgctagacct   1020
tgcatcccca agagcttcgg ctacagcagc gtcgtgtgcg tgtgcaatgc cacctactgc   1080
gacagcttcg accctcctac ctttcctgct ctgggcacct tcagcagata cgagagcacc   1140
agatccggca gacggatgga actgagcatg ggacccatcc aggccaatca cacaggcact   1200
ggcctgctgc tgacactgca gcctgagcag aaattccaga aagtgaaagg cttcggcgga   1260
gccatgacag atgccgccgc tctgaatatc ctggctctgt ctccaccagc tcagaacctg   1320
ctgctcaaga gctacttcag cgaggaaggc atcggctaca acatcatcag agtgcccatg   1380
gccagctgcg acttcagcat caggacctac acctacgccg acacacccga cgatttccag   1440
ctgcacaact tcagcctgcc tgaagaggac accaagctga agatccctct gatccacaga   1500
gccctgcagc tggcacaaag acccgtgtca ctgctggcct ctccatggac atctcccacc   1560
tggctgaaaa caaatggcgc cgtgaatggc aagggcagcc tgaaaggcca acctggcgac   1620
atctaccacc agacctgggc cagatacttc gtgaagttcc tggacgccta tgccgagcac   1680
aagctgcagt tttgggccgt gacagccgag aacgaacctt ctgctggact gctgagcggc   1740
taccccttc agtgcctggg ctttacaccc gagcaccagc gggactttat cgcccgtgat   1800
ctgggaccca cactggccaa tagcacccac cataatgtgc ggctgctgat gctggacgac   1860
cagagactgc ttctgcccca ctgggctaaa gtggtgctga cagatcctga ggccgccaaa   1920
tacgtgcacg gaatcgccgt gcactggtat ctggactttc tggcccctgc caaggccaca   1980
ctgggagaga cacacagact gttccccaac accatgctgt tcgccagcga agcctgtgtg   2040
ggcagcaagt tttgggaaca gagcgtgcgg ctcggcagct gggatagagg catgcagtac   2100
agccacagca tcatcaccaa cctgctgtac cacgtcgtcg gctggaccga ctggaatctg   2160
gccctgaatc ctgaaggcgg ccctaactgg gtccgaaact tcgtggacag ccccatcatc   2220
gtggacatca ccaaggacac cttctacaag cagcccatgt tctaccacct gggacacttc   2280
agcaagttca tccccgaggg ctctcagcgc gttggactgg tggcttccca gaagaacgat   2340
ctggacgccg tggctctgat gcaccctgat ggatctgctg tggtggtggt cctgaaccgc   2400
agcagcaaag atgtgcccct gaccatcaag gatcccgccg tgggattcct ggaaacaatc   2460
agccctggct actccatcca cacctacctg tggcgtagac aggagggcag aggaagtctt   2520
ctgacatgcg gagacgtgga agagaatccc ggccctatgg agaagggccc cgtgcgcgcc   2580
cccgccgaga agccccgcgg cgcccgctgc agcaacggct tccccgagcg cgacccccccc   2640
cgccccggcc ccagccgccc cgccgagaag cccccccgcc ccgaggccaa gagcgcccag   2700
cccgccgacg gctggaaggg cgagcgcccc cgcagcgagg aggacaacga gctgaacctg   2760
cccaacctgg ccgccgccta cagcagcatc ctgagcagcc tgggcgagaa cccccagcgc   2820
cagggcctgc tgaagacccc ctggcgcgcc gccagcgcca tgcagttctt caccaagggc   2880
taccaggaga ccatcagcga cgtgctgaac gacgccatct tcgacgagga ccacgacgag   2940
atggtgatcg tgaaggacat cgacatgttc agcatgtgcg agcaccacct ggtgcccttc   3000
gtgggcaagg tgcacatcgg ctacctgccc aacaagcagg tgctgggcct gagcaagctg   3060
```

gcccgcatcg tggagatcta cagccgccgc ctgcaggtgc aggagcgcct gaccaagcag 3120
atcgccgtgg ccatcaccga ggccctgcgc cccgccggcg tgggcgtggt ggtggaggcc 3180
acccacatgt gcatggtgat gcgcggcgtg cagaagatga acagcaagac cgtgaccagc 3240
accatgctgg gcgtgttccg cgaggacccc aagacccgcg aggagttcct gaccctgatc 3300
cgcagctgac aattgttaat taagtttaaa ccctcgaggc cgcaagctta tcgataatca 3360
acctctggat tacaaaattt gtgaaagatt gactggtatt cttaactatg ttgctccttt 3420
tacgctatgt ggatacgctg ctttaatgcc tttgtatcat gctattgctt cccgtatggc 3480
tttcattttc tcctccttgt ataaatcctg gttgctgtct ctttatgagg agttgtggcc 3540
cgttgtcagg caacgtggcg tggtgtgcac tgtgtttgct gacgcaaccc ccactggttg 3600
gggcattgcc accacctgtc agctcctttc cgggactttc gctttccccc tccctattgc 3660
cacggcggaa ctcatcgccg cctgccttgc ccgctgctgg acaggggctc ggctgttggg 3720
cactgacaat tccgtggtgt tgtcggggaa atcatcgtcc tttccttggc tgctcgcctg 3780
tgttgccacc tggattctgc gcgggacgtc cttctgctac gtcccttcgg ccctcaatcc 3840
agcggacctt ccttcccgcg gcctgctgcc ggctctgcgg cctcttccgc gtcttcgcct 3900
tcgccctcag acgagtcgga tctccctttg ggccgcctcc ccgcatcgat accgtcgact 3960
agagctcgct gatcagcctc gactgtgcct tctagttgcc agccatctgt tgtttgcccc 4020
tcccccgtgc cttccttgac cctggaaggt gccactccca ctgtcctttc ctaataaaat 4080
gaggaaattg catcgcattg tctgagtagg tgtcattcta ttctgggggg tggggtgggg 4140
caggacagca agggggagga ttgggaagac aatagcaggc atgctgggga gagatccacg 4200
ataacaaaca gctttttttgg ggtgaacata ttgactgaat tccctgcagg ttggccactc 4260
cctctctgcg cgctcgctcg ctcactgagg ccgcccgggc aaagcccggg cgtcgggcga 4320
cctttggtcg cccggcctca gtgagcgagc gagcgcgcag agagggagtg gccaactcca 4380
tcactagggg ttcctgcggc cgctcgtacg gtctcgagga attcctgcag gataacttgc 4440
caacctcatt ctaaaatgta tatagaagcc caaaagacaa taacaaaaat attcttgtag 4500
aacaaaatgg gaaagaatgt tccactaaat atcaagattt agagcaaagc atgagatgtg 4560
tggggataga cagtgaggct gataaaatag agtagagctc agaaacagac ccattgatat 4620
atgtaagtga cctatgaaaa aaatatggca ttttacaatg ggaaaatgat ggtctttttc 4680
ttttttagaa aaacagggaa atatatttat atgtaaaaaa taaaagggaa cccatatgtc 4740
ataccataca cacaaaaaaa ttccagtgaa ttataagtct aaatggagaa ggcaaaactt 4800
taaatctttt agaaaataat atagaagcat gcagaccagc ctggccaaca tgatgaaacc 4860
ctctctacta ataataaaat cagtagaact actcaggact actttgagtg ggaagtcctt 4920
ttctatgaag acttctttgg ccaaaattag gctctaaatg caaggagata gtgcatcatg 4980
cctggctgca cttactgata aatgatgtta tcaccatctt taaccaaatg cacaggaaca 5040
agttatggta ctgatgtgct ggattgagaa ggagctctac ttccttgaca ggacacattt 5100
gtatcaactt aaaaaagcag atttttgcca gcagaactat tcattcagag gtaggaaact 5160
tagaatagat gatgtcactg attagcatgg cttccccatc tccacagctg cttcccaccc 5220
aggttgccca cagttgagtt tgtccagtgc tcagggctgc ccactctcag taagaagccc 5280
cacaccagcc cctctccaaa tatgttggct gttccttcca ttaaagtgac cccactttag 5340
agcagcaagt ggatttctgt ttcttacagt tcaggaagga ggagtcagct gtgagaacct 5400
ggagcctgag atgcttctaa gtcccactgc tactggggtc agggaagcca gactccagca 5460

```
tcagcagtca ggagcactaa gcccttgcca acatcctgtt tctcagagaa actgcttcca   5520
ttataatggt tgtccttttt taagctatca agccaaacaa ccagtgtcta ccattattct   5580
catcacctga agccaagggt tctagcaaaa gtcaagctgt cttgtaatgg ttgatgtgcc   5640
tccagcttct gtcttcagtc actccactct tagcctgctc tgaatcaact ctgaccacag   5700
ttccctggag cccctgccac ctgctgcccc tgccaccttc tccatctgca gtgctgtgca   5760
gccttctgca ctcttgcaga gctaataggt ggagacttga aggaagagga ggaaagtttc   5820
tcataaatagc cttgctgcaa gctcaaatgg gaggtgggca ctgtgcccag gagccttgga   5880
gcaaaggctg tgcccaacct ctgactgcat ccaggtttgg tcttgacaga gataagaagc   5940
cctggctttt ggagccaaaa tctaggtcag acttaggcag gattctcaaa gtttatcagc   6000
agaacatgag gcagaagacc ctttctgctc cagcttcttc aggctcaacc ttcatcagaa   6060
tagatagaaa gagaggctgt gagggttctt aaaacagaag caaatctgac tcagagaata   6120
aacaacctcc tagtaaacta cagcttagac agagcatctg gtggtgagtg tgctcagtgt   6180
cctactcaac tgtctggtat cagccctcat gaggacttct cttctttccc tcatagacct   6240
ccatctctgt tttccttagc ctgcagaaat ctggatggct attcacagaa tgcctgtgct   6300
ttcagagttg catttttttct ctggtattct ggttcaagca tttgaaggta ggaaaggttc   6360
tccaagtgca agaaagccag ccctgagcct caactgcctg gctagtgtgg tcagtaggat   6420
gcaaaggctg ttgaatgcca caaggccaaa ctttaacctg tgtaccacaa gcctagcagc   6480
agaggcagct ctgctcactg gaactctctg tcttctttct cctgagcctt ttcttttcct   6540
gagttttcta gctctcctca accttacctc tgccctaccc aggacaaacc caagagccac   6600
tgtttctgtg atgtcctctc cagccctaat taggcatcat gacttcagcc tgaccttcca   6660
tgctcagaag cagtgctaat ccacttcaga tgagctgctc tatgcaacac aggcagagcc   6720
tacaaacctt tgcaccagag ccctccacat atcagtgttt gttcatactc acttcaacag   6780
caaatgtgac tgctgagatt aagattttac acaagatggt ctgtaatttc acagttagtt   6840
ttatcccatt aggtatgaaa gaattagcat aattcccctt aaacatgaat gaatcttaga   6900
tttttaata aatagttttg gaagtaaaga cagagacatc aggagcacaa ggaatagcct   6960
gagaggacaa acagaacaag aaagagtctg gaaatacaca ggatgttctt ggcctcctca   7020
aagcaagtgc aagcagatag taccagcagc cccaggctat cagagcccag tgaagagaag   7080
taccatgaaa gccacagctc taaccaccct gttccagagt gacagacagt ccccaagaca   7140
agccagcctg agccagagag agaactgcaa gagaaagttt ctaatttagg ttctgttaga   7200
ttcagacaag tgcaggtcat cctctctcca cagctactca cctctccagc ctaacaaagc   7260
ctgcagtcca cactccaacc ctggtgtctc acctcctagc ctctcccaac atcctgctct   7320
ctgaccatct tctgcatctc tcatctcacc atctcccact gtctacagcc tactcttgca   7380
actaccatct catttctga catcctgtct acatcttctg ccatactctg ccatctacca   7440
taccacctct taccatctac cacaccatct tttatctcca tccctctcag aagcctccaa   7500
gctgaatcct gctttatgtg ttcatctcag cccctgcatg gaaagctgac cccagaggca   7560
gaactattcc cagagagctt ggccaagaaa aacaaaacta ccagcctggc caggctcagg   7620
agtagtaagc tgcagtgtct gttgtgttct agcttcaaca gctgcaggag ttccactctc   7680
aaatgctcca catttctcac atcctcctga ttctggtcac tacccatctt caaagaacag   7740
aatatctcac atcagcatac tgtgaaggac tagtcatggg tgcagctgct cagagctgca   7800
```

```
aagtcattct ggatggtgga gagcttacaa acatttcatg atgctccccc cgctctgatg   7860
gctggagccc aatccctaca cagactcctg ctgtatgtgt tttcctttca ctctgagcca   7920
cagccagagg gcaggcattc agtctcctct tcaggctggg gctggggcac tgagaactca   7980
cccaacacct tgctctcact ccttctgcaa aacaagaaag agctttgtgc tgcagtagcc   8040
atgaagaatg aaaggaaggc tttaactaaa aaatgtcaga gattattttc aaccccttac   8100
tgtggatcac cagcaaggag gaaacacaac acagagacat tttttcccct caaattatca   8160
aaagaatcac tgcatttgtt aaagagagca actgaatcag gaagcagagt tttgaacata   8220
tcagaagtta ggaatctgca tcagagacaa atgcagtcat ggttgtttgc tgcataccag   8280
ccctaatcat tagaagcctc atggacttca aacatcattc cctctgacaa gatgctctag   8340
cctaactcca tgagataaaa taaatctgcc tttcagagcc aaagaagagt ccaccagctt   8400
cttctcagtg tgaacaagag ctccagtcag gttagtcagt ccagtgcagt agaggagacc   8460
agtctgcatc ctctaatttt caaaggcaag aagatttgtt taccctggac accaggcaca   8520
agtgaggtca cagagctctt agatatgcag tcctcatgag tgaggagact aaagcgcatg   8580
ccatcaagac ttcagtgtag agaaaacctc caaaaaagcc tcctcactac ttctggaata   8640
gctcagaggc cgaggcggcc tcggcctctg cataaataaa aaaaattagt cagccatggg   8700
gcggagaatg ggcggaactg ggcggagtta ggggcgggat gggcggagtt aggggcggga   8760
ctatggttgc tgactaattg agatgcatgc tttgcatact tctgcctgct ggggagcctg   8820
gggactttcc acacctggtt gctgactaat tgagatgcat gctttgcata cttctgcctg   8880
ctggggagcc tggggacttt ccacacccta actgacacac attccacagc tgcattaatg   8940
aatcggccaa cgcgcgggga gaggcggttt gcgtattggg cgctcttccg cttcctcgct   9000
cactgactcg ctgcgctcgg tcgttcggct gcggcgagcg gtatcagctc actcaaaggc   9060
ggtaatacgg ttatccacag aatcagggga taacgcagga aagaacatgt gagcaaaagg   9120
ccagcaaaag gccaggaacc gtaaaaaggc cgcgttgctg gcgtttttcc ataggctccg   9180
cccccctgac gagcatcaca aaaatcgacg ctcaagtcag aggtggcgaa acccgacagg   9240
actataaaga taccaggcgt ttccccctgg aagctccctc gtgcgctctc ctgttccgac   9300
cctgccgctt accggatacc tgtccgcctt tctcccttcg ggaagcgtgg cgctttctca   9360
tagctcacgc tgtaggtatc tcagttcggt gtaggtcgtt cgctccaagc tgggctgtgt   9420
gcacgaaccc cccgttcagc ccgaccgctg cgccttatcc ggtaactatc gtcttgagtc   9480
caacccggta agacacgact tatcgccact ggcagcagcc actggtaaca ggattagcag   9540
agcgaggtat gtaggcggtg ctacagagtt cttgaagtgg tggcctaact acggctacac   9600
tagaagaaca gtatttggta tctgcgctct gctgaagcca gttaccttcg gaaaaagagt   9660
tggtagctct tgatccggca aacaaaccac cgctggtagc ggtggttttt ttgtttgcaa   9720
gcagcagatt acgcgcagaa aaaaaggatc tcaagaagat cctttgatct tttctacggg   9780
gtctgacgct cagtggaacg aaaactcacg ttaagggatt ttggtcatga gattatcaaa   9840
aaggatcttc acctagatcc ttttaaatta aaaatgaagt tttaaatcaa tctaaagtat   9900
atatgagtaa acttggtctg acagttacca atgcttaatc agtgaggcac ctatctcagc   9960
gatctgtcta tttcgttcat ccatagttgc ctgactcctg caaaccacgt tgtgtctcaa  10020
aatctctgat gttacattgc acaagataaa aatatatcat catgaacaat aaaactgtct  10080
gcttacataa acagtaatac aaggggtgtt atgagccata ttcaacggga aacgtcttgc  10140
tcgaggccgc gattaaattc caacatggat gctgatttat atgggtataa atgggctcgc  10200
```

```
gataatgtcg ggcaatcagg tgcgacaatc tatcgattgt atgggaagcc cgatgcgcca  10260
gagttgtttc tgaaacatgg caaaggtagc gttgccaatg atgttacaga tgagatggtc  10320
agactaaact ggctgacgga atttatgcct cttccgacca tcaagcattt tatccgtact  10380
cctgatgatg catggttact caccactgcg atccccggga aaacagcatt ccaggtatta  10440
gaagaatatc ctgattcagg tgaaaatatt gttgatgcgc tggcagtgtt cctgcgccgg  10500
ttgcattcga ttcctgtttg taattgtcct tttaacagcg atcgcgtatt tcgtctcgct  10560
caggcgcaat cacgaatgaa taacggtttg gttgatgcga gtgattttga tgacgagcgt  10620
aatggctggc ctgttgaaca agtctggaaa gaaatgcata agcttttgcc attctcaccg  10680
gattcagtcg tcactcatgg tgatttctca cttgataacc ttatttttga cgaggggaaa  10740
ttaataggtt gtattgatgt tggacgagtc ggaatcgcag accgatacca ggatcttgcc  10800
atcctatgga actgcctcgg tgagttttct ccttcattac agaaacggct ttttcaaaaa  10860
tatggtattg ataatcctga tatgaataaa ttgcagtttc atttgatgct cgatgagttt  10920
ttctaagggc ggcctgccac catacccacg ccgaaacaag cgctcatgag cccgaagtgg  10980
cgagcccgat cttccccatc ggtgatgtcg gcgatatagg cgccagcaac cgcacctgtg  11040
gcgccggtga tgagggcgcg ccaagtcgac gtccggcagt c                      11081
```

<210> SEQ ID NO 52
<211> LENGTH: 10940
<212> TYPE: DNA
<213> ORGANISM: Artificial sequence
<220> FEATURE:
<223> OTHER INFORMATION: Synthetic polynucleotide

<400> SEQUENCE: 52

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg agggcggagt    300
tagggcggag ccaatcagcg tgcgccgttc cgaaagttgc cttttatggc tgggcggaga    360
atgggcggtg aacgccgatg attatataag gacgcgccgg gtgtggcaca gctagttccg    420
tcgcagccgg gatttgggtc gcggttcttg tttgtggatc cctgtgatcg tcacttggta    480
agtcactgac tgtctatgcc tgggaaaggg tgggcaggag atggggcagt gcaggaaaag    540
tggcactatg aaccctcctg gtggcgaggg gagggggtg gtcctcgaac gccttgcaga    600
actggcctgg atacagagtg gaccggctgg ccccatctgg aagacttcga gatacactgt    660
tgtcttactg cgctcaacag tgtatctcga agtcttccaa atggtgccag ccatcgcagc    720
ggggtgcagg aaatgggggc agcccccctt tttggctatc cttccacgtg ttcttttttg    780
tatcttttgt gtttcctaga aaacatctca gtcaccaccg cagccctagg aatgcatcta    840
gacaattgta ctaaccttct tctctttcct ctcctgacag tccggaaagc caccatgggc    900
agccgcgacc acctgttcaa ggtgctggtg gtgggcgacg ccgccgtggg caagaccagc    960
ctggtgcagc gctacagcca ggacagcttc agcaagcact acaagagcac cgtgggcgtg   1020
gacttcgccc tgaaggtgct gcagtggagc gactacgaga tcgtgcgcct gcagctgtgg   1080
gacatcgccg gccaggagcg cttcaccagc atgacccgcc tgtactaccg cgacgccagc   1140
```

```
gcctgcgtga tcatgttcga cgtgaccaac gccaccacct tcagcaacag ccagcgctgg   1200
aagcaggacc tggacagcaa gctgaccctg cccaacggcg agcccgtgcc ctgcctgctg   1260
ctggccaaca agtgcgacct gagcccctgg gccgtgagcc gcgaccagat cgaccgcttc   1320
agcaaggaga acggcttcac cggctggacc gagaccagcg tgaaggagaa caagaacatc   1380
aacgaggcca tgcgcgtgct gatcgagaag atgatgcgca acagcaccga ggacatcatg   1440
agcctgagca cccagggcga ctacatcaac ctgcagacca agagcagcag ctggagctgc   1500
tgcgagggca gaggaagtct tctgacatgc ggagacgtgg aagagaatcc cggccctatg   1560
gaattcagca gccccagcag agaggaatgc cccaagcctc tgagccgggt gtcaatcatg   1620
gccggatctc tgacaggact gctgctgctt caggccgtgt cttgggcttc tggcgctaga   1680
ccttgcatcc ccaagagctt cggctacagc agcgtcgtgt gcgtgtgcaa tgccacctac   1740
tgcgacagct tcgaccctcc tacctttcct gctctgggca ccttcagcag atacgagagc   1800
accagatccg gcagacggat ggaactgagc atggacccca tccaggccaa tcacacaggc   1860
actggcctgc tgctgacact gcagcctgag cagaaattcc agaaagtgaa aggcttcggc   1920
ggagccatga cagatgccgc cgctctgaat atcctggctc tgtctccacc agctcagaac   1980
ctgctgctca agagctactt cagcgaggaa ggcatcggct acaacatcat cagagtgccc   2040
atggccagct gcgacttcag catcaggacc tacacctacg ccgacacacc cgacgatttc   2100
cagctgcaca acttcagcct gcctgaagag gacaccaagc tgaagatccc tctgatccac   2160
agagccctgc agctggcaca aagacccgtg tcactgctgg cctctccatg gacatctccc   2220
acctggctga aaacaaatgg cgccgtgaat ggcaagggca gcctgaaagg ccaacctggc   2280
gacatctacc accagacctg ggccagatac ttcgtgaagt tcctggacgc ctatgccgag   2340
cacaagctgc agttttgggc cgtgacagcc gagaacgaac cttctgctgg actgctgagc   2400
ggctacccct ttcagtgcct gggctttaca cccgagcacc agcgggactt tatcgcccgt   2460
gatctgggac ccacactggc caatagcacc caccataatg tgcggctgct gatgctggac   2520
gaccagagac tgcttctgcc ccactgggct aaagtggtgc tgacagatcc tgaggccgcc   2580
aaatacgtgc acggaatcgc cgtgcactgg tatctggact ttctggcccc tgccaaggcc   2640
acactgggag agacacacag actgttcccc aacaccatgc tgttcgccag cgaagcctgt   2700
gtgggcagca agttttggga acagagcgtg cggctcggca gctgggatag aggcatgcag   2760
tacagccaca gcatcatcac caacctgctg taccacgtcg tcggctggac cgactggaat   2820
ctggccctga atcctgaagg cggccctaac tgggtccgaa acttcgtgga cagccccatc   2880
atcgtggaca tcaccaagga caccttctac aagcagccca tgttctacca cctgggacac   2940
ttcagcaagt tcatccccga gggctctcag cgcgttggac tggtggcttc ccagaagaac   3000
gatctggacg ccgtggctct gatgcaccct gatggatctg ctgtggtggt ggtcctgaac   3060
cgcagcagca aagatgtgcc cctgaccatc aaggatcccg ccgtgggatt cctggaaaca   3120
atcagccctg gctactccat ccacacctac ctgtggcgta gacagtgaca attgttaatt   3180
aagtttaaac cctcgaggcc gcaagcttat cgataatcaa cctctggatt acaaaatttg   3240
tgaaagattg actggtattc ttaactatgt tgctcctttt acgctatgtg gatacgctgc   3300
tttaatgcct ttgtatcatg ctattgcttc ccgtatggct ttcattttct cctccttgta   3360
taaatcctgg ttgctgtctc tttatgagga gttgtggccc gttgtcaggc aacgtggcgt   3420
ggtgtgcact gtgtttgctg acgcaacccc cactggttgg ggcattgcca ccacctgtca   3480
gctcctttcc gggactttcg ctttcccct ccctattgcc acggcggaac tcatcgccgc   3540
```

```
ctgccttgcc cgctgctgga caggggctcg gctgttgggc actgacaatt ccgtggtgtt   3600
gtcggggaaa tcatcgtcct ttccttggct gctcgcctgt gttgccacct ggattctgcg   3660
cgggacgtcc ttctgctacg tcccttcggc cctcaatcca gcggaccttc cttcccgcgg   3720
cctgctgccg gctctgcggc ctcttccgcg tcttcgcctt cgccctcaga cgagtcggat   3780
ctccctttgg gccgcctccc cgcatcgata ccgtcgacta gagctcgctg atcagcctcg   3840
actgtgcctt ctagttgcca gccatctgtt gtttgcccct cccccgtgcc ttccttgacc   3900
ctggaaggtg ccactcccac tgtcctttcc taataaaatg aggaaattgc atcgcattgt   3960
ctgagtaggt gtcattctat tctggggggt ggggtggggc aggacagcaa gggggaggat   4020
tgggaagaca atagcaggca tgctggggag agatccacga taacaaacag ctttttttggg   4080
gtgaacatat tgactgaatt ccctgcaggt tggccactcc ctctctgcgc gctcgctcgc   4140
tcactgaggc cgcccgggca aagcccgggc gtcgggcgac ctttggtcgc ccggcctcag   4200
tgagcgagcg agcgcgcaga gagggagtgg ccaactccat cactaggggt tcctgcggcc   4260
gctcgtacgg tctcgaggaa ttcctgcagg ataacttgcc aacctcattc taaaatgtat   4320
atagaagccc aaaagacaat aacaaaaata ttcttgtaga acaaaatggg aaagaatgtt   4380
ccactaaata tcaagattta gagcaaagca tgagatgtgt ggggatagac agtgaggctg   4440
ataaaataga gtagagctca gaaacagacc cattgatata tgtaagtgac ctatgaaaaa   4500
aatatggcat tttacaatgg gaaaatgatg gtctttttct tttttagaaa aacagggaaa   4560
tatatttata tgtaaaaaat aaaagggaac ccatatgtca taccatacac acaaaaaaat   4620
tccagtgaat tataagtcta aatggagaag gcaaaacttt aaatctttta gaaaataata   4680
tagaagcatg cagaccagcc tggccaacat gatgaaaccc tctctactaa taataaaatc   4740
agtagaacta ctcaggacta ctttgagtgg gaagtccttt tctatgaaga cttctttggc   4800
caaaattagg ctctaaatgc aaggagatag tgcatcatgc ctggctgcac ttactgataa   4860
atgatgttat caccatcttt aaccaaatgc acaggaacaa gttatggtac tgatgtgctg   4920
gattgagaag gagctctact tccttgacag gacacatttg tatcaactta aaaaagcaga   4980
tttttgccag cagaactatt cattcagagg taggaaactt agaatagatg atgtcactga   5040
ttagcatggc ttccccatct ccacagctgc ttcccaccca ggttgcccac agttgagttt   5100
gtccagtgct cagggctgcc cactctcagt aagaagcccc acaccagccc ctctccaaat   5160
atgttggctg ttccttccat taaagtgacc ccactttaga gcagcaagtg gatttctgtt   5220
tcttacagtt caggaaggag gagtcagctg tgagaacctg gagcctgaga tgcttctaag   5280
tcccactgct actggggtca gggaagccag actccagcat cagcagtcag gagcactaag   5340
cccttgccaa catcctgttt ctcagagaaa ctgcttccat tataatggtt gtcctttttt   5400
aagctatcaa gccaaacaac cagtgtctac cattattctc atcacctgaa gccaagggtt   5460
ctagcaaaag tcaagctgtc ttgtaatggt tgatgtgcct ccagcttctg tcttcagtca   5520
ctccactctt agcctgctct gaatcaactc tgaccacagt tccctggagc ccctgccacc   5580
tgctgcccct gccaccttct ccatctgcag tgctgtgcag ccttctgcac tcttgcagag   5640
ctaataggtg gagacttgaa ggaagaggag gaaagtttct cataatagcc ttgctgcaag   5700
ctcaaatggg aggtgggcac tgtgcccagg agccttggag caaaggctgt gcccaacctc   5760
tgactgcatc caggtttggt cttgacagag ataagaagcc ctggcttttg gagccaaaat   5820
ctaggtcaga cttaggcagg attctcaaag tttatcagca gaacatgagg cagaagaccc   5880
```

-continued

```
tttctgctcc agcttcttca ggctcaacct tcatcagaat agatagaaag agaggctgtg   5940
agggttctta aaacagaagc aaatctgact cagagaataa acaacctcct agtaaactac   6000
agcttagaca gagcatctgg tggtgagtgt gctcagtgtc ctactcaact gtctggtatc   6060
agccctcatg aggacttctc ttctttccct catagacctc catctctgtt ttccttagcc   6120
tgcagaaatc tggatggcta ttcacagaat gcctgtgctt tcagagttgc atttttctc   6180
tggtattctg gttcaagcat ttgaaggtag gaaaggttct ccaagtgcaa gaaagccagc   6240
cctgagcctc aactgcctgg ctagtgtggt cagtaggatg caaaggctgt tgaatgccac   6300
aaggccaaac tttaacctgt gtaccacaag cctagcagca gaggcagctc tgctcactgg   6360
aactctctgt cttctttctc ctgagccttt tcttttcctg agttttctag ctctcctcaa   6420
ccttacctct gccctaccca ggacaaaccc aagagccact gtttctgtga tgtcctctcc   6480
agccctaatt aggcatcatg acttcagcct gaccttccat gctcagaagc agtgctaatc   6540
cacttcagat gagctgctct atgcaacaca ggcagagcct acaaaccttt gcaccagagc   6600
cctccacata tcagtgtttg ttcatactca cttcaacagc aaatgtgact gctgagatta   6660
agattttaca caagatggtc tgtaatttca cagttagttt tatcccatta ggtatgaaag   6720
aattagcata attcccctta aacatgaatg aatcttagat tttttaataa atagttttgg   6780
aagtaaagac agagacatca ggagcacaag gaatagcctg agaggacaaa cagaacaaga   6840
aagagtctgg aaatacacag gatgttcttg gcctcctcaa agcaagtgca agcagatagt   6900
accagcagcc ccaggctatc agagcccagt gaagagaagt accatgaaag ccacagctct   6960
aaccaccctg ttccagagtg acagacagtc cccaagacaa gccagcctga gccagagaga   7020
gaactgcaag agaaagtttc taatttaggt tctgttagat tcagacaagt gcaggtcatc   7080
ctctctccac agctactcac ctctccagcc taacaaagcc tgcagtccac actccaaccc   7140
tggtgtctca cctcctagcc tctcccaaca tcctgctctc tgaccatctt ctgcatctct   7200
catctcacca tctcccactg tctacagcct actcttgcaa ctaccatctc attttctgac   7260
atcctgtcta catcttctgc catactctgc catctaccat accacctctt accatctacc   7320
acaccatctt ttatctccat ccctctcaga agcctccaag ctgaatcctg ctttatgtgt   7380
tcatctcagc ccctgcatgg aaagctgacc ccagaggcag aactattccc agagagcttg   7440
gccaagaaaa acaaaactac cagcctggcc aggctcagga gtagtaagct gcagtgtctg   7500
ttgtgttcta gcttcaacag ctgcaggagt tccactctca aatgctccac atttctcaca   7560
tcctcctgat tctggtcact acccatcttc aaagaacaga atatctcaca tcagcatact   7620
gtgaaggact agtcatgggt gcagctgctc agagctgcaa agtcattctg gatggtggag   7680
agcttacaaa catttcatga tgctccccc gctctgatgg ctggagccca atccctacac   7740
agactcctgc tgtatgtgtt ttcctttcac tctgagccac agccagaggg caggcattca   7800
gtctcctctt caggctgggg ctggggcact gagaactcac ccaacacctt gctctcactc   7860
cttctgcaaa acaagaaaga gctttgtgct gcagtagcca tgaagaatga aaggaaggct   7920
ttaactaaaa aatgtcagag attattttca acccccttact gtggatcacc agcaaggagg   7980
aaacacaaca cagagacatt ttttcccctc aaattatcaa aagaatcact gcatttgtta   8040
aagagagcaa ctgaatcagg aagcagagtt ttgaacatat cagaagttag gaatctgcat   8100
cagagacaaa tgcagtcatg gttgtttgct gcataccagc cctaatcatt agaagcctca   8160
tggacttcaa acatcattcc ctctgacaag atgctctagc ctaactccat gagataaaat   8220
aaatctgcct ttcagagcca aagaagagtc caccagcttc ttctcagtgt gaacaagagc   8280
```

```
tccagtcagg ttagtcagtc cagtgcagta gaggagacca gtctgcatcc tctaattttc   8340
aaaggcaaga agatttgttt accctggaca ccaggcacaa gtgaggtcac agagctctta   8400
gatatgcagt cctcatgagt gaggagacta aagcgcatgc catcaagact tcagtgtaga   8460
gaaaacctcc aaaaaagcct cctcactact tctggaatag ctcagaggcc gaggcggcct   8520
cggcctctgc ataaataaaa aaaattagtc agccatgggg cggagaatgg gcggaactgg   8580
gcggagttag gggcgggatg ggcggagtta ggggcgggac tatggttgct gactaattga   8640
gatgcatgct ttgcatactt ctgcctgctg gggagcctgg ggactttcca cacctggttg   8700
ctgactaatt gagatgcatg ctttgcatac ttctgcctgc tggggagcct ggggactttc   8760
cacaccctaa ctgacacaca ttccacagct gcattaatga atcggccaac gcgcggggag   8820
aggcggtttg cgtattgggc gctcttccgc ttcctcgctc actgactcgc tgcgctcggt   8880
cgttcggctg cggcgagcgg tatcagctca ctcaaaggcg gtaatacggt tatccacaga   8940
atcaggggat aacgcaggaa agaacatgtg agcaaaaggc cagcaaaagg ccaggaaccg   9000
taaaaaggcc gcgttgctgg cgtttttcca taggctccgc ccccctgacg agcatcacaa   9060
aaatcgacgc tcaagtcaga ggtggcgaaa cccgacagga ctataaagat accaggcgtt   9120
tccccctgga agctccctcg tgcgctctcc tgttccgacc ctgccgctta ccggatacct   9180
gtccgccttt ctcccttcgg gaagcgtggc gctttctcat agctcacgct gtaggtatct   9240
cagttcggtg taggtcgttc gctccaagct gggctgtgtg cacgaacccc ccgttcagcc   9300
cgaccgctgc gccttatccg gtaactatcg tcttgagtcc aacccggtaa gacacgactt   9360
atcgccactg gcagcagcca ctggtaacag gattagcaga gcgaggtatg taggcggtgc   9420
tacagagttc ttgaagtggt ggcctaacta cggctacact agaagaacag tatttggtat   9480
ctgcgctctg ctgaagccag ttaccttcgg aaaaagagtt ggtagctctt gatccggcaa   9540
acaaaccacc gctggtagcg gtggtttttt tgtttgcaag cagcagatta cgcgcagaaa   9600
aaaaggatct caagaagatc ctttgatctt ttctacgggg tctgacgctc agtggaacga   9660
aaactcacgt taagggattt tggtcatgag attatcaaaa aggatcttca cctagatcct   9720
tttaaattaa aaatgaagtt ttaaatcaat ctaaagtata tatgagtaaa cttggtctga   9780
cagttaccaa tgcttaatca gtgaggcacc tatctcagcg atctgtctat ttcgttcatc   9840
catagttgcc tgactcctgc aaaccacgtt gtgtctcaaa atctctgatg ttacattgca   9900
caagataaaa atatatcatc atgaacaata aaactgtctg cttacataaa cagtaataca   9960
aggggtgtta tgagccatat tcaacgggaa acgtcttgct cgaggccgcg attaaattcc  10020
aacatggatg ctgatttata tgggtataaa tgggctcgcg ataatgtcgg gcaatcaggt  10080
gcgacaatct atcgattgta tgggaagccc gatgcgccag agttgtttct gaaacatggc  10140
aaaggtagcg ttgccaatga tgttacagat gagatggtca gactaaactg gctgacggaa  10200
tttatgcctc ttccgaccat caagcatttt atccgtactc ctgatgatgc atggttactc  10260
accactgcga tccccgggaa aacagcattc caggtattag aagaatatcc tgattcaggt  10320
gaaaatattg ttgatgcgct ggcagtgttc ctgcgccggt tgcattcgat tcctgtttgt  10380
aattgtcctt ttaacagcga tcgcgtattt cgtctcgctc aggcgcaatc acgaatgaat  10440
aacggtttgg ttgatgcgag tgattttgat gacgagcgta atggctggcc tgttgaacaa  10500
gtctggaaag aaatgcataa gcttttgcca ttctcaccgg attcagtcgt cactcatggt  10560
gatttctcac ttgataacct tatttttgac gaggggaaat taataggttg tattgatgtt  10620
```

ggacgagtcg gaatcgcaga ccgataccag gatcttgcca tcctatggaa ctgcctcggt 10680
gagttttctc cttcattaca gaaacggctt tttcaaaaat atggtattga taatcctgat 10740
atgaataaat tgcagtttca tttgatgctc gatgagtttt tctaagggcg gcctgccacc 10800
atacccacgc cgaaacaagc gctcatgagc ccgaagtggc gagcccgatc ttccccatcg 10860
gtgatgtcgg cgatataggc gccagcaacc gcacctgtgg cgccggtgat gagggcgcgc 10920
caagtcgacg tccggcagtc 10940

<210> SEQ ID NO 53
<211> LENGTH: 10934
<212> TYPE: DNA
<213> ORGANISM: Artificial sequence
<220> FEATURE:
<223> OTHER INFORMATION: Synthetic polynucleotide

<400> SEQUENCE: 53
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg agggcggagt 300
tagggcggag ccaatcagcg tgcgccgttc cgaaagttgc cttttatggc tgggcggaga 360
atgggcggtg aacgccgatg attatataag gacgcgccgg gtgtggcaca gctagttccg 420
tcgcagccgg gatttgggtc gcggttcttg tttgtggatc cctgtgatcg tcacttggta 480
agtcactgac tgtctatgcc tgggaaaggg tgggcaggag atggggcagt gcaggaaaag 540
tggcactatg aaccctcctg gtggcgaggg gagggggggtg gtcctcgaac gccttgcaga 600
actggcctgg atacagagtg gaccggctgg ccccatctgg aagacttcga gatacactgt 660
tgtcttactg cgctcaacag tgtatctcga agtcttccaa atggtgccag ccatcgcagc 720
ggggtgcagg aaatgggggc agcccccctt tttggctatc cttccacgtg ttcttttttg 780
tatcttttgt gtttcctaga aaacatctca gtcaccaccg cagccctagg aatgcatcta 840
gacaattgta ctaaccttct tctctttcct ctcctgacag tccggaaagc caccatggaa 900
ttcagcagcc ccagcagaga ggaatgcccc aagcctctga gccgggtgtc aatcatggcc 960
ggatctctga caggactgct gctgcttcag gccgtgtctt gggcttctgg cgctagacct 1020
tgcatcccca agagcttcgg ctacagcagc gtcgtgtgcg tgtgcaatgc cacctactgc 1080
gacagcttcg accctcctac ctttcctgct ctgggcacct tcagcagata cgagagcacc 1140
agatccggca gacggatgga actgagcatg ggacccatcc aggccaatca cacaggcact 1200
ggcctgctgc tgacactgca gcctgagcag aaattccaga aagtgaaagg cttcggcgga 1260
gccatgacag atgccgccgc tctgaatatc ctggctctgt ctccaccagc tcagaacctg 1320
ctgctcaaga gctacttcag cgaggaaggc atcggctaca acatcatcag agtgcccatg 1380
gccagctgcg acttcagcat caggacctac acctacgccg acacacccga cgatttccag 1440
ctgcacaact tcagcctgcc tgaagaggac accaagctga agatccctct gatccacaga 1500
gccctgcagc tggcacaaag acccgtgtca ctgctggcct ctccatggac atctcccacc 1560
tggctgaaaa caaatggcgc cgtgaatggc aagggcagcc tgaaaggcca acctggcgac 1620
atctaccacc agacctgggc cagatacttc gtgaagttcc tggacgccta tgccgagcac 1680
aagctgcagt tttgggccgt gacagccgag aacgaacctt ctgctggact gctgagcggc 1740

```
taccccttc agtgcctggg ctttacaccc gagcaccagc gggactttat cgcccgtgat   1800
ctgggaccca cactggccaa tagcacccac cataatgtgc ggctgctgat gctggacgac   1860
cagagactgc ttctgcccca ctgggctaaa gtggtgctga cagatcctga ggccgccaaa   1920
tacgtgcacg gaatcgccgt gcactggtat ctggactttc tggcccctgc caaggccaca   1980
ctgggagaga cacacagact gttccccaac accatgctgt tcgccagcga agcctgtgtg   2040
ggcagcaagt tttgggaaca gagcgtgcgg ctcggcagct gggatagagg catgcagtac   2100
agccacagca tcatcaccaa cctgctgtac cacgtcgtcg gctggaccga ctggaatctg   2160
gccctgaatc ctgaaggcgg ccctaactgg gtccgaaact tcgtggacag ccccatcatc   2220
gtggacatca ccaaggacac cttctacaag cagcccatgt tctaccacct gggacacttc   2280
agcaagttca tccccgaggg ctctcagcgc gttggactgg tggcttccca gaagaacgat   2340
ctggacgccg tggctctgat gcaccctgat ggatctgctg tggtggtggt cctgaaccgc   2400
agcagcaaag atgtgcccct gaccatcaag gatcccgccg tgggattcct ggaaacaatc   2460
agccctggct actccatcca cacctacctg tggcgtagac agtgattgtg gccgaaccgc   2520
cgaactcaga ggccggcccc agaaaacccg agcgagtagg gggcggcgcg caggagggag   2580
gagaactggg ggcgcgggag gctggtgggt gtgggggtg gagatgtaga agatgtgacg   2640
ccgcggcccg gcgggtgcca gattagcgga cgcggtgccc gcggttgcaa cgggatcccg   2700
ggcgctgcag cttgggaggc ggctctcccc aggcggcgtc cgcggagaca cccatccgtg   2760
aaccccaggt cccgggccgc cggctcgccg cgcaccaggg gccggcggac agaagagcgg   2820
ccgagcggct cgaggctggg ggaccgcggg cgcggccgcg cgctgccggg cgggaggctg   2880
gggggccggg gccggggccg tgccccggag cgggtcggag gccggggccg gggccggggg   2940
acggcggctc cccgcgcggc tccagcggct cggggatccc ggccgggccc cgcagggacc   3000
atgatggaga agggccccgt gcgcgccccc gccgagaagc cccgcggcgc ccgctgcagc   3060
aacggcttcc ccgagcgcga cccccccgc cccggcccca gccgccccgc cgagaagccc   3120
ccccgccccg aggccaagag cgcccagccc gccgacggct ggaagggcga gcgcccccgc   3180
agcgaggagg acaacgagct gaacctgccc aacctggccg ccgcctacag cagcatcctg   3240
agcagcctgg gcgagaaccc ccagcgccag ggcctgctga agaccccctg gcgcgccgcc   3300
agcgccatgc agttcttcac caagggctac caggagacca tcagcgacgt gctgaacgac   3360
gccatcttcg acgaggacca cgacgagatg gtgatcgtga aggacatcga catgttcagc   3420
atgtgcgagc accacctggt gcccttcgtg ggcaaggtgc acatcggcta cctgcccaac   3480
aagcaggtgc tgggcctgag caagctggcc cgcatcgtgg agatctacag ccgccgcctg   3540
caggtgcagg agcgcctgac caagcagatc gccgtggcca tcaccgaggc cctgcgcccc   3600
gccggcgtgg gcgtggtggt ggaggccacc cacatgtgca tggtgatgcg cggcgtgcag   3660
aagatgaaca gcaagaccgt gaccagcacc atgctgggcg tgttccgcga ggaccccaag   3720
acccgcgagg agttcctgac cctgatccgc agctgacaat tgttaattaa gtttaaaccc   3780
tcgaggccgc aagccgcatc gataccgtcg actagagctc gctgatcagc ctcgactgtg   3840
ccttctagtt gccagccatc tgttgtttgc ccctcccccg tgccttcctt gaccctggaa   3900
ggtgccactc ccactgtcct ttcctaataa aatgaggaaa ttgcatcgca ttgtctgagt   3960
aggtgtcatt ctattctggg gggtggggtg gggcaggaca gcaaggggga ggattgggaa   4020
gacaatagca ggcatgctgg ggagagatcc acgataacaa acagcttttt tggggtgaac   4080
```

```
atattgactg aattccctgc aggttggcca ctccctctct gcgcgctcgc tcgctcactg   4140
aggccgcccg ggcaaagccc gggcgtcggg cgacctttgg tcgcccggcc tcagtgagcg   4200
agcgagcgcg cagagaggga gtggccaact ccatcactag gggttcctgc ggccgctcgt   4260
acggtctcga ggaattcctg caggataact tgccaacctc attctaaaat gtatatagaa   4320
gcccaaaaga caataacaaa aatattcttg tagaacaaaa tgggaaagaa tgttccacta   4380
aatatcaaga tttagagcaa agcatgagat gtgtggggat agacagtgag gctgataaaa   4440
tagagtagag ctcagaaaca gacccattga tatatgtaag tgacctatga aaaaaatatg   4500
gcattttaca atgggaaaat gatggtcttt ttcttttta gaaaaacagg gaaatatatt   4560
tatatgtaaa aaataaaagg gaacccatat gtcataccat acacacaaaa aaattccagt   4620
gaattataag tctaaatgga gaaggcaaaa ctttaaatct tttagaaaat aatatagaag   4680
catgcagacc agcctggcca acatgatgaa accctctcta ctaataataa aatcagtaga   4740
actactcagg actactttga gtgggaagtc cttttctatg aagacttctt tggccaaaat   4800
taggctctaa atgcaaggag atagtgcatc atgcctggct gcacttactg ataaatgatg   4860
ttatcaccat ctttaaccaa atgcacagga acaagttatg gtactgatgt gctggattga   4920
gaaggagctc tacttccttg acaggacaca tttgtatcaa cttaaaaaag cagatttttg   4980
ccagcagaac tattcattca gaggtaggaa acttagaata gatgatgtca ctgattagca   5040
tggcttcccc atctccacag ctgcttccca cccaggttgc ccacagttga gtttgtccag   5100
tgctcagggc tgcccactct cagtaagaag ccccacacca gcccctctcc aaatatgttg   5160
gctgttcctt ccattaaagt gaccccactt tagagcagca agtggatttc tgtttcttac   5220
agttcaggaa ggaggagtca gctgtgagaa cctggagcct gagatgcttc taagtcccac   5280
tgctactggg gtcagggaag ccagactcca gcatcagcag tcaggagcac taagcccttg   5340
ccaacatcct gtttctcaga gaaactgctt ccattataat ggttgtcctt ttttaagcta   5400
tcaagccaaa caaccagtgt ctaccattat tctcatcacc tgaagccaag ggttctagca   5460
aaagtcaagc tgtcttgtaa tggttgatgt gcctccagct tctgtcttca gtcactccac   5520
tcttagcctg ctctgaatca actctgacca cagttccctg gagcccctgc cacctgctgc   5580
ccctgccacc ttctccatct gcagtgctgt gcagccttct gcactcttgc agagctaata   5640
ggtggagact tgaaggaaga ggaggaaagt ttctcataat agccttgctg caagctcaaa   5700
tgggaggtgg gcactgtgcc caggagcctt ggagcaaagg ctgtgcccaa cctctgactg   5760
catccaggtt tggtcttgac agagataaga agccctggct tttggagcca aaatctaggt   5820
cagacttagg caggattctc aaagtttatc agcagaacat gaggcagaag accctttctg   5880
ctccagcttc ttcaggctca accttcatca gaatagatag aaagagaggc tgtgagggtt   5940
cttaaaacag aagcaaatct gactcagaga ataaacaacc tcctagtaaa ctacagctta   6000
gacagagcat ctggtggtga gtgtgctcag tgtcctactc aactgtctgg tatcagccct   6060
catgaggact tctcttcttt ccctcataga cctccatctc tgttttcctt agcctgcaga   6120
aatctggatg gctattcaca gaatgcctgt gctttcagag ttgcattttt tctctggtat   6180
tctggttcaa gcatttgaag gtaggaaagg ttctccaagt gcaagaaagc cagccctgag   6240
cctcaactgc ctggctagtg tggtcagtag gatgcaaagg ctgttgaatg ccacaaggcc   6300
aaactttaac ctgtgtacca caagcctagc agcagaggca gctctgctca ctggaactct   6360
ctgtcttctt tctcctgagc cttttctttt cctgagtttt ctagctctcc tcaaccttac   6420
ctctgcccta cccaggacaa acccaagagc cactgtttct gtgatgtcct ctccagccct   6480
```

```
aattaggcat catgacttca gcctgacctt ccatgctcag aagcagtgct aatccacttc   6540
agatgagctg ctctatgcaa cacaggcaga gcctacaaac ctttgcacca gagccctcca   6600
catatcagtg tttgttcata ctcacttcaa cagcaaatgt gactgctgag attaagattt   6660
tacacaagat ggtctgtaat ttcacagtta gttttatccc attaggtatg aaagaattag   6720
cataattccc cttaaacatg aatgaatctt agatttttta ataaatagtt ttggaagtaa   6780
agacagagac atcaggagca caaggaatag cctgagagga caaacagaac aagaaagagt   6840
ctggaaatac acaggatgtt cttggcctcc tcaaagcaag tgcaagcaga tagtaccagc   6900
agccccaggc tatcagagcc cagtgaagag aagtaccatg aaagccacag ctctaaccac   6960
cctgttccag agtgacagac agtccccaag acaagccagc ctgagccaga gagagaactg   7020
caagagaaag tttctaattt aggttctgtt agattcagac aagtgcaggt catcctctct   7080
ccacagctac tcacctctcc agcctaacaa agcctgcagt ccacactcca accctggtgt   7140
ctcacctcct agcctctccc aacatcctgc tctctgacca tcttctgcat ctctcatctc   7200
accatctccc actgtctaca gcctactctt gcaactacca tctcattttc tgacatcctg   7260
tctacatctt ctgccatact ctgccatcta ccataccacc tcttaccatc taccacacca   7320
tcttttatct ccatccctct cagaagcctc caagctgaat cctgctttat gtgttcatct   7380
cagcccctgc atggaaagct gaccccagag gcagaactat tcccagagag cttggccaag   7440
aaaaacaaaa ctaccagcct ggccaggctc aggagtagta agctgcagtg tctgttgtgt   7500
tctagcttca acagctgcag gagttccact ctcaaatgct ccacatttct cacatcctcc   7560
tgattctggt cactacccat cttcaaagaa cagaatatct cacatcagca tactgtgaag   7620
gactagtcat gggtgcagct gctcagagct gcaaagtcat tctggatggt ggagagctta   7680
caaacatttc atgatgctcc ccccgctctg atggctggag cccaatccct acacagactc   7740
ctgctgtatg tgttttcctt tcactctgag ccacagccag agggcaggca ttcagtctcc   7800
tcttcaggct ggggctgggg cactgagaac tcacccaaca ccttgctctc actccttctg   7860
caaaacaaga aagagctttg tgctgcagta gccatgaaga atgaaaggaa ggctttaact   7920
aaaaaatgtc agagattatt ttcaacccct tactgtggat caccagcaag gaggaaacac   7980
aacacagaga catttttccc cctcaaatta tcaaaagaat cactgcattt gttaaagaga   8040
gcaactgaat caggaagcag agttttgaac atatcagaag ttaggaatct gcatcagaga   8100
caaatgcagt catggttgtt tgctgcatac cagccctaat cattagaagc ctcatggact   8160
tcaaacatca ttccctctga caagatgctc tagcctaact ccatgagata aaataaatct   8220
gcctttcaga gccaaagaag agtccaccag cttcttctca gtgtgaacaa gagctccagt   8280
caggttagtc agtccagtgc agtagaggag accagtctgc atcctctaat tttcaaaggc   8340
aagaagattt gtttaccctg gacaccaggc acaagtgagg tcacagagct cttagatatg   8400
cagtcctcat gagtgaggag actaaagcgc atgccatcaa gacttcagtg tagagaaaac   8460
ctccaaaaaa gcctcctcac tacttctgga atagctcaga ggccgaggcg gcctcggcct   8520
ctgcataaat aaaaaaaatt agtcagccat ggggcggaga atgggcggaa ctgggcggag   8580
ttaggggcgg gatgggcgga gttaggggcg ggactatggt tgctgactaa ttgagatgca   8640
tgctttgcat acttctgcct gctggggagc ctggggactt tccacacctg gttgctgact   8700
aattgagatg catgctttgc atacttctgc ctgctgggga gcctggggac tttccacacc   8760
ctaactgaca cacattccac agctgcatta atgaatcggc caacgcgcgg ggagaggcgg   8820
```

```
tttgcgtatt gggcgctctt ccgcttcctc gctcactgac tcgctgcgct cggtcgttcg   8880
gctgcggcga gcggtatcag ctcactcaaa ggcggtaata cggttatcca cagaatcagg   8940
ggataacgca ggaaagaaca tgtgagcaaa aggccagcaa aaggccagga accgtaaaaa   9000
ggccgcgttg ctggcgtttt tccataggct ccgcccccct gacgagcatc acaaaaatcg   9060
acgctcaagt cagaggtggc gaaacccgac aggactataa agataccagg cgtttccccc   9120
tggaagctcc ctcgtgcgct ctcctgttcc gaccctgccg cttaccggat acctgtccgc   9180
ctttctccct tcgggaagcg tggcgctttc tcatagctca cgctgtaggt atctcagttc   9240
ggtgtaggtc gttcgctcca agctgggctg tgtgcacgaa ccccccgttc agcccgaccg   9300
ctgcgcctta tccggtaact atcgtcttga gtccaacccg gtaagacacg acttatcgcc   9360
actggcagca gccactggta acaggattag cagagcgagg tatgtaggcg gtgctacaga   9420
gttcttgaag tggtggccta actacggcta cactagaaga acagtatttg gtatctgcgc   9480
tctgctgaag ccagttacct tcggaaaaag agttggtagc tcttgatccg gcaaacaaac   9540
caccgctggt agcggtggtt tttttgtttg caagcagcag attacgcgca gaaaaaaagg   9600
atctcaagaa gatcctttga tcttttctac ggggtctgac gctcagtgga acgaaaactc   9660
acgttaaggg attttggtca tgagattatc aaaaaggatc ttcacctaga tccttttaaa   9720
ttaaaaatga agttttaaat caatctaaag tatatatgag taaacttggt ctgacagtta   9780
ccaatgctta atcagtgagg cacctatctc agcgatctgt ctatttcgtt catccatagt   9840
tgcctgactc ctgcaaacca cgttgtgtct caaaatctct gatgttacat tgcacaagat   9900
aaaaatatat catcatgaac aataaaactg tctgcttaca taaacagtaa tacaaggggt   9960
gttatgagcc atattcaacg ggaaacgtct tgctcgaggc cgcgattaaa ttccaacatg  10020
gatgctgatt tatatgggta taaatgggct cgcgataatg tcgggcaatc aggtgcgaca  10080
atctatcgat tgtatgggaa gcccgatgcg ccagagttgt ttctgaaaca tggcaaaggt  10140
agcgttgcca atgatgttac agatgagatg gtcagactaa actggctgac ggaatttatg  10200
cctcttccga ccatcaagca ttttatccgt actcctgatg atgcatggtt actcaccact  10260
gcgatccccg ggaaaacagc attccaggta ttagaagaat atcctgattc aggtgaaaat  10320
attgttgatg cgctggcagt gttcctgcgc cggttgcatt cgattcctgt ttgtaattgt  10380
ccttttaaca gcgatcgcgt atttcgtctc gctcaggcgc aatcacgaat gaataacggt  10440
ttggttgatg cgagtgattt tgatgacgag cgtaatggct ggcctgttga acaagtctgg  10500
aaagaaatgc ataagctttt gccattctca ccggattcag tcgtcactca tggtgatttc  10560
tcacttgata accttatttt tgacgagggg aaattaatag gttgtattga tgttggacga  10620
gtcggaatcg cagaccgata ccaggatctt gccatcctat ggaactgcct cggtgagttt  10680
tctccttcat tacagaaacg gctttttcaa aaatatggta ttgataatcc tgatatgaat  10740
aaattgcagt ttcatttgat gctcgatgag tttttctaag ggcggcctgc caccataccc  10800
acgccgaaac aagcgctcat gagcccgaag tggcgagccc gatcttcccc atcggtgatg  10860
tcggcgatat aggcgccagc aaccgcacct gtggcgccgg tgatgagggc gcgccaagtc  10920
gacgtccggc agtc                                                    10934
```

<210> SEQ ID NO 54
<211> LENGTH: 11138
<212> TYPE: DNA
<213> ORGANISM: Artificial sequence
<220> FEATURE:
<223> OTHER INFORMATION: Synthetic polynucleotide

<400> SEQUENCE: 54

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg agtaagtcac    300
tgactgtcta tgcctgggaa agggtgggca ggagatgggg cagtgcagga aaagtggcac    360
tatgaaccct cctggtggcg aggggagggg ggtggtcctc gaacgccttg cagaactggc    420
ctggatacag agtggaccgg ctggccccat ctggaagact tcgagataca ctgttgtctt    480
actgcgctca acagtgtatc tcgaagtctt ccaaatggtg ccagccatcg cagcggggtg    540
caggaaatgg gggcagcccc cctttttggc tatccttcca cgtgttcttt tttgtatctt    600
ttgtgtttcc tagaaaacat ctcagtcacc accgtgatat cacaaggtcc cagggctggg    660
gtcagaaatt ctctcccgag ggaatgaagc cacaggagcc aagagcagga ggaccaaggc    720
cctggcgaag gccgtggcct cgttcaagta aaagatccta gtacagtgca ggtcccaatg    780
tgtactagga tcttttactt gaacggggac gccggcatcc gggctcagga ccccccctctc    840
tgccagaggc accaacacca gagttcacaa atcagtctcc tgccctttgc atgtagcaaa    900
gcagccctag gaatgcatct agacaattgt actaaccttc ttctctttcc tctcctgaca    960
gtccggaaag ccaccatgcc caccacccag cagagccccc aggacgagca ggagaagctg   1020
ctggacgagg ccatccaggc cgtgaaggtg cagagcttcc agatgaagcg ctgcctggac   1080
aagaacaagc tgatggacgc cctgaagcac gccagcaaca tgctgggcga gctgcgcacc   1140
agcatgctga gccccaagag ctactacgag ctgtacatgg ccatcagcga cgagctgcac   1200
tacctggagg tgtacctgac cgacgagttc gccaagggcc gcaaggtggc cgacctgtac   1260
gagctggtgc agtacgccgg caacatcatc ccccgcctgt acctgctgat caccgtgggc   1320
gtggtgtacg tgaagagctt cccccagagc cgcaaggaca tcctgaagga cctggtggag   1380
atgtgccgcg gcgtgcagca ccccctgcgc ggcctgttcc tgcgcaacta cctgctgcag   1440
tgcacccgca acatcctgcc cgacgagggc gagcccaccg acgaggagac caccggcgac   1500
atcagcgaca gcatggactt cgtgctgctg aacttcgccg agatgaacaa gctgtgggtg   1560
cgcatgcagc accagggcca cagccgcgac cgcgagaagc gcgagcgcga gcgccaggag   1620
ctgcgcatcc tggtgggcac caacctggtg cgcctgagcc agctggaggg cgtgaacgtg   1680
gagcgctaca agcagatcgt gctgaccggc atcctggagc aggtggtgaa ctgccgcgac   1740
gccctggccc aggagtacct gatggagtgc atcatccagg tgttccccga cgagttccac   1800
ctgcagaccc tgaacccctt cctgcgcgcc tgcgccgagc tgcaccagaa cgtgaacgtg   1860
aagaacatca tcatcgccct gatcgaccgc ctggccctgt tcgcccaccg cgaggacggc   1920
cccggcatcc ccgccgacat caagctgttc gacatcttca gccagcaggt ggccaccgtg   1980
atccagagcc gccaggacat gcccagcgag gacgtggtga gcctgcaggt gagcctgatc   2040
aacctggcca tgaagtgcta ccccgaccgc gtggactacg tggacaaggt gctggagacc   2100
accgtggaga tcttcaacaa gctgaacctg gagcacatcg ccaccagcag cgccgtgagc   2160
aaggagctga cccgcctgct gaagatcccc gtggacacct acaacaacat cctgaccgtg   2220
ctgaagctga agcacttcca cccccctgttc gagtacttcg actacgagag ccgcaagagc   2280
```

-continued

```
atgagctgct acgtgctgag caacgtgctg gactacaaca ccgagatcgt gagccaggac   2340
caggtggaca gcatcatgaa cctggtgagc accctgatcc aggaccagcc cgaccagccc   2400
gtggaggacc ccgaccccga ggacttcgcc gacgagcaga gcctggtggg ccgcttcatc   2460
cacctgctgc gcagcgagga ccccgaccag cagtacctga tcctgaacac cgcccgcaag   2520
cacttcggcg ccggcggcaa ccagcgcatc cgcttcaccc tgcccccct ggtgttcgcc   2580
gcctaccagc tggccttccg ctacaaggag aacagcaagg tggacgacaa gtgggagaag   2640
aagtgccaga agatcttcag cttcgcccac cagaccatca gcgccctgat caaggccgag   2700
ctggccgagc tgcccctgcg cctgttcctg cagggcgccc tggccgccgg cgagatcggc   2760
ttcgagaacc acgagaccgt ggcctacgag ttcatgagcc aggccttcag cctgtacgag   2820
gacgagatca gcgacagcaa ggcccagctg gccgccatca ccctgatcat cggcaccttc   2880
gagcgcatga agtgcttcag cgaggagaac cacgagcccc tgcgcaccca gtgcgccctg   2940
gccgccagca agctgctgaa gaagcccgac cagggccgcg ccgtgagcac ctgcgcccac   3000
ctgttctgga gcggccgcaa caccgacaag aacggcgagg agctgcacgg cggcaagcgc   3060
gtgatggagt gcctgaagaa ggccctgaag atcgccaacc agtgcatgga ccccagcctg   3120
caggtgcagc tgttcatcga gatcctgaac cgctacatct acttctacga gaaggagaac   3180
gacgccgtga ccatccaggt gctgaaccag ctgatccaga agatccgcga ggacctgccc   3240
aacctggaga gcagcgagga gaccgagcag atcaacaagc acttccacaa caccctggag   3300
cacctgcgcc tgcgccgcga gagccccgag agcgagggcc ccatctacga gggcctgatc   3360
ctgtgacaat tgttaattaa gtttaaaccc tcgaggccgc aagcttatcg ataatcaacc   3420
tctggattac aaaatttgtg aaagattgac tggtattctt aactatgttg ctccttttac   3480
gctatgtgga tacgctgctt taatgccttt gtatcatgct attgcttccc gtatggcttt   3540
cattttctcc tccttgtata aatcctggtt gctgtctctt tatgaggagt tgtggcccgt   3600
tgtcaggcaa cgtggcgtgg tgtgcactgt gtttgctgac gcaaccccca ctggttgggg   3660
cattgccacc acctgtcagc tcctttccgg gactttcgct ttccccctcc ctattgccac   3720
ggcggaactc atcgccgcct gccttgcccg ctgctggaca ggggctcggc tgttgggcac   3780
tgacaattcc gtggtgttgt cggggaaatc atcgtccttt ccttggctgc tcgcctgtgt   3840
tgccacctgg attctgcgcg ggacgtcctt ctgctacgtc ccttcggccc tcaatccagc   3900
ggaccttcct tcccgcggcc tgctgccggc tctgcggcct cttccgcgtc ttcgccttcg   3960
ccctcagacg agtcggatct ccctttgggc cgcctccccg catcgatacc gtcgactaga   4020
gctcgctgat cagcctcgac tgtgccttct agttgccagc catctgttgt ttgcccctcc   4080
cccgtgcctt ccttgaccct ggaaggtgcc actcccactg tcctttccta ataaaatgag   4140
gaaattgcat cgcattgtct gagtaggtgt cattctattc tggggggtgg ggtggggcag   4200
gacagcaagg gggaggattg ggaagacaat agcaggcatg ctggggagag atccacgata   4260
acaaacagct tttttggggt gaacatattg actgaattcc ctgcaggttg gccactccct   4320
ctctgcgcgc tcgctcgctc actgaggccg cccgggcaaa gcccgggcgt cgggcgacct   4380
ttggtcgccc ggcctcagtg agcgagcgag cgcgcagaga gggagtggcc aactccatca   4440
ctaggggttc ctgcggccgc tcgtacggtc tcgaggaatt cctgcaggat aacttgccaa   4500
cctcattcta aaatgtatat agaagcccaa aagacaataa caaaaatatt cttgtagaac   4560
aaaatgggaa agaatgttcc actaaatatc aagatttaga gcaaagcatg agatgtgtgg   4620
ggatagacag tgaggctgat aaaatagagt agagctcaga aacagaccca ttgatatatg   4680
```

```
taagtgacct atgaaaaaaa tatggcattt tacaatggga aaatgatggt ctttttcttt   4740
tttagaaaaa cagggaaata tatttatatg taaaaaataa aagggaaccc atatgtcata   4800
ccatacacac aaaaaaattc cagtgaatta taagtctaaa tggagaaggc aaaactttaa   4860
atcttttaga aaataatata gaagcatgca gaccagcctg gccaacatga tgaaaccctc   4920
tctactaata ataaaatcag tagaactact caggactact ttgagtggga agtccttttc   4980
tatgaagact tctttggcca aaattaggct ctaaatgcaa ggagatagtg catcatgcct   5040
ggctgcactt actgataaat gatgttatca ccatctttaa ccaaatgcac aggaacaagt   5100
tatggtactg atgtgctgga ttgagaagga gctctacttc cttgacagga cacatttgta   5160
tcaacttaaa aaagcagatt tttgccagca gaactattca ttcagaggta ggaaacttag   5220
aatagatgat gtcactgatt agcatggctt ccccatctcc acagctgctt cccacccagg   5280
ttgcccacag ttgagtttgt ccagtgctca gggctgccca ctctcagtaa gaagccccac   5340
accagcccct ctccaaatat gttggctgtt ccttccatta aagtgacccc actttagagc   5400
agcaagtgga tttctgtttc ttacagttca ggaaggagga gtcagctgtg agaacctgga   5460
gcctgagatg cttctaagtc ccactgctac tggggtcagg gaagccagac tccagcatca   5520
gcagtcagga gcactaagcc cttgccaaca tcctgtttct cagagaaact gcttccatta   5580
taatggttgt cctttttttaa gctatcaagc caaacaacca gtgtctacca ttattctcat   5640
cacctgaagc caagggttct agcaaaagtc aagctgtctt gtaatggttg atgtgcctcc   5700
agcttctgtc ttcagtcact ccactcttag cctgctctga atcaactctg accacagttc   5760
cctggagccc ctgccacctg ctgcccctgc caccttctcc atctgcagtg ctgtgcagcc   5820
ttctgcactc ttgcagagct aataggtgga gacttgaagg aagaggagga aagtttctca   5880
taatagcctt gctgcaagct caaatgggag gtgggcactg tgcccaggag ccttggagca   5940
aaggctgtgc ccaacctctg actgcatcca ggtttggtct tgacagagat aagaagccct   6000
ggcttttgga gccaaaatct aggtcagact taggcaggat tctcaaagtt tatcagcaga   6060
acatgaggca gaagaccctt tctgctccag cttcttcagg ctcaaccttc atcagaatag   6120
atagaaagag aggctgtgag ggttcttaaa acagaagcaa atctgactca gagaataaac   6180
aacctcctag taaactacag cttagacaga gcatctggtg gtgagtgtgc tcagtgtcct   6240
actcaactgt ctggtatcag ccctcatgag gacttctctt ctttccctca tagacctcca   6300
tctctgtttt ccttagcctg cagaaatctg gatggctatt cacagaatgc ctgtgctttc   6360
agagttgcat tttttctctg gtattctggt tcaagcattt gaaggtagga aaggttctcc   6420
aagtgcaaga aagccagccc tgagcctcaa ctgcctggct agtgtggtca gtaggatgca   6480
aaggctgttg aatgccacaa ggccaaactt taacctgtgt accacaagcc tagcagcaga   6540
ggcagctctg ctcactggaa ctctctgtct tctttctcct gagccttttc ttttcctgag   6600
ttttctagct ctcctcaacc ttacctctgc cctacccagg acaaacccaa gagccactgt   6660
ttctgtgatg tcctctccag ccctaattag gcatcatgac ttcagcctga ccttccatgc   6720
tcagaagcag tgctaatcca cttcagatga gctgctctat gcaacacagg cagagcctac   6780
aaacctttgc accagagccc tccacatatc agtgtttgtt catactcact tcaacagcaa   6840
atgtgactgc tgagattaag attttacaca agatggtctg taatttcaca gttagtttta   6900
tcccattagg tatgaaagaa ttagcataat tccccttaaa catgaatgaa tcttagattt   6960
tttaataaat agttttggaa gtaaagacag agacatcagg agcacaagga atagcctgag   7020
```

```
aggacaaaca gaacaagaaa gagtctggaa atacacagga tgttcttggc ctcctcaaag   7080
caagtgcaag cagatagtac cagcagcccc aggctatcag agcccagtga agagaagtac   7140
catgaaagcc acagctctaa ccaccctgtt ccagagtgac agacagtccc caagacaagc   7200
cagcctgagc cagagagaga actgcaagag aaagtttcta atttaggttc tgttagattc   7260
agacaagtgc aggtcatcct ctctccacag ctactcacct ctccagccta acaaagcctg   7320
cagtccacac tccaaccctg gtgtctcacc tcctagcctc tcccaacatc ctgctctctg   7380
accatcttct gcatctctca tctcaccatc tcccactgtc tacagcctac tcttgcaact   7440
accatctcat tttctgacat cctgtctaca tcttctgcca tactctgcca tctaccatac   7500
cacctcttac catctaccac accatctttt atctccatcc ctctcagaag cctccaagct   7560
gaatcctgct ttatgtgttc atctcagccc ctgcatggaa agctgacccc agaggcagaa   7620
ctattcccag agagcttggc caagaaaaac aaaactacca gcctggccag gctcaggagt   7680
agtaagctgc agtgtctgtt gtgttctagc ttcaacagct gcaggagttc cactctcaaa   7740
tgctccacat ttctcacatc ctcctgattc tggtcactac ccatcttcaa agaacagaat   7800
atctcacatc agcatactgt gaaggactag tcatgggtgc agctgctcag agctgcaaag   7860
tcattctgga tggtggagag cttacaaaca tttcatgatg ctcccccgc tctgatggct    7920
ggagcccaat ccctacacag actcctgctg tatgtgtttt cctttcactc tgagccacag   7980
ccagagggca ggcattcagt ctcctcttca ggctggggct ggggcactga gaactcaccc   8040
aacaccttgc tctcactcct tctgcaaaac aagaaagagc tttgtgctgc agtagccatg   8100
aagaatgaaa ggaaggcttt aactaaaaaa tgtcagagat tattttcaac cccttactgt   8160
ggatcaccag caaggaggaa acacaacaca gagacatttt ttcccctcaa attatcaaaa   8220
gaatcactgc atttgttaaa gagagcaact gaatcaggaa gcagagtttt gaacatatca   8280
gaagttagga atctgcatca gagacaaatg cagtcatggt tgtttgctgc ataccagccc   8340
taatcattag aagcctcatg gacttcaaac atcattccct ctgacaagat gctctagcct   8400
aactccatga gataaaataa atctgccttt cagagccaaa gaagagtcca ccagcttctt   8460
ctcagtgtga acaagagctc cagtcaggtt agtcagtcca gtgcagtaga ggagaccagt   8520
ctgcatcctc taattttcaa aggcaagaag atttgtttac cctggacacc aggcacaagt   8580
gaggtcacag agctcttaga tatgcagtcc tcatgagtga ggagactaaa gcgcatgcca   8640
tcaagacttc agtgtagaga aaacctccaa aaaagcctcc tcactacttc tggaatagct   8700
cagaggccga ggcggcctcg gcctctgcat aaataaaaaa aattagtcag ccatggggcg   8760
gagaatgggc ggaactgggc ggagttaggg gcgggatggg cggagttagg ggcgggacta   8820
tggttgctga ctaattgaga tgcatgcttt gcatacttct gcctgctggg gagcctgggg   8880
actttccaca cctggttgct gactaattga gatgcatgct ttgcatactt ctgcctgctg   8940
gggagcctgg ggactttcca caccctaact gacacacatt ccacagctgc attaatgaat   9000
cggccaacgc gcggggagag gcggtttgcg tattgggcgc tcttccgctt cctcgctcac   9060
tgactcgctg cgctcggtcg ttcggctgcg gcgagcggta tcagctcact caaaggcggt   9120
aatacggtta tccacagaat caggggataa cgcaggaaag aacatgtgag caaaaggcca   9180
gcaaaaggcc aggaaccgta aaaaggccgc gttgctggcg tttttccata ggctccgccc   9240
ccctgacgag catcacaaaa atcgacgctc aagtcagagg tggcgaaacc cgacaggact   9300
ataaagatac caggcgtttc cccctggaag ctccctcgtg cgctctcctg ttccgaccct   9360
gccgcttacc ggatacctgt ccgcctttct cccttcggga agcgtggcgc tttctcatag   9420
```

```
ctcacgctgt aggtatctca gttcggtgta ggtcgttcgc tccaagctgg gctgtgtgca   9480

cgaacccccc gttcagcccg accgctgcgc cttatccggt aactatcgtc ttgagtccaa   9540

cccggtaaga cacgacttat cgccactggc agcagccact ggtaacagga ttagcagagc   9600

gaggtatgta ggcggtgcta cagagttctt gaagtggtgg cctaactacg gctacactag   9660

aagaacagta tttggtatct gcgctctgct gaagccagtt accttcggaa aaagagttgg   9720

tagctcttga tccggcaaac aaaccaccgc tggtagcggt ggtttttttg tttgcaagca   9780

gcagattacg cgcagaaaaa aaggatctca agaagatcct ttgatctttt ctacggggtc   9840

tgacgctcag tggaacgaaa actcacgtta agggattttg gtcatgagat tatcaaaaag   9900

gatcttcacc tagatccttt taaattaaaa atgaagtttt aaatcaatct aaagtatata   9960

tgagtaaact tggtctgaca gttaccaatg cttaatcagt gaggcaccta tctcagcgat  10020

ctgtctattt cgttcatcca tagttgcctg actcctgcaa accacgttgt gtctcaaaat  10080

ctctgatgtt acattgcaca agataaaaat atatcatcat gaacaataaa actgtctgct  10140

tacataaaca gtaatacaag gggtgttatg agccatattc aacgggaaac gtcttgctcg  10200

aggccgcgat taaattccaa catggatgct gatttatatg ggtataaatg ggctcgcgat  10260

aatgtcgggc aatcaggtgc gacaatctat cgattgtatg ggaagcccga tgcgccagag  10320

ttgtttctga aacatggcaa aggtagcgtt gccaatgatg ttacagatga gatggtcaga  10380

ctaaactggc tgacggaatt tatgcctctt ccgaccatca agcattttat ccgtactcct  10440

gatgatgcat ggttactcac cactgcgatc cccgggaaaa cagcattcca ggtattagaa  10500

gaatatcctg attcaggtga aaatattgtt gatgcgctgg cagtgttcct gcgccggttg  10560

cattcgattc ctgtttgtaa ttgtcctttt aacagcgatc gcgtatttcg tctcgctcag  10620

gcgcaatcac gaatgaataa cggtttggtt gatgcgagtg attttgatga cgagcgtaat  10680

ggctggcctg ttgaacaagt ctggaaagaa atgcataagc ttttgccatt ctcaccggat  10740

tcagtcgtca ctcatggtga tttctcactt gataacctta tttttgacga ggggaaatta  10800

ataggttgta ttgatgttgg acgagtcgga atcgcagacc gataccagga tcttgccatc  10860

ctatggaact gcctcggtga gttttctcct tcattacaga aacggctttt tcaaaaatat  10920

ggtattgata atcctgatat gaataaattg cagtttcatt tgatgctcga tgagtttttc  10980

taagggcggc ctgccaccat acccacgccg aaacaagcgc tcatgagccc gaagtggcga  11040

gcccgatctt ccccatcggt gatgtcggcg atataggcgc cagcaaccgc acctgtggcg  11100

ccggtgatga gggcgcgcca agtcgacgtc cggcagtc                          11138
```

<210> SEQ ID NO 55
<211> LENGTH: 242
<212> TYPE: PRT
<213> ORGANISM: Artificial sequence
<220> FEATURE:
<223> OTHER INFORMATION: Synthetic polypeptide

<400> SEQUENCE: 55

```
Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
            20                  25                  30

Glu Glu Cys Thr Val Thr Gly Phe Leu Arg Asp Lys Leu Gln Tyr Arg
        35                  40                  45

Ser Arg Leu Gln Tyr Met Lys His Tyr Phe Pro Ile Asn Tyr Lys Ile
```

```
    50                  55                  60

Ser Val Pro Tyr Glu Gly Val Phe Arg Ile Ala Asn Val Thr Arg Leu
65                  70                  75                  80

Gln Arg Ala Gln Val Ser Glu Arg Glu Leu Arg Tyr Leu Trp Val Leu
                85                  90                  95

Val Ser Leu Ser Ala Thr Glu Ser Val Gln Asp Val Leu Leu Glu Gly
            100                 105                 110

His Pro Ser Trp Lys Tyr Leu Gln Glu Val Glu Thr Leu Leu Leu Asn
        115                 120                 125

Val Gln Gln Gly Leu Thr Asp Val Glu Val Ser Pro Lys Val Glu Ser
    130                 135                 140

Val Leu Ser Leu Leu Asn Ala Pro Gly Pro Asn Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Ser Val Leu Asn Trp Gln Asp Cys Glu
            180                 185                 190

Val Pro Ser Pro Gln Ser Cys Ser Pro Glu Pro Ser Leu Gln Tyr Ala
        195                 200                 205

Ala Thr Gln Leu Tyr Pro Pro Pro Pro Trp Ser Pro Ser Ser Pro Pro
    210                 215                 220

His Ser Thr Gly Ser Val Arg Pro Val Arg Ala Gln Gly Glu Gly Leu
225                 230                 235                 240

Leu Pro
```

<210> SEQ ID NO 56
<211> LENGTH: 729
<212> TYPE: DNA
<213> ORGANISM: Artificial sequence
<220> FEATURE:
<223> OTHER INFORMATION: Synthetic polynucleotide

<400> SEQUENCE: 56

```
atgccccgcg gcttcacctg gctgcgctac ctgggcatct tcctgggcgt ggccctgggc     60

aacgagcccc tggagatgtg gcccctgacc cagaacgagg agtgcaccgt gaccggcttc    120

ctgcgcgaca agctgcagta ccgcagccgc ctgcagtaca tgaagcacta cttccccatc    180

aactacaaga tcagcgtgcc ctacgagggc gtgttccgca tcgccaacgt gacccgcctg    240

cagcgcgccc aggtgagcga gcgcgagctg cgctacctgt gggtgctggt gagcctgagc    300

gccaccgaga gcgtgcagga cgtgctgctg gagggccacc ccagctggaa gtacctgcag    360

gaggtggaga ccctgctgct gaacgtgcag cagggcctga ccgacgtgga ggtgagcccc    420

aaggtggaga gcgtgctgag cctgctgaac gcccccggcc ccaacctgaa gctggtgcgc    480

cccaaggccc tgctggacaa ctgcttccgc gtgatggagc tgctgtactg cagctgctgc    540

aagcagagca gcgtgctgaa ctggcaggac tgcgaggtgc ccagccccca gagctgcagc    600

cccgagccca gcctgcagta cgccgccacc cagctgtacc cccccccccc ctggagcccc    660

agcagccccc cccacagcac cggcagcgtg cgccccgtgc gcgcccaggg cgagggcctg    720

ctgccctaa                                                            729
```

<210> SEQ ID NO 57
<211> LENGTH: 230
<212> TYPE: PRT
<213> ORGANISM: Artificial sequence
<220> FEATURE:

<223> OTHER INFORMATION: Synthetic polypeptide

<400> SEQUENCE: 57

```
Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45

Ala Trp Cys Arg Gln Leu Gly Glu Lys Gly Pro Cys Gln Arg Val Val
    50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
        115                 120                 125

Leu Ala Asp Pro Leu Asp His Arg Asp Ala Gly Asp Leu Trp Phe Pro
    130                 135                 140

Gly Glu Ser Glu Ser Phe Glu Asp Ala His Val Glu His Ser Ile Ser
145                 150                 155                 160

Arg Ser Leu Leu Glu Gly Glu Ile Pro Phe Pro Pro Thr Ser Ile Leu
                165                 170                 175

Leu Leu Leu Ala Cys Ile Phe Leu Ile Lys Ile Leu Ala Ala Ser Ala
            180                 185                 190

Leu Trp Ala Ala Ala Trp His Gly Gln Lys Pro Gly Thr His Pro Pro
        195                 200                 205

Ser Glu Leu Asp Cys Gly His Asp Pro Gly Tyr Gln Leu Gln Thr Leu
    210                 215                 220

Pro Gly Leu Arg Asp Thr
225                 230
```

<210> SEQ ID NO 58
<211> LENGTH: 690
<212> TYPE: DNA
<213> ORGANISM: Artificial sequence
<220> FEATURE:
<223> OTHER INFORMATION: Synthetic polynucleotide

<400> SEQUENCE: 58

```
atggagcccc tgcgcctgct gatcctgctg ttcgtgaccg agctgagcgg cgcccacaac      60

accaccgtgt tccagggcgt ggccggccag agcctgcagg tgagctgccc ctacgacagc     120

atgaagcact ggggccgccg caaggcctgg tgccgccagc tgggcgagaa gggcccctgc     180

cagcgcgtgg tgagcaccca caacctgtgg ctgctgagct tcctgcgccg ctggaacggc     240

agcaccgcca tcaccgacga caccctgggc ggcaccctga ccatcaccct gcgcaacctg     300

cagccccacg acgccggcct gtaccagtgc cagagcctgc acggcagcga ggccgacacc     360

ctgcgcaagg tgctggtgga ggtgctggcc gacccccctgg accaccgcga cgccggcgac     420

ctgtggttcc ccggcgagag cgagagcttc gaggacgccc acgtggagca cagcatcagc     480

cgcagcctgc tggagggcga gatccccttc ccccccacca gcatcctgct gctgctggcc     540

tgcatcttcc tgatcaagat cctggccgcc agcgccctgt gggccgccgc ctggcacggc     600
```

```
cagaagcccg gcacccaccc ccccagcgag ctggactgcg gccacgaccc cggctaccag    660

ctgcagaccc tgcccggcct gcgcgacacc                                     690


<210> SEQ ID NO 59
<211> LENGTH: 11060
<212> TYPE: DNA
<213> ORGANISM: Artificial sequence
<220> FEATURE:
<223> OTHER INFORMATION: Synthetic polynucleotide

<400> SEQUENCE: 59

ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg agggcggagt    300

tagggcggag ccaatcagcg tgcgccgttc cgaaagttgc cttttatggc tgggcggaga    360

atgggcggtg aacgccgatg attatataag gacgcgccgg gtgtggcaca gctagttccg    420

tcgcagccgg gatttgggtc gcggttcttg tttgtggatc cctgtgatcg tcacttggta    480

agtcactgac tgtctatgcc tgggaaaggg tgggcaggag atggggcagt gcaggaaaag    540

tggcactatg aaccctcctg gtggcgaggg gaggggggtg gtcctcgaac gccttgcaga    600

actggcctgg atacagagtg gaccggctgg ccccatctgg aagacttcga gatacactgt    660

tgtcttactg cgctcaacag tgtatctcga agtcttccaa atggtgccag ccatcgcagc    720

ggggtgcagg aaatgggggc agcccccctt tttggctatc cttccacgtg ttcttttttg    780

tatcttttgt gtttcctaga aaacatctca gtcaccaccg cagccctagg aatgcatcta    840

gacaattgta ctaaccttct tctctttcct ctcctgacag tccggaaagc caccatggaa    900

ttcagcagcc ccagcagaga ggaatgcccc aagcctctga gccgggtgtc aatcatggcc    960

ggatctctga caggactgct gctgcttcag gccgtgtctt gggcttctgg cgctagacct   1020

tgcatcccca agagcttcgg ctacagcagc gtcgtgtgcg tgtgcaatgc cacctactgc   1080

gacagcttcg accctcctac ctttcctgct ctgggcacct tcagcagata cgagagcacc   1140

agatccggca gacggatgga actgagcatg ggacccatcc aggccaatca cacaggcact   1200

ggcctgctgc tgacactgca gcctgagcag aaattccaga aagtgaaagg cttcggcgga   1260

gccatgacag atgccgccgc tctgaatatc ctggctctgt ctccaccagc tcagaacctg   1320

ctgctcaaga gctacttcag cgaggaaggc atcggctaca acatcatcag agtgcccatg   1380

gccagctgcg acttcagcat caggacctac acctacgccg acacacccga cgatttccag   1440

ctgcacaact tcagcctgcc tgaagaggac accaagctga agatccctct gatccacaga   1500

gccctgcagc tggcacaaag acccgtgtca ctgctggcct ctccatggac atctcccacc   1560

tggctgaaaa caaatggcgc cgtgaatggc aagggcagcc tgaaaggcca acctggcgac   1620

atctaccacc agacctgggc cagatacttc gtgaagttcc tggacgccta tgccgagcac   1680

aagctgcagt tttgggccgt gacagccgag aacgaacctt ctgctggact gctgagcggc   1740

taccccttc agtgcctggg ctttacaccc gagcaccagc gggactttat cgcccgtgat    1800

ctgggaccca cactggccaa tagcacccac cataatgtgc ggctgctgat gctggacgac   1860

cagagactgc ttctgcccca ctgggctaaa gtggtgctga cagatcctga ggccgccaaa   1920

tacgtgcacg gaatcgccgt gcactggtat ctggactttc tggcccctgc caaggccaca   1980
```

```
ctgggagaga cacacagact gttccccaac accatgctgt tcgccagcga agcctgtgtg   2040
ggcagcaagt tttgggaaca gagcgtgcgg ctcggcagct gggatagagg catgcagtac   2100
agccacagca tcatcaccaa cctgctgtac cacgtcgtcg gctggaccga ctggaatctg   2160
gccctgaatc ctgaaggcgg ccctaactgg gtccgaaact tcgtggacag ccccatcatc   2220
gtggacatca ccaaggacac cttctacaag cagcccatgt tctaccacct gggacacttc   2280
agcaagttca tccccgaggg ctctcagcgc gttggactgg tggcttccca gaagaacgat   2340
ctggacgccg tggctctgat gcaccctgat ggatctgctg tggtggtggt cctgaaccgc   2400
agcagcaaag atgtgcccct gaccatcaag gatcccgccg tgggattcct ggaaacaatc   2460
agccctggct actccatcca cacctacctg tggcgtagac aggagggcag aggaagtctt   2520
ctgacatgcg gagacgtgga agagaatccc ggccctatgc ccgcggctt cacctggctg   2580
cgctacctgg gcatcttcct gggcgtggcc ctgggcaacg agcccctgga gatgtggccc   2640
ctgacccaga acgaggagtg caccgtgacc ggcttcctgc gcgacaagct gcagtaccgc   2700
agccgcctgc agtacatgaa gcactacttc cccatcaact acaagatcag cgtgccctac   2760
gagggcgtgt tccgcatcgc caacgtgacc cgcctgcagc gcgcccaggt gagcgagcgc   2820
gagctgcgct acctgtgggt gctggtgagc ctgagcgcca ccgagagcgt gcaggacgtg   2880
ctgctggagg gccaccccag ctggaagtac ctgcaggagg tggagaccct gctgctgaac   2940
gtgcagcagg gcctgaccga cgtggaggtg agccccaagg tggagagcgt gctgagcctg   3000
ctgaacgccc ccggccccaa cctgaagctg gtgcgcccca aggccctgct ggacaactgc   3060
ttccgcgtga tggagctgct gtactgcagc tgctgcaagc agagcagcgt gctgaactgg   3120
caggactgcg aggtgcccag cccccagagc tgcagccccg agcccagcct gcagtacgcc   3180
gccacccagc tgtacccccc cccccctgg agccccagca gccccccca cagcaccggc   3240
agcgtgcgcc ccgtgcgcgc ccagggcgag ggcctgctgc cctaatgaca attgttaatt   3300
aagtttaaac cctcgaggcc gcaagcttat cgataatcaa cctctggatt acaaaatttg   3360
tgaaagattg actggtattc ttaactatgt tgctcctttt acgctatgtg gatacgctgc   3420
tttaatgcct ttgtatcatg ctattgcttc ccgtatggct ttcattttct cctccttgta   3480
taaatcctgg ttgctgtctc tttatgagga gttgtggccc gttgtcaggc aacgtggcgt   3540
ggtgtgcact gtgtttgctg acgcaacccc cactggttgg ggcattgcca ccacctgtca   3600
gctcctttcc gggactttcg ctttccccct ccctattgcc acggcggaac tcatcgccgc   3660
ctgccttgcc cgctgctgga caggggctcg gctgttgggc actgacaatt ccgtggtgtt   3720
gtcggggaaa tcatcgtcct ttccttggct gctcgcctgt gttgccacct ggattctgcg   3780
cgggacgtcc ttctgctacg tcccttcggc cctcaatcca gcggaccttc cttcccgcgg   3840
cctgctgccg gctctgcggc ctcttccgcg tcttcgcctt cgccctcaga cgagtcggat   3900
ctccctttgg gccgcctccc cgcatcgata ccgtcgacta gagctcgctg atcagcctcg   3960
actgtgcctt ctagttgcca gccatctgtt gtttgcccct cccccgtgcc ttccttgacc   4020
ctggaaggtg ccactcccac tgtcctttcc taataaaatg aggaaattgc atcgcattgt   4080
ctgagtaggt gtcattctat tctggggggt ggggtggggc aggacagcaa gggggaggat   4140
tgggaagaca atagcaggca tgctggggag agatccacga taacaaacag ctttttttggg   4200
gtgaacatat tgactgaatt ccctgcaggt tggccactcc ctctctgcgc gctcgctcgc   4260
tcactgaggc cgcccgggca aagcccgggc gtcgggcgac ctttggtcgc ccggcctcag   4320
```

```
tgagcgagcg agcgcgcaga gagggagtgg ccaactccat cactaggggt tcctgcggcc   4380
gctcgtacgg tctcgaggaa ttcctgcagg ataacttgcc aacctcattc taaaatgtat   4440
atagaagccc aaaagacaat aacaaaaata ttcttgtaga acaaaatggg aaagaatgtt   4500
ccactaaata tcaagattta gagcaaagca tgagatgtgt ggggatagac agtgaggctg   4560
ataaaataga gtagagctca gaaacagacc cattgatata tgtaagtgac ctatgaaaaa   4620
aatatggcat tttacaatgg gaaaatgatg gtctttttct tttttagaaa aacagggaaa   4680
tatatttata tgtaaaaaat aaaagggaac ccatatgtca taccatacac acaaaaaaat   4740
tccagtgaat tataagtcta aatggagaag gcaaaacttt aaatctttta gaaaataata   4800
tagaagcatg cagaccagcc tggccaacat gatgaaaccc tctctactaa taataaaatc   4860
agtagaacta ctcaggacta ctttgagtgg gaagtccttt tctatgaaga cttctttggc   4920
caaaattagg ctctaaatgc aaggagatag tgcatcatgc ctggctgcac ttactgataa   4980
atgatgttat caccatcttt aaccaaatgc acaggaacaa gttatggtac tgatgtgctg   5040
gattgagaag gagctctact tccttgacag gacacatttg tatcaactta aaaaagcaga   5100
tttttgccag cagaactatt cattcagagg taggaaactt agaatagatg atgtcactga   5160
ttagcatggc ttccccatct ccacagctgc ttcccaccca ggttgcccac agttgagttt   5220
gtccagtgct cagggctgcc cactctcagt aagaagcccc acaccagccc ctctccaaat   5280
atgttggctg ttccttccat taaagtgacc ccactttaga gcagcaagtg gatttctgtt   5340
tcttacagtt caggaaggag gagtcagctg tgagaacctg gagcctgaga tgcttctaag   5400
tcccactgct actggggtca gggaagccag actccagcat cagcagtcag gagcactaag   5460
cccttgccaa catcctgttt ctcagagaaa ctgcttccat tataatggtt gtcctttttt   5520
aagctatcaa gccaaacaac cagtgtctac cattattctc atcacctgaa gccaagggtt   5580
ctagcaaaag tcaagctgtc ttgtaatggt tgatgtgcct ccagcttctg tcttcagtca   5640
ctccactctt agcctgctct gaatcaactc tgaccacagt tccctggagc ccctgccacc   5700
tgctgcccct gccaccttct ccatctgcag tgctgtgcag ccttctgcac tcttgcagag   5760
ctaataggtg gagacttgaa ggaagaggag gaaagtttct cataatagcc ttgctgcaag   5820
ctcaaatggg aggtgggcac tgtgcccagg agccttggag caaaggctgt gcccaacctc   5880
tgactgcatc caggtttggt cttgacagag ataagaagcc ctggcttttg gagccaaaat   5940
ctaggtcaga cttaggcagg attctcaaag tttatcagca gaacatgagg cagaagaccc   6000
tttctgctcc agcttcttca ggctcaacct tcatcagaat agatagaaag agaggctgtg   6060
agggttctta aaacagaagc aaatctgact cagagaataa acaacctcct agtaaactac   6120
agcttagaca gagcatctgg tggtgagtgt gctcagtgtc ctactcaact gtctggtatc   6180
agccctcatg aggacttctc ttctttccct catagacctc catctctgtt ttccttagcc   6240
tgcagaaatc tggatggcta ttcacagaat gcctgtgctt tcagagttgc atttttctc    6300
tggtattctg gttcaagcat ttgaaggtag gaaaggttct ccaagtgcaa gaaagccagc   6360
cctgagcctc aactgcctgg ctagtgtggt cagtaggatg caaaggctgt tgaatgccac   6420
aaggccaaac tttaacctgt gtaccacaag cctagcagca gaggcagctc tgctcactgg   6480
aactctctgt cttctttctc ctgagccttt tcttttcctg agttttctag ctctcctcaa   6540
ccttacctct gccctaccca ggacaaaccc aagagccact gtttctgtga tgtcctctcc   6600
agccctaatt aggcatcatg acttcagcct gaccttccat gctcagaagc agtgctaatc   6660
cacttcagat gagctgctct atgcaacaca ggcagagcct acaaaccttt gcaccagagc   6720
```

```
cctccacata tcagtgtttg ttcatactca cttcaacagc aaatgtgact gctgagatta   6780
agattttaca caagatggtc tgtaatttca cagttagttt tatcccatta ggtatgaaag   6840
aattagcata attcccctta aacatgaatg aatcttagat tttttaataa atagttttgg   6900
aagtaaagac agagacatca ggagcacaag gaatagcctg agaggacaaa cagaacaaga   6960
aagagtctgg aaatacacag gatgttcttg gcctcctcaa agcaagtgca agcagatagt   7020
accagcagcc ccaggctatc agagcccagt gaagagaagt accatgaaag ccacagctct   7080
aaccaccctg ttccagagtg acagacagtc cccaagacaa gccagcctga gccagagaga   7140
gaactgcaag agaaagtttc taatttaggt tctgttagat tcagacaagt gcaggtcatc   7200
ctctctccac agctactcac ctctccagcc taacaaagcc tgcagtccac actccaaccc   7260
tggtgtctca cctcctagcc tctcccaaca tcctgctctc tgaccatctt ctgcatctct   7320
catctcacca tctcccactg tctacagcct actcttgcaa ctaccatctc attttctgac   7380
atcctgtcta catcttctgc catactctgc catctaccat accacctctt accatctacc   7440
acaccatctt ttatctccat ccctctcaga agcctccaag ctgaatcctg ctttatgtgt   7500
tcatctcagc ccctgcatgg aaagctgacc ccagaggcag aactattccc agagagcttg   7560
gccaagaaaa acaaaactac cagcctggcc aggctcagga gtagtaagct gcagtgtctg   7620
ttgtgttcta gcttcaacag ctgcaggagt tccactctca aatgctccac atttctcaca   7680
tcctcctgat tctggtcact acccatcttc aaagaacaga atatctcaca tcagcatact   7740
gtgaaggact agtcatgggt gcagctgctc agagctgcaa agtcattctg gatggtggag   7800
agcttacaaa catttcatga tgctccccc gctctgatgg ctggagccca atccctacac   7860
agactcctgc tgtatgtgtt ttcctttcac tctgagccac agccagaggg caggcattca   7920
gtctcctctt caggctgggg ctggggcact gagaactcac ccaacacctt gctctcactc   7980
cttctgcaaa acaagaaaga gctttgtgct gcagtagcca tgaagaatga aaggaaggct   8040
ttaactaaaa aatgtcagag attattttca accccttact gtggatcacc agcaaggagg   8100
aaacacaaca cagagacatt ttttcccctc aaattatcaa aagaatcact gcatttgtta   8160
aagagagcaa ctgaatcagg aagcagagtt ttgaacatat cagaagttag gaatctgcat   8220
cagagacaaa tgcagtcatg gttgtttgct gcataccagc cctaatcatt agaagcctca   8280
tggacttcaa acatcattcc ctctgacaag atgctctagc ctaactccat gagataaaat   8340
aaatctgcct ttcagagcca aagaagagtc caccagcttc ttctcagtgt gaacaagagc   8400
tccagtcagg ttagtcagtc cagtgcagta gaggagacca gtctgcatcc tctaattttc   8460
aaaggcaaga agatttgttt accctggaca ccaggcacaa gtgaggtcac agagctctta   8520
gatatgcagt cctcatgagt gaggagacta aagcgcatgc catcaagact tcagtgtaga   8580
gaaaacctcc aaaaaagcct cctcactact tctggaatag ctcagaggcc gaggcggcct   8640
cggcctctgc ataaataaaa aaaattagtc agccatgggg cggagaatgg gcggaactgg   8700
gcggagttag gggcgggatg ggcggagtta ggggcgggac tatggttgct gactaattga   8760
gatgcatgct ttgcatactt ctgcctgctg gggagcctgg ggactttcca cacctggttg   8820
ctgactaatt gagatgcatg ctttgcatac ttctgcctgc tggggagcct ggggactttc   8880
cacaccctaa ctgacacaca ttccacagct gcattaatga atcggccaac gcgcggggag   8940
aggcggtttg cgtattgggc gctcttccgc ttcctcgctc actgactcgc tgcgctcggt   9000
cgttcggctg cggcgagcgg tatcagctca ctcaaaggcg gtaatacggt tatccacaga   9060
```

atcaggggat aacgcaggaa agaacatgtg agcaaaaggc cagcaaaagg ccaggaaccg 9120
taaaaaggcc gcgttgctgg cgtttttcca taggctccgc ccccctgacg agcatcacaa 9180
aaatcgacgc tcaagtcaga ggtggcgaaa cccgacagga ctataaagat accaggcgtt 9240
tccccctgga agctccctcg tgcgctctcc tgttccgacc ctgccgctta ccggatacct 9300
gtccgccttt ctcccttcgg gaagcgtggc gctttctcat agctcacgct gtaggtatct 9360
cagttcggtg taggtcgttc gctccaagct gggctgtgtg cacgaacccc ccgttcagcc 9420
cgaccgctgc gccttatccg gtaactatcg tcttgagtcc aacccggtaa gacacgactt 9480
atcgccactg gcagcagcca ctggtaacag gattagcaga gcgaggtatg taggcggtgc 9540
tacagagttc ttgaagtggt ggcctaacta cggctacact agaagaacag tatttggtat 9600
ctgcgctctg ctgaagccag ttaccttcgg aaaaagagtt ggtagctctt gatccggcaa 9660
acaaaccacc gctggtagcg gtggtttttt tgtttgcaag cagcagatta cgcgcagaaa 9720
aaaaggatct caagaagatc ctttgatctt ttctacgggg tctgacgctc agtggaacga 9780
aaactcacgt taagggattt tggtcatgag attatcaaaa aggatcttca cctagatcct 9840
tttaaattaa aaatgaagtt ttaaatcaat ctaaagtata tatgagtaaa cttggtctga 9900
cagttaccaa tgcttaatca gtgaggcacc tatctcagcg atctgtctat ttcgttcatc 9960
catagttgcc tgactcctgc aaaccacgtt gtgtctcaaa atctctgatg ttacattgca 10020
caagataaaa atatatcatc atgaacaata aaactgtctg cttacataaa cagtaataca 10080
aggggtgtta tgagccatat tcaacgggaa acgtcttgct cgaggccgcg attaaattcc 10140
aacatggatg ctgatttata tgggtataaa tgggctcgcg ataatgtcgg gcaatcaggt 10200
gcgacaatct atcgattgta tgggaagccc gatgcgccag agttgtttct gaaacatggc 10260
aaaggtagcg ttgccaatga tgttacagat gagatggtca gactaaactg gctgacggaa 10320
tttatgcctc ttccgaccat caagcatttt atccgtactc ctgatgatgc atggttactc 10380
accactgcga tccccgggaa aacagcattc caggtattag aagaatatcc tgattcaggt 10440
gaaaatattg ttgatgcgct ggcagtgttc ctgcgccggt tgcattcgat tcctgtttgt 10500
aattgtcctt ttaacagcga tcgcgtattt cgtctcgctc aggcgcaatc acgaatgaat 10560
aacggtttgg ttgatgcgag tgattttgat gacgagcgta atggctggcc tgttgaacaa 10620
gtctggaaag aaatgcataa gcttttgcca ttctcaccgg attcagtcgt cactcatggt 10680
gatttctcac ttgataacct tatttttgac gaggggaaat taataggttg tattgatgtt 10740
ggacgagtcg gaatcgcaga ccgataccag gatcttgcca tcctatggaa ctgcctcggt 10800
gagttttctc cttcattaca gaaacggctt tttcaaaaat atggtattga taatcctgat 10860
atgaataaat tgcagtttca tttgatgctc gatgagtttt tctaagggcg gcctgccacc 10920
atacccacgc cgaaacaagc gctcatgagc ccgaagtggc gagcccgatc ttccccatcg 10980
gtgatgtcgg cgatataggc gccagcaacc gcacctgtgg cgccggtgat gagggcgcgc 11040
caagtcgacg tccggcagtc 11060

<210> SEQ ID NO 60
<211> LENGTH: 10913
<212> TYPE: DNA
<213> ORGANISM: Artificial sequence
<220> FEATURE:
<223> OTHER INFORMATION: Synthetic polynucleotide

<400> SEQUENCE: 60
ttggccactc cctctctgcg cgctcgctcg ctcactgagg ccgggcgacc aaaggtcgcc 60

```
cgacgcccgg gctttgcccg ggcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg agggcggagt    300
tagggcggag ccaatcagcg tgcgccgttc cgaaagttgc cttttatggc tgggcggaga    360
atgggcggtg aacgccgatg attatataag gacgcgccgg gtgtggcaca gctagttccg    420
tcgcagccgg gatttgggtc gcggttcttg tttgtggatc cctgtgatcg tcacttggta    480
agtcactgac tgtctatgcc tgggaaaggg tgggcaggag atggggcagt gcaggaaaag    540
tggcactatg aaccctcctg gtggcgaggg gaggggggtg gtcctcgaac gccttgcaga    600
actggcctgg atacagagtg gaccggctgg ccccatctgg aagacttcga gatacactgt    660
tgtcttactg cgctcaacag tgtatctcga agtcttccaa atggtgccag ccatcgcagc    720
ggggtgcagg aaatgggggc agcccccctt tttggctatc cttccacgtg ttcttttttg    780
tatcttttgt gtttcctaga aaacatctca gtcaccaccg cagccctagg aatgcatcta    840
gacaattgta ctaaccttct tctctttcct ctcctgacag tccggaaagc caccatggaa    900
ttcagcagcc ccagcagaga ggaatgcccc aagcctctga gccgggtgtc aatcatggcc    960
ggatctctga caggactgct gctgcttcag gccgtgtctt gggcttctgg cgctagacct   1020
tgcatcccca agagcttcgg ctacagcagc gtcgtgtgcg tgtgcaatgc cacctactgc   1080
gacagcttcg accctcctac ctttcctgct ctgggcacct tcagcagata cgagagcacc   1140
agatccggca gacggatgga actgagcatg ggacccatcc aggccaatca cacaggcact   1200
ggcctgctgc tgacactgca gcctgagcag aaattccaga aagtgaaagg cttcggcgga   1260
gccatgacag atgccgccgc tctgaatatc ctggctctgt ctccaccagc tcagaacctg   1320
ctgctcaaga gctacttcag cgaggaaggc atcggctaca acatcatcag agtgcccatg   1380
gccagctgcg acttcagcat caggacctac acctacgccg acacacccga cgatttccag   1440
ctgcacaact tcagcctgcc tgaagaggac accaagctga agatccctct gatccacaga   1500
gccctgcagc tggcacaaag acccgtgtca ctgctggcct ctccatggac atctcccacc   1560
tggctgaaaa caaatggcgc cgtgaatggc aagggcagcc tgaaaggcca acctggcgac   1620
atctaccacc agacctgggc cagatacttc gtgaagttcc tggacgccta tgccgagcac   1680
aagctgcagt tttgggccgt gacagccgag aacgaacctt ctgctggact gctgagcggc   1740
taccccttc agtgcctggg ctttacaccc gagcaccagc gggactttat cgcccgtgat   1800
ctgggaccca cactggccaa tagcacccac cataatgtgc ggctgctgat gctggacgac   1860
cagagactgc ttctgcccca ctgggctaaa gtggtgctga cagatcctga ggccgccaaa   1920
tacgtgcacg gaatcgccgt gcactggtat ctggactttc tggcccctgc caaggccaca   1980
ctgggagaga cacacagact gttccccaac accatgctgt tcgccagcga agcctgtgtg   2040
ggcagcaagt tttgggaaca gagcgtgcgg ctcggcagct gggatagagg catgcagtac   2100
agccacagca tcatcaccaa cctgctgtac cacgtcgtcg gctggaccga ctggaatctg   2160
gccctgaatc ctgaaggcgg ccctaactgg gtccgaaact tcgtggacag ccccatcatc   2220
gtggacatca ccaaggacac cttctacaag cagcccatgt tctaccacct gggacacttc   2280
agcaagttca tccccgaggg ctctcagcgc gttggactgg tggcttccca gaagaacgat   2340
ctggacgccg tggctctgat gcaccctgat ggatctgctg tggtggtggt cctgaaccgc   2400
```

```
agcagcaaag atgtgcccct gaccatcaag gatcccgccg tgggattcct ggaaacaatc   2460
agccctggct actccatcca cacctacctg tggcgtagac agtgattgtg gccgaaccgc   2520
cgaactcaga ggccggcccc agaaaacccg agcgagtagg gggcggcgcg caggagggag   2580
gagaactggg ggcgcgggag gctggtgggt gtgggggtg gagatgtaga agatgtgacg    2640
ccgcggcccg gcgggtgcca gattagcgga cgcggtgccc gcggttgcaa cgggatcccg   2700
ggcgctgcag cttgggaggc ggctctcccc aggcggcgtc cgcggagaca cccatccgtg   2760
aaccccaggt cccgggccgc cggctcgccg cgcaccaggg gccggcggac agaagagcgg   2820
ccgagcggct cgaggctggg ggaccgcggg cgcggccgcg cgctgccggg cgggaggctg   2880
gggggccggg gccggggccg tgccccggag cgggtcggag gccggggccg gggccggggg   2940
acggcggctc cccgcgcggc tccagcggct cggggatccc ggccgggccc cgcagggacc   3000
atgatgcccc gcggcttcac ctggctgcgc tacctgggca tcttcctggg cgtggccctg   3060
ggcaacgagc ccctggagat gtggcccctg acccagaacg aggagtgcac cgtgaccggc   3120
ttcctgcgcg acaagctgca gtaccgcagc cgcctgcagt acatgaagca ctacttcccc   3180
atcaactaca agatcagcgt gccctacgag ggcgtgttcc gcatcgccaa cgtgacccgc   3240
ctgcagcgcg cccaggtgag cgagcgcgag ctgcgctacc tgtgggtgct ggtgagcctg   3300
agcgccaccg agagcgtgca ggacgtgctg ctggagggcc accccagctg gaagtacctg   3360
caggaggtgg agaccctgct gctgaacgtg cagcagggcc tgaccgacgt ggaggtgagc   3420
cccaaggtgg agagcgtgct gagcctgctg aacgcccccg gccccaacct gaagctggtg   3480
cgccccaagg ccctgctgga caactgcttc cgcgtgatgg agctgctgta ctgcagctgc   3540
tgcaagcaga gcagcgtgct gaactggcag gactgcgagg tgcccagccc ccagagctgc   3600
agccccgagc ccagcctgca gtacgccgcc acccagctgt accccccccc cccctggagc   3660
cccagcagcc ccccccacag caccggcagc gtgcgccccg tgcgcgccca gggcgagggc   3720
ctgctgccct aatgacaatt gttaattaag tttaaaccct cgaggccgca agccgcatcg   3780
ataccgtcga ctagagctcg ctgatcagcc tcgactgtgc cttctagttg ccagccatct   3840
gttgtttgcc cctcccccgt gccttccttg accctggaag gtgccactcc cactgtcctt   3900
tcctaataaa atgaggaaat tgcatcgcat tgtctgagta ggtgtcattc tattctgggg   3960
ggtggggtgg ggcaggacag caagggggag gattgggaag acaatagcag gcatgctggg   4020
gagagatcca cgataacaaa cagctttttt ggggtgaaca tattgactga attccctgca   4080
ggttggccac tccctctctg cgcgctcgct cgctcactga ggccgcccgg gcaaagcccg   4140
ggcgtcgggc gacctttggt cgcccggcct cagtgagcga gcgagcgcgc agagagggag   4200
tggccaactc catcactagg ggttcctgcg gccgctcgta cggtctcgag gaattcctgc   4260
aggataactt gccaacctca ttctaaaatg tatatagaag cccaaaagac aataacaaaa   4320
atattcttgt agaacaaaat gggaaagaat gttccactaa atatcaagat ttagagcaaa   4380
gcatgagatg tgtggggata gacagtgagg ctgataaaat agagtagagc tcagaaacag   4440
acccattgat atatgtaagt gacctatgaa aaaaatatgg cattttacaa tgggaaaatg   4500
atggtctttt tcttttttag aaaaacaggg aaatatattt atatgtaaaa aataaaaggg   4560
aacccatatg tcataccata cacacaaaaa aattccagtg aattataagt ctaaatggag   4620
aaggcaaaac tttaaatctt ttagaaaata atatagaagc atgcagacca gcctggccaa   4680
catgatgaaa ccctctctac taataataaa atcagtagaa ctactcagga ctactttgag   4740
tgggaagtcc ttttctatga agacttcttt ggccaaaatt aggctctaaa tgcaaggaga   4800
```

```
tagtgcatca tgcctggctg cacttactga taaatgatgt tatcaccatc tttaaccaaa   4860
tgcacaggaa caagttatgg tactgatgtg ctggattgag aaggagctct acttccttga   4920
caggacacat ttgtatcaac ttaaaaaagc agatttttgc cagcagaact attcattcag   4980
aggtaggaaa cttagaatag atgatgtcac tgattagcat ggcttcccca tctccacagc   5040
tgcttcccac ccaggttgcc cacagttgag tttgtccagt gctcagggct gcccactctc   5100
agtaagaagc cccacaccag cccctctcca aatatgttgg ctgttccttc cattaaagtg   5160
accccacttt agagcagcaa gtggatttct gtttcttaca gttcaggaag gaggagtcag   5220
ctgtgagaac ctggagcctg agatgcttct aagtcccact gctactgggg tcagggaagc   5280
cagactccag catcagcagt caggagcact aagcccttgc caacatcctg tttctcagag   5340
aaactgcttc cattataatg gttgtccttt tttaagctat caagccaaac aaccagtgtc   5400
taccattatt ctcatcacct gaagccaagg gttctagcaa aagtcaagct gtcttgtaat   5460
ggttgatgtg cctccagctt ctgtcttcag tcactccact cttagcctgc tctgaatcaa   5520
ctctgaccac agttccctgg agcccctgcc acctgctgcc cctgccacct tctccatctg   5580
cagtgctgtg cagccttctg cactcttgca gagctaatag gtggagactt gaaggaagag   5640
gaggaaagtt tctcataata gccttgctgc aagctcaaat gggaggtggg cactgtgccc   5700
aggagccttg gagcaaaggc tgtgcccaac ctctgactgc atccaggttt ggtcttgaca   5760
gagataagaa gccctggctt ttggagccaa aatctaggtc agacttaggc aggattctca   5820
aagtttatca gcagaacatg aggcagaaga ccctttctgc tccagcttct tcaggctcaa   5880
ccttcatcag aatagataga aagagaggct gtgagggttc ttaaaacaga agcaaatctg   5940
actcagagaa taaacaacct cctagtaaac tacagcttag acagagcatc tggtggtgag   6000
tgtgctcagt gtcctactca actgtctggt atcagccctc atgaggactt ctcttctttc   6060
cctcatagac ctccatctct gttttcctta gcctgcagaa atctggatgg ctattcacag   6120
aatgcctgtg ctttcagagt tgcatttttt ctctggtatt ctggttcaag catttgaagg   6180
taggaaaggt tctccaagtg caagaaagcc agccctgagc ctcaactgcc tggctagtgt   6240
ggtcagtagg atgcaaaggc tgttgaatgc cacaaggcca aactttaacc tgtgtaccac   6300
aagcctagca gcagaggcag ctctgctcac tggaactctc tgtcttcttt ctcctgagcc   6360
ttttcttttc ctgagttttc tagctctcct caaccttacc tctgccctac ccaggacaaa   6420
cccaagagcc actgtttctg tgatgtcctc tccagcccta attaggcatc atgacttcag   6480
cctgaccttc catgctcaga agcagtgcta atccacttca gatgagctgc tctatgcaac   6540
acaggcagag cctacaaacc tttgcaccag agccctccac atatcagtgt ttgttcatac   6600
tcacttcaac agcaaatgtg actgctgaga ttaagatttt acacaagatg gtctgtaatt   6660
tcacagttag ttttatccca ttaggtatga aagaattagc ataattcccc ttaaacatga   6720
atgaatctta gatttttttaa taaatagttt tggaagtaaa gacagagaca tcaggagcac   6780
aaggaatagc ctgagaggac aaacagaaca agaaagagtc tggaaataca caggatgttc   6840
ttggcctcct caaagcaagt gcaagcagat agtaccagca gccccaggct atcagagccc   6900
agtgaagaga agtaccatga aagccacagc tctaaccacc ctgttccaga gtgacagaca   6960
gtccccaaga caagccagcc tgagccagag agagaactgc aagagaaagt ttctaattta   7020
ggttctgtta gattcagaca agtgcaggtc atcctctctc cacagctact cacctctcca   7080
gcctaacaaa gcctgcagtc cacactccaa ccctggtgtc tcacctccta gcctctccca   7140
```

```
acatcctgct ctctgaccat cttctgcatc tctcatctca ccatctccca ctgtctacag   7200
cctactcttg caactaccat ctcattttct gacatcctgt ctacatcttc tgccatactc   7260
tgccatctac cataccacct cttaccatct accacaccat cttttatctc catccctctc   7320
agaagcctcc aagctgaatc ctgctttatg tgttcatctc agcccctgca tggaaagctg   7380
accccagagg cagaactatt cccagagagc ttggccaaga aaaacaaaac taccagcctg   7440
gccaggctca ggagtagtaa gctgcagtgt ctgttgtgtt ctagcttcaa cagctgcagg   7500
agttccactc tcaaatgctc cacatttctc acatcctcct gattctggtc actacccatc   7560
ttcaaagaac agaatatctc acatcagcat actgtgaagg actagtcatg ggtgcagctg   7620
ctcagagctg caaagtcatt ctggatggtg gagagcttac aaacatttca tgatgctccc   7680
cccgctctga tggctggagc ccaatcccta cacagactcc tgctgtatgt gttttccttt   7740
cactctgagc cacagccaga gggcaggcat tcagtctcct cttcaggctg gggctggggc   7800
actgagaact cacccaacac cttgctctca ctccttctgc aaaacaagaa agagctttgt   7860
gctgcagtag ccatgaagaa tgaaaggaag gctttaacta aaaaatgtca gagattattt   7920
tcaacccctt actgtggatc accagcaagg aggaaacaca acacagagac atttttttccc   7980
ctcaaattat caaaagaatc actgcatttg ttaaagagag caactgaatc aggaagcaga   8040
gttttgaaca tatcagaagt taggaatctg catcagagac aaatgcagtc atggttgttt   8100
gctgcatacc agccctaatc attagaagcc tcatggactt caaacatcat tccctctgac   8160
aagatgctct agcctaactc catgagataa aataaatctg cctttcagag ccaaagaaga   8220
gtccaccagc ttcttctcag tgtgaacaag agctccagtc aggttagtca gtccagtgca   8280
gtagaggaga ccagtctgca tcctctaatt ttcaaaggca agaagatttg tttaccctgg   8340
acaccaggca caagtgaggt cacagagctc ttagatatgc agtcctcatg agtgaggaga   8400
ctaaagcgca tgccatcaag acttcagtgt agagaaaacc tccaaaaaag cctcctcact   8460
acttctggaa tagctcagag gccgaggcgg cctcggcctc tgcataaata aaaaaaatta   8520
gtcagccatg gggcggagaa tgggcggaac tgggcggagt taggggcggg atgggcggag   8580
ttaggggcgg gactatggtt gctgactaat tgagatgcat gctttgcata cttctgcctg   8640
ctggggagcc tggggacttt ccacacctgg ttgctgacta attgagatgc atgctttgca   8700
tacttctgcc tgctggggag cctggggact ttccacaccc taactgacac acattccaca   8760
gctgcattaa tgaatcggcc aacgcgcggg gagaggcggt ttgcgtattg ggcgctcttc   8820
cgcttcctcg ctcactgact cgctgcgctc ggtcgttcgg ctgcggcgag cggtatcagc   8880
tcactcaaag gcggtaatac ggttatccac agaatcaggg gataacgcag gaaagaacat   8940
gtgagcaaaa ggccagcaaa aggccaggaa ccgtaaaaag gccgcgttgc tggcgttttt   9000
ccataggctc cgcccccctg acgagcatca caaaaatcga cgctcaagtc agaggtggcg   9060
aaacccgaca ggactataaa gataccaggc gtttccccct ggaagctccc tcgtgcgctc   9120
tcctgttccg accctgccgc ttaccggata cctgtccgcc tttctccctt cgggaagcgt   9180
ggcgctttct catagctcac gctgtaggta tctcagttcg gtgtaggtcg ttcgctccaa   9240
gctgggctgt gtgcacgaac cccccgttca gcccgaccgc tgcgccttat ccggtaacta   9300
tcgtcttgag tccaacccgg taagacacga cttatcgcca ctggcagcag ccactggtaa   9360
caggattagc agagcgaggt atgtaggcgg tgctacagag ttcttgaagt ggtggcctaa   9420
ctacggctac actagaagaa cagtatttgg tatctgcgct ctgctgaagc cagttacctt   9480
cggaaaaaga gttggtagct cttgatccgg caaacaaacc accgctggta gcggtggttt   9540
```

```
ttttgtttgc aagcagcaga ttacgcgcag aaaaaaagga tctcaagaag atcctttgat   9600
cttttctacg gggtctgacg ctcagtggaa cgaaaactca cgttaaggga ttttggtcat   9660
gagattatca aaaaggatct tcacctagat ccttttaaat taaaaatgaa gttttaaatc   9720
aatctaaagt atatatgagt aaacttggtc tgacagttac caatgcttaa tcagtgaggc   9780
acctatctca gcgatctgtc tatttcgttc atccatagtt gcctgactcc tgcaaaccac   9840
gttgtgtctc aaaatctctg atgttacatt gcacaagata aaaatatatc atcatgaaca   9900
ataaaactgt ctgcttacat aaacagtaat acaaggggtg ttatgagcca tattcaacgg   9960
gaaacgtctt gctcgaggcc gcgattaaat tccaacatgg atgctgattt atatgggtat  10020
aaatgggctc gcgataatgt cgggcaatca ggtgcgacaa tctatcgatt gtatgggaag  10080
cccgatgcgc cagagttgtt tctgaaacat ggcaaaggta gcgttgccaa tgatgttaca  10140
gatgagatgg tcagactaaa ctggctgacg gaatttatgc ctcttccgac catcaagcat  10200
tttatccgta ctcctgatga tgcatggtta ctcaccactg cgatccccgg gaaaacagca  10260
ttccaggtat tagaagaata tcctgattca ggtgaaaata ttgttgatgc gctggcagtg  10320
ttcctgcgcc ggttgcattc gattcctgtt tgtaattgtc cttttaacag cgatcgcgta  10380
tttcgtctcg ctcaggcgca atcacgaatg aataacggtt tggttgatgc gagtgatttt  10440
gatgacgagc gtaatggctg gcctgttgaa caagtctgga aagaaatgca taagcttttg  10500
ccattctcac cggattcagt cgtcactcat ggtgatttct cacttgataa ccttattttt  10560
gacgagggga aattaatagg ttgtattgat gttggacgag tcggaatcgc agaccgatac  10620
caggatcttg ccatcctatg gaactgcctc ggtgagtttt ctccttcatt acagaaacgg  10680
ctttttcaaa aatatggtat tgataatcct gatatgaata aattgcagtt tcatttgatg  10740
ctcgatgagt ttttctaagg gcggcctgcc accataccca cgccgaaaca agcgctcatg  10800
agcccgaagt ggcgagcccg atcttcccca tcggtgatgt cggcgatata ggcgccagca  10860
accgcacctg tggcgccggt gatgagggcg cgccaagtcg acgtccggca gtc         10913
```

<210> SEQ ID NO 61
<211> LENGTH: 11209
<212> TYPE: DNA
<213> ORGANISM: Artificial sequence
<220> FEATURE:
<223> OTHER INFORMATION: Synthetic polynucleotide

<400> SEQUENCE: 61

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg agggcggagt    300
tagggcggag ccaatcagcg tgcgccgttc cgaaagttgc cttttatggc tgggcggaga    360
atgggcggtg aacgccgatg attatataag gacgcgccgg gtgtggcaca gctagttccg    420
tcgcagccgg gatttgggtc gcggttcttg tttgtggatc cctgtgatcg tcacttggta    480
agtcactgac tgtctatgcc tgggaaaggg tgggcaggag atggggcagt gcaggaaaag    540
tggcactatg aaccctgcag ccctaggaat gcatctagac aattgtacta accttcttct    600
ctttcctctc ctgacagtcc ggaaagccac catggaattc agcagcccca gcagagagga    660
```

```
atgccccaag cctctgagcc gggtgtcaat catggccgga tctctgacag gactgctgct    720
gcttcaggcc gtgtcttggg cttctggcgc tagaccttgc atccccaaga gcttcggcta    780
cagcagcgtc gtgtgcgtgt gcaatgccac ctactgcgac agcttcgacc ctcctacctt    840
tcctgctctg ggcaccttca gcagatacga gagcaccaga tccggcagac ggatggaact    900
gagcatggga cccatccagg ccaatcacac aggcactggc ctgctgctga cactgcagcc    960
tgagcagaaa ttccagaaag tgaaaggctt cggcggagcc atgacagatg ccgccgctct   1020
gaatatcctg gctctgtctc caccagctca gaacctgctg ctcaagagct acttcagcga   1080
ggaaggcatc ggctacaaca tcatcagagt gcccatggcc agctgcgact tcagcatcag   1140
gacctacacc tacgccgaca cacccgacga tttccagctg cacaacttca gcctgcctga   1200
agaggacacc aagctgaaga tccctctgat ccacagagcc ctgcagctgg cacaaagacc   1260
cgtgtcactg ctggcctctc catggacatc tcccacctgg ctgaaaacaa atggcgccgt   1320
gaatggcaag ggcagcctga aaggccaacc tggcgacatc taccaccaga cctgggccag   1380
atacttcgtg aagttcctgg acgcctatgc cgagcacaag ctgcagtttt gggccgtgac   1440
agccgagaac gaaccttctg ctggactgct gagcggctac ccctttcagt gcctgggctt   1500
tacacccgag caccagcggg actttatcgc ccgtgatctg ggacccacac tggccaatag   1560
cacccaccat aatgtgcggc tgctgatgct ggacgaccag agactgcttc tgccccactg   1620
ggctaaagtg gtgctgacag atcctgaggc cgccaaatac gtgcacggaa tcgccgtgca   1680
ctggtatctg gactttctgg cccctgccaa ggccacactg ggagagacac acagactgtt   1740
ccccaacacc atgctgttcg ccagcgaagc ctgtgtgggc agcaagtttt gggaacagag   1800
cgtgcggctc ggcagctggg atagaggcat gcagtacagc cacagcatca tcaccaacct   1860
gctgtaccac gtcgtcggct ggaccgactg gaatctggcc ctgaatcctg aaggcggccc   1920
taactgggtc cgaaacttcg tggacagccc catcatcgtg gacatcacca aggacacctt   1980
ctacaagcag cccatgttct accacctggg acacttcagc aagttcatcc ccgagggctc   2040
tcagcgcgtt ggactggtgg cttcccagaa gaacgatctg gacgccgtgg ctctgatgca   2100
ccctgatgga tctgctgtgg tggtggtcct gaaccgcagc agcaaagatg tgcccctgac   2160
catcaaggat cccgccgtgg gattcctgga aacaatcagc cctggctact ccatccacac   2220
ctacctgtgg cgtagacagt gacaattgtt aattaagttt aaaccctcga ggccgcaagc   2280
cgcatcgata ccgtcgacta gagctcgctg atcagcctcg actgtgcctt ctagttgcca   2340
gccatctgtt gtttgcccct cccccgtgcc ttccttgacc ctggaaggtg ccactcccac   2400
tgtcctttcc taataaaatg aggaaattgc atcgcattgt ctgagtaggt gtcattctat   2460
tctggggggt ggggtggggc aggacagcaa gggggaggat tgggaagaca atagcaggca   2520
tgctggggag agatccacga taacaaacag ctttttgggg ggatatcaaa ctgcctgttt   2580
gggcttctca tttcttacct cccctccct ctcccacctg ctactgggtg catctctgct   2640
ccccccttcc ccagcagatg gttacctttg ggctgttgct ttcttgtcac catctgagtt   2700
ctcagacgct ggaaagccat gttctcggct ctgtgaatga caatgctgac tggagtgctg   2760
cccctctgta aagggctggg tgtggatggt cacaagcccc tcacatgcct cagccaagag   2820
gaagtagtac aggggtcagc ccagaggtcc aggggaaagg agtggaaacc gatttcccca   2880
ccaagggagg ggcctgtacc tcagctgttc ccatagctta cttgccacaa ctgccaagca   2940
agtttcgctg agtttgacac atggatccct gtggatcaac tgccctagga ctccgtttgc   3000
acccatgtga cactgttgac tttgccctga cgaagcaggg ccaacagtcc cctaacttaa   3060
```

```
ttacaaaaac taatgactaa gagagaggtg gctagagctg aggcccctga gtcaggctgt   3120
gggtgggatc atctccagta caggaagtga gactttcatt tcctcctttc caagagaggg   3180
ctgagggagc agggttgagc aactggtgca gacagcctag ctggactttg ggtgaggcgg   3240
ttcagccata tcgaattctg ctggggctac tggcaggtaa ggaggaagga ggctgagggg   3300
agggggcccc tgggagggag cctgccctgg gttgctaacc atctcctctc tgccaaaagt   3360
ccggaaagcc accatggagc ccctgcgcct gctgatcctg ctgttcgtga ccgagctgag   3420
cggcgcccac aacaccaccg tgttccaggg cgtggccggc cagagcctgc aggtgagctg   3480
cccctacgac agcatgaagc actggggccg ccgcaaggcc tggtgccgcc agctgggcga   3540
gaagggcccc tgccagcgcg tggtgagcac ccacaacctg tggctgctga gcttcctgcg   3600
ccgctggaac ggcagcaccg ccatcaccga cgacaccctg ggcggcaccc tgaccatcac   3660
cctgcgcaac ctgcagcccc acgacgccgg cctgtaccag tgccagagcc tgcacggcag   3720
cgaggccgac accctgcgca aggtgctggt ggaggtgctg gccgaccccc tggaccaccg   3780
cgacgccggc gacctgtggt tccccggcga gagcgagagc ttcgaggacg cccacgtgga   3840
gcacagcatc agccgcagcc tgctggaggg cgagatcccc ttcccccccca ccagcatcct   3900
gctgctgctg gcctgcatct tcctgatcaa gatcctggcc gccagcgccc tgtgggccgc   3960
cgcctggcac ggccagaagc ccggcaccca cccccccagc gagctggact gcggccacga   4020
ccccggctac cagctgcaga ccctgcccgg cctgcgcgac acctgaccca ggggactcag   4080
cggccgctcg agtctagagg gcccgtttaa acccgctgat cagcctcgaa gacatgataa   4140
gatacattga tgagtttgga caaaccacaa caagaatgca gtgaaaaaaa tgctttattt   4200
gtgaaatttg tgatgctatt gctttatttg taaccattat aagctgcaat aaacaagtta   4260
acaacaacaa ttgcattcat tttatgtttc aggttcaggg ggagatgtgg gaggtttttt   4320
aaagcaagta aaacctctac aaatgtggta tgaacatatt gactgaattc cctgcaggtt   4380
ggccactccc tctctgcgcg ctcgctcgct cactgaggcc gcccgggcaa agcccgggcg   4440
tcgggcgacc tttggtcgcc cggcctcagt gagcgagcga gcgcgcagag agggagtggc   4500
caactccatc actaggggtt cctgcggccg ctcgtacggt ctcgaggaat tcctgcagga   4560
taacttgcca acctcattct aaaatgtata tagaagccca aaagacaata acaaaaatat   4620
tcttgtagaa caaaatggga aagaatgttc cactaaatat caagatttag agcaaagcat   4680
gagatgtgtg gggatagaca gtgaggctga taaaatagag tagagctcag aaacagaccc   4740
attgatatat gtaagtgacc tatgaaaaaa atatggcatt ttacaatggg aaaatgatgg   4800
tctttttctt ttttagaaaa acagggaaat atatttatat gtaaaaaata aaagggaacc   4860
catatgtcat accatacaca caaaaaaatt ccagtgaatt ataagtctaa atggagaagg   4920
caaaacttta aatcttttag aaaataatat agaagcatgc agaccagcct ggccaacatg   4980
atgaaaccct ctctactaat aataaaatca gtagaactac tcaggactac tttgagtggg   5040
aagtcctttt ctatgaagac ttctttggcc aaaattaggc tctaaatgca aggagatagt   5100
gcatcatgcc tggctgcact tactgataaa tgatgttatc accatcttta accaaatgca   5160
caggaacaag ttatggtact gatgtgctgg attgagaagg agctctactt ccttgacagg   5220
acacatttgt atcaacttaa aaaagcagat ttttgccagc agaactattc attcagaggt   5280
aggaaactta gaatagatga tgtcactgat tagcatggct tccccatctc cacagctgct   5340
tcccacccag gttgcccaca gttgagtttg tccagtgctc agggctgccc actctcagta   5400
```

```
agaagcccca caccagcccc tctccaaata tgttggctgt tccttccatt aaagtgaccc   5460
cactttagag cagcaagtgg atttctgttt cttacagttc aggaaggagg agtcagctgt   5520
gagaacctgg agcctgagat gcttctaagt cccactgcta ctggggtcag ggaagccaga   5580
ctccagcatc agcagtcagg agcactaagc ccttgccaac atcctgtttc tcagagaaac   5640
tgcttccatt ataatggttg tccttttta agctatcaag ccaaacaacc agtgtctacc    5700
attattctca tcacctgaag ccaagggttc tagcaaaagt caagctgtct tgtaatggtt   5760
gatgtgcctc cagcttctgt cttcagtcac tccactctta gcctgctctg aatcaactct   5820
gaccacagtt ccctggagcc cctgccacct gctgcccctg ccaccttctc catctgcagt   5880
gctgtgcagc cttctgcact cttgcagagc taataggtgg agacttgaag gaagaggagg   5940
aaagtttctc ataatagcct tgctgcaagc tcaaatggga ggtgggcact gtgcccagga   6000
gccttggagc aaaggctgtg cccaacctct gactgcatcc aggtttggtc ttgacagaga   6060
taagaagccc tggcttttgg agccaaaatc taggtcagac ttaggcagga ttctcaaagt   6120
ttatcagcag aacatgaggc agaagaccct ttctgctcca gcttcttcag gctcaacctt   6180
catcagaata gatagaaaga gaggctgtga gggttcttaa aacagaagca aatctgactc   6240
agagaataaa caacctccta gtaaactaca gcttagacag agcatctggt ggtgagtgtg   6300
ctcagtgtcc tactcaactg tctggtatca gccctcatga ggacttctct tctttccctc   6360
atagacctcc atctctgttt tccttagcct gcagaaatct ggatggctat tcacagaatg   6420
cctgtgcttt cagagttgca tttttctct ggtattctgg ttcaagcatt tgaaggtagg    6480
aaaggttctc caagtgcaag aaagccagcc ctgagcctca actgcctggc tagtgtggtc   6540
agtaggatgc aaaggctgtt gaatgccaca aggccaaact ttaacctgtg taccacaagc   6600
ctagcagcag aggcagctct gctcactgga actctctgtc ttctttctcc tgagcctttt   6660
cttttcctga gttttctagc tctcctcaac cttacctctg ccctacccag gacaaaccca   6720
agagccactg tttctgtgat gtcctctcca gccctaatta ggcatcatga cttcagcctg   6780
accttccatg ctcagaagca gtgctaatcc acttcagatg agctgctcta tgcaacacag   6840
gcagagccta caaacctttg caccagagcc ctccacatat cagtgtttgt tcatactcac   6900
ttcaacagca aatgtgactg ctgagattaa gattttacac aagatggtct gtaatttcac   6960
agttagtttt atcccattag gtatgaaaga attagcataa ttccccttaa acatgaatga   7020
atcttagatt ttttaataaa tagttttgga agtaaagaca gagacatcag gagcacaagg   7080
aatagcctga gaggacaaac agaacaagaa agagtctgga aatacacagg atgttcttgg   7140
cctcctcaaa gcaagtgcaa gcagatagta ccagcagccc caggctatca gagcccagtg   7200
aagagaagta ccatgaaagc cacagctcta accaccctgt tccagagtga cagacagtcc   7260
ccaagacaag ccagcctgag ccagagagag aactgcaaga gaaagtttct aatttaggtt   7320
ctgttagatt cagacaagtg caggtcatcc tctctccaca gctactcacc tctccagcct   7380
aacaaagcct gcagtccaca ctccaaccct ggtgtctcac ctcctagcct ctcccaacat   7440
cctgctctct gaccatcttc tgcatctctc atctcaccat ctcccactgt ctacagccta   7500
ctcttgcaac taccatctca ttttctgaca tcctgtctac atcttctgcc atactctgcc   7560
atctaccata ccacctctta ccatctacca caccatcttt tatctccatc cctctcagaa   7620
gcctccaagc tgaatcctgc tttatgtgtt catctcagcc cctgcatgga aagctgaccc   7680
cagaggcaga actattccca gagagcttgg ccaagaaaaa caaaactacc agcctggcca   7740
ggctcaggag tagtaagctg cagtgtctgt tgtgttctag cttcaacagc tgcaggagtt   7800
```

```
ccactctcaa atgctccaca tttctcacat cctcctgatt ctggtcacta cccatcttca   7860
aagaacagaa tatctcacat cagcatactg tgaaggacta gtcatgggtg cagctgctca   7920
gagctgcaaa gtcattctgg atggtggaga gcttacaaac atttcatgat gctccccccg   7980
ctctgatggc tggagcccaa tccctacaca gactcctgct gtatgtgttt tcctttcact   8040
ctgagccaca gccagagggc aggcattcag tctcctcttc aggctggggc tggggcactg   8100
agaactcacc caacaccttg ctctcactcc ttctgcaaaa caagaaagag ctttgtgctg   8160
cagtagccat gaagaatgaa aggaaggctt taactaaaaa atgtcagaga ttattttcaa   8220
ccccttactg tggatcacca gcaaggagga aacacaacac agagacattt tttcccctca   8280
aattatcaaa agaatcactg catttgttaa agagagcaac tgaatcagga agcagagttt   8340
tgaacatatc agaagttagg aatctgcatc agagacaaat gcagtcatgg ttgtttgctg   8400
cataccagcc ctaatcatta gaagcctcat ggacttcaaa catcattccc tctgacaaga   8460
tgctctagcc taactccatg agataaaata aatctgcctt tcagagccaa agaagagtcc   8520
accagcttct tctcagtgtg aacaagagct ccagtcaggt tagtcagtcc agtgcagtag   8580
aggagaccag tctgcatcct ctaattttca aaggcaagaa gatttgttta ccctggacac   8640
caggcacaag tgaggtcaca gagctcttag atatgcagtc ctcatgagtg aggagactaa   8700
agcgcatgcc atcaagactt cagtgtagag aaaacctcca aaaaagcctc ctcactactt   8760
ctggaatagc tcagaggccg aggcggcctc ggcctctgca taaataaaaa aaattagtca   8820
gccatggggc ggagaatggg cggaactggg cggagttagg ggcgggatgg gcggagttag   8880
gggcgggact atggttgctg actaattgag atgcatgctt tgcatacttc tgcctgctgg   8940
ggagcctggg gactttccac acctggttgc tgactaattg agatgcatgc tttgcatact   9000
tctgcctgct ggggagcctg gggactttcc acaccctaac tgacacacat tccacagctg   9060
cattaatgaa tcggccaacg cgcggggaga ggcggtttgc gtattgggcg ctcttccgct   9120
tcctcgctca ctgactcgct gcgctcggtc gttcggctgc ggcgagcggt atcagctcac   9180
tcaaaggcgg taatacggtt atccacagaa tcaggggata acgcaggaaa gaacatgtga   9240
gcaaaaggcc agcaaaaggc caggaaccgt aaaaaggccg cgttgctggc gtttttccat   9300
aggctccgcc cccctgacga gcatcacaaa aatcgacgct caagtcagag gtggcgaaac   9360
ccgacaggac tataaagata ccaggcgttt ccccctggaa gctccctcgt gcgctctcct   9420
gttccgaccc tgccgcttac cggatacctg tccgcctttc tcccttcggg aagcgtggcg   9480
ctttctcata gctcacgctg taggtatctc agttcggtgt aggtcgttcg ctccaagctg   9540
ggctgtgtgc acgaaccccc cgttcagccc gaccgctgcg ccttatccgg taactatcgt   9600
cttgagtcca acccggtaag acacgactta tcgccactgg cagcagccac tggtaacagg   9660
attagcagag cgaggtatgt aggcggtgct acagagttct tgaagtggtg gcctaactac   9720
ggctacacta gaagaacagt atttggtatc tgcgctctgc tgaagccagt taccttcgga   9780
aaaagagttg gtagctcttg atccggcaaa caaaccaccg ctggtagcgg tggttttttt   9840
gtttgcaagc agcagattac gcgcagaaaa aaaggatctc aagaagatcc tttgatcttt   9900
tctacggggt ctgacgctca gtggaacgaa aactcacgtt aagggatttt ggtcatgaga   9960
ttatcaaaaa ggatcttcac ctagatcctt ttaaattaaa aatgaagttt taaatcaatc  10020
taaagtatat atgagtaaac ttggtctgac agttaccaat gcttaatcag tgaggcacct  10080
atctcagcga tctgtctatt tcgttcatcc atagttgcct gactcctgca aaccacgttg  10140
```

```
tgtctcaaaa tctctgatgt tacattgcac aagataaaaa tatatcatca tgaacaataa  10200

aactgtctgc ttacataaac agtaatacaa ggggtgttat gagccatatt caacgggaaa  10260

cgtcttgctc gaggccgcga ttaaattcca acatggatgc tgatttatat gggtataaat  10320

gggctcgcga taatgtcggg caatcaggtg cgacaatcta tcgattgtat gggaagcccg  10380

atgcgccaga gttgtttctg aaacatggca aaggtagcgt tgccaatgat gttacagatg  10440

agatggtcag actaaactgg ctgacggaat ttatgcctct tccgaccatc aagcatttta  10500

tccgtactcc tgatgatgca tggttactca ccactgcgat ccccgggaaa acagcattcc  10560

aggtattaga agaatatcct gattcaggtg aaaatattgt tgatgcgctg gcagtgttcc  10620

tgcgccggtt gcattcgatt cctgtttgta attgtccttt taacagcgat cgcgtatttc  10680

gtctcgctca ggcgcaatca cgaatgaata acggtttggt tgatgcgagt gattttgatg  10740

acgagcgtaa tggctggcct gttgaacaag tctggaaaga aatgcataag cttttgccat  10800

tctcaccgga ttcagtcgtc actcatggtg atttctcact tgataacctt atttttgacg  10860

aggggaaatt aataggttgt attgatgttg gacgagtcgg aatcgcagac cgataccagg  10920

atcttgccat cctatggaac tgcctcggtg agttttctcc ttcattacag aaacggcttt  10980

ttcaaaaata tggtattgat aatcctgata tgaataaatt gcagtttcat ttgatgctcg  11040

atgagttttt ctaagggcgg cctgccacca tacccacgcc gaaacaagcg ctcatgagcc  11100

cgaagtggcg agcccgatct tccccatcgg tgatgtcggc gatataggcg ccagcaaccg  11160

cacctgtggc gccggtgatg agggcgcgcc aagtcgacgt ccggcagtc             11209
```

<210> SEQ ID NO 62
<211> LENGTH: 11459
<212> TYPE: DNA
<213> ORGANISM: Artificial sequence
<220> FEATURE:
<223> OTHER INFORMATION: Synthetic polynucleotide

<400> SEQUENCE: 62

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg aattcggtac    300

cctagttatt aatagtaatc aattacgggg tcattagttc atagcccata tatggagttc    360

cgcgttacat aacttacggt aaatggcccg cctggctgac cgcccaacga cccccgccca    420

ttgacgtcaa taatgacgta tgttcccata gtaacgccaa tagggacttt ccattgacgt    480

caatgggtgg actatttacg gtaaactgcc cacttggcag tacatcaagt gtatcatatg    540

ccaagtacgc cccctattga cgtcaatgac ggtaaatggc ccgcctggca ttatgcccag    600

tacatgacct tatgggactt tcctacttgg cagtacatct acgtattagt catcgctatt    660

accatggtcg aggtgagccc cacgttctgc ttcactctcc ccatctcccc cccctcccca    720

cccccaattt tgtatttatt tatttttaa ttattttgtg cagcgatggg ggcggggggg    780

gggggggggc gcgcgccagg cggggcgggg cggggcgagg ggcggggcgg ggcgaggcgg    840

agaggtgcgg cggcagccaa tcagagcggc gcgctccgaa agtttccttt tatggcgagg    900

cggcggcggc ggcggcccta taaaaagcga agcgcgcggc gggcgggagt cgctgcgacg    960

ctgccttcgc cccgtgcccc gctccgccgc cgcctcgcgc cgcccgcccc ggctctgact   1020
```

```
gaccgcgtta ctcccacagg tgagcgggcg ggacggccct tctcctccgg gctgtaatta   1080
gcgcttggtt taatgacggc ttgttttctg tggctgcgtg aaagccttga ggggctccgg   1140
gagctagagc ctctgctaac catgttcatg ccttcttctt tttcctacag ctcctgggca   1200
acgtgctggt tattgtgctg tctcatcatt ttggcaaaga attcctcgaa gatccgaagg   1260
gaaagtcttc cacgactgtg ggatccgttc gaagatatca ccggttgagc caccatggaa   1320
ttcagcagcc ccagcagaga ggaatgcccc aagcctctga gccgggtgtc aatcatggcc   1380
ggatctctga caggactgct gctgcttcag gccgtgtctt gggcttctgg cgctagacct   1440
tgcatcccca agagcttcgg ctacagcagc gtcgtgtgcg tgtgcaatgc cacctactgc   1500
gacagcttcg accctcctac ctttcctgct ctgggcacct tcagcagata cgagagcacc   1560
agatccggca gacggatgga actgagcatg ggacccatcc aggccaatca cacaggcact   1620
ggcctgctgc tgacactgca gcctgagcag aaattccaga aagtgaaagg cttcggcgga   1680
gccatgacag atgccgccgc tctgaatatc ctggctctgt ctccaccagc tcagaacctg   1740
ctgctcaaga gctacttcag cgaggaaggc atcggctaca acatcatcag agtgcccatg   1800
gccagctgcg acttcagcat caggacctac acctacgccg acacacccga cgatttccag   1860
ctgcacaact tcagcctgcc tgaagaggac accaagctga agatccctct gatccacaga   1920
gccctgcagc tggcacaaag acccgtgtca ctgctggcct ctccatggac atctcccacc   1980
tggctgaaaa caaatggcgc cgtgaatggc aagggcagcc tgaaaggcca acctggcgac   2040
atctaccacc agacctgggc cagatacttc gtgaagttcc tggacgccta tgccgagcac   2100
aagctgcagt tttgggccgt gacagccgag aacgaacctt ctgctggact gctgagcggc   2160
taccccttc agtgcctggg ctttacaccc gagcaccagc gggactttat cgcccgtgat   2220
ctgggaccca cactggccaa tagcacccac cataatgtgc ggctgctgat gctggacgac   2280
cagagactgc ttctgcccca ctgggctaaa gtggtgctga cagatcctga ggccgccaaa   2340
tacgtgcacg gaatcgccgt gcactggtat ctggactttc tggcccctgc caaggccaca   2400
ctgggagaga cacacagact gttccccaac accatgctgt tcgccagcga agcctgtgtg   2460
ggcagcaagt tttgggaaca gagcgtgcgg ctcggcagct gggatagagg catgcagtac   2520
agccacagca tcatcaccaa cctgctgtac cacgtcgtcg gctggaccga ctggaatctg   2580
gccctgaatc ctgaaggcgg ccctaactgg gtccgaaact tcgtggacag ccccatcatc   2640
gtggacatca ccaaggacac cttctacaag cagcccatgt tctaccacct gggacacttc   2700
agcaagttca tccccgaggg ctctcagcgc gttggactgg tggcttccca gaagaacgat   2760
ctggacgccg tggctctgat gcaccctgat ggatctgctg tggtggtggt cctgaaccgc   2820
agcagcaaag atgtgcccct gaccatcaag gatcccgccg tgggattcct ggaaacaatc   2880
agccctggct actccatcca cacctacctg tggcgtagac agtgacaatt gttaattaag   2940
tttaaaccct cgaggccgca agccgcatcg ataccgtcga ctagagctcg ctgatcagcc   3000
tcgactgtgc cttctagttg ccagccatct gttgtttgcc cctcccccgt gccttccttg   3060
accctggaag gtgccactcc cactgtcctt tcctaataaa atgaggaaat tgcatcgcat   3120
tgtctgagta ggtgtcattc tattctgggg ggtggggtgg ggcaggacag caagggggag   3180
gattgggaag acaatagcag gcatgctggg gagagatcca cgataacaaa cagcttttt    3240
gggggggcgg agttagggcg gagccaatca gcgtgcgccg ttccgaaagt tgccttttat   3300
ggctgggcgg agaatgggcg gtgaacgccg atgattatat aaggacgcgc cgggtgtggc   3360
```

```
acagctagtt ccgtcgcagc cgggatttgg gtcgcggttc ttgtttgtgg atccctgtga   3420
tcgtcacttg gtaagtcact gactgtctat gcctgggaaa gggtgggcag gagatggggc   3480
agtgcaggaa aagtggcact atgaaccctg cagccctagg aatgcatcta gacaattgta   3540
ctaaccttct tctctttcct ctcctgacag tccggaaagc caccatgccc cgcggcttca   3600
cctggctgcg ctacctgggc atcttcctgg gcgtggccct gggcaacgag cccctggaga   3660
tgtggcccct gacccagaac gaggagtgca ccgtgaccgg cttcctgcgc gacaagctgc   3720
agtaccgcag ccgcctgcag tacatgaagc actacttccc catcaactac aagatcagcg   3780
tgccctacga gggcgtgttc cgcatcgcca acgtgacccg cctgcagcgc gcccaggtga   3840
gcgagcgcga gctgcgctac ctgtgggtgc tggtgagcct gagcgccacc gagagcgtgc   3900
aggacgtgct gctggagggc caccccagct ggaagtacct gcaggaggtg gagaccctgc   3960
tgctgaacgt gcagcagggc ctgaccgacg tggaggtgag ccccaaggtg gagagcgtgc   4020
tgagcctgct gaacgccccc ggccccaacc tgaagctggt gcgccccaag gccctgctgg   4080
acaactgctt ccgcgtgatg gagctgctgt actgcagctg ctgcaagcag agcagcgtgc   4140
tgaactggca ggactgcgag gtgcccagcc cccagagctg cagccccgag cccagcctgc   4200
agtacgccgc cacccagctg tacccccccc cccccctggag ccccagcagc cccccccaca   4260
gcaccggcag cgtgcgcccc gtgcgcgccc agggcgaggg cctgctgccc taatgaccca   4320
ggggactcag cggccgctcg agtctagagg gcccgtttaa acccgctgat cagcctcgaa   4380
gacatgataa gatacattga tgagtttgga caaaccacaa caagaatgca gtgaaaaaaa   4440
tgctttattt gtgaaatttg tgatgctatt gctttatttg taaccattat aagctgcaat   4500
aaacaagtta acaacaacaa ttgcattcat tttatgtttc aggttcaggg ggagatgtgg   4560
gaggtttttt aaagcaagta aaacctctac aaatgtggta tgaacatatt gactgaattc   4620
cctgcaggtt ggccactccc tctctgcgcg ctcgctcgct cactgaggcc gcccgggcaa   4680
agcccgggcg tcgggcgacc tttggtcgcc cggcctcagt gagcgagcga gcgcgcagag   4740
agggagtggc caactccatc actaggggtt cctgcggccg ctcgtacggt ctcgaggaat   4800
tcctgcagga taacttgcca acctcattct aaaatgtata tagaagccca aaagacaata   4860
acaaaaatat tcttgtagaa caaaatggga aagaatgttc cactaaatat caagatttag   4920
agcaaagcat gagatgtgtg gggatagaca gtgaggctga taaaatagag tagagctcag   4980
aaacagaccc attgatatat gtaagtgacc tatgaaaaaa atatggcatt ttacaatggg   5040
aaaatgatgg tctttttctt ttttagaaaa acagggaaat atatttatat gtaaaaaata   5100
aaagggaacc catatgtcat accatacaca caaaaaaatt ccagtgaatt ataagtctaa   5160
atggagaagg caaaacttta aatcttttag aaaataatat agaagcatgc agaccagcct   5220
ggccaacatg atgaaaccct ctctactaat aataaaatca gtagaactac tcaggactac   5280
tttgagtggg aagtcctttt ctatgaagac ttctttggcc aaaattaggc tctaaatgca   5340
aggagatagt gcatcatgcc tggctgcact tactgataaa tgatgttatc accatcttta   5400
accaaatgca caggaacaag ttatggtact gatgtgctgg attgagaagg agctctactt   5460
ccttgacagg acacatttgt atcaacttaa aaaagcagat ttttgccagc agaactattc   5520
attcagaggt aggaaactta gaatagatga tgtcactgat tagcatggct tccccatctc   5580
cacagctgct tcccacccag gttgcccaca gttgagtttg tccagtgctc agggctgccc   5640
actctcagta agaagcccca caccagcccc tctccaaata tgttggctgt tccttccatt   5700
aaagtgaccc cactttagag cagcaagtgg atttctgttt cttacagttc aggaaggagg   5760
```

```
agtcagctgt gagaacctgg agcctgagat gcttctaagt cccactgcta ctggggtcag   5820
ggaagccaga ctccagcatc agcagtcagg agcactaagc ccttgccaac atcctgtttc   5880
tcagagaaac tgcttccatt ataatggttg tcctttttta agctatcaag ccaaacaacc   5940
agtgtctacc attattctca tcacctgaag ccaagggttc tagcaaaagt caagctgtct   6000
tgtaatggtt gatgtgcctc cagcttctgt cttcagtcac tccactctta gcctgctctg   6060
aatcaactct gaccacagtt ccctggagcc cctgccacct gctgcccctg ccaccttctc   6120
catctgcagt gctgtgcagc cttctgcact cttgcagagc taataggtgg agacttgaag   6180
gaagaggagg aaagtttctc ataatagcct tgctgcaagc tcaaatggga ggtgggcact   6240
gtgcccagga gccttggagc aaaggctgtg cccaacctct gactgcatcc aggtttggtc   6300
ttgacagaga taagaagccc tggcttttgg agccaaaatc taggtcagac ttaggcagga   6360
ttctcaaagt ttatcagcag aacatgaggc agaagaccct ttctgctcca gcttcttcag   6420
gctcaacctt catcagaata gatagaaaga gaggctgtga gggttcttaa aacagaagca   6480
aatctgactc agagaataaa caacctccta gtaaactaca gcttagacag agcatctggt   6540
ggtgagtgtg ctcagtgtcc tactcaactg tctggtatca gccctcatga ggacttctct   6600
tctttccctc atagacctcc atctctgttt tccttagcct gcagaaatct ggatggctat   6660
tcacagaatg cctgtgcttt cagagttgca ttttttctct ggtattctgg ttcaagcatt   6720
tgaaggtagg aaaggttctc caagtgcaag aaagccagcc ctgagcctca actgcctggc   6780
tagtgtggtc agtaggatgc aaaggctgtt gaatgccaca aggccaaact ttaacctgtg   6840
taccacaagc ctagcagcag aggcagctct gctcactgga actctctgtc ttctttctcc   6900
tgagcctttt cttttcctga gttttctagc tctcctcaac cttacctctg ccctacccag   6960
gacaaaccca agagccactg tttctgtgat gtcctctcca gccctaatta ggcatcatga   7020
cttcagcctg accttccatg ctcagaagca gtgctaatcc acttcagatg agctgctcta   7080
tgcaacacag gcagagccta caaacctttg caccagagcc ctccacatat cagtgtttgt   7140
tcatactcac ttcaacagca aatgtgactg ctgagattaa gattttacac aagatggtct   7200
gtaatttcac agttagtttt atcccattag gtatgaaaga attagcataa ttccccttaa   7260
acatgaatga atcttagatt ttttaataaa tagttttgga agtaaagaca gagacatcag   7320
gagcacaagg aatagcctga gaggacaaac agaacaagaa agagtctgga aatacacagg   7380
atgttcttgg cctcctcaaa gcaagtgcaa gcagatagta ccagcagccc caggctatca   7440
gagcccagtg aagagaagta ccatgaaagc cacagctcta accaccctgt tccagagtga   7500
cagacagtcc ccaagacaag ccagcctgag ccagagagag aactgcaaga gaaagtttct   7560
aatttaggtt ctgttagatt cagacaagtg caggtcatcc tctctccaca gctactcacc   7620
tctccagcct aacaaagcct gcagtccaca ctccaaccct ggtgtctcac ctcctagcct   7680
ctcccaacat cctgctctct gaccatcttc tgcatctctc atctcaccat ctcccactgt   7740
ctacagccta ctcttgcaac taccatctca ttttctgaca tcctgtctac atcttctgcc   7800
atactctgcc atctaccata ccacctctta ccatctacca caccatcttt tatctccatc   7860
cctctcagaa gcctccaagc tgaatcctgc tttatgtgtt catctcagcc cctgcatgga   7920
aagctgaccc cagaggcaga actattccca gagagcttgg ccaagaaaaa caaaactacc   7980
agcctggcca ggctcaggag tagtaagctg cagtgtctgt tgtgttctag cttcaacagc   8040
tgcaggagtt ccactctcaa atgctccaca tttctcacat cctcctgatt ctggtcacta   8100
```

```
cccatcttca aagaacagaa tatctcacat cagcatactg tgaaggacta gtcatgggtg   8160
cagctgctca gagctgcaaa gtcattctgg atggtggaga gcttacaaac atttcatgat   8220
gctccccccg ctctgatggc tggagcccaa tccctacaca gactcctgct gtatgtgttt   8280
tcctttcact ctgagccaca gccagagggc aggcattcag tctcctcttc aggctggggc   8340
tggggcactg agaactcacc caacaccttg ctctcactcc ttctgcaaaa caagaaagag   8400
ctttgtgctg cagtagccat gaagaatgaa aggaaggctt taactaaaaa atgtcagaga   8460
ttattttcaa ccccttactg tggatcacca gcaaggagga aacacaacac agagacattt   8520
tttcccctca aattatcaaa agaatcactg catttgttaa agagagcaac tgaatcagga   8580
agcagagttt tgaacatatc agaagttagg aatctgcatc agagacaaat gcagtcatgg   8640
ttgtttgctg cataccagcc ctaatcatta gaagcctcat ggacttcaaa catcattccc   8700
tctgacaaga tgctctagcc taactccatg agataaaata aatctgcctt tcagagccaa   8760
agaagagtcc accagcttct tctcagtgtg aacaagagct ccagtcaggt tagtcagtcc   8820
agtgcagtag aggagaccag tctgcatcct ctaattttca aaggcaagaa gatttgttta   8880
ccctggacac caggcacaag tgaggtcaca gagctcttag atatgcagtc ctcatgagtg   8940
aggagactaa agcgcatgcc atcaagactt cagtgtagag aaaacctcca aaaaagcctc   9000
ctcactactt ctggaatagc tcagaggccg aggcggcctc ggcctctgca taaataaaaa   9060
aaattagtca gccatggggc ggagaatggg cggaactggg cggagttagg ggcgggatgg   9120
gcggagttag gggcgggact atggttgctg actaattgag atgcatgctt tgcatacttc   9180
tgcctgctgg ggagcctggg gactttccac acctggttgc tgactaattg agatgcatgc   9240
tttgcatact tctgcctgct ggggagcctg gggactttcc acaccctaac tgacacacat   9300
tccacagctg cattaatgaa tcggccaacg cgcggggaga ggcggtttgc gtattgggcg   9360
ctcttccgct tcctcgctca ctgactcgct gcgctcggtc gttcggctgc ggcgagcggt   9420
atcagctcac tcaaaggcgg taatacggtt atccacagaa tcaggggata acgcaggaaa   9480
gaacatgtga gcaaaaggcc agcaaaaggc caggaaccgt aaaaaggccg cgttgctggc   9540
gtttttccat aggctccgcc cccctgacga gcatcacaaa aatcgacgct caagtcagag   9600
gtggcgaaac ccgacaggac tataaagata ccaggcgttt ccccctggaa gctccctcgt   9660
gcgctctcct gttccgaccc tgccgcttac cggatacctg tccgcctttc tcccttcggg   9720
aagcgtggcg ctttctcata gctcacgctg taggtatctc agttcggtgt aggtcgttcg   9780
ctccaagctg ggctgtgtgc acgaaccccc cgttcagccc gaccgctgcg ccttatccgg   9840
taactatcgt cttgagtcca acccggtaag acacgactta tcgccactgg cagcagccac   9900
tggtaacagg attagcagag cgaggtatgt aggcggtgct acagagttct tgaagtggtg   9960
gcctaactac ggctacacta gaagaacagt atttggtatc tgcgctctgc tgaagccagt  10020
taccttcgga aaaagagttg gtagctcttg atccggcaaa caaaccaccg ctggtagcgg  10080
tggttttttt gtttgcaagc agcagattac gcgcagaaaa aaaggatctc aagaagatcc  10140
tttgatcttt tctacggggt ctgacgctca gtggaacgaa aactcacgtt aagggatttt  10200
ggtcatgaga ttatcaaaaa ggatcttcac ctagatcctt ttaaattaaa aatgaagttt  10260
taaatcaatc taaagtatat atgagtaaac ttggtctgac agttaccaat gcttaatcag  10320
tgaggcacct atctcagcga tctgtctatt tcgttcatcc atagttgcct gactcctgca  10380
aaccacgttg tgtctcaaaa tctctgatgt tacattgcac aagataaaaa tatatcatca  10440
tgaacaataa aactgtctgc ttacataaac agtaatacaa ggggtgttat gagccatatt  10500
```

```
caacgggaaa cgtcttgctc gaggccgcga ttaaattcca acatggatgc tgatttatat  10560

gggtataaat gggctcgcga taatgtcggg caatcaggtg cgacaatcta tcgattgtat  10620

gggaagcccg atgcgccaga gttgtttctg aaacatggca aaggtagcgt tgccaatgat  10680

gttacagatg agatggtcag actaaactgg ctgacggaat ttatgcctct tccgaccatc  10740

aagcatttta tccgtactcc tgatgatgca tggttactca ccactgcgat ccccgggaaa  10800

acagcattcc aggtattaga agaatatcct gattcaggtg aaaatattgt tgatgcgctg  10860

gcagtgttcc tgcgccggtt gcattcgatt cctgtttgta attgtccttt taacagcgat  10920

cgcgtatttc gtctcgctca ggcgcaatca cgaatgaata acggtttggt tgatgcgagt  10980

gattttgatg acgagcgtaa tggctggcct gttgaacaag tctggaaaga aatgcataag  11040

cttttgccat tctcaccgga ttcagtcgtc actcatggtg atttctcact tgataacctt  11100

atttttgacg aggggaaatt aataggttgt attgatgttg gacgagtcgg aatcgcagac  11160

cgataccagg atcttgccat cctatggaac tgcctcggtg agttttctcc ttcattacag  11220

aaacggcttt ttcaaaaata tggtattgat aatcctgata tgaataaatt gcagtttcat  11280

ttgatgctcg atgagttttt ctaagggcgg cctgccacca tacccacgcc gaaacaagcg  11340

ctcatgagcc cgaagtggcg agcccgatct tccccatcgg tgatgtcggc gatataggcg  11400

ccagcaaccg cacctgtggc gccggtgatg agggcgcgcc aagtcgacgt ccggcagtc   11459
```

<210> SEQ ID NO 63
<211> LENGTH: 274
<212> TYPE: PRT
<213> ORGANISM: Artificial sequence
<220> FEATURE:
<223> OTHER INFORMATION: Synthetic polypeptide

<400> SEQUENCE: 63

```
Met Gly Lys Ser Leu Ser His Leu Pro Leu His Ser Ser Lys Glu Asp
1               5                   10                  15

Ala Tyr Asp Gly Val Thr Ser Glu Asn Met Arg Asn Gly Leu Val Asn
            20                  25                  30

Ser Glu Val His Asn Glu Asp Gly Arg Asn Gly Asp Val Ser Gln Phe
        35                  40                  45

Pro Tyr Val Glu Phe Thr Gly Arg Asp Ser Val Thr Cys Pro Thr Cys
    50                  55                  60

Gln Gly Thr Gly Arg Ile Pro Arg Gly Gln Glu Asn Gln Leu Val Ala
65                  70                  75                  80

Leu Ile Pro Tyr Ser Asp Gln Arg Leu Arg Pro Arg Arg Thr Lys Leu
                85                  90                  95

Tyr Val Met Ala Ser Val Phe Val Cys Leu Leu Leu Ser Gly Leu Ala
            100                 105                 110

Val Phe Phe Leu Phe Pro Arg Ser Ile Asp Val Lys Tyr Ile Gly Val
        115                 120                 125

Lys Ser Ala Tyr Val Ser Tyr Asp Val Gln Lys Arg Thr Ile Tyr Leu
    130                 135                 140

Asn Ile Thr Asn Thr Leu Asn Ile Thr Asn Asn Asn Tyr Tyr Ser Val
145                 150                 155                 160

Glu Val Glu Asn Ile Thr Ala Gln Val Gln Phe Ser Lys Thr Val Ile
                165                 170                 175

Gly Lys Ala Arg Leu Asn Asn Ile Thr Ile Ile Gly Pro Leu Asp Met
            180                 185                 190
```

```
Lys Gln Ile Asp Tyr Thr Val Pro Thr Val Ile Ala Glu Glu Met Ser
        195                 200                 205

Tyr Met Tyr Asp Phe Cys Thr Leu Ile Ser Ile Lys Val His Asn Ile
    210                 215                 220

Val Leu Met Met Gln Val Thr Val Thr Thr Thr Tyr Phe Gly His Ser
225                 230                 235                 240

Glu Gln Ile Ser Gln Glu Arg Tyr Gln Tyr Val Asp Cys Gly Arg Asn
                245                 250                 255

Thr Thr Tyr Gln Leu Gly Gln Ser Glu Tyr Leu Asn Val Leu Gln Pro
            260                 265                 270

Gln Gln
```

<210> SEQ ID NO 64
<211> LENGTH: 825
<212> TYPE: DNA
<213> ORGANISM: Artificial sequence
<220> FEATURE:
<223> OTHER INFORMATION: Synthetic polynucleotide

<400> SEQUENCE: 64

```
atgggcaaga gcctgagcca cctgcccctg cacagcagca aggaggacgc ctacgacggc     60

gtgaccagcg agaacatgcg caacggcctg gtgaacagcg aggtgcacaa cgaggacggc    120

cgcaacggcg acgtgagcca gttcccctac gtggagttca ccggccgcga cagcgtgacc    180

tgccccacct gccagggcac cggccgcatc cccgcggcc aggagaacca gctggtggcc     240

ctgatcccct acagcgacca gcgcctgcgc ccccgccgca ccaagctgta cgtgatggcc    300

agcgtgttcg tgtgcctgct gctgagcggc ctggccgtgt tcttcctgtt cccccgcagc    360

atcgacgtga agtacatcgg cgtgaagagc gcctacgtga gctacgacgt gcagaagcgc    420

accatctacc tgaacatcac caacaccctg aacatcacca acaacaacta ctacagcgtg    480

gaggtggaga acatcaccgc ccaggtgcag ttcagcaaga ccgtgatcgg caaggcccgc    540

ctgaacaaca tcaccatcat cggcccccctg gacatgaagc agatcgacta caccgtgccc   600

accgtgatcg ccgaggagat gagctacatg tacgacttct gcaccctgat cagcatcaag    660

gtgcacaaca tcgtgctgat gatgcaggtg accgtgacca ccacctactt cggccacagc    720

gagcagatca gccaggagcg ctaccagtac gtggactgcg gccgcaacac cacctaccag    780

ctgggccaga gcgagtacct gaacgtgctg cagccccagc agtaa                    825
```

<210> SEQ ID NO 65
<211> LENGTH: 267
<212> TYPE: DNA
<213> ORGANISM: Artificial sequence
<220> FEATURE:
<223> OTHER INFORMATION: Synthetic polynucleotide

<400> SEQUENCE: 65

```
gtgatatcac aaggtcccag ggctggggtc agaaattctc tcccgaggga atgaagccac     60

aggagccaag agcaggagga ccaaggccct ggcgaaggcc gtggcctcgt tcaagtaaaa    120

gatcctagta cagtgcaggt cccaatgtgt actaggatct tttacttgaa cggggacgcc    180

ggcatccggg ctcaggaccc ccctctctgc cagaggcacc aacaccagag ttcacaaatc    240

agtctcctgc cctttgcatg tagcaaa                                        267
```

<210> SEQ ID NO 66
<211> LENGTH: 267
<212> TYPE: DNA

<213> ORGANISM: Artificial sequence
<220> FEATURE:
<223> OTHER INFORMATION: Synthetic polynucleotide

<400> SEQUENCE: 66

```
tttgctacat gcaaagggca ggagactgat ttgtgaactc tggtgttggt gcctctggca     60

gagagggggg tcctgagccc ggatgccggc gtccccgttc aagtaaaaga tcctagtaca    120

cattgggacc tgcactgtac taggatcttt tacttgaacg aggccacggc cttcgccagg    180

gccttggtcc tcctgctctt ggctcctgtg gcttcattcc ctcgggagag aatttctgac    240

cccagccctg ggaccttgtg atatcac                                        267
```

<210> SEQ ID NO 67
<211> LENGTH: 593
<212> TYPE: PRT
<213> ORGANISM: Artificial sequence
<220> FEATURE:
<223> OTHER INFORMATION: Synthetic polypeptide

<400> SEQUENCE: 67

```
Met Trp Thr Leu Val Ser Trp Val Ala Leu Thr Ala Gly Leu Val Ala
1               5                   10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

Trp Pro Thr Thr Leu Ser Arg His Leu Gly Gly Pro Cys Gln Val Asp
    50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
        115                 120                 125

Ser Gln Phe Glu Cys Pro Asp Phe Ser Thr Cys Cys Val Met Val Asp
    130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Ser Val Met Cys
        195                 200                 205

Pro Asp Ala Arg Ser Arg Cys Pro Asp Gly Ser Thr Cys Cys Glu Leu
    210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
            260                 265                 270

Lys Leu Pro Ala His Thr Val Gly Asp Val Lys Cys Asp Met Glu Val
        275                 280                 285
```

```
Ser Cys Pro Asp Gly Tyr Thr Cys Cys Arg Leu Gln Ser Gly Ala Trp
    290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
            340                 345                 350

Ser Leu Pro Asp Pro Gln Ala Leu Lys Arg Asp Val Pro Cys Asp Asn
        355                 360                 365

Val Ser Ser Cys Pro Ser Ser Asp Thr Cys Cys Gln Leu Thr Ser Gly
    370                 375                 380

Glu Trp Gly Cys Cys Pro Ile Pro Glu Ala Val Cys Cys Ser Asp His
385                 390                 395                 400

Gln His Cys Cys Pro Gln Gly Tyr Thr Cys Val Ala Glu Gly Gln Cys
                405                 410                 415

Gln Arg Gly Ser Glu Ile Val Ala Gly Leu Glu Lys Met Pro Ala Arg
            420                 425                 430

Arg Ala Ser Leu Ser His Pro Arg Asp Ile Gly Cys Asp Gln His Thr
        435                 440                 445

Ser Cys Pro Val Gly Gln Thr Cys Cys Pro Ser Leu Gly Gly Ser Trp
    450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
                485                 490                 495

Lys Glu Val Val Ser Ala Gln Pro Ala Thr Phe Leu Ala Arg Ser Pro
            500                 505                 510

His Val Gly Val Lys Asp Val Glu Cys Gly Glu Gly His Phe Cys His
        515                 520                 525

Asp Asn Gln Thr Cys Cys Arg Asp Asn Arg Gln Gly Trp Ala Cys Cys
    530                 535                 540

Pro Tyr Arg Gln Gly Val Cys Cys Ala Asp Arg Arg His Cys Cys Pro
545                 550                 555                 560

Ala Gly Phe Arg Cys Ala Ala Arg Gly Thr Lys Cys Leu Arg Arg Glu
                565                 570                 575

Ala Pro Arg Trp Asp Ala Pro Leu Arg Asp Pro Ala Leu Arg Gln Leu
            580                 585                 590

Leu
```

<210> SEQ ID NO 68
<211> LENGTH: 1779
<212> TYPE: DNA
<213> ORGANISM: Artificial sequence
<220> FEATURE:
<223> OTHER INFORMATION: Synthetic polynucleotide

<400> SEQUENCE: 68

```
atgtggaccc tggtgagctg ggtggccctg accgccggcc tggtggccgg cacccgctgc     60

cccgacggcc agttctgccc cgtggcctgc tgcctggacc ccggcggcgc cagctacagc    120

tgctgccgcc ccctgctgga caagtggccc accaccctga gccgccacct gggcggcccc    180

tgccaggtgg acgcccactg cagcgccggc cacagctgca tcttcaccgt gagcggcacc    240

agcagctgct gccccttccc cgaggccgtg gcctgcggcg acggccacca ctgctgcccc    300
```

```
cgcggcttcc actgcagcgc cgacggccgc agctgcttcc agcgcagcgg caacaacagc    360

gtgggcgcca tccagtgccc cgacagccag ttcgagtgcc ccgacttcag cacctgctgc    420

gtgatggtgg acggcagctg ggctgctgc cccatgcccc aggccagctg ctgcgaggac    480

cgcgtgcact gctgccccca cggcgccttc tgcgacctgg tgcacacccg ctgcatcacc    540

cccaccggca cccacccccct ggccaagaag ctgcccgccc agcgcaccaa ccgcgccgtg    600

gccctgagca gcagcgtgat gtgccccgac gcccgcagcc gctgccccga cggcagcacc    660

tgctgcgagc tgcccagcgg caagtacggc tgctgcccca tgcccaacgc cacctgctgc    720

agcgaccacc tgcactgctg cccccaggac accgtgtgcg acctgatcca gagcaagtgc    780

ctgagcaagg agaacgccac caccgacctg ctgaccaagc tgcccgccca caccgtgggc    840

gacgtgaagt gcgacatgga ggtgagctgc cccgacggct acacctgctg ccgcctgcag    900

agcggcgcct ggggctgctg ccccttcacc caggccgtgt gctgcgagga ccacatccac    960

tgctgccccg ccggcttcac ctgcgacacc cagaagggca cctgcgagca gggcccccac   1020

caggtgccct ggatggagaa ggcccccgcc cacctgagcc tgcccgaccc ccaggccctg   1080

aagcgcgacg tgccctgcga caacgtgagc agctgcccca gcagcgacac ctgctgccag   1140

ctgaccagcg gcgagtgggg ctgctgcccc atccccgagg ccgtgtgctg cagcgaccac   1200

cagcactgct gcccccaggg ctacacctgc gtggccgagg gccagtgcca gcgcggcagc   1260

gagatcgtgg ccggcctgga gaagatgccc gcccgccgcg ccagcctgag ccacccccgc   1320

gacatcggct gcgaccagca caccagctgc cccgtgggcc agacctgctg ccccagcctg   1380

ggcggcagct gggcctgctg ccagctgccc cacgccgtgt gctgcgagga ccgccagcac   1440

tgctgccccg ccggctacac ctgcaacgtg aaggcccgca gctgcgagaa ggaggtggtg   1500

agcgcccagc ccgccacctt cctggcccgc agcccccacg tgggcgtgaa ggacgtggag   1560

tgcggcgagg gccacttctg ccacgacaac cagacctgct gccgcgacaa ccgccagggc   1620

tgggcctgct gcccctaccg ccagggcgtg tgctgcgccg accgccgcca ctgctgcccc   1680

gccggcttcc gctgcgccgc ccgcggcacc aagtgcctgc gccgcgaggc cccccgctgg   1740

gacgcccccc tgcgcgaccc cgccctgcgc cagctgctg                          1779
```

<210> SEQ ID NO 69
<211> LENGTH: 10871
<212> TYPE: DNA
<213> ORGANISM: Artificial sequence
<220> FEATURE:
<223> OTHER INFORMATION: Synthetic polynucleotide

<400> SEQUENCE: 69

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg aattcggtac    300

ctagttatta atagtaatca attacggggt cattagttca tagcccatat atggagttcc    360

gcgttacata acttacggta aatggcccgc ctggctgacc gcccaacgac ccccgcccat    420

tgacgtcaat aatgacgtat gttcccatag taacgccaat agggactttc cattgacgtc    480

aatgggtgga gtatttacgg taaactgccc acttggcagt acatcaagtg tatcatatgc    540
```

```
caagtacgcc ccctattgac gtcaatgacg gtaaatggcc cgcctggcat tatgcccagt    600
acatgacctt atgggacttt cctacttggc agtacatcta cgtattagtc atcgctatta    660
ccatggtcga ggtgagcccc acgttctgct tcactctccc catctccccc ccctccccac    720
ccccaatttt gtatttattt atttttttaat tattttgtgc agcgatgggg gcgggggggg    780
gggggggcg cgcgccaggc ggggcggggc ggggcgaggg gcggggcggg gcgaggcgga    840
gaggtgcggc ggcagccaat cagagcggcg cgctccgaaa gtttcctttt atggcgaggc    900
ggcggcggcg gcggccctat aaaaagcgaa gcgcgcggcg ggcgggagtc gctgcgacgc    960
tgccttcgcc ccgtgccccg ctccgccgcc gcctcgcgcc gcccgccccg gctctgactg   1020
accgcgttac tcccacaggt gagcgggcgg gacggccctt ctcctccggg ctgtaattag   1080
cgcttggttt aatgacggct tgtttctttt ctgtggctgc gtgaaagcct tgaggggctc   1140
cgggagctag agcctctgct aaccatgttc atgccttctt ctttttccta cagctcctgg   1200
gcaacgtgct ggttattgtg ctgtctcatc attttggcaa agaattcctc gaagatccga   1260
agggaaagtc ttccacgact gtgggatccg ttcgaagata tcaccggttg agccaccatg   1320
tggaccctgg tgagctgggt ggccctgacc gccggcctgg tggccggcac ccgctgcccc   1380
gacggccagt tctgccccgt ggcctgctgc ctggaccccg gcggcgccag ctacagctgc   1440
tgccgccccc tgctggacaa gtggcccacc accctgagcc gccacctggg cggcccctgc   1500
caggtggacg cccactgcag cgccggccac agctgcatct tcaccgtgag cggcaccagc   1560
agctgctgcc ccttccccga ggccgtggcc tgcggcgacg gccaccactg ctgcccccgc   1620
ggcttccact gcagcgccga cggccgcagc tgcttccagc gcagcggcaa caacagcgtg   1680
ggcgccatcc agtgccccga cagccagttc gagtgccccg acttcagcac ctgctgcgtg   1740
atggtggacg gcagctgggg ctgctgcccc atgccccagg ccagctgctg cgaggaccgc   1800
gtgcactgct gcccccacgg cgccttctgc gacctggtgc acacccgctg catcaccccc   1860
accggcaccc accccctggc caagaagctg cccgcccagc gcaccaaccg cgccgtggcc   1920
ctgagcagca gcgtgatgtg ccccgacgcc cgcagccgct gccccgacgg cagcacctgc   1980
tgcgagctgc ccagcggcaa gtacggctgc tgccccatgc ccaacgccac ctgctgcagc   2040
gaccacctgc actgctgccc ccaggacacc gtgtgcgacc tgatccagag caagtgcctg   2100
agcaaggaga acgccaccac cgacctgctg accaagctgc ccgcccacac cgtgggcgac   2160
gtgaagtgcg acatggaggt gagctgcccc gacggctaca cctgctgccg cctgcagagc   2220
ggcgcctggg gctgctgccc cttcacccag gccgtgtgct gcgaggacca catccactgc   2280
tgccccgccg gcttcacctg cgacacccag aagggcacct gcgagcaggg cccccaccag   2340
gtgccctgga tggagaaggc cccccgcccac ctgagcctgc ccgaccccca ggccctgaag   2400
cgcgacgtgc cctgcgacaa cgtgagcagc tgccccagca gcgacacctg ctgccagctg   2460
accagcggcg agtggggctg ctgccccatc cccgaggccg tgtgctgcag cgaccaccag   2520
cactgctgcc cccagggcta cacctgcgtg gccgagggcc agtgccagcg cggcagcgag   2580
atcgtggccg gcctggagaa gatgcccgcc cgccgcgcca gcctgagcca cccccgcgac   2640
atcggctgcg accagcacac cagctgcccc gtgggccaga cctgctgccc cagcctgggc   2700
ggcagctggg cctgctgcca gctgccccac gccgtgtgct gcgaggaccg ccagcactgc   2760
tgccccgccg gctacacctg caacgtgaag gcccgcagct gcgagaagga ggtggtgagc   2820
gcccagcccg ccaccttcct ggcccgcagc ccccacgtgg gcgtgaagga cgtggagtgc   2880
ggcgagggcc acttctgcca cgacaaccag acctgctgcc gcgacaaccg ccagggctgg   2940
```

```
gcctgctgcc cctaccgcca gggcgtgtgc tgcgccgacc gccgccactg ctgccccgcc   3000
ggcttccgct gcgccgcccg cggcaccaag tgcctgcgcc gcgaggcccc ccgctgggac   3060
gccccccctgc gcgaccccgc cctgcgccag ctgctgtgac aattgttaat taagtttaaa   3120
ccctcgaggc cgcaagctta tcgataatca acctctggat tacaaaattt gtgaaagatt   3180
gactggtatt cttaactatg ttgctccttt tacgctatgt ggatacgctg ctttaatgcc   3240
tttgtatcat gctattgctt cccgtatggc tttcattttc tcctccttgt ataaatcctg   3300
gttgctgtct ctttatgagg agttgtggcc cgttgtcagg caacgtggcg tggtgtgcac   3360
tgtgtttgct gacgcaaccc ccactggttg gggcattgcc accacctgtc agctcctttc   3420
cgggactttc gctttccccc tccctattgc cacggcggaa ctcatcgccg cctgccttgc   3480
ccgctgctgg acaggggctc ggctgttggg cactgacaat tccgtggtgt tgtcggggaa   3540
atcatcgtcc tttccttggc tgctcgcctg tgttgccacc tggattctgc gcgggacgtc   3600
cttctgctac gtcccttcgg ccctcaatcc agcggacctt ccttcccgcg gcctgctgcc   3660
ggctctgcgg cctcttccgc gtcttcgcct tcgccctcag acgagtcgga tctccctttg   3720
ggccgcctcc ccgcatcgat accgtcgact agagctcgct gatcagcctc gactgtgcct   3780
tctagttgcc agccatctgt tgtttgcccc tcccccgtgc cttccttgac cctggaaggt   3840
gccactccca ctgtcctttc ctaataaaat gaggaaattg catcgcattg tctgagtagg   3900
tgtcattcta ttctgggggg tggggtgggg caggacagca agggggagga ttgggaagac   3960
aatagcaggc atgctgggga gagatccacg ataacaaaca gctttttttgg ggtgaacata   4020
ttgactgaat tccctgcagg ttggccactc cctctctgcg cgctcgctcg ctcactgagg   4080
ccgcccgggc aaagcccggg cgtcgggcga cctttggtcg cccggcctca gtgagcgagc   4140
gagcgcgcag agagggagtg gccaactcca tcactagggg ttcctgcggc cgctcgtacg   4200
gtctcgagga attcctgcag gataacttgc caacctcatt ctaaaatgta tatagaagcc   4260
caaaagacaa taacaaaaat attcttgtag aacaaaatgg gaaagaatgt tccactaaat   4320
atcaagattt agagcaaagc atgagatgtg tggggataga cagtgaggct gataaaatag   4380
agtagagctc agaaacagac ccattgatat atgtaagtga cctatgaaaa aaatatggca   4440
ttttacaatg ggaaaatgat ggtctttttc tttttttagaa aaacagggaa atatatttat   4500
atgtaaaaaa taaaagggaa cccatatgtc ataccataca cacaaaaaaa ttccagtgaa   4560
ttataagtct aaatggagaa ggcaaaactt taaatctttt agaaaataat atagaagcat   4620
gcagaccagc ctggccaaca tgatgaaacc ctctctacta ataataaaat cagtagaact   4680
actcaggact actttgagtg ggaagtcctt ttctatgaag acttctttgg ccaaaattag   4740
gctctaaatg caaggagata gtgcatcatg cctggctgca cttactgata aatgatgtta   4800
tcaccatctt taaccaaatg cacaggaaca agttatggta ctgatgtgct ggattgagaa   4860
ggagctctac ttccttgaca ggacacattt gtatcaactt aaaaaagcag atttttgcca   4920
gcagaactat tcattcagag gtaggaaact tagaatagat gatgtcactg attagcatgg   4980
cttccccatc tccacagctg cttcccaccc aggttgccca cagttgagtt tgtccagtgc   5040
tcagggctgc ccactctcag taagaagccc cacaccagcc cctctccaaa tatgttggct   5100
gttccttcca ttaaagtgac ccccactttag agcagcaagt ggatttctgt ttcttacagt   5160
tcaggaagga ggagtcagct gtgagaacct ggagcctgag atgcttctaa gtcccactgc   5220
tactggggtc agggaagcca gactccagca tcagcagtca ggagcactaa gcccttgcca   5280
```

```
acatcctgtt tctcagagaa actgcttcca ttataatggt tgtccttttt taagctatca   5340
agccaaacaa ccagtgtcta ccattattct catcacctga agccaagggt tctagcaaaa   5400
gtcaagctgt cttgtaatgg ttgatgtgcc tccagcttct gtcttcagtc actccactct   5460
tagcctgctc tgaatcaact ctgaccacag ttccctggag cccctgccac ctgctgcccc   5520
tgccaccttc tccatctgca gtgctgtgca gccttctgca ctcttgcaga gctaataggt   5580
ggagacttga aggaagagga ggaaagtttc tcataatagc cttgctgcaa gctcaaatgg   5640
gaggtgggca ctgtgcccag gagccttgga gcaaaggctg tgcccaacct ctgactgcat   5700
ccaggtttgg tcttgacaga gataagaagc cctggctttt ggagccaaaa tctaggtcag   5760
acttaggcag gattctcaaa gtttatcagc agaacatgag gcagaagacc ctttctgctc   5820
cagcttcttc aggctcaacc ttcatcagaa tagatagaaa gagaggctgt gagggttctt   5880
aaaacagaag caaatctgac tcagagaata aacaacctcc tagtaaacta cagcttagac   5940
agagcatctg gtggtgagtg tgctcagtgt cctactcaac tgtctggtat cagccctcat   6000
gaggacttct cttctttccc tcatagacct ccatctctgt tttccttagc ctgcagaaat   6060
ctggatggct attcacagaa tgcctgtgct ttcagagttg catttttttct ctggtattct   6120
ggttcaagca tttgaaggta ggaaaggttc tccaagtgca agaaagccag ccctgagcct   6180
caactgcctg gctagtgtgg tcagtaggat gcaaaggctg ttgaatgcca caaggccaaa   6240
ctttaacctg tgtaccacaa gcctagcagc agaggcagct ctgctcactg gaactctctg   6300
tcttctttct cctgagcctt ttcttttcct gagttttcta gctctcctca accttacctc   6360
tgccctaccc aggacaaacc caagagccac tgtttctgtg atgtcctctc cagccctaat   6420
taggcatcat gacttcagcc tgaccttcca tgctcagaag cagtgctaat ccacttcaga   6480
tgagctgctc tatgcaacac aggcagagcc tacaaacctt tgcaccagag ccctccacat   6540
atcagtgttt gttcatactc acttcaacag caaatgtgac tgctgagatt aagattttac   6600
acaagatggt ctgtaatttc acagttagtt ttatcccatt aggtatgaaa gaattagcat   6660
aattcccctt aaacatgaat gaatcttaga ttttttaata aatagttttg gaagtaaaga   6720
cagagacatc aggagcacaa ggaatagcct gagaggacaa acagaacaag aaagagtctg   6780
gaaatacaca ggatgttctt ggcctcctca aagcaagtgc aagcagatag taccagcagc   6840
cccaggctat cagagcccag tgaagagaag taccatgaaa gccacagctc taaccaccct   6900
gttccagagt gacagacagt ccccaagaca agccagcctg agccagagag agaactgcaa   6960
gagaaagttt ctaatttagg ttctgttaga ttcagacaag tgcaggtcat cctctctcca   7020
cagctactca cctctccagc ctaacaaagc ctgcagtcca cactccaacc ctggtgtctc   7080
acctcctagc ctctcccaac atcctgctct ctgaccatct tctgcatctc tcatctcacc   7140
atctcccact gtctacagcc tactcttgca actaccatct cattttctga catcctgtct   7200
acatcttctg ccatactctg ccatctacca taccacctct taccatctac cacaccatct   7260
tttatctcca tccctctcag aagcctccaa gctgaatcct gctttatgtg ttcatctcag   7320
cccctgcatg gaaagctgac cccagaggca gaactattcc cagagagctt ggccaagaaa   7380
aacaaaacta ccagcctggc caggctcagg agtagtaagc tgcagtgtct gttgtgttct   7440
agcttcaaca gctgcaggag ttccactctc aaatgctcca catttctcac atcctcctga   7500
ttctggtcac tacccatctt caaagaacag aatatctcac atcagcatac tgtgaaggac   7560
tagtcatggg tgcagctgct cagagctgca aagtcattct ggatggtgga gagcttacaa   7620
acatttcatg atgctccccc cgctctgatg gctggagccc aatccctaca cagactcctg   7680
```

```
ctgtatgtgt tttcctttca ctctgagcca cagccagagg gcaggcattc agtctcctct   7740
tcaggctggg gctggggcac tgagaactca cccaacacct tgctctcact ccttctgcaa   7800
aacaagaaag agctttgtgc tgcagtagcc atgaagaatg aaaggaaggc tttaactaaa   7860
aaatgtcaga gattattttc aaccccttac tgtggatcac cagcaaggag gaaacacaac   7920
acagagacat tttttcccct caaattatca aaagaatcac tgcatttgtt aaagagagca   7980
actgaatcag gaagcagagt tttgaacata tcagaagtta ggaatctgca tcagagacaa   8040
atgcagtcat ggttgtttgc tgcataccag ccctaatcat tagaagcctc atggacttca   8100
aacatcattc cctctgacaa gatgctctag cctaactcca tgagataaaa taaatctgcc   8160
tttcagagcc aaagaagagt ccaccagctt cttctcagtg tgaacaagag ctccagtcag   8220
gttagtcagt ccagtgcagt agaggagacc agtctgcatc ctctaatttt caaaggcaag   8280
aagatttgtt taccctggac accaggcaca agtgaggtca cagagctctt agatatgcag   8340
tcctcatgag tgaggagact aaagcgcatg ccatcaagac ttcagtgtag agaaaacctc   8400
caaaaaagcc tcctcactac ttctggaata gctcagaggc cgaggcggcc tcggcctctg   8460
cataaataaa aaaaattagt cagccatggg gcggagaatg ggcggaactg ggcggagtta   8520
ggggcgggat gggcggagtt aggggcggga ctatggttgc tgactaattg agatgcatgc   8580
tttgcatact tctgcctgct ggggagcctg gggactttcc acacctggtt gctgactaat   8640
tgagatgcat gctttgcata cttctgcctg ctggggagcc tggggacttt ccacacccta   8700
actgacacac attccacagc tgcattaatg aatcggccaa cgcgcgggga gaggcggttt   8760
gcgtattggg cgctcttccg cttcctcgct cactgactcg ctgcgctcgg tcgttcggct   8820
gcggcgagcg gtatcagctc actcaaaggc ggtaatacgg ttatccacag aatcagggga   8880
taacgcagga aagaacatgt gagcaaaagg ccagcaaaag gccaggaacc gtaaaaaggc   8940
cgcgttgctg gcgtttttcc ataggctccg cccccctgac gagcatcaca aaaatcgacg   9000
ctcaagtcag aggtggcgaa acccgacagg actataaaga taccaggcgt ttccccctgg   9060
aagctccctc gtgcgctctc ctgttccgac cctgccgctt accggatacc tgtccgcctt   9120
tctcccttcg ggaagcgtgg cgctttctca tagctcacgc tgtaggtatc tcagttcggt   9180
gtaggtcgtt cgctccaagc tgggctgtgt gcacgaaccc cccgttcagc ccgaccgctg   9240
cgccttatcc ggtaactatc gtcttgagtc caacccggta agacacgact tatcgccact   9300
ggcagcagcc actggtaaca ggattagcag agcgaggtat gtaggcggtg ctacagagtt   9360
cttgaagtgg tggcctaact acggctacac tagaagaaca gtatttggta tctgcgctct   9420
gctgaagcca gttaccttcg gaaaaagagt tggtagctct tgatccggca aacaaaccac   9480
cgctggtagc ggtggttttt ttgtttgcaa gcagcagatt acgcgcagaa aaaaaggatc   9540
tcaagaagat cctttgatct tttctacggg gtctgacgct cagtggaacg aaaactcacg   9600
ttaagggatt ttggtcatga gattatcaaa aaggatcttc acctagatcc ttttaaatta   9660
aaaatgaagt tttaaatcaa tctaaagtat atatgagtaa acttggtctg acagttacca   9720
atgcttaatc agtgaggcac ctatctcagc gatctgtcta tttcgttcat ccatagttgc   9780
ctgactcctg caaaccacgt tgtgtctcaa aatctctgat gttacattgc acaagataaa   9840
aatatatcat catgaacaat aaaactgtct gcttacataa acagtaatac aaggggtgtt   9900
atgagccata ttcaacggga aacgtcttgc tcgaggccgc gattaaattc caacatggat   9960
gctgatttat atgggtataa atgggctcgc gataatgtcg ggcaatcagg tgcgacaatc  10020
```

```
tatcgattgt atgggaagcc cgatgcgcca gagttgtttc tgaaacatgg caaaggtagc  10080

gttgccaatg atgttacaga tgagatggtc agactaaact ggctgacgga atttatgcct  10140

cttccgacca tcaagcattt tatccgtact cctgatgatg catggttact caccactgcg  10200

atccccggga aaacagcatt ccaggtatta gaagaatatc ctgattcagg tgaaaatatt  10260

gttgatgcgc tggcagtgtt cctgcgccgg ttgcattcga ttcctgtttg taattgtcct  10320

tttaacagcg atcgcgtatt tcgtctcgct caggcgcaat cacgaatgaa taacggtttg  10380

gttgatgcga gtgattttga tgacgagcgt aatggctggc ctgttgaaca agtctggaaa  10440

gaaatgcata agcttttgcc attctcaccg gattcagtcg tcactcatgg tgatttctca  10500

cttgataacc ttatttttga cgaggggaaa ttaataggtt gtattgatgt tggacgagtc  10560

ggaatcgcag accgatacca ggatcttgcc atcctatgga actgcctcgg tgagttttct  10620

ccttcattac agaaacggct ttttcaaaaa tatggtattg ataatcctga tatgaataaa  10680

ttgcagtttc atttgatgct cgatgagttt ttctaagggc ggcctgccac catacccacg  10740

ccgaaacaag cgctcatgag cccgaagtgg cgagcccgat cttccccatc ggtgatgtcg  10800

gcgatatagg cgccagcaac cgcacctgtg gcgccggtga tgagggcgcg ccaagtcgac  10860

gtccggcagt c                                                       10871
```

<210> SEQ ID NO 70
<211> LENGTH: 4151
<212> TYPE: DNA
<213> ORGANISM: Artificial sequence
<220> FEATURE:
<223> OTHER INFORMATION: Synthetic polynucleotide

<400> SEQUENCE: 70

```
gggaggttac gcgttcgtcg actactagtg ggtaccagag cgggcggagt tagggcggag    60

ccaatcagcg tgcgccgttc cgaaagttgc cttttatggc tgggcggaga atgggcggtg   120

aacgccgatg attatataag gacgcgccgg gtgtggcaca gctagttccg tcgcagccgg   180

gatttgggtc gcggttcttg tttgtggatc cctgtgatcg tcacttggta agtcactgac   240

tgtctatgcc tgggaaaggg tgggcaggag atggggcagt gcaggaaaag tggcactatg   300

aaccctgcag ccctaggaat gcatctagac aattgtacta accttcttct ctttcctctc   360

ctgacagtcc ggaaagccac catgtacgcc ctgttcctgc tggccagcct gctgggcgcc   420

gccctggccg gccccgtgct gggcctgaag gagtgcaccc gcggcagcgc cgtgtggtgc   480

cagaacgtga agaccgccag cgactgcggc gccgtgaagc actgcctgca gaccgtgtgg   540

aacaagccca ccgtgaagag cctgccctgc gacatctgca aggacgtggt gaccgccgcc   600

ggcgacatgc tgaaggacaa cgccaccgag gaggagatcc tggtgtacct ggagaagacc   660

tgcgactggc tgcccaagcc caacatgagc gccagctgca aggagatcgt ggacagctac   720

ctgcccgtga tcctggacat catcaagggc gagatgagcc gccccggcga ggtgtgcagc   780

gccctgaacc tgtgcgagag cctgcagaag cacctggccg agctgaacca ccagaagcag   840

ctggagagca acaagatccc cgagctggac atgaccgagg tggtggcccc cttcatggcc   900

aacatccccc tgctgctgta cccccaggac ggcccccgca gcaagcccca gcccaaggac   960

aacggcgacg tgtgccagga ctgcatccag atggtgaccg acatccagac cgccgtgcgc  1020

accaacagca ccttcgtgca ggccctggtg gagcacgtga aggaggagtg cgaccgcctg  1080

ggccccggca tggccgacat ctgcaagaac tacatcagcc agtacagcga gatcgccatc  1140

cagatgatga tgcacatgca gcccaaggag atctgcgccc tggtgggctt ctgcgacgag  1200
```

```
gtgaaggaga tgcccatgca gaccctggtg cccgccaagg tggccagcaa gaacgtgatc   1260
cccgccctgg agctggtgga gcccatcaag aagcacgagg tgcccgccaa gagcgacgtg   1320
tactgcgagg tgtgcgagtt cctggtgaag gaggtgacca agctgatcga caacaacaag   1380
accgagaagg agatcctgga cgccttcgac aagatgtgca gcaagctgcc caagagcctg   1440
agcgaggagt gccaggaggt ggtggacacc tacggcagca gcatcctgag catcctgctg   1500
gaggaggtga gccccgagct ggtgtgcagc atgctgcacc tgtgcagcgg cacccgcctg   1560
cccgccctga ccgtgcacgt gacccagccc aaggacggcg gcttctgcga ggtgtgcaag   1620
aagctggtgg gctacctgga ccgcaacctg gagaagaaca gcaccaagca ggagatcctg   1680
gccgccctgg agaagggctg cagcttcctg cccgacccct accagaagca gtgcgaccag   1740
ttcgtggccg agtacgagcc cgtgctgatc gagatcctgg tggaggtgat ggaccccagc   1800
ttcgtgtgcc tgaagatcgg cgcctgcccc agcgcccaca agcccctgct gggcaccgag   1860
aagtgcatct ggggccccag ctactggtgc cagaacaccg agaccgccgc ccagtgcaac   1920
gccgtggagc actgcaagcg ccacgtgtgg aacagaagaa agagaggaag tggagagggc   1980
agaggaagtc ttctgacatg cggagacgtg gaagagaatc ccggccctat gtggaccctg   2040
gtgagctggg tggccctgac cgccggcctg gtggccggca cccgctgccc cgacggccag   2100
ttctgccccg tggcctgctg cctggacccc ggcggcgcca gctacagctg ctgccgcccc   2160
ctgctggaca agtggcccac caccctgagc cgccacctgg gcggcccctg ccaggtggac   2220
gcccactgca gcgccggcca cagctgcatc ttcaccgtga gcggcaccag cagctgctgc   2280
cccttccccg aggccgtggc ctgcggcgac ggccaccact gctgcccccg cggcttccac   2340
tgcagcgccg acggccgcag ctgcttccag cgcagcggca acaacagcgt gggcgccatc   2400
cagtgccccg acagccagtt cgagtgcccc gacttcagca cctgctgcgt gatggtggac   2460
ggcagctggg gctgctgccc catgccccag gccagctgct gcgaggaccg cgtgcactgc   2520
tgcccccacg gcgccttctg cgacctggtg cacacccgct gcatcacccc caccggcacc   2580
cacccccctgg ccaagaagct gcccgcccag cgcaccaacc gcgccgtggc cctgagcagc   2640
agcgtgatgt gccccgacgc ccgcagccgc tgccccgacg gcagcacctg ctgcgagctg   2700
cccagcggca agtacggctg ctgccccatg cccaacgcca cctgctgcag cgaccacctg   2760
cactgctgcc cccaggacac cgtgtgcgac ctgatccaga gcaagtgcct gagcaaggag   2820
aacgccacca ccgacctgct gaccaagctg cccgcccaca ccgtgggcga cgtgaagtgc   2880
gacatggagg tgagctgccc cgacggctac acctgctgcc gcctgcagag cggcgcctgg   2940
ggctgctgcc ccttcaccca ggccgtgtgc tgcgaggacc acatccactg ctgccccgcc   3000
ggcttcacct gcgacaccca gaagggcacc tgcgagcagg gcccccacca ggtgccctgg   3060
atggagaagg cccccgccca cctgagcctg cccgaccccc aggccctgaa gcgcgacgtg   3120
ccctgcgaca acgtgagcag ctgccccagc agcgacacct gctgccagct gaccagcggc   3180
gagtggggct gctgccccat ccccgaggcc gtgtgctgca gcgaccacca gcactgctgc   3240
ccccagggct acacctgcgt ggccgagggc cagtgccagc gcggcagcga gatcgtggcc   3300
ggcctggaga agatgcccgc ccgccgcgcc agcctgagcc acccccgcga catcggctgc   3360
gaccagcaca ccagctgccc cgtgggccag acctgctgcc ccagcctggg cggcagctgg   3420
gcctgctgcc agctgcccca cgccgtgtgc tgcgaggacc gccagcactg ctgccccgcc   3480
ggctacacct gcaacgtgaa ggcccgcagc tgcgagaagg aggtggtgag cgcccagccc   3540
```

gccaccttcc tggcccgcag cccccacgtg ggcgtgaagg acgtggagtg cggcgagggc 3600
cacttctgcc acgacaacca gacctgctgc cgcgacaacc gccagggctg ggcctgctgc 3660
ccctaccgcc agggcgtgtg ctgcgccgac cgccgccact gctgccccgc cggcttccgc 3720
tgcgccgccc gcggcaccaa gtgcctgcgc cgcgaggccc cccgctggga cgccccccctg 3780 cgcgaccccg ccctgcgcca gctgctgtga caattgttaa ttaagtttaa accctcgagg 3840
ccgcaagcaa taaaatatct ttattttcat tacatctgtg tgttggtttt ttgtgtgaca 3900
attgttaatt aagtttaaac gttcgaggcc gcaagcgaga tccacgataa caaacagctt 3960
ttttggggtg aacatattga ctgaattccc tgcaggttgg ccactccctc tctgcgcgct 4020
cgctcgctca ctgaggccgc ccgggcaaag cccgggcgtc gggcgacctt tggtcgcccg 4080
gcctcagtga gcgagcgagc gcgcagagag ggagtggcca actccatcac taggggttcc 4140
tgcggccgct c 4151

<210> SEQ ID NO 71
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 71
aagagggtgt tctctatgta ggc 23

<210> SEQ ID NO 72
<211> LENGTH: 22
<212> TYPE: DNA
<213> ORGANISM: Artificial sequence
<220> FEATURE:
<223> OTHER INFORMATION: Synthetic polynucleotide

<400> SEQUENCE: 72
gctcctccaa catttgtcac tt 22

<210> SEQ ID NO 73
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 73
acacagtacc taccgttata gca 23

<210> SEQ ID NO 74
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 74
tgttgtcaca gtaacttgca tca 23

<210> SEQ ID NO 75
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 75
ctgggctaca ctgagcacc 19

<210> SEQ ID NO 76
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 76
aagtggtcgt tgagggcaat g 21

<210> SEQ ID NO 77
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 77
tattagatct gatggccgcg 20

<210> SEQ ID NO 78
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 78
tccatcacta ggggttcctg 20

<210> SEQ ID NO 79
<211> LENGTH: 4013
<212> TYPE: DNA
<213> ORGANISM: Artificial Sequence
<220> FEATURE:
<223> OTHER INFORMATION: Synthetic polynucleotide

<400> SEQUENCE: 79
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
ctagttatta atagtaatca attacggggt cattagttca tagcccatat atggagttcc 360
gcgttacata acttacggta aatggcccgc ctggctgacc gcccaacgac ccccgcccat 420
tgacgtcaat aatgacgtat gttcccatag taacgccaat agggactttc cattgacgtc 480
aatgggtgga gtatttacgg taaactgccc acttggcagt acatcaagtg tatcatatgc 540
caagtacgcc ccctattgac gtcaatgacg gtaaatggcc cgcctggcat tatgcccagt 600
acatgacctt atgggacttt cctacttggc agtacatcta cgtattagtc atcgctatta 660
ccatggtcga ggtgagcccc acgttctgct tcactctccc catctccccc ccctccccac 720
ccccaatttt gtatttattt atttttttaat tattttgtgc agcgatgggg gcgggggggg 780 gggggggcg cgcgccaggc ggggcggggc ggggcgaggg gcggggcggg gcgaggcgga 840
gaggtgcggc ggcagccaat cagagcggcg cgctccgaaa gtttcctttt atggcgaggc 900

```
ggcggcggcg gcggccctat aaaaagcgaa gcgcgcggcg ggcgggagtc gctgcgcgct    960
gccttcgccc cgtgccccgc tccgccgccg cctcgcgccg cccgccccgg ctctgactga   1020
ccgcgttact cccacaggtg agcgggcggg acggcccttc tcctccgggc tgtaattagc   1080
gcttggttta atgacggctt gtttcttttc tgtggctgcg tgaaagcctt gaggggctcc   1140
gggagctaga gcctctgcta accatgttca tgccttcttc tttttcctac agctcctggg   1200
caacgtgctg gttattgtgc tgtctcatca ttttggcaaa gaattcctcg aagatccgaa   1260
gggaaagtct tccacgactg tgggatccgt tcgaagatat caccggttga gccaccatgg   1320
aattcagcag ccccagcaga gaggaatgcc ccaagcctct gagccgggtg tcaatcatgg   1380
ccggatctct gacaggactg ctgctgcttc aggccgtgtc ttgggcttct ggcgctagac   1440
cttgcatccc caagagcttc ggctacagca gcgtcgtgtg cgtgtgcaat gccacctact   1500
gcgacagctt cgaccctcct acctttcctg ctctgggcac cttcagcaga tacgagagca   1560
ccagatccgg cagacggatg gaactgagca tgggacccat ccaggccaat cacacaggca   1620
ctggcctgct gctgacactg cagcctgagc agaaattcca gaaagtgaaa ggcttcggcg   1680
gagccatgac agatgccgcc gctctgaata tcctggctct gtctccacca gctcagaacc   1740
tgctgctcaa gagctacttc agcgaggaag gcatcggcta caacatcatc agagtgccca   1800
tggccagctg cgacttcagc atcaggacct acacctacgc cgacacaccc gacgatttcc   1860
agctgcacaa cttcagcctg cctgaagagg acaccaagct gaagatccct ctgatccaca   1920
gagccctgca gctggcacaa agacccgtgt cactgctggc ctctccatgg acatctccca   1980
cctggctgaa aacaaatggc gccgtgaatg gcaagggcag cctgaaaggc caacctggcg   2040
acatctacca ccagacctgg gccagatact tcgtgaagtt cctggacgcc tatgccgagc   2100
acaagctgca gttttgggcc gtgacagccg agaacgaacc ttctgctgga ctgctgagcg   2160
gctacccctt tcagtgcctg ggctttacac ccgagcacca gcgggacttt atcgcccgtg   2220
atctgggacc cacactggcc aatagcaccc accataatgt gcggctgctg atgctggacg   2280
accagagact gcttctgccc cactgggcta aagtggtgct gacagatcct gaggccgcca   2340
aatacgtgca cggaatcgcc gtgcactggt atctggactt tctggcccct gccaaggcca   2400
cactgggaga gacacacaga ctgttcccca acaccatgct gttcgccagc gaagcctgtg   2460
tgggcagcaa gttttgggaa cagagcgtgc ggctcggcag ctgggataga ggcatgcagt   2520
acagccacag catcatcacc aacctgctgt accacgtcgt cggctggacc gactggaatc   2580
tggccctgaa tcctgaaggc ggccctaact gggtccgaaa cttcgtggac agccccatca   2640
tcgtggacat caccaaggac accttctaca agcagcccat gttctaccac ctgggacact   2700
tcagcaagtt catccccgag ggctctcagc gcgttggact ggtggcttcc cagaagaacg   2760
atctggacgc cgtggctctg atgcaccctg atggatctgc tgtggtggtg gtcctgaacc   2820
gcagcagcaa agatgtgccc ctgaccatca aggatcccgc cgtgggattc ctggaaacaa   2880
tcagccctgg ctactccatc cacacctacc tgtggcgtag acagtgacaa ttgttaatta   2940
agtttaaacc ctcgaggccg caagcttatc gataatcaac ctctggatta caaaatttgt   3000
gaaagattga ctggtattct taactatgtt gctcctttta cgctatgtgg atacgctgct   3060
ttaatgcctt tgtatcatgc tattgcttcc cgtatggctt tcattttctc ctccttgtat   3120
aaatcctggt tgctgtctct ttatgaggag ttgtggcccg ttgtcaggca acgtggcgtg   3180
gtgtgcactg tgtttgctga cgcaaccccc actggttggg gcattgccac cacctgtcag   3240
ctcctttccg ggactttcgc tttccccctc cctattgcca cggcggaact catcgccgcc   3300
```

tgccttgccc gctgctggac aggggctcgg ctgttgggca ctgacaattc cgtggtgttg 3360
tcggggaaat catcgtcctt tccttggctg ctcgcctgtg ttgccacctg gattctgcgc 3420
gggacgtcct tctgctacgt cccttcggcc ctcaatccag cggaccttcc ttcccgcggc 3480
ctgctgccgg ctctgcggcc tcttccgcgt cttcgccttc gccctcagac gagtcggatc 3540
tccctttggg ccgcctcccc gcatcgatac cgtcgactag agctcgctga tcagcctcga 3600
ctgtgccttc tagttgccag ccatctgttg tttgcccctc ccccgtgcct tccttgaccc 3660
tggaaggtgc cactcccact gtcctttcct aataaaatga ggaaattgca tcgcattgtc 3720
tgagtaggtg tcattctatt ctggggggtg gggtggggca ggacagcaag ggggaggatt 3780
gggaagacaa tagcaggcat gctggggaga gatccacgat aacaaacagc tttttttgggg 3840 tgaacatatt gactgaattc cctgcaggtt ggccactccc tctctgcgcg ctcgctcgct 3900
cactgaggcc gcccgggcaa agcccgggcg tcgggcgacc tttggtcgcc cggcctcagt 3960
gagcgagcga gcgcgcagag agggagtggc caactccatc actaggggtt cct 4013

<210> SEQ ID NO 80
<211> LENGTH: 4013
<212> TYPE: DNA
<213> ORGANISM: Artificial Sequence
<220> FEATURE:
<223> OTHER INFORMATION: Synthetic polynucleotide

<400> SEQUENCE: 80
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
ctagttatta atagtaatca attacggggt cattagttca tagcccatat atggagttcc 360
gcgttacata acttacggta aatggcccgc ctggctgacc gcccaacgac ccccgcccat 420
tgacgtcaat aatgacgtat gttcccatag taacgccaat agggactttc cattgacgtc 480
aatgggtgga gtatttacgg taaactgccc acttggcagt acatcaagtg tatcatatgc 540
caagtacgcc ccctattgac gtcaatgacg gtaaatggcc cgcctggcat tatgcccagt 600
acatgacctt atgggacttt cctacttggc agtacatcta cgtattagtc atcgctatta 660
ccatggtcga ggtgagcccc acgttctgct tcactctccc catctccccc ccctccccac 720
ccccaatttt gtatttattt atttttttaat tattttgtgc agcgatgggg gcgggggggg 780 gggggggcgcg cgcgccaggc ggggcggggc ggggcgaggg gcggggcggg gcgaggcgga 840
gaggtgcggc ggcagccaat cagagcggcg cgctccgaaa gtttcctttt atggcgaggc 900
ggcggcggcg gcggccctat aaaaagcgaa gcgcgcggcg ggcgggagtc gctgcgcgct 960
gccttcgccc cgtgccccgc tccgccgccg cctcgcgccg cccgccccgg ctctgactga 1020
ccgcgttact cccacaggtg agcgggcggg acggcccttc tcctccgggc tgtaattagc 1080
gcttggttta atgacggctt gtttcttttc tgtggctgcg tgaaagcctt gaggggctcc 1140
gggagctaga gcctctgcta accatgttca tgccttcttc tttttcctac agctcctggg 1200
caacgtgctg gttattgtgc tgtctcatca ttttggcaaa gaattcctcg aagatccgaa 1260
gggaaagtct tccacgactg tgggatccgt tcgaagatat caccggttga gccaccatgg 1320

```
aattcagcag ccccagcaga gaggaatgcc ccaagcctct gagccgggtg tcaatcatgg   1380
ccggatctct gacaggactg ctgctgcttc aggccgtgtc ttgggcttct ggcgctagac   1440
cttgcatccc caagagcttc ggctacagca gcgtcgtgtg cgtgtgcaat gccacctact   1500
gcgacagctt cgaccctcct acctttcctg ctctgggcac cttcagcaga tacgagagca   1560
ccagatccgg cagacggatg gaactgagca tgggacccat ccaggccaat cacacaggca   1620
ctggcctgct gctgacactg cagcctgagc agaaattcca gaaagtgaaa ggcttcggcg   1680
gagccatgac agatgccgcc gctctgaata tcctggctct gtctccacca gctcagaacc   1740
tgctgctcaa gagctacttc agcgaggaag gcatcggcta caacatcatc agagtgccca   1800
tggccagctg cgacttcagc atcaggacct acacctacgc cgacacaccc gacgatttcc   1860
agctgcacaa cttcagcctg cctgaagagg acaccaagct gaagatccct ctgatccaca   1920
gagccctgca gctggcacaa agacccgtgt cactgctggc ctctccatgg acatctccca   1980
cctggctgaa aacaaatggc gccgtgaatg gcaagggcag cctgaaaggc caacctggcg   2040
acatctacca ccagacctgg gccagatact tcgtgaagtt cctggacgcc tatgccgagc   2100
acaagctgca gttttgggcc gtgacagccg agaacgaacc ttctgctgga ctgctgagcg   2160
gctacccctt tcagtgcctg ggctttacac ccgagcacca gcgggacttt atcgcccgtg   2220
atctgggacc cacactggcc aatagcaccc accataatgt gcggctgctg atgctggacg   2280
accagagact gcttctgccc cactgggcta aagtggtgct gacagatcct gaggccgcca   2340
aatacgtgca cggaatcgcc gtgcactggt atctggactt tctggcccct gccaaggcca   2400
cactgggaga gacacacaga ctgttcccca acaccatgct gttcgccagc gaagcctgtg   2460
tgggcagcaa gttttgggaa cagagcgtgc ggctcggcag ctgggataga ggcatgcagt   2520
acagccacag catcatcacc aacctgctgt accacgtcgt cggctggacc gactggaatc   2580
tggccctgaa tcctgaaggc ggccctaact gggtccgaaa cttcgtggac agccccatca   2640
tcgtggacat caccaaggac accttctaca agcagcccat gttctaccac ctgggacact   2700
tcagcaagtt catccccgag ggctctcagc gcgttggact ggtggcttcc cagaagaacg   2760
atctggacgc cgtggctctg atgcaccctg atggatctgc tgtggtggtg gtcctgaacc   2820
gcagcagcaa agatgtgccc ctgaccatca aggatcccgc cgtgggattc ctggaaacaa   2880
tcagccctgg ctactccatc cacacctacc tgtggcgtag acagtgacaa ttgttaatta   2940
agtttaaacc ctcgaggccg caagcttatc gataatcaac ctctggatta caaaatttgt   3000
gaaagattga ctggtattct taactatgtt gctcctttta cgctatgtgg atacgctgct   3060
ttaatgcctt tgtatcatgc tattgcttcc cgtatggctt tcattttctc ctccttgtat   3120
aaatcctggt tgctgtctct ttatgaggag ttgtggcccg ttgtcaggca acgtggcgtg   3180
gtgtgcactg tgtttgctga cgcaaccccc actggttggg gcattgccac cacctgtcag   3240
ctcctttccg ggactttcgc tttccccctc cctattgcca cggcggaact catcgccgcc   3300
tgccttgccc gctgctggac aggggctcgg ctgttgggca ctgacaattc cgtggtgttg   3360
tcggggaaat catcgtcctt tccttggctg ctcgcctgtg ttgccacctg gattctgcgc   3420
gggacgtcct tctgctacgt cccttcggcc ctcaatccag cggaccttcc ttcccgcggc   3480
ctgctgccgg ctctgcggcc tcttccgcgt cttcgccttc gccctcagac gagtcggatc   3540
tccctttggg ccgcctcccc gcatcgatac cgtcgactag agctcgctga tcagcctcga   3600
ctgtgccttc tagttgccag ccatctgttg tttgcccctc ccccgtgcct tccttgaccc   3660
tggaaggtgc cactcccact gtcctttcct aataaaatga ggaaattgca tcgcattgtc   3720
```

tgagtaggtg tcattctatt ctggggggtg gggtggggca ggacagcaag gggaggatt 3780 gggaagacaa tagcaggcat gctggggaga gatccacgat aacaaacagc tttttttgggg 3840 tgaacatatt gactgaattc cctgcaggtt ggccactccc tctctgcgcg ctcgctcgct 3900
cactgaggcc gcccgggcaa agcccgggcg tcgggcgacc tttggtcgcc cggcctcagt 3960
gagcgagcga gcgcgcagag agggagtggc caactccatc actaggggtt cct 4013

<210> SEQ ID NO 81
<211> LENGTH: 4162
<212> TYPE: DNA
<213> ORGANISM: Artificial Sequence
<220> FEATURE:
<223> OTHER INFORMATION: Synthetic polynucleotide

<400> SEQUENCE: 81
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
ctagttatta atagtaatca attacggggt cattagttca tagcccatat atggagttcc 360
gcgttacata acttacggta aatggcccgc ctggctgacc gcccaacgac ccccgcccat 420
tgacgtcaat aatgacgtat gttcccatag taacgccaat agggactttc cattgacgtc 480
aatgggtgga gtatttacgg taaactgccc acttggcagt acatcaagtg tatcatatgc 540
caagtacgcc ccctattgac gtcaatgacg gtaaatggcc cgcctggcat tatgcccagt 600
acatgacctt atgggacttt cctacttggc agtacatcta cgtattagtc atcgctatta 660
ccatggtcga ggtgagcccc acgttctgct tcactctccc catctccccc ccctccccac 720
ccccaatttt gtatttattt atttttaat tattttgtgc agcgatgggg gcgggggggg 780 gggggggcg cgcgccaggc ggggcggggc ggggcgaggg gcggggcggg gcgaggcgga 840
gaggtgcggc ggcagccaat cagagcggcg cgctccgaaa gtttcctttt atggcgaggc 900
ggcggcggcg gcggccctat aaaaagcgaa gcgcgcggcg ggcgggagtc gctgcgacgc 960
tgccttcgcc ccgtgccccg ctccgccgcc gcctcgcgcc gcccgccccg gctctgactg 1020
accgcgttac tcccacaggt gagcgggcgg gacggccctt ctcctcagcg ctgtaattag 1080
cgcttggttt aatgacggct tgttggaggc ttgctgaagg ctgtatgctg ttgtctttag 1140
aaataagtgg tagtcaagtg aagccacaga tgtgactacc acttatttct aaaaggacac 1200
aaggcctgtt actagcactc acatggaaca aatggccacc gtgggaggat gacaatttct 1260
gtggctgcgt gaaagccttg aggggctccg ggagctagag cctctgctaa ccatgttcat 1320
gccttcttct ttttcctaca gctcctgggc aacgtgctgg ttattgtgct gtctcatcat 1380
tttggcaaag aattcctcga agatccgaag ggaaagtctt ccacgactgt gggatccgtt 1440
cgaagatatc accggttgag ccaccatgga attcagcagc cccagcagag aggaatgccc 1500
caagcctctg agccgggtgt caatcatggc cggatctctg acaggactgc tgctgcttca 1560
ggccgtgtct tgggcttctg gcgctagacc ttgcatcccc aagagcttcg gctacagcag 1620
cgtcgtgtgc gtgtgcaatg ccacctactg cgacagcttc gaccctccta cctttcctgc 1680
tctgggcacc ttcagcagat acgagagcac cagatccggc agacggatgg aactgagcat 1740

```
gggacccatc caggccaatc acacaggcac tggcctgctg ctgacactgc agcctgagca   1800
gaaattccag aaagtgaaag gcttcggcgg agccatgaca gatgccgccg ctctgaatat   1860
cctggctctg tctccaccag ctcagaacct gctgctcaag agctacttca gcgaggaagg   1920
catcggctac aacatcatca gagtgcccat ggccagctgc gacttcagca tcaggaccta   1980
cacctacgcc gacacacccg acgatttcca gctgcacaac ttcagcctgc ctgaagagga   2040
caccaagctg aagatccctc tgatccacag agccctgcag ctggcacaaa gacccgtgtc   2100
actgctggcc tctccatgga catctcccac ctggctgaaa acaaatggcg ccgtgaatgg   2160
caagggcagc ctgaaaggcc aacctggcga catctaccac cagacctggg ccagatactt   2220
cgtgaagttc ctggacgcct atgccgagca caagctgcag ttttgggccg tgacagccga   2280
gaacgaacct tctgctggac tgctgagcgg ctaccccttt cagtgcctgg gctttacacc   2340
cgagcaccag cgggacttta tcgcccgtga tctgggaccc acactggcca atagcaccca   2400
ccataatgtg cggctgctga tgctggacga ccagagactg cttctgcccc actgggctaa   2460
agtggtgctg acagatcctg aggccgccaa atacgtgcac ggaatcgccg tgcactggta   2520
tctggacttt ctggcccctg ccaaggccac actgggagag acacacagac tgttccccaa   2580
caccatgctg ttcgccagcg aagcctgtgt gggcagcaag ttttgggaac agagcgtgcg   2640
gctcggcagc tgggatagag gcatgcagta cagccacagc atcatcacca acctgctgta   2700
ccacgtcgtc ggctggaccg actggaatct ggccctgaat cctgaaggcg gccctaactg   2760
ggtccgaaac ttcgtggaca gccccatcat cgtggacatc accaaggaca ccttctacaa   2820
gcagcccatg ttctaccacc tgggacactt cagcaagttc atccccgagg gctctcagcg   2880
cgttggactg gtggcttccc agaagaacga tctggacgcc gtggctctga tgcaccctga   2940
tggatctgct gtggtggtgg tcctgaaccg cagcagcaaa gatgtgcccc tgaccatcaa   3000
ggatcccgcc gtgggattcc tggaaacaat cagccctggc tactccatcc acacctacct   3060
gtggcgtaga cagtgacaat tgttaattaa gtttaaaccc tcgaggccgc aagcttatcg   3120
ataatcaacc tctggattac aaaatttgtg aaagattgac tggtattctt aactatgttg   3180
ctccttttac gctatgtgga tacgctgctt taatgccttt gtatcatgct attgcttccc   3240
gtatggcttt cattttctcc tccttgtata aatcctggtt gctgtctctt tatgaggagt   3300
tgtggcccgt tgtcaggcaa cgtggcgtgg tgtgcactgt gtttgctgac gcaaccccca   3360
ctggttgggg cattgccacc acctgtcagc tcctttccgg gactttcgct ttccccctcc   3420
ctattgccac ggcggaactc atcgccgcct gccttgcccg ctgctggaca ggggctcggc   3480
tgttgggcac tgacaattcc gtggtgttgt cggggaaatc atcgtccttt ccttggctgc   3540
tcgcctgtgt tgccacctgg attctgcgcg ggacgtcctt ctgctacgtc ccttcggccc   3600
tcaatccagc ggaccttcct tcccgcggcc tgctgccggc tctgcggcct cttccgcgtc   3660
ttcgccttcg ccctcagacg agtcggatct ccctttgggc cgcctccccg catcgatacc   3720
gtcgactaga gctcgctgat cagcctcgac tgtgccttct agttgccagc catctgttgt   3780
ttgcccctcc cccgtgcctt ccttgaccct ggaaggtgcc actcccactg tcctttccta   3840
ataaaatgag gaaattgcat cgcattgtct gagtaggtgt cattctattc tggggggtgg   3900
ggtggggcag gacagcaagg gggaggattg ggaagacaat agcaggcatg ctggggagag   3960
atccacgata acaaacagct tttttggggc ccacatgtac actgaattcc ctgcaggttg   4020
gccactccct ctctgcgcgc tcgctcgctc actgaggccg cccgggcaaa gcccgggcgt   4080
cgggcgacct ttggtcgccc ggcctcagtg agcgagcgag cgcgcagaga gggagtggcc   4140
```

aactccatca ctaggggttc ct 4162

<210> SEQ ID NO 82
<211> LENGTH: 4184
<212> TYPE: DNA
<213> ORGANISM: Artificial Sequence
<220> FEATURE:
<223> OTHER INFORMATION: Synthetic polynucleotide

<400> SEQUENCE: 82
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
ctagttatta atagtaatca attacggggt cattagttca tagcccatat atggagttcc 360
gcgttacata acttacggta aatggcccgc ctggctgacc gcccaacgac ccccgcccat 420
tgacgtcaat aatgacgtat gttcccatag taacgccaat agggactttc cattgacgtc 480
aatgggtgga gtatttacgg taaactgccc acttggcagt acatcaagtg tatcatatgc 540
caagtacgcc ccctattgac gtcaatgacg gtaaatggcc cgcctggcat tatgcccagt 600
acatgacctt atgggacttt cctacttggc agtacatcta cgtattagtc atcgctatta 660
ccatggtcga ggtgagcccc acgttctgct tcactctccc catctccccc ccctccccac 720
ccccaatttt gtatttattt atttttaat tattttgtgc agcgatgggg gcgggggggg 780 gggggggcg cgcgccaggc ggggcggggc ggggcgaggg gcggggcggg gcgaggcgga 840
gaggtgcggc ggcagccaat cagagcggcg cgctccgaaa gtttcctttt atggcgaggc 900
ggcggcggcg gcggccctat aaaaagcgaa gcgcgcggcg ggcgggagtc gctgcgcgct 960
gccttcgccc cgtgccccgc tccgccgccg cctcgcgccg cccgccccgg ctctgactga 1020
ccgcgttact cccacaggtg agcgggcggg acggcccttc tcctccgggc tgtaattagc 1080
gcttggttta atgacggctt gtttcttttc tgtggctgcg tgaaagcctt gaggggctcc 1140
gggagctaga gcctctgcta accatgttca tgccttcttc tttttcctac agctcctggg 1200
caacgtgctg gttattgtgc tgtctcatca ttttggcaaa gaattcctcg aagatccgaa 1260
gggaaagtct tccacgactg tgggatccgt tcgaagatat caccggttga gccaccatgt 1320
ggaccctggt gagctgggtg gccctgaccg ccggcctggt ggccggcacc cgctgccccg 1380
acggccagtt ctgccccgtg gcctgctgcc tggaccccgg cggcgccagc tacagctgct 1440
gccgccccct gctggacaag tggcccacca ccctgagccg ccacctgggc ggcccctgcc 1500
aggtggacgc ccactgcagc gccggccaca gctgcatctt caccgtgagc ggcaccagca 1560
gctgctgccc cttccccgag gccgtggcct gcggcgacgg ccaccactgc tgcccccgcg 1620
gcttccactg cagcgccgac ggccgcagct gcttccagcg cagcggcaac aacagcgtgg 1680
gcgccatcca gtgccccgac agccagttcg agtgccccga cttcagcacc tgctgcgtga 1740
tggtggacgg cagctggggc tgctgcccca tgccccaggc cagctgctgc gaggaccgcg 1800
tgcactgctg cccccacggc gccttctgcg acctggtgca cacccgctgc atcaccccca 1860
ccggcaccca ccccctggcc aagaagctgc ccgcccagcg caccaaccgc gccgtggccc 1920
tgagcagcag cgtgatgtgc cccgacgccc gcagccgctg ccccgacggc agcacctgct 1980

```
gcgagctgcc cagcggcaag tacggctgct gccccatgcc caacgccacc tgctgcagcg   2040
accacctgca ctgctgcccc caggacaccg tgtgcgacct gatccagagc aagtgcctga   2100
gcaaggagaa cgccaccacc gacctgctga ccaagctgcc cgcccacacc gtgggcgacg   2160
tgaagtgcga catggaggtg agctgccccg acggctacac ctgctgccgc ctgcagagcg   2220
gcgcctgggg ctgctgcccc ttcacccagg ccgtgtgctg cgaggaccac atccactgct   2280
gccccgccgg cttcacctgc gacacccaga agggcacctg cgagcagggc ccccaccagg   2340
tgccctggat ggagaaggcc cccgcccacc tgagcctgcc cgacccccag gccctgaagc   2400
gcgacgtgcc ctgcgacaac gtgagcagct gccccagcag cgacacctgc tgccagctga   2460
ccagcggcga gtggggctgc tgccccatcc ccgaggccgt gtgctgcagc gaccaccagc   2520
actgctgccc ccagggctac acctgcgtgg ccgagggcca gtgccagcgc ggcagcgaga   2580
tcgtggccgg cctggagaag atgcccgccc gccgcgccag cctgagccac ccccgcgaca   2640
tcggctgcga ccagcacacc agctgccccg tgggccagac ctgctgcccc agcctgggcg   2700
gcagctgggc ctgctgccag ctgcccccacg ccgtgtgctg cgaggaccgc cagcactgct   2760
gccccgccgg ctacacctgc aacgtgaagg cccgcagctg cgagaaggag gtggtgagcg   2820
cccagcccgc caccttcctg gcccgcagcc cccacgtggg cgtgaaggac gtggagtgcg   2880
gcgagggcca cttctgccac gacaaccaga cctgctgccg cgacaaccgc cagggctggg   2940
cctgctgccc ctaccgccag ggcgtgtgct gcgccgaccg ccgccactgc tgccccgccg   3000
gcttccgctg cgccgcccgc ggcaccaagt gcctgcgccg cgaggccccc cgctgggacg   3060
ccccccctgcg cgaccccgcc ctgcgccagc tgctgtgaca attgttaatt aagtttaaac   3120
cctcgaggcc gcaagcttat cgataatcaa cctctggatt acaaaatttg tgaaagattg   3180
actggtattc ttaactatgt tgctcctttt acgctatgtg gatacgctgc tttaatgcct   3240
ttgtatcatg ctattgcttc ccgtatggct ttcattttct cctccttgta taaatcctgg   3300
ttgctgtctc tttatgagga gttgtggccc gttgtcaggc aacgtggcgt ggtgtgcact   3360
gtgtttgctg acgcaacccc cactggttgg ggcattgcca ccacctgtca gctcctttcc   3420
gggactttcg ctttcccct ccctattgcc acggcggaac tcatcgccgc ctgccttgcc   3480
cgctgctgga caggggctcg gctgttgggc actgacaatt ccgtggtgtt gtcggggaaa   3540
tcatcgtcct ttccttggct gctcgcctgt gttgccacct ggattctgcg cgggacgtcc   3600
ttctgctacg tcccttcggc cctcaatcca gcggaccttc cttcccgcgg cctgctgccg   3660
gctctgcggc ctcttccgcg tcttcgcctt cgccctcaga cgagtcggat ctccctttgg   3720
gccgcctccc cgcatcgata ccgtcgacta gagctcgctg atcagcctcg actgtgcctt   3780
ctagttgcca gccatctgtt gtttgcccct cccccgtgcc ttccttgacc ctggaaggtg   3840
ccactcccac tgtcctttcc taataaaatg aggaaattgc atcgcattgt ctgagtaggt   3900
gtcattctat tctggggggt ggggtggggc aggacagcaa gggggaggat tgggaagaca   3960
atagcaggca tgctggggag agatccacga taacaaacag ctttttttggg gcccacatgt   4020
acactgaatt ccctgcaggt tggccactcc ctctctgcgc gctcgctcgc tcactgaggc   4080
cgcccgggca aagcccgggc gtcgggcgac ctttggtcgc ccggcctcag tgagcgagcg   4140
agcgcgcaga gagggagtgg ccaactccat cactaggggt tcct                    4184
```

<210> SEQ ID NO 83
<211> LENGTH: 4184
<212> TYPE: DNA
<213> ORGANISM: Artificial Sequence
<220> FEATURE:
<223> OTHER INFORMATION: Synthetic polynucleotide

<400> SEQUENCE: 83

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg aattcggtac    300
ctagttatta atagtaatca attacggggt cattagttca tagcccatat atggagttcc    360
gcgttacata acttacggta aatggcccgc ctggctgacc gcccaacgac ccccgcccat    420
tgacgtcaat aatgacgtat gttcccatag taacgccaat agggactttc cattgacgtc    480
aatgggtgga gtatttacgg taaactgccc acttggcagt acatcaagtg tatcatatgc    540
caagtacgcc ccctattgac gtcaatgacg gtaaatggcc cgcctggcat tatgcccagt    600
acatgacctt atgggacttt cctacttggc agtacatcta cgtattagtc atcgctatta    660
ccatggtcga ggtgagcccc acgttctgct tcactctccc catctccccc ccctccccac    720
ccccaatttt gtatttattt atttttaat tattttgtgc agcgatgggg gcgggggggg    780
ggggggggcg cgcgccaggc ggggcggggc ggggcgaggg gcggggcggg gcgaggcgga    840
gaggtgcggc ggcagccaat cagagcggcg cgctccgaaa gtttcctttt atggcgaggc    900
ggcggcggcg gcggccctat aaaaagcgaa gcgcgcggcg ggcgggagtc gctgcgcgct    960
gccttcgccc cgtgccccgc tccgccgccg cctcgcgccg cccgccccgg ctctgactga   1020
ccgcgttact cccacaggtg agcgggcggg acggcccttc tcctccgggc tgtaattagc   1080
gcttggttta atgacggctt gtttcttttc tgtggctgcg tgaaagcctt gaggggctcc   1140
gggagctaga gcctctgcta accatgttca tgccttcttc tttttcctac agctcctggg   1200
caacgtgctg gttattgtgc tgtctcatca ttttggcaaa gaattcctcg aagatccgaa   1260
gggaaagtct tccacgactg tgggatccgt tcgaagatat caccggttga gccaccatgt   1320
ggaccctggt gagctgggtg gccctgaccg ccggcctggt ggccggcacc cgctgccccg   1380
acggccagtt ctgccccgtg gcctgctgcc tggacccccgg cggcgccagc tacagctgct   1440
gccgccccct gctggacaag tggcccacca ccctgagccg ccacctgggc ggcccctgcc   1500
aggtggacgc ccactgcagc gccggccaca gctgcatctt caccgtgagc ggcaccagca   1560
gctgctgccc cttccccgag gccgtggcct gcggcgacgg ccaccactgc tgcccccgcg   1620
gcttccactg cagcgccgac ggccgcagct gcttccagcg cagcggcaac aacagcgtgg   1680
gcgccatcca gtgccccgac agccagttcg agtgccccga cttcagcacc tgctgcgtga   1740
tggtggacgg cagctggggc tgctgcccca tgccccaggc cagctgctgc gaggaccgcg   1800
tgcactgctg cccccacggc gccttctgcg acctggtgca cacccgctgc atcaccccca   1860
ccggcaccca cccccctggcc aagaagctgc ccgcccagcg caccaaccgc gccgtggccc   1920
tgagcagcag cgtgatgtgc cccgacgccc gcagccgctg ccccgacggc agcacctgct   1980
gcgagctgcc cagcggcaag tacggctgct gccccatgcc caacgccacc tgctgcagcg   2040
accacctgca ctgctgcccc caggacaccg tgtgcgacct gatccagagc aagtgcctga   2100
gcaaggagaa cgccaccacc gacctgctga ccaagctgcc cgcccacacc gtgggcgacg   2160
tgaagtgcga catggaggtg agctgccccg acggctacac ctgctgccgc ctgcagagcg   2220
```

gcgcctgggg ctgctgcccc ttcacccagg ccgtgtgctg cgaggaccac atccactgct 2280
gccccgccgg cttcacctgc gacacccaga agggcacctg cgagcagggc ccccaccagg 2340
tgccctggat ggagaaggcc cccgcccacc tgagcctgcc cgacccccag gccctgaagc 2400
gcgacgtgcc ctgcgacaac gtgagcagct gccccagcag cgacacctgc tgccagctga 2460
ccagcggcga gtggggctgc tgccccatcc ccgaggccgt gtgctgcagc gaccaccagc 2520
actgctgccc ccagggctac acctgcgtgg ccgagggcca gtgccagcgc ggcagcgaga 2580
tcgtggccgg cctggagaag atgcccgccc gccgcgccag cctgagccac ccccgcgaca 2640
tcggctgcga ccagcacacc agctgccccg tgggccagac ctgctgcccc agcctgggcg 2700
gcagctgggc ctgctgccag ctgccccacg ccgtgtgctg cgaggaccgc cagcactgct 2760
gccccgccgg ctacacctgc aacgtgaagg cccgcagctg cgagaaggag gtggtgagcg 2820
cccagcccgc caccttcctg gcccgcagcc cccacgtggg cgtgaaggac gtggagtgcg 2880
gcgagggcca cttctgccac gacaaccaga cctgctgccg cgacaaccgc cagggctggg 2940
cctgctgccc ctaccgccag ggcgtgtgct gcgccgaccg ccgccactgc tgccccgccg 3000
gcttccgctg cgccgcccgc ggcaccaagt gcctgcgccg cgaggccccc cgctgggacg 3060 ccccccctgcg cgaccccgcc ctgcgccagc tgctgtgaca attgttaatt aagtttaaac 3120
cctcgaggcc gcaagcttat cgataatcaa cctctggatt acaaaatttg tgaaagattg 3180
actggtattc ttaactatgt tgctcctttt acgctatgtg gatacgctgc tttaatgcct 3240
ttgtatcatg ctattgcttc ccgtatggct ttcattttct cctccttgta taaatcctgg 3300
ttgctgtctc tttatgagga gttgtggccc gttgtcaggc aacgtggcgt ggtgtgcact 3360
gtgtttgctg acgcaacccc cactggttgg ggcattgcca ccacctgtca gctcctttcc 3420
gggactttcg ctttccccct ccctattgcc acggcggaac tcatcgccgc ctgccttgcc 3480
cgctgctgga caggggctcg gctgttgggc actgacaatt ccgtggtgtt gtcggggaaa 3540
tcatcgtcct ttccttggct gctcgcctgt gttgccacct ggattctgcg cgggacgtcc 3600
ttctgctacg tcccttcggc cctcaatcca gcggaccttc cttcccgcgg cctgctgccg 3660
gctctgcggc ctcttccgcg tcttcgcctt cgccctcaga cgagtcggat ctccctttgg 3720
gccgcctccc cgcatcgata ccgtcgacta gagctcgctg atcagcctcg actgtgcctt 3780
ctagttgcca gccatctgtt gtttgcccct cccccgtgcc ttccttgacc ctggaaggtg 3840
ccactcccac tgtcctttcc taataaaatg aggaaattgc atcgcattgt ctgagtaggt 3900
gtcattctat tctggggggt ggggtggggc aggacagcaa gggggaggat tgggaagaca 3960
atagcaggca tgctggggag agatccacga taacaaacag ctttttttggg gcccacatgt 4020 acactgaatt ccctgcaggt tggccactcc ctctctgcgc gctcgctcgc tcactgaggc 4080
cgcccgggca aagcccgggc gtcgggcgac ctttggtcgc ccggcctcag tgagcgagcg 4140
agcgcgcaga gagggagtgg ccaactccat cactaggggt tcct 4184

<210> SEQ ID NO 84
<211> LENGTH: 4578
<212> TYPE: DNA
<213> ORGANISM: Artificial Sequence
<220> FEATURE:
<223> OTHER INFORMATION: Synthetic polynucleotide

<400> SEQUENCE: 84
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120

```
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
aaaaaaattg tcatcctccc acggtggcca tttgttccat gtgagtgcta gtaacaggcc    300
ttgtgtcctt tgtagactat ttgcacactg catctgtggc ttcactcagt gtgcaaatag    360
tctacaagac aacagcatac agccttcagc aagcctccag tggtctcata cagaacttat    420
aagattccca aatccaaaga catttcacgt ttatggtgat ttcccagaac acatagcgac    480
atgcaaatat tgcagggcgc cactcccctg tccctcacag ccatcttcct gccagggcgc    540
acgcgcgctg ggtgttcccg cctagtgaca ctgggcccgc gattccttgg agcgggttga    600
tgacgtcagc gtttcccatg gtgaagcttg gatctgatcc ctaggttcta gaaccggtga    660
cgtctcccat ggtgaagctt ggatctgaat tcggtaccta gttattaata gtaatcaatt    720
acggggtcat tagttcatag cccatatatg gagttccgcg ttacataact tacggtaaat    780
ggcccgcctg gctgaccgcc caacgacccc cgcccattga cgtcaataat gacgtatgtt    840
cccatagtaa cgccaatagg gactttccat tgacgtcaat gggtggagta tttacggtaa    900
actgcccact tggcagtaca tcaagtgtat catatgccaa gtacgccccc tattgacgtc    960
aatgacggta aatggcccgc ctggcattat gcccagtaca tgaccttatg ggactttcct   1020
acttggcagt acatctacgt attagtcatc gctattacca tggtcgaggt gagccccacg   1080
ttctgcttca ctctccccat ctcccccccc tccccacccc caattttgta tttatttatt   1140
ttttaattat tttgtgcagc gatgggggcg gggggggggg gggggcgcgc gccaggcggg   1200
gcggggcggg gcgaggggcg gggcggggcg aggcggagag gtgcggcggc agccaatcag   1260
agcggcgcgc tccgaaagtt tccttttatg gcgaggcggc ggcggcggcg gccctataaa   1320
aagcgaagcg cgcggcgggc gggagtcgct gcgacgctgc cttcgccccg tgccccgctc   1380
cgccgccgcc tcgcgccgcc cgccccggct ctgactgacc gcgttactcc cacaggtgag   1440
cgggcgggac ggcccttctc ctccgggctg taattagcgc ttggtttaat gacggcttgt   1500
ttctgtggc tgcgtgaaag ccttgagggg ctccgggagc tagagcctct gctaaccatg   1560
ttcatgcctt cttctttttc ctacagctcc tgggcaacgt gctggttatt gtgctgtctc   1620
atcattttgg caaagaattc ctcgaagatc cgaagggaaa gtcttccacg actgtgggat   1680
ccgttcgaag atatcaccgg ttgagccacc atgtggaccc tggtgagctg ggtggccctg   1740
accgccggcc tggtggccgg cacccgctgc cccgacggcc agttctgccc cgtggcctgc   1800
tgcctggacc ccggcggcgc cagctacagc tgctgccgcc ccctgctgga caagtggccc   1860
accaccctga gccgccacct gggcggcccc tgccaggtgg acgcccactg cagcgccggc   1920
cacagctgca tcttcaccgt gagcggcacc agcagctgct gccccttccc cgaggccgtg   1980
gcctgcggcg acggccacca ctgctgcccc cgcggcttcc actgcagcgc cgacggccgc   2040
agctgcttcc agcgcagcgg caacaacagc gtgggcgcca tccagtgccc cgacagccag   2100
ttcgagtgcc ccgacttcag cacctgctgc gtgatggtgg acggcagctg gggctgctgc   2160
cccatgcccc aggccagctg ctgcgaggac cgcgtgcact gctgccccca cggcgccttc   2220
tgcgacctgg tgcacacccg ctgcatcacc cccaccggca cccacccccct ggccaagaag   2280
ctgcccgccc agcgcaccaa ccgcgccgtg gccctgagca gcagcgtgat gtgccccgac   2340
gcccgcagcc gctgccccga cggcagcacc tgctgcgagc tgcccagcgg caagtacggc   2400
tgctgcccca tgcccaacgc cacctgctgc agcgaccacc tgcactgctg cccccaggac   2460
```

```
accgtgtgcg acctgatcca gagcaagtgc ctgagcaagg agaacgccac caccgacctg   2520
ctgaccaagc tgcccgccca caccgtgggc gacgtgaagt gcgacatgga ggtgagctgc   2580
cccgacggct acacctgctg ccgcctgcag agcggcgcct ggggctgctg ccccttcacc   2640
caggccgtgt gctgcgagga ccacatccac tgctgccccg ccggcttcac ctgcgacacc   2700
cagaagggca cctgcgagca gggcccccac caggtgccct ggatggagaa ggcccccgcc   2760
cacctgagcc tgcccgaccc ccaggccctg aagcgcgacg tgccctgcga caacgtgagc   2820
agctgcccca gcagcgacac ctgctgccag ctgaccagcg gcgagtgggg ctgctgcccc   2880
atccccgagg ccgtgtgctg cagcgaccac cagcactgct gcccccaggg ctacacctgc   2940
gtggccgagg gccagtgcca gcgcggcagc gagatcgtgg ccggcctgga gaagatgccc   3000
gcccgccgcg ccagcctgag ccacccccgc gacatcggct gcgaccagca caccagctgc   3060
cccgtgggcc agacctgctg ccccagcctg ggcggcagct gggcctgctg ccagctgccc   3120
cacgccgtgt gctgcgagga ccgccagcac tgctgccccg ccggctacac ctgcaacgtg   3180
aaggcccgca gctgcgagaa ggaggtggtg agcgcccagc ccgccacctt cctggcccgc   3240
agcccccacg tgggcgtgaa ggacgtggag tgcggcgagg gccacttctg ccacgacaac   3300
cagacctgct gccgcgacaa ccgccagggc tgggcctgct gcccctaccg ccagggcgtg   3360
tgctgcgccg accgccgcca ctgctgcccc gccggcttcc gctgcgccgc ccgcggcacc   3420
aagtgcctgc gccgcgaggc cccccgctgg gacgcccccc tgcgcgaccc cgccctgcgc   3480
cagctgctgt gacaattgtt aattaagttt aaaccctcga ggccgcaagc ttatcgataa   3540
tcaacctctg gattacaaaa tttgtgaaag attgactggt attcttaact atgttgctcc   3600
ttttacgcta tgtggatacg ctgctttaat gcctttgtat catgctattg cttcccgtat   3660
ggctttcatt ttctcctcct tgtataaatc ctggttgctg tctctttatg aggagttgtg   3720
gcccgttgtc aggcaacgtg gcgtggtgtg cactgtgttt gctgacgcaa cccccactgg   3780
ttggggcatt gccaccacct gtcagctcct ttccgggact ttcgctttcc ccctccctat   3840
tgccacggcg gaactcatcg ccgcctgcct tgcccgctgc tggacagggg ctcggctgtt   3900
gggcactgac aattccgtgg tgttgtcggg gaaatcatcg tcctttcctt ggctgctcgc   3960
ctgtgttgcc acctggattc tgcgcgggac gtccttctgc tacgtccctt cggccctcaa   4020
tccagcggac cttccttccc gcggcctgct gccggctctg cggcctcttc cgcgtcttcg   4080
ccttcgccct cagacgagtc ggatctccct ttgggccgcc tccccgcatc gataccgtcg   4140
actagagctc gctgatcagc ctcgactgtg ccttctagtt gccagccatc tgttgtttgc   4200
ccctcccccg tgccttcctt gaccctggaa ggtgccactc ccactgtcct ttcctaataa   4260
aatgaggaaa ttgcatcgca ttgtctgagt aggtgtcatt ctattctggg gggtggggtg   4320
gggcaggaca gcaaggggga ggattgggaa gacaatagca ggcatgctgg ggagagatcc   4380
acgataacaa acagcttttt tggggtgaac atattgactg aattccctgc aggttggcca   4440
ctccctctct gcgcgctcgc tcgctcactg aggccgcccg ggcaaagccc gggcgtcggg   4500
cgacctttgg tcgcccggcc tcagtgagcg agcgagcgcg cagagaggga gtggccaact   4560
ccatcactag gggttcct                                                 4578
```

<210> SEQ ID NO 85
<211> LENGTH: 4162
<212> TYPE: DNA
<213> ORGANISM: Artificial Sequence
<220> FEATURE:
<223> OTHER INFORMATION: Synthetic polynucleotide

<400> SEQUENCE: 85

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg aattcggtac    300
ctagttatta atagtaatca attacggggt cattagttca tagcccatat atggagttcc    360
gcgttacata acttacggta aatggcccgc ctggctgacc gcccaacgac ccccgcccat    420
tgacgtcaat aatgacgtat gttcccatag taacgccaat agggactttc cattgacgtc    480
aatgggtgga gtatttacgg taaactgccc acttggcagt acatcaagtg tatcatatgc    540
caagtacgcc ccctattgac gtcaatgacg gtaaatggcc cgcctggcat tatgcccagt    600
acatgacctt atgggacttt cctacttggc agtacatcta cgtattagtc atcgctatta    660
ccatggtcga ggtgagcccc acgttctgct tcactctccc catctccccc ccctccccac    720
ccccaatttt gtatttattt atttttaat tattttgtgc agcgatgggg gcgggggggg    780
gggggggcg cgcgccaggc ggggcggggc ggggcgaggg gcggggcggg gcgaggcgga    840
gaggtgcggc ggcagccaat cagagcggcg cgctccgaaa gtttcctttt atggcgaggc    900
ggcggcggcg gcggccctat aaaaagcgaa gcgcgcggcg ggcgggagtc gctgcgacgc    960
tgccttcgcc ccgtgccccg ctccgccgcc gcctcgcgcc gcccgccccg gctctgactg   1020
accgcgttac tcccacaggt gagcgggcgg gacggccctt ctcctcagcg ctgtaattag   1080
cgcttggttt aatgacggct tgttggaggc ttgctgaagg ctgtatgctg ttgtctttag   1140
aaataagtgg tagtcaagtg aagccacaga tgtgactacc acttatttct aaaaggacac   1200
aaggcctgtt actagcactc acatggaaca aatggccacc gtgggaggat gacaatttct   1260
gtggctgcgt gaaagccttg aggggctccg ggagctagag cctctgctaa ccatgttcat   1320
gccttcttct ttttcctaca gctcctgggc aacgtgctgg ttattgtgct gtctcatcat   1380
tttggcaaag aattcctcga agatccgaag ggaaagtctt ccacgactgt gggatccgtt   1440
cgaagatatc accggttgag ccaccatgga attcagcagc cccagcagag aggaatgccc   1500
caagcctctg agccgggtgt caatcatggc cggatctctg acaggactgc tgctgcttca   1560
ggccgtgtct tgggcttctg gcgctagacc ttgcatcccc aagagcttcg gctacagcag   1620
cgtcgtgtgc gtgtgcaatg ccacctactg cgacagcttc gaccctccta cctttcctgc   1680
tctgggcacc ttcagcagat acgagagcac cagatccggc agacggatgg aactgagcat   1740
gggacccatc caggccaatc acacaggcac tggcctgctg ctgacactgc agcctgagca   1800
gaaattccag aaagtgaaag gcttcggcgg agccatgaca gatgccgccg ctctgaatat   1860
cctggctctg tctccaccag ctcagaacct gctgctcaag agctacttca gcgaggaagg   1920
catcggctac aacatcatca gagtgcccat ggccagctgc gacttcagca tcaggaccta   1980
cacctacgcc gacacacccg acgatttcca gctgcacaac ttcagcctgc ctgaagagga   2040
caccaagctg aagatccctc tgatccacag agccctgcag ctggcacaaa gacccgtgtc   2100
actgctggcc tctccatgga catctcccac ctggctgaaa acaaatggcg ccgtgaatgg   2160
caagggcagc ctgaaaggcc aacctggcga catctaccac cagacctggg ccagatactt   2220
cgtgaagttc ctggacgcct atgccgagca caagctgcag ttttgggccg tgacagccga   2280
```

```
gaacgaacct tctgctggac tgctgagcgg ctaccccttt cagtgcctgg gctttacacc   2340

cgagcaccag cgggacttta tcgcccgtga tctgggaccc acactggcca atagcaccca   2400

ccataatgtg cggctgctga tgctggacga ccagagactg cttctgcccc actgggctaa   2460

agtggtgctg acagatcctg aggccgccaa atacgtgcac ggaatcgccg tgcactggta   2520

tctggacttt ctggcccctg ccaaggccac actgggagag acacacagac tgttccccaa   2580

caccatgctg ttcgccagcg aagcctgtgt gggcagcaag ttttgggaac agagcgtgcg   2640

gctcggcagc tgggatagag gcatgcagta cagccacagc atcatcacca acctgctgta   2700

ccacgtcgtc ggctggaccg actggaatct ggccctgaat cctgaaggcg gccctaactg   2760

ggtccgaaac ttcgtggaca gccccatcat cgtggacatc accaaggaca ccttctacaa   2820

gcagcccatg ttctaccacc tgggacactt cagcaagttc atccccgagg gctctcagcg   2880

cgttggactg gtggcttccc agaagaacga tctggacgcc gtggctctga tgcaccctga   2940

tggatctgct gtggtggtgg tcctgaaccg cagcagcaaa gatgtgcccc tgaccatcaa   3000

ggatcccgcc gtgggattcc tggaaacaat cagccctggc tactccatcc acacctacct   3060

gtggcgtaga cagtgacaat tgttaattaa gtttaaaccc tcgaggccgc aagcttatcg   3120

ataatcaacc tctggattac aaaatttgtg aaagattgac tggtattctt aactatgttg   3180

ctccttttac gctatgtgga tacgctgctt taatgccttt gtatcatgct attgcttccc   3240

gtatggcttt cattttctcc tccttgtata aatcctggtt gctgtctctt tatgaggagt   3300

tgtggcccgt tgtcaggcaa cgtggcgtgg tgtgcactgt gtttgctgac gcaaccccca   3360

ctggttgggg cattgccacc acctgtcagc tcctttccgg gactttcgct ttccccctcc   3420

ctattgccac ggcggaactc atcgccgcct gccttgcccg ctgctggaca ggggctcggc   3480

tgttgggcac tgacaattcc gtggtgttgt cggggaaatc atcgtccttt ccttggctgc   3540

tcgcctgtgt tgccacctgg attctgcgcg ggacgtcctt ctgctacgtc ccttcggccc   3600

tcaatccagc ggaccttcct tcccgcggcc tgctgccggc tctgcggcct cttccgcgtc   3660

ttcgccttcg ccctcagacg agtcggatct ccctttgggc cgcctccccg catcgatacc   3720

gtcgactaga gctcgctgat cagcctcgac tgtgccttct agttgccagc catctgttgt   3780

ttgcccctcc cccgtgcctt ccttgaccct ggaaggtgcc actcccactg tcctttccta   3840

ataaaatgag gaaattgcat cgcattgtct gagtaggtgt cattctattc tggggggtgg   3900

ggtggggcag gacagcaagg gggaggattg ggaagacaat agcaggcatg ctggggagag   3960

atccacgata acaaacagct tttttggggc ccacatgtac actgaattcc ctgcaggttg   4020

gccactccct ctctgcgcgc tcgctcgctc actgaggccg cccgggcaaa gcccgggcgt   4080

cgggcgacct ttggtcgccc ggcctcagtg agcgagcgag cgcgcagaga gggagtggcc   4140

aactccatca ctaggggttc ct                                             4162
```

<210> SEQ ID NO 86
<211> LENGTH: 3977
<212> TYPE: DNA
<213> ORGANISM: Artificial Sequence
<220> FEATURE:
<223> OTHER INFORMATION: Synthetic polynucleotide

<400> SEQUENCE: 86

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgctag ctctgggtat ttaagcccga gtgagcacgc    180
```

```
agggtctcca ttttgaagcg ggaggttacg cgttcgtcga ctactagtgg gtaccagagc    240
tccctaggtt ctagaaccgg tgacgtctcc catggtgaag cttggatctg aattcggtac    300
ctagttatta atagtaatca attacggggt cattagttca tagcccatat atggagttcc    360
gcgttacata acttacggta aatggcccgc ctggctgacc gcccaacgac ccccgcccat    420
tgacgtcaat aatgacgtat gttcccatag taacgccaat agggactttc cattgacgtc    480
aatgggtgga gtatttacgg taaactgccc acttggcagt acatcaagtg tatcatatgc    540
caagtacgcc ccctattgac gtcaatgacg gtaaatggcc cgcctggcat tatgcccagt    600
acatgacctt atgggacttt cctacttggc agtacatcta cgtattagtc atcgctatta    660
ccatggtcga ggtgagcccc acgttctgct tcactctccc catctccccc ccctccccac    720
ccccaatttt gtatttattt atttttaat tattttgtgc agcgatgggg gcgggggggg    780
ggggggggcg cgcgccaggc ggggcggggc ggggcgaggg gcggggcggg gcgaggcgga    840
gaggtgcggc ggcagccaat cagagcggcg cgctccgaaa gtttcctttt atggcgaggc    900
ggcggcggcg gcggccctat aaaaagcgaa gcgcgcggcg ggcgggagtc gctgcgcgct    960
gccttcgccc cgtgccccgc tccgccgccg cctcgcgccg cccgccccgg ctctgactga   1020
ccgcgttact cccacaggtg agcgggcggg acggcccttc tcctccgggc tgtaattagc   1080
gcttggttta atgacggctt gtttcttttc tgtggctgcg tgaaagcctt gaggggctcc   1140
gggagctaga gcctctgcta accatgttca tgccttcttc tttttcctac agctcctggg   1200
caacgtgctg gttattgtgc tgtctcatca ttttggcaaa gaattcctcg aagatccgaa   1260
gggaaagtct tccacgactg tgggatccgt tcgaagatat caccggttga gccaccatgt   1320
acgccctgtt cctgctggcc agcctgctgg gcgccgccct ggccggcccc gtgctgggcc   1380
tgaaggagtg cacccgcggc agcgccgtgt ggtgccagaa cgtgaagacc gccagcgact   1440
gcggcgccgt gaagcactgc ctgcagaccg tgtggaacaa gcccaccgtg aagagcctgc   1500
cctgcgacat ctgcaaggac gtggtgaccg ccgccggcga catgctgaag gacaacgcca   1560
ccgaggagga gatcctggtg tacctggaga agacctgcga ctggctgccc aagcccaaca   1620
tgagcgccag ctgcaaggag atcgtggaca gctacctgcc cgtgatcctg gacatcatca   1680
agggcgagat gagccgcccc ggcgaggtgt gcagcgccct gaacctgtgc gagagcctgc   1740
agaagcacct ggccgagctg aaccaccaga agcagctgga gagcaacaag atccccgagc   1800
tggacatgac cgaggtggtg gccccctca tggccaacat cccccgctg ctgtaccccc   1860
aggacggccc ccgcagcaag ccccagccca aggacaacgg cgacgtgtgc caggactgca   1920
tccagatggt gaccgacatc cagaccgccg tgcgcaccaa cagcaccttc gtgcaggccc   1980
tggtggagca cgtgaaggag gagtgcgacc gcctgggccc cggcatggcc gacatctgca   2040
agaactacat cagccagtac agcgagatcg ccatccagat gatgatgcac atgcagccca   2100
aggagatctg cgccctggtg ggcttctgcg acgaggtgaa ggagatgccc atgcagaccc   2160
tggtgcccgc caaggtggcc agcaagaacg tgatccccgc cctggagctg gtggagccca   2220
tcaagaagca cgaggtgccc gccaagagcg acgtgtactg cgaggtgtgc gagttcctgg   2280
tgaaggaggt gaccaagctg atcgacaaca acaagaccga gaaggagatc ctggacgcct   2340
tcgacaagat gtgcagcaag ctgcccaaga gcctgagcga ggagtgccag gaggtggtgg   2400
acacctacgg cagcagcatc ctgagcatcc tgctggagga ggtgagcccc gagctggtgt   2460
gcagcatgct gcacctgtgc agcggcaccc gcctgcccgc cctgaccgtg cacgtgaccc   2520
```

```
agcccaagga cggcggcttc tgcgaggtgt gcaagaagct ggtgggctac ctggaccgca   2580

acctggagaa gaacagcacc aagcaggaga tcctggccgc cctggagaag ggctgcagct   2640

tcctgcccga cccctaccag aagcagtgcg accagttcgt ggccgagtac gagcccgtgc   2700

tgatcgagat cctggtggag gtgatggacc ccagcttcgt gtgcctgaag atcggcgcct   2760

gccccagcgc ccacaagccc ctgctgggca ccgagaagtg catctggggc cccagctact   2820

ggtgccagaa caccgagacc gccgcccagt gcaacgccgt ggagcactgc aagcgccacg   2880

tgtggaactg acaattgtta attaagttta aaccctcgag gccgcaagct tatcgataat   2940

caacctctgg attacaaaat ttgtgaaaga ttgactggta ttcttaacta tgttgctcct   3000

tttacgctat gtggatacgc tgctttaatg cctttgtatc atgctattgc ttcccgtatg   3060

gctttcattt tctcctcctt gtataaatcc tggttgctgt ctctttatga ggagttgtgg   3120

cccgttgtca ggcaacgtgg cgtggtgtgc actgtgtttg ctgacgcaac ccccactggt   3180

tggggcattg ccaccacctg tcagctcctt tccgggactt tcgctttccc cctccctatt   3240

gccacggcgg aactcatcgc cgcctgcctt gcccgctgct ggacaggggc tcggctgttg   3300

ggcactgaca attccgtggt gttgtcgggg aaatcatcgt cctttccttg gctgctcgcc   3360

tgtgttgcca cctggattct gcgcgggacg tccttctgct acgtcccttc ggccctcaat   3420

ccagcggacc ttccttcccg cggcctgctg ccggctctgc ggcctcttcc gcgtcttcgc   3480

cttcgccctc agacgagtcg gatctccctt tgggccgcct ccccgcatcg ataccgtcga   3540

ctagagctcg ctgatcagcc tcgactgtgc cttctagttg ccagccatct gttgtttgcc   3600

cctcccccgt gccttccttg accctggaag gtgccactcc cactgtcctt tcctaataaa   3660

atgaggaaat tgcatcgcat tgtctgagta ggtgtcattc tattctgggg ggtggggtgg   3720

ggcaggacag caagggggag gattgggaag acaatagcag gcatgctggg gagagatcca   3780

cgataacaaa cagctttttt ggggcccaca tgtacactga attccctgca ggttggccac   3840

tccctctctg cgcgctcgct cgctcactga ggccgcccgg gcaaagcccg ggcgtcgggc   3900

gacctttggt cgcccggcct cagtgagcga gcgagcgcgc agagagggag tggccaactc   3960

catcactagg ggttcct                                                  3977
```

<210> SEQ ID NO 87
<211> LENGTH: 4013
<212> TYPE: DNA
<213> ORGANISM: Artificial Sequence
<220> FEATURE:
<223> OTHER INFORMATION: Synthetic polynucleotide

<400> SEQUENCE: 87

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg aattcggtac    300

ctagttatta atagtaatca attacggggt cattagttca tagcccatat atggagttcc    360

gcgttacata acttacggta aatggcccgc ctggctgacc gcccaacgac ccccgcccat    420

tgacgtcaat aatgacgtat gttcccatag taacgccaat agggactttc cattgacgtc    480

aatgggtgga gtatttacgg taaactgccc acttggcagt acatcaagtg tatcatatgc    540

caagtacgcc ccctattgac gtcaatgacg gtaaatggcc cgcctggcat tatgcccagt    600
```

```
acatgacctt atgggacttt cctacttggc agtacatcta cgtattagtc atcgctatta    660
ccatggtcga ggtgagcccc acgttctgct tcactctccc catctccccc ccctccccac    720
ccccaatttt gtatttattt atttttttaat tattttgtgc agcgatgggg gcgggggggg    780
ggggggggcg cgcgccaggc ggggcggggc ggggcgaggg gcggggcggg gcgaggcgga    840
gaggtgcggc ggcagccaat cagagcggcg cgctccgaaa gtttcctttt atggcgaggc    900
ggcggcggcg gcggccctat aaaaagcgaa gcgcgcggcg ggcgggagtc gctgcgcgct    960
gccttcgccc cgtgccccgc tccgccgccg cctcgcgccg cccgccccgg ctctgactga   1020
ccgcgttact cccacaggtg agcgggcggg acggcccttc tcctccgggc tgtaattagc   1080
gcttggttta atgacggctt gtttcttttc tgtggctgcg tgaaagcctt gaggggctcc   1140
gggagctaga gcctctgcta accatgttca tgccttcttc tttttcctac agctcctggg   1200
caacgtgctg gttattgtgc tgtctcatca ttttggcaaa gaattcctcg aagatccgaa   1260
gggaaagtct tccacgactg tgggatccgt tcgaagatat caccggttga gccaccatgg   1320
aattcagcag ccccagcaga gaggaatgcc ccaagcctct gagccgggtg tcaatcatgg   1380
ccggatctct gacaggactg ctgctgcttc aggccgtgtc ttgggcttct ggcgctagac   1440
cttgcatccc caagagcttc ggctacagca gcgtcgtgtg cgtgtgcaat gccacctact   1500
gcgacagctt cgaccctcct acctttcctg ctctgggcac cttcagcaga tacgagagca   1560
ccagatccgg cagacggatg gaactgagca tgggacccat ccaggccaat cacacaggca   1620
ctggcctgct gctgacactg cagcctgagc agaaattcca gaaagtgaaa ggcttcggcg   1680
gagccatgac agatgccgcc gctctgaata tcctggctct gtctccacca gctcagaacc   1740
tgctgctcaa gagctacttc agcgaggaag gcatcggcta caacatcatc agagtgccca   1800
tggccagctg cgacttcagc atcaggacct acacctacgc cgacacaccc gacgatttcc   1860
agctgcacaa cttcagcctg cctgaagagg acaccaagct gaagatccct ctgatccaca   1920
gagccctgca gctggcacaa agacccgtgt cactgctggc ctctccatgg acatctccca   1980
cctggctgaa aacaaatggc gccgtgaatg gcaagggcag cctgaaaggc caacctggcg   2040
acatctacca ccagacctgg gccagatact tcgtgaagtt cctggacgcc tatgccgagc   2100
acaagctgca gttttgggcc gtgacagccg agaacgaacc ttctgctgga ctgctgagcg   2160
gctacccctt tcagtgcctg ggctttacac ccgagcacca gcgggacttt atcgcccgtg   2220
atctgggacc cacactggcc aatagcaccc accataatgt gcggctgctg atgctggacg   2280
accagagact gcttctgccc cactgggcta aagtggtgct gacagatcct gaggccgcca   2340
aatacgtgca cggaatcgcc gtgcactggt atctggactt tctggcccct gccaaggcca   2400
cactgggaga gacacacaga ctgttcccca acaccatgct gttcgccagc gaagcctgtg   2460
tgggcagcaa gttttgggaa cagagcgtgc ggctcggcag ctgggataga ggcatgcagt   2520
acagccacag catcatcacc aacctgctgt accacgtcgt cggctggacc gactggaatc   2580
tggccctgaa tcctgaaggc ggccctaact gggtccgaaa cttcgtggac agccccatca   2640
tcgtggacat caccaaggac accttctaca agcagcccat gttctaccac ctgggacact   2700
tcagcaagtt catccccgag ggctctcagc gcgttggact ggtggcttcc cagaagaacg   2760
atctggacgc cgtggctctg atgcaccctg atggatctgc tgtggtggtg gtcctgaacc   2820
gcagcagcaa agatgtgccc ctgaccatca aggatcccgc cgtgggattc ctggaaacaa   2880
tcagccctgg ctactccatc cacacctacc tgtggcgtag acagtgacaa ttgttaatta   2940
```

```
agtttaaacc ctcgaggccg caagcttatc gataatcaac ctctggatta caaaatttgt   3000
gaaagattga ctggtattct taactatgtt gctcctttta cgctatgtgg atacgctgct   3060
ttaatgcctt tgtatcatgc tattgcttcc cgtatggctt tcattttctc ctccttgtat   3120
aaatcctggt tgctgtctct ttatgaggag ttgtggcccg ttgtcaggca acgtggcgtg   3180
gtgtgcactg tgtttgctga cgcaaccccc actggttggg gcattgccac cacctgtcag   3240
ctcctttccg ggactttcgc tttccccctc cctattgcca cggcggaact catcgccgcc   3300
tgccttgccc gctgctggac aggggctcgg ctgttgggca ctgacaattc cgtggtgttg   3360
tcggggaaat catcgtcctt tccttggctg ctcgcctgtg ttgccacctg gattctgcgc   3420
gggacgtcct tctgctacgt cccttcggcc ctcaatccag cggaccttcc ttcccgcggc   3480
ctgctgccgg ctctgcggcc tcttccgcgt cttcgccttc gccctcagac gagtcggatc   3540
tccctttggg ccgcctcccc gcatcgatac cgtcgactag agctcgctga tcagcctcga   3600
ctgtgccttc tagttgccag ccatctgttg tttgcccctc ccccgtgcct tccttgaccc   3660
tggaaggtgc cactcccact gtcctttcct aataaaatga ggaaattgca tcgcattgtc   3720
tgagtaggtg tcattctatt ctggggggtg gggtggggca ggacagcaag ggggaggatt   3780
gggaagacaa tagcaggcat gctggggaga gatccacgat aacaaacagc tttttttgggg  3840
tgaacatatt gactgaattc cctgcaggtt ggccactccc tctctgcgcg ctcgctcgct   3900
cactgaggcc gcccgggcaa agcccgggcg tcgggcgacc tttggtcgcc cggcctcagt   3960
gagcgagcga gcgcgcagag agggagtggc caactccatc actaggggtt cct          4013
```

<210> SEQ ID NO 88
<211> LENGTH: 4625
<212> TYPE: DNA
<213> ORGANISM: Artificial Sequence
<220> FEATURE:
<223> OTHER INFORMATION: Synthetic polynucleotide

<400> SEQUENCE: 88

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg agggcggagt    300
tagggcggag ccaatcagcg tgcgccgttc cgaaagttgc cttttatggc tgggcggaga    360
atgggcggtg aacgccgatg attatataag gacgcgccgg gtgtggcaca gctagttccg    420
tcgcagccgg gatttgggtc gcggttcttg tttgtggatc cctgtgatcg tcacttggta    480
agtcactgac tgtctatgcc tgggaaaggg tgggcaggag atggggcagt gcaggaaaag    540
tggcactatg aaccctgcag ccctaggaat gcatctagac aattgtacta accttcttct    600
ctttcctctc ctgacagtcc ggaaagccac catggaattc agcagcccca gcagagagga    660
atgccccaag cctctgagcc gggtgtcaat catggccgga tctctgacag gactgctgct    720
gcttcaggcc gtgtcttggg cttctggcgc tagaccttgc atccccaaga gcttcggcta    780
cagcagcgtc gtgtgcgtgt gcaatgccac ctactgcgac agcttcgacc ctcctacctt    840
tcctgctctg ggcaccttca gcagatacga gagcaccaga tccggcagac ggatggaact    900
gagcatggga cccatccagg ccaatcacac aggcactggc ctgctgctga cactgcagcc    960
tgagcagaaa ttccagaaag tgaaaggctt cggcggagcc atgacagatg ccgccgctct   1020
```

```
gaatatcctg gctctgtctc caccagctca gaacctgctg ctcaagagct acttcagcga   1080
ggaaggcatc ggctacaaca tcatcagagt gcccatggcc agctgcgact tcagcatcag   1140
gacctacacc tacgccgaca cacccgacga tttccagctg cacaacttca gcctgcctga   1200
agaggacacc aagctgaaga tccctctgat ccacagagcc ctgcagctgg cacaaagacc   1260
cgtgtcactg ctggcctctc catggacatc tcccacctgg ctgaaaacaa atggcgccgt   1320
gaatggcaag ggcagcctga aaggccaacc tggcgacatc taccaccaga cctgggccag   1380
atacttcgtg aagttcctgg acgcctatgc cgagcacaag ctgcagtttt gggccgtgac   1440
agccgagaac gaaccttctg ctggactgct gagcggctac ccctttcagt gcctgggctt   1500
tacacccgag caccagcggg actttatcgc ccgtgatctg ggacccacac tggccaatag   1560
cacccaccat aatgtgcggc tgctgatgct ggacgaccag agactgcttc tgccccactg   1620
ggctaaagtg gtgctgacag atcctgaggc cgccaaatac gtgcacggaa tcgccgtgca   1680
ctggtatctg gactttctgg cccctgccaa ggccacactg ggagagacac acagactgtt   1740
ccccaacacc atgctgttcg ccagcgaagc ctgtgtgggc agcaagtttt gggaacagag   1800
cgtgcggctc ggcagctggg atagaggcat gcagtacagc cacagcatca tcaccaacct   1860
gctgtaccac gtcgtcggct ggaccgactg gaatctggcc ctgaatcctg aaggcggccc   1920
taactgggtc cgaaacttcg tggacagccc catcatcgtg gacatcacca aggacacctt   1980
ctacaagcag cccatgttct accacctggg acacttcagc aagttcatcc ccgagggctc   2040
tcagcgcgtt ggactggtgg cttcccagaa gaacgatctg gacgccgtgg ctctgatgca   2100
ccctgatgga tctgctgtgg tggtggtcct gaaccgcagc agcaaagatg tgcccctgac   2160
catcaaggat cccgccgtgg gattcctgga aacaatcagc cctggctact ccatccacac   2220
ctacctgtgg cgtagacaga gaagaaagag aggaagtgga gagggcagag gaagtcttct   2280
gacatgcgga gacgtggaag agaatcccgg ccctatggcc gagtggctgc tgagcgccag   2340
ctggcagcgc cgcgccaagg ccatgaccgc cgccgccggc agcgccggcc gcgccgccgt   2400
gcccctgctg ctgtgcgccc tgctggcccc cggcggcgcc tacgtgctgg acgacagcga   2460
cggcctgggc cgcgagttcg acggcatcgg cgccgtgagc ggcggcggcg ccaccagccg   2520
cctgctggtg aactaccccg agccctaccg cagccagatc ctggactacc tgttcaagcc   2580
caacttcggc gccagcctgc acatcctgaa ggtggagatc ggcggcgacg gccagaccac   2640
cgacggcacc gagcccagcc acatgcacta cgccctggac gagaactact tccgcggcta   2700
cgagtggtgg ctgatgaagg aggccaagaa gcgcaacccc aacatcaccc tgatcggcct   2760
gccctggagc ttccccggct ggctgggcaa gggcttcgac tggccctacg tgaacctgca   2820
gctgaccgcc tactacgtgg tgacctggat cgtgggcgcc aagcgctacc acgacctgga   2880
catcgactac atcggcatct ggaacgagcg cagctacaac gccaactaca tcaagatcct   2940
gcgcaagatg ctgaactacc agggcctgca gcgcgtgaag atcatcgcca gcgacaacct   3000
gtgggagagc atcagcgcca gcatgctgct ggacgccgag ctgttcaagg tggtggacgt   3060
gatcggcgcc cactaccccg gcacccacag cgccaaggac gccaagctga ccggcaagaa   3120
gctgtggagc agcgaggact tcagcaccct gaacagcgac atgggcgccg gctgctgggg   3180
ccgcatcctg aaccagaact acatcaacgg ctacatgacc agcaccatcg cctggaacct   3240
ggtggccagc tactacgagc agctgcccta cggccgctgc ggcctgatga ccgcccagga   3300
gccctggagc ggccactacg tggtggagag ccccgtgtgg gtgagcgccc acaccaccca   3360
```

```
gttcacccag cccggctggt actacctgaa gaccgtgggc cacctggaga agggcggcag   3420

ctacgtggcc ctgaccgacg gcctgggcaa cctgaccatc atcatcgaga ccatgagcca   3480

caagcacagc aagtgcatcc gcccctteet gccctacttc aacgtgagcc agcagttcgc   3540

caccttcgtg ctgaagggca gcttcagcga gatccccgag ctgcaggtgt ggtacaccaa   3600

gctgggcaag accagcgagc gcttcctgtt caagcagctg gacagcctgt ggctgctgga   3660

cagcgacggc agcttcaccc tgagcctgca cgaggacgag ctgttcaccc tgaccaccct   3720

gaccaccggc cgcaagggca gctacccccct gccccccaag agccagccct tccccagcac   3780

ctacaaggac gacttcaacg tggactaccc cttcttcagc gaggccccca acttcgccga   3840

ccagaccggc gtgttcgagt acttcaccaa catcgaggac cccggcgagc accacttcac   3900

cctgcgccag gtgctgaacc agcgccccat cacctgggcc gccgacgcca gcaacaccat   3960

cagcatcatc ggcgactaca actggaccaa cctgaccatc aagtgcgacg tgtacatcga   4020

gacccccgac accggcggcg tgttcatcgc cggccgcgtg aacaagggcg gcatcctgat   4080

ccgcagcgcc cgcggcatct tcttctggat cttcgccaac ggcagctacc gcgtgaccgg   4140

cgacctggcc ggctggatca tctacgccct gggccgcgtg gaggtgaccg ccaagaagtg   4200

gtacaccctg accctgacca tcaagggcca cttcaccagc ggcatgctga acgacaagag   4260

cctgtggacc gacatccccg tgaacttccc caagaacggc tgggccgcca tcggcaccca   4320

cagcttcgag ttcgcccagt tcgacaactt cctggtggag gccacccgct gacaattgtt   4380

aattaagttt aaaccctcga ggccgcaagc aataaaatat ctttattttc attacatctg   4440

tgtgttggtt ttttgtgttg tacactgaat tccctgcagg ttggccactc cctctctgcg   4500

cgctcgctcg ctcactgagg ccgcccgggc aaagcccggg cgtcgggcga cctttggtcg   4560

cccggcctca gtgagcgagc gagcgcgcag agagggagtg gccaactcca tcactagggg   4620

ttcct                                                             4625
```

```
<210> SEQ ID NO 89
<211> LENGTH: 4606
<212> TYPE: DNA
<213> ORGANISM: Artificial Sequence
<220> FEATURE:
<223> OTHER INFORMATION: Synthetic polynucleotide

<400> SEQUENCE: 89

ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg agggcggagt    300

tagggcggag ccaatcagcg tgcgccgttc cgaaagttgc cttttatggc tgggcggaga    360

atgggcggtg aacgccgatg attatataag gacgcgccgg gtgtggcaca gctagttccg    420

tcgcagccgg gatttgggtc gcggttcttg tttgtggatc cctgtgatcg tcacttggta    480

agtcactgac tgtctatgcc tgggaaaggg tgggcaggag atggggcagt gcaggaaaag    540

tggcactatg aaccctcctg gtggcgaggg gaggggggtg gtcctcgaac gccttgcaga    600

actggcctgg atacagagtg gaccggctgg ccccatctgg aagacttcga gatacactgt    660

tgtcttactg cgctcaacag tgtatctcga agtcttccaa atggtgccag ccatcgcagc    720

ggggtgcagg aaatgggggc agcccccctt tttggctatc cttccacgtg ttcttttttg    780
```

```
tatcttttgt gtttcctaga aaacatctca gtcaccaccg cagccctagg aatgcatcta    840
gacaattgta ctaaccttct tctctttcct ctcctgacag tccggaaagc caccatgtac    900
gccctgttcc tgctggccag cctgctgggc gccgccctgg ccggccccgt gctgggcctg    960
aaggagtgca cccgcggcag cgccgtgtgg tgccagaacg tgaagaccgc cagcgactgc   1020
ggcgccgtga agcactgcct gcagaccgtg tggaacaagc ccaccgtgaa gagcctgccc   1080
tgcgacatct gcaaggacgt ggtgaccgcc gccggcgaca tgctgaagga caacgccacc   1140
gaggaggaga tcctggtgta cctggagaag acctgcgact ggctgcccaa gcccaacatg   1200
agcgccagct gcaaggagat cgtggacagc tacctgcccg tgatcctgga catcatcaag   1260
ggcgagatga gccgccccgg cgaggtgtgc agcgccctga acctgtgcga gagcctgcag   1320
aagcacctgg ccgagctgaa ccaccagaag cagctggaga gcaacaagat ccccgagctg   1380
gacatgaccg aggtggtggc cccctcatg gccaacatcc ccctgctgct gtacccccag   1440
gacggccccc gcagcaagcc ccagcccaag gacaacggcg acgtgtgcca ggactgcatc   1500
cagatggtga ccgacatcca gaccgccgtg cgcaccaaca gcaccttcgt gcaggccctg   1560
gtggagcacg tgaaggagga gtgcgaccgc ctgggccccg gcatggccga catctgcaag   1620
aactacatca gccagtacag cgagatcgcc atccagatga tgatgcacat gcagcccaag   1680
gagatctgcg ccctggtggg cttctgcgac gaggtgaagg agatgcccat gcagaccctg   1740
gtgcccgcca aggtggccag caagaacgtg atccccgccc tggagctggt ggagcccatc   1800
aagaagcacg aggtgcccgc caagagcgac gtgtactgcg aggtgtgcga gttcctggtg   1860
aaggaggtga ccaagctgat cgacaacaac aagaccgaga aggagatcct ggacgccttc   1920
gacaagatgt gcagcaagct gcccaagagc ctgagcgagg agtgccagga ggtggtggac   1980
acctacggca gcagcatcct gagcatcctg ctggaggagg tgagccccga gctggtgtgc   2040
agcatgctgc acctgtgcag cggcacccgc ctgcccgccc tgaccgtgca cgtgacccag   2100
cccaaggacg gcggcttctg cgaggtgtgc aagaagctgg tgggctacct ggaccgcaac   2160
ctggagaaga acagcaccaa gcaggagatc ctggccgccc tggagaaggg ctgcagcttc   2220
ctgcccgacc cctaccagaa gcagtgcgac cagttcgtgg ccgagtacga gcccgtgctg   2280
atcgagatcc tggtggaggt gatggacccc agcttcgtgt gcctgaagat cggcgcctgc   2340
cccagcgccc acaagcccct gctgggcacc gagaagtgca tctggggccc cagctactgg   2400
tgccagaaca ccgagaccgc cgcccagtgc aacgccgtgg agcactgcaa gcgccacgtg   2460
tggaacagaa gaaagagagg aagtggagag ggcagaggaa gtcttctgac atgcggagac   2520
gtggaagaga atcccggccc tatggaattc agcagcccca gcagagagga atgccccaag   2580
cctctgagcc gggtgtcaat catggccgga tctctgacag gactgctgct gcttcaggcc   2640
gtgtcttggg cttctggcgc tagaccttgc atccccaaga gcttcggcta cagcagcgtc   2700
gtgtgcgtgt gcaatgccac ctactgcgac agcttcgacc ctcctacctt tcctgctctg   2760
ggcaccttca gcagatacga gagcaccaga tccggcagac ggatggaact gagcatggga   2820
cccatccagg ccaatcacac aggcactggc ctgctgctga cactgcagcc tgagcagaaa   2880
ttccagaaag tgaaaggctt cggcggagcc atgacagatg ccgccgctct gaatatcctg   2940
gctctgtctc caccagctca gaacctgctg ctcaagagct acttcagcga ggaaggcatc   3000
ggctacaaca tcatcagagt gcccatggcc agctgcgact tcagcatcag gacctacacc   3060
tacgccgaca cacccgacga tttccagctg cacaacttca gcctgcctga agaggacacc   3120
```

```
aagctgaaga tccctctgat ccacagagcc ctgcagctgg cacaaagacc cgtgtcactg   3180

ctggcctctc catggacatc tcccacctgg ctgaaaacaa atggcgccgt gaatggcaag   3240

ggcagcctga aaggccaacc tggcgacatc taccaccaga cctgggccag atacttcgtg   3300

aagttcctgg acgcctatgc cgagcacaag ctgcagtttt gggccgtgac agccgagaac   3360

gaaccttctg ctggactgct gagcggctac ccctttcagt gcctgggctt tacacccgag   3420

caccagcggg actttatcgc ccgtgatctg ggacccacac tggccaatag cacccaccat   3480

aatgtgcggc tgctgatgct ggacgaccag agactgcttc tgccccactg ggctaaagtg   3540

gtgctgacag atcctgaggc cgccaaatac gtgcacggaa tcgccgtgca ctggtatctg   3600

gactttctgg cccctgccaa ggccacactg ggagagacac acagactgtt ccccaacacc   3660

atgctgttcg ccagcgaagc ctgtgtgggc agcaagtttt gggaacagag cgtgcggctc   3720

ggcagctggg atagaggcat gcagtacagc cacagcatca tcaccaacct gctgtaccac   3780

gtcgtcggct ggaccgactg gaatctggcc ctgaatcctg aaggcggccc taactgggtc   3840

cgaaacttcg tggacagccc catcatcgtg gacatcacca aggacacctt ctacaagcag   3900

cccatgttct accacctggg acacttcagc aagttcatcc ccgagggctc tcagcgcgtt   3960

ggactggtgg cttcccagaa gaacgatctg gacgccgtgg ctctgatgca ccctgatgga   4020

tctgctgtgg tggtggtcct gaaccgcagc agcaaagatg tgcccctgac catcaaggat   4080

cccgccgtgg gattcctgga aacaatcagc cctggctact ccatccacac ctacctgtgg   4140

cgtagacagt gacaattgtt aattaagttt aaaccctcga ggccgcaagc cgcatcgata   4200

ccgtcgacta gagctcgctg atcagcctcg actgtgcctt ctagttgcca gccatctgtt   4260

gtttgcccct cccccgtgcc ttccttgacc ctggaaggtg ccactcccac tgtcctttcc   4320

taataaaatg aggaaattgc atcgcattgt ctgagtaggt gtcattctat tctggggggt   4380

ggggtggggc aggacagcaa gggggaggat tgggaagaca atagcaggca tgctggggat   4440

gtacactgaa ttccctgcag gttggccact ccctctctgc gcgctcgctc gctcactgag   4500

gccgcccggg caaagcccgg gcgtcgggcg acctttggtc gcccggcctc agtgagcgag   4560

cgagcgcgca gagagggagt ggccaactcc atcactaggg gttcct                  4606
```

```
<210> SEQ ID NO 90
<211> LENGTH: 10870
<212> TYPE: DNA
<213> ORGANISM: Artificial Sequence
<220> FEATURE:
<223> OTHER INFORMATION: Nucleotide sequence of first strand of PR006A
      vector

<400> SEQUENCE: 90
```

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg aattcggtac    300

ctagttatta atagtaatca attacggggt cattagttca tagcccatat atggagttcc    360

gcgttacata acttacggta aatggcccgc ctggctgacc gcccaacgac ccccgcccat    420

tgacgtcaat aatgacgtat gttcccatag taacgccaat agggactttc cattgacgtc    480

aatgggtgga gtatttacgg taaactgccc acttggcagt acatcaagtg tatcatatgc    540
```

```
caagtacgcc ccctattgac gtcaatgacg gtaaatggcc cgcctggcat tatgcccagt    600
acatgacctt atgggacttt cctacttggc agtacatcta cgtattagtc atcgctatta    660
ccatggtcga ggtgagcccc acgttctgct tcactctccc catctccccc ccctccccac    720
ccccaatttt gtatttattt atttttaat tattttgtgc agcgatgggg gcggggggg      780
gggggggcg cgcgccaggc ggggcggggc ggggcgaggg gcggggcggg gcgaggcgga     840
gaggtgcggc ggcagccaat cagagcggcg cgctccgaaa gtttcctttt atggcgaggc    900
ggcggcggcg gcggccctat aaaaagcgaa gcgcgcggcg ggcgggagtc gctgcgcgct    960
gccttcgccc cgtgccccgc tccgccgccg cctcgcgccg cccgccccgg ctctgactga   1020
ccgcgttact cccacaggtg agcgggcggg acggcccttc tcctccgggc tgtaattagc   1080
gcttggttta atgacggctt gtttcttttc tgtggctgcg tgaaagcctt gaggggctcc   1140
gggagctaga gcctctgcta accatgttca tgccttcttc tttttcctac agctcctggg   1200
caacgtgctg gttattgtgc tgtctcatca ttttggcaaa gaattcctcg aagatccgaa   1260
gggaaagtct tccacgactg tgggatccgt tcgaagatat caccggttga gccaccatgt   1320
ggaccctggt gagctgggtg gccctgaccg ccggcctggt ggccggcacc cgctgccccg   1380
acggccagtt ctgccccgtg gcctgctgcc tggaccccgg cggcgccagc tacagctgct   1440
gccgccccct gctggacaag tggcccacca ccctgagccg ccacctgggc ggcccctgcc   1500
aggtggacgc ccactgcagc gccggccaca gctgcatctt caccgtgagc ggcaccagca   1560
gctgctgccc cttccccgag gccgtggcct gcggcgacgg ccaccactgc tgcccccgcg   1620
gcttccactg cagcgccgac ggccgcagct gcttccagcg cagcggcaac aacagcgtgg   1680
gcgccatcca gtgccccgac agccagttcg agtgccccga cttcagcacc tgctgcgtga   1740
tggtggacgg cagctggggc tgctgcccca tgccccaggc cagctgctgc gaggaccgcg   1800
tgcactgctg cccccacggc gccttctgcg acctggtgca cacccgctgc atcacccccca   1860
ccggcaccca ccccctggcc aagaagctgc ccgcccagcg caccaaccgc gccgtggccc   1920
tgagcagcag cgtgatgtgc cccgacgccc gcagccgctg ccccgacggc agcacctgct   1980
gcgagctgcc cagcggcaag tacggctgct gccccatgcc caacgccacc tgctgcagcg   2040
accacctgca ctgctgcccc caggacaccg tgtgcgacct gatccagagc aagtgcctga   2100
gcaaggagaa cgccaccacc gacctgctga ccaagctgcc cgcccacacc gtgggcgacg   2160
tgaagtgcga catggaggtg agctgccccg acggctacac ctgctgccgc ctgcagagcg   2220
gcgcctgggg ctgctgcccc ttcacccagg ccgtgtgctg cgaggaccac atccactgct   2280
gccccgccgg cttcacctgc gacacccaga agggcacctg cgagcagggc ccccaccagg   2340
tgccctggat ggagaaggcc cccgcccacc tgagcctgcc cgacccccag gccctgaagc   2400
gcgacgtgcc ctgcgacaac gtgagcagct gccccagcag cgacacctgc tgccagctga   2460
ccagcggcga gtggggctgc tgccccatcc ccgaggccgt gtgctgcagc gaccaccagc   2520
actgctgccc ccagggctac acctgcgtgg ccgagggcca gtgccagcgc ggcagcgaga   2580
tcgtggccgg cctggagaag atgcccgccc gccgcgccag cctgagccac ccccgcgaca   2640
tcggctgcga ccagcacacc agctgccccg tgggccagac ctgctgcccc agcctgggcg   2700
gcagctgggc ctgctgccag ctgccccacg ccgtgtgctg cgaggaccgc cagcactgct   2760
gccccgccgg ctacacctgc aacgtgaagg cccgcagctg cgagaaggag gtggtgagcg   2820
cccagcccgc caccttcctg gcccgcagcc cccacgtggg cgtgaaggac gtggagtgcg   2880
gcgagggcca cttctgccac gacaaccaga cctgctgccg cgacaaccgc cagggctggg   2940
```

```
cctgctgccc ctaccgccag ggcgtgtgct gcgccgaccg ccgccactgc tgccccgccg   3000
gcttccgctg cgccgcccgc ggcaccaagt gcctgcgccg cgaggccccc cgctgggacg   3060
ccccccctgcg cgaccccgcc ctgcgccagc tgctgtgaca attgttaatt aagtttaaac   3120
cctcgaggcc gcaagcttat cgataatcaa cctctggatt acaaaatttg tgaaagattg   3180
actggtattc ttaactatgt tgctcctttt acgctatgtg gatacgctgc tttaatgcct   3240
ttgtatcatg ctattgcttc ccgtatggct ttcattttct cctccttgta taaatcctgg   3300
ttgctgtctc tttatgagga gttgtggccc gttgtcaggc aacgtggcgt ggtgtgcact   3360
gtgtttgctg acgcaacccc cactggttgg ggcattgcca ccacctgtca gctcctttcc   3420
gggactttcg ctttccccct ccctattgcc acggcggaac tcatcgccgc ctgccttgcc   3480
cgctgctgga caggggctcg gctgttgggc actgacaatt ccgtggtgtt gtcggggaaa   3540
tcatcgtcct ttccttggct gctcgcctgt gttgccacct ggattctgcg cgggacgtcc   3600
ttctgctacg tcccttcggc cctcaatcca gcggaccttc cttcccgcgg cctgctgccg   3660
gctctgcggc ctcttccgcg tcttcgcctt cgccctcaga cgagtcggat ctccctttgg   3720
gccgcctccc cgcatcgata ccgtcgacta gagctcgctg atcagcctcg actgtgcctt   3780
ctagttgcca gccatctgtt gtttgcccct cccccgtgcc ttccttgacc ctggaaggtg   3840
ccactcccac tgtcctttcc taataaaatg aggaaattgc atcgcattgt ctgagtaggt   3900
gtcattctat tctggggggt ggggtggggc aggacagcaa gggggaggat tgggaagaca   3960
atagcaggca tgctggggag agatccacga taacaaacag ctttttgggg gcccacatgt   4020
acactgaatt ccctgcaggt tggccactcc ctctctgcgc gctcgctcgc tcactgaggc   4080
cgcccgggca aagcccgggc gtcgggcgac ctttggtcgc ccggcctcag tgagcgagcg   4140
agcgcgcaga gagggagtgg ccaactccat cactaggggt tcctgcggcc gctcgtacgg   4200
tctcgaggaa ttcctgcagg ataacttgcc aacctcattc taaaatgtat atagaagccc   4260
aaaagacaat aacaaaaata ttcttgtaga acaaaatggg aaagaatgtt ccactaaata   4320
tcaagattta gagcaaagca tgagatgtgt ggggatagac agtgaggctg ataaaataga   4380
gtagagctca gaaacagacc cattgatata tgtaagtgac ctatgaaaaa aatatggcat   4440
tttacaatgg gaaaatgatg gtctttttct tttttagaaa aacagggaaa tatatttata   4500
tgtaaaaaat aaaagggaac ccatatgtca taccatacac acaaaaaaat tccagtgaat   4560
tataagtcta aatggagaag gcaaaacttt aaatctttta gaaaataata tagaagcatg   4620
cagaccagcc tggccaacat gatgaaaccc tctctactaa taataaaatc agtagaacta   4680
ctcaggacta ctttgagtgg gaagtccttt tctatgaaga cttctttggc caaaattagg   4740
ctctaaatgc aaggagatag tgcatcatgc ctggctgcac ttactgataa atgatgttat   4800
caccatcttt aaccaaatgc acaggaacaa gttatggtac tgatgtgctg gattgagaag   4860
gagctctact tccttgacag gacacatttg tatcaactta aaaaagcaga tttttgccag   4920
cagaactatt cattcagagg taggaaactt agaatagatg atgtcactga ttagcatggc   4980
ttccccatct ccacagctgc ttcccaccca ggttgcccac agttgagttt gtccagtgct   5040
cagggctgcc cactctcagt aagaagcccc acaccagccc ctctccaaat atgttggctg   5100
ttccttccat taaagtgacc ccactttaga gcagcaagtg gatttctgtt tcttacagtt   5160
caggaaggag gagtcagctg tgagaacctg gagcctgaga tgcttctaag tcccactgct   5220
actggggtca gggaagccag actccagcat cagcagtcag gagcactaag cccttgccaa   5280
```

```
catcctgttt ctcagagaaa ctgcttccat tataatggtt gtcctttttt aagctatcaa   5340
gccaaacaac cagtgtctac cattattctc atcacctgaa gccaagggtt ctagcaaaag   5400
tcaagctgtc ttgtaatggt tgatgtgcct ccagcttctg tcttcagtca ctccactctt   5460
agcctgctct gaatcaactc tgaccacagt tccctggagc cctgccacc tgctgcccct    5520
gccaccttct ccatctgcag tgctgtgcag ccttctgcac tcttgcagag ctaataggtg   5580
gagacttgaa ggaagaggag gaaagtttct cataatagcc ttgctgcaag ctcaaatggg   5640
aggtgggcac tgtgcccagg agccttggag caaaggctgt gcccaacctc tgactgcatc   5700
caggtttggt cttgacagag ataagaagcc ctggcttttg gagccaaaat ctaggtcaga   5760
cttaggcagg attctcaaag tttatcagca gaacatgagg cagaagaccc tttctgctcc   5820
agcttcttca ggctcaacct tcatcagaat agatagaaag agaggctgtg agggttctta   5880
aaacagaagc aaatctgact cagagaataa acaacctcct agtaaactac agcttagaca   5940
gagcatctgg tggtgagtgt gctcagtgtc ctactcaact gtctggtatc agccctcatg   6000
aggacttctc ttctttccct catagacctc catctctgtt ttccttagcc tgcagaaatc   6060
tggatggcta ttcacagaat gcctgtgctt tcagagttgc attttttctc tggtattctg   6120
gttcaagcat ttgaaggtag gaaaggttct ccaagtgcaa gaaagccagc cctgagcctc   6180
aactgcctgg ctagtgtggt cagtaggatg caaaggctgt tgaatgccac aaggccaaac   6240
tttaacctgt gtaccacaag cctagcagca gaggcagctc tgctcactgg aactctctgt   6300
cttctttctc ctgagccttt tcttttcctg agttttctag ctctcctcaa ccttacctct   6360
gccctaccca ggacaaaccc aagagccact gtttctgtga tgtcctctcc agccctaatt   6420
aggcatcatg acttcagcct gaccttccat gctcagaagc agtgctaatc cacttcagat   6480
gagctgctct atgcaacaca ggcagagcct acaaaccttt gcaccagagc cctccacata   6540
tcagtgtttg ttcatactca cttcaacagc aaatgtgact gctgagatta agattttaca   6600
caagatggtc tgtaatttca cagttagttt tatcccatta ggtatgaaag aattagcata   6660
attcccctta aacatgaatg aatcttagat tttttaataa atagttttgg aagtaaagac   6720
agagacatca ggagcacaag gaatagcctg agaggacaaa cagaacaaga aagagtctgg   6780
aaatacacag gatgttcttg gcctcctcaa agcaagtgca agcagatagt accagcagcc   6840
ccaggctatc agagcccagt gaagagaagt accatgaaag ccacagctct aaccaccctg   6900
ttccagagtg acagacagtc cccaagacaa gccagcctga gccagagaga gaactgcaag   6960
agaaagtttc taatttaggt tctgttagat tcagacaagt gcaggtcatc ctctctccac   7020
agctactcac ctctccagcc taacaaagcc tgcagtccac actccaaccc tggtgtctca   7080
cctcctagcc tctcccaaca tcctgctctc tgaccatctt ctgcatctct catctcacca   7140
tctcccactg tctacagcct actcttgcaa ctaccatctc attttctgac atcctgtcta   7200
catcttctgc catactctgc catctaccat accacctctt accatctacc acaccatctt   7260
ttatctccat ccctctcaga agcctccaag ctgaatcctg ctttatgtgt tcatctcagc   7320
ccctgcatgg aaagctgacc ccagaggcag aactattccc agagagcttg gccaagaaaa   7380
acaaaactac cagcctggcc aggctcagga gtagtaagct gcagtgtctg ttgtgttcta   7440
gcttcaacag ctgcaggagt tccactctca aatgctccac atttctcaca tcctcctgat   7500
tctggtcact acccatcttc aaagaacaga atatctcaca tcagcatact gtgaaggact   7560
agtcatgggt gcagctgctc agagctgcaa agtcattctg gatggtggag agcttacaaa   7620
catttcatga tgctcccccc gctctgatgg ctggagccca atccctacac agactcctgc   7680
```

```
tgtatgtgtt ttcctttcac tctgagccac agccagaggg caggcattca gtctcctctt   7740
caggctgggg ctggggcact gagaactcac ccaacacctt gctctcactc cttctgcaaa   7800
acaagaaaga gctttgtgct gcagtagcca tgaagaatga aaggaaggct ttaactaaaa   7860
aatgtcagag attattttca accccttact gtggatcacc agcaaggagg aaacacaaca   7920
cagagacatt ttttcccctc aaattatcaa aagaatcact gcatttgtta aagagagcaa   7980
ctgaatcagg aagcagagtt ttgaacatat cagaagttag gaatctgcat cagagacaaa   8040
tgcagtcatg gttgtttgct gcataccagc cctaatcatt agaagcctca tggacttcaa   8100
acatcattcc ctctgacaag atgctctagc ctaactccat gagataaaat aaatctgcct   8160
ttcagagcca aagaagagtc caccagcttc ttctcagtgt gaacaagagc tccagtcagg   8220
ttagtcagtc cagtgcagta gaggagacca gtctgcatcc tctaattttc aaaggcaaga   8280
agatttgttt accctggaca ccaggcacaa gtgaggtcac agagctctta gatatgcagt   8340
cctcatgagt gaggagacta aagcgcatgc catcaagact tcagtgtaga gaaaacctcc   8400
aaaaaagcct cctcactact tctggaatag ctcagaggcc gaggcggcct cggcctctgc   8460
ataaataaaa aaaattagtc agccatgggg cggagaatgg gcggaactgg gcggagttag   8520
gggcgggatg ggcggagtta ggggcgggac tatggttgct gactaattga gatgcatgct   8580
ttgcatactt ctgcctgctg gggagcctgg ggactttcca cacctggttg ctgactaatt   8640
gagatgcatg ctttgcatac ttctgcctgc tggggagcct ggggactttc cacaccctaa   8700
ctgacacaca ttccacagct gcattaatga atcggccaac gcgcggggag aggcggtttg   8760
cgtattgggc gctcttccgc ttcctcgctc actgactcgc tgcgctcggt cgttcggctg   8820
cggcgagcgg tatcagctca ctcaaaggcg gtaatacggt tatccacaga atcaggggat   8880
aacgcaggaa agaacatgtg agcaaaaggc cagcaaaagg ccaggaaccg taaaaaggcc   8940
gcgttgctgg cgtttttcca taggctccgc ccccctgacg agcatcacaa aaatcgacgc   9000
tcaagtcaga ggtggcgaaa cccgacagga ctataaagat accaggcgtt tccccctgga   9060
agctccctcg tgcgctctcc tgttccgacc ctgccgctta ccggatacct gtccgccttt   9120
ctcccttcgg gaagcgtggc gctttctcat agctcacgct gtaggtatct cagttcggtg   9180
taggtcgttc gctccaagct gggctgtgtg cacgaacccc ccgttcagcc cgaccgctgc   9240
gccttatccg gtaactatcg tcttgagtcc aacccggtaa gacacgactt atcgccactg   9300
gcagcagcca ctggtaacag gattagcaga gcgaggtatg taggcggtgc tacagagttc   9360
ttgaagtggt ggcctaacta cggctacact agaagaacag tatttggtat ctgcgctctg   9420
ctgaagccag ttaccttcgg aaaaagagtt ggtagctctt gatccggcaa acaaaccacc   9480
gctggtagcg gtggtttttt tgtttgcaag cagcagatta cgcgcagaaa aaaaggatct   9540
caagaagatc ctttgatctt ttctacgggg tctgacgctc agtggaacga aaactcacgt   9600
taagggattt tggtcatgag attatcaaaa aggatcttca cctagatcct tttaaattaa   9660
aaatgaagtt ttaaatcaat ctaaagtata tatgagtaaa cttggtctga cagttaccaa   9720
tgcttaatca gtgaggcacc tatctcagcg atctgtctat ttcgttcatc catagttgcc   9780
tgactcctgc aaaccacgtt gtgtctcaaa atctctgatg ttacattgca caagataaaa   9840
atatatcatc atgaacaata aaactgtctg cttacataaa cagtaataca aggggtgtta   9900
tgagccatat tcaacgggaa acgtcttgct cgaggccgcg attaaattcc aacatggatg   9960
ctgatttata tgggtataaa tgggctcgcg ataatgtcgg gcaatcaggt gcgacaatct  10020
```

```
atcgattgta tgggaagccc gatgcgccag agttgtttct gaaacatggc aaaggtagcg  10080

ttgccaatga tgttacagat gagatggtca gactaaactg gctgacggaa tttatgcctc  10140

ttccgaccat caagcatttt atccgtactc ctgatgatgc atggttactc accactgcga  10200

tccccgggaa aacagcattc caggtattag aagaatatcc tgattcaggt gaaaatattg  10260

ttgatgcgct ggcagtgttc ctgcgccggt tgcattcgat tcctgtttgt aattgtcctt  10320

ttaacagcga tcgcgtattt cgtctcgctc aggcgcaatc acgaatgaat aacggtttgg  10380

ttgatgcgag tgattttgat gacgagcgta atggctggcc tgttgaacaa gtctggaaag  10440

aaatgcataa gcttttgcca ttctcaccgg attcagtcgt cactcatggt gatttctcac  10500

ttgataacct tatttttgac gaggggaaat taataggttg tattgatgtt ggacgagtcg  10560

gaatcgcaga ccgataccag gatcttgcca tcctatggaa ctgcctcggt gagttttctc  10620

cttcattaca gaaacggctt tttcaaaaat atggtattga taatcctgat atgaataaat  10680

tgcagtttca tttgatgctc gatgagtttt tctaagggcg gcctgccacc atacccacgc  10740

cgaaacaagc gctcatgagc ccgaagtggc gagcccgatc ttccccatcg gtgatgtcgg  10800

cgatataggc gccagcaacc gcacctgtgg cgccggtgat gagggcgcgc caagtcgacg  10860

tccggcagtc                                                         10870
```

<210> SEQ ID NO 91
<211> LENGTH: 10870
<212> TYPE: DNA
<213> ORGANISM: Artificial Sequence
<220> FEATURE:
<223> OTHER INFORMATION: Nucleotide sequence of second strand of PR006A vector

<400> SEQUENCE: 91

```
gactgccgga cgtcgacttg gcgcgccctc atcaccggcg ccacaggtgc ggttgctggc     60

gcctatatcg ccgacatcac cgatggggaa gatcgggctc gccacttcgg gctcatgagc    120

gcttgtttcg gcgtgggtat ggtggcaggc cgcccttaga aaaactcatc gagcatcaaa    180

tgaaactgca atttattcat atcaggatta tcaataccat atttttgaaa aagccgtttc    240

tgtaatgaag gagaaaactc accgaggcag ttccatagga tggcaagatc ctggtatcgg    300

tctgcgattc cgactcgtcc aacatcaata caacctatta atttcccctc gtcaaaaata    360

aggttatcaa gtgagaaatc accatgagtg acgactgaat ccggtgagaa tggcaaaagc    420

ttatgcattt ctttccagac ttgttcaaca ggccagccat tacgctcgtc atcaaaatca    480

ctcgcatcaa ccaaaccgtt attcattcgt gattgcgcct gagcgagacg aaatacgcga    540

tcgctgttaa aaggacaatt acaaacagga atcgaatgca accggcgcag gaacactgcc    600

agcgcatcaa caatattttc acctgaatca ggatattctt ctaatacctg gaatgctgtt    660

ttcccgggga tcgcagtggt gagtaaccat gcatcatcag gagtacggat aaaatgcttg    720

atggtcggaa gaggcataaa ttccgtcagc cagtttagtc tgaccatctc atctgtaaca    780

tcattggcaa cgctaccttt gccatgtttc agaaacaact ctggcgcatc gggcttccca    840

tacaatcgat agattgtcgc acctgattgc ccgacattat cgcgagccca tttataccca    900

tataaatcag catccatgtt ggaatttaat cgcggcctcg agcaagacgt ttcccgttga    960

atatggctca taacacccct tgtattactg tttatgtaag cagacagttt tattgttcat   1020

gatgatatat ttttatcttg tgcaatgtaa catcagagat tttgagacac aacgtggttt   1080

gcaggagtca ggcaactatg gatgaacgaa atagacagat cgctgagata ggtgcctcac   1140
```

-continued

```
tgattaagca ttggtaactg tcagaccaag tttactcata tatactttag attgatttaa   1200
aacttcattt ttaatttaaa aggatctagg tgaagatcct ttttgataat ctcatgacca   1260
aaatccctta acgtgagttt tcgttccact gagcgtcaga ccccgtagaa aagatcaaag   1320
gatcttcttg agatcctttt tttctgcgcg taatctgctg cttgcaaaca aaaaaaccac   1380
cgctaccagc ggtggtttgt ttgccggatc aagagctacc aactcttttt ccgaaggtaa   1440
ctggcttcag cagagcgcag ataccaaata ctgttcttct agtgtagccg tagttaggcc   1500
accacttcaa gaactctgta gcaccgccta catacctcgc tctgctaatc ctgttaccag   1560
tggctgctgc cagtggcgat aagtcgtgtc ttaccgggtt ggactcaaga cgatagttac   1620
cggataaggc gcagcggtcg ggctgaacgg ggggttcgtg cacacagccc agcttggagc   1680
gaacgaccta caccgaactg agatacctac agcgtgagct atgagaaagc gccacgcttc   1740
ccgaagggag aaaggcggac aggtatccgg taagcggcag ggtcggaaca ggagagcgca   1800
cgagggagct tccaggggga aacgcctggt atctttatag tcctgtcggg tttcgccacc   1860
tctgacttga gcgtcgattt ttgtgatgct cgtcaggggg gcggagccta tggaaaaacg   1920
ccagcaacgc ggccttttta cggttcctgg ccttttgctg gccttttgct cacatgttct   1980
ttcctgcgtt atcccctgat tctgtggata accgtattac cgcctttgag tgagctgata   2040
ccgctcgccg cagccgaacg accgagcgca gcgagtcagt gagcgaggaa gcggaagagc   2100
gcccaatacg caaaccgcct ctccccgcgc gttggccgat tcattaatgc agctgtggaa   2160
tgtgtgtcag ttagggtgtg gaaagtcccc aggctcccca gcaggcagaa gtatgcaaag   2220
catgcatctc aattagtcag caaccaggtg tggaaagtcc ccaggctccc cagcaggcag   2280
aagtatgcaa agcatgcatc tcaattagtc agcaaccata gtcccgcccc taactccgcc   2340
catcccgccc ctaactccgc ccagttccgc ccattctccg ccccatggct gactaatttt   2400
ttttatttat gcagaggccg aggccgcctc ggcctctgag ctattccaga agtagtgagg   2460
aggctttttt ggaggttttc tctacactga agtcttgatg gcatgcgctt tagtctcctc   2520
actcatgagg actgcatatc taagagctct gtgacctcac ttgtgcctgg tgtccagggt   2580
aaacaaatct tcttgccttt gaaaattaga ggatgcagac tggtctcctc tactgcactg   2640
gactgactaa cctgactgga gctcttgttc acactgagaa gaagctggtg gactcttctt   2700
tggctctgaa aggcagattt attttatctc atggagttag gctagagcat cttgtcagag   2760
ggaatgatgt ttgaagtcca tgaggcttct aatgattagg gctggtatgc agcaaacaac   2820
catgactgca tttgtctctg atgcagattc ctaacttctg atatgttcaa aactctgctt   2880
cctgattcag ttgctctctt taacaaatgc agtgattctt ttgataattt gaggggaaaa   2940
aatgtctctg tgttgtgttt cctccttgct ggtgatccac agtaaggggt tgaaaataat   3000
ctctgacatt ttttagttaa agccttcctt tcattcttca tggctactgc agcacaaagc   3060
tctttcttgt tttgcagaag gagtgagagc aaggtgttgg gtgagttctc agtgccccag   3120
ccccagcctg aagaggagac tgaatgcctg ccctctggct gtggctcaga gtgaaaggaa   3180
aacacataca gcaggagtct gtgtagggat tgggctccag ccatcagagc ggggggagca   3240
tcatgaaatg tttgtaagct ctccaccatc cagaatgact ttgcagctct gagcagctgc   3300
acccatgact agtccttcac agtatgctga tgtgagatat tctgttcttt gaagatgggt   3360
agtgaccaga atcaggagga tgtgagaaat gtggagcatt tgagagtgga actcctgcag   3420
ctgttgaagc tagaacacaa cagacactgc agcttactac tcctgagcct ggccaggctg   3480
gtagttttgt ttttcttggc caagctctct gggaatagtt ctgcctctgg ggtcagcttt   3540
```

```
ccatgcaggg gctgagatga acacataaag caggattcag cttggaggct tctgagaggg   3600
atggagataa aagatggtgt ggtagatggt aagaggtggt atggtagatg gcagagtatg   3660
gcagaagatg tagacaggat gtcagaaaat gagatggtag ttgcaagagt aggctgtaga   3720
cagtgggaga tggtgagatg agagatgcag aagatggtca gagagcagga tgttgggaga   3780
ggctaggagg tgagacacca gggttggagt gtggactgca ggctttgtta ggctggagag   3840
gtgagtagct gtggagagag gatgacctgc acttgtctga atctaacaga acctaaatta   3900
gaaactttct cttgcagttc tctctctggc tcaggctggc ttgtcttggg gactgtctgt   3960
cactctggaa cagggtggtt agagctgtgg ctttcatggt acttctcttc actgggctct   4020
gatagcctgg ggctgctggt actatctgct tgcacttgct ttgaggaggc caagaacatc   4080
ctgtgtattt ccagactctt tcttgttctg tttgtcctct caggctattc cttgtgctcc   4140
tgatgtctct gtctttactt ccaaaactat ttattaaaaa atctaagatt cattcatgtt   4200
taaggggaat tatgctaatt ctttcatacc taatgggata aaactaactg tgaaattaca   4260
gaccatcttg tgtaaaatct taatctcagc agtcacattt gctgttgaag tgagtatgaa   4320
caaacactga tatgtggagg gctctggtgc aaaggtttgt aggctctgcc tgtgttgcat   4380
agagcagctc atctgaagtg gattagcact gcttctgagc atggaaggtc aggctgaagt   4440
catgatgcct aattagggct ggagaggaca tcacagaaac agtggctctt gggtttgtcc   4500
tgggtagggc agaggtaagg ttgaggagag ctagaaaact caggaaaaga aaaggctcag   4560
gagaaagaag acagagagtt ccagtgagca gagctgcctc tgctgctagg cttgtggtac   4620
acaggttaaa gtttggcctt gtggcattca acagcctttg catcctactg accacactag   4680
ccaggcagtt gaggctcagg gctggctttc ttgcacttgg agaacctttc ctaccttcaa   4740
atgcttgaac cagaatacca gagaaaaaat gcaactctga aagcacaggc attctgtgaa   4800
tagccatcca gatttctgca ggctaaggaa aacagagatg gaggtctatg agggaaagaa   4860
gagaagtcct catgagggct gataccagac agttgagtag gacactgagc acactcacca   4920
ccagatgctc tgtctaagct gtagtttact aggaggttgt ttattctctg agtcagattt   4980
gcttctgttt taagaaccct cacagcctct ctttctatct attctgatga aggttgagcc   5040
tgaagaagct ggagcagaaa gggtcttctg cctcatgttc tgctgataaa ctttgagaat   5100
cctgcctaag tctgacctag attttggctc caaaagccag ggcttcttat ctctgtcaag   5160
accaaacctg gatgcagtca gaggttgggc acagcctttg ctccaaggct cctgggcaca   5220
gtgcccacct cccatttgag cttgcagcaa ggctattatg agaaactttc ctcctcttcc   5280
ttcaagtctc cacctattag ctctgcaaga gtgcagaagg ctgcacagca ctgcagatgg   5340
agaaggtggc aggggcagca ggtggcaggg gctccaggga actgtggtca gagttgattc   5400
agagcaggct aagagtggag tgactgaaga cagaagctgg aggcacatca accattacaa   5460
gacagcttga cttttgctag aacccttggc ttcaggtgat gagaataatg gtagacactg   5520
gttgtttggc ttgatagctt aaaaaaggac aaccattata atggaagcag tttctctgag   5580
aaacaggatg ttggcaaggg cttagtgctc ctgactgctg atgctggagt ctggcttccc   5640
tgaccccagt agcagtggga cttagaagca tctcaggctc caggttctca cagctgactc   5700
ctccttcctg aactgtaaga aacagaaatc cacttgctgc tctaaagtgg ggtcacttta   5760
atggaaggaa cagccaacat atttggagag gggctggtgt ggggcttctt actgagagtg   5820
ggcagccctg agcactggac aaactcaact gtgggcaacc tgggtgggaa gcagctgtgg   5880
```

```
agatggggaa gccatgctaa tcagtgacat catctattct aagtttccta cctctgaatg   5940
aatagttctg ctggcaaaaa tctgcttttt taagttgata caaatgtgtc ctgtcaagga   6000
agtagagctc cttctcaatc cagcacatca gtaccataac ttgttcctgt gcatttggtt   6060
aaagatggtg ataacatcat ttatcagtaa gtgcagccag gcatgatgca ctatctcctt   6120
gcatttagag cctaattttg gccaaagaag tcttcataga aaaggacttc ccactcaaag   6180
tagtcctgag tagttctact gattttatta ttagtagaga gggtttcatc atgttggcca   6240
ggctggtctg catgcttcta tattattttc taaaagattt aaagttttgc cttctccatt   6300
tagacttata attcactgga atttttttgt gtgtatggta tgacatatgg gttccctttt   6360
atttttaca tataaatata tttccctgtt tttctaaaaa agaaaaagac catcattttc   6420
ccattgtaaa atgccatatt tttttcatag gtcacttaca tatatcaatg ggtctgtttc   6480
tgagctctac tctattttat cagcctcact gtctatcccc acacatctca tgctttgctc   6540
taaatcttga tatttagtgg aacattcttt cccattttgt tctacaagaa tatttttgtt   6600
attgtctttt gggcttctat atacatttta gaatgaggtt ggcaagttat cctgcaggaa   6660
ttcctcgaga ccgtacgagc ggccgcagga acccctagtg atggagttgg ccactccctc   6720
tctgcgcgct cgctcgctca ctgaggccgg gcgaccaaag gtcgcccgac gcccgggctt   6780
tgcccgggcg gcctcagtga gcgagcgagc gcgcagagag ggagtggcca acctgcaggg   6840
aattcagtgt acatgtgggc cccaaaaaag ctgtttgtta tcgtggatct ctccccagca   6900
tgcctgctat tgtcttccca atcctccccc ttgctgtcct gccccacccc accccccaga   6960
atagaatgac acctactcag acaatgcgat gcaatttcct cattttatta ggaaaggaca   7020
gtgggagtgg caccttccag ggtcaaggaa ggcacggggg aggggcaaac aacagatggc   7080
tggcaactag aaggcacagt cgaggctgat cagcgagctc tagtcgacgg tatcgatgcg   7140
gggaggcggc ccaaagggag atccgactcg tctgagggcg aaggcgaaga cgcggaagag   7200
gccgcagagc cggcagcagg ccgcgggaag gaaggtccgc tggattgagg gccgaaggga   7260
cgtagcagaa ggacgtcccg cgcagaatcc aggtggcaac acaggcgagc agccaaggaa   7320
aggacgatga tttccccgac aacaccacgg aattgtcagt gcccaacagc cgagcccctg   7380
tccagcagcg ggcaaggcag gcggcgatga gttccgccgt ggcaataggg agggggaaag   7440
cgaaagtccc ggaaaggagc tgacaggtgg tggcaatgcc ccaaccagtg gggggttgcgt  7500
cagcaaacac agtgcacacc acgccacgtt gcctgacaac gggccacaac tcctcataaa   7560
gagacagcaa ccaggattta tacaaggagg agaaaatgaa agccatacgg gaagcaatag   7620
catgatacaa aggcattaaa gcagcgtatc cacatagcgt aaaaggagca acatagttaa   7680
gaataccagt caatctttca caaattttgt aatccagagg ttgattatcg ataagcttgc   7740
ggcctcgagg gtttaaactt aattaacaat tgtcacagca gctggcgcag ggcggggtcg   7800
cgcagggggg cgtcccagcg gggggcctcg cggcgcaggc acttggtgcc gcgggcggcg   7860
cagcggaagc cggcggggca gcagtggcgg cggtcggcgc agcacacgcc ctggcggtag   7920
gggcagcagg cccagccctg gcggttgtcg cggcagcagg tctggttgtc gtggcagaag   7980
tggccctcgc cgcactccac gtccttcacg cccacgtggg ggctgcgggc caggaaggtg   8040
gcgggctggg cgctcaccac ctccttctcg cagctgcggg ccttcacgtt gcaggtgtag   8100
ccggcggggc agcagtgctg gcggtcctcg cagcacacgg cgtggggcag ctggcagcag   8160
gcccagctgc cgcccaggct ggggcagcag gtctggccca cggggcagct ggtgtgctgg   8220
tcgcagccga tgtcgcgggg gtggctcagg ctggcgcggc gggcgggcat cttctccagg   8280
```

```
ccggccacga tctcgctgcc gcgctggcac tggccctcgg ccacgcaggt gtagccctgg   8340
gggcagcagt gctggtggtc gctgcagcac acggcctcgg ggatggggca gcagccccac   8400
tcgccgctgg tcagctggca gcaggtgtcg ctgctggggc agctgctcac gttgtcgcag   8460
ggcacgtcgc gcttcagggc ctgggggtcg ggcaggctca ggtgggcggg ggccttctcc   8520
atccagggca cctggtgggg gccctgctcg caggtgccct tctgggtgtc gcaggtgaag   8580
ccggcggggc agcagtggat gtggtcctcg cagcacacgg cctgggtgaa ggggcagcag   8640
ccccaggcgc cgctctgcag gcggcagcag gtgtagccgt cggggcagct cacctccatg   8700
tcgcacttca cgtcgcccac ggtgtgggcg ggcagcttgg tcagcaggtc ggtggtggcg   8760
ttctccttgc tcaggcactt gctctggatc aggtcgcaca cggtgtcctg gggcagcag    8820
tgcaggtggt cgctgcagca ggtggcgttg ggcatggggc agcagccgta cttgccgctg   8880
ggcagctcgc agcaggtgct gccgtcgggg cagcggctgc gggcgtcggg gcacatcacg   8940
ctgctgctca gggccacggc gcggttggtg cgctgggcgg gcagcttctt ggccaggggg   9000
tgggtgccgg tgggggtgat gcagcgggtg tgcaccaggt cgcagaaggc gccgtggggg   9060
cagcagtgca cgcggtcctc gcagcagctg gcctggggca tggggcagca gccccagctg   9120
ccgtccacca tcacgcagca ggtgctgaag tcggggcact cgaactggct gtcggggcac   9180
tggatggcgc ccacgctgtt gttgccgctg cgctggaagc agctgcggcc gtcggcgctg   9240
cagtggaagc cgcgggggca gcagtggtgg ccgtcgccgc aggccacggc ctcggggaag   9300
gggcagcagc tgctggtgcc gctcacggtg aagatgcagc tgtggccggc gctgcagtgg   9360
gcgtccacct ggcaggggcc gcccaggtgg cggctcaggg tggtgggcca cttgtccagc   9420
agggggcggc agcagctgta gctggcgccg ccggggtcca ggcagcaggc cacggggcag   9480
aactggccgt cggggcagcg ggtgccggcc accaggccgg cggtcagggc cacccagctc   9540
accagggtcc acatggtggc tcaaccggtg atatcttcga acggatccca cagtcgtgga   9600
agactttccc ttcggatctt cgaggaattc tttgccaaaa tgatgagaca gcacaataac   9660
cagcacgttg cccaggagct gtaggaaaaa gaagaaggca tgaacatggt tagcagaggc   9720
tctagctccc ggagcccctc aaggctttca cgcagccaca gaaaagaaac aagccgtcat   9780
taaaccaagc gctaattaca gcccggagga gaagggccgt cccgcccgct cacctgtggg   9840
agtaacgcgg tcagtcagag ccggggcggg cggcgcgagg cggcggcgga gcggggcacg   9900
gggcgaaggc agcgcgcagc gactcccgcc cgccgcgcgc ttcgcttttt atagggccgc   9960
cgccgccgcc gcctcgccat aaaaggaaac tttcggagcg cgccgctctg attggctgcc  10020
gccgcacctc tccgcctcgc cccgccccgc ccctcgcccc gccccgcccc gcctggcgcg  10080
cgcccccccc cccccccgc ccccatcgct gcacaaaata attaaaaaat aaataaatac  10140
aaaattgggg gtggggaggg gggggagatg gggagagtga agcagaacgt ggggctcacc  10200
tcgaccatgg taatagcgat gactaatacg tagatgtact gccaagtagg aaagtcccat  10260
aaggtcatgt actgggcata atgccaggcg ggccatttac cgtcattgac gtcaataggg  10320
ggcgtacttg gcatatgata cacttgatgt actgccaagt gggcagttta ccgtaaatac  10380
tccacccatt gacgtcaatg gaaagtccct attggcgtta ctatgggaac atacgtcatt  10440
attgacgtca atgggcgggg gtcgttgggc ggtcagccag gcgggccatt taccgtaagt  10500
tatgtaacgc ggaactccat atatgggcta tgaactaatg accccgtaat tgattactat  10560
taataactag gtaccgaatt cagatccaag cttcaccatg ggagacgtca ccggttctag  10620
```

-continued

```
aacctaggga gctctggtac ccactagtag tcgacgaacg cgtaacctcc cgcttcaaaa  10680

tggagaccct gcgtgctcac tcgggcttaa atacccagag ctagcaggaa cccctagtga  10740

tggagttggc cactccctct ctgcgcgctc gctcgctcac tgaggccgcc cgggcaaagc  10800

ccgggcgtcg ggcgaccttt ggtcgcccgg cctcagtgag cgagcgagcg cgcagagagg  10860

gagtggccaa                                                         10870
```

GENE THERAPIES FOR LYSOSOMAL DISORDERS

CROSS-REFERENCE TO RELATED APPLICATIONS

This application claims priority to U.S. Provisional Patent Application No. 62/988,665, filed on Mar. 12, 2020, U.S. Provisional Patent Application No. 62/960,471, filed on Jan. 13, 2020, U.S. Provisional Patent Application No. 62/954,089, filed on Dec. 27, 2019, U.S. Provisional Patent Application No. 62/934,450, filed on Nov. 12, 2019 and U.S. Provisional Patent Application No. 62/831,846, filed on Apr. 10, 2019. The disclosure of each of these applications is incorporated herein by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: PRVL_010_05US_SeqList.txt, date recorded: Apr. 10, 2020, file size 612,902 bytes).

FIELD

The disclosure relates to the field of gene therapy and methods of using same.

BACKGROUND

Gaucher disease is a rare inborn error of glycosphingolipid metabolism due to deficiency of lysosomal acid β-glucocerebrosidase (Gcase, "GBA"). Patients suffer from non-CNS symptoms and findings including hepatosplenomegaly, bone marrow insufficiency leading to pancytopenia, lung disorders and fibrosis, and bone defects. In addition, a significant number of patients suffer from neurological manifestations, including defective saccadic eye movements and gaze, seizures, cognitive deficits, developmental delay, and movement disorders including Parkinson's disease. Several therapeutics exist that address the peripheral disease and the principal clinical manifestations in hematopoietic bone marrow and viscera, including enzyme replacement therapies as described below, chaperone-like small molecule drugs that bind to defective Gcase and improve stability, and substrate reduction therapy that block the production of substrate that accumulate in Gaucher disease leading to symptoms and findings. However, other aspects of Gaucher disease (particularly those affecting the skeleton and brain) appear refractory to treatment.

Progranulin (PGRN) is an additional protein linked to lysosomal function. PGRN is encoded by the GRN gene. GRN haploinsufficiency in humans leads to an approximately 90% risk of developing FTD-GRN (fronto-temporal dementia with GRN mutation), a neurodegenerative disease characterized by impairment of executive function, changes in behavior, and language difficulties, accompanied by atrophy of the frontal and temporal lobes. No disease-modifying therapies are available for patients with FTD.

SUMMARY

Provided herein is a method for treating a subject having or suspected of having fronto-temporal dementia with a GRN mutation, the method comprising administering to the subject a recombinant adeno-associated virus (rAAV) comprising: (i) a rAAV vector comprising a nucleic acid comprising an expression construct comprising a promoter operably linked to a transgene insert encoding a PGRN protein, wherein the transgene insert comprises the nucleotide sequence of SEQ ID NO: 68; and (ii) an AAV9 capsid protein. In some embodiments, the rAAV is administered to a subject at a dose ranging from about $1\times10^{13}$ vector genomes (vg) to about $7\times10^{14}$ vg. In some embodiments, the rAAV is administered via an injection into the cisterna magna.

In some embodiments, the promoter operably linked to a transgene insert encoding a PGRN protein is a chicken beta actin (CBA) promoter. In some embodiments, the rAAV vector further comprises a cytomegalovirus (CMV) enhancer. In some embodiments, the rAAV vector further comprises a Woodchuck Hepatitis Virus Posttranscriptional Regulatory Element (WPRE). In some embodiments, the rAAV vector further comprises a Bovine Growth Hormone polyA signal tail. In some embodiments, the nucleic acid comprises two adeno-associated virus inverted terminal repeats (ITR) sequences flanking the expression construct. In some embodiments, each ITR sequence is a wild-type AAV2 ITR sequence. In some embodiments, the rAAV vector further comprises a TRY region between the 5' ITR and the expression construct, wherein the TRY region comprises SEQ ID NO: 28.

Provided herein is a method for treating a subject having or suspected of having fronto-temporal dementia with a GRN mutation, the method comprising administering to the subject a rAAV comprising: (i) a rAAV vector comprising a nucleic acid comprising, in 5' to 3' order: (a) an AAV2 ITR; (b) a CMV enhancer; (c) a CBA promoter; (d) a transgene insert encoding a PGRN protein, wherein the transgene insert comprises the nucleotide sequence of SEQ ID NO: 68; (e) a WPRE; (f) a Bovine Growth Hormone polyA signal tail; and (g) an AAV2 ITR; and (ii) an AAV9 capsid protein. In some embodiments, the rAAV is administered to a subject at a dose ranging from about $1\times10^{13}$ vg to about 7×10" vg. In some embodiments, the rAAV is administered via an injection into the cisterna magna.

In some embodiments, the rAAV is administered in a formulation comprising about 20 mM Tris, pH 8.0, about 1 mM $MgCl_2$, about 200 mM NaCl, and about 0.001% w/v poloxamer 188.

Provided herein is a pharmaceutical composition comprising (i) a rAAV comprising: (a) a rAAV vector comprising a nucleic acid comprising an expression construct comprising a promoter operably linked to a transgene insert encoding a PGRN protein, wherein the transgene insert comprises the nucleotide sequence of SEQ ID NO: 68; and (b) an AAV9 capsid protein; and (ii) about 20 mM Tris, pH 8.0, (iii) about 1 mM $MgCl_2$, (iv) about 200 mM NaCl, and (v) about 0.001% w/v poloxamer 188.

Provided herein is a rAAV comprising: (a) a rAAV vector comprising a nucleic acid comprising an expression construct comprising a promoter operably linked to a transgene insert encoding a PGRN protein, wherein the transgene insert comprises the nucleotide sequence of SEQ ID NO: 68; and (b) an AAV9 capsid protein, for use in a method of treating fronto-temporal dementia with a GRN mutation in a subject.

Provided herein is a method of quantifying a PGRN protein level in a cerebrospinal fluid (CSF) sample, the method comprising: (1) diluting the CSF sample in a master mix containing dithiothreitol (DTT) and sample buffer; (2) loading the diluted CSF sample, an anti-progranulin antibody, a secondary antibody that detects the anti-progranulin antibody, luminol and peroxide into wells of a capillary cartridge; (3) loading the capillary cartridge into an automated Western blot immunoassay instrument; (4) using the automated Western blot immunoassay instrument to calculate signal intensity, peak area, and signal-to-noise ratio; and (5) quantifying a progranulin protein level in the CSF sample as the peak area of immunoreactivity to the anti-progranulin antibody.

BRIEF DESCRIPTION OF THE DRAWINGS

FIG. 36A shows data for overexpression of TREM2. FIG. 36B shows data for overexpression of GBA1 from the same construct.

FIG. 52D: Neurons were lysed, and the Triton-X insoluble protein fraction was isolated and analyzed on the Protein Simple Western Jess system with an anti-TDP-43 antibody (#12892-AP-1). A band corresponding to TDP-43 was detected, and the area under the curve was quantified for each band and normalized to the total protein concentration of the insoluble fraction. The y-axis depicts the amount of insoluble TDP-43 as a percent of excipient treated levels normalized separately for each FTD-GRN cell line (n=3; mean±SEM). FIG. 52D shows that PR006 treatment decreased insoluble TDP-43, a hallmark of FTD-GRN pathology, in FTD-GRN neuronal cultures. FIG. 52F: Quantification of nuclear TDP-43 signal from immunofluorescence images of iPSC-derived neurons treated with PR006A. The TDP-43 signal intensity per nucleus in excipient or PR006A treated FTD-GRN neurons was determined; the y-axis depicts the TDP-43 signal intensity per nucleus as a percent of the TDP-43 signal intensity per nucleus of excipient treated Control neurons (n=145-306 cells; mean±SEM). TDP-43 was measured using an anti-TDP-43 antibody (#12892-AP-1) and nuclear area was determined by DAPI stain. FIG. 52F shows that PR006 treatment increased nuclear TDP-43 expression levels in FTD-GRN neuronal cultures to near wild-type control levels. Statistics were determined using an unpaired t-test, =p<0.01, *=p<0.001.

FIG. 53A-FIG. 53C are a series of bar graphs depicting the results of experiments analyzing biodistribution and progranulin expression in the CNS in adult dose-ranging PR006A FTD-GRN mouse model study. 4-month-old Grn KO mice were given PR006A or excipient by ICV administration. They were sacrificed 3 months after the treatment with excipient (red) or PR006A at dose of $1.1\times10^{9}$ vg ($2.7\times10^{9}$ vg/g brain), $1.1\times10^{19}$ vg ($2.7\times10^{19}$ vg/g brain), or $1.1\times10^{11}$ vg ($2.7\times10^{11}$ vg/g brain) (blue) for biochemical endpoints in the CNS. FIG. 53A: Presence of vector genomes was assessed in the cerebral cortex and spinal cord, and biodistribution is shown as vector genomes per μg of gDNA on a log scale (n=8-10/group; mean±SEM). Vector genome presence was quantified by qPCR using a vector reference standard curve. Dashed line (at 50 vector genomes/μg gDNA) represents the threshold for positive vector presence. FIG. 53B: PR006A-encoded GRN RNA expression was assessed by quantitative RT-PCR (qRT-PCR) in the cerebral cortex (n=8-10/group; mean±SEM). The number of GRN copies (specific to our codon optimized PR006A sequence) was normalized to 1 μg of total RNA and is shown on a log scale. FIG. 53C: Progranulin protein levels were measured using a human-specific progranulin ELISA in the brain and spinal cord (n=8-10/group; mean±SEM). Tissue progranulin levels were normalized to total protein concentration. The lower limit of quantitation (LLOQ) is indicated by a dashed gray line. For tissue ELISA assays, LLOQ (ng/mg) values are determined by dividing the assay LLOQ (ng/mL) by the total protein concentration average from all samples. A simple line corresponding to the treatment group legend color on the x-axis without error bars indicates that all animals in that group were 0. Statistical analysis was conducted using ANOVA followed by Dunnett's test to compare to the excipient treated Grn KO mouse group; *=p<0.05, =p<0.01, *=p<0.001. vg=vector genomes; LLOQ=lower limit of quantitation; SC=spinal cord.

FIG. 53D: Presence of vector genomes was assessed, and biodistribution is shown as vector genomes per μg of gDNA on a log scale (n=8-10/group; mean±SEM). Vector genome presence was quantified by qPCR using a vector reference standard curve. Dashed line (at 50 vector genomes/μg gDNA) represents the threshold for positive vector presence. FIG. 53E: Progranulin protein levels were measured using an ELISA (n=8-10/group; mean±SEM). Tissue progranulin levels were normalized to total protein concentration. A simple line corresponding to the treatment group legend color on the x-axis without error bars indicates that all animals in that group were 0. Statistical analysis was conducted using ANOVA followed by Dunnett's test to compare to the excipient treated Grn KO mouse group; *=p<0.05, ***=p<0.001. vg=vector genomes.

FIG. 53G: Lipofuscin accumulation (autofluorescent lipofuscin granules) was semi-quantitatively scored in H&E-stained sections in different brain regions by a blinded board-certified pathologist according to the following grading scheme: 0=no lipofuscin observed; 1=very small granules of lipofuscin (<2 μm) scattered throughout region; 2=increased density of small granule accumulation, and/or development of larger granules (>2-3 μm); 3=multifocal regions with a high density of lipofuscin granules visible from a low objective power; 4=widespread lipofuscin accumulation.

Lipofuscin severity scores in the cerebral cortex, hippocampus, and thalamus/hypothalamus brain regions is shown (n=8-10/group). FIG. 53H: IHC analysis of ubiquitin was performed and quantified in the cerebral cortex, hippocampus, and thalamus. The size of above-threshold immunoreactive objects (immunoreactive object size [μm2] is shown for ubiquitin (n=8-10/group; mean±SEM). Statistics were determined by ANOVA followed by Dunnett's test to compare to the excipient treated Grn KO mouse group, *=p<0.05, =p<0.01, *=p<0.001. vg=vector genomes; WT=wildtype.

FIG. 53I: Gene expression (mRNA levels) of Tnf and Cd68 was measured by qRT-PCR in the somatosensory cortex (mean±SEM; n=8-10/group). Gene expression was normalized to the housekeeping gene Ppib. FIG. 53J-FIG. 53K: IHC analysis of Iba1 (FIG. 53J) and GFAP (FIG. 53K) was performed and quantified in fixed brain sections in the cerebral cortex, hippocampus, and thalamus. The percent of the area of interest that is covered by above-threshold objects (immunoreactive area [%]) is shown (mean±SEM; n=8-10/group). Statistics were determined using ANOVA with Dunnett's adjustment comparing each group to the excipient treated Grn KO mouse group, *=p<0.05, ***=p<0.001. vg=vector genomes; WT=wildtype.

FIG. 53L: Cellular Component: Vacuole (GO: 0005773), FIG. 53M: Lysosome, and FIG. 53N: Complement System (HALLMARK pathway) (median±range; n=8-10/group). Statistical analysis was conducted using ANOVA followed by Dunnett's test to compare to the excipient-treated Grn KO mouse group while controlling for the family-wise Type I error rate, ***=p<0.001. GSVA=gene set variation analysis; vg=vector genomes; WT=wildtype.

FIG. 59A-FIG. 59C are a series of bar graphs depicting the results of experiments analyzing biodistribution and progranulin expression in the CNS in an aged FTD-GRN mouse model following PR006A treatment. Tissue samples were collected from 18-month old Grn KO mice 2 months after receiving ICV excipient (red) or $9.7\times10^{10}$ vg ($2.4\times10^{11}$ vg/g brain) PR006A (blue). FIG. 59A: Presence of vector genomes was assessed in the cerebral cortex and spinal cord (mean±SEM; n=4/group). Biodistribution is shown as vector genomes per 1 μg of gDNA on a log scale. Vector genome presence was quantified by qPCR using a vector reference standard curve. Dashed line (at 50 vector genomes/ng gDNA) represents the threshold for positive vector presence. FIG. 59B-FIG. 59C: Progranulin protein levels were measured using an ELISA in CNS tissues (brain and spinal cord (FIG. 59B)), and CSF (FIG. 59C) (mean±SEM; n=4/group). Tissue progranulin levels were normalized to total protein concentration, and CSF levels of progranulin were normalized to fluid volume. The lower limit of quantitation (LLOQ) is indicated by a dashed gray line. For tissue ELISA assays, LLOQ (ng/mg) values were determined by dividing the assay LLOQ (ng/mL) by the total protein concentration average from all samples. A simple red line on the x-axis without error bars indicates that all animals in that group were 0. Statistical analyses were performed using Kruskal-Wallis; *=p<0.05, =p<0.01, *=p<0.001. vg=vector genomes; LLOQ=lower limit of quantitation; SC=spinal cord.

FIG. 59D: Representative lipofuscin images from the thalamus/hypothalamus region of brain sections. White arrowheads indicate examples of lipofuscin accumulation. A summary of lipofuscin severity scores in the cerebral cortex, hippocampus, and thalamus/hypothalamus of H&E-stained slides from brain sections that were evaluated for autofluorescent lipofuscin granules is provided. Lipofuscin accumulation was semi-quantitatively scored by a blinded board-certified pathologist according to the following grading scheme: 0=no lipofuscin observed; 1=very small granules of lipofuscin (<2 μm) scattered throughout region; 2=increased density of small granule accumulation, and/or development of larger granules (>2-3 μm); 3=multifocal regions with a high density of lipofuscin granules visible from a low objective power; 4=widespread lipofuscin accumulation. FIG. 59E: IHC analysis of ubiquitin (n=4/group) was performed and quantified in the cerebral cortex, hippocampus, and thalamus. The positive cell density (cells/mm$^2$) for each region is shown (mean±SEM). Statistics were determined using a t-test, *=p<0.05, **=p<0.01. vg=vector genomes.

FIG. 59F: Gene expression of Tnf and Cd68 was measured by qRT-PCR in the somatosensory cortex (mean±SEM; n=4/group). Gene expression was normalized to the housekeeping gene Ppib. (FIG. 59G) Protein expression of the proinflammatory cytokine TNFα was measured in the cerebral cortex using a Mesoscale Discovery mouse pro-inflammatory cytokine assay (mean±SEM; n=4/group). Cerebral cortices were homogenized, and protein expression levels were normalized to total protein concentration of tissue lysates. FIG. 59H-FIG. 59I: IHC analysis of Iba1 (FIG. 59H) and GFAP (FIG. 59I) was performed and quantified in fixed brain sections. A compilation of the positive cell density (cells/mm$^2$) from the three brain regions analyzed (cerebral cortex, hippocampus, and thalamus) is shown (mean±SEM; n=3-4/group). Statistical analyses were performed using a t-test, *=p<0.05. vg=vector genomes.

FIG. 62A: Presence of vector genomes was assessed in the liver, heart, lung, kidney, spleen, and gonads (mean±SEM; n=4/group). Biodistribution is shown as vector genomes per μg of gDNA on a log scale. Vector genome presence was quantified by qPCR using a vector reference standard. FIG. 62B: Progranulin protein levels were measured using an ELISA (mean±SEM; n=4/group). Tissue progranulin levels were normalized to total protein concentration. A simple red line on the x-axis without error bars indicates that all animals in that group were 0. Statistical analyses were performed using Kruskal-Wallis; *=p<0.05, =p<0.01, *=p<0.001. vg=vector genomes.

DETAILED DESCRIPTION

Figure 1:
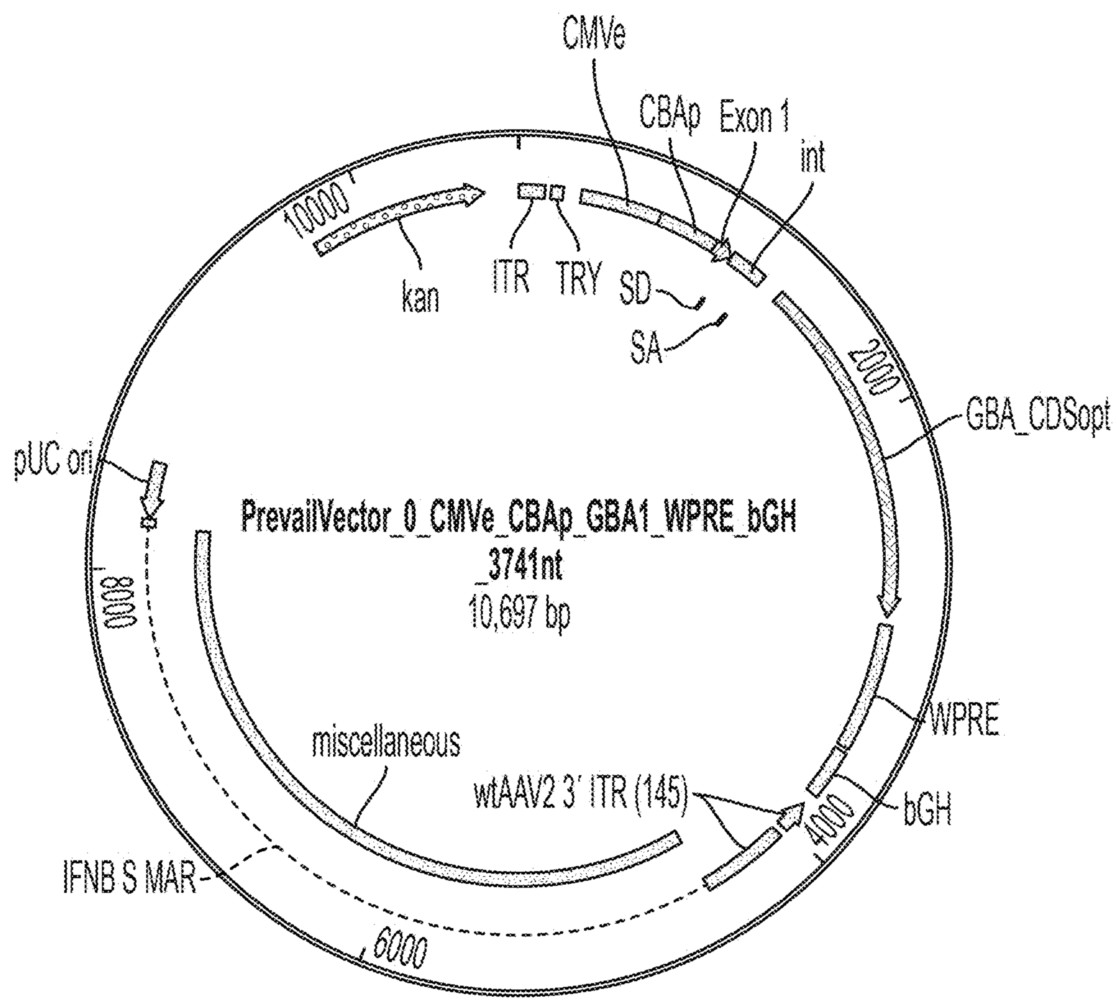
FIG. 1 is a schematic depicting one embodiment of a vector comprising an expression construct encoding Gcase (e.g., GBA1 or a portion thereof).
Figure 2:
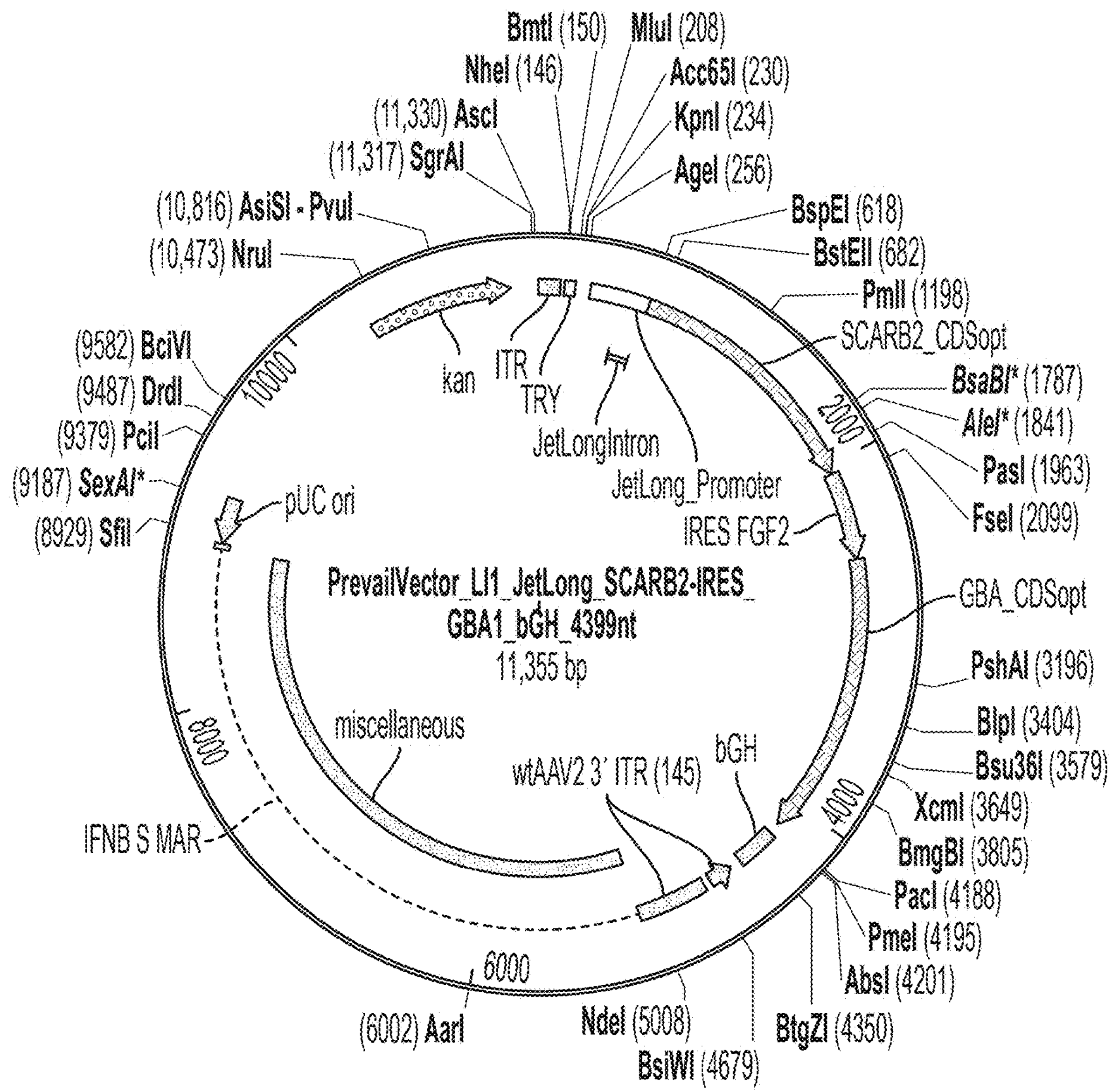
FIG. 2 is a schematic depicting one embodiment of a vector comprising an expression construct encoding Gcase (e.g., GBA1 or a portion thereof) and LIMP2 (SCARB2) or a portion thereof. The coding sequences of Gcase and LIMP2 are separated by an internal ribosomal entry site (IRES).
Figure 3:
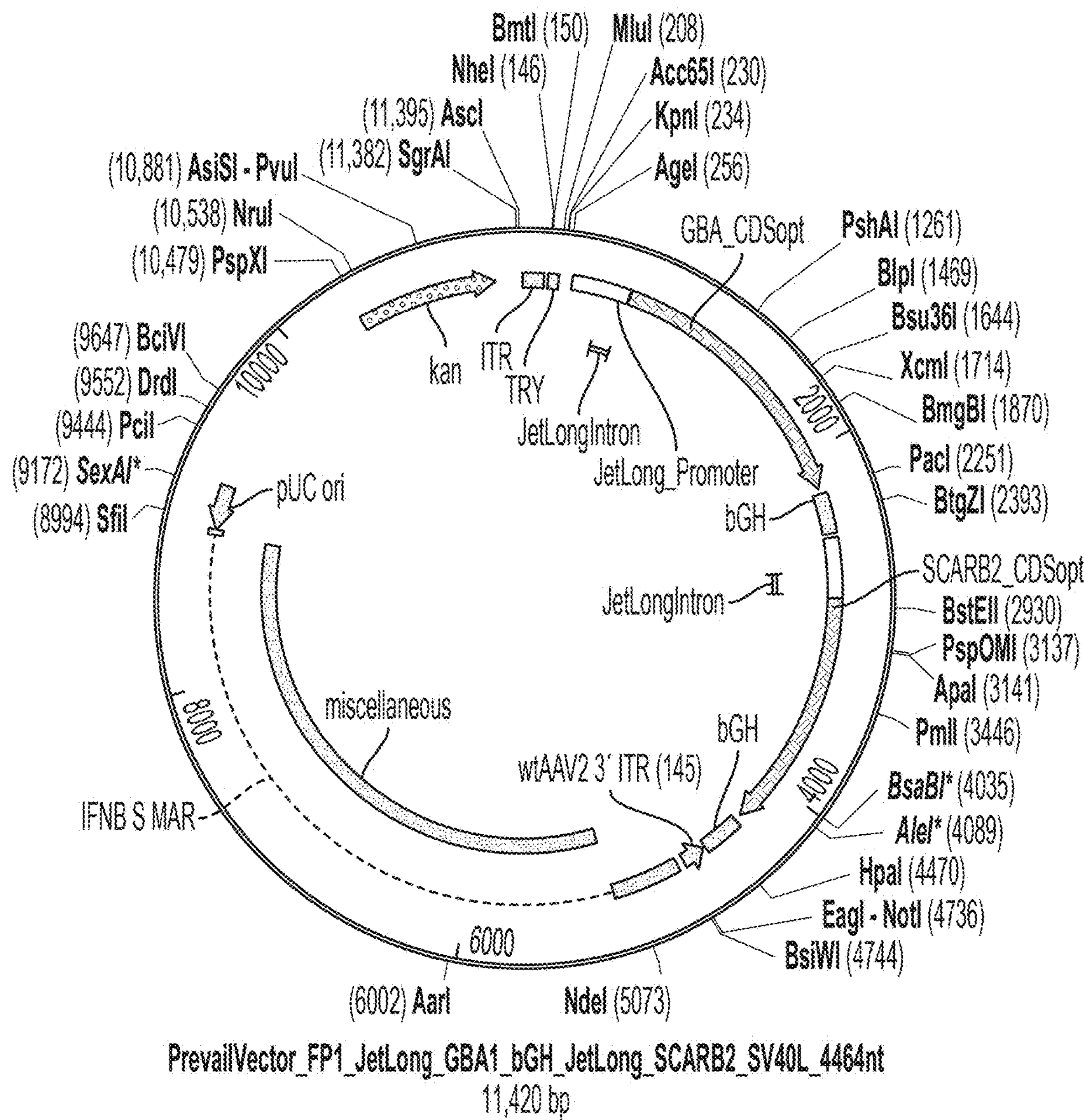
FIG. 3 is a schematic depicting one embodiment of a vector comprising an expression construct encoding Gcase (e.g., GBA1 or a portion thereof) and LIMP2 (SCARB2) or a portion thereof. Expression of the coding sequences of Gcase and LIMP2 are each driven by a separate promoter.

The disclosure is based, in part, on compositions and methods for expression of combinations of certain gene products (e.g., gene products associated with CNS disease) in a subject. A gene product can be a protein, a fragment (e.g., portion) of a protein, an interfering nucleic acid that inhibits a CNS disease-associated gene, etc. In some embodiments, a gene product is a protein or a protein fragment encoded by a CNS disease-associated gene. In some embodiments, a gene product is an interfering nucleic acid (e.g., shRNA, siRNA, miRNA, amiRNA, etc.) that inhibits a CNS disease-associated gene.

A CNS disease-associated gene refers to a gene encoding a gene product that is genetically, biochemically or functionally associated with a CNS disease, such as FTD (frontotemporal dementia) or PD (Parkinson's disease). For example, individuals having a pathogenic mutation in the GRN gene (which encodes the protein PGRN) have an increased risk of developing FTD compared to individuals that do not have a mutation in GRN. Similarly, individuals having mutations in the GBA1 gene (which encodes the protein Gcase), have been observed to be have an increased risk of developing PD compared to individuals that do not have a mutation in GBA1 In another example, PD is associated with accumulation of protein aggregates comprising α-Synuclein (α-Syn) protein; accordingly, SNCA (which encodes α-Syn) is a PD-associated gene. In some embodiments, an expression cassette described herein encodes a wild-type or non-mutant form of a CNS disease-associated gene (or coding sequence thereof). Examples of CNS disease-associated genes are listed in Table 1.

TABLE 1

Examples of CNS disease-associated genes

| Name | Gene | Function | NCBI Accession No. |
|---|---|---|---|
| Lysosome membrane protein 2 | SCARB2/LIMP2 | lysosomal receptor for glucosylceramidase (GBA targeting) | NP_005497.1 (Isoform 1), NP_001191184.1 (Isoform 2) |
| Prosaposin | PSAP | precursor for saposins A, B, C, and D, which localize to the lysosomal compartment and facilitate the catabolism of glycosphingolipids with short oligosaccharide groups | AAH01503.1, AAH07612.1, AAH04275.1, AAA60303.1 |
| beta-Glucocerebrosidase | GBA1 | cleaves the beta-glucosidic linkage of glucocerebroside | NP_001005742.1 (Isoform 1), NP_001165282.1 (Isoform 2), NP_001165283.1 (Isoform 3) |
| Non-lysosomal Glucosylceramidase | GBA2 | catalyzes the conversion of glucosylceramide to free glucose and ceramide | NP_065995.1 (Isoform 1), NP_001317589.1 (Isoform 2) |
| Galactosylceramidase | GALC | removes galactose from ceramide derivatives | EAW81359.1 (Isoform CRA_a), EAW81360.1 (Isoform CRA_b), EAW81362.1 (Isoform CRA_c) |
| Sphingomyelin phosphodiesterase 1 | SMPDI | converts sphingomyelin to ceramide | EAW68726.1 (Isoform CRA_a), EAW68727.1 (Isoform CRA_b), EAW68728.1 (Isoform CRA_c), EAW68729.1 (Isoform CRA_d) |

TABLE 1-continued

| Examples of CNS disease-associated genes | | | |
|---|---|---|---|
| Name | Gene | Function | NCBI Accession No. |
| Cathepsin B | CTSB | thiol protease believed to participate in intracellular degradation and turnover of proteins; also implicated in tumor invasion and metastasis | AAC37547.1, AAH95408.1, AAH10240.1 |
| RAB7, member RAS oncogene family-like 1 | RAB7L1 | regulates vesicular transport | AAH02585.1 |
| Vacuolar protein sorting-associated protein 35 | VPS35 | component of retromer cargo-selective complex | NP_060676.2 |
| GTP cyclohydrolase 1 | GCH1 | responsible for hydrolysis of guanosine triphosphate to form 7.8-dihydroneopterin triphosphate | AAH25415.1 |
| Interleukin 34 | IL34 | increases growth or survival of monocytes; elicits activity by binding the Colony stimulating factor 1 receptor | AAH29804.1 |
| Triggering receptor expressed on myeloid cells 2 | TREM2 | forms a receptor signaling complex with the TYRO protein tyrosine kinase binding protein; functions in immune response and may be involved in chronic inflammation | AAF69824.1 |
| Progranulin | PGRN | plays a role in development, inflammation, cell proliferation and protein homeostasis | NP_002087.1 |

In addition to Gaucher disease patients (who possess mutations in both chromosomal alleles of GBA1 gene), patients with mutations in only one allele of GBA1 are at highly increased risk of Parkinson's disease (PD). The severity of PD symptoms—which include gait difficulty, a tremor at rest, rigidity, and often depression, sleep difficulties, and cognitive decline—correlate with the degree of enzyme activity reduction. Thus, Gaucher disease patients have the most severe course, whereas patient with a single mild mutation in GBA1 typically have a more benign course. Mutation carriers are also at high risk of other PD-related disorders, including Lewy Body Dementia, characterized by executive dysfunction, psychosis, and a PD-like movement disorder, and multi-system atrophy, with characteristic motor and cognitive impairments. No therapies exist that alter the inexorable course of these disorders.

Deficits in enzymes such as Gcase (e.g., the gene product of GBA1 gene), as well as common variants in many genes implicated in lysosome function or trafficking of macromolecules to the lysosome (e.g., Lysosomal Membrane Protein 1 (LIMP), also referred to as SCARB2), have been associated with increased PD risk and/or risk of Gaucher disease (e.g., neuronopathic Gaucher disease, such as Type 2 Gaucher disease or Type 3 Gaucher disease). The disclosure is based, in part, on expression constructs (e.g., vectors) encoding one or more genes, for example Gcase, GBA2, prosaposin, progranulin (PGRN), LIMP2, GALC, CTSB, SMPD1, GCH1, RAB7, VPS35, IL-34, TREM2, TMEM106B, or a combination of any of the foregoing (or portions thereof), associated with central nervous system (CNS) diseases, for example Gaucher disease, PD, etc. In some embodiments, combinations of gene products described herein act together (e.g., synergistically) to reduce one or more signs and symptoms of a CNS disease when expressed in a subject.

Accordingly, in some aspects, the disclosure provides an isolated nucleic acid comprising an expression construct encoding a Gcase (e.g., the gene product of GBA1 gene). In some embodiments, the isolated nucleic acid comprises a Gcase-encoding sequence that has been codon optimized (e.g., codon optimized for expression in mammalian cells, for example human cells). In some embodiments, the nucleic acid sequence encoding the Gcase encodes a protein comprising an amino acid sequence as set forth in SEQ ID NO: 14 (e.g., as set forth in NCBI Reference Sequence NP 000148.2). In some embodiments, the isolated nucleic acid comprises the sequence set forth in SEQ ID NO: 15. In some embodiments the expression construct comprises adeno-associated virus (AAV) inverted terminal repeats (ITRs), for example AAV ITRs flanking the nucleic acid sequence encoding the Gcase protein.

In some aspects, the disclosure provides an isolated nucleic acid comprising an expression construct encoding Prosaposin (e.g., the gene product of PSAP gene). In some embodiments, the isolated nucleic acid comprises a prosaposin-encoding sequence that has been codon optimized (e.g., codon optimized for expression in mammalian cells, for example human cells). In some embodiments, the nucleic acid sequence encoding the prosaposin encodes a protein comprising an amino acid sequence as set forth in SEQ ID NO: 16 (e.g., as set forth in NCBI Reference Sequence NP 002769.1). In some embodiments, the isolated nucleic acid comprises the sequence set forth in SEQ ID NO: 17. In some embodiments the expression construct comprises adeno-associated virus (AAV) inverted terminal repeats (ITRs), for example AAV ITRs flanking the nucleic acid sequence encoding the prosaposin protein.

In some aspects, the disclosure provides an isolated nucleic acid comprising an expression construct encoding LIMP2/SCARB2 (e.g., the gene product of SCARB2 gene). In some embodiments, the isolated nucleic acid comprises a SCARB2-encoding sequence that has been codon optimized (e.g., codon optimized for expression in mammalian cells, for example human cells). In some embodiments, the nucleic acid sequence encoding the LIMP2/SCARB2 encodes a protein comprising an amino acid sequence as set forth in SEQ ID NO: 18 (e.g., as set forth in NCBI Reference Sequence NP 005497.1). In some embodiments, the isolated nucleic acid comprises the sequence set forth in SEQ ID NO: 29. In some embodiments the expression construct comprises adeno-associated virus (AAV) inverted terminal repeats (ITRs), for example AAV ITRs flanking the nucleic acid sequence encoding the SCARB2 protein.

In some aspects, the disclosure provides an isolated nucleic acid comprising an expression construct encoding GBA2 protein (e.g., the gene product of GBA2 gene). In some embodiments, the isolated nucleic acid comprises a GBA2-encoding sequence that has been codon optimized (e.g., codon optimized for expression in mammalian cells, for example human cells). In some embodiments, the nucleic acid sequence encoding the GBA2 encodes a protein comprising an amino acid sequence as set forth in SEQ ID NO: 30 (e.g., as set forth in NCBI Reference Sequence NP 065995.1). In some embodiments, the isolated nucleic acid comprises the sequence set forth in SEQ ID NO: 31. In some embodiments the expression construct comprises adeno-associated virus (AAV) inverted terminal repeats (ITRs), for example AAV ITRs flanking the nucleic acid sequence encoding the GBA2 protein.

In some aspects, the disclosure provides an isolated nucleic acid comprising an expression construct encoding GALC protein (e.g., the gene product of GALC gene). In some embodiments, the isolated nucleic acid comprises a GALC-encoding sequence that has been codon optimized (e.g., codon optimized for expression in mammalian cells, for example human cells). In some embodiments, the nucleic acid sequence encoding the GALC encodes a protein comprising an amino acid sequence as set forth in SEQ ID NO: 33 (e.g., as set forth in NCBI Reference Sequence NP 000144.2). In some embodiments, the isolated nucleic acid comprises the sequence set forth in SEQ ID NO: 34. In some embodiments the expression construct comprises adeno-associated virus (AAV) inverted terminal repeats (ITRs), for example AAV ITRs flanking the nucleic acid sequence encoding the GALC protein.

In some aspects, the disclosure provides an isolated nucleic acid comprising an expression construct encoding CTSB protein (e.g., the gene product of CTSB gene). In some embodiments, the isolated nucleic acid comprises a CTSB-encoding sequence that has been codon optimized (e.g., codon optimized for expression in mammalian cells, for example human cells). In some embodiments, the nucleic acid sequence encoding the CTSB encodes a protein comprising an amino acid sequence as set forth in SEQ ID NO: 35 (e.g., as set forth in NCBI Reference Sequence NP 001899.1). In some embodiments, the isolated nucleic acid comprises the sequence set forth in SEQ ID NO: 36. In some embodiments the expression construct comprises adeno-associated virus (AAV) inverted terminal repeats (ITRs), for example AAV ITRs flanking the nucleic acid sequence encoding the CTSB protein.

In some aspects, the disclosure provides an isolated nucleic acid comprising an expression construct encoding SMPD1 protein (e.g., the gene product of SMPD1 gene). In some embodiments, the isolated nucleic acid comprises a SMPD1-encoding sequence that has been codon optimized (e.g., codon optimized for expression in mammalian cells, for example human cells). In some embodiments, the nucleic acid sequence encoding the SMPD1 encodes a protein comprising an amino acid sequence as set forth in SEQ ID NO: 37 (e.g., as set forth in NCBI Reference Sequence NP_000534.3). In some embodiments, the isolated nucleic acid comprises the sequence set forth in SEQ ID NO: 38. In some embodiments the expression construct comprises adeno-associated virus (AAV) inverted terminal repeats (ITRs), for example AAV ITRs flanking the nucleic acid sequence encoding the SMPD1 protein.

In some aspects, the disclosure provides an isolated nucleic acid comprising an expression construct encoding GCH1 protein (e.g., the gene product of GCH1 gene). In some embodiments, the isolated nucleic acid comprises a GCH1-encoding sequence that has been codon optimized (e.g., codon optimized for expression in mammalian cells, for example human cells). In some embodiments, the nucleic acid sequence encoding the GCH1 encodes a protein comprising an amino acid sequence as set forth in SEQ ID NO: 45 (e.g., as set forth in NCBI Reference Sequence NP_000534.3). In some embodiments, the isolated nucleic acid comprises the sequence set forth in SEQ ID NO: 46. In some embodiments the expression construct comprises adeno-associated virus (AAV) inverted terminal repeats (ITRs), for example AAV ITRs flanking the nucleic acid sequence encoding the GCH1 protein.

In some aspects, the disclosure provides an isolated nucleic acid comprising an expression construct encoding RAB7L protein (e.g., the gene product of RAB7L gene). In some embodiments, the isolated nucleic acid comprises a RAB7L-encoding sequence that has been codon optimized (e.g., codon optimized for expression in mammalian cells, for example human cells). In some embodiments, the nucleic acid sequence encoding the RAB7L encodes a protein comprising an amino acid sequence as set forth in SEQ ID NO: 47 (e.g., as set forth in NCBI Reference Sequence NP_003920.1). In some embodiments, the isolated nucleic acid comprises the sequence set forth in SEQ ID NO: 48. In some embodiments the expression construct comprises adeno-associated virus (AAV) inverted terminal repeats (ITRs), for example AAV ITRs flanking the nucleic acid sequence encoding the RAB7L protein.

In some aspects, the disclosure provides an isolated nucleic acid comprising an expression construct encoding VPS35 protein (e.g., the gene product of VPS35 gene). In some embodiments, the isolated nucleic acid comprises a VPS35-encoding sequence that has been codon optimized (e.g., codon optimized for expression in mammalian cells, for example human cells). In some embodiments, the nucleic acid sequence encoding the VPS35 encodes a protein comprising an amino acid sequence as set forth in SEQ ID NO: 49 (e.g., as set forth in NCBI Reference Sequence NP_060676.2). In some embodiments, the isolated nucleic acid comprises the sequence set forth in SEQ ID NO: 50. In some embodiments the expression construct comprises adeno-associated virus (AAV) inverted terminal repeats (ITRs), for example AAV ITRs flanking the nucleic acid sequence encoding the VPS35 protein.

In some aspects, the disclosure provides an isolated nucleic acid comprising an expression construct encoding IL-34 protein (e.g., the gene product of IL34 gene). In some embodiments, the isolated nucleic acid comprises a IL-34-encoding sequence that has been codon optimized (e.g., codon optimized for expression in mammalian cells, for example human cells). In some embodiments, the nucleic acid sequence encoding the IL-34 encodes a protein comprising an amino acid sequence as set forth in SEQ ID NO: 55 (e.g., as set forth in NCBI Reference Sequence NP_689669.2). In some embodiments, the isolated nucleic acid comprises the sequence set forth in SEQ ID NO: 56. In some embodiments the expression construct comprises adeno-associated virus (AAV) inverted terminal repeats (ITRs), for example AAV ITRs flanking the nucleic acid sequence encoding the IL-34 protein.

In some aspects, the disclosure provides an isolated nucleic acid comprising an expression construct encoding TREM2 protein (e.g., the gene product of TREMgene). In some embodiments, the isolated nucleic acid comprises a TREM2-encoding sequence that has been codon optimized (e.g., codon optimized for expression in mammalian cells, for example human cells). In some embodiments, the nucleic acid sequence encoding the TREM2 encodes a protein comprising an amino acid sequence as set forth in SEQ ID NO: 57 (e.g., as set forth in NCBI Reference Sequence NP_061838.1). In some embodiments, the isolated nucleic acid comprises the sequence set forth in SEQ ID NO: 58. In some embodiments the expression construct comprises adeno-associated virus (AAV) inverted terminal repeats (ITRs), for example AAV ITRs flanking the nucleic acid sequence encoding the TREM2 protein.

In some aspects, the disclosure provides an isolated nucleic acid comprising an expression construct encoding TMEM106B protein (e.g., the gene product of TMEM106B gene). In some embodiments, the isolated nucleic acid comprises a TMEM106B-encoding sequence that has been codon optimized (e.g., codon optimized for expression in mammalian cells, for example human cells). In some embodiments, the nucleic acid sequence encoding the TMEM106B encodes a protein comprising an amino acid sequence as set forth in SEQ ID NO: 63 (e.g., as set forth in NCBI Reference Sequence NP_060844.2). In some embodiments, the isolated nucleic acid comprises the sequence set forth in SEQ ID NO: 64. In some embodiments the expression construct comprises adeno-associated virus (AAV) inverted terminal repeats (ITRs), for example AAV ITRs flanking the nucleic acid sequence encoding the TMEM106B protein.

In some aspects, the disclosure provides an isolated nucleic acid comprising an expression construct encoding progranulin (e.g., the gene product of PGRN gene). In some embodiments, the isolated nucleic acid comprises a prosaposin-encoding sequence that has been codon optimized (e.g., codon optimized for expression in mammalian cells, for example human cells). In some embodiments, the nucleic acid sequence encoding the progranulin (PGRN) encodes a protein comprising an amino acid sequence as set forth in SEQ ID NO: 67 (e.g., as set forth in NCBI Reference Sequence NP_002078.1). In some embodiments, the isolated nucleic acid comprises the sequence set forth in SEQ ID NO: 68. In some embodiments the expression construct comprises adeno-associated virus (AAV) inverted terminal repeats (ITRs), for example AAV ITRs flanking the nucleic acid sequence encoding the prosaposin protein.

In some aspects, the disclosure provides an isolated nucleic acid comprising an expression construct encoding a first gene product and a second gene product, wherein each gene product independently is selected from the gene products, or portions thereof, set forth in Table 1.

In some embodiments, a first gene product or a second gene product is a Gcase protein, or a portion thereof. In some embodiments, a first gene product is a Gcase protein and a second gene product is selected from GBA2, prosaposin, progranulin, LIMP2, GALC, CTSB, SMPD1, GCH1, RAB7, VPS35, IL-34, TREM2, and TMEM106B.

In some embodiments, an expression construct encodes (e.g., alone or in addition to another gene product) an interfering nucleic acid (e.g., shRNA, miRNA, dsRNA, etc.). In some embodiments, an interfering nucleic acid inhibits expression of α-Synuclein (α-Synuclein). In some embodiments, an interfering nucleic acid that targets α-Synuclein comprises a sequence set forth in any one of SEQ ID NOs: 20-25. In some embodiments, an interfering nucleic acid that targets α-Synuclein binds to (e.g., hybridizes with) a sequence set forth in any one of SEQ ID NO: 20-25.

In some embodiments, an interfering nucleic acid inhibits expression of TMEM106B. In some embodiments, an interfering nucleic acid that targets TMEM106B comprises a sequence set forth in SEQ ID NO: 64 or 65. In some embodiments, an interfering nucleic acid that targets TMEM106B binds to (e.g., hybridizes with) a sequence set forth in SEQ ID NO: 64 or 65.

In some embodiments, an expression construct further comprises one or more promoters. In some embodiments, a promoter is a chicken-beta actin (CBA) promoter, a CAG promoter, a CD68 promoter, or a JeT promoter. In some embodiments, a promoter is a RNA pol II promoter (or an RNA pol III promoter (e.g., U6, etc.).

In some embodiments, an expression construct further comprises an internal ribosomal entry site (IRES). In some embodiments, an IRES is located between a first gene product and a second gene product.

In some embodiments, an expression construct further comprises a self-cleaving peptide coding sequence. In some embodiments, a self-cleaving peptide is a T2A peptide.

In some embodiments, an expression construct comprises two adeno-associated virus (AAV) inverted terminal repeat (ITR) sequences. In some embodiments, ITR sequences flank a first gene product and a second gene product (e.g., are arranged as follows from 5'-end to 3'-end: ITR-first gene product-second gene product-ITR). In some embodiments, one of the ITR sequences of an isolated nucleic acid lacks a functional terminal resolution site (trs). For example, in some embodiments, one of the ITRs is a ΔITR.

The disclosure relates, in some aspects, to rAAV vectors comprising an ITR having a modified "D" region (e.g., a D sequence that is modified relative to wild-type AAV2 ITR, SEQ ID NO: 29). In some embodiments, the ITR having the modified D region is the 5' ITR of the rAAV vector. In some embodiments, a modified "D" region comprises an "S"

sequence, for example as set forth in SEQ ID NO: 26. In some embodiments, the ITR having the modified "D" region is the 3' ITR of the rAAV vector. In some embodiments, a modified "D" region comprises a 3'ITR in which the "D" region is positioned at the 3' end of the ITR (e.g., on the outside or terminal end of the ITR relative to the transgene insert of the vector). In some embodiments, a modified "D" region comprises a sequence as set forth in SEQ ID NO: 26 or 27.

In some embodiments, an isolated nucleic acid (e.g., an rAAV vector) comprises a TRY region. In some embodiments, a TRY region comprises the sequence set forth in SEQ ID NO: 28.

In some embodiments, an isolated nucleic acid described by the disclosure comprises or consists of, or encodes a peptide having, the sequence set forth in any one of SEQ ID NOs: 1-91.

In some aspects, the disclosure provides a vector comprising an isolated nucleic acid as described by the disclosure. In some embodiments, a vector is a plasmid, or a viral vector. In some embodiments, a viral vector is a recombinant AAV (rAAV) vector or a Baculovirus vector. In some embodiments, an rAAV vector is single-stranded (e.g., single-stranded DNA).

In some embodiments, the disclosure provides a host cell comprising an isolated nucleic acid as described by the disclosure or a vector as described by the disclosure.

In some embodiments, the disclosure provides a recombinant adeno-associated virus (rAAV) comprising a capsid protein and an isolated nucleic acid or a vector as described by the disclosure.

In some embodiments, a capsid protein is capable of crossing the blood-brain barrier, for example an AAV9 capsid protein or an AAVrh.10 capsid protein. In some embodiments, an rAAV transduces neuronal cells and non-neuronal cells of the central nervous system (CNS).

In some aspects, the disclosure provides a method for treating a subject having or suspected of having or suspected of having a central nervous system (CNS) disease, the method comprising administering to the subject a composition (e.g., a composition comprising an isolated nucleic acid or a vector or a rAAV) as described by the disclosure. In some embodiments, the CNS disease is a neurodegenerative disease, such as a neurodegenerative disease listed in Table 12. In some embodiments, the CNS disease is a synucleinopathy, such as a synucleinopathy listed in Table 13. In some embodiments, the CNS disease is a tauopathy, such as a tauopathy listed in Table 14. In some embodiments, the CNS disease is a lysosomal storage disease, such as a lysosomal storage disease listed in Table 15. In some embodiments, the lysosomal storage disease is neuronopathic Gaucher disease, such as Type 2 Gaucher disease or Type 3 Gaucher disease.

In some embodiments, the disclosure provides a method for treating a subject having or suspected of having Parkinson's disease, the method comprising administering to the subject a composition (e.g., a composition comprising an isolated nucleic acid or a vector or a rAAV) as described by the disclosure.

In some embodiments, the disclosure provides a method for treating a subject having or suspected of having frontotemporal dementia (FTD), FTD with GRN mutation, FTD with tau mutation, FTD with C9orf72 mutation, ceroid lipofuscinosis, Parkinson's disease, Alzheimer's disease, corticobasal degeneration, motor neuron disease, or Gaucher disease, the method comprising administering to the subject an rAAV encoding Progranulin (PGRN), wherein the PGRN is encoded by the nucleic acid sequence in SEQ ID NO:68; and wherein the rAAV comprises a capsid protein having an AAV9 serotype.

In some embodiments, the disclosure provides a method for treating a subject having or suspected of having FTD with a GRN mutation, the method comprising administering to the subject an rAAV encoding Progranulin (PGRN), wherein the PGRN is encoded by the nucleic acid sequence in SEQ ID NO:68; and wherein the rAAV comprises a capsid protein having an AAV9 serotype. In some embodiments, the rAAV is administered to a subject at a dose of about $3.5\times10^{13}$ vector genomes (vg), about $7.0\times10^{13}$ vg, or about $1.4\times10^{14}$ vg. In some embodiments, the rAAV is administered via an injection into the cisterna magna.

In some embodiments, a composition comprises a nucleic acid (e.g., an rAAV genome, for example encapsidated by AAV capsid proteins) that encodes two or more gene products (e.g., CNS disease-associated gene products), for example 2, 3, 4, 5, or more gene products described in this application. In some embodiments, a composition comprises two or more (e.g., 2, 3, 4, 5, or more) different nucleic acids (e.g., two or more rAAV genomes, for example separately encapsidated by AAV capsid proteins), each encoding one or more different gene products. In some embodiments, two or more different compositions are administered to a subject, each composition comprising one or more nucleic acids encoding different gene products. In some embodiments, different gene products are operably linked to the same promoter type (e.g., the same promoter). In some embodiments, different gene products are operably linked to different promoters.

Isolated Nucleic Acids and Vectors

An isolated nucleic acid may be DNA or RNA. The disclosure provides, in some aspects, isolated nucleic acids (e.g., rAAV vectors) comprising an expression construct encoding one or more PD-associated genes, for example a Gcase (e.g., the gene product of GBA1 gene) or a portion thereof. Gcase, also referred to as (3-glucocerebrosidase or GBA, refers to a lysosomal protein that cleaves the beta-glucosidic linkage of the chemical glucocerebroside, an intermediate in glycolipid metabolism. In humans, Gcase is encoded by the GBA1 gene, located on chromosome 1. In some embodiments, GBA1 encodes a peptide that is represented by NCBI Reference Sequence NP_000148.2 (SEQ ID NO: 14). In some embodiments, an isolated nucleic acid comprises a Gcase-encoding sequence that has been codon optimized (e.g., codon optimized for expression in mammalian cells, for example human cells), such as the sequence set forth in SEQ ID NO: 15.

In some aspects, the disclosure provides an isolated nucleic acid comprising an expression construct encoding Prosaposin (e.g., the gene product of PSAP gene). Prosaposin is a precursor glycoprotein for sphingolipid activator proteins (saposins) A, B, C, and D, which facilitate the catabolism of glycosphingolipids with short oligosaccharide groups. In humans, the PSAP gene is located on chromosome 10. In some embodiments, PSAP encodes a peptide that is represented by NCBI Reference Sequence NP_002769.1 (e.g., SEQ ID NO: 16). In some embodiments, an isolated nucleic acid comprises a prosaposin-encoding sequence that has been codon optimized (e.g., codon optimized for expression in mammalian cells, for example human cells), such as the sequence set forth in SEQ ID NO: 17.

Aspects of the disclosure relate to an isolated nucleic acid comprising an expression construct encoding LIMP2/SCARB2 (e.g., the gene product of SCARB2 gene).

SCARB2 refers to a membrane protein that regulates lysosomal and endosomal transport within a cell. In humans, SCARB2 gene is located on chromosome 4. In some embodiments, the SCARB2 gene encodes a peptide that is represented by NCBI Reference Sequence NP_005497.1 (SEQ ID NO: 18). In some embodiments, an isolated nucleic acid comprises the sequence set forth in SEQ ID NO: 19. In some embodiments the isolated nucleic acid comprises a SCARB2-encoding sequence that has been codon optimized.

Aspects of the disclosure relate to an isolated nucleic acid comprising an expression construct encoding GBA2 protein (e.g., the gene product of GBA2 gene). GBA2 protein refers to non-lysosomal glucosylceramidase. In humans, GBA2 gene is located on chromosome 9. In some embodiments, the GBA2 gene encodes a peptide that is represented by NCBI Reference Sequence NP_065995.1 (SEQ ID NO: 30). In some embodiments, an isolated nucleic acid comprises the sequence set forth in SEQ ID NO: 31. In some embodiments the isolated nucleic acid comprises a GBA2-encoding sequence that has been codon optimized.

Aspects of the disclosure relate to an isolated nucleic acid comprising an expression construct encoding GALC protein (e.g., the gene product of GALC gene). GALC protein refers to galactosylceramidase (or galactocerebrosidase), which is an enzyme that hydrolyzes galactose ester bonds of galactocerebroside, galactosylsphingosine, lactosylceramide, and monogalactosyldiglyceride. In humans, GALC gene is located on chromosome 14. In some embodiments, the GALC gene encodes a peptide that is represented by NCBI Reference Sequence NP_000144.2 (SEQ ID NO: 33). In some embodiments, an isolated nucleic acid comprises the sequence set forth in SEQ ID NO: 34. In some embodiments the isolated nucleic acid comprises a GALC-encoding sequence that has been codon optimized.

Aspects of the disclosure relate to an isolated nucleic acid comprising an expression construct encoding CTSB protein (e.g., the gene product of CTSB gene). CTSB protein refers to cathepsin B, which is a lysosomal cysteine protease that plays an important role in intracellular proteolysis. In humans, CTSB gene is located on chromosome 8. In some embodiments, the CTSB gene encodes a peptide that is represented by NCBI Reference Sequence NP_001899.1 (SEQ ID NO: 35). In some embodiments, an isolated nucleic acid comprises the sequence set forth in SEQ ID NO: 36. In some embodiments the isolated nucleic acid comprises a CTSB-encoding sequence that has been codon optimized.

Aspects of the disclosure relate to an isolated nucleic acid comprising an expression construct encoding SMPD1 protein (e.g., the gene product of SMPD1 gene). SMPD1 protein refers to sphingomyelin phosphodiesterase 1, which is a hydrolase enzyme that is involved in sphingolipid metabolism. In humans, SMPD1 gene is located on chromosome 11. In some embodiments, the SMPD1 gene encodes a peptide that is represented by NCBI Reference Sequence NP_000534.3 (SEQ ID NO: 37). In some embodiments, an isolated nucleic acid comprises the sequence set forth in SEQ ID NO: 38. In some embodiments the isolated nucleic acid comprises a SMPD1-encoding sequence that has been codon optimized.

Aspects of the disclosure relate to an isolated nucleic acid comprising an expression construct encoding GCH1 protein (e.g., the gene product of GCH1 gene). GCH1 protein refers to GTP cyclohydrolase I, which is a hydrolase enzyme that is part of the folate and biopterin biosynthesis pathways. In humans, GCH1 gene is located on chromosome 14. In some embodiments, the GCH1 gene encodes a peptide that is represented by NCBI Reference Sequence NP_000152.1 (SEQ ID NO: 45). In some embodiments, an isolated nucleic acid comprises the sequence set forth in SEQ ID NO: 46. In some embodiments the isolated nucleic acid comprises a GCH1-encoding sequence that has been codon optimized.

Aspects of the disclosure relate to an isolated nucleic acid comprising an expression construct encoding RAB7L protein (e.g., the gene product of RAB7L gene). RAB7L protein refers to RAB7, member RAS oncogene family-like 1, which is a GTP binding protein. In humans, RAB7L gene is located on chromosome 1. In some embodiments, the RAB7L gene encodes a peptide that is represented by NCBI Reference Sequence NP_003920.1 (SEQ ID NO: 47). In some embodiments, an isolated nucleic acid comprises the sequence set forth in SEQ ID NO: 48. In some embodiments the isolated nucleic acid comprises a RAB7L-encoding sequence that has been codon optimized.

Aspects of the disclosure relate to an isolated nucleic acid comprising an expression construct encoding VPS35 protein (e.g., the gene product of VPS35 gene). VPS35 protein refers to vacuolar protein sorting-associated protein 35, which is part of a protein complex involved in retrograde transport of proteins from endosomes to the trans-Golgi network. In humans, VPS35 gene is located on chromosome 16. In some embodiments, the VPS35 gene encodes a peptide that is represented by NCBI Reference Sequence NP_060676.2 (SEQ ID NO: 49). In some embodiments, an isolated nucleic acid comprises the sequence set forth in SEQ ID NO: 50. In some embodiments the isolated nucleic acid comprises a VPS35-encoding sequence that has been codon optimized.

Aspects of the disclosure relate to an isolated nucleic acid comprising an expression construct encoding IL-34 protein (e.g., the gene product of IL34 gene). IL-34 protein refers to interleukin 34, which is a cytokine that increases growth and survival of monocytes. In humans, IL34 gene is located on chromosome 16. In some embodiments, the IL34 gene encodes a peptide that is represented by NCBI Reference Sequence NP_689669.2 (SEQ ID NO: 55). In some embodiments, an isolated nucleic acid comprises the sequence set forth in SEQ ID NO: 56. In some embodiments the isolated nucleic acid comprises a IL-34-encoding sequence that has been codon optimized.

Aspects of the disclosure relate to an isolated nucleic acid comprising an expression construct encoding TREM2 protein (e.g., the gene product of TREM2 gene). TREM2 protein refers to triggering receptor expressed on myeloid cells 2, which is an immunoglobulin superfamily receptor found on myeloid cells. In humans, TREM2 gene is located on chromosome 6. In some embodiments, the TREM2 gene encodes a peptide that is represented by NCBI Reference Sequence NP_061838.1 (SEQ ID NO: 57). In some embodiments, the isolated nucleic acid comprises the sequence set forth in SEQ ID NO: 58. In some embodiments an isolated nucleic acid comprises a TREM2-encoding sequence that has been codon optimized.

Aspects of the disclosure relate to an isolated nucleic acid comprising an expression construct encoding TMEM106B protein (e.g., the gene product of TMEM106B gene). TMEM106B protein refers to transmembrane protein 106B, which is a protein involved in dendrite morphogenesis and regulation of lysosomal trafficking. In humans, TMEM106B gene is located on chromosome 7. In some embodiments, the TMEM106B gene encodes a peptide that is represented by NCBI Reference Sequence NP_060844.2 (SEQ ID NO: 62). In some embodiments, an isolated nucleic acid comprises the sequence set forth in SEQ ID NO: 63. In some embodiments the isolated nucleic acid comprises a TMEM106B-encoding sequence that has been codon optimized.

Aspects of the disclosure relate to an isolated nucleic acid comprising an expression construct encoding progranulin protein (e.g., the gene product of PGRN gene). PGRN protein refers to progranulin, which is a protein involved in development, inflammation, cell proliferation and protein homeostasis. In humans, the PGRN gene is located on chromosome 17. In some embodiments, the PGRN gene encodes a peptide that is represented by NCBI Reference Sequence NP_002078.1 (SEQ ID NO: 67). In some embodiments, an isolated nucleic acid comprises the sequence set forth in SEQ ID NO: 68. In some embodiments the isolated nucleic acid comprises a PGRN-encoding sequence that has been codon optimized. In some embodiments, the nucleic acid further comprises a chicken β-actin (CBA) promoter and a cytomegalovirus enhancer (CMVe).

In some aspects, the disclosure provides an automated Western blot immunoassay to quantify a PGRN protein level in a cerebrospinal fluid (CSF) sample. In some embodiments, the immunoassay is a capillary-based automated Western blot immunoassay platform, where all steps, such as protein separation, immunoprobing, washing, and detection by chemiluminescence, occur in a capillary cartridge. In some embodiments, a CSF sample is from a human or a non-human primate. In some aspects, the immunoassay allows detection of differences in PGRN protein levels in the presence of circulating antibody. In some aspects, the disclosure provides a method of quantifying a progranulin protein level in a CSF sample, the method comprising: (1) diluting the CSF sample (e.g., a 4-fold dilution); (2) loading the CSF sample; an anti-progranulin antibody; a secondary antibody that detects the anti-progranulin antibody, luminol, and peroxide into wells of a capillary cartridge; (3) loading the capillary cartridge into an automated Western blot immunoassay instrument; (4) using the automated Western blot immunoassay instrument to calculate one or more of: signal intensity, peak area, signal-to-noise ratio and total protein normalization parameters; and (5) quantifying a progranulin protein level in the CSF sample as the peak area of immunoreactivity to the anti-progranulin antibody. In some embodiments, the CSF sample is diluted in a master mix comprising dithiothreitol (DTT) and sample buffer. The master mix may further comprise other proprietary components. In some aspects, the anti-progranulin antibody detects human progranulin. In some embodiments, a progranulin protein level is quantified from the calculated parameters using software that controls the automated Western blot immunoassay instrument. In some embodiments, the software is Compass software for Simple Western™ (ProteinSimple, San Jose, CA).

In some embodiments, the disclosure provides a method of quantifying a progranulin protein level in a cerebrospinal fluid (CSF) sample, the method comprising: (1) diluting the CSF sample (e.g., a 4-fold dilution) in a master mix containing dithiothreitol (DTT) and sample buffer; (2) loading the diluted CSF sample, an anti-progranulin antibody; a secondary antibody that detects the anti-progranulin antibody, luminol, and peroxide into wells of a capillary cartridge; (3) loading the capillary cartridge into an automated Western blot immunoassay instrument; (4) using the automated Western blot immunoassay instrument to calculate signal intensity, peak area, and signal-to-noise ratio; and (5) quantifying a progranulin protein level in the CSF sample as the peak area of immunoreactivity to the anti-progranulin antibody.

In some aspects, the disclosure provides an isolated nucleic acid comprising an expression construct encoding a first gene product and a second gene product, wherein each gene product independently is selected from the gene products, or portions thereof, set forth in Table 1.

In some embodiments, an isolated nucleic acid or vector (e.g., rAAV vector) described by the disclosure comprises or consists of a sequence set forth in any one of SEQ ID NOs: 1-91. In some embodiments, an isolated nucleic acid or vector (e.g., rAAV vector) described by the disclosure comprises or consists of a sequence that is complementary (e.g., the complement of) a sequence set forth in any one of SEQ ID NOs: 1-91. In some embodiments, an isolated nucleic acid or vector (e.g., rAAV vector) described by the disclosure comprises or consists of a sequence that is a reverse complement of a sequence set forth in any one of SEQ ID NOs: 1-91. In some embodiments, an isolated nucleic acid or vector (e.g., rAAV vector) described by the disclosure comprises or consists of a portion of a sequence set forth in any one of SEQ ID NOs: 1-91. A portion may comprise at least 25%, 50%, 60%, 70%, 80%, 90%, 95%, or 99% of a sequence set forth in any one of SEQ ID NOs: 1-91. In some embodiments, a nucleic acid sequence described by the disclosure is a nucleic acid sense strand (e.g., 5' to 3' strand), or in the context of a viral sequences a plus (+) strand. In some embodiments, a nucleic acid sequence described by the disclosure is a nucleic acid antisense strand (e.g., 3' to 5' strand), or in the context of viral sequences a minus (−) strand.

In some embodiments, a gene product is encoded by a coding portion (e.g., a cDNA) of a naturally occurring gene. In some embodiments, a first gene product is a protein (or a fragment thereof) encoded by the GBA1 gene. In some embodiments, a gene product is a protein (or a fragment thereof) encoded by another gene listed in Table 1, for example the SCARB2/LIMP2 gene or the PSAP gene. However, the skilled artisan recognizes that the order of expression of a first gene product (e.g., Gcase) and a second gene product (e.g., LIMP2, etc.) can generally be reversed (e.g., LIMP2 is the first gene product and Gcase is the second gene product). In some embodiments, a gene product is a fragment (e.g., portion) of a gene listed in Table 1. A protein fragment may comprise about 50%, about 60%, about 70%, about 80% about 90% or about 99% of a protein encoded by the genes listed in Table 1. In some embodiments, a protein fragment comprises between 50% and 99.9% (e.g., any value between 50% and 99.9%) of a protein encoded by a gene listed in Table 1.

In some embodiments, an expression construct is monocistronic (e.g., the expression construct encodes a single fusion protein comprising a first gene product and a second gene product). In some embodiments, an expression construct is polycistronic (e.g., the expression construct encodes two distinct gene products, for example two different proteins or protein fragments).

A polycistronic expression vector may comprise a one or more (e.g., 1, 2, 3, 4, 5, or more) promoters. Any suitable promoter can be used, for example, a constitutive promoter, an inducible promoter, an endogenous promoter, a tissue-specific promoter (e.g., a CNS-specific promoter), etc. In some embodiments, a promoter is a chicken beta-actin promoter (CBA promoter), a CAG promoter (for example as described by Alexopoulou et al. (2008) *BMC Cell Biol.* 9:2; doi: 10.1186/1471-2121-9-2), a CD68 promoter, or a JeT promoter (for example as described by Tornoe et al. (2002) Gene 297 (1-2):21-32). In some embodiments, a promoter is operably-linked to a nucleic acid sequence encoding a first gene product, a second gene product, or a first gene product and a second gene product. In some embodiments, an expression cassette comprises one or more additional regulatory sequences, including but not limited to transcription factor binding sequences, intron splice sites, poly(A) addition sites, enhancer sequences, repressor binding sites, or any combination of the foregoing.

In some embodiments, a nucleic acid sequence encoding a first gene product and a nucleic acid sequence encoding a second gene product are separated by a nucleic acid sequence encoding an internal ribosomal entry site (IRES). Examples of IRES sites are described, for example, by Mokrejs et al. (2006) *Nucleic Acids Res.* 34 (Database issue):D125-30. In some embodiments, a nucleic acid sequence encoding a first gene product and a nucleic acid sequence encoding a second gene product are separated by a nucleic acid sequence encoding a self-cleaving peptide. Examples of self-cleaving peptides include but are not limited to T2A, P2A, E2A, F2A, BmCPV 2A, and BmIFV 2A, and those described by Liu et al. (2017) *Sci Rep.* 7: 2193. In some embodiments, the self-cleaving peptide is a T2A peptide.

Pathologically, disorders such as PD and Gaucher disease are associated with accumulation of protein aggregates composed largely of α-Synuclein (α-Syn) protein. Accordingly, in some embodiments, isolated nucleic acids described herein comprise an inhibitory nucleic acid that reduces or prevents expression of α-Syn protein. A sequence encoding an inhibitory nucleic acid may be placed in an untranslated region (e.g., intron, 5'UTR, 3'UTR, etc.) of the expression vector.

In some embodiments, an inhibitory nucleic acid is positioned in an intron of an expression construct, for example in an intron upstream of the sequence encoding a first gene product. An inhibitory nucleic acid can be a double stranded RNA (dsRNA), siRNA, shRNA, micro RNA (miRNA), artificial miRNA (amiRNA), or an RNA aptamer. Generally, an inhibitory nucleic acid binds to (e.g., hybridizes with) between about 6 and about 30 (e.g., any integer between 6 and 30, inclusive) contiguous nucleotides of a target RNA (e.g., mRNA). In some embodiments, the inhibitory nucleic acid molecule is an miRNA or an amiRNA, for example an miRNA that targets SNCA (the gene encoding α-Syn protein) or TMEM106B (e.g., the gene encoding TMEM106B protein). In some embodiments, the miRNA does not comprise any mismatches with the region of SNCA mRNA to which it hybridizes (e.g., the miRNA is "perfected"). In some embodiments, the inhibitory nucleic acid is an shRNA (e.g., an shRNA targeting SNCA or TMEM106B). In some embodiments, an inhibitory nucleic acid is an artificial miRNA (amiRNA) that includes a miR-155 scaffold and a SNCA or TMEM106B targeting sequence.

The skilled artisan recognizes that when referring to nucleic acid sequences comprising or encoding inhibitory nucleic acids (e.g., dsRNA, siRNA, miRNA, amiRNA, etc.) any one or more thymidine (T) nucleotides or uridine (U) nucleotides in a sequence provided herein may be replaced with any other nucleotide suitable for base pairing (e.g., via a Watson-Crick base pair) with an adenosine nucleotide. For example, T may be replaced with U, and U may be replaced with T.

An isolated nucleic acid as described herein may exist on its own, or as part of a vector. Generally, a vector can be a plasmid, cosmid, phagemid, bacterial artificial chromosome (BAC), or a viral vector (e.g., adenoviral vector, adeno-associated virus (AAV) vector, retroviral vector, baculoviral vector, etc.). In some embodiments, the vector is a plasmid (e.g., a plasmid comprising an isolated nucleic acid as described herein). In some embodiments, an rAAV vector is single-stranded (e.g., single-stranded DNA). In some embodiments, the vector is a recombinant AAV (rAAV) vector. In some embodiments, a vector is a Baculovirus vector (e.g., an *Autographa californica* nuclear polyhedrosis (AcNPV) vector).

Typically an rAAV vector (e.g., rAAV genome) comprises a transgene (e.g., an expression construct comprising one or more of each of the following: promoter, intron, enhancer sequence, protein coding sequence, inhibitory RNA coding sequence, polyA tail sequence, etc.) flanked by two AAV inverted terminal repeat (ITR) sequences. In some embodiments the transgene of an rAAV vector comprises an isolated nucleic acid as described by the disclosure. In some embodiments, each of the two ITR sequences of an rAAV vector is a full-length ITR (e.g., approximately 145 bp in length, and containing functional Rep binding site (RBS) and terminal resolution site (trs)). In some embodiments, one of the ITRs of an rAAV vector is truncated (e.g., shortened or not full-length). In some embodiments, a truncated ITR lacks a functional terminal resolution site (trs) and is used for production of self-complementary AAV vectors (scAAV vectors). In some embodiments, a truncated ITR is a ΔITR, for example as described by McCarty et al. (2003) *Gene Ther.* 10(26):2112-8.

Figure 20:
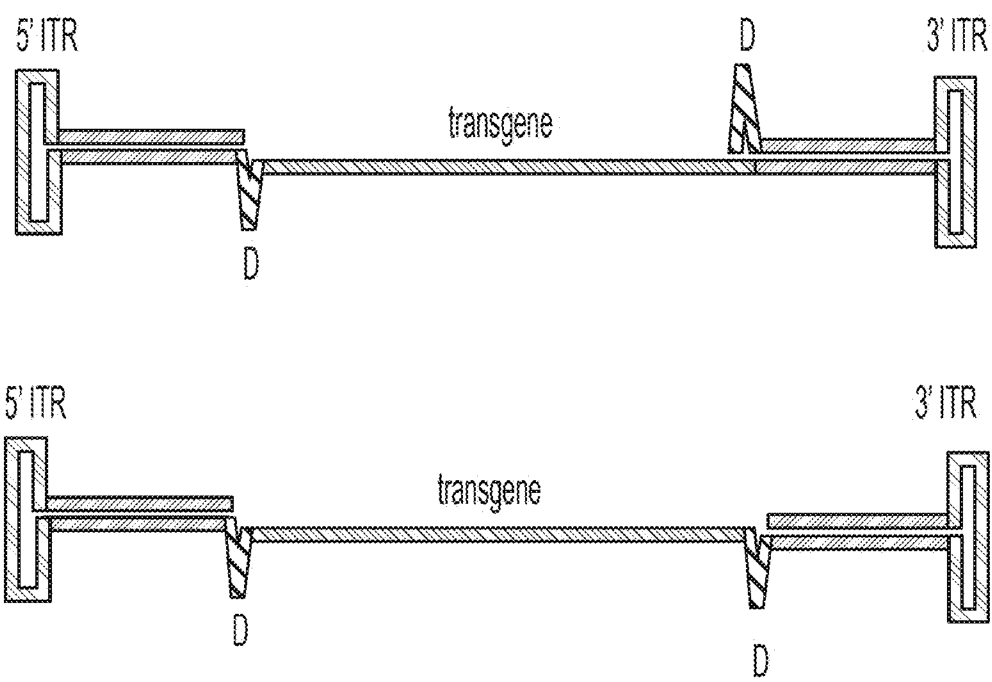
FIG. 20 is a schematic depicting an rAAV vectors comprising a "D" region located on the "outside" of the ITR (e.g., proximal to the terminus of the ITR relative to the transgene insert or expression construct) (top) and a wild-type rAAV vectors having ITRs on the "inside" of the vector (e.g., proximal to the transgene insert of the vector).
Figure 21:
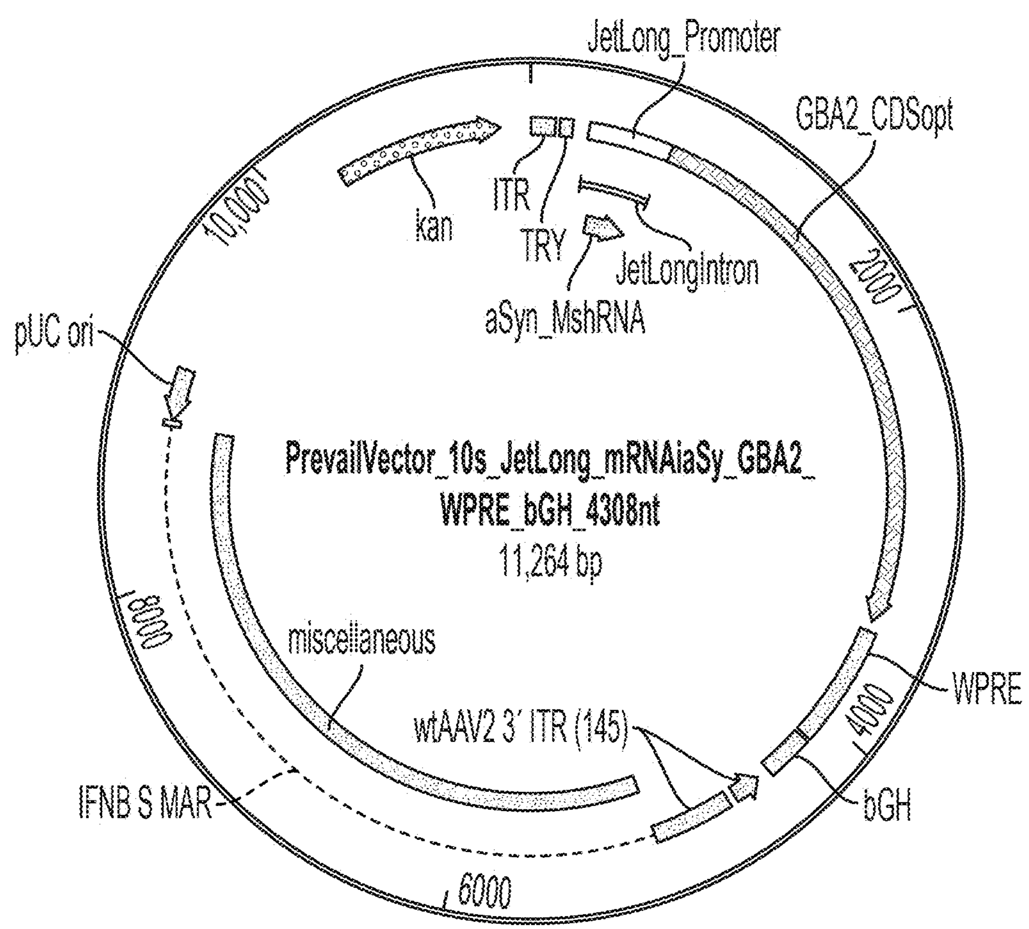
FIG. 21 a schematic depicting one embodiment of a vector comprising an expression construct encoding GBA2 or a portion thereof, and an interfering RNA for α-Syn.
Figure 22:
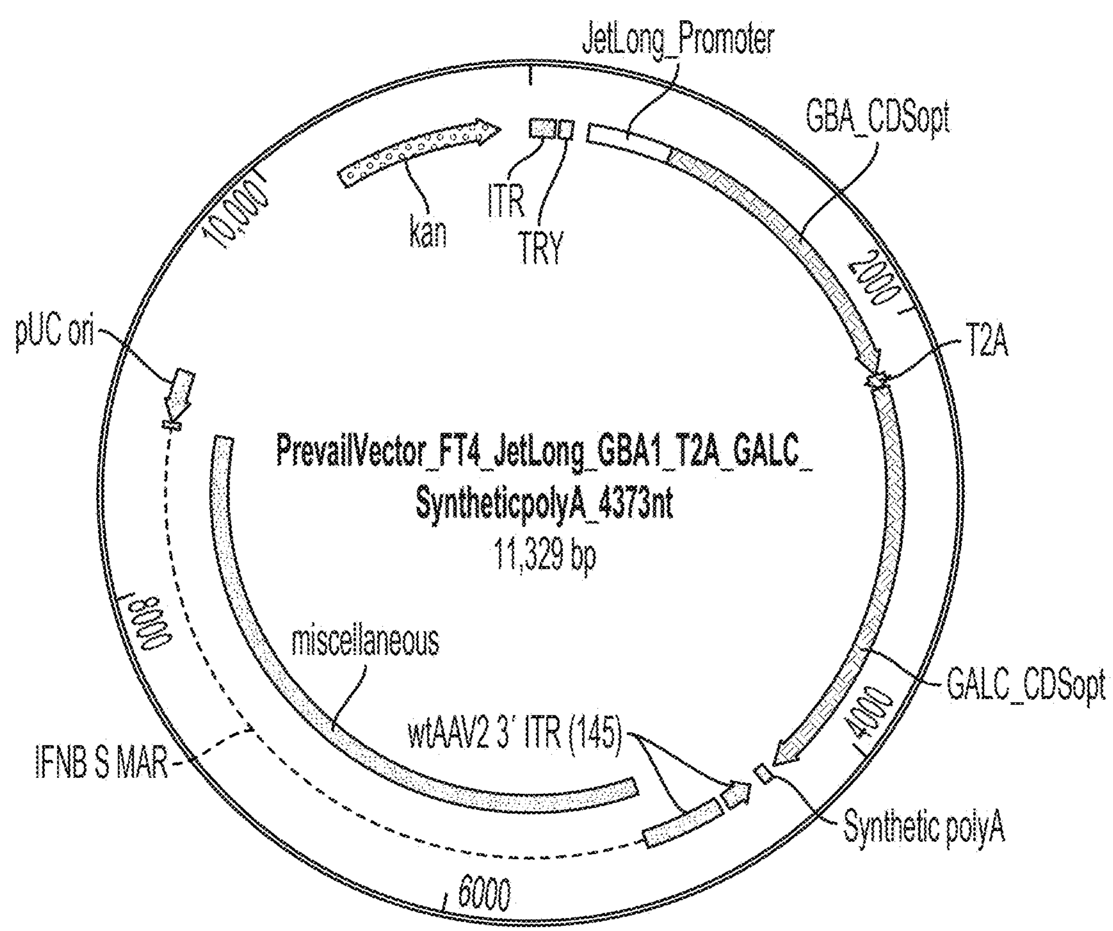
FIG. 22 is a schematic depicting one embodiment of a vector comprising an expression construct encoding Gcase (e.g., GBA1 or a portion thereof) and Galactosylceramidase (e.g., GALC or a portion thereof). Expression of the coding sequences of Gcase and Galactosylceramidase are separated by a T2A self-cleaving peptide sequence.
Figure 23:
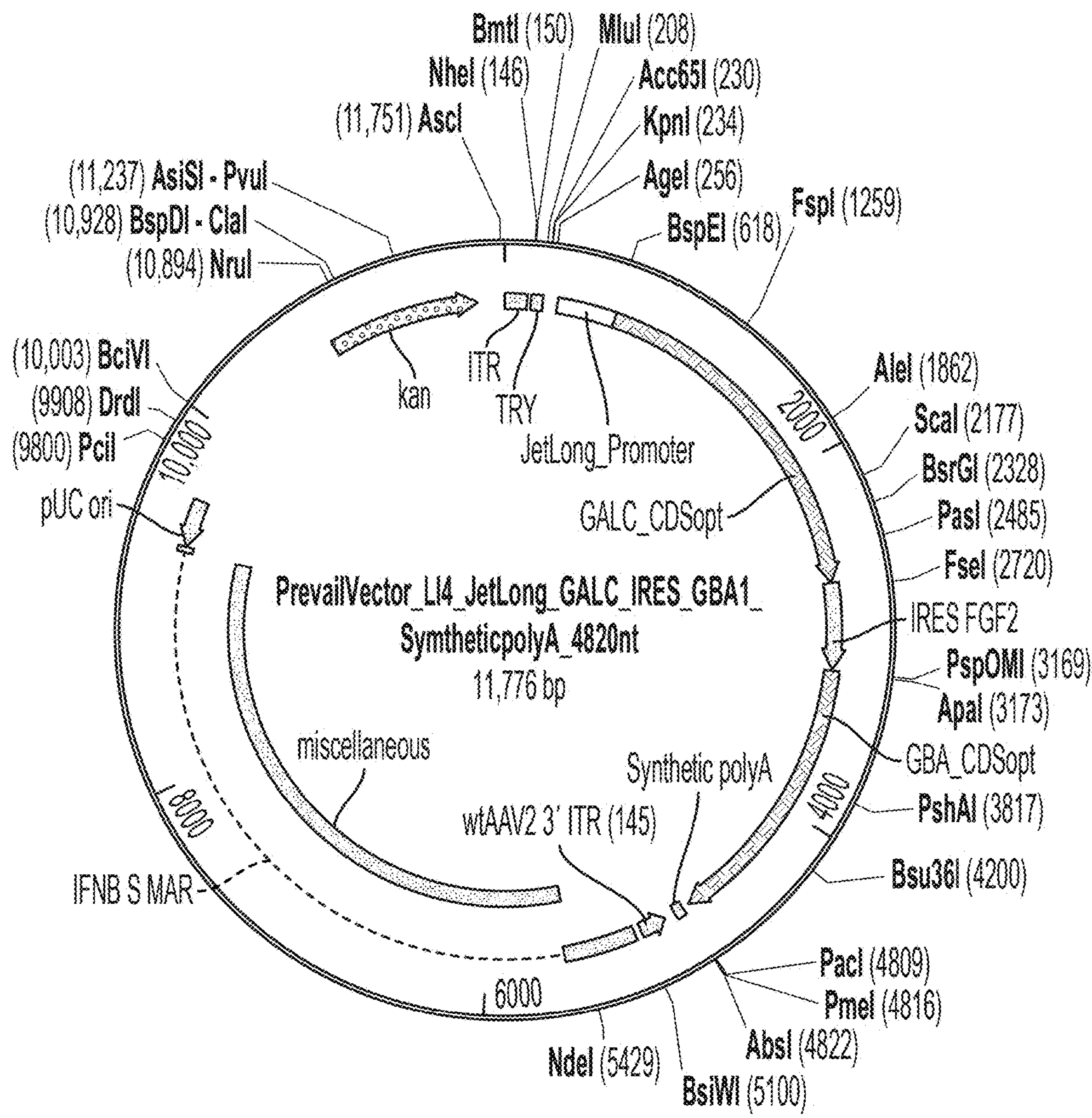
FIG. 23 is a schematic depicting one embodiment of a vector comprising an expression construct encoding Gcase (e.g., GBA1 or a portion thereof) and Galactosylceramidase (e.g., GALC or a portion thereof). Expression of the coding sequences of Gcase and Galactosylceramidase are separated by a T2A self-cleaving peptide sequence.
Figure 24:
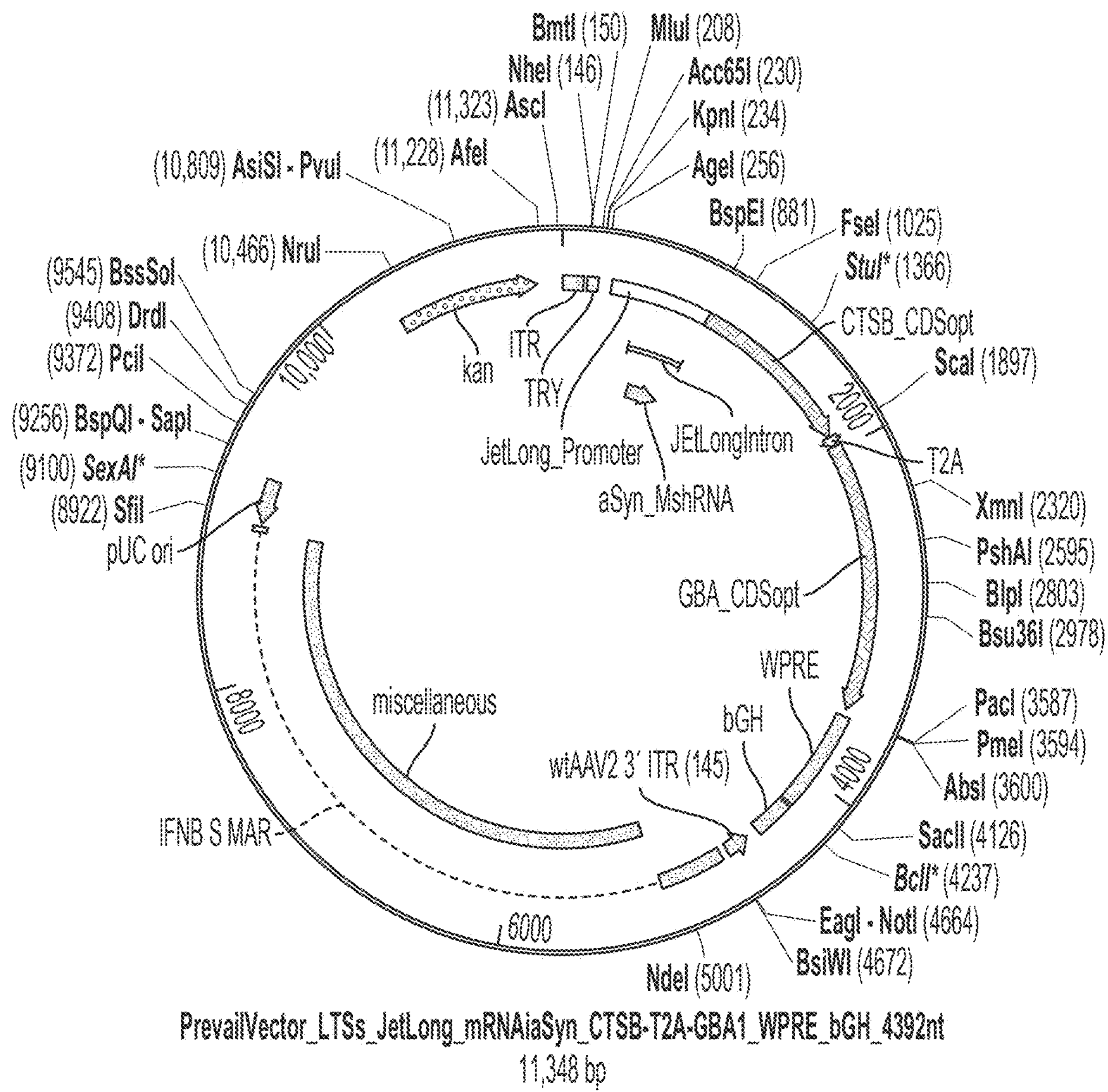
FIG. 24 is a schematic depicting one embodiment of a vector comprising an expression construct encoding Gcase (e.g., GBA1 or a portion thereof), Cathepsin B (e.g., CTSB or a portion thereof), and an interfering RNA for α-Syn. Expression of the coding sequences of Gcase and Cathepsin B are separated by a T2A self-cleaving peptide sequence.
Figure 25:
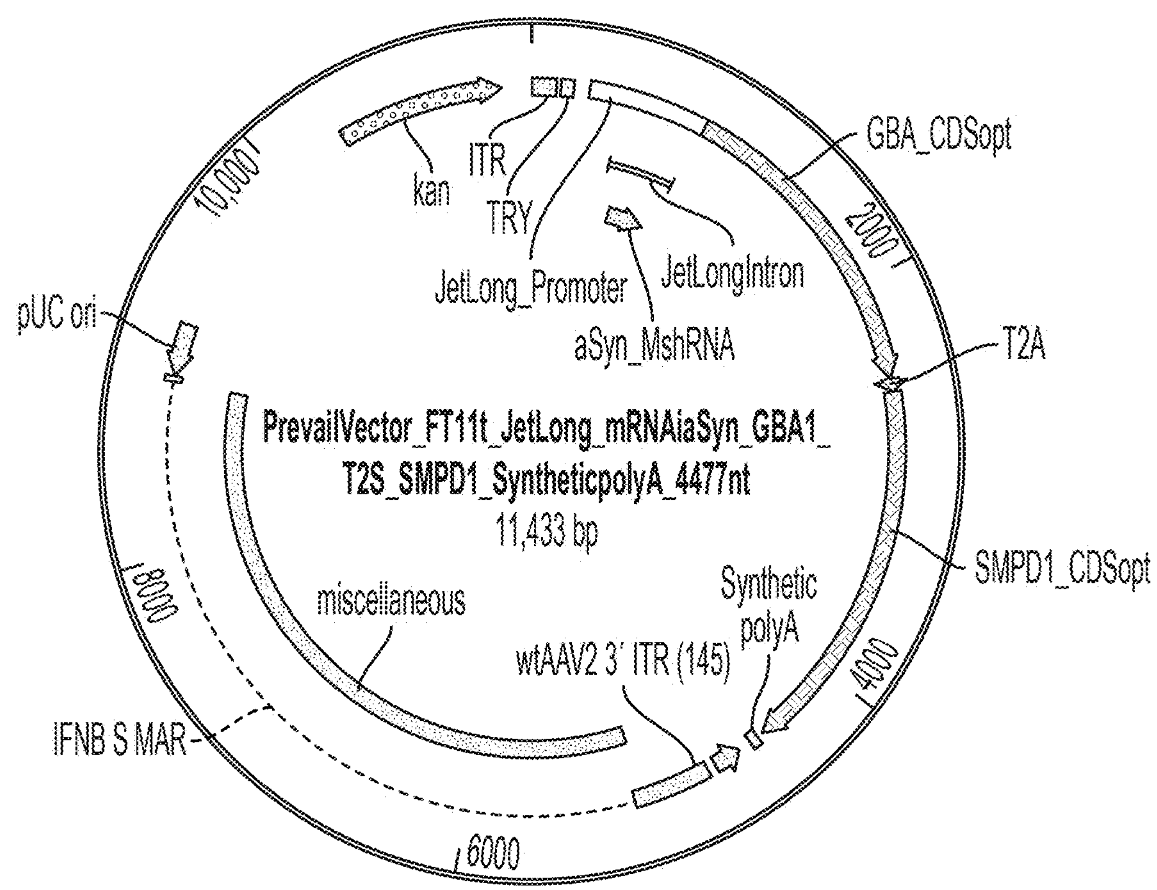
FIG. 25 is a schematic depicting one embodiment of a vector comprising an expression construct encoding Gcase (e.g., GBA1 or a portion thereof), Sphingomyelin phosphodiesterase 1 (e.g., SMPD1 a portion thereof, and an interfering RNA for α-Syn.
Figure 26:
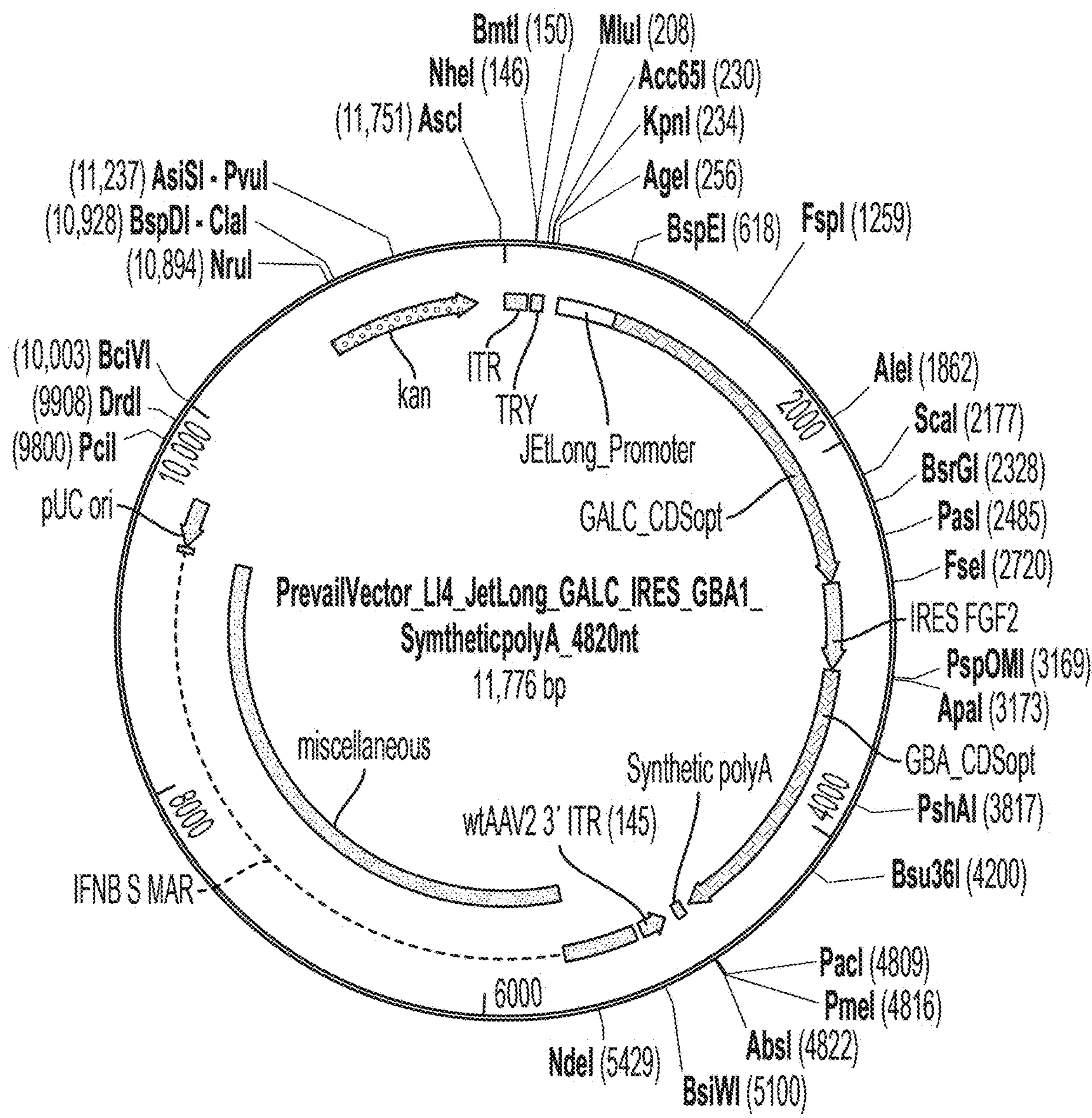
FIG. 26 is a schematic depicting one embodiment of a vector comprising an expression construct encoding Gcase (e.g., GBA1 or a portion thereof) and Galactosylceramidase (e.g., GALC or a portion thereof). The coding sequences of Gcase and Galactosylceramidase are separated by an internal ribosomal entry site (IRES).
Figure 27:
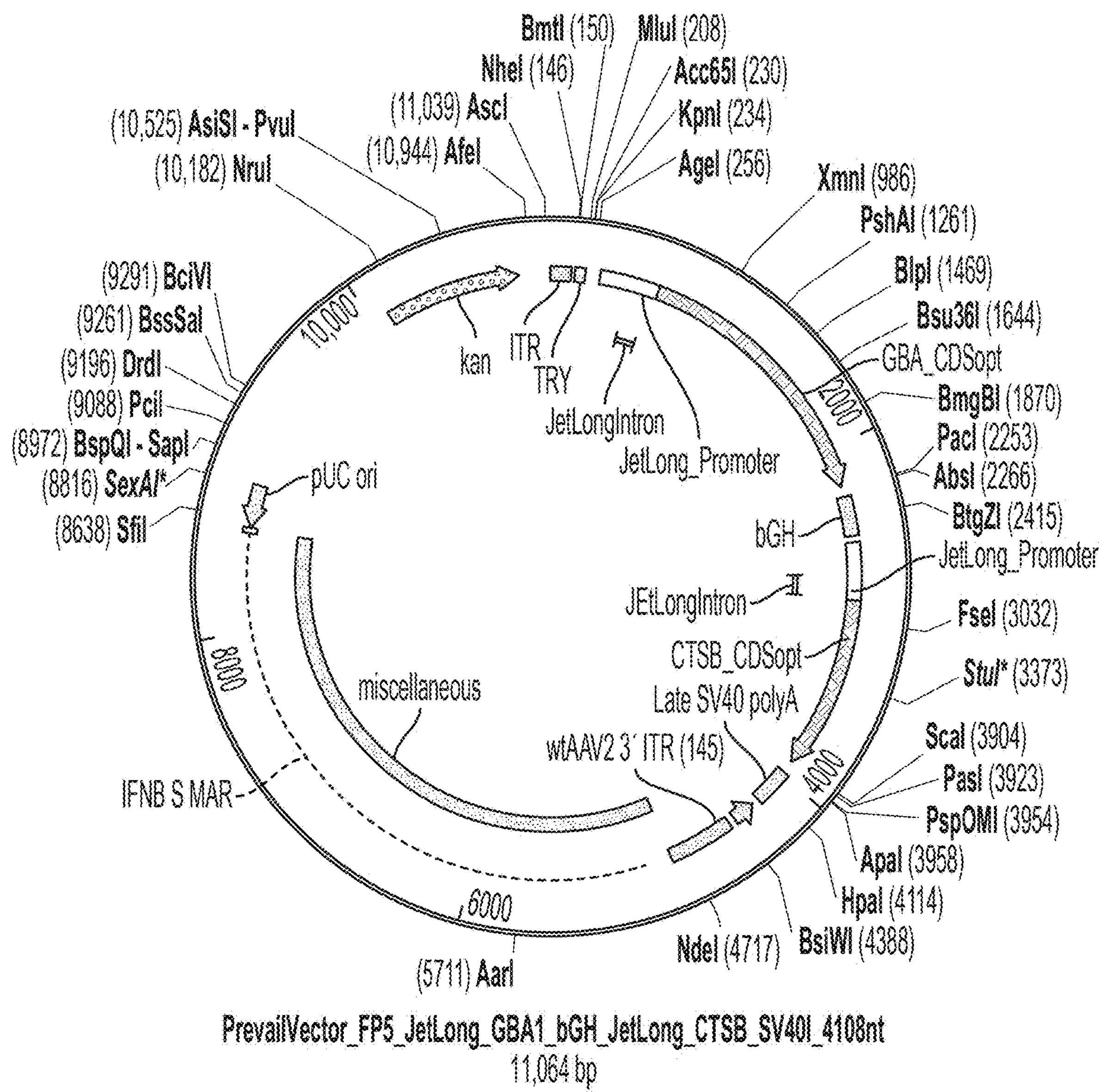
FIG. 27 is a schematic depicting one embodiment of a vector comprising an expression construct encoding Gcase (e.g., GBA1 or a portion thereof) and Cathepsin B (e.g., CTSB or a portion thereof). Expression of the coding sequences of Gcase and Cathepsin B are each driven by a separate promoter.
Figure 28:
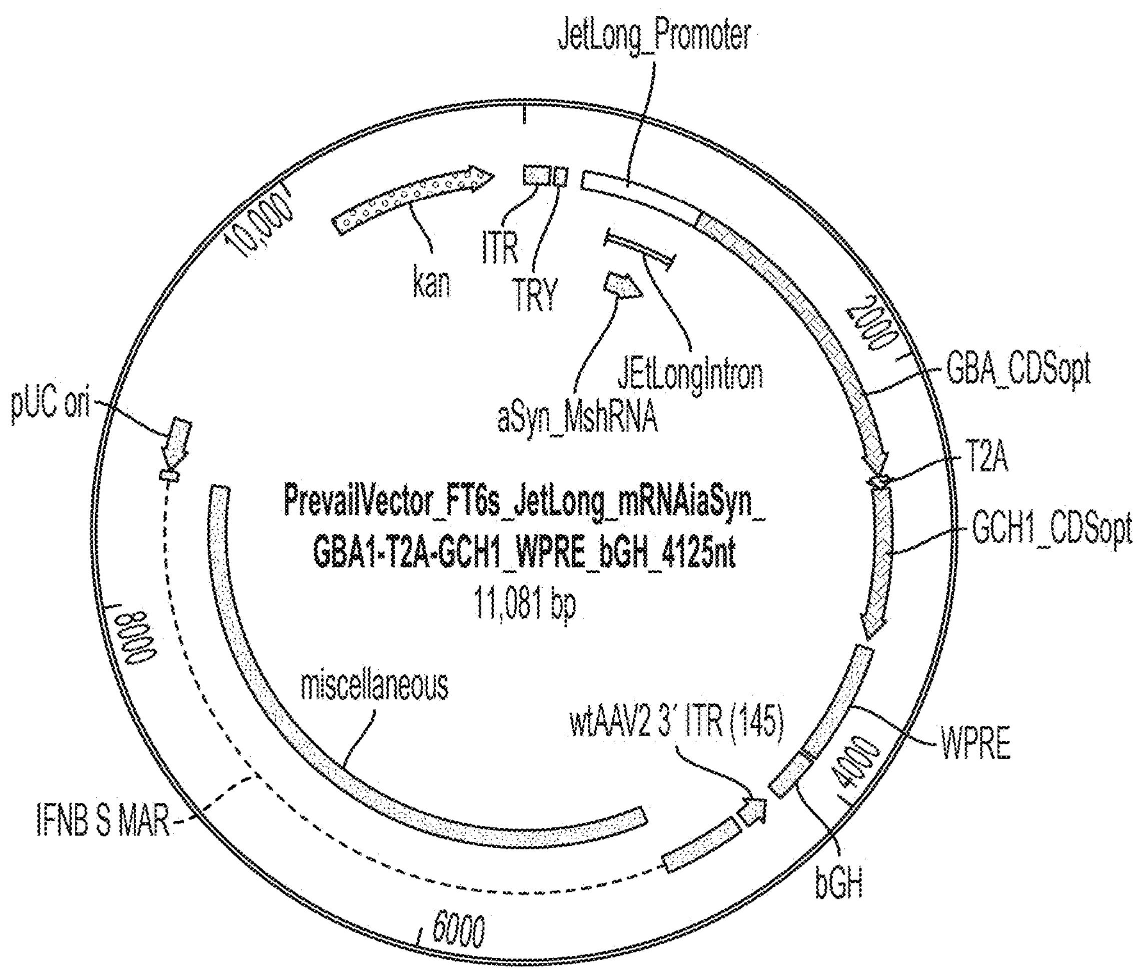
FIG. 28 is a schematic depicting one embodiment of a vector comprising an expression construct encoding Gcase (e.g., GBA1 or a portion thereof), GCH1 (e.g., GCH1 or a portion thereof), and an interfering RNA for α-Syn. The coding sequences of Gcase and GCH1 are separated by an T2A self-cleaving peptide sequence
Figure 29:
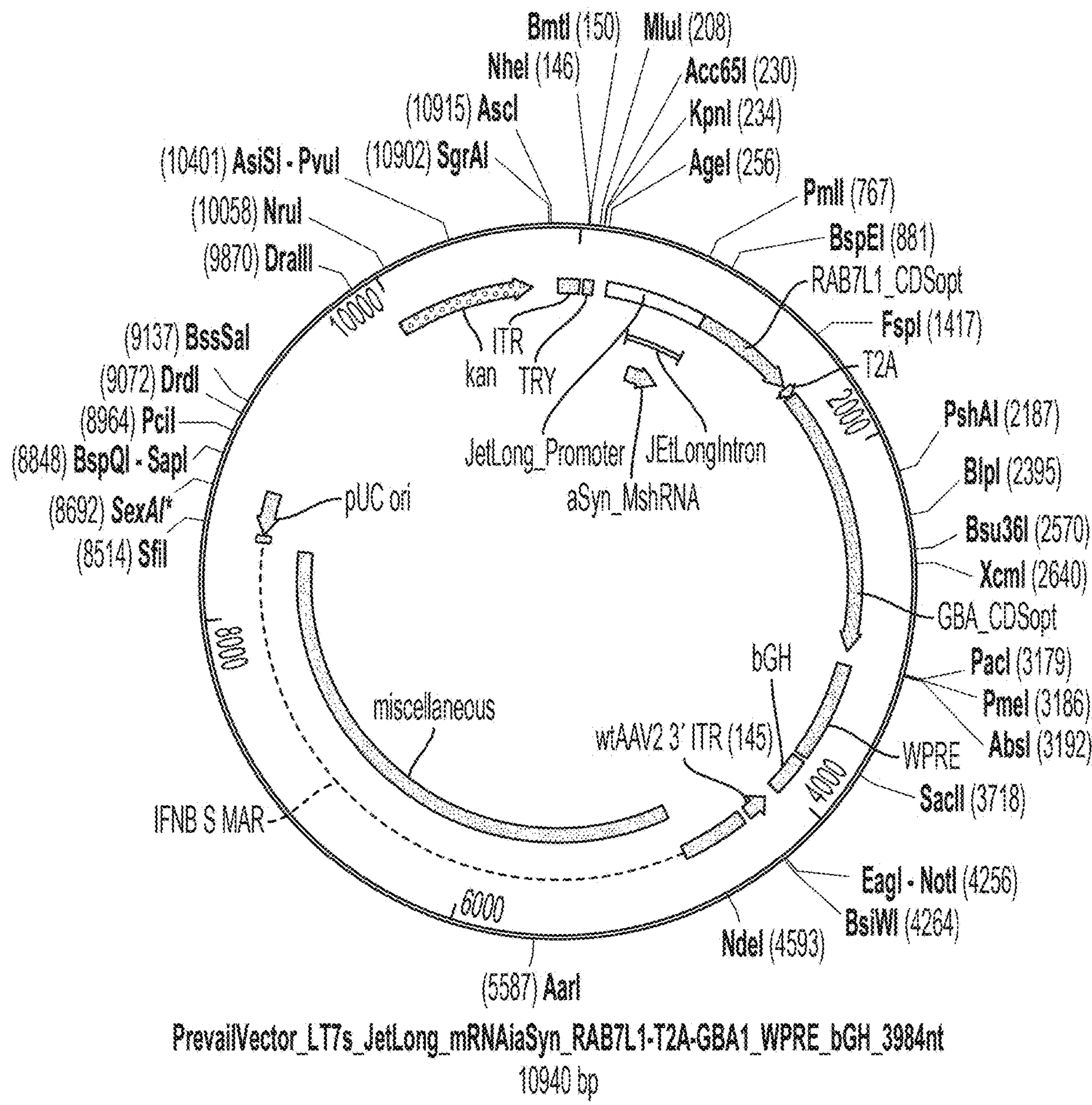
FIG. 29 is a schematic depicting one embodiment of a vector comprising an expression construct encoding Gcase (e.g., GBA1 or a portion thereof), RAB7L1 (e.g., RAB7L1 or a portion thereof), and an interfering RNA for α-Syn. The coding sequences of Gcase and RAB7L1 are separated by an T2A self-cleaving peptide sequence.
Figure 30:
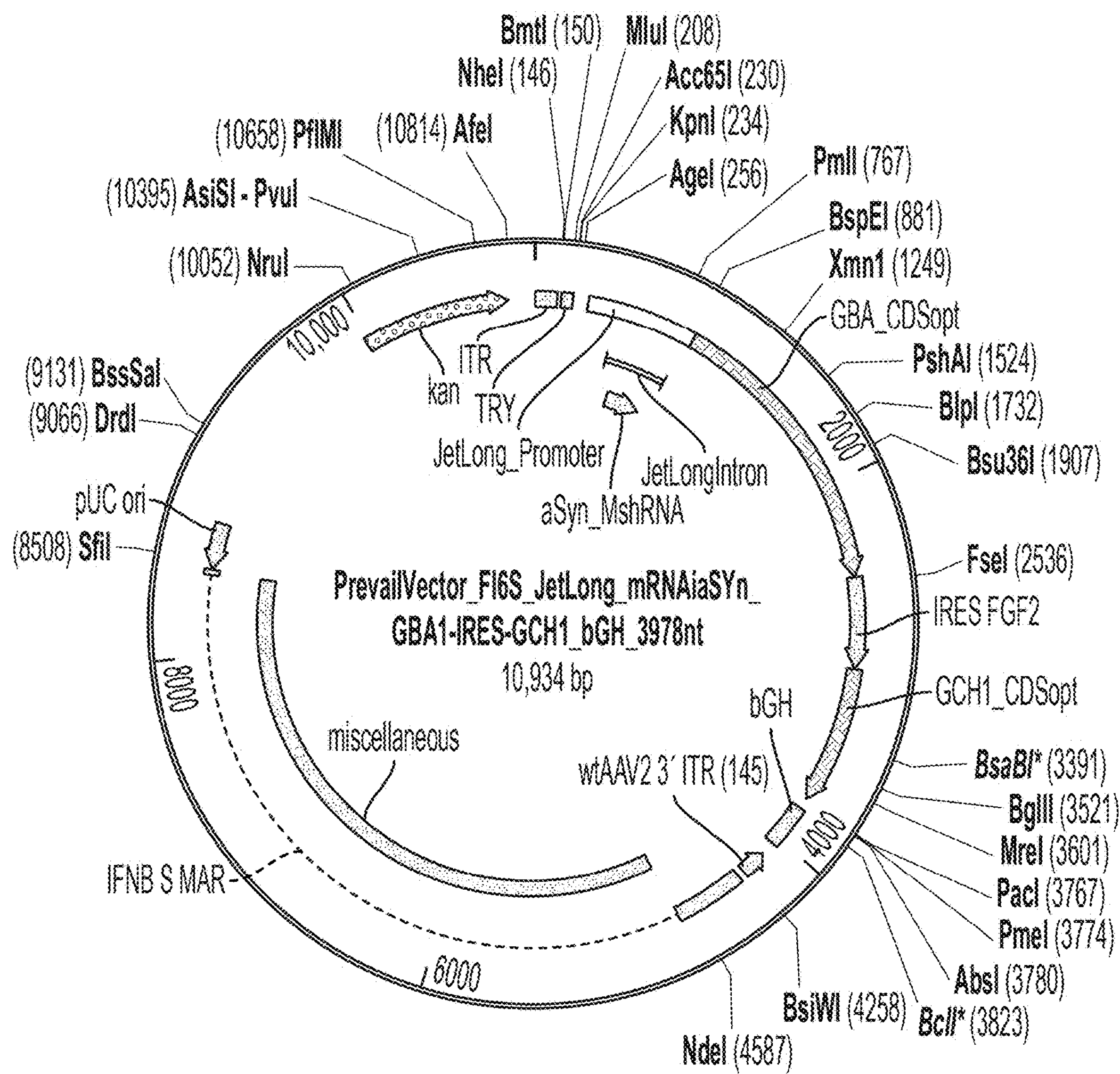
FIG. 30 is a schematic depicting one embodiment of a vector comprising an expression construct encoding Gcase (e.g., GBA1 or a portion thereof), GCH1 (e.g., GCH1 or a portion thereof), and an interfering RNA for α-Syn. Expression of the coding sequences of Gcase and GCH1 are an internal ribosomal entry site (IRES).
Figure 31:
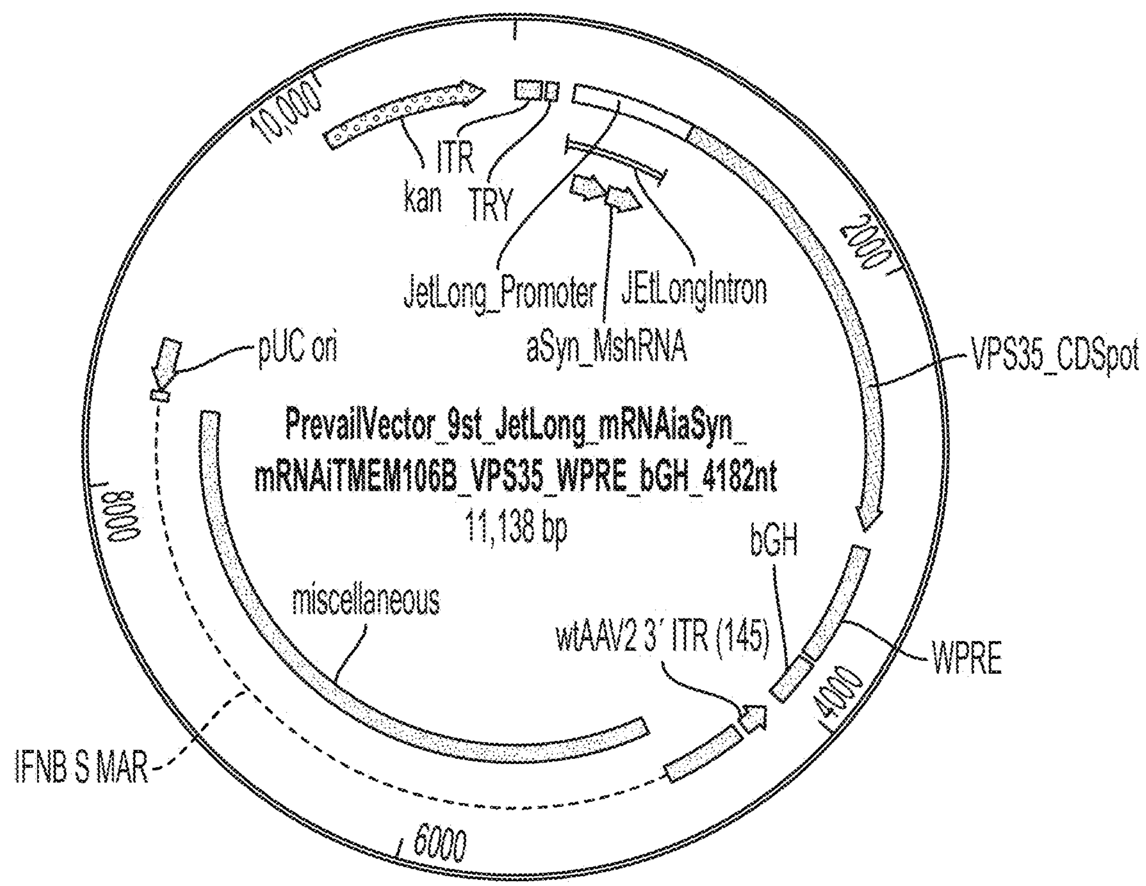
FIG. 31 is a schematic depicting one embodiment of a vector comprising an expression construct encoding VPS35 (e.g., VPS35 or a portion thereof) and interfering RNAs for α-Syn and TMEM106B.
Figure 32:
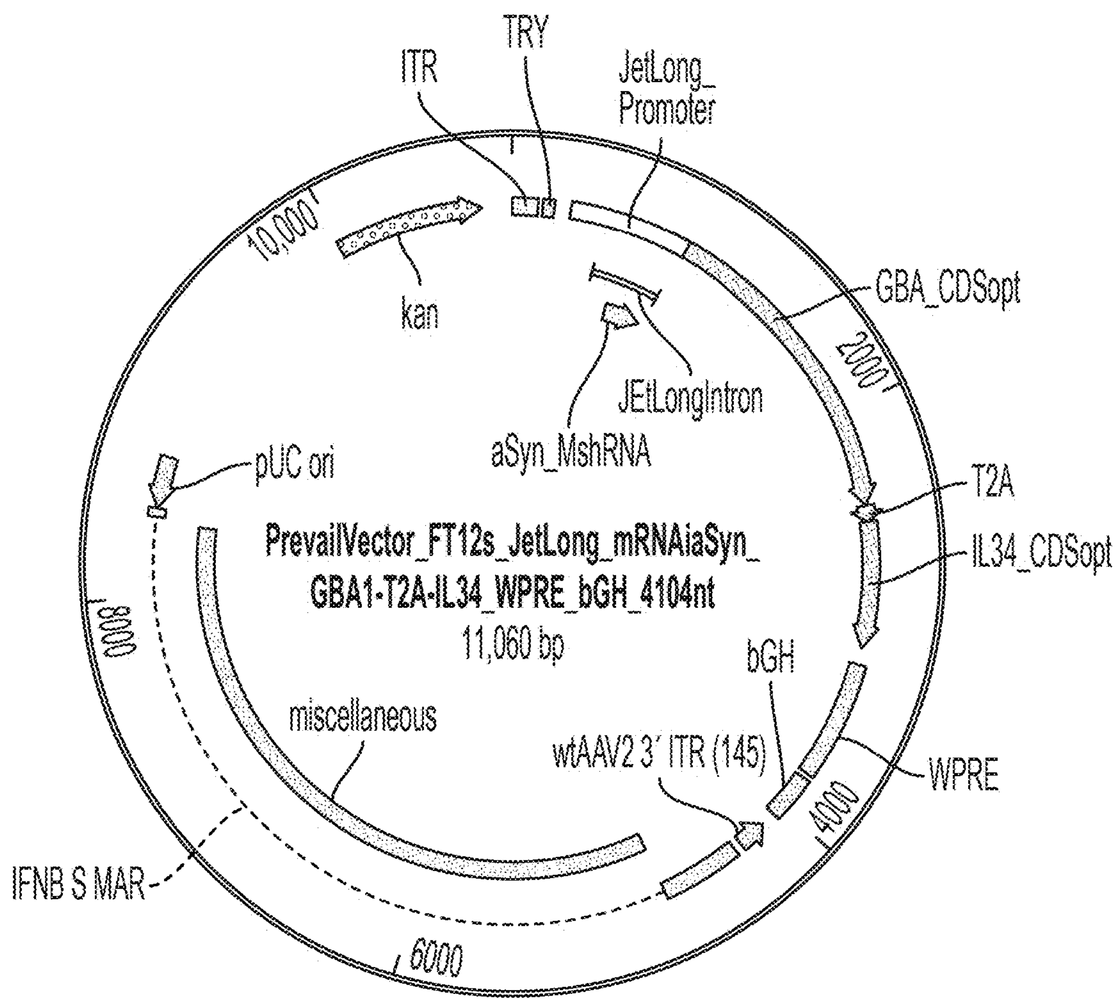
FIG. 32 is a schematic depicting one embodiment of a vector comprising an expression construct encoding Gcase (e.g., GBA1 or a portion thereof), IL-34 (e.g., IL34 or a portion thereof), and an interfering RNA for α-Syn. The coding sequences of Gcase and IL-34 are separated by T2A self-cleaving peptide sequence.
Figure 33:
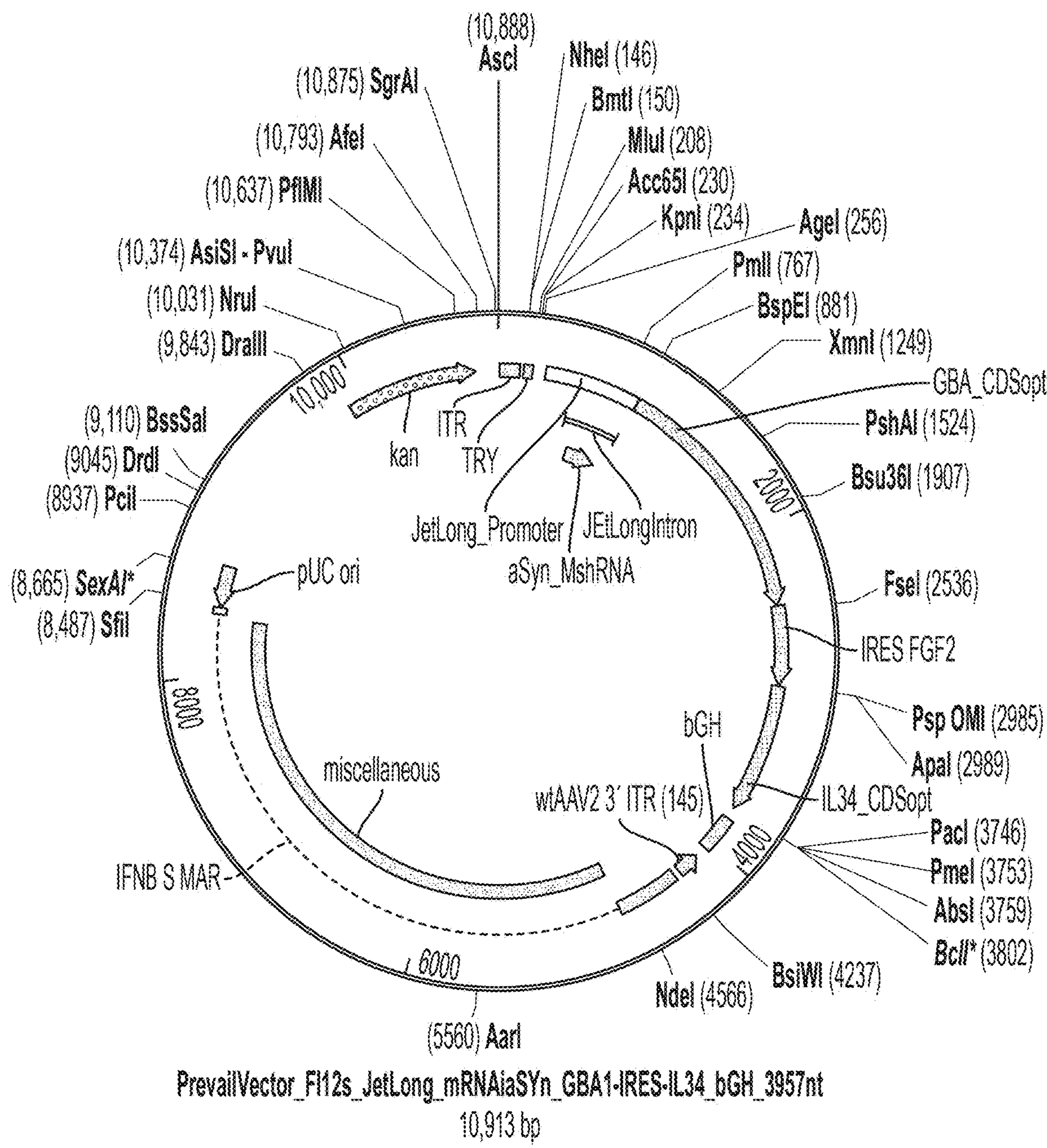
FIG. 33 is a schematic depicting one embodiment of a vector comprising an expression construct encoding Gcase (e.g., GBA1 or a portion thereof) and IL-34 (e.g., IL34 or a portion thereof). The coding sequences of Gcase and IL-34 are separated by an internal ribosomal entry site (IRES).
Figure 34:
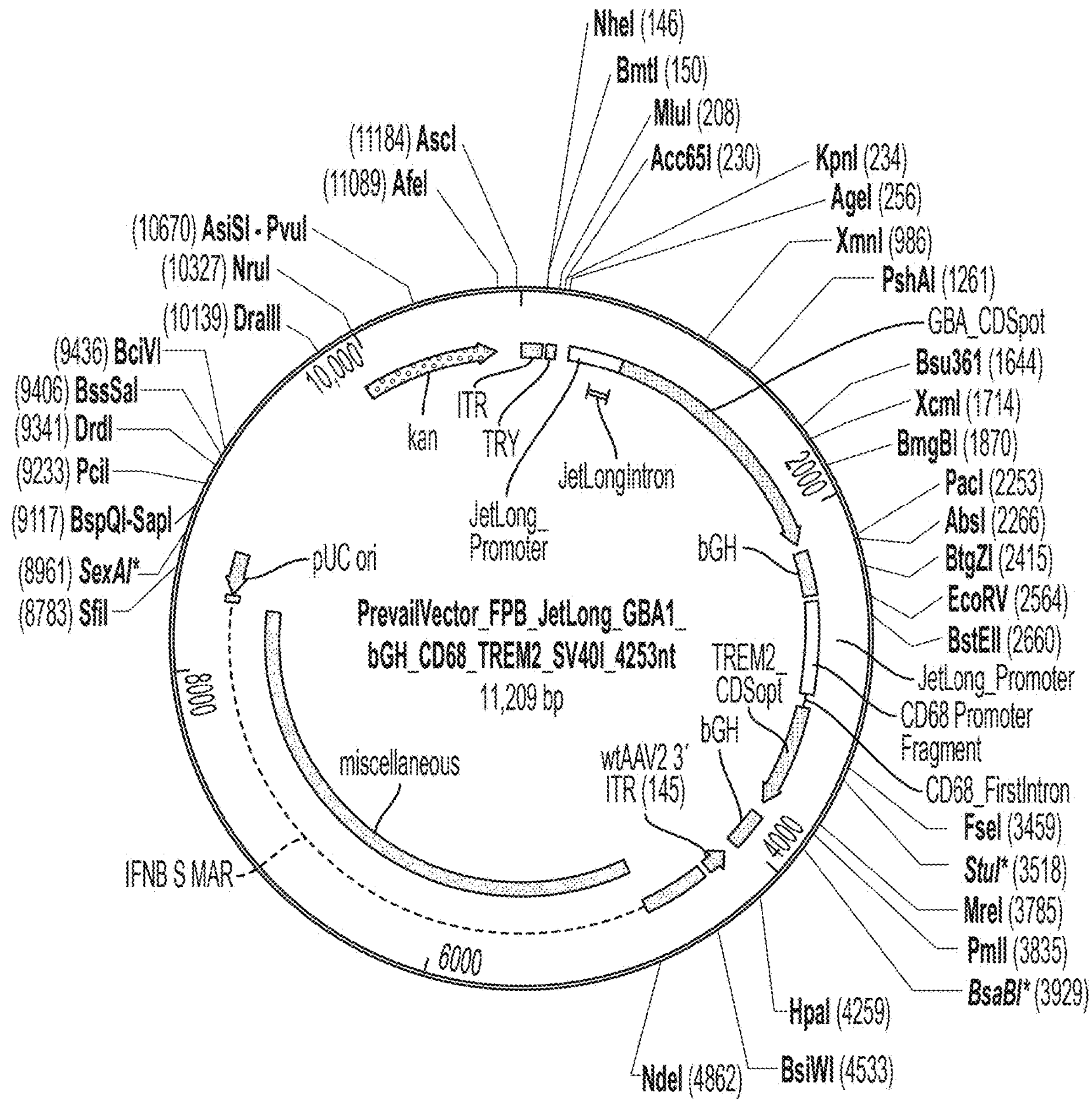
FIG. 34 is a schematic depicting one embodiment of a vector comprising an expression construct encoding Gcase (e.g., GBA1 or a portion thereof) and TREM2 (e.g., TREM2 or a portion thereof). Expression of the coding sequences of Gcase and TREM2 are each driven by a separate promoter.
Figure 35:
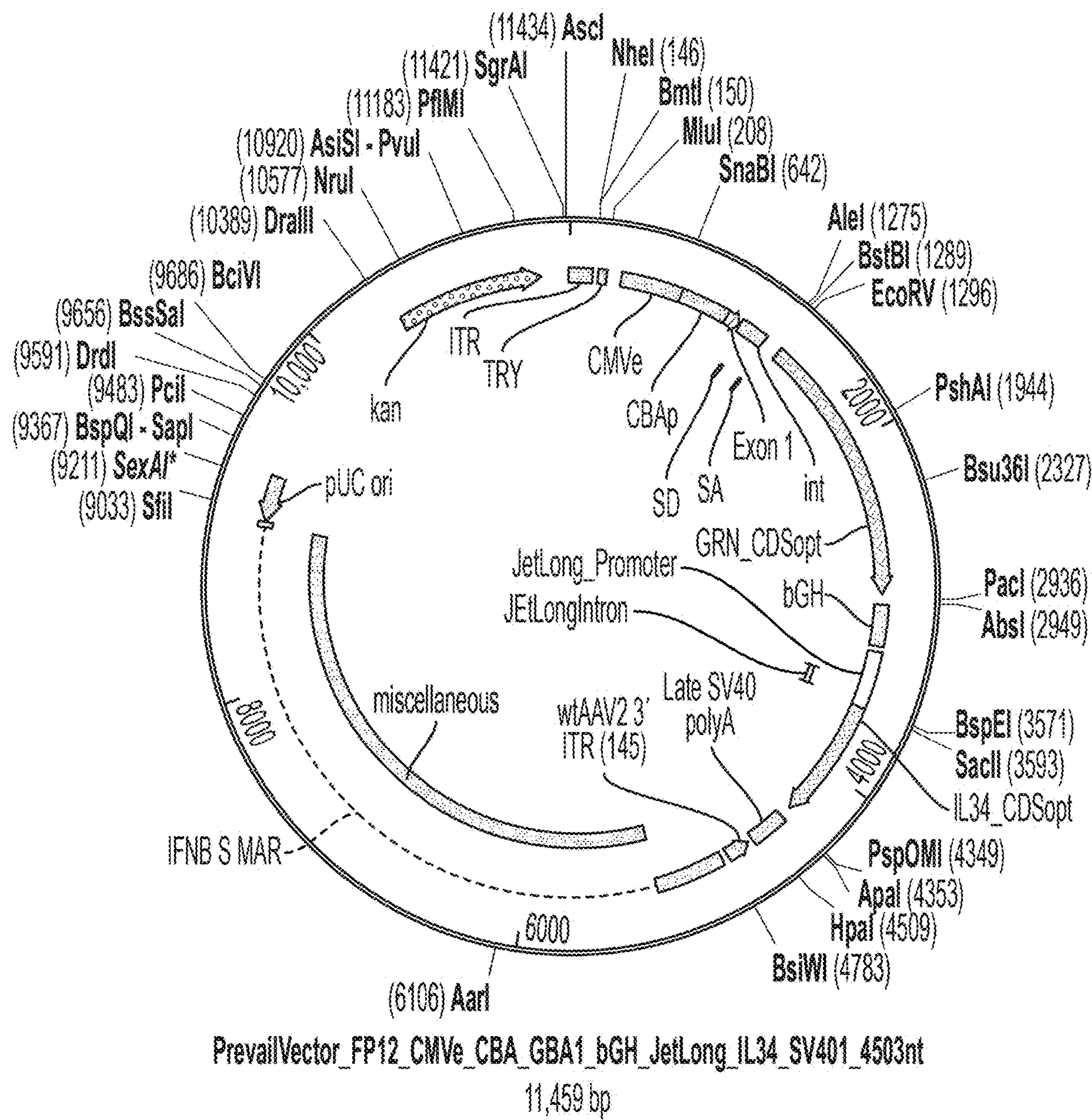
FIG. 35 is a schematic depicting one embodiment of a vector comprising an expression construct encoding Gcase (e.g., GBA1 or a portion thereof) and IL-34 (e.g., IL34 or a portion thereof). Expression of the coding sequences of Gcase and IL-34 are each driven by a separate promoter.

Aspects of the disclosure relate to isolated nucleic acids (e.g., rAAV vectors) comprising an ITR having one or more modifications (e.g., nucleic acid additions, deletions, substitutions, etc.) relative to a wild-type AAV ITR, for example relative to wild-type AAV2 ITR (e.g., SEQ ID NO: 29). The structure of wild-type AAV2 ITR is shown in FIG. 20. Generally, a wild-type ITR comprises a 125 nucleotide region that self-anneals to form a palindromic double-stranded T-shaped, hairpin structure consisting of two cross arms (formed by sequences referred to as B/B' and C/C', respectively), a longer stem region (formed by sequences A/A'), and a single-stranded terminal region referred to as the "D" region (FIG. 20). Generally, the "D" region of an ITR is positioned between the stem region formed by the A/A' sequences and the insert containing the transgene of the rAAV vector (e.g., positioned on the "inside" of the ITR relative to the terminus of the ITR or proximal to the transgene insert or expression construct of the rAAV vector). In some embodiments, a "D" region comprises the sequence set forth in SEQ ID NO: 27. The "D" region has been observed to play an important role in encapsidation of rAAV vectors by capsid proteins, for example as disclosed by Ling et al. (2015) *J Mol Genet Med* 9(3).

The disclosure is based, in part, on the surprising discovery that rAAV vectors comprising a "D" region located on the "outside" of the ITR (e.g., proximal to the terminus of the ITR relative to the transgene insert or expression construct) are efficiently encapsidated by AAV capsid proteins than rAAV vectors having ITRs with unmodified (e.g., wild-type) ITRs. In some embodiments, rAAV vectors having a modified "D" sequence (e.g., a "D" sequence in the "outside" position) have reduced toxicity relative to rAAV vectors having wild-type ITR sequences.

In some embodiments, a modified "D" sequence comprises at least one nucleotide substitution relative to a wild-type "D" sequence (e.g., SEQ ID NO: 27). A modified "D" sequence may have at least 1, 2, 3, 4, 5, 6, 7, 8, 9, 10, or more than 10 nucleotide substitutions relative to a wild-type "D" sequence (e.g., SEQ ID NO: 27). In some embodiments, a modified "D" sequence comprises at least 10, 11, 12, 13, 14, 15, 16, 17, 18, or 19 nucleic acid substitutions relative to a wild-type "D" sequence (e.g., SEQ ID NO: 27). In some embodiments, a modified "D" sequence is between about 10% and about 99% (e.g., 10%, 15%, 20%, 25%, 30%, 40%, 45%, 50%, 55%, 60%, 65%, 70%, 75%, 80%, 85%, 90%, 95%, or 99%) identical to a wild-type "D" sequence (e.g., SEQ ID NO: 27). In some embodiments, a modified "D" sequence comprises the sequence set forth in SEQ ID NO: 26, also referred to as an "S" sequence as described in Wang et al. (1995) *J Mol Biol* 250(5):573-80.

An isolated nucleic acid or rAAV vector as described by the disclosure may further comprise a "TRY" sequence, for example as set forth in SEQ ID NO: 28 or as described by Francois et al., (2005) *J. Virol.* 79(17):11082-11094. In some embodiments, a TRY sequence is positioned between an ITR (e.g. a 5' ITR) and an expression construct (e.g. a transgene-encoding insert) of an isolated nucleic acid or rAAV vector.

In some aspects, the disclosure relates to Baculovirus vectors comprising an isolated nucleic acid or rAAV vector as described by the disclosure. In some embodiments, the Baculovirus vector is an *Autographa californica* nuclear polyhedrosis (AcNPV) vector, for example as described by Urabe et al. (2002) *Hum Gene Ther* 13(16):1935-43 and Smith et al. (2009) *Mol Ther* 17(11):1888-1896.

In some aspects, the disclosure provides a host cell comprising an isolated nucleic acid or vector as described herein. A host cell can be a prokaryotic cell or a eukaryotic cell. For example, a host cell can be a mammalian cell, bacterial cell, yeast cell, insect cell, etc. In some embodiments, a host cell is a mammalian cell, for example a HEK293T cell. In some embodiments, a host cell is a bacterial cell, for example an *E. coli* cell.

rAAVs

In some aspects, the disclosure relates to recombinant AAVs (rAAVs) comprising a transgene that encodes a nucleic acid as described herein (e.g., an rAAV vector as described herein). The term "rAAVs" generally refers to viral particles comprising an rAAV vector encapsidated by one or more AAV capsid proteins. An rAAV described by the disclosure may comprise a capsid protein having a serotype selected from AAV1, AAV2, AAV3, AAV4, AAV5, AAV6, AAV7, AAV8, AAV9, and AAV10. In some embodiments, an rAAV comprises a capsid protein from a non-human host, for example a rhesus AAV capsid protein such as AAVrh.10, AAVrh.39, etc. In some embodiments, an rAAV described by the disclosure comprises a capsid protein that is a variant of a wild-type capsid protein, such as a capsid protein variant that includes at least 1, 2, 3, 4, 5, 6, 7, 8, 9, 10, or more than 10 (e.g., 15, 20 25, 50, 100, etc.) amino acid substitutions (e.g., mutations) relative to the wild-type AAV capsid protein from which it is derived. In some embodiments, an AAV capsid protein variant is an AAV1RX capsid protein, for example as described by Albright et al. *Mol Ther.* 2018 Feb. 7; 26(2):510-523. In some embodiments, a capsid protein variant is an AAV TM6 capsid protein, for example as described by Rosario et al. *Mol Ther Methods Clin Dev.* 2016; 3: 16026.

In some embodiments, rAAVs described by the disclosure readily spread through the CNS, particularly when introduced into the CSF space or directly into the brain parenchyma. Accordingly, in some embodiments, rAAVs described by the disclosure comprise a capsid protein that is capable of crossing the blood-brain barrier (BBB). For example, in some embodiments, an rAAV comprises a capsid protein having an AAV9 or AAVrh.10 serotype. Production of rAAVs is described, for example, by Samulski et al. (1989) *J Virol.* 63(9):3822-8 and Wright (2009) *Hum Gene Ther.* 20(7): 698-706. In some embodiments, an rAAV comprises a capsid protein that specifically or preferentially targets myeloid cells, for example microglial cells.

Figure 64:
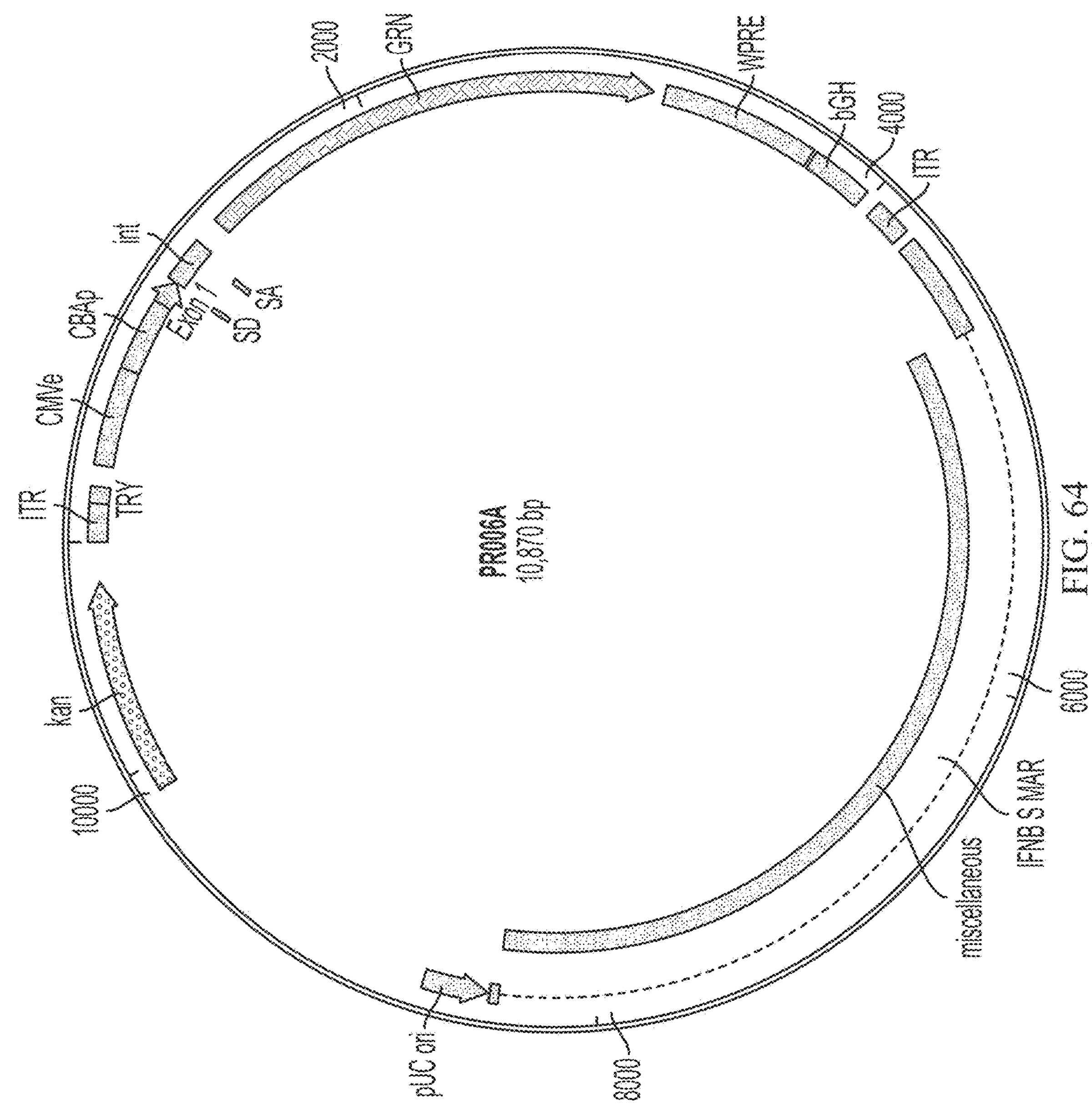
FIG. 64 is a schematic depicting one embodiment of a recombinant adeno-associated virus vector (PR006A) comprising an expression construct encoding human progranulin. "bp" refers to "base pairs". "kan" refers to a gene that confers resistance to kanamycin. "GRN" refers to "progranulin". "ITR" refers to an adeno-associated virus inverted terminal repeat sequence. "TRY" refers to a sequence comprising three transcriptional regulatory activation sites: TATA, RBS, and YY1. "CBAp" refers to a chicken β-actin promoter. "CMVe" refers to a cytomegalovirus enhancer. "WPRE" refers to a woodchuck hepatitis virus post-transcriptional regulatory element. "bGH" refers to a bovine Growth Hormone polyA signal tail. "int" refers to an intron. The nucleotide sequences of the two strands of PR006A are provided in SEQ ID NOs: 90 and 91.

In some embodiments, the disclosure provides an rAAV referred to as "PR006A". PR006A is a rAAV that delivers a functional human GRN gene, leading to increased expression of functional human PGRN. The PR006A vector insert comprises the chicken β-actin (CBA) promoter element, comprising 4 parts: the cytomegalovirus (CMV) enhancer, CBA promoter, exon 1, and intron (int) to constitutively express a codon-optimized coding sequence of human GRN (SEQ ID NO:68). The 3' region also contains a woodchuck hepatitis virus post-transcriptional regulatory element (WPRE) followed by a bovine growth hormone polyadenylation signal tail. Three well described transcriptional regulatory activation sites are included at the 5' end of the promoter region: TATA, RBS, and YY1 (see, e.g., Francois et al., (2005) *J. Virol.* 79(17):11082-11094). The flanking inverted terminal repeats (ITRs) allow for the correct packaging of the intervening sequences. The backbone contains the gene to confer resistance to kanamycin as well as a stuffer sequence to prevent reverse packaging. A schematic depicting the rAAV vector is shown in FIG. 64. SEQ ID NO 90 provides the nucleotide sequence of the first strand (in 5' to 3' order) of the PR006A vector shown in FIG. 64. SEQ ID NO 91 provides the nucleotide sequence of the second strand (in 5' to 3' order) of the PR006A vector shown in FIG. 64. PR006A comprises AAV9 capsid proteins.

In some embodiments, an rAAV as described by the disclosure (e.g., comprising a recombinant rAAV genome encapsidated by AAV capsid proteins to form an rAAV capsid particle) is produced in a Baculovirus vector expression system (BEVS). Production of rAAVs using BEVS are described, for example by Urabe et al. (2002) Hum Gene Ther 13(16):1935-43, Smith et al. (2009) Mol Ther 17(11): 1888-1896, U.S. Pat. Nos. 8,945,918, 9,879,282, and International PCT Publication WO 2017/184879. However, an rAAV can be produced using any suitable method (e.g., using recombinant rep and cap genes). In some embodiments, an rAAV as disclosed herein is produced in HEK293 (human embryonic kidney) cells.

Pharmaceutical Compositions

In some aspects, the disclosure provides pharmaceutical compositions comprising an isolated nucleic acid or rAAV as described herein and a pharmaceutically acceptable carrier. As used herein, the term "pharmaceutically acceptable" refers to a material, such as a carrier or diluent, which does not abrogate the biological activity or properties of the compound, and is relatively non-toxic, e.g., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

Compositions (e.g., pharmaceutical compositions) provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

In some embodiments, the disclosure provides a PR006A finished drug product comprising the PR006A rAAV described above presented in aqueous solution. In some embodiments, the final formulation buffer comprises about 20 mM Tris [pH 8.0], about 1 mM $MgCl_2$, about 200 mM NaCl, and about 0.001% [w/v] poloxamer 188. In some embodiments, the finished drug product and the final formulation buffer are suitable for intra-cisterna *magna* (ICM) injection.

Methods

Aspects of the disclosure relate to compositions for expression of one or more CNS disease-associated gene products in a subject to treat CNS-associated diseases. The one or more CNS disease-associated gene products may be encoded by one or more isolated nucleic acids or rAAV vectors. In some embodiments, a subject is administered a single vector (e.g., isolated nucleic acid, rAAV, etc.) encoding one or more (1, 2, 3, 4, 5, or more) gene products. In some embodiments, a subject is administered a plurality (e.g., 2, 3, 4, 5, or more) vectors (e.g., isolated nucleic acids, rAAVs, etc.), where each vector encodes a different CNS disease-associated gene product.

A CNS-associated disease may be a neurodegenerative disease, synucleinopathy, tauopathy, or a lysosomal storage disease. Examples of neurodegenerative diseases and their associated genes are listed in Table 12.

A "synucleinopathy" refers to a disease or disorder characterized by the accumulation of alpha-Synuclein (the gene product of SNCA) in a subject (e.g., relative to a healthy subject, for example a subject not having a synucleinopathy). Examples of synucleinopathies and their associated genes are listed in Table 13.

A "tauopathy" refers to a disease or disorder characterized by accumulation of abnormal Tau protein in a subject (e.g., relative to a healthy subject not having a tauopathy). Examples of tauopathies and their associated genes are listed in Table 14.

A "lysosomal storage disease" refers to a disease characterized by abnormal build-up of toxic cellular products in lysosomes of a subject. Examples of lysosomal storage diseases and their associated genes are listed in Table 15.

As used herein "treat" or "treating" refers to (a) preventing or delaying onset of a CNS disease; (b) reducing severity of a CNS disease; (c) reducing or preventing development of symptoms characteristic of a CNS disease; (d) and/or preventing worsening of symptoms characteristic of a CNS disease. Symptoms of CNS disease may include, for example, motor dysfunction (e.g., shaking, rigidity, slowness of movement, difficulty with walking, paralysis), cognitive dysfunction (e.g., dementia, depression, anxiety, psychosis), difficulty with memory, emotional and behavioral dysfunction.

The disclosure is based, in part, on compositions for expression of combinations of PD-associated gene products in a subject that act together (e.g., synergistically) to treat Parkinson's disease.

Accordingly, in some aspects, the disclosure provides a method for treating a subject having or suspected of having Parkinson's disease, the method comprising administering to the subject a composition (e.g., a composition comprising an isolated nucleic acid or a vector or a rAAV) as described by the disclosure.

The disclosure is based, in part, on compositions for expression of one or more CNS-disease associated gene products in a subject to treat Gaucher disease. In some embodiments, the Gaucher disease is a neuronopathic Gaucher disease, for example Type 2 Gaucher disease or Type 3 Gaucher disease. In some embodiments, a subject having Gaucher disease does not have PD or PD symptoms.

Accordingly, in some aspects, the disclosure provides a method for treating a subject having or suspected of having neuronopathic Gaucher disease, the method comprising administering to the subject a composition (e.g., a composition comprising an isolated nucleic acid or a vector or a rAAV) as described by the disclosure.

The disclosure is based, in part, on compositions for expression of one or more CNS-disease associated gene products in a subject to treat Alzheimer's disease or frontotemporal dementia (FTD). In some embodiments, the subject does not have Alzheimer's disease. In some embodiments, the subject has FTD and does not have Alzheimer's disease. In some embodiments, the subject has FTD with GRN (progranulin) mutation. In some embodiments, the subject has FTD with GRN mutation, and the subject is heterozygous for a GRN mutation (e.g., a pathogenic GRN mutation). In some embodiments, a GRN mutation is a null mutation (e.g., a nonsense, a frameshift, or a splice site mutations, or a complete or partial (exonic) gene deletion). In some embodiments, a GRN mutation is a pathogenic mutation with proven functional deleterious effect. In some embodiments, a GRN mutation is a missense pathogenic mutation. In some embodiments, a GRN mutation is listed in the Molgen FTD database (molgen.ua.ac.be). In some embodiments, a GRN mutation produces a low plasma PGRN level (<70 ng/mL) in a subject.

In some embodiments, the subject has FTD, FTD with GRN mutation, FTD with tau mutation, FTD with C9orf72 mutation, neuronal ceroid lipofuscinosis, Parkinson's disease, Alzheimer's disease, corticobasal degeneration, motor neuron disease, or Gaucher disease.

In some embodiments, the subject has symptomatic FTD (e.g., behavioral-variant FTD (bvFTD), primary progressive aphasia (PPA)-FTD, FTD with corticobasal syndrome, or a combination of syndromes).

Accordingly, in some aspects, the disclosure provides a method for treating a subject having or suspected of having FTD with GRN mutation, the method comprising administering to the subject a composition (e.g., a composition comprising an isolated nucleic acid or a vector or a rAAV) as described by the disclosure.

In some embodiments, a subject having Alzheimer's disease or FTD (e.g. FTD with GRN mutation) is administered an rAAV encoding Progranulin (PGRN) or a portion thereof. In some embodiments, a subject having Alzheimer's disease or FTD (e.g. FTD with GRN mutation) is administered an rAAV encoding PGRN or a portion thereof, wherein the PGRN protein is encoded by a codon-optimized nucleic acid sequence or the nucleic acid sequence in SEQ ID NO:68. In some embodiments, the PGRN protein comprises the amino acid sequence in SEQ ID NO:67 or a portion thereof. In some embodiments, the rAAV encoding PGRN comprises a capsid protein having an AAV9 serotype.

In some embodiments, a composition comprising an rAAV encoding PGRN for treating FTD (e.g. FTD with GRN mutation) is administered to a subject at a dose ranging from about $1\times10^{12}$ vector genomes (vg) to about $1\times10^{15}$ vg or from about $1\times10^{13}$ vg to about $7\times10^{14}$ vg, or from about $1\times10^{13}$ vg to about $5\times10^{14}$ vg, or from about $2\times10^{13}$ vg to about $2\times10^{14}$ vg, or from about $3\times10^{13}$ vg to about $2\times10^{14}$ vg, or from about $3.5\times10^{13}$ vg to about $1.4\times10^{14}$ vg. In some embodiments, a composition comprising an rAAV encoding PGRN for treating FTD (e.g. FTD with GRN mutation) is administered to a subject at a dose of about $2\times10^{13}$ vg, about $3\times10^{13}$ vg, about $4\times10^{13}$ vg, about $5\times10^{13}$ vg, about $6\times10^{13}$ vg, about $7\times10^{13}$ vg, about $8\times10^{13}$ vg, about $9\times10^{13}$ vg, about $1\times10^{14}$ vg, or about $2\times10^{14}$ vg.

In some aspects, the disclosure provides a method for treating a subject having or suspected of having FTD (e.g. FTD with GRN mutation), the method comprising administering to the subject a composition comprising an rAAV encoding PGRN, wherein the composition is administered at a dose of about $3.5\times10^{13}$ vector genomes (vg), about $7.0\times10^{13}$ vg, or about $1.4\times10^{14}$ vg.

In some aspects, the disclosure provides a method for treating a subject having or suspected of having FTD (e.g. FTD with GRN mutation), the method comprising administering to the subject a composition comprising an rAAV encoding PGRN, wherein the composition is administered at a dose of about $1\times10^{14}$ vector genomes (vg), about $2.0\times10^{14}$ vg, or about $4.0\times10^{14}$ vg.

In some embodiments, a composition comprising an rAAV encoding PGRN for treating FTD (e.g. FTD with GRN mutation) to a subject as a single dose, and the composition is not administered to the subject subsequently.

In some embodiments, the composition comprising the rAAV is delivered via a single suboccipital injection into the cisterna magna. In some embodiments, the injection into the cisterna magna is performed under radiographic guidance.

In some embodiments, the disclosure provides a method for treating a symptom of a subject having or suspected of having FTD with GRN mutation, the method comprising administering to the subject a composition comprising an rAAV encoding the sequence for functional Progranulin (PGRN) protein, wherein the PGRN protein is encoded by a codon-optimized nucleic acid sequence or the nucleic acid sequence in SEQ ID NO:68. In some embodiments, a symptom of FTD with GRN mutation may be a personality change, impairment of executive function, disinhibition, apathy, slow speech production, misuse of grammar, multimodal agnosia, semantic aphasia, or impaired word comprehension. In some embodiments, the rAAV encoding PGRN comprises a capsid protein having an AAV9 serotype.

In some embodiments, the disclosure provides a method for reducing lipofuscin accumulation in the brain of a subject having or suspected of having FTD with GRN mutation, the method comprising administering to the subject a composition comprising an rAAV encoding Progranulin (PGRN), wherein the PGRN protein is encoded by a codon-optimized nucleic acid sequence or the nucleic acid sequence in SEQ ID NO:68. In some aspects, the disclosure provides a method for reducing ubiquitin accumulation in the brain of a subject having or suspected of having FTD with GRN mutation, the method comprising administering to the subject a composition comprising an rAAV encoding Progranulin (PGRN), wherein the PGRN protein is encoded by a codon-optimized nucleic acid sequence or the nucleic acid sequence in SEQ ID NO:68. In some aspects, the disclosure provides a method for reducing gene expression and/or protein expression of TNFα and/or CD68 in the brain of a subject having or suspected of having FTD with GRN mutation, the method comprising administering to the subject a composition comprising an rAAV encoding Progranulin (PGRN), wherein the PGRN protein is encoded by a codon-optimized nucleic acid sequence or the nucleic acid sequence in SEQ ID NO:68. In some aspects, the disclosure provides a method for increasing the maturation of cathepsin D in the brain of a subject having or suspected of having FTD with GRN mutation, the method comprising administering to the subject a composition comprising an rAAV encoding Progranulin (PGRN), wherein the PGRN protein is encoded by a codon-optimized nucleic acid sequence or the nucleic acid sequence in SEQ ID NO:68. In some aspects, the disclosure provides a method for increasing the level of nuclear TDP-43 (transactive response DNA binding protein 43 kDa) protein in the brain of a subject having or suspected of having FTD with GRN mutation, the method comprising administering to the subject a composition comprising an rAAV encoding Progranulin (PGRN), wherein the PGRN protein is encoded by a codon-optimized nucleic acid sequence or the nucleic acid sequence in SEQ ID NO:68. In some embodiments, the disclosure provides a method for reducing a level of neurofilament light chain (NFL) in blood or CSF of a subject having or suspected of having FTD with GRN mutation, the method comprising administering to the subject a composition comprising an rAAV encoding Progranulin (PGRN), wherein the PGRN protein is encoded by a codon-optimized nucleic acid sequence or the nucleic acid sequence in SEQ ID NO:68. In some embodiments, the rAAV encoding PGRN comprises a capsid protein having an AAV9 serotype.

A subject is typically a mammal, preferably a human. In some embodiments, a subject is between the ages of 1 month old and 10 years old (e.g., 1 month, 2 months, 3 months, 4, months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 3, years, 4 years, 5 years, 6 years, 7 years, 8 years, 9 years, 10 years, or any age therebetween). In some embodiments, a subject is between 2 years old and 20 years old. In some embodiments, a subject is between 30 years old and 100 years old. In some embodiments, a subject is older than 55 years old.

In some embodiments, a composition is administered directly to the CNS of the subject, for example by direct injection into the brain and/or spinal cord of the subject. Examples of CNS-direct administration modalities include but are not limited to intracerebral injection, intraventricular injection, intracisternal injection, intraparenchymal injection, intrathecal injection, and any combination of the foregoing. In some embodiments, a composition is administered to a subject by intra-cisterna magna (ICM) injection. In some embodiments, direct injection into the CNS of a subject results in transgene expression (e.g., expression of the first gene product, second gene product, and if applicable, third gene product) in the midbrain, striatum and/or cerebral cortex of the subject. In some embodiments, direct injection into the CNS results in transgene expression (e.g., expression of the first gene product, second gene product, and if applicable, third gene product) in the spinal cord and/or CSF of the subject.

In some embodiments, direct injection to the CNS of a subject comprises convection enhanced delivery (CED). Convection enhanced delivery is a therapeutic strategy that involves surgical exposure of the brain and placement of a small-diameter catheter directly into a target area of the brain, followed by infusion of a therapeutic agent (e.g., a composition or rAAV as described herein) directly to the brain of the subject. CED is described, for example by Debinski et al. (2009) Expert Rev Neurother. 9(10):1519-27.

In some embodiments, a composition is administered peripherally to a subject, for example by peripheral injection. Examples of peripheral injection include subcutaneous injection, intravenous injection, intra-arterial injection, intraperitoneal injection, or any combination of the foregoing. In some embodiments, the peripheral injection is intra-arterial injection, for example injection into the carotid artery of a subject.

In some embodiments, a composition (e.g., a composition comprising an isolated nucleic acid or a vector or a rAAV) as described by the disclosure is administered both peripherally and directly to the CNS of a subject. For example, in some embodiments, a subject is administered a composition by intra-arterial injection (e.g., injection into the carotid artery) and by intraparenchymal injection (e.g., intraparenchymal injection by CED). In some embodiments, the direct injection to the CNS and the peripheral injection are simultaneous (e.g., happen at the same time). In some embodiments, the direct injection occurs prior (e.g., between 1 minute and 1 week, or more before) to the peripheral injection. In some embodiments, the direct injection occurs after (e.g., between 1 minute and 1 week, or more after) the peripheral injection.

In some embodiments, a subject is administered an immunosuppressant prior to (e.g., between 1 month and 1 minute prior to) or at the same time as a composition as described herein. In some embodiments, the immunosuppressant is a corticosteroid (e.g., prednisone, budesonide, etc.), an mTOR inhibitor (e.g., sirolimus, everolimus, etc.), an antibody (e.g., adalimumab, etanercept, natalizumab, etc.), or methotrexate.

The amount of composition (e.g., a composition comprising an isolated nucleic acid or a vector or a rAAV) as described by the disclosure administered to a subject will vary depending on the administration method. For example, in some embodiments, a rAAV as described herein is administered to a subject at a titer between about $10^9$ Genome copies (GC)/kg and about $10^{14}$ GC/kg (e.g., about $10^9$ GC/kg, about $10^{10}$ GC/kg, about $10^{11}$ GC/kg, about $10^{12}$ GC/kg, about $10^{12}$ GC/kg, or about $10^{14}$ GC/kg). In some embodiments, a subject is administered a high titer (e.g., $>10^{12}$ Genome Copies GC/kg of an rAAV) by injection to the CSF space, or by intraparenchymal injection. In some embodiments, a rAAV as described herein is administered to a subject at a dose ranging from about $1\times10^{10}$ vector genomes (vg) to about $1\times10^{17}$ vg by intravenous injection. In some embodiments, a rAAV as described herein is administered to a subject at a dose ranging from about $1\times10^{10}$ vg to about $1\times10^{16}$ vg by injection into the cisterna magna.

A composition (e.g., a composition comprising an isolated nucleic acid or a vector or a rAAV) as described by the disclosure can be administered to a subject once or multiple times (e.g., 2, 3, 4, 5, 6, 7, 8, 9, 10, 20, or more) times. In some embodiments, a composition is administered to a subject continuously (e.g., chronically), for example via an infusion pump.

EXAMPLES

Example 1: rAAV Vectors

AAV vectors are generated using cells, such as HEK293 cells for triple-plasmid transfection. The ITR sequences flank an expression construct comprising a promoter/enhancer element for each transgene of interest, a 3' polyA signal, and posttranslational signals such as the WPRE element. Multiple gene products can be expressed simultaneously such as GBA1 and LIMP2 and/or Prosaposin, by fusion of the protein sequences; or using a 2A peptide linker, such as T2A or P2A, which leads 2 peptide fragments with added amino acids due to prevention of the creation of a peptide bond; or using an IRES element; or by expression with 2 separate expression cassettes. The presence of a short intronic sequence that is efficiently spliced, upstream of the expressed gene, can improve expression levels. shRNAs and other regulatory RNAs can potentially be included within these sequences. Examples of expression constructs described by the disclosure are shown in FIGS. 1-8, 21-35, 39, 41-51 and 64 and in Table 2 below.

TABLE 2

| Name | Promoter 1 | shRNA | CDS1 | PolyA 1 | Bicistronic element | Promoter 2 | CDS2 | PolyA2 | Length between ITRs |
|---|---|---|---|---|---|---|---|---|---|
| CMVe_CBAp_GBA1_WPRE_bGH | CBA | | GBA1 | WPRE-bGH | | | | | 3741 |
| LT1s_JetLong_mRNAiaSYn_SCARB2-T2A-GBA1_bGH | JetLong | aSyn | SCARB2 | bGH | T2A | | GBA1 | | 4215 |
| LI1_JetLong_SCARB2-IRES-GBA1_bGH | JetLong | | SCARB2 | bGH | IRES | | GBA1 | | 4399 |
| FP1_JetLong_GBA1_bGH_JetLong_SCARB2_SV40L | JetLong | | GBA1 | bGH | | JetLong | SCARB2 | SV40L | 4464 |
| PrevailVector_LT2s_JetLong_mRNAiaSYn_PSAP-T2A-GBA1_bGH_4353nt | JetLong | aSyn | PSAP | bGH | T2A | — | GBA1 | — | 4353 |
| PrevailVector_LI2_JetLong_PSAP_TRES_GBA1_SymtheticpolyA_4337nt | JetLong | — | PSAP | Synthetic pA | IRES | — | GBA1 | — | 4337 |
| PrevailVector_10s_JetLong_mRNAiaSy_GBA2_WPRE_bGH_4308nt | JetLong | aSyn | GBA2 | WPRE_bGH | — | — | — | — | 4308 |
| PrevailVector_FT4_JetLong_GBA1_T2A_GALC_SyntheticpolyA_4373nt | JetLong | — | GBA1 | Synthetic pA | T2A | — | GALC | — | 4373 |
| PrevailVector_LT4_JetLong_GALC_T2A_GBA1_SyntheticpolyA_4373nt | JetLong | — | GALC | Synthetic pA | T2A | — | GBA1 | — | 4373 |
| PrevailVector_LT5s_JetLong_mRNAiaSyn_CTSB-T2A-GBA1_WPRE_bGH_4392nt | JetLong | aSyn | CTSB | WPRE_bGH | T2A | — | GBA1 | — | 4392 |
| Prevail_Vector_FT11t_JetLong_mRNAiaSyn_GBA1_T2S_SMPD1_SyntheticpolyA_4477nt | JetLong | aSyn | GBA1 | Synthetic pA | T2A | — | SMPD1 | — | 4477 |
| PrevailVector_LI4_JetLong_GALC_TRES_GBA1_SymtheticpolyA_4820nt | JetLong | — | GALC | Synthetic pA | IRES | — | GBA1 | — | 4820 |
| PrevailVector_FP5_JetLong_GBA1_bGH_JetLong_CTSB_SV40l_4108nt | JetLong | — | GBA1 | bGH | — | JetLong | CTSB | SV40L | 4108 |
| PrevailVector_FT6s_JetLong_mRNAiaSyn_GBA1-T2A-GCH1_WPRE_bGH_4125nt | JetLong | aSyn | GBA1 | WPRE_bGH | T2A | — | GCH1 | — | 4125 |
| PrevailVector_LT7s_JetLong_mRNAiaSyn_RAB7L1-T2A-GBA1_WPRE_bGH_3984nt | JetLong | aSyn | RAB7L1 | WPRE_bGH | T2A | — | GBA1 | — | 3984 |
| PrevailVector_FI6s_JetLong_mRNAiaSYn_GBA1-IRES-GCH1_bGH_3978nt | JetLong | aSyn | GBA1 | bGH | IRES | — | GCH1 | — | 3978 |
| PrevailVector_9st_JetLong_mRNAiaSyn_mRNAiTMEM106B_VPS35_WPRE_bGH_4182nt | JetLong | aSyn & TMEM106B | VPS35 | WPRE_bGH | — | — | — | — | 4182 |
| PrevailVector_FT12s_JetLong_mRNAiaSyn_GBA1-T2A-IL34_WPRE_bGH_4104nt | JetLong | aSyn | GBA1 | WPRE_bGH | T2A | — | IL34 | — | 4104 |
| PrevailVector_FI12s_JetLong_mRNAiaSYn_GBA1-IRES-IL34_bGH_3957nt | JetLong | aSyn | GBA1 | bGH | IRES | — | IL34 | — | 3957 |
| PrevailVector_FP8_JetLong_GBA1_bGH_CD68_TREM2_SV40l_4253nt | JetLong | — | GBA1 | bGH | — | CD68 | TREM2 | SV40L | 4253 |
| PrevailVector_FP12_CMVe_CBA_GBA1_bGH_JetLong_IL34_SV40l_4503nt | CBA | | GBA1 | bGH | | JetLong | IL34 | SV40L | 4503 |

Example 2: Cell Based Assays of Viral Transduction into GBA-Deficient Cells

Cells deficient in GBA1 are obtained, for example as fibroblasts from GD patients, monocytes, or hES cells, or patient-derived induced pluripotent stem cells (iPSCs). These cells accumulate substrates such as glucosylceramide and glucosylsphingosine (GlcCer and GlcSph). Treatment of wild-type or mutant cultured cell lines with Gcase inhibitors, such as CBE, is also be used to obtain GBA deficient cells.

Using such cell models, lysosomal defects are quantified in terms of accumulation of protein aggregates, such as of α-Synuclein with an antibody for this protein or phospho-αSyn, followed by imaging using fluorescent microscopy. Imaging for lysosomal abnormalities by ICC for protein markers such as LAMP1, LAMP2, LIMP1, LIMP2, or using dyes such as Lysotracker, or by uptake through the endocytic compartment of fluorescent dextran or other markers is also performed. Imaging for autophagy marker accumulation due to defective fusion with the lysosome, such as for LC3, can also be performed. Western blotting and/or ELISA is used to quantify abnormal accumulation of these markers. Also, the accumulation of glycolipid substrates and products of GBA1 is measured using standard approaches.

Therapeutic endpoints (e.g., reduction of PD-associated pathology) are measured in the context of expression of transduction of the AAV vectors, to confirm and quantify activity and function. Gcase can is also quantified using protein ELISA measures, or by standard Gcase activity assays.

Example 3: In Vivo Assays Using Mutant Mice

This example describes in vivo assays of AAV vectors using mutant mice. In vivo studies of AAV vectors as above in mutant mice are performed using assays described, for example, by Liou et al. (2006) *J. Biol. Chem.* 281(7): 4242-4253, Sun et al. (2005) *J. Lipid Res.* 46:2102-2113, and Farfel-Becker et al. (2011) *Dis. Model Mech.* 4(6):746-752.

The intrathecal or intraventricular delivery of vehicle control and AAV vectors (e.g., at a dose of $2\times10^{11}$ vg/mouse) are performed using concentrated AAV stocks, for example at an injection volume between 5-10 pt. Intraparenchymal delivery by convection enhanced delivery is performed.

Treatment is initiated either before onset of symptoms, or subsequent to onset. Endpoints measured are the accumulation of substrate in the CNS and CSF, accumulation of Gcase enzyme by ELISA and of enzyme activity, motor and cognitive endpoints, lysosomal dysfunction, and accumulation of α-Synuclein monomers, protofibrils or fibrils.

Example 4: Chemical Models of Disease

This example describes in vivo assays of AAV vectors using a chemically-induced mouse model of Gaucher disease (e.g., the CBE mouse model). In vivo studies of these AAV vectors are performed in a chemically-induced mouse model of Gaucher disease, for example as described by Vardi et al. (2016) *J Pathol.* 239(4):496-509.

Intrathecal or intraventricular delivery of vehicle control and AAV vectors (e.g., at a dose of $2\times10^{11}$ vg/mouse) are performed using concentrated AAV stocks, for example with injection volume between 5-10 μL. Intraparenchymal delivery by convection enhanced delivery is performed. Peripheral delivery is achieved by tail vein injection.

Treatment is initiated either before onset of symptoms, or subsequent to onset. Endpoints measured are the accumulation of substrate in the CNS and CSF, accumulation of Gcase enzyme by ELISA and of enzyme activity, motor and cognitive endpoints, lysosomal dysfunction, and accumulation of α-Synuclein monomers, protofibrils or fibrils.

Example 5: Clinical Trials in PD, LBD, Gaucher Disease Patients

In some embodiments, patients having certain forms of Gaucher disease (e.g., GD1) have an increased risk of developing Parkinson's disease (PD) or Lewy body dementia (LBD). This Example describes clinical trials to assess the safety and efficacy of rAAVs as described by the disclosure, in patients having Gaucher disease, PD and/or LBD.

Clinical trials of such vectors for treatment of Gaucher disease, PD and/or LBD are performed using a study design similar to that described in Grabowski et al. (1995) *Ann. Intern. Med.* 122(1):33-39.

Example 6: Treatment of Peripheral Disease

In some embodiments, patients having certain forms of Gaucher disease exhibit symptoms of peripheral neuropathy, for example as described in Biegstraaten et al. (2010) *Brain* 133(10):2909-2919.

This example describes in vivo assays of AAV vectors as described herein for treatment of peripheral neuropathy associated with Gaucher disease (e.g., Type 1 Gaucher disease). Briefly, Type 1 Gaucher disease patients identified as having signs or symptoms of peripheral neuropathy are administered a rAAV as described by the disclosure. In some embodiments, the peripheral neuropathic signs and symptoms of the subject are monitored, for example using methods described in Biegstraaten et al., after administration of the rAAV.

Levels of transduced gene products as described by the disclosure present in patients (e.g., in serum of a patient, in peripheral tissue (e.g., liver tissue, spleen tissue, etc.)) of a patient are assayed, for example by Western blot analysis, enzymatic functional assays, or imaging studies.

Example 7: Treatment of CNS Forms

This example describes in vivo assays of rAAVs as described herein for treatment of CNS forms of Gaucher disease. Briefly, Gaucher disease patients identified as having a CNS form of Gaucher disease (e.g., Type 2 or Type 3 Gaucher disease) are administered a rAAV as described by the disclosure. Levels of transduced gene products as described by the disclosure present in the CNS of patients (e.g., in serum of the CNS of a patient, in cerebrospinal fluid (CSF) of a patient, or in CNS tissue of a patient) are assayed, for example by Western blot analysis, enzymatic functional assays, or imaging studies.

Example 8: Gene Therapy of Parkinson's Disease in Subjects Having Mutations in GBA1

This example describes administration of a recombinant adeno-associated virus (rAAV) encoding GBA1 to a subject having Parkinson's disease characterized by a mutation in GBA/gene.

The rAAV-GBA1 vector insert contains the CBA promoter element (CBA), consisting of four parts: the CMV enhancer (CMVe), CBA promoter (CBAp), Exon 1, and intron (int) to constitutively express the codon optimized coding sequence (CDS) of human GBA1 (maroon). The 3' region also contains a Woodchuck hepatitis virus Posttranscriptional Regulatory Element (WPRE) followed by a bovine Growth Hormone polyA signal (bGH polyA) tail. The flanking ITRs allow for the correct packaging of the intervening sequences. Two variants of the 5' ITR sequence (FIG. 7, inset box, bottom sequence) were evaluated; these variants have several nucleotide differences within the 20-nucleotide "D" region of the ITR, which is believed to impact the efficiency of packaging and expression. The rAAV-GBA1 vector product contains the "D" domain nucleotide sequence shown in FIG. 7 (inset box, top sequence). A variant vector harbors a mutant "D" domain (termed an "S" domain herein, with the nucleotide changes shown by shading), performed similarly in preclinical studies. The backbone contains the gene to confer resistance to kanamycin as well as a stuffer sequence to prevent reverse packaging. A schematic depicting a rAAV-GBA1 vector is shown in FIG. 8. The rAAV-GBA1 vector is packaged into an rAAV using AAV9 serotype capsid proteins.

rAAV-GBA1 is administered to a subject as a single dose via a fluoroscopy guided sub-occipital injection into the cisterna magna (intracisternal magna; ICM). One embodiment of a rAAV-GBA1 dosing regimen study is as follows:

A single dose of rAAV-GBA1 is administered to patients (N=12) at one of two dose levels (3e13 vg (low dose); 1e14 vg (high dose), etc.) which are determined based on the results of nonclinical pharmacology and toxicology studies.

Initial studies were conducted in a chemical mouse model involving daily delivery of conduritol-b-epoxide (CBE), an inhibitor of GCase to assess the efficacy and safety of the rAAV-GBA1 vector and a rAAV-GBA1 S-variant construct (as described further below). Additionally, initial studies were performed in a genetic mouse model, which carries a homozygous GBA1 mutation and is partially deficient in saposins (4L/PS-NA). Additional dose-ranging studies in mice and nonhuman primates (NHPs) are conducted to further evaluate vector safety and efficacy.

Figure 7:
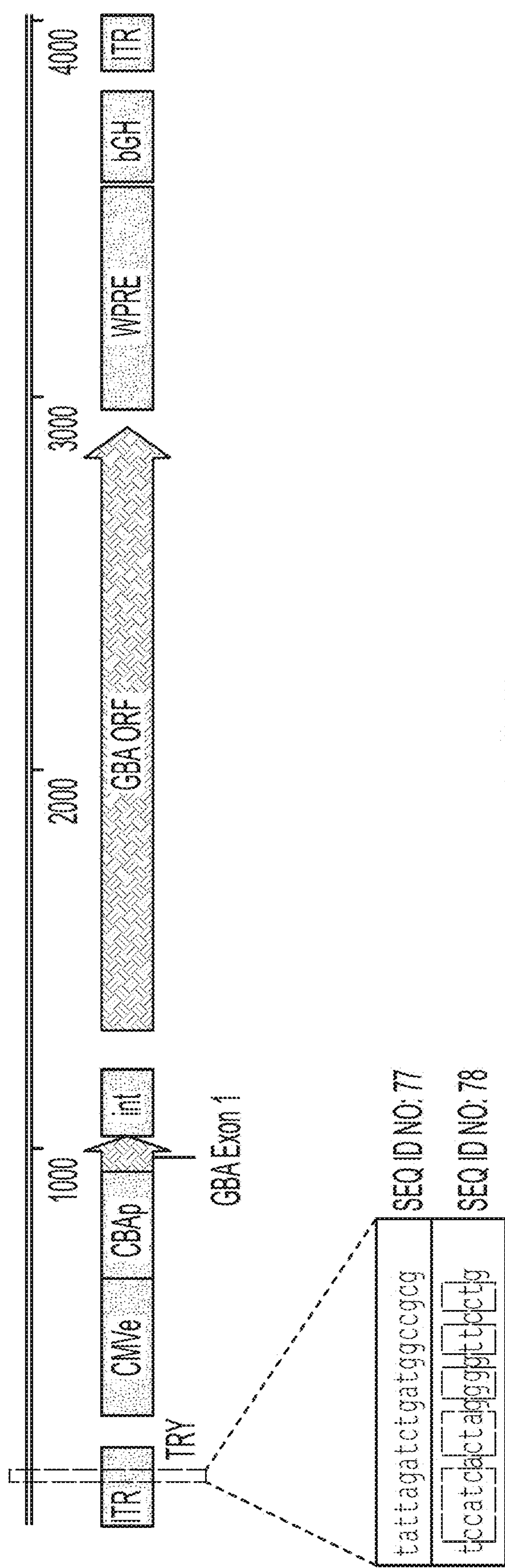
FIG. 7 is a schematic depicting one embodiment of a vector comprising an expression construct encoding a Gcase (e.g., GBA1 or a portion thereof). In this embodiment, the vector comprises a CBA promoter element (CBA), consisting of four parts: the CMV enhancer (CMVe), CBA promoter (CBAp), Exon 1, and intron (int) to constitutively express the codon optimized coding sequence of human GBA1. The 3' region also contains a WPRE regulatory element followed by a bGH polyA tail. Three transcriptional regulatory activation sites are included at the 5' end of the promoter region: TATA, RBS, and YY1. The flanking ITRs allow for the correct packaging of the intervening sequences. Two variants of the 5' ITR sequence (inset box) were evaluated; these have several nucleotide differences within the 20-nucleotide "D" region of wild-type AAV2 ITR. In some embodiments, an rAAV vector contains the "D" domain nucleotide sequence shown on the top line. In some embodiments, a rAAV vector comprises a mutant "D" domain (e.g., an "S" domain, with the nucleotide changes shown on the bottom line).
Figure 8:
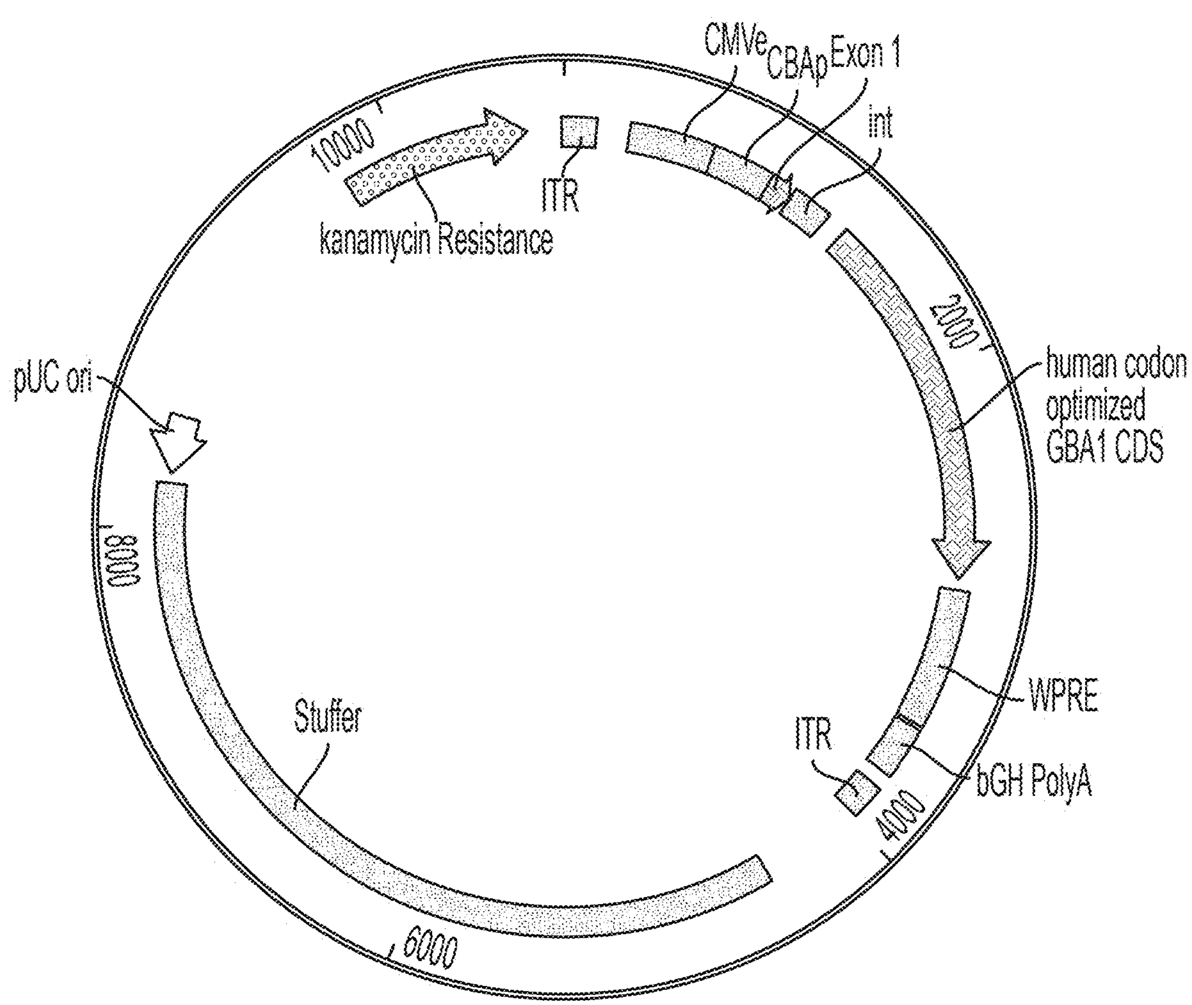
FIG. 8 is a schematic depicting one embodiment of the vector described in FIG. 6

Two slightly different versions of the 5' inverted terminal repeat (ITR) in the AAV backbone were tested to assess manufacturability and transgene expression (FIG. 7). The 20 bp "D" domain within the 145 bp 5' ITR is thought to be necessary for optimal viral vector production, but mutations within the "D" domain have also been reported to increase transgene expression in some cases. Thus, in addition to the viral vector rAAV-GBA1, which harbors an intact "D" domain, a second vector form with a mutant D domain (termed an "S" domain herein) was also evaluated. Both rAAV-GBA1 and the variant express the same transgene. While both vectors produced virus that was efficacious in vivo as detailed below, rAAV-GBA1, which contains a wild-type "D" domain, was selected for further development.

Figure 9:
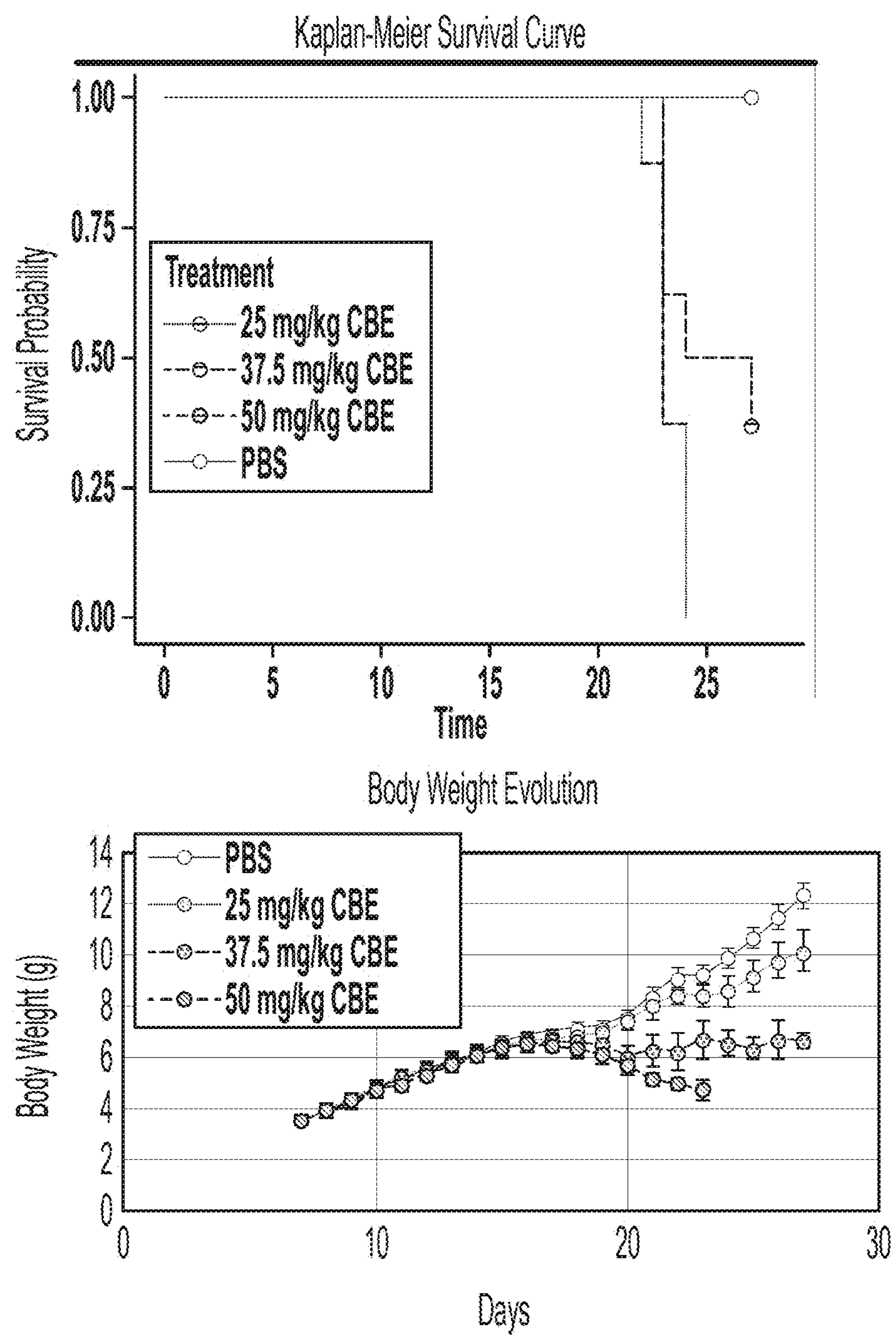
FIG. 9 shows representative data for delivery of an rAAV comprising a transgene encoding a Gcase (e.g., GBA1 or a portion thereof) in a CBE mouse model of Parkinson's disease. Daily IP delivery of PBS vehicle, 25 mg/kg CBE, 37.5 mg/kg CBE, or 50 mg/kg CBE (left to right) initiated at P8. Survival (top left) was checked two times a day and weight (top right) was checked daily. All groups started with n=8. Behavior was assessed by total distance traveled in Open Field (bottom left) at P23 and latency to fall on Rotarod (bottom middle) at P24. Levels of the GCase substrates were analyzed in the cortex of mice in the PBS and 25 mg/kg CBE treatment groups both with (Day 3) and without (Day 1) CBE withdrawal. Aggregate GluSph and GalSph levels (bottom right) are shown as pmol per mg wet weight of the tissue. Means are presented. Error bars are SEM. *$p<0.05$; $p<0.01$; *$p<0.001$, nominal p-values for treatment groups by linear regression.
Figure 9:
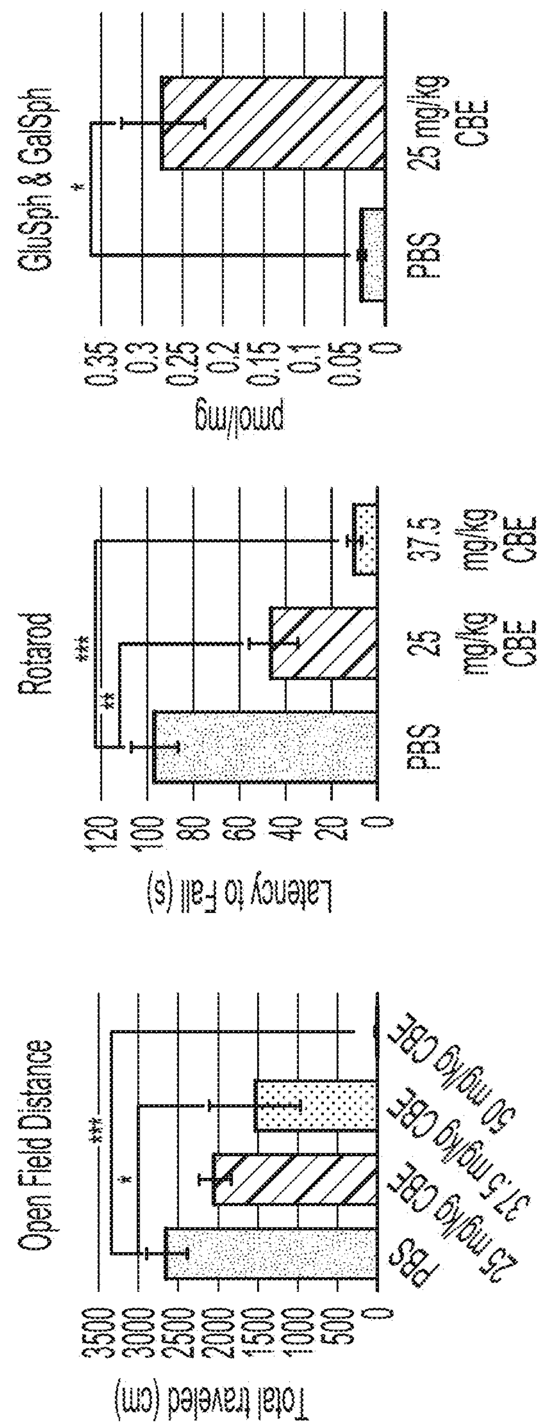

To establish the CBE model of GCase deficiency, juvenile mice were dosed with CBE, a specific inhibitor of GCase. Mice were given CBE by IP injection daily, starting at postnatal day 8 (P8). Three different CBE doses (25 mg/kg, 37.5 mg/kg, 50 mg/kg) and PBS were tested to establish a model that exhibits a behavioral phenotype (FIG. 9). Higher doses of CBE led to lethality in a dose-dependent manner. All mice treated with 50 mg/kg CBE died by P23, and 5 of the 8 mice treated with 37.5 mg/kg CBE died by P27. There was no lethality in mice treated with 25 mg/kg CBE. Whereas CBE-injected mice showed no general motor deficits in the open field assay (traveling the same distance and at the same velocity as mice given PBS), CBE-treated mice exhibited a motor coordination and balance deficit as measured by the rotarod assay.

Mice surviving to the end of the study were sacrificed on the day after their last CBE dose (P27, "Day 1") or after three days of CBE withdrawal (P29, "Day 3"). Lipid analysis was performed on the cortex of mice given 25 mg/kg CBE to evaluate the accumulation of GCase substrates in both the Day 1 and Day 3 cohorts. GluSph and GalSph levels (measured in aggregate in this example) were significantly accumulated in the CBE-treated mice compared to PBS-treated controls, consistent with GCase insufficiency.

Figure 10:
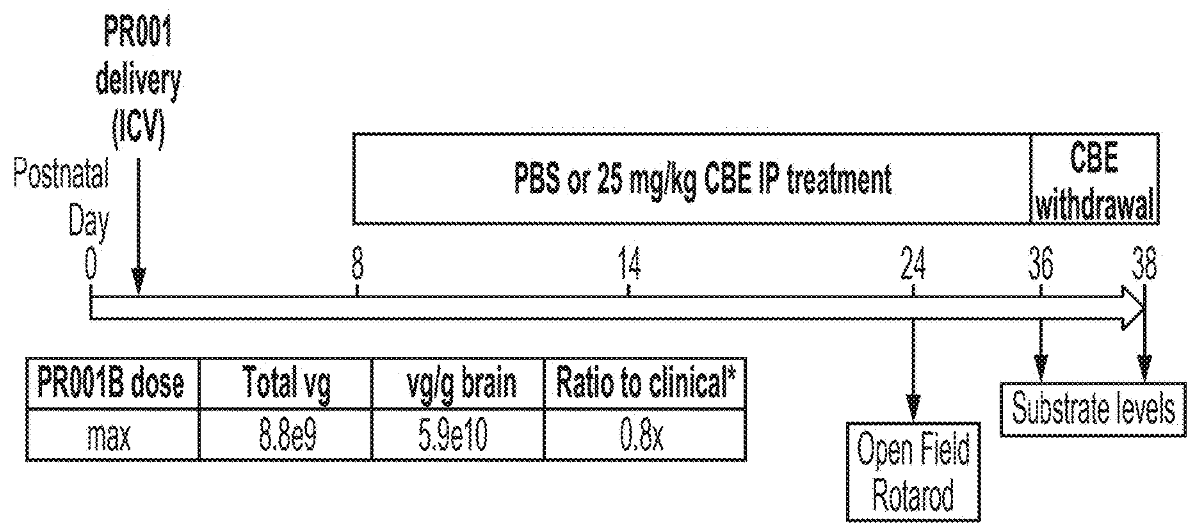
FIG. 10 is a schematic depicting one embodiment of a study design for maximal rAAV dose in a CBE mouse model. Briefly, rAAV was delivered by ICV injection at P3, and daily CBE treatment was initiated at P8. Behavior was assessed in the Open Field and Rotarod assays at P24-25 and substrate levels were measured at P36 and P38.

Based on the study described above, the 25 mg/kg CBE dose was selected since it produced behavioral deficits without impacting survival. To achieve widespread GBA1 distribution throughout the brain and transgene expression during CBE treatment, rAAV-GBA1 or excipient was delivered by intracerebroventricular (ICV) injection at postnatal day 3 (P3) followed by daily IP CBE or PBS treatment initiated at P8 (FIG. 10).

Figure 11:
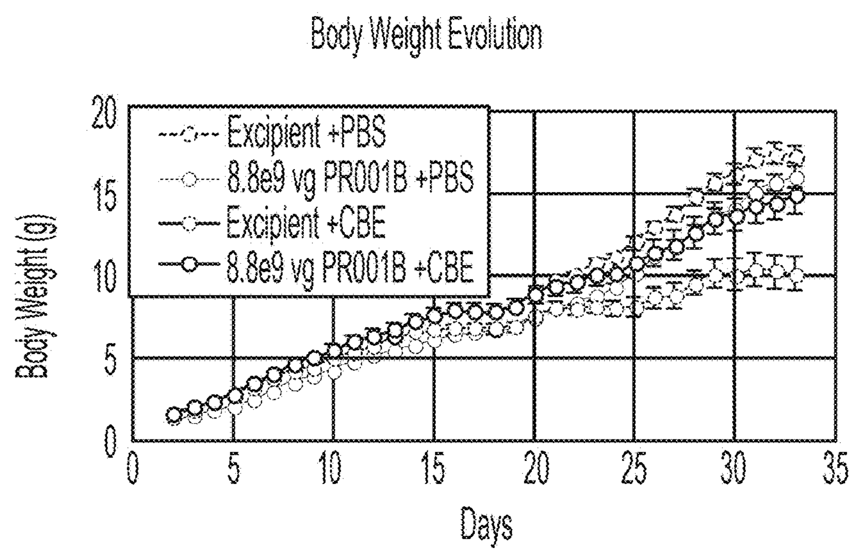
FIG. 11 shows representative data for in-life assessment of maximal rAAV dose in a CBE mouse model. At P3, mice were treated with either excipient or 8.8e9 vg rAAV-GBA1 via ICV delivery. Daily IP delivery of either PBS or 25 mg/kg CBE was initiated at P8. At the end of the study, half the mice were sacrificed one day after their last CBE dose at P36 (Day 1) while the remaining half went through 3 days of CBE withdrawal before sacrifice at P38 (Day3). All treatment groups (excipient+PBS n=8, rAAV-GBA1+PBS n=7, excipient+CBE n=8, and variant+CBE n=9) were weighed daily (top left), and the weight at P36 was analyzed (top right). Behavior was assessed by total distance traveled in Open Field at P23 (bottom left) and latency to fall on Rotarod at P24 (bottom right), evaluated for each animal as the median across 3 trials. Due to lethality, n=7 for the excipient+CBE group for the behavioral assays, while n=8 for all other groups. Means across animals are presented. Error bars are SEM. *$p<0.05$; ***$p<0.001$, nominal p-values for treatment groups by linear regression in the CBE-treated animals.
Figure 11:
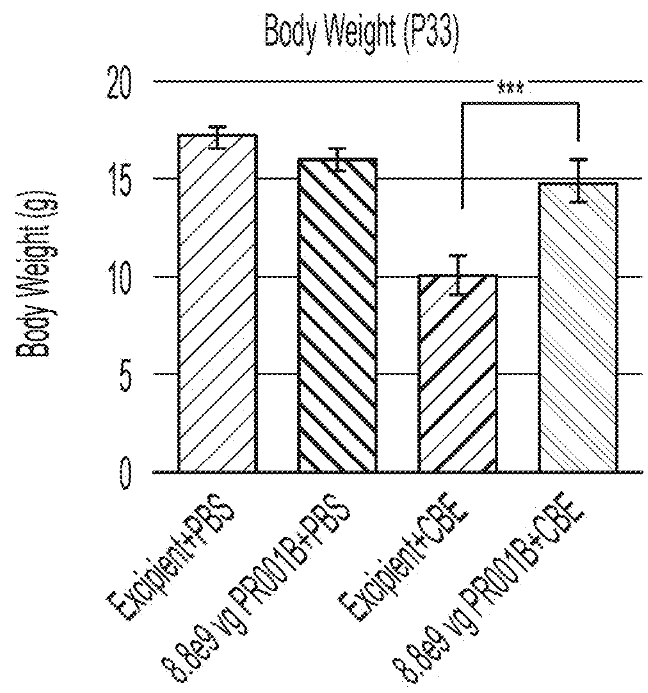
Figure 11:
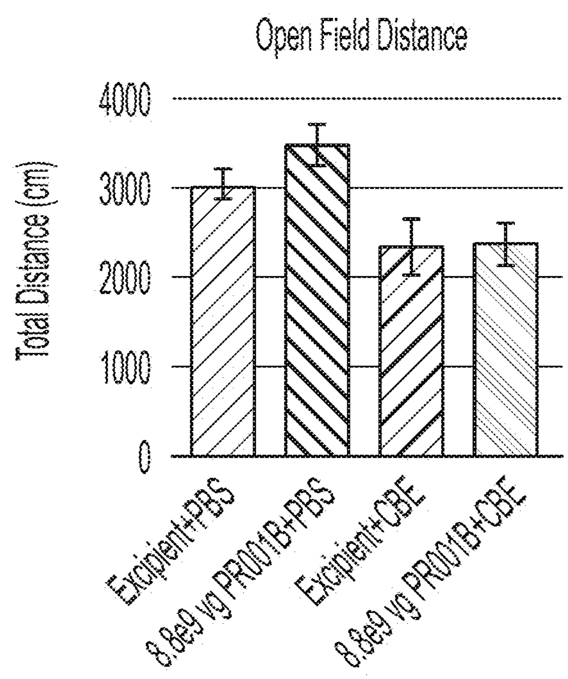
Figure 11:
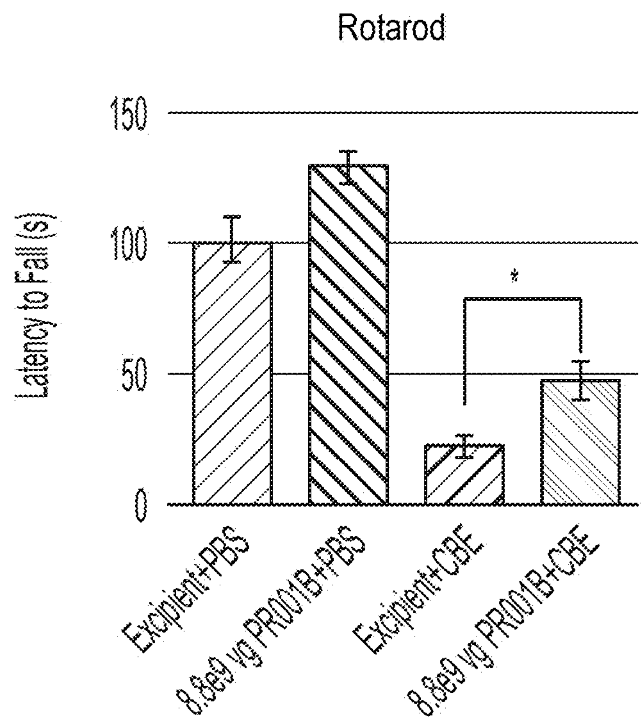

CBE-treated mice that received rAAV-GBA1 performed statistically significantly better on the rotarod than those that received excipient (FIG. 11). Mice in the variant treatment group did not differ from excipient treated mice in terms of other behavioral measures, such as the total distance traveled during testing (FIG. 11).

Figure 12:
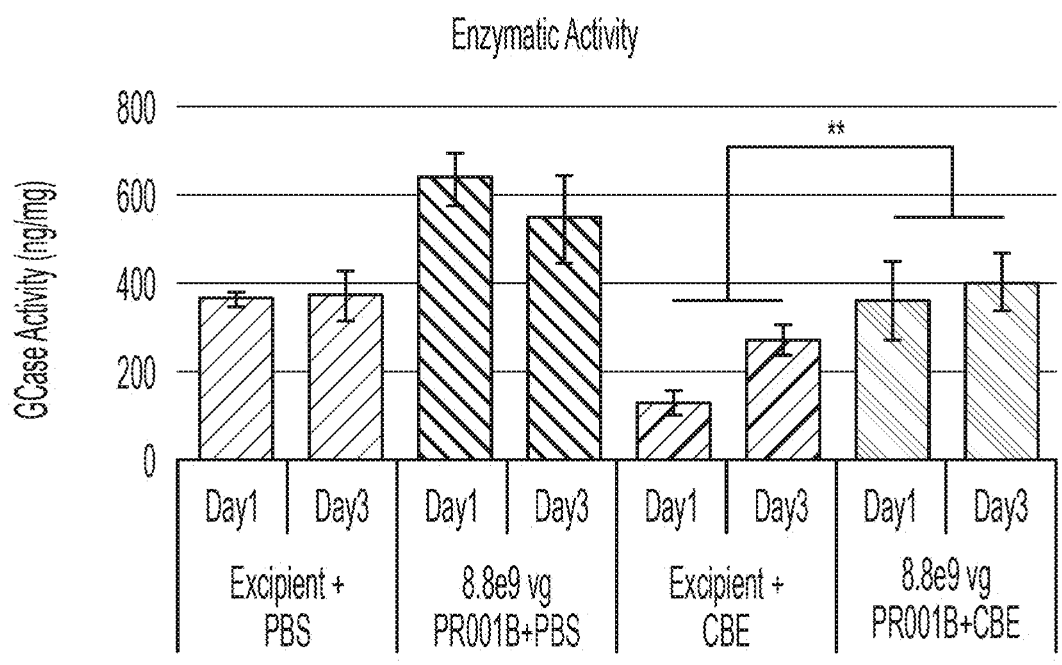
FIG. 12 shows representative data for biochemical assessment of maximal rAAV dose in a CBE mouse model. The cortex of all treatment groups (excipient+PBS n=8, variant+PBS n=7, excipient+CBE n=7, and variant+CBE n=9) was used to measure GCase activity (top left), GluSph levels (top right), GluCer levels (bottom left), and vector genomes (bottom right) in the groups before (Day 1) or after (Day 3) CBE withdrawal. Biodistribution is shown as vector genomes per 1 μg of genomic DNA. Means are presented. Error bars are SEM. (*)$p<0.1$; $p<0.01$; *$p<0.001$, nominal p-values for treatment groups by linear regression in the CBE-treated animals, with collection days and gender corrected for as covariates.
Figure 12:
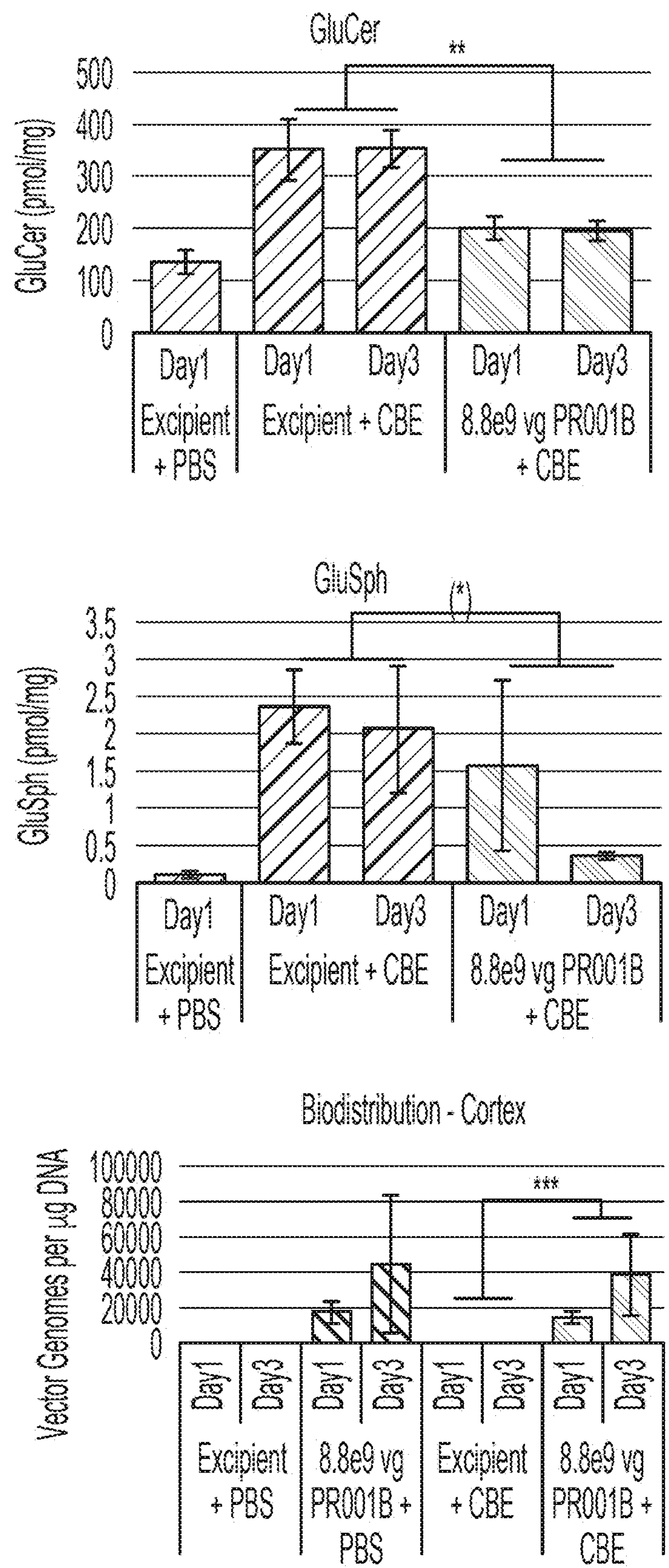

At the completion of the in-life study, half of the mice were sacrificed the day after the last CBE dose (P36, "Day 1") or after three days of CBE withdrawal (P38, "Day 3") for biochemical analysis (FIG. 12). Using a fluorometric enzyme assay performed in biological triplicate, GCase activity was assessed in the cortex. GCase activity was increased in mice that were treated with rAAV-GBA1, while CBE treatment reduced GCase activity. Additionally, mice that received both CBE and rAAV-GBA1 had GCase activity levels that were similar to the PBS-treated group, indicating that delivery of rAAV-GBA1 is able to overcome the inhibition of GCase activity induced by CBE treatment. Lipid analysis was performed on the motor cortex of the mice to examine levels of the substrates GluCer and GluSph. Both lipids accumulated in the brains of mice given CBE, and rAAV-GBA1 treatment significantly reduced substrate accumulation.

Figure 13:
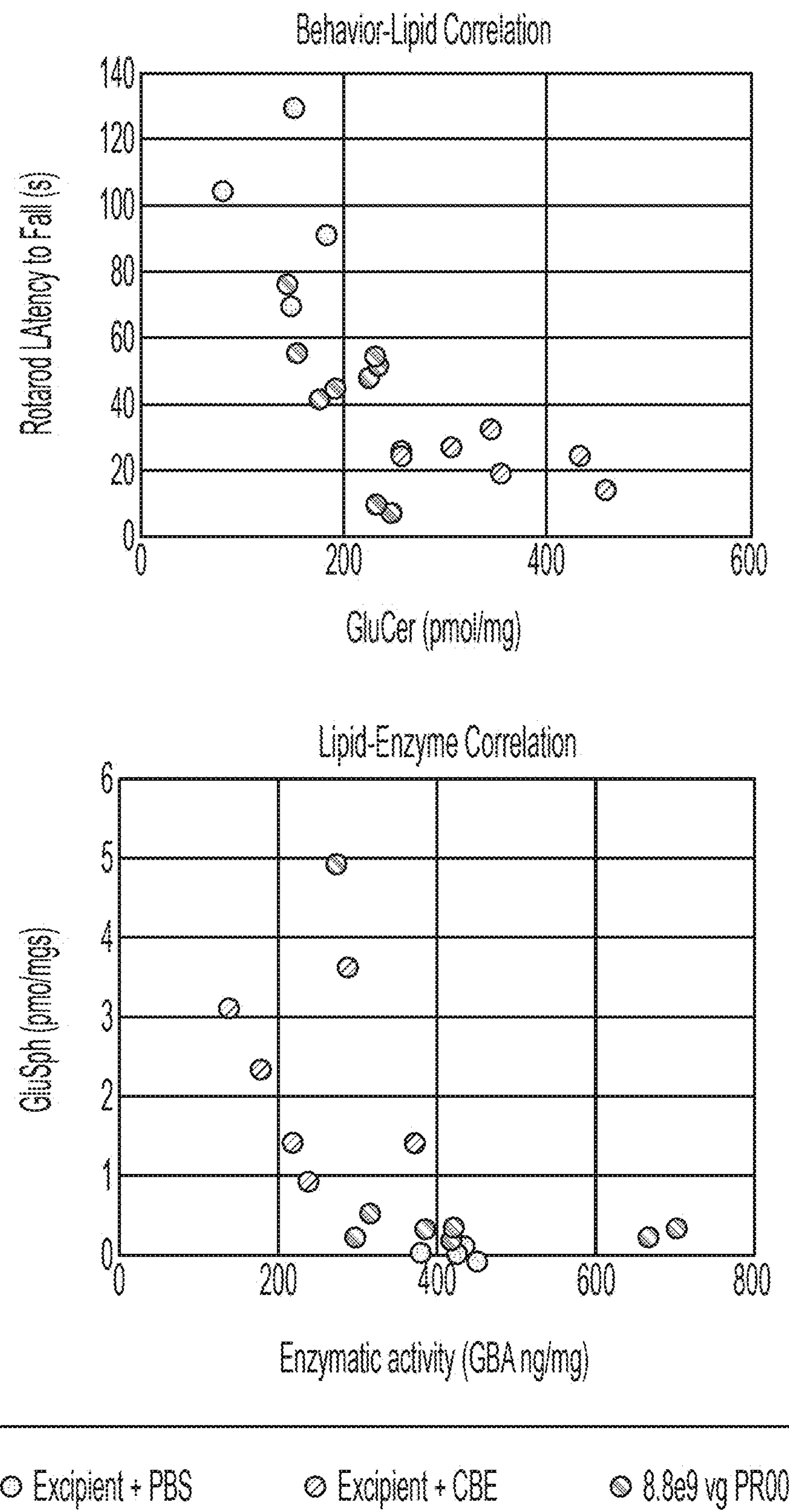
FIG. 13 shows representative data for behavioral and biochemical correlations in a CBE mouse model after administration of excipient+PBS, excipient+CBE, and variant+CBE treatment groups. Across treatment groups, performance on Rotarod was negatively correlated with GluCer accumulation (A, p=0.0012 by linear regression), and GluSph accumulation was negatively correlated with increased GCase activity (B, p=0.0086 by linear regression).
Figure 14:
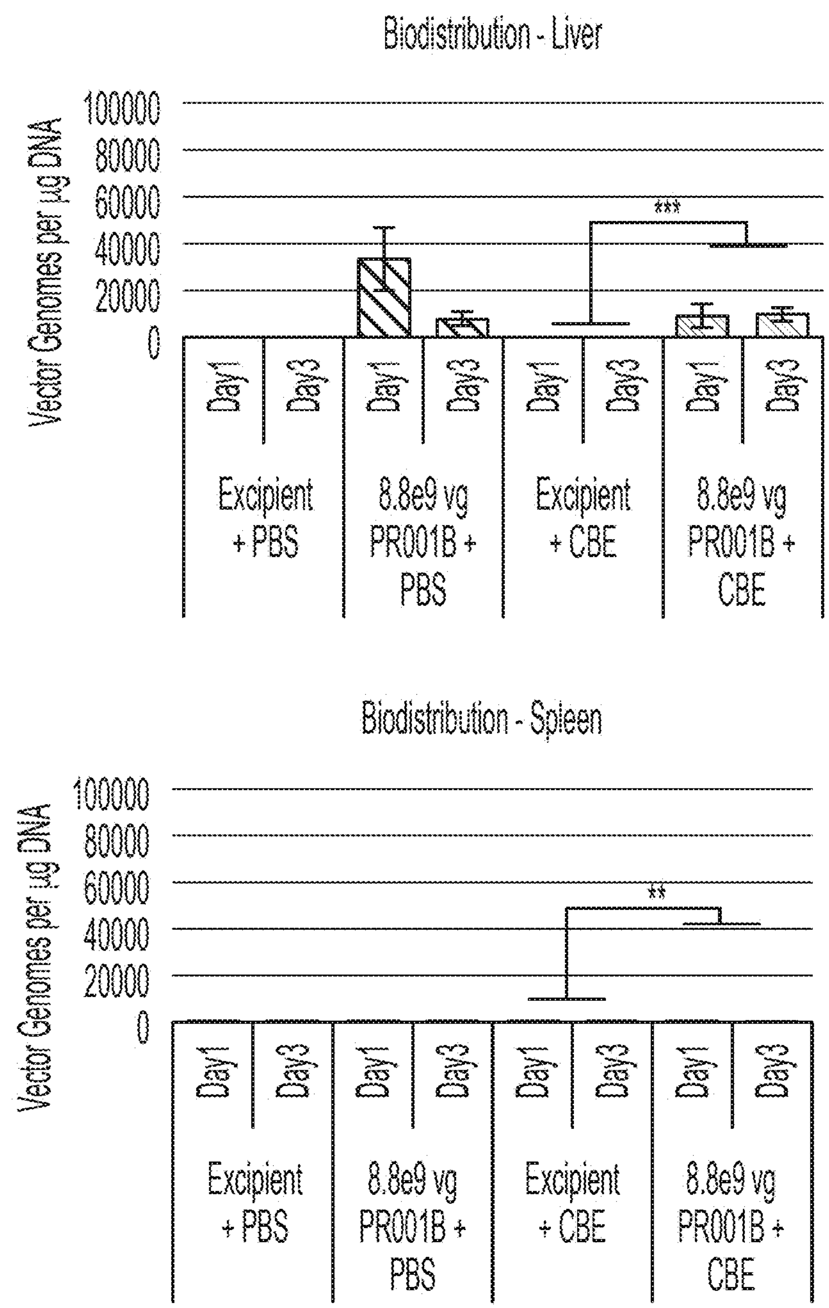
FIG. 14 shows representative data for biodistribution of variant in a CBE mouse model. Presence of vector genomes was assessed in the liver, spleen, kidney, and gonads for all treatment groups (excipient+PBS n=8, variant+PBS n=7, excipient+CBE n=7, and variant+CBE n=9). Biodistribution is shown as vector genomes per 1 μg of genomic DNA. Vector genome presence was quantified by quantitative PCR using a vector reference standard curve; genomic DNA concentration was evaluated by A260 optical density measurement. Means are presented. Error bars are SEM. *p<0.05; p<0.01; *p<0.001, nominal p-values for treatment groups by linear regression in the CBE-treated animals, with collection days and gender corrected for as covariates.
Figure 14:
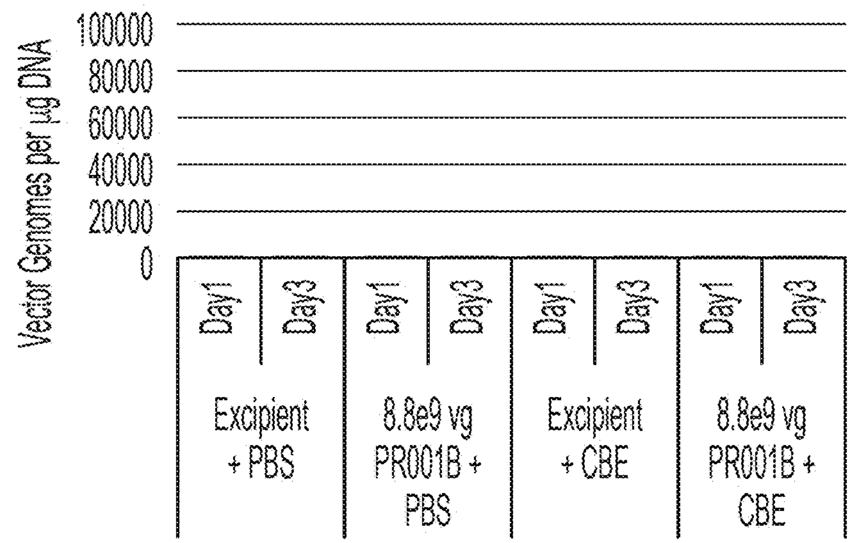
Figure 14:
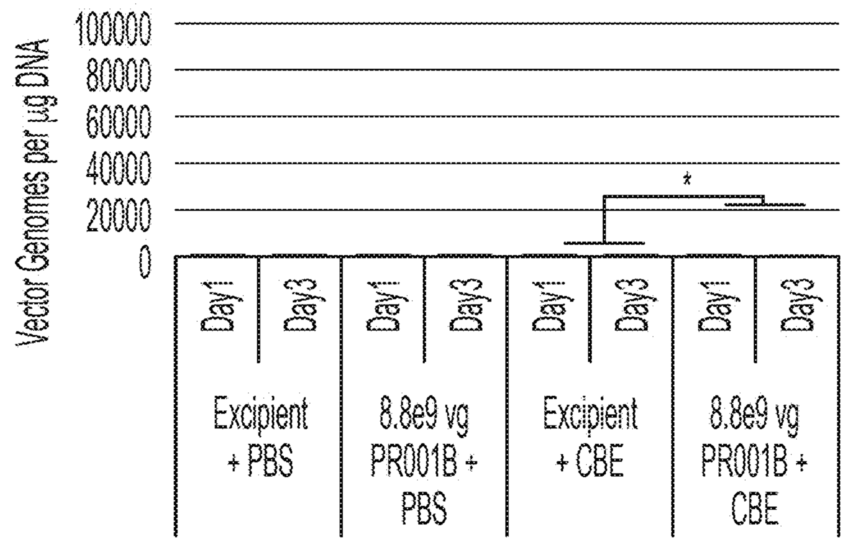

Lipid levels were negatively correlated with both GCase activity and performance on the Rotarod across treatment groups. The increased GCase activity after rAAV-GBA1 administration was associated with substrate reduction and enhanced motor function (FIG. 13). As shown in FIG. 14, preliminary biodistribution was assessed by vector genome presence, as measured by qPCR (with >100 vector genomes per 1 μg genomic DNA defined as positive). Mice that received rAAV-GBA1, both with and without CBE, were positive for rAAV-GBA1 vector genomes in the cortex, indicating that ICV delivery results in rAAV-GBA1 delivery to the cortex. Additionally, vector genomes were detected in the liver, few in spleen, and none in the heart, kidney or gonads. For all measures, there was no statistically significant difference between the Day 1 and Day 3 groups.

A larger study in the CBE model further explored efficacious doses of rAAV-GBA1 in the CBE model. Using the 25 mg/kg CBE dose model, excipient or rAAV-GBA1 was delivered via ICV at P3, and daily IP PBS or CBE treatment initiated at P8. Given the similarity between the groups with and without CBE withdrawal observed in the previous studies, all mice were sacrificed one day after the final CBE dose (P38-40). The effect of three different rAAV-GBA1 doses was assessed, resulting in the following five groups, with 10 mice (5M/5F) per group:

Excipient ICV+PBS IP

Excipient ICV+25 mg/kg CBE IP 3.2e9 vg (2.13e10 vg/g brain) rAAV-GBA1 ICV+25 mg/kg CBE IP 1.0e10 vg (6.67e10 vg/g brain) rAAV-GBA1 ICV+25 mg/kg CBE IP 3.2e10 vg (2.13e11 vg/g brain) rAAV-GBA1 ICV+25 mg/kg CBE IP.

Figure 15:
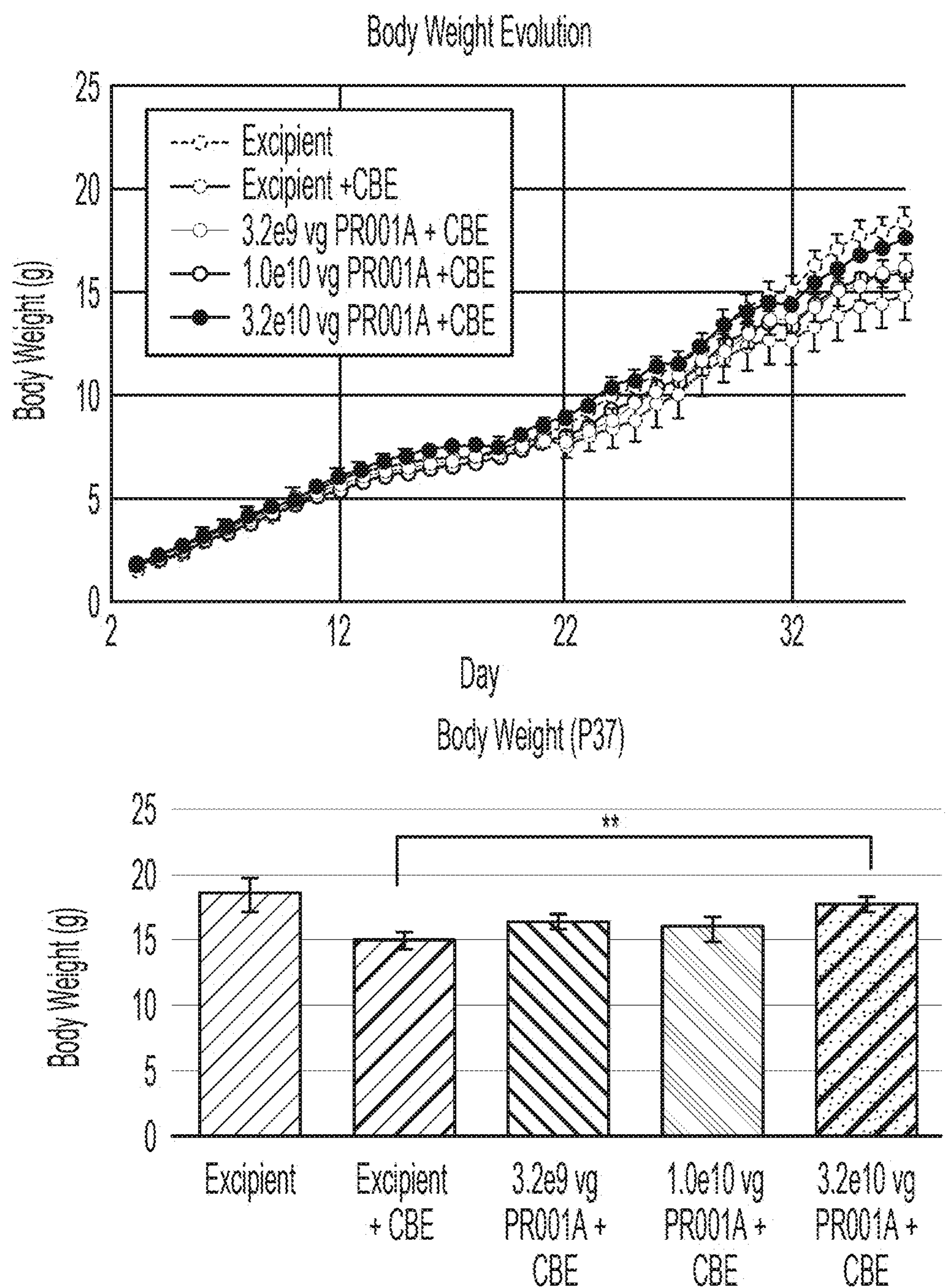
FIG. 15 shows representative data for in-life assessment of rAAV dose ranging in a CBE mouse model. Mice received excipient or one of three different doses of rAAV-GBA1 by ICV delivery at P3: 3.2e9 vg, 1.0e10 vg, or 3.2e10 vg. At P8, daily IP treatment of 25 mg/kg CBE was initiated. Mice that received excipient and CBE or excipient and PBS served as controls. All treatment groups started with n=10 (5M/5F) per group. All mice were sacrificed one day after their final CBE dose (P38-P40). All treatment groups were weighed daily, and their weight was analyzed at P36. Motor performance was assessed by latency to fall on Rotarod at P24 and latency to traverse the Tapered Beam at P30. Due to early lethality, the number of mice participating in the behavioral assays was: excipient+PBS n=10, excipient+CBE n=9, and 3.2e9 vg rAAV-GBA1+CBE n=6, 1.0e10 vg rAAV-GBA1+CBE n=10, 3.2e10 vg rAAV-GBA1+CBE n=7. Means are presented. Error bars are SEM; * p<0.05; **p<0.01 for nominal p-values by linear regression in the CBE-treated groups, with gender corrected for as a covariate.
Figure 15:
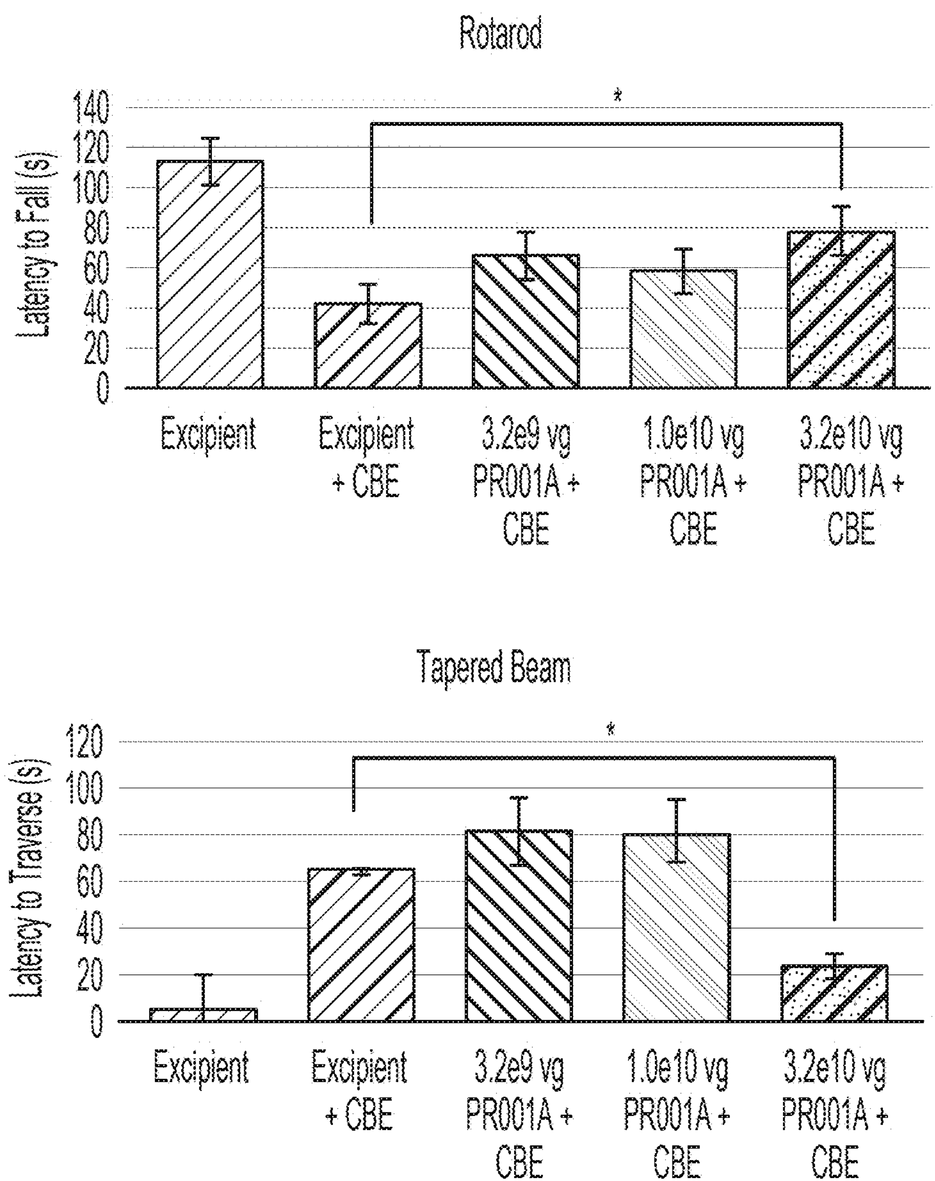

The highest dose of rAAV-GBA1 rescued the CBE treatment-related failure to gain weight at P37. Additionally, this dose resulted in a statistically significant increase in performance on the rotarod and tapered beam compared to the Excipient+CBE treated group (FIG. 15). Lethality was observed in several groups, including both excipient-treated and rAAV-GBA1-treated groups (Excipient+PBS: 0; Excipient+25 mg/kg CBE: 1; 3.2e9 vg rAAV-GBA1+25 mg/kg CBE: 4; 1.0e10 vg rAAV-GBA1+25 mg/kg CBE: 0; 3.2e10 vg rAAV-GBA1+25 mg/kg CBE: 3).

Figure 16:
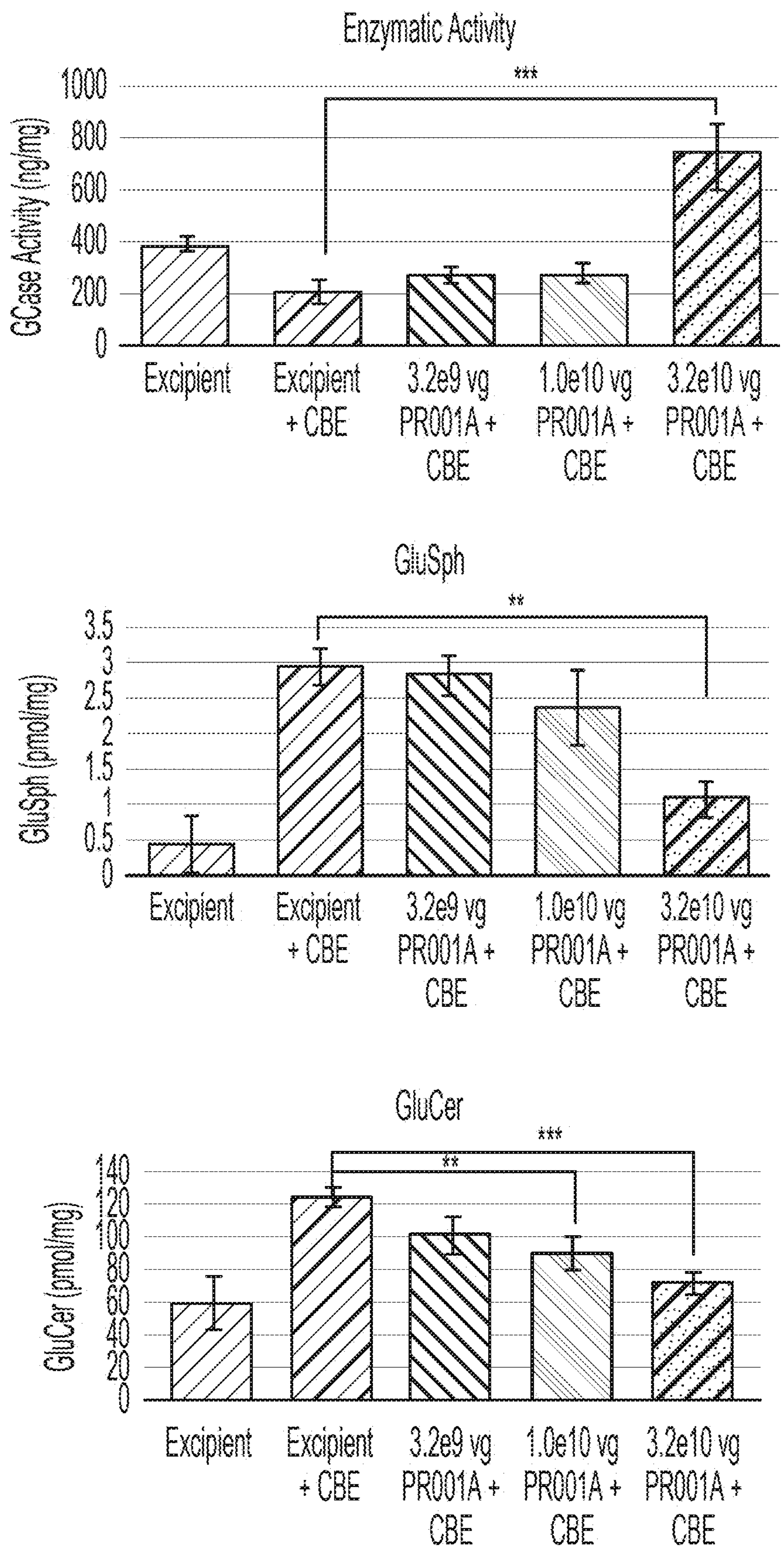
FIG. 16 shows representative data for biochemical assessment of rAAV dose ranging in a CBE mouse model. The cortex of all treatment groups (excipient+PBS n=10, excipient+CBE n=9, and 3.2e9 vg rAAV-GBA1+CBE n=6, 1.0e10 vg rAAV-GBA1+CBE n=10, 3.2e10 vg rAAV-GBA1+CBE n=7) was used to measure GCase activity, GluSph levels, GluCer levels, and vector genomes. GCase activity is shown as ng of GCase per mg of total protein. GluSph and GluCer levels are shown as pmol per mg wet weight of the tissue. Biodistribution is shown as vector genomes per 1 μg of genomic DNA. Vector genome presence was quantified by quantitative PCR using a vector reference standard curve; genomic DNA concentration was evaluated by A260 optical density measurement. Vector genome presence was also measured in the liver (E). Means are presented. Error bars are SEM. p<0.01; *p<0.001 for nominal p-values by linear regression in the CBE-treated groups, with gender corrected for as a covariate.
Figure 16:
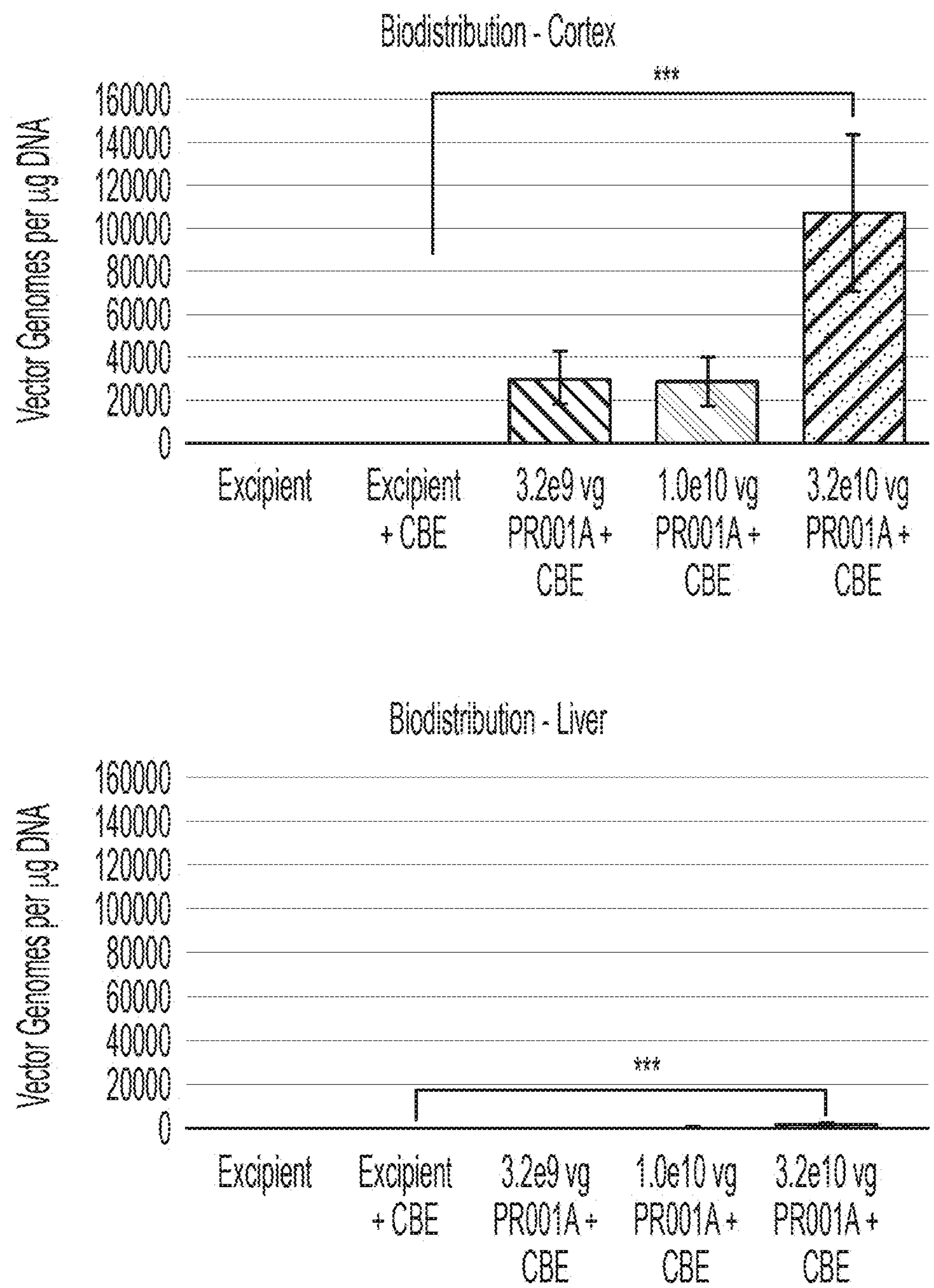

At the completion of the in-life study, mice were sacrificed for biochemical analysis (FIG. 16). GCase activity in the cortex was assessed in biological triplicates by a fluorometric assay. CBE-treated mice showed reduced GCase activity whereas mice that received a high rAAV-GBA1 dose showed a statistically significant increase in GCase activity compared to CBE treatment. CBE-treated mice also had accumulation of GluCer and GluSph, both of which were rescued by administering a high dose of rAAV-GBA1.

In addition to the established chemical CBE model, rAAV-GBA1 is also evaluated in the 4L/PS-NA genetic model, which is homozygous for the V394L GD mutation in Gbal and is also partially deficient in saposins, which affect GCase localization and activity. These mice exhibit motor strength, coordination, and balance deficits, as evidenced by their performance in the beam walk, rotarod, and wire hang assays. Typically the lifespan of these mice is less than 22 weeks. In an initial study, 3 μl of maximal titer virus was delivered by ICV at P23, with a final dose of 2.4e10 vg (6.0e10 vg/g brain). With 6 mice per group, the treatment groups were:

WT+Excipient ICV

4L/PS-NA+Excipient ICV

4L/PS-NA+2.4e10 vg (6.0e10 vg/g brain) rAAV-GBA1 ICV

Figure 17:
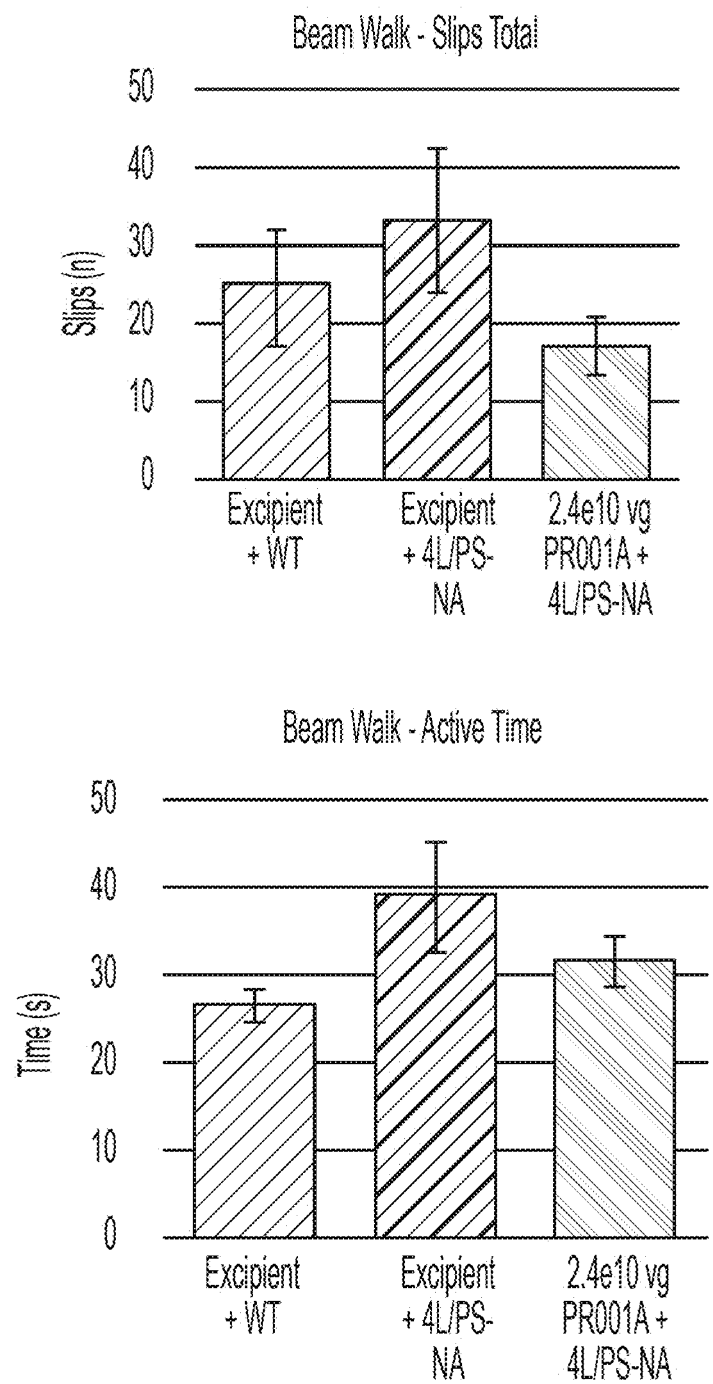
FIG. 17 shows representative data for tapered beam analysis in maximal dose rAAV-GBA1 in a genetic mouse model. Motor performance of the treatment groups (WT+excipient, n=5), 4L/PS-NA+excipient (n=6), and 4L/PS-NA+rAAV-GBA1 (n=5)) was assayed by Beam Walk 4 weeks post rAAV-GBA1 administration. The total slips and active time are shown as total over 5 trials on different beams. Speed and slips per speed are shown as the average over 5 trials on different beams. Means are presented. Error bars are SEM.
Figure 17:
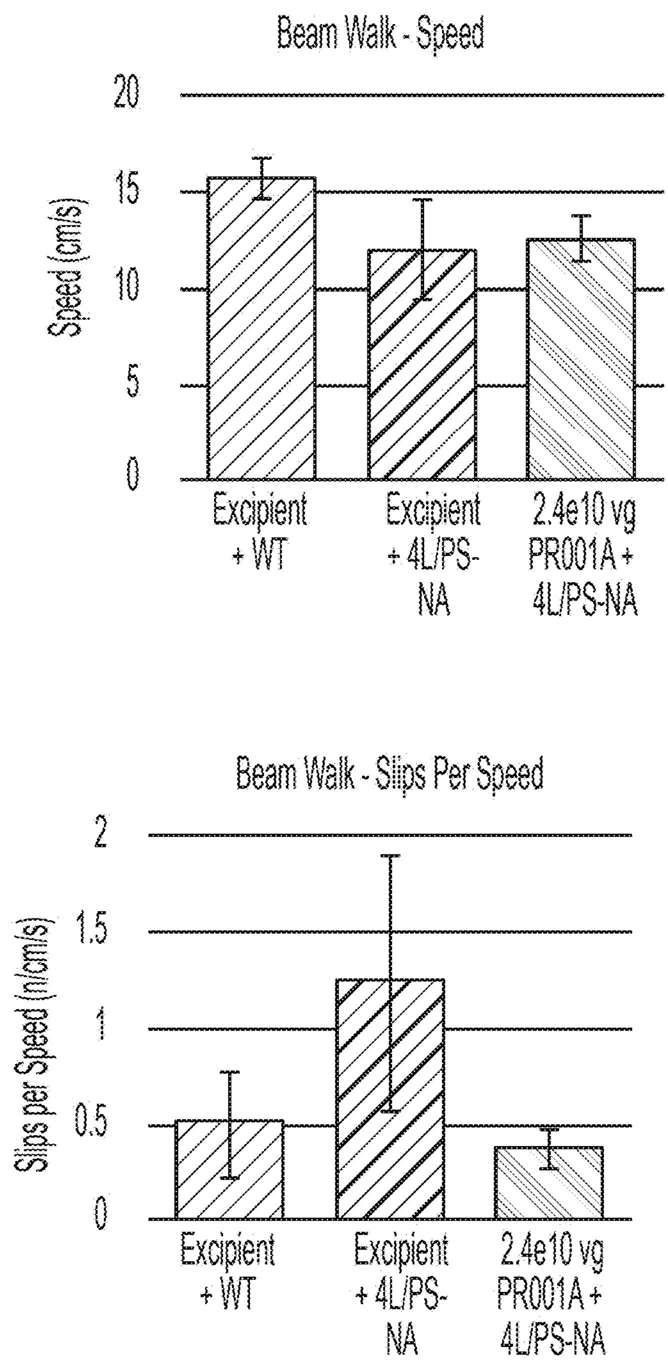

Motor performance by the beam walk test was assessed 4 weeks post-rAAV-GBA1 delivery. The group of mutant mice that received rAAV-GBA1 showed a trend towards fewer total slips and fewer slips per speed when compared to mutant mice treated with excipient, restoring motor function to near WT levels (FIG. 17). Since the motor phenotypes become more severe as these mice age, their performance on this and other behavioral tests is assessed at later time points. At the completion of the in-life study, lipid levels, GCase activity, and biodistribution are assessed in these mice.

Additional lower doses of rAAV-GBA1 are currently being tested using the CBE model, corresponding to 0.03×, 0.1×, and 1× the proposed phase 1 high clinical dose. Each group includes 10 mice (5M/5F) per group:

Excipient ICV

Excipient ICV+25 mg/kg CBE IP 3.2e8 vg (2.13e9 vg/g brain) rAAV-GBA1 ICV+25 mg/kg CBE IP 1.0e9 vg (6.67e9 vg/g brain) rAAV-GBA1 ICV+25 mg/kg CBE IP 1.0e10 vg (6.67e10 vg/g brain) rAAV-GBA1 ICV+25 mg/kg CBE IP.

In addition to motor phenotypes, lipid levels and GCase activity are assessed in the cortex. Time course of treatments and analyses are also performed.

A larger dose ranging study was initiated to evaluate efficacy and safety data. 10 4L/PS-NA mice (5M/5F per group) were injected with 10 μl of rAAV-GBA1. Using an allometric brain weight calculation, the doses correlate to 0.15×, 1.5×, 4.4×, and 14.5× the proposed phase 1 high clinical dose. The injection groups consist of:

WT+Excipient ICV

4L/PS-NA+Excipient ICV

4L/PS-NA+4.3e9 vg (1.1e10 vg/g brain) rAAV-GBA1 ICV

4L/PS-NA+4.3e10 vg (1.1e11 vg/g/brain) rAAV-GBA1 ICV

4L/PS-NA+1.3e11 vg (3.2e11 vg/g brain) rAAV-GBA1 ICV

4L/PS-NA+4.3e11 vg (1.1e12 vg/g brain) rAAV-GBA1 ICV.

Figure 18:
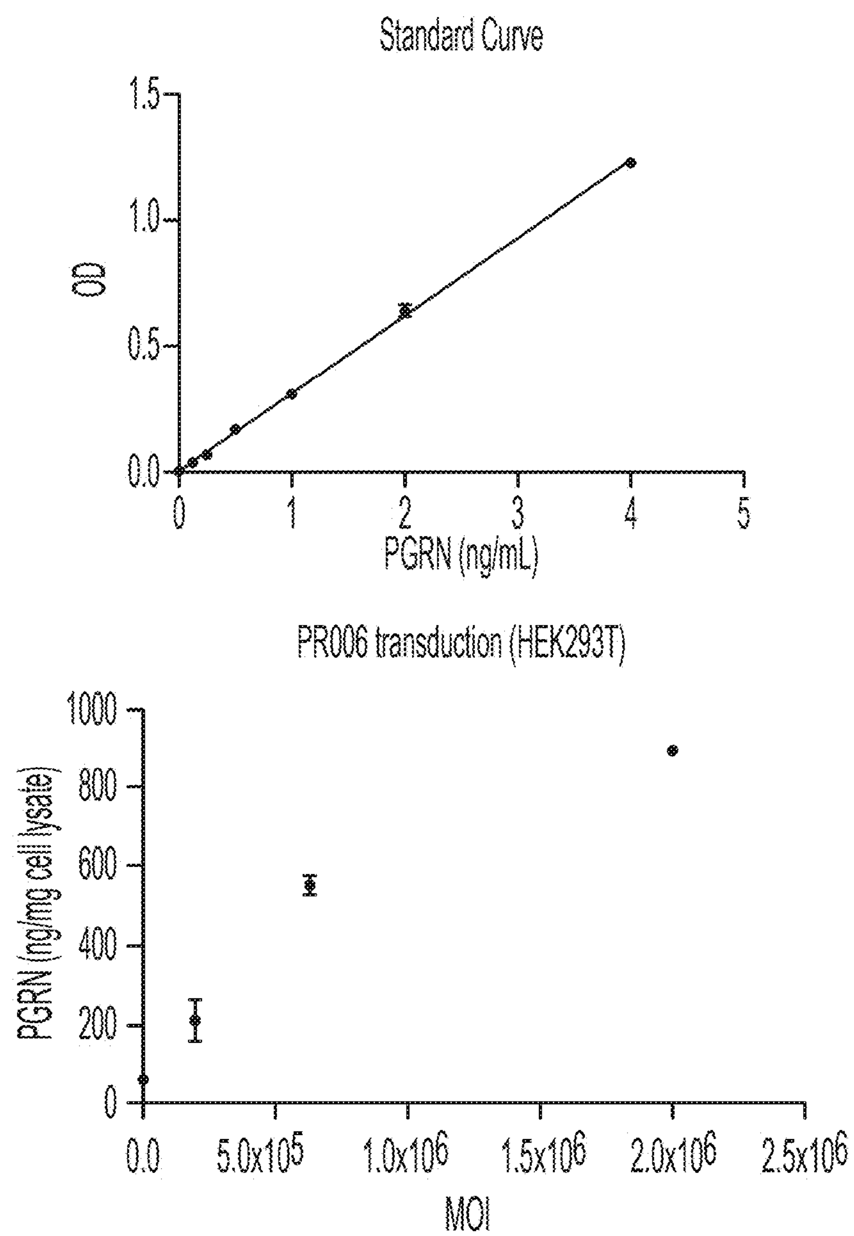
FIG. 18 shows representative data for in vitro expression of rAAV constructs encoding progranulin (PGRN) protein. The left panel shows a standard curve of progranulin (PGRN) ELISA assay. The bottom panel shows a dose-response of PGRN expression measured by ELISA assay in cell lysates of HEK293T cells transduced with rAAV. MOI=multiplicity of infection (vector genomes per cell).

Example 9: In Vitro Analysis of rAAV Vectors rAAV constructs were tested in vitro and in vivo. FIG. 18 shows representative data for in vitro expression of rAAV constructs encoding progranulin (PGRN) protein. The left panel shows a standard curve of progranulin (PGRN) ELISA assay. The bottom panel shows a dose-response of PGRN expression measured by ELISA assay in cell lysates of HEK293T cells transduced with rAAV. MOI=multiplicity of infection (vector genomes per cell).

Figure 19:
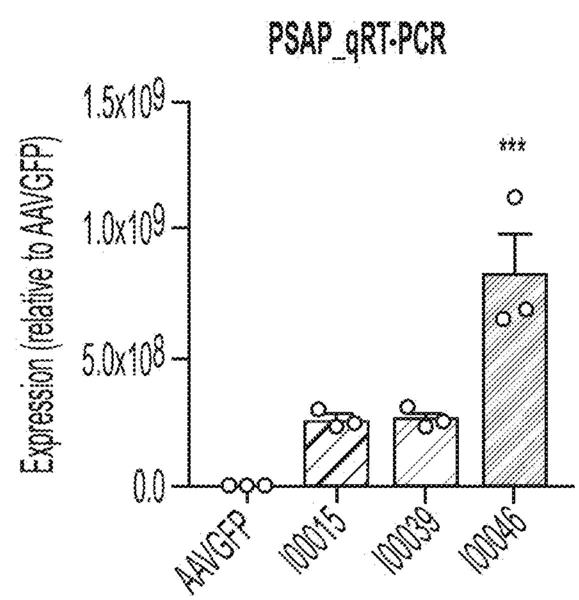
FIG. 19 shows representative data for in vitro expression of rAAV constructs encoding GBA1 in combination with Prosaposin (PSAP), SCARB2, and/or one or more inhibitory nucleic acids. Data indicate transfection of HEK293 cells with each construct resulted in overexpression of the transgenes of interest relative to mock transfected cells.
Figure 19:
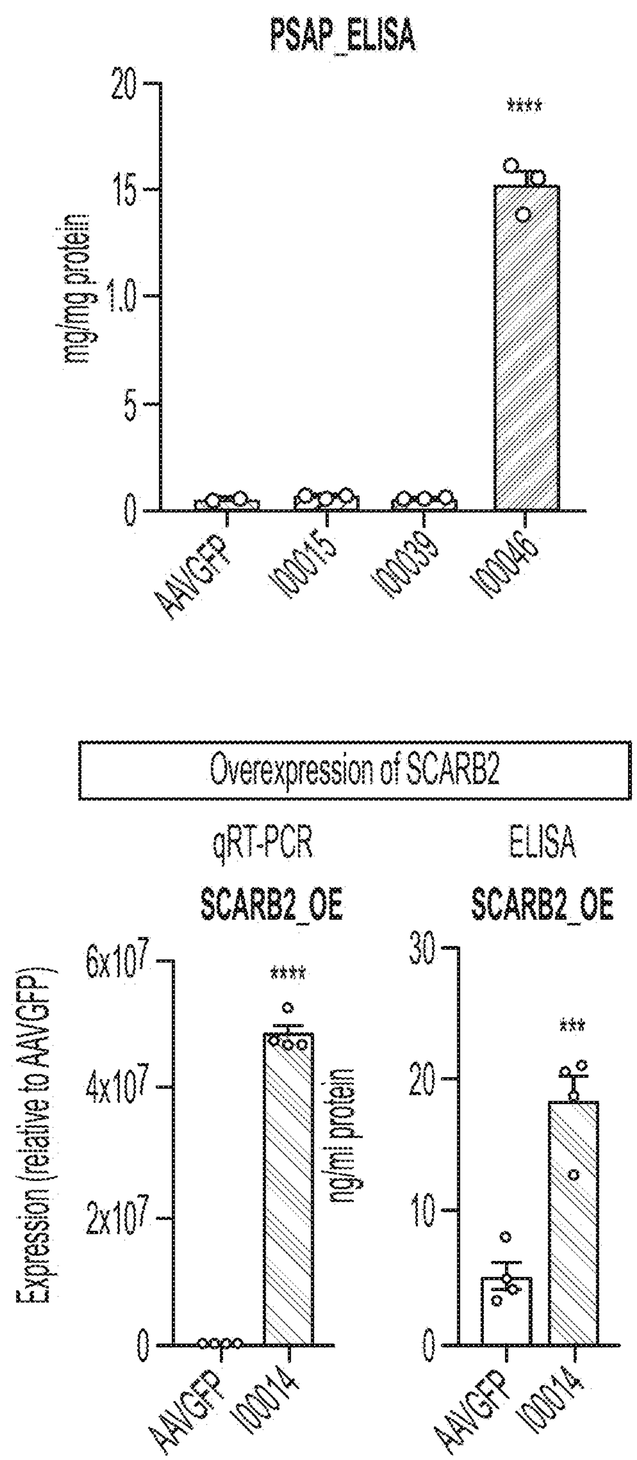
Figure 19:
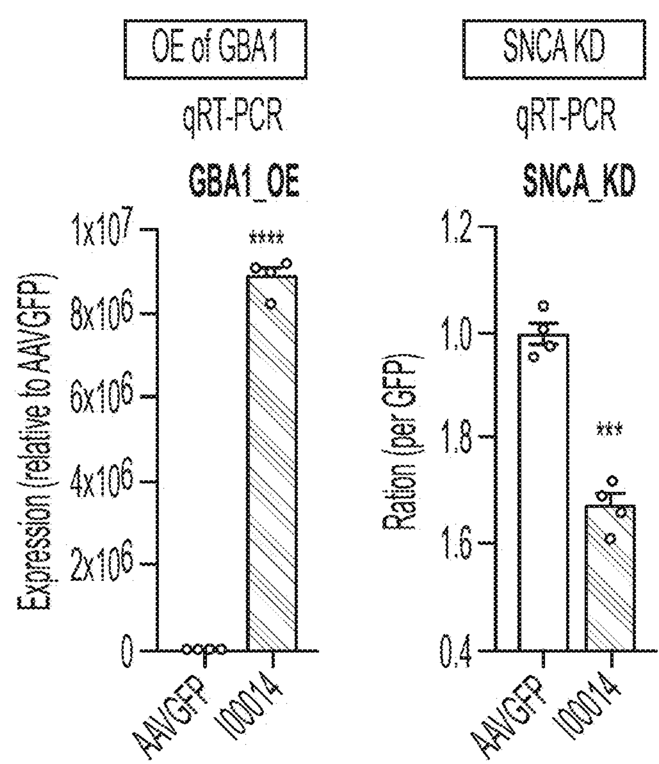

A pilot study was performed to assess in vitro activity of rAAV vectors encoding Prosaposin (PSAP) and SCARB2, alone or in combination with GBA1 and/or one or more inhibitory RNAs. One construct encoding PSAP and progranulin (PGRN) was also tested. Vectors tested include those shown in Table 3. "Opt" refers to a nucleic acid sequence codon optimized for expression in mammalian cells (e.g., human cells). FIG. 19 shows representative data indicating that transfection of HEK293 cells with each of the constructs resulted in overexpression of the corresponding gene product compared to mock transfected cells.

Figure 36A:
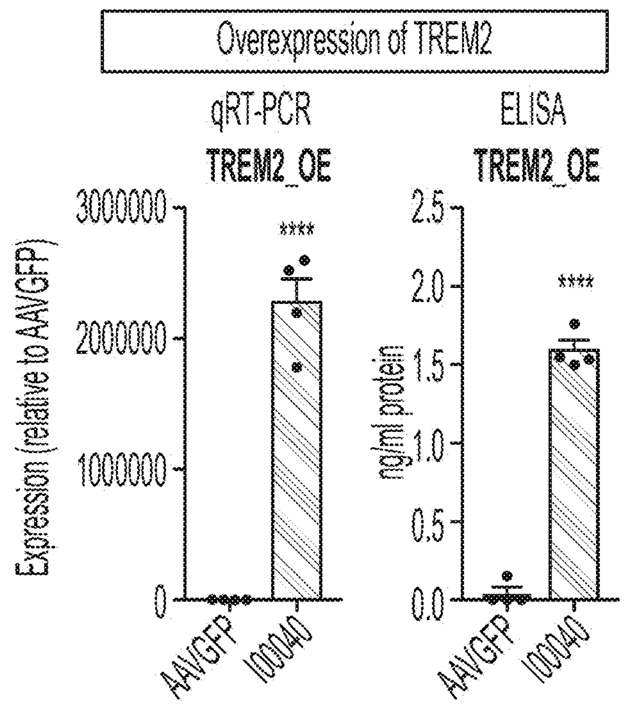
FIG. 36A-FIG. 36B show representative data for overexpression of TREM2 and GBA1 in HEK293 cells relative to control transduced cells, as measured by qPCR and ELISA.
Figure 36B:
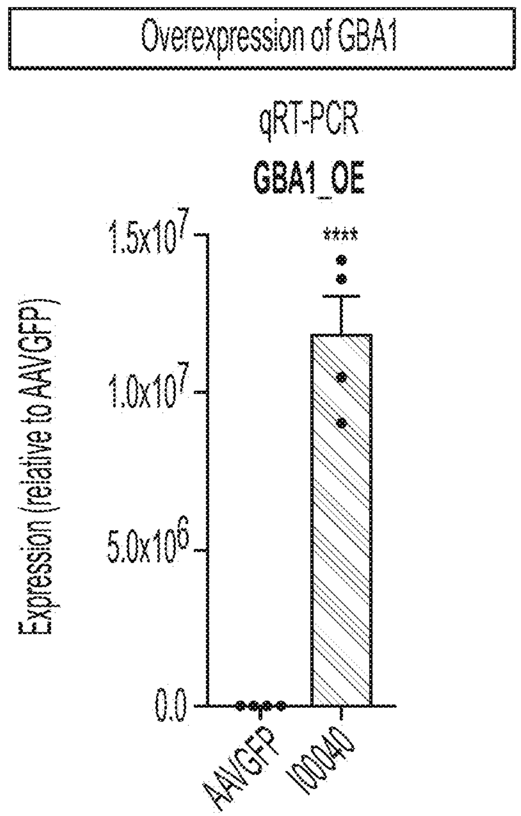

A pilot study was performed to assess in vitro activity of rAAV vectors encoding TREM2, alone or in combination with one or more inhibitory RNAs. Vectors tested include those shown in Table 3. "Opt" refers to a nucleic acid sequence codon optimized for expression in mammalian cells (e.g., human cells). FIGS. 36A-36B show representative data indicating that transfection of HEK293 cells with each of the constructs resulted in overexpression of the corresponding gene product compared to mock transfected cells.

TABLE 3

| ID | Promoter | Inhibitory RNA | Promoter | Transgene |
|---|---|---|---|---|
| I00015 | JL_intronic | SNCA | JetLong | Opt-PSAP_GBA1 |
| I00039 | — | — | JetLong | Opt-PSAP-GRN |
| I00046 | — | — | CBA | Opt-PSAP |
| I00014 | JetLong | SNCA | JetLong | Opt-SCARB2_GBA1 |
| I00040 | | | JL, CD68 | opt-GBA1, TREM2 |

Example 10: Testing of SNCA and TMEM106B shRNA Constructs

HEK293 Cells

Human embryonic kidney 293 cell line (HEK293) were used in this study (#85120602, Sigma-Aldrich). HEK293 cells were maintained in culture media (D-MEM [#11995065, Thermo Fisher Scientific] supplemented with 10% fetal bovine serum [FBS] [#10082147, Thermo Fisher Scientific]) containing 100 units/ml penicillin and 100 μg/ml streptomycin (#15140122, Thermo Fisher Scientific).

Plasmid Transfection

Plasmid transfection was performed using Lipofectamine 2000 transfection reagent (#11668019, Thermo Fisher Scientific) according to the manufacture's instruction. Briefly, HEK293 cells (#12022001, Sigma-Aldrich) were plated at the density of $3\times10^5$ cells/ml in culture media without antibiotics. On the following day, the plasmid and Lipofectamine 2000 reagent were combined in Opti-MEM solution (#31985062, Thermo Fisher Scientific). After 5 minutes, the mixtures were added into the HEK293 culture. After 72 hours, the cells were harvested for RNA or protein extraction, or subjected to the imaging analyses. For imaging analyses, the plates were pre-coated with 0.01% poly-L-Lysine solution (P8920, Sigma-Aldrich) before the plating of cells.

Gene Expression Analysis by Quantitative Real-Time PCR (qRT-PCR)

Relative gene expression levels were determined by quantitative real-time PCR (qRT-PCR) using Power SYBR Green Cells-to-CT Kit (#4402955, Thermo Fisher Scientific) according to the manufacturer's instruction. The candidate plasmids were transiently transfected into HEK293 cells plated on 48-well plates ($7.5\times10^4$ cells/well) using Lipofectamine 2000 transfection reagent (0.5 μg plasmid and 1.5 μl reagent in 50 μl Opti-MEM solution). After 72 hours, RNA was extracted from the cells and used for reverse transcription to synthesize cDNA according to the manufacturer's instruction. For quantitative PCR analysis, 2-5 μl of cDNA products were amplified in duplicates using gene specific primer pairs (250 nM final concentration) with Power SYBR Green PCR Master Mix (#4367659, Thermo Fisher Scientific). The primer sequences for SNCA, TMEM106B, and GAPDH genes were: 5'-AAG AGG GTG TTC TCT ATG TAG GC-3' (SEQ ID NO: 71), 5'-GCT CCT CCA ACA TTT GTC ACT T-3' (SEQ ID NO: 72) for SNCA, 5'-ACA CAG TAC CTA CCG TTA TAG CA-3' (SEQ ID NO: 73), 5'-TGT TGT CAC AGT AAC TTG CAT CA-3' (SEQ ID NO: 74) for TME114,106B, and 5'-CTG GGC TAC ACT GAG CAC C-3' (SEQ ID NO: 75), 5'-AAG TGG TCG TTG AGG GCA ATG-3' (SEQ ID NO: 76) for GAPDH. Quantitative PCR was performed in a QuantStudio 3 Real-Time PCR system (Thermo Fisher Scientific). Expression levels were normalized by the housekeeping gene GAPDH and calculated using the comparative CT method.

Fluorescence Imaging Analysis

EGFP reporter plasmids, which contain 3'-UTR of human SNCA gene at downstream of EGFP coding region, were used for the validation of SNCA and TMEM106B knockdown plasmids. EGFP reporter plasmids and candidate knockdown plasmids were simultaneously transfected into HEK293 cells plated on poly-L-Lysine coated 96-well plates ($3.0\times10^4$ cells/well) using Lipofectamine 2000 transfection reagent (0.04 μg reporter plasmid, 0.06 μg knockdown plasmid and 0.3 μl reagent in 10 ut Opti-MEM solution). After 72 hours, the fluorescent intensities of EGFP signal were measured at excitation 488 nm/emission 512 nm using Varioskan LUX multimode reader (Thermo Fisher Scientific). Cells were fixed with 4% PFA at RT for 10 minutes, and incubated with D-PBS containing 40 μg/ml 7-aminoactinomycin D (7-AAD) for 30 min at RT. After washing with D-PBS, the fluorescent intensities of 7-AAD signal were measured at excitation 546 nm/emission 647 nm using Varioskan reader to quantify cell number. Normalized EGFP signal per 7-AAD signal levels were compared with the control knockdown samples.

Enzyme-Linked Immunosorbent Assay (ELISA)

α-Synuclein reporter plasmids, which contain 3'-UTR of human SNCA gene or TMEM106B gene downstream of SNCA coding region, were used for the validation of knockdown plasmids at the protein level. Levels of α-synuclein protein were determined by ELISA (#KHB0061, Thermo Fisher Scientific) using the lysates extracted from HEK293 cells. The candidate plasmids were transiently transfected into HEK293 cells plated on 48-well plates ($7.5\times10^4$ cells/well) using Lipofectamine 2000 transfection reagent (0.1 μg reporter plasmid, 0.15 μg knockdown plasmid and 0.75 μl reagent in 25 μl Opti-MEM solution). After 72 hours, cells were lysed in radioimmunoprecipitation assay (RIPA) buffer (#89900, Thermo Fisher Scientific) supplemented with protease inhibitor cocktail (#P8340, Sigma-Aldrich), and sonicated for a few seconds. After incubation on ice for 30 min, the lysates were centrifuged at 20,000×g at 4° C. for 15 min, and the supernatant was collected. Protein levels were quantified. Plates were read in a Varioskan plate reader at 450 nm, and concentrations were calculated using SoftMax Pro 5 software. Measured protein concentrations were normalized to total protein concentration determined with a bicinchoninic acid assay (#23225, Thermo Fisher Scientific)

.

Figure 37:
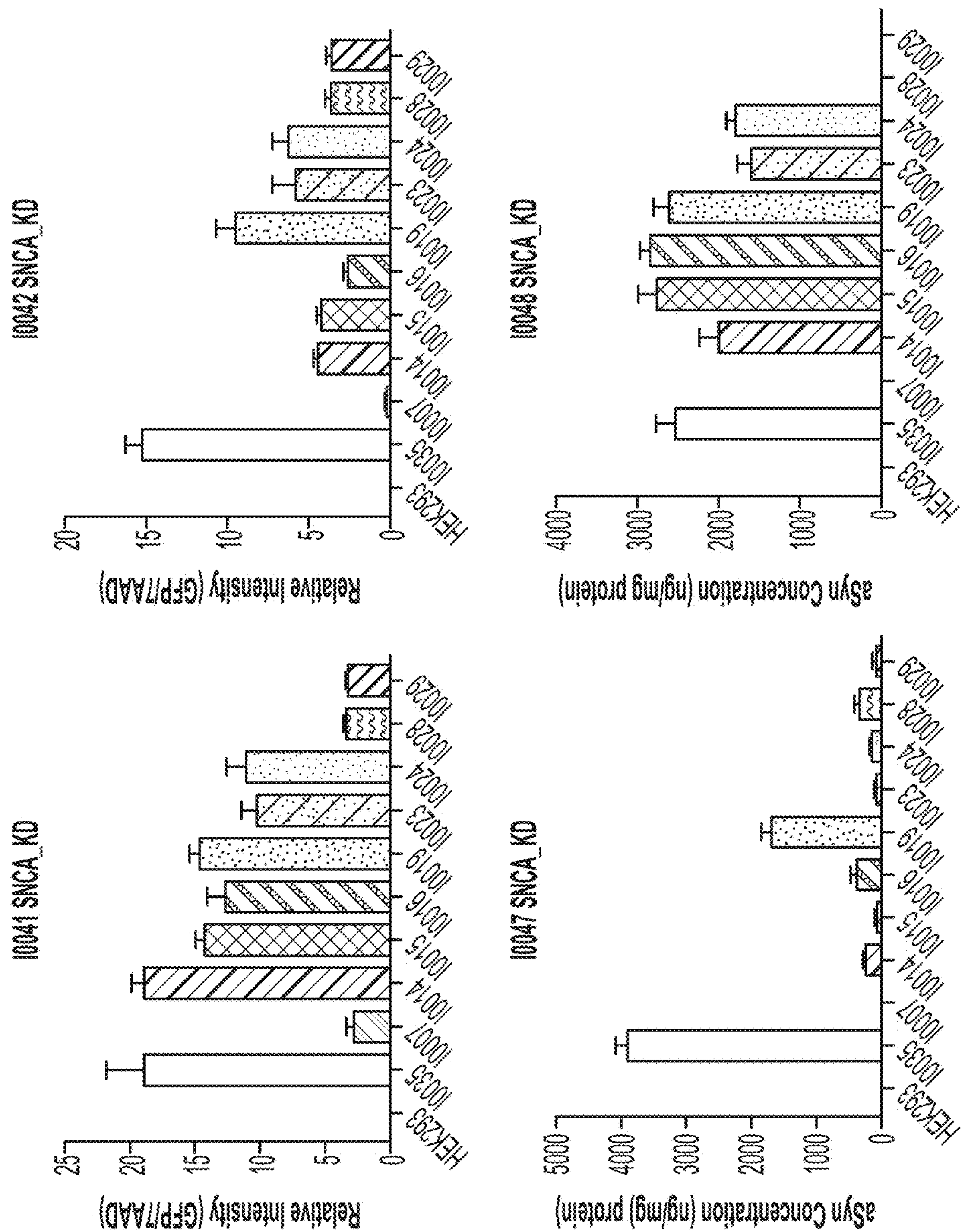
FIG. 37 shows representative data indicating successful silencing of SNCA in vitro by GFP reporter assay (top) and α-Syn assay (bottom).
Figure 38:
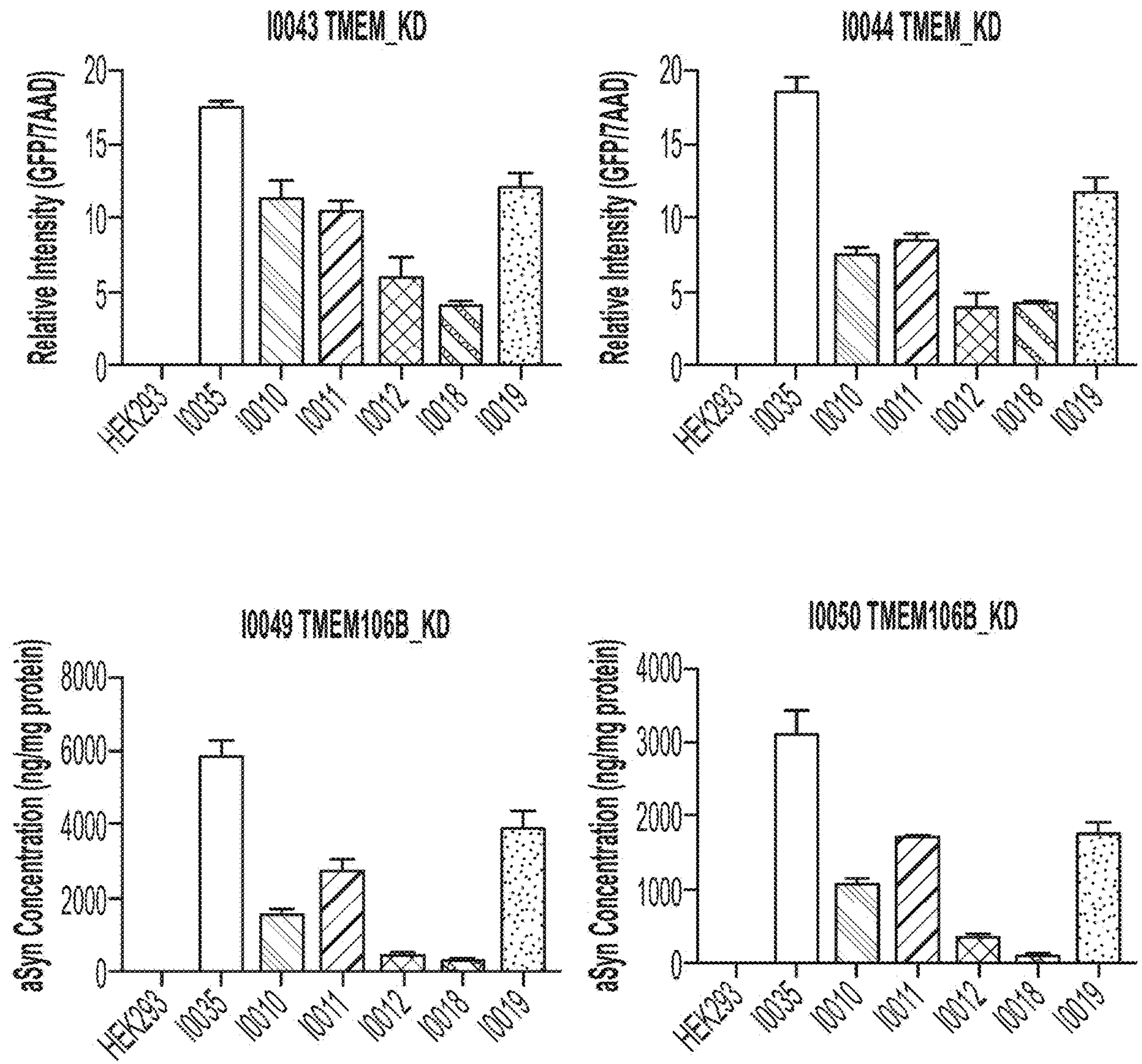
FIG. 38 shows representative data indicating successful silencing of TMEA106B in vitro by GFP reporter assay (top) and α-Syn assay (bottom).

FIG. 37 and Table 4 show representative data indicating successful silencing of SNCA in vitro by GFP reporter assay (top) and α-Syn assay (bottom). FIG. 38 and Table 5 show representative data indicating successful silencing of TMEM106B in vitro by GFP reporter assay (top) and α-Syn assay (bottom).

TABLE 4

| ID | Promoter | Knockdown | Promoter | Overexpress |
|---|---|---|---|---|
| I00007 | CMV_intronic | SNCA_mi | CMV | opt-GBA1 |
| I00008 | H1 | SNCA_sh | CMV | opt-GBA1 |
| I00009 | H1 | SNCA_Pubsh4 | CMV | opt-GBA1 |
| I00014 | JL_intronic | SNCA_mi | JetLong | opt-SCARB2_GBA |
| I00015 | JL_intronic | SNCA_mi | JetLong | opt-PSAP_GBA |
| I00016 | JL_intronic | SNCA_mi | JetLong | opt-CTSB_GBA |
| I00019 | JL_intronic | SNCA_TMEM_mi | JetLong | opt-VPS35 |
| I00023 | JL_intronic | SNCA_mi | JetLong | opt-GBA1_IL34 |
| I00024 | JL_intronic | SNCA_mi | JetLong | opt-GBA2 |
| I00028 | intronic | SNCA_Broadsh | CMV | opt-GBA1 |
| I00029 | intronic | SNCA_Pubsh4 | CMV | opt-GBA1 |

TABLE 5

| ID | Promoter | Knockdown | Promoter | Overexpress |
|---|---|---|---|---|
| I00010 | H1 | TMEM_Pubsh | CMV | opt-GRN |
| I00011 | JL_intronic | TMEM_mi | JetLong | opt-GBA1_GRN |
| I00012 | H1 | TMEM_sh | CMV | opt-GRN |
| I00019 | JL_intronic | SNCA_TMEM_mi | JetLong | opt-VPS35 |

Example 11: ITR "D" Sequence Placement and Cell Transduction

Figure 40:
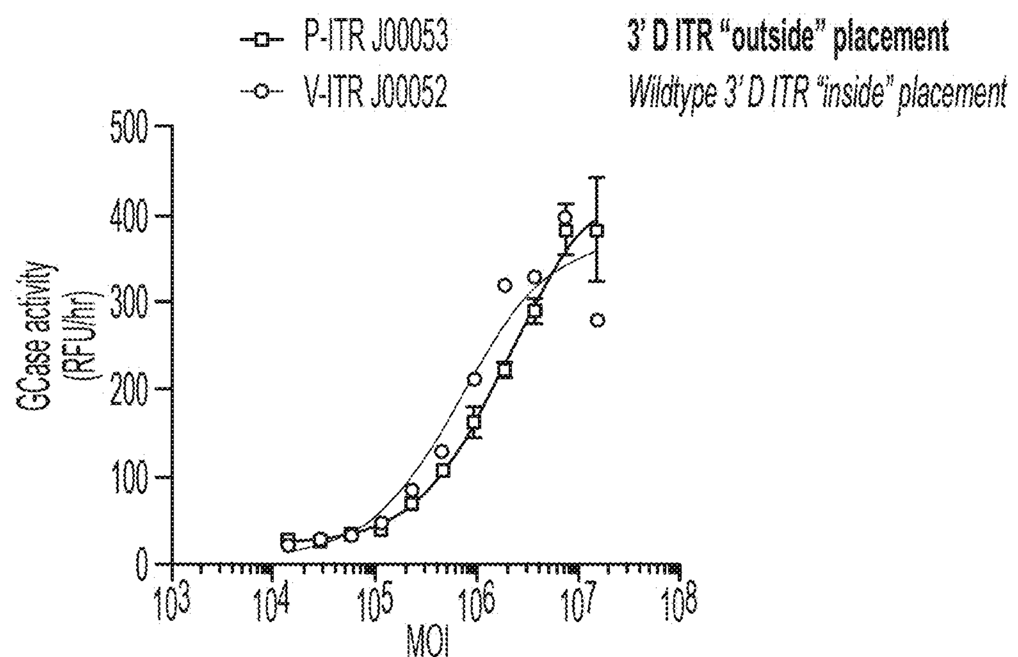
FIG. 40 shows data for transduction of HEK293 cells using rAAVs having ITRs with wild-type (circles) or alternative (e.g., "outside"; squares) placement of the "D" sequence. The rAAVs having ITRs placed on the "outside" were able to transduce cells as efficiently as rAAVs having wild-type ITRs.
Figure 41:
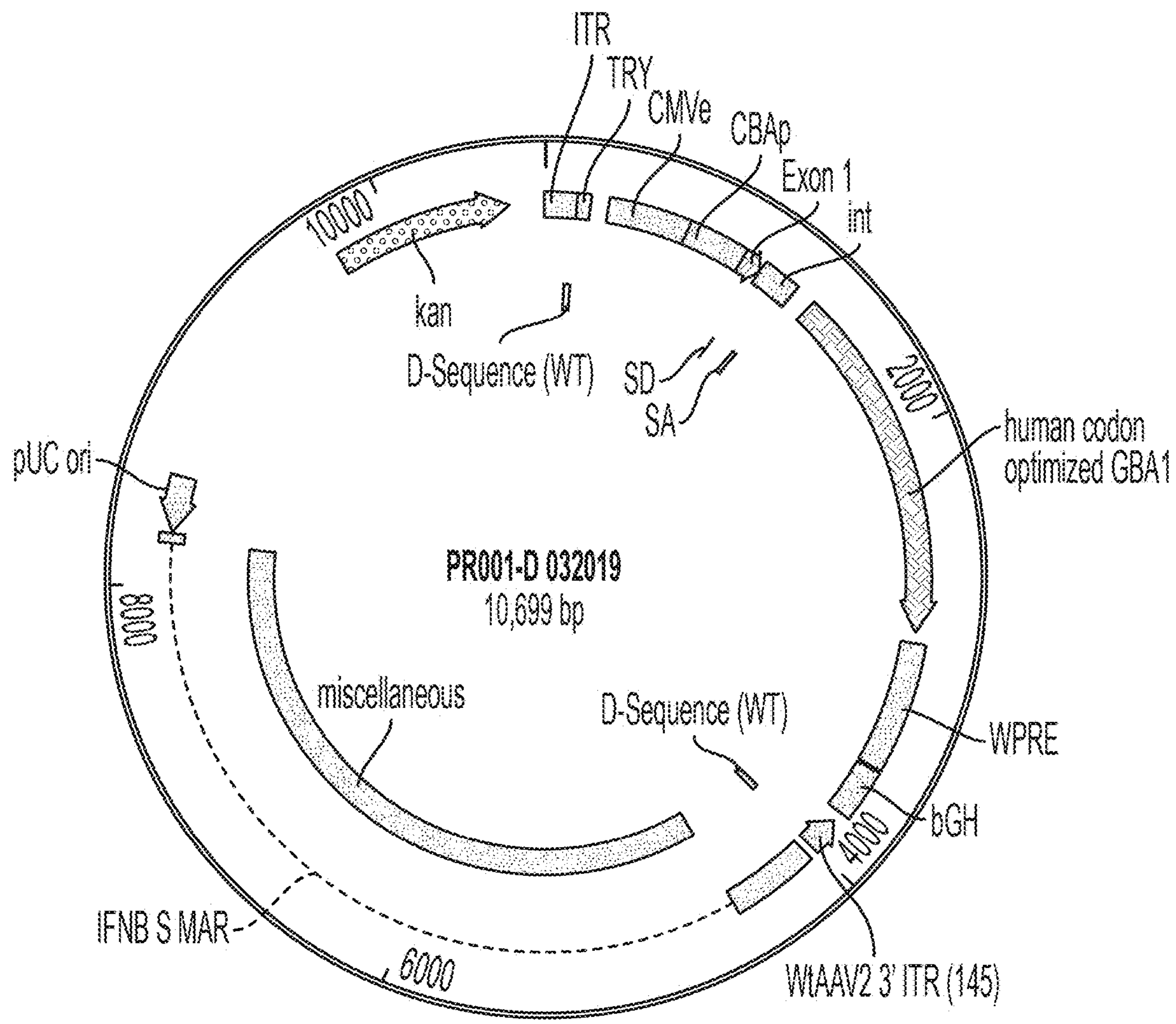
FIG. 41 is a schematic depicting one embodiment of a vector comprising an expression construct encoding Gcase (e.g., GBA1 or a portion thereof).
Figure 42:
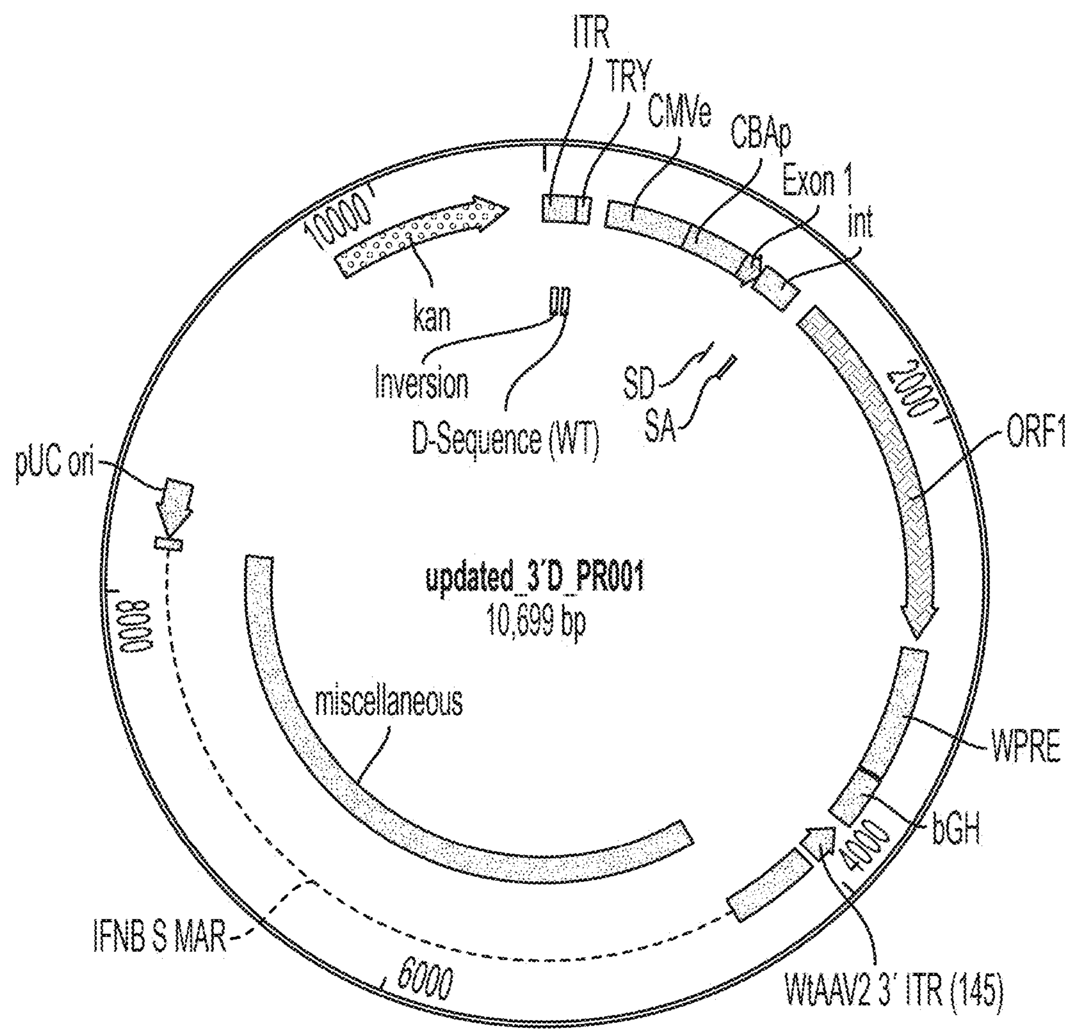
FIG. 42 is a schematic depicting one embodiment of a vector comprising an expression construct encoding Gcase (e.g., GBA1 or a portion thereof).
Figure 43:
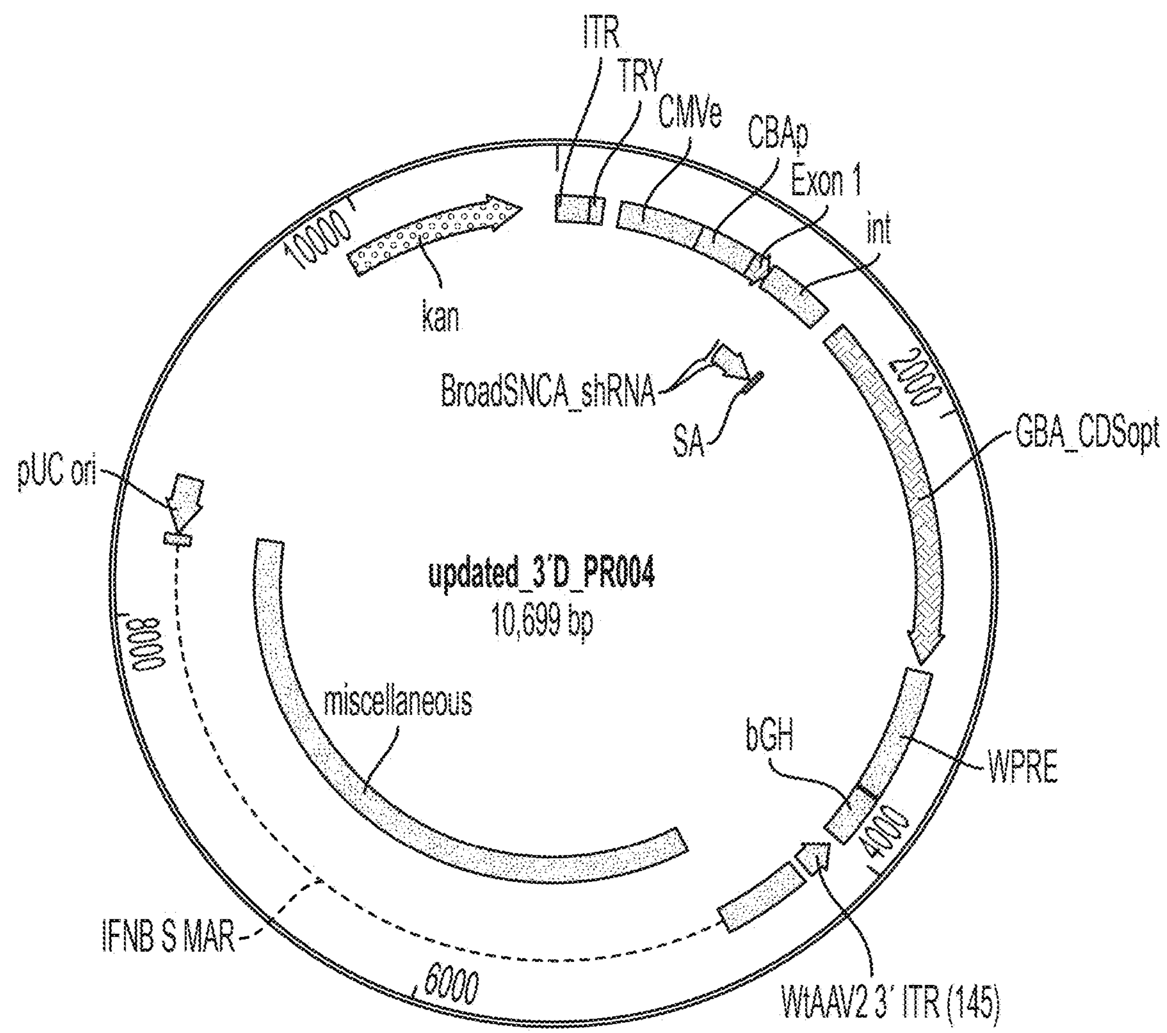
FIG. 43 is a schematic depicting one embodiment of a vector comprising an expression construct encoding Gcase (e.g., GBA1 or a portion thereof) and an interfering RNA for α-Syn.
Figure 44:
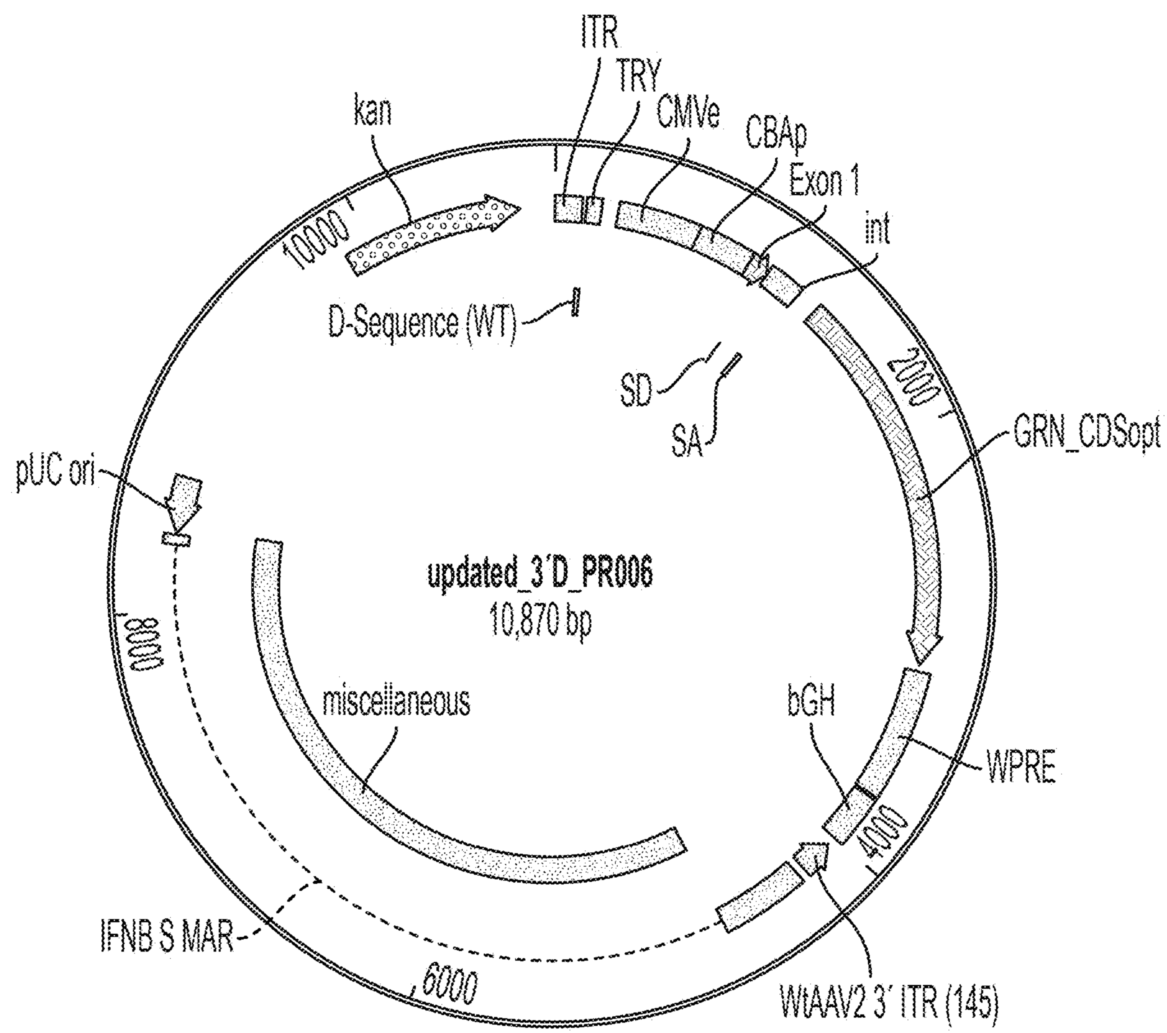
FIG. 44 is a schematic depicting one embodiment of a vector comprising an expression construct encoding PGRN.
Figure 45:
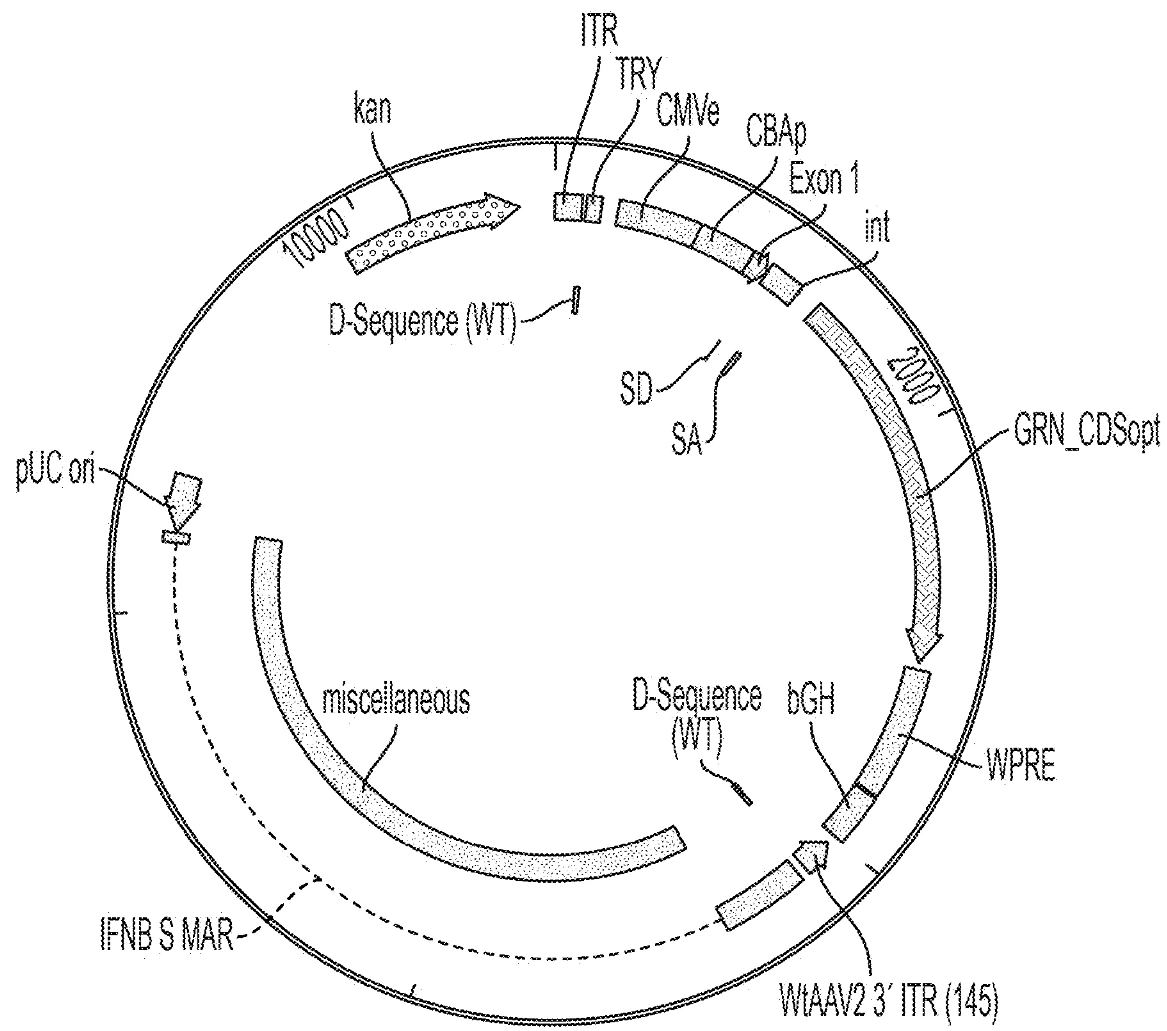
FIG. 45 is a schematic depicting one embodiment of a vector comprising an expression construct encoding PGRN.
Figure 46:
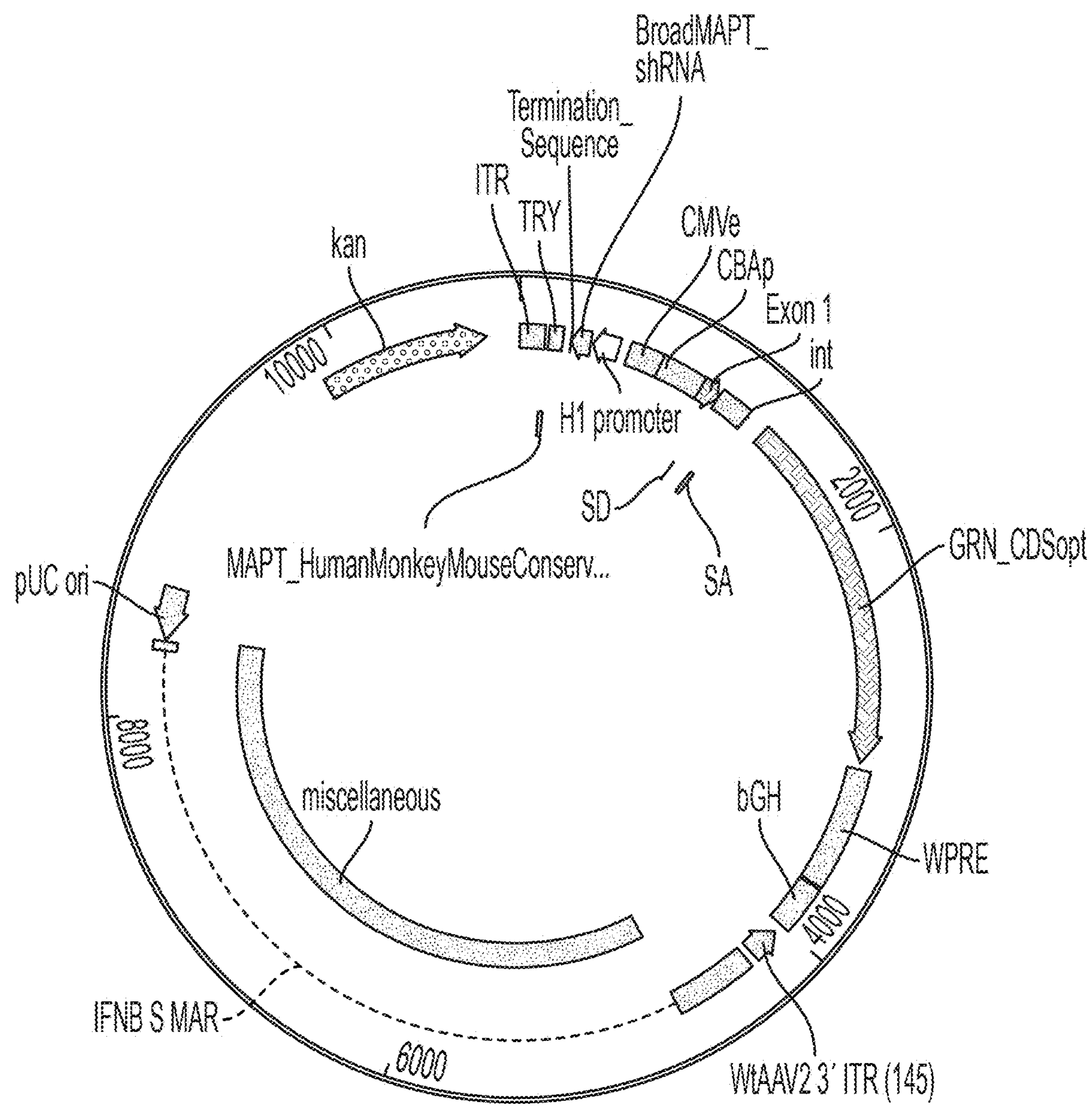
FIG. 46 is a schematic depicting one embodiment of a vector comprising an expression construct encoding PGRN and an interfering RNA for microtubule-associated protein tau (MAPT).
Figure 47:
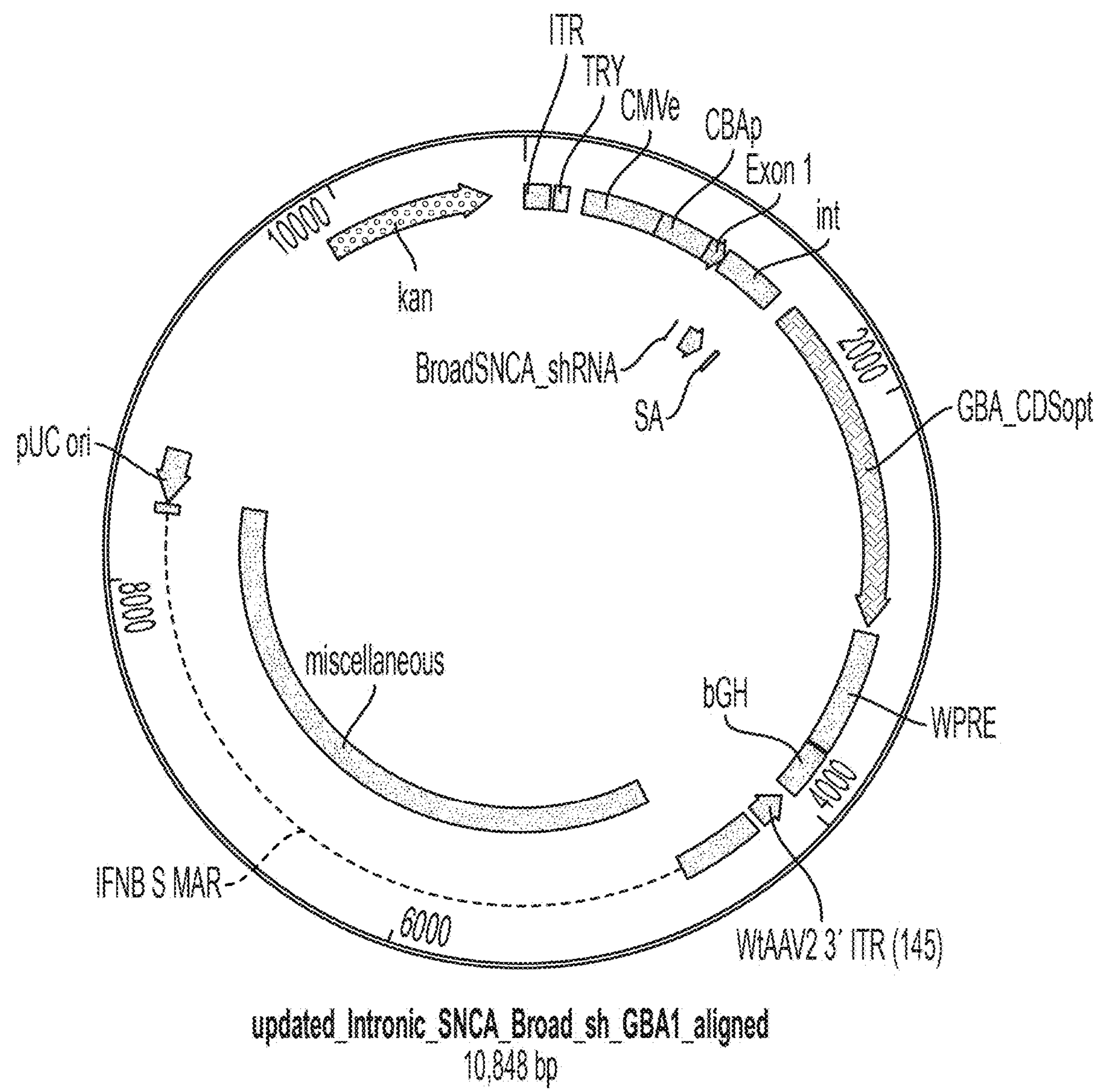
FIG. 47 is a schematic depicting one embodiment of a vector comprising an expression construct encoding Gcase (e.g., GBA1 or a portion thereof) and an interfering RNA for α-Syn.
Figure 48:
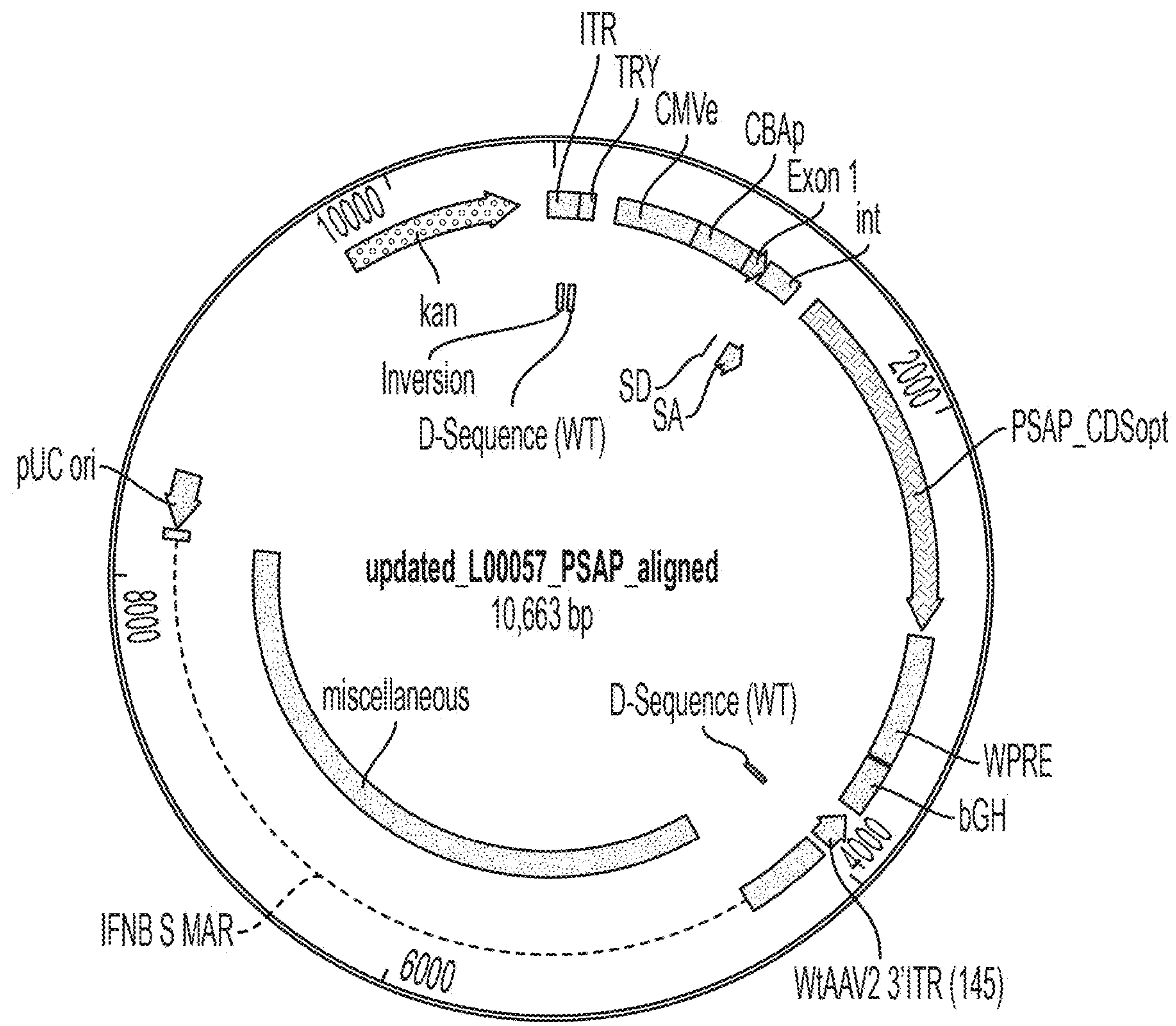
FIG. 48 is a schematic depicting one embodiment of a vector comprising an expression construct encoding PSAP.
Figure 49:
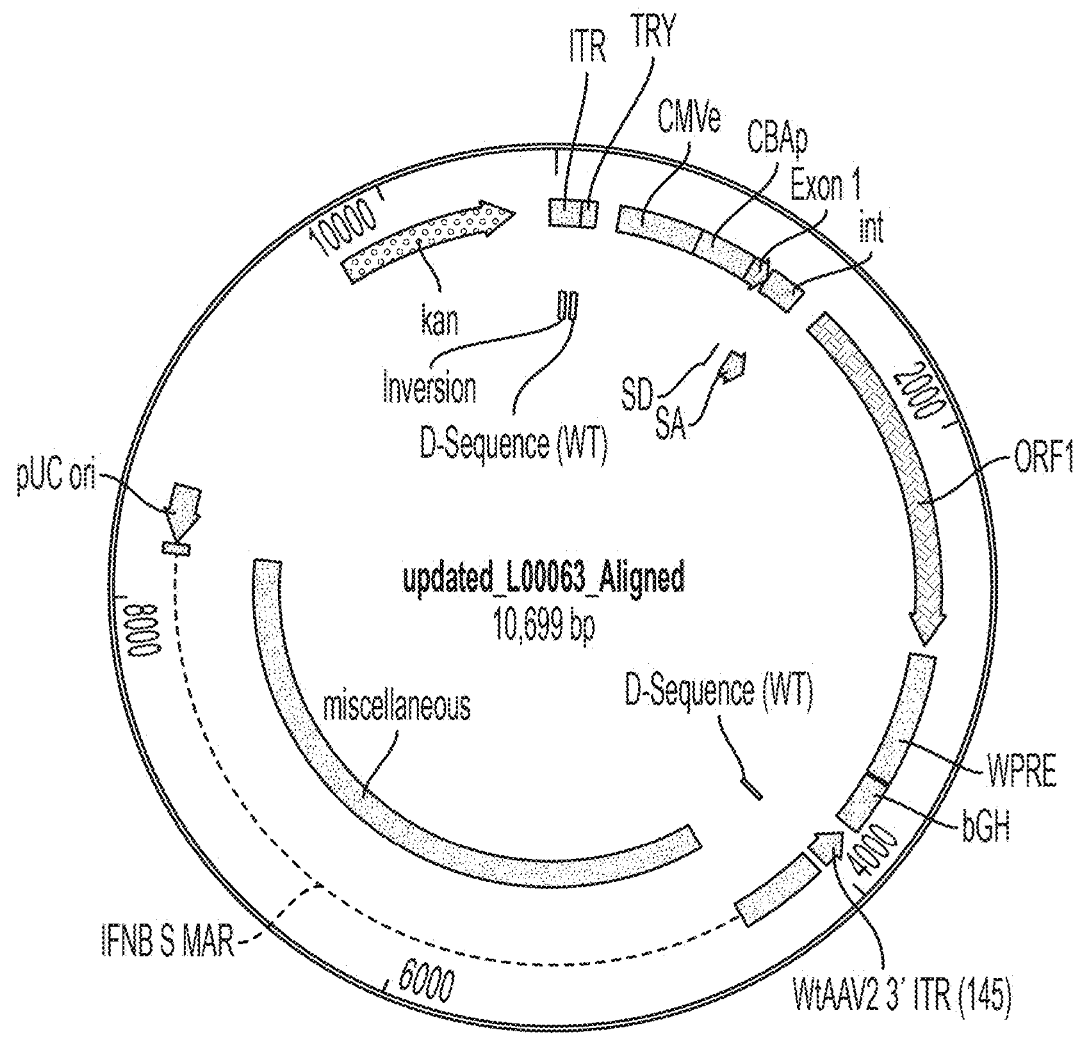
FIG. 49 is a schematic depicting one embodiment of a vector comprising an expression construct encoding Gcase (e.g., GBA1 or a portion thereof).
Figure 50:
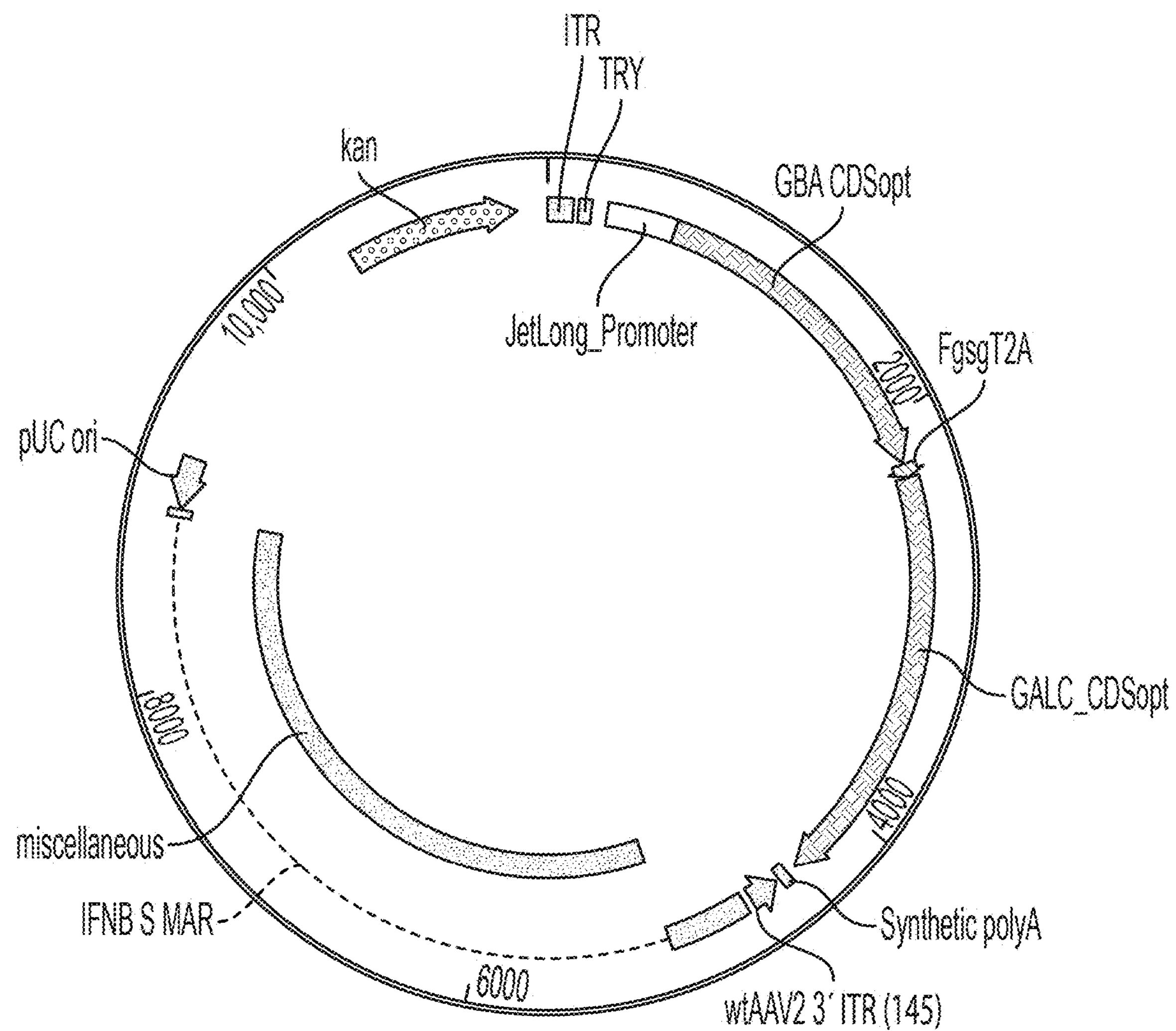
FIG. 50 is a schematic depicting one embodiment of a vector comprising an expression construct encoding Gcase (e.g., GBA1 or a portion thereof) and Galactosylceramidase (e.g., GALC or a portion thereof).
Figure 51:
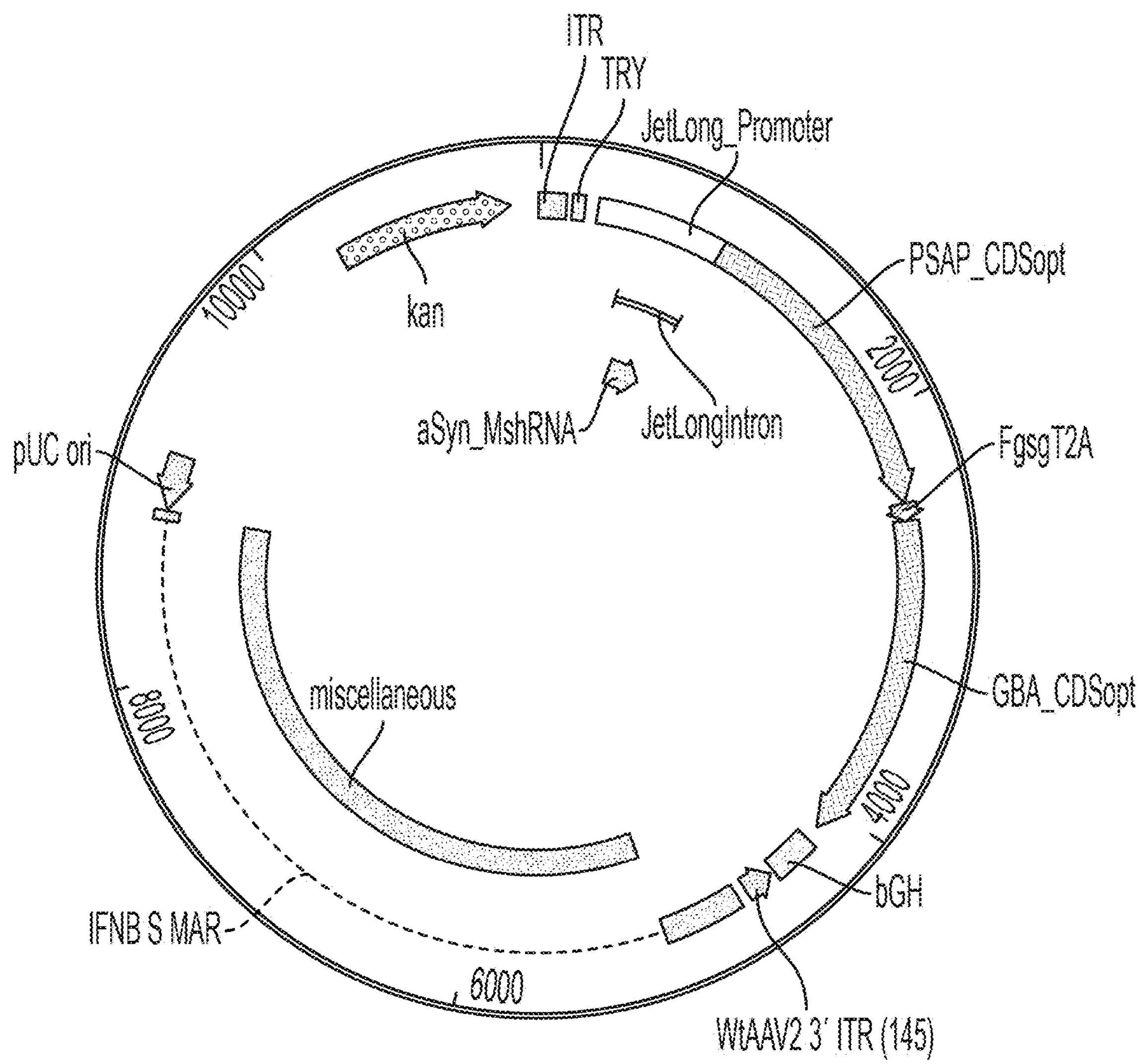
FIG. 51 is a schematic depicting one embodiment of a plasmid comprising an rAAV vector that includes an expression construct encoding Gcase (e.g., GBA1 or a portion thereof), Prosaposin (e.g., PSAP or a portion thereof), and an interfering RNA for α-Syn.

The effect of placement of ITR "D" sequence on cell transduction of rAAV vectors was investigated. HEK293 cells were transduced with Gcase-encoding rAAVs having 1) wild-type ITRs (e.g., "D" sequences proximal to the transgene insert and distal to the terminus of the ITR) or 2) ITRs with the "D" sequence located on the "outside" of the vector (e.g., "D" sequence located proximal to the terminus of the ITR and distal to the transgene insert), as shown in FIG. 20. Surprisingly, data indicate that rAAVs having the "D" sequence located in the "outside" position retain the ability to be packaged and transduce cells efficiently (FIG. 40).

Example 12: In Vitro Testing of Progranulin rAAVs

Figure 39:
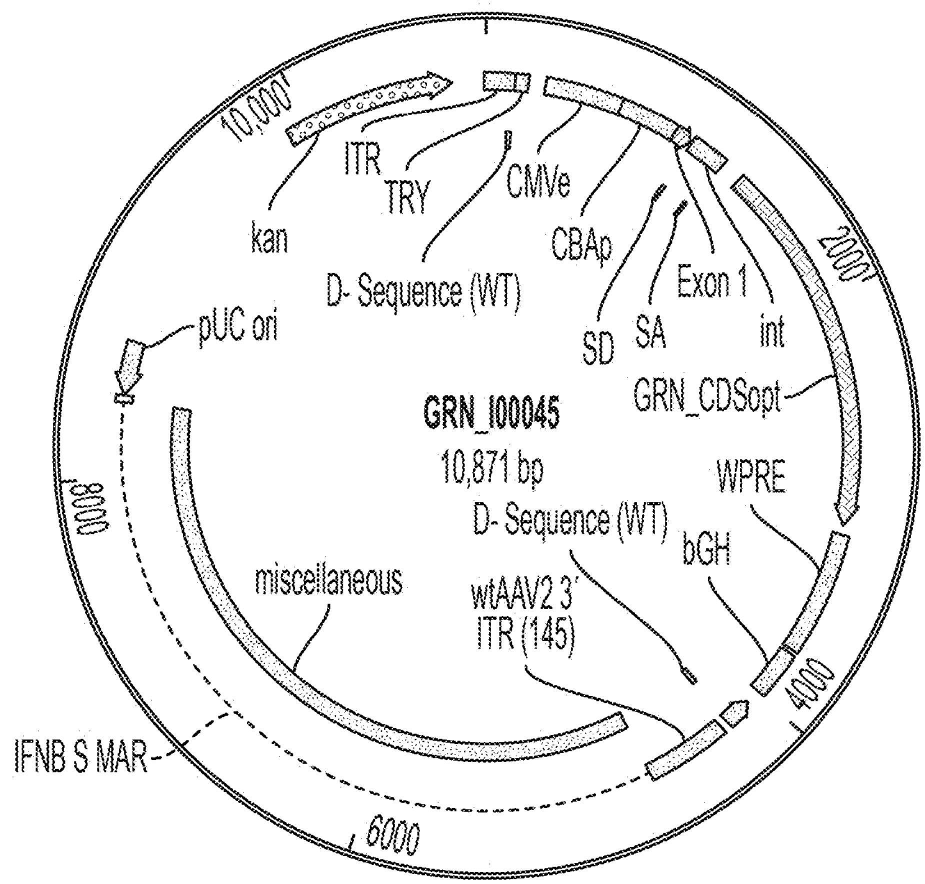
FIG. 39 is a schematic depicting one embodiment of a vector comprising an expression construct encoding PGRN.

FIG. 39 is a schematic depicting one embodiment of a vector comprising an expression construct encoding PGRN. Progranulin is overexpressed in the CNS of rodents deficient in GRN, either heterozygous or homozygous for GRN deletion, by injection of an rAAV vector encoding PGRN (e.g., codon-optimized PGRN), either by intraparenchymal or intrathecal injection such as into the cisterna magna.

Mice are injected at 2 months or 6 months of age, and aged to 6 months or 12 months and analyzed for one or more of the following: expression level of GRN at the RNA and protein levels, behavioral assays (e.g., improved movement), survival assays (e.g., improved survival), microglia and inflammatory markers, gliosis, neuronal loss, Lipofuscinosis, and/or Lysosomal marker accumulation rescue, such as LAMP1. Assays on PGRN-deficient mice are described, for example by Arrant et al. (2017) *Brain* 140: 1477-1465; Arrant et al. (2018) 1 Neuroscience 38(9):2341-2358; and Amado et al. (2018) doi:https://doi.org/10.1101/30869; the entire contents of which are incorporated herein by reference.

Example 13: In Vitro and In Vivo Testing of Progranulin rAAV

In vitro and in vivo assays were performed to analyze the effects of an rAAV construct (PR006 (also referred to as PR006A); see FIG. 64) encoding progranulin (PGRN) protein. PR006 comprises a capsid having an AAV9 serotype.

In Vitro Nonclinical Studies

Progranulin Expression Derived from PR006A in HEK293T Cells

Figure 60:
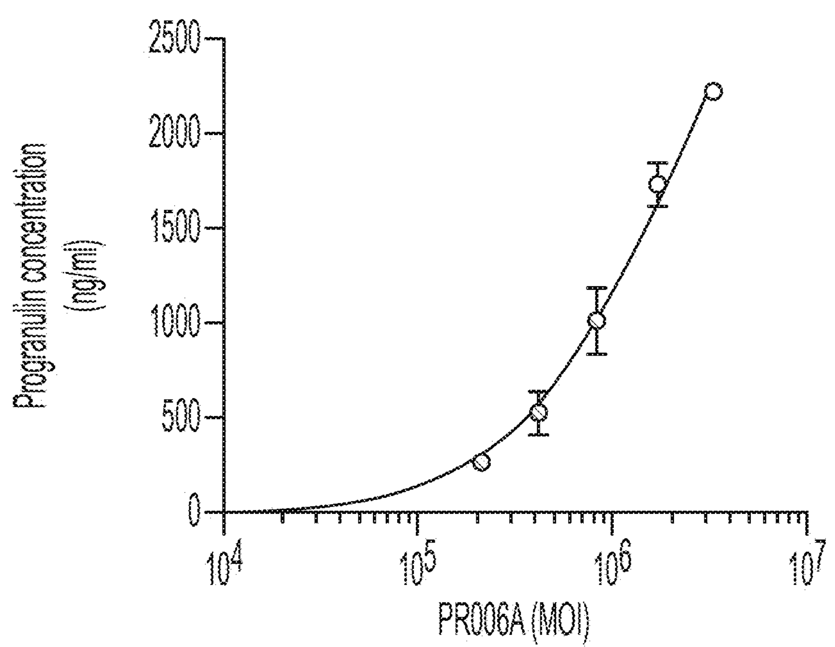
FIG. 60 is a graph depicting a dose-response curve of HEK293T cells transduced with PR006A (n=2; mean±SEM). An equal number of cells were transduced with varying amounts of PR006A. After 72 hours, progranulin protein levels in the cell media were measured using an ELISA assay.

The ability of PR006A to induce progranulin protein production in a cellular context was investigated. HEK293T cells were transduced with PR006A over a range of multiplicities of infection (MOI) ranging from $2.1\times10^5$ to $3.3\times10^6$ vector genomes (vg)/cell. PR006A transduction resulted in a robust, dose-dependent increase in progranulin protein expression and secretion into the cell media (FIG. 60). Substantially lower progranulin protein levels, reflecting the expression derived from the endogenous human GRN gene, were detected in a negative control group treated with excipient (the intended clinical vehicle) alone.

Efficacy in FTD-GRN iPSC-Derived Neurons

An assay was performed to analyze the efficacy of the rAAV construct in vitro in human FTD-GRN (Frontotemporal dementia with GRN mutation) neuronal cultures. Cell lines were obtained from the National Institute of Neurological Disorders and Stroke (NINDS) Human Cell and Data Repository (NHCDR): Materials ND50015 (FTD-GRN, M1L), ND50060 (FTD-GRN, R493X) and ND38555 (control, wild-type) (see Table 6).

TABLE 6

Summary of iPSC cell line characteristics

| Cell Line | NINDS Cell Line ID # | Clinical Diagnosis of FTD? | GRN mutation | Age | Gender | Source Cell/ Reprogramming Method |
|---|---|---|---|---|---|---|
| FTD-GRN #1 | ND50015 | Yes | MIL | 54 | F | Fibroblast/Episomal plasmids |
| FTD-GRN #2 | ND50060 | At risk (sibling affected at 62 yrs) | R493X | 60 | M | Fibroblast/Episomal plasmids |
| Control | ND38555 | No | N/A | 48 | F | Fibroblast/Retroviral plasmids |

To establish a cellular model that is pathologically relevant to FTD-GRN, iPSCs from each line were differentiated into neuronal cells using a two-step protocol. In the first step, iPSCs were differentiated into proliferating neuronal stem cell (NSC) lines, which lacked expression of pluripotency markers (i.e., Oct4 and SSEA1) and gained expression of neuronal stem cell markers (i.e., SOX2, Nestin, SOX1, and PAX6), as detected by immunofluorescence labeling.

Figure 52A:
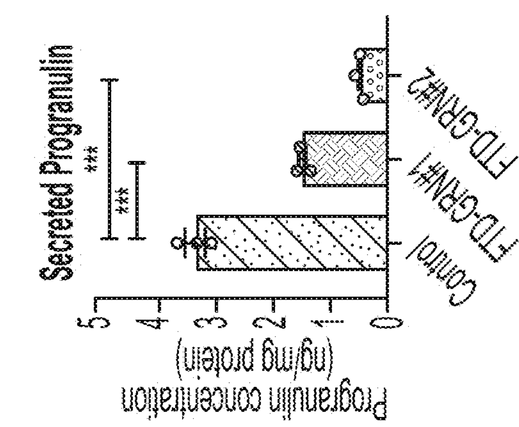
FIG. 52A shows that iPSC-derived neuronal stem cell (NSC) lines from patients with FTD-GRN mutations secreted less progranulin than NSC lines derived from healthy control subjects. Statistics were determined using an unpaired t-test; *=$p<0.05$, =$p<0.01$, *=$p<0.001$. Data is presented as mean±SEM.

Control and FTD-GRN NSC lines were seeded at an equal density, and 48 hours later, progranulin expression was measured by an enzyme-linked immunosorbent assay (ELISA) in cell lysates (intracellular progranulin) (FIG. 52E) and cell media (secreted progranulin) (FIG. 52A). Progranulin expression was normalized to total protein concentration to account for differences in cell number (n=3; mean±SEM). The NSC lines with heterozygous GRN mutations had significantly lower intracellular and secreted progranulin levels compared to Control NSCs, with FTD-GRN NSCs expressing ~25-50% of endogenous progranulin levels. This suggested that this FTD-GRN cell model recapitulates the clinical progranulin deficiency observed in FTD-GRN patients, who express one third to one half of normal progranulin levels in the plasma (Finch et al., *Brain* 132, 583-591 (2009); Ghidoni et al., *Neurology* 71, 1235-1239, (2008); Sleegers et al., *Ann Neurol* 65, 603-609 (2009)).

Figure 52B:
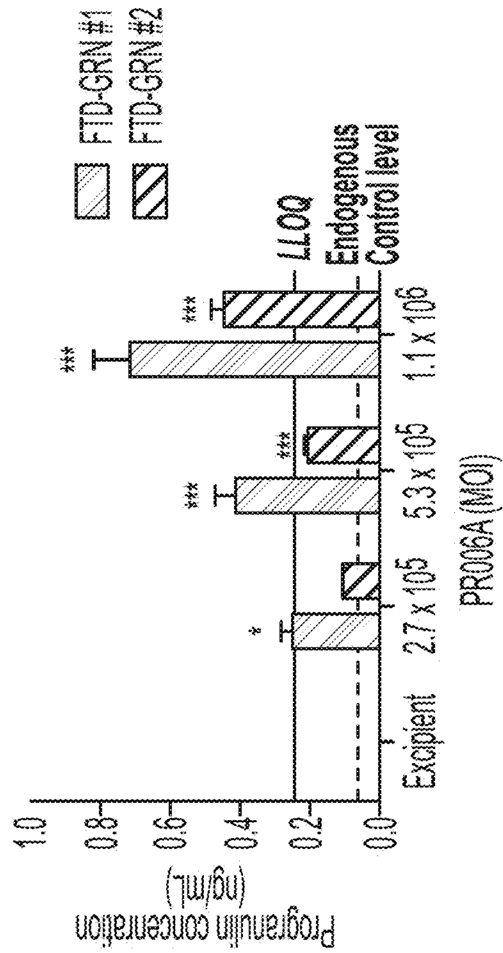
FIG. 52B shows results from dose-ranging PR006A transduction in FTD-GRN mutation carrier neuronal cultures. NSCs were seeded at an equal density and differentiated into neurons. On day 7, neurons were transduced with excipient or the indicated amounts of PR006A for 72 hours. Secreted progranulin expression was measured from the cell media by ELISA and normalized to volume (n=3-4; mean±SEM). Black dashed line represents endogenous levels of secreted progranulin from Control neurons (excipient-treated). Secreted progranulin was not detectable in excipient-treated FTD-GRN neurons. Statistics were determined using ANOVA followed by Tukey HSD and statistical comparison of each condition to excipient-treated Control neurons is indicated on the graph, *=$p<0.05$, ***=$p<0.001$. LLOQ=lower limit of quantitation; MOI=multiplicity of infection.
Figure 52C:
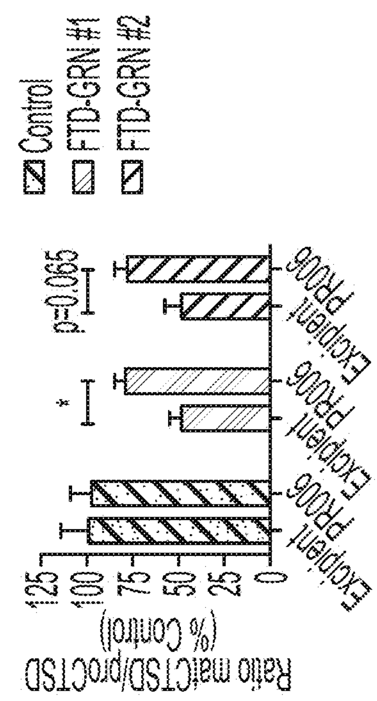
FIG. 52C shows that PR006 treatment of neuronal cultures rescued the defective maturation of a key lysosomal protease, cathepsin D, in FTD-GRN neuronal cultures. NSCs were seeded at equal concentrations and differentiated into neurons. On day 7, neurons were transduced with excipient or PR006A at an MOI of $5.3\times10^5$ for 72 hours. Neurons were lysed, and lysates were analyzed on the Protein Simple Western Jess system with an anti-cathepsin D (CTSD) primary antibody. Bands corresponding to both the mature cathepsin D (matCTSD) and pro-cathepsin D (proCTSD) were detected, and the area under the curve was quantified for each band and normalized to an internal total protein normalization signal. The matCTSD/proCTSD ratio in excipient or PR006A treated FTD-GRN neurons was determined; the y-axis depicts the matCTSD/proCTSD ratio as a percent of the ratio of excipient-treated Control neurons (n=3; mean±SEM). Statistics were determined using a paired t-test, *=$p<0.05$.
Figure 52D:
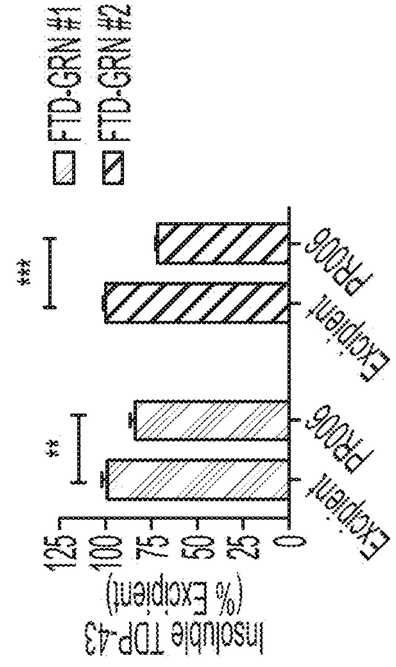
FIG. 52D and FIG. 52F show that PR006A reduces TDP-43 pathology in FTD-GRN neuronal cultures. NSCs were seeded at equal concentrations and differentiated into neurons. On day 7, neurons were transduced with excipient or PR006A at an MOI of $5.3\times10^5$ and collected 21 days after transduction.
Figure 52F:
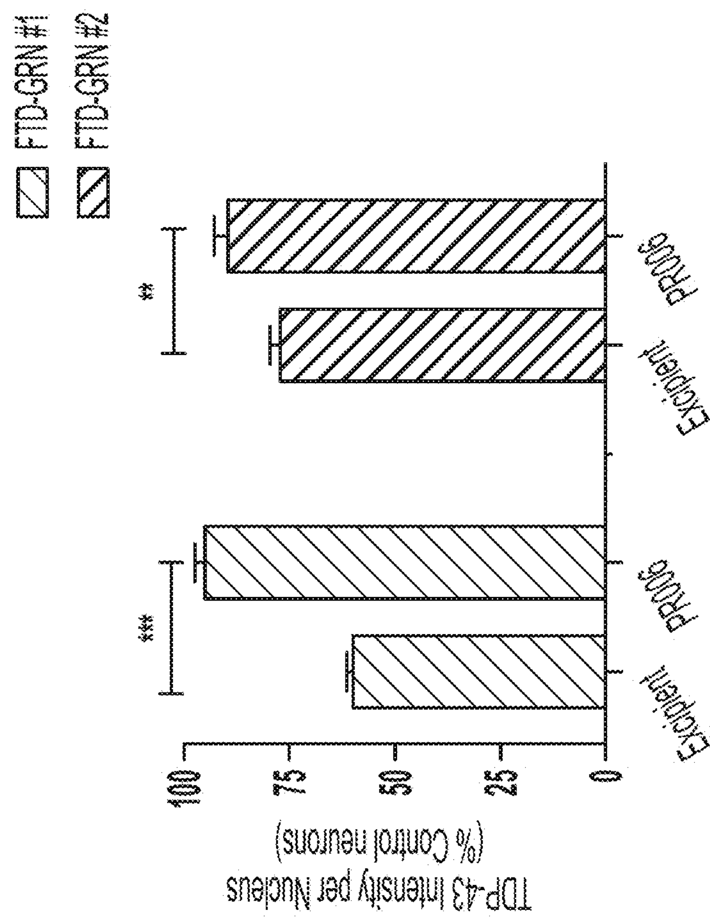
Figure 52E:
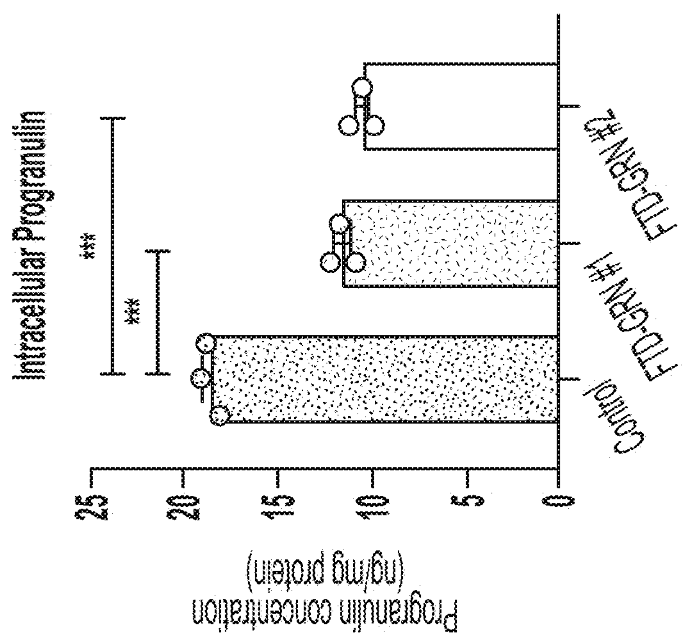
FIG. 52E shows that iPSC-derived NSC lines from patients with FTD-GRN mutations expressed less progranulin than NSC lines derived from healthy control subjects. Statistics were determined using an unpaired t-test; *=p<0.05, =p<0.01, *=p<0.001. Data is presented as mean±SEM.
Figure 52G:
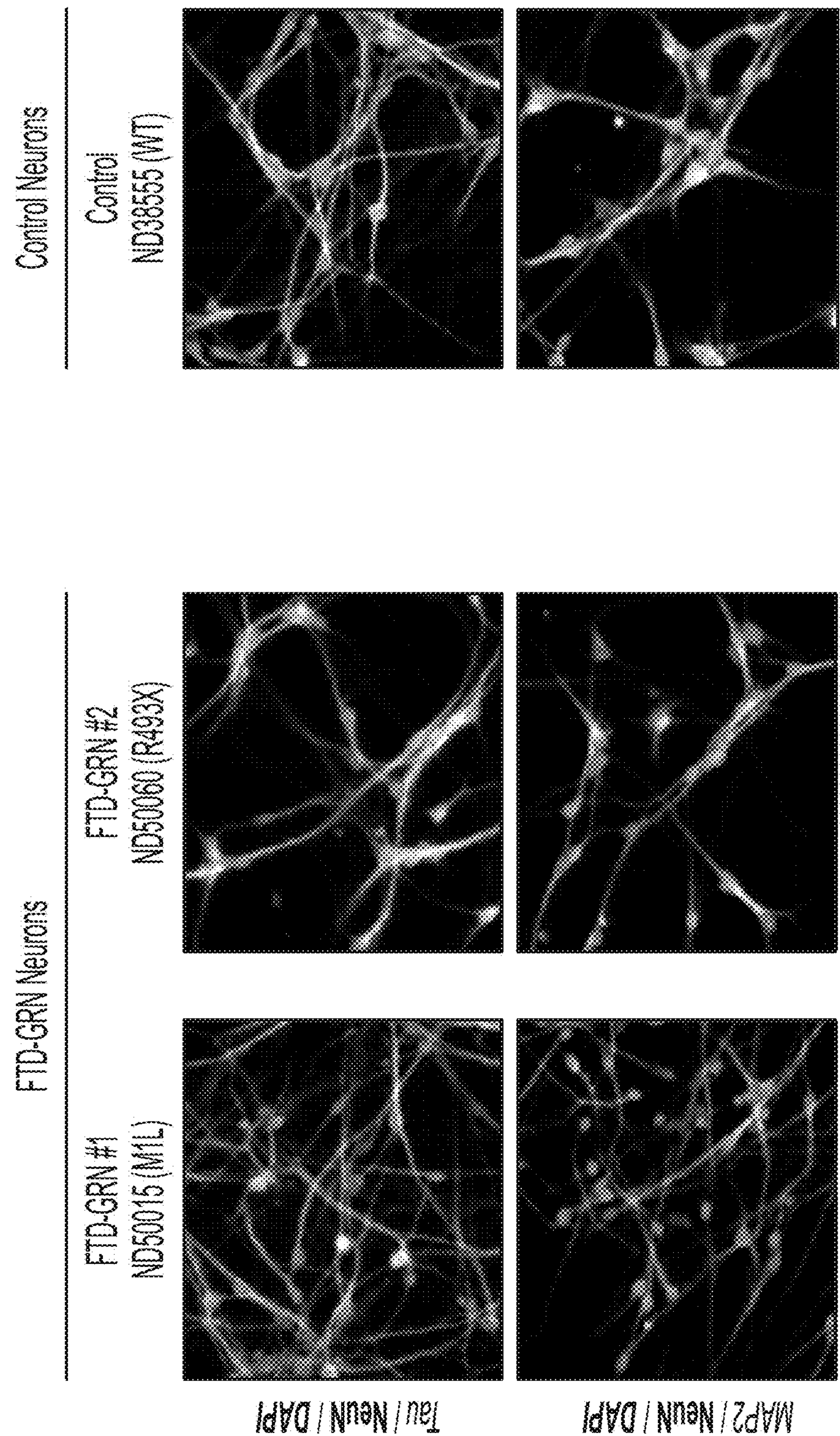
FIG. 52G is a series of images showing that neuronal stem cell (NSC) lines from human FTD-GRN and human control cell lines were successfully differentiated into neuronal cultures. Control and FTD-GRN NSC lines (FTD-GRN #1 and FTD-GRN #2) were differentiated into neurons after a period of 7 days, as indicated by cell morphology and immunofluorescence staining for neuronal markers (NeuN [red]; MAP2 or Tau as labeled at left [green]). DAPI (blue) was used to stain the nucleus.

NSCs from all cell lines were differentiated into neuronal cultures. After establishing that the iPSC-derived NSCs exhibit reduced progranulin expression, the lines were differentiated into neurons to generate a clinically representative cell type for nonclinical efficacy studies of PR006A. NSCs were seeded into neuronal differentiation media, terminally differentiated into postmitotic neurons for a period of 7 days, and then assessed for expression of neuronal markers (i.e., MAP2, NeuN, Tau, Tuj1, NF-H) by immunofluorescence (FIG. 52G). Both Control and FTD-GRN iPSC-derived NSC lines efficiently differentiated into neurons using this protocol.

FTD-GRN iPSC-derived neuronal cultures were used to evaluate the efficacy of PR006A in vitro. FTD-GRN neurons were treated with excipient or PR006A at MOIs of $2.7\times10^5$, $5.3\times10^5$, or $1.1\times10^6$ vg/cell. PR006 transduction resulted in a robust, dose-dependent expression of secreted progranulin, as measured by ELISA, in all cell lines (FIG. 52B). Excipient-treated Control and FTD-GRN neurons were assessed for endogenous progranulin levels. Control neurons expressed endogenous secreted progranulin, while no secreted progranulin was detected in FTD-GRN neurons (FIG. 52B). Linear regression analysis confirmed a significant correlation between PR006A dose and progranulin levels across both FTD-GRN cell lines ($p=3.5\times10^{-13}$). These results demonstrate that treatment with PR006A results in elevated secretion of progranulin in the FTD-GRN neuronal model.

Progranulin is known to stimulate maturation of the lysosomal protease cathepsin D (CTSD), whose loss of function has also been implicated in lysosomal storage disorders and neurodegeneration. CTSD is expressed as an inactive full-length pro-protein (proCTSD) that undergoes proteolytic processing into an enzymatically active mature protease (matCTSD). Progranulin has been reported to act as a molecular chaperone that binds to proCTSD to enhance its maturation into the matCTSD protease. In FTD-GRN neuronal cultures, PR006 transduction rescued the defective maturation of cathepsin D (FIG. 52C). Control, FTD-GRN #1, and FTD-GRN #2 neurons were transduced with PR006A or excipient. An MOI of $5.3\times10^5$ PR006A was used for efficacy experiments since it restored progranulin levels to at least 2-fold those of Control cells (FIG. 52B). To evaluate efficacy, proCTSD and matCTSD expression levels were measured in cell lysates using the automated a Simple Western™ (Jess) platform (FIG. 52C). Excipient-treated FTD-GRN neurons had a lower ratio of matCTSD to proCTSD as compared to excipient-treated Control neurons; PR006A treatment significantly increased the ratio in both FTD-GRN neuronal lines (FIG. 52C). In Control neurons, the ratio of matCTSD to proCTSD was not significantly altered by PR006A treatment. These findings demonstrate that PR006A restores a lysosomal function-related phenotype in FTD-GRN neurons.

In normal neurons, TDP-43 (transactive response DNA binding protein 43 kDa) protein is localized in the nucleus. In post-mortem brains of FTD-GRN patients, aggregation of TDP-43 in the cytoplasm of neurons is observed, and nuclear accumulation of TDP-43 is reduced. FTD neurons have decreased nuclear TDP-43, leading to aggregation and downstream toxicity in neurons. Since Grn KO mice do not fully recapitulate this TDP-43 pathology, induced pluripotent stem cell (iPSC)-derived neurons are a valuable FTD-GRN model to study TDP-43 biology. Decreased accumulation of TDP-43 in the nucleus, and increased accumulation of insoluble TDP-43, have been reported in iPSC-derived neurons from patients with FTD-GRN, relative to control neurons that do not carry a GRN mutation, as described by Valdez et al. (Human Molecular Genetics 26, 4861-4872 (2017)). PR006A transduction of neuronal cultures from both FTD-GRN mutation carrier lines reversed TDP-43 abnormalities, resulting in decreased insoluble TDP-43 (measured using the Simple Western™ (Jess) platform (FIG. 52D)) and increased nuclear localization of TDP-43 (measured using immunofluorescence (FIG. 52F)).

To summarize, PR006 transduction restored defective maturation in the lysosomal enzyme, cathepsin D, and improved abnormal TDP-43 pathology in FTD-GRN neurons.

In Vivo Nonclinical Studies

Efficacy and Biodistribution in Aged Grn Knockout Mice

PR006A efficacy in vivo and the maximal dose PR006A were evaluated in the Grn knockout (KO) mouse model. In the Grn KO mouse model used in these studies (B6(Cg)-$Grn^{tm1.1Aidi}$/J (Jackson Laboratory, Bar Harbor, ME), exons 1-4 are deleted from the target progranulin (Grn) gene (Yin et al., *J Exp Med* 207, 117-128 (2010)). These animals have a complete loss of progranulin, display age-dependent phenotypes including lysosomal alterations, neuronal lipofuscin accumulation, ubiquitin accumulation, microgliosis, and neuroinflammation, and are therefore widely used to model FTD-GRN. All attempts were made to eliminate bias from the study; mice were assigned to treatment groups that were balanced for gender and body weight, and a blinded assessment of experimental endpoints was conducted by qualified personnel.

In the initial studies, PR006A was delivered to aged Grn KO mice at a dose of $9.7\times10^{10}$ vg ($2.4\times10^{11}$ vg/g brain), which was the highest achievable dose at the time of the study due to injection volume constraints and the physical titer of the virus lot used for the study. Aged mice were used since many of the FTD-GRN-related phenotypes, including CNS inflammation and microgliosis, develop in an age dependent manner, with the most pronounced manifestation of phenotypes occurring between 12-24 months of age.

Figure 61:
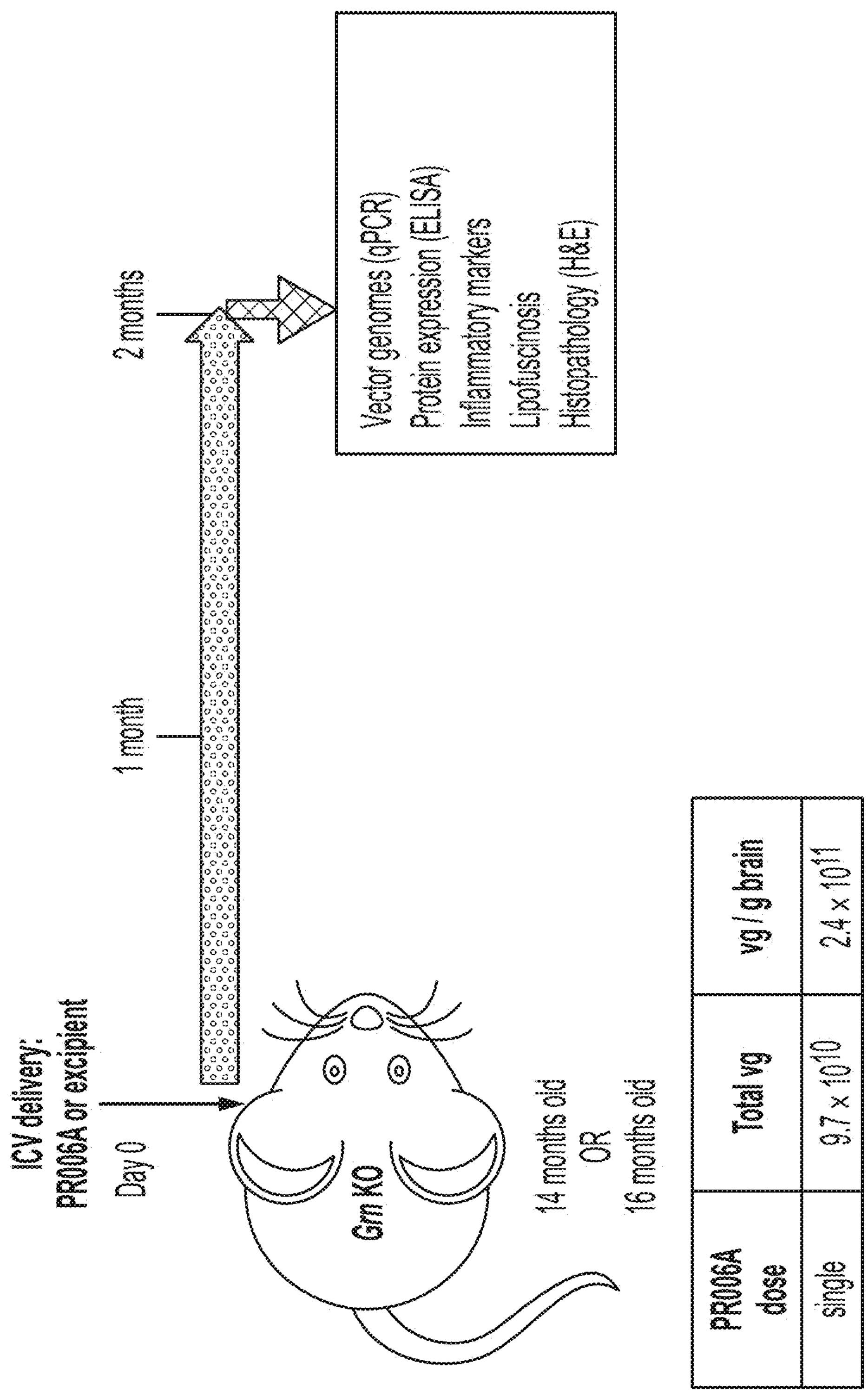
FIG. 61 is a diagram of a study design for maximal dose PR006A in an aged FTD-GRN mouse model. 10 μl excipient (control) or PR006A at a dose of $9.7\times10^{10}$ vg ($2.4\times10^{11}$ vg/g brain) was delivered by ICV injection to two cohorts of Grn KO mice: (1) 16 months old at time of injection (n=4-5/group; PRV-2018-027) and (2) 14 months old at time of injection (n=1/excipient-treated group; n=3/PR006A-treated group; PRV-2019-002). The animals were sacrificed two months post-injection. CNS and peripheral tissues were collected to analyze PR006A biodistribution (qPCR), progranulin protein expression (ELISA), and histopathology (H&E). Expression of proinflammatory markers, lipofuscin accumulation, and ubiquitin accumulation were assessed in the brain.

In the studies with aged Grn KO mice, PR006A was administered by single intracerebroventricular (ICV) injection. 10 μl excipient (the intended clinical vehicle; 20 mM Tris pH 8.0, 200 mM NaCl, and 1 mM $MgCl_2$+0.001% Pluronic F68) or $9.7\times10^{10}$ vg PR006A ($2.4\times10^{11}$ vg/g brain [based on an adult mouse brain weight of 400 mg]) was delivered by ICV injection into two cohorts of aged Grn KO mice: (1) 16-months-old at time of injection (n=4/group; PRV-2018-027; FIG. 61) and (2) 14-months-old at time of injection (planned n=3/group; PRV-2019-002; FIG. 61). The animals were sacrificed two months post-injection.

In study PRV-2018-027, a single dose of PR006A was delivered to 16-month-old mice with the following treatment groups:

| Model | ICV | ICV dose | N |
|---|---|---|---|
| Grn KO | Excipient | N/A | 4 (2 M/2 F) |
| Grn KO | PR006A | $9.7\times10^{10}$ vg ($2.4\times10^{11}$ vg/g brain) | 5 (3 M/2 F) |

Due to unforeseen study deviations (errors in genotyping and premature loss of animals), study PRV-2019-002 (14-month-old cohort) enrolled only 1 mouse in the excipient-treated group instead of the planned n=3. The low sample number made statistical analysis impossible, and therefore this study is excluded from further discussion here. However, the findings from the study were comparable to those from study PRV-2018-027.

Biodistribution and Progranulin Expression:

Biodistribution was determined by measuring vector genome presence using a qPCR assay that meets the current U.S. Food and Drug Administration Center for Biologics Evaluation and Research (CBER)/Office of Tissues and Advanced Therapies (OTAT) standards for PCR sensitivity (with >50 vector genomes per 1 μg genomic DNA defined as positive). All mice that received PR006A were positive for vector genomes in the cerebral cortex and spinal cord, indicating that ICV administration successfully results in PR006A transduction in the brain and CNS (FIG. 59A). ICV PR006A resulted in significant levels of human progranulin protein in the CNS (brain, spinal cord) of the Grn KO mice, whereas, as expected, human progranulin was not detectable in the mice that received excipient (FIG. 59B). Since progranulin is primarily a secreted protein, expression in the CSF can be considered a surrogate of protein production within the brain and represents a potential translational endpoint for FTD-GRN patients who have decreased CSF progranulin levels. We were able to detect human progranulin in the CSF of PR006A-treated mice, but because of the small sample volume and the technical limitations of obtaining sufficient volume of CSF in mice, the measurements of CSF progranulin level were below the lower limit of quantitation (LLOQ) of the assay (FIG. 59C).

Figure 62B:
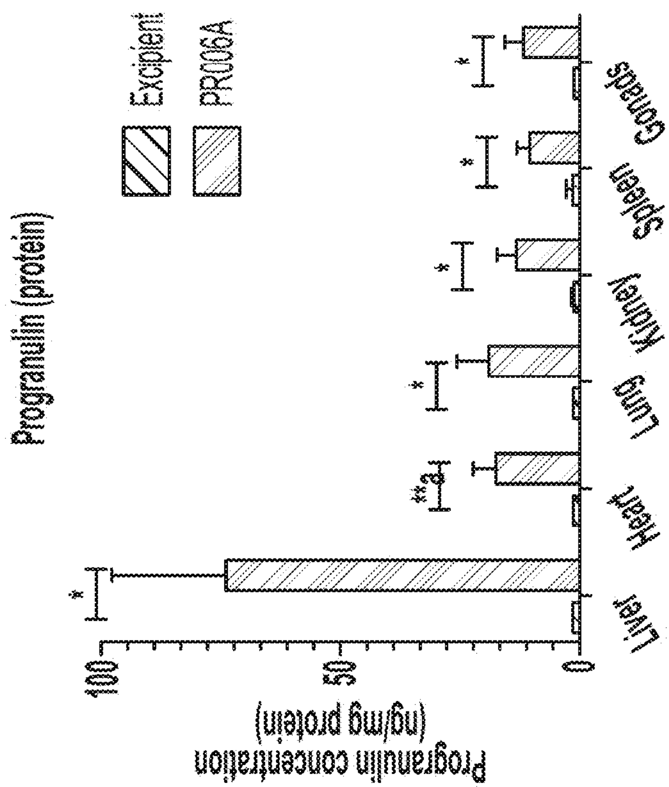
FIG. 62A-FIG. 62B are bar graphs showing results for peripheral tissue biodistribution and progranulin expression in an aged FTD-GRN mouse model following PR006A treatment. Tissue samples were collected from 18-month old Grn KO mice 2 months after receiving ICV excipient (red) or $9.7\times10^{10}$ vg ($2.4\times10^{11}$ vg/g brain) PR006A (blue).
Figure 62A:
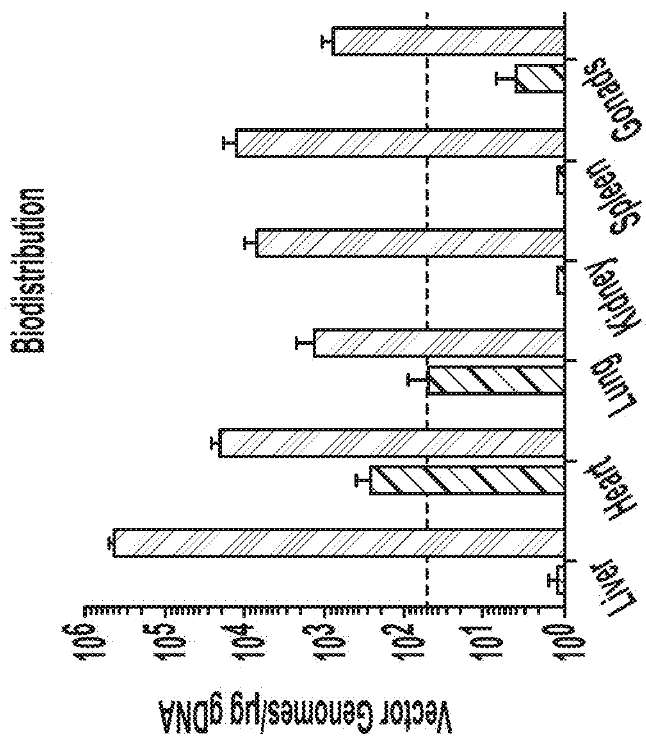

ICV administration also resulted in broad vector genome presence and progranulin protein levels in peripheral tissues, including liver, heart, lung, kidney, spleen, and gonads (FIG. 62A-FIG. 62B). In addition, significant levels of human progranulin were detectable in plasma of the PR006A-treated Grn KO mice. As expected, human progranulin was not detected in the excipient treated Grn KO mice.

Figure 59D:
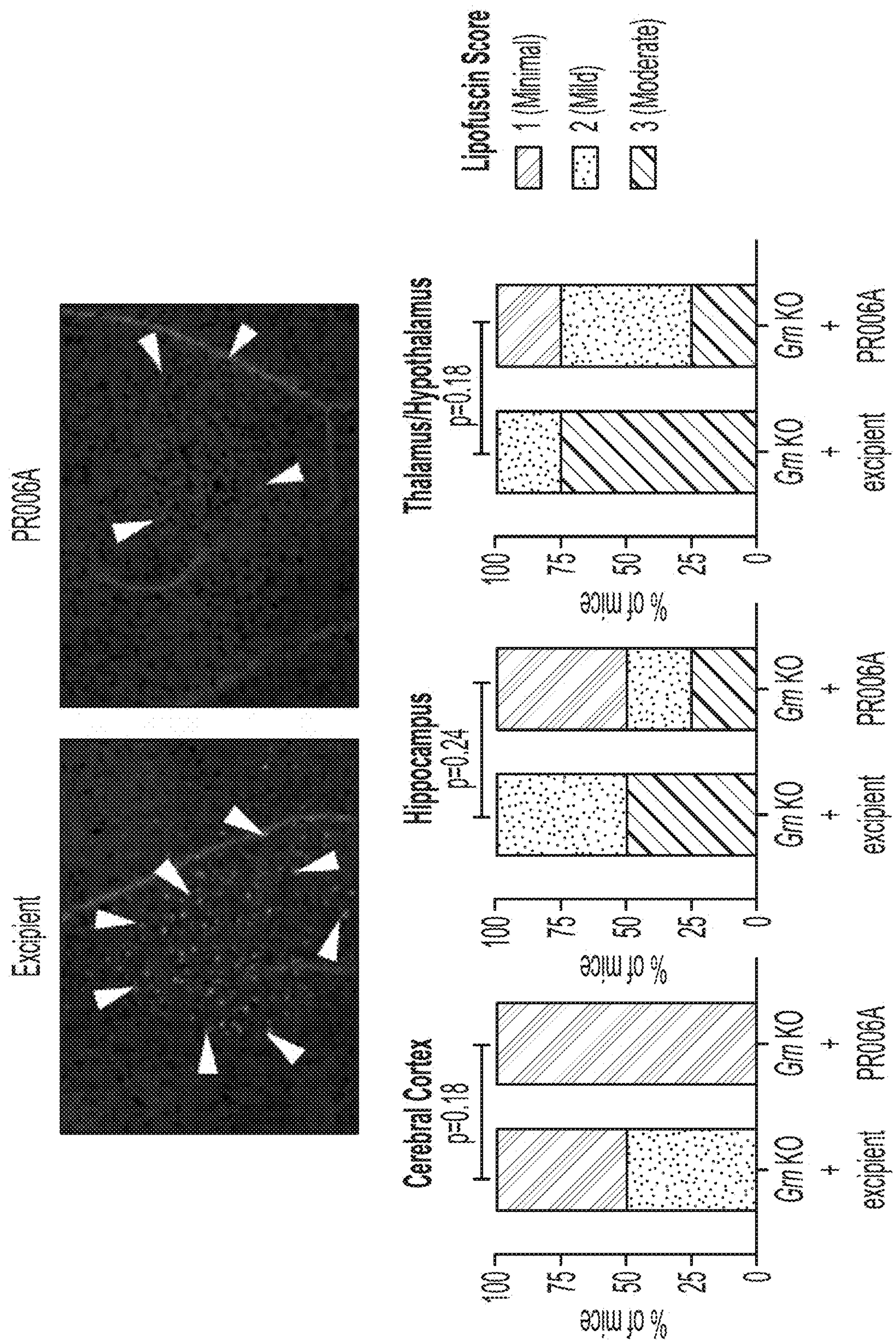
FIG. 59D-FIG. 59E are a series of bar graphs and images depicting the results of experiments showing reduced lysosomal and neuropathology defects in an aged FTD-GRN mouse model following PR006A treatment. Tissue samples were collected from 18-month old Grn KO mice 2 months after receiving ICV excipient (red) or $9.7\times10^{10}$ vg ($2.4\times10^{11}$ vg/g brain) PR006A (blue). Lipofuscinosis was analyzed by scoring of H&E-stained brain sections by a pathologist.
Figures 59E, 59F, 59G:
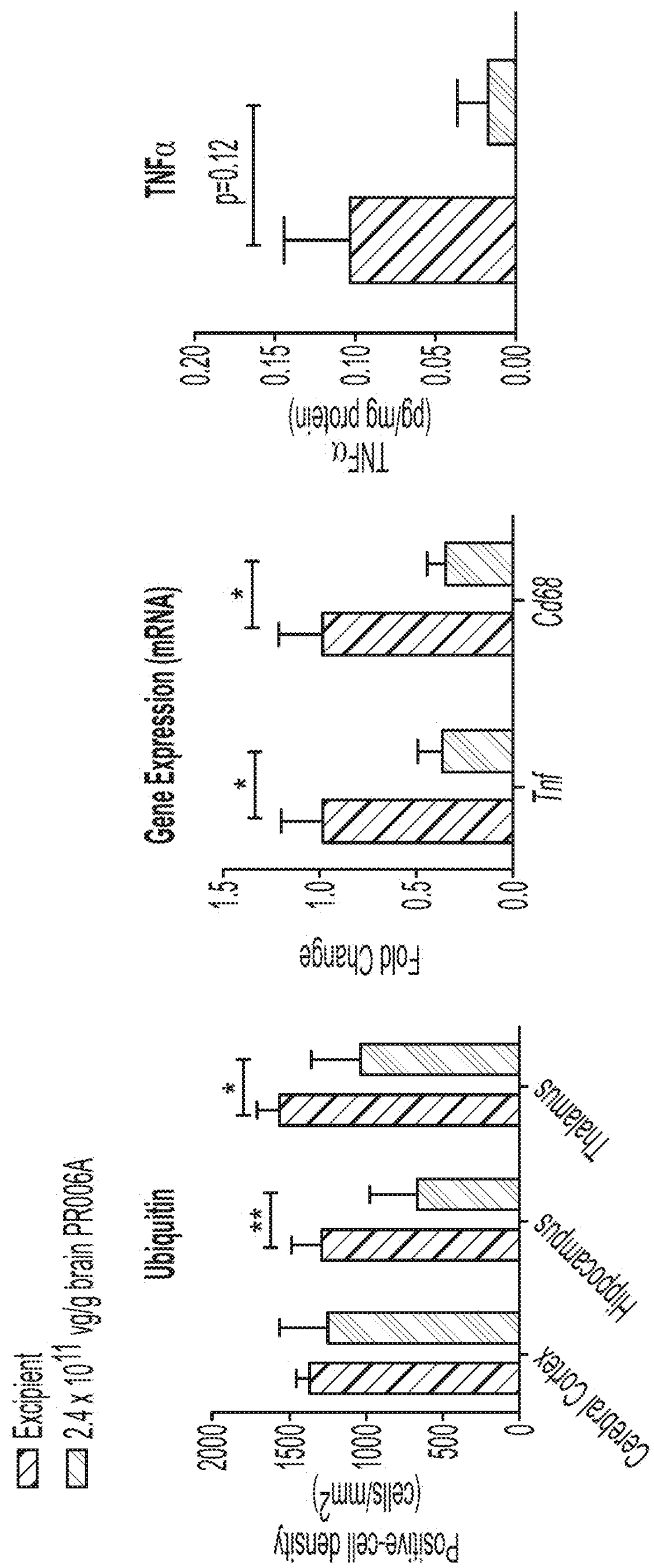
FIG. 59F-FIG. 59I are a series of bar graphs depicting the results of experiments showing decreased neuroinflammation markers in an aged FTD-GRN mouse model following PR006A treatment. Tissue samples were collected from 18-month old Grn KO mice 2 months after receiving ICV excipient (red) or $9.7\times10^{10}$ vg ($2.4\times10^{11}$ vg/g brain) PR006A (blue).

Lipofuscin Accumulation:

Accumulation of neuronal lipofuscin, an electron-dense, autofluorescent material that accumulates progressively over time in lysosomes of postmitotic cells and is an indicator of lysosomal dysfunction, is a hallmark age-dependent phenotype of Grn KO mice. Lipofuscin accumulation was assessed using two independent methods in adjacent brain sections: (1) in a more clinical approach, lipofuscin accumulation in the brain was scored by a blinded pathologist on a scale of 0 (no lipofuscin observed) to 4 (widespread lipofuscin accumulation) and (2) in a more quantitative approach, lipofuscin autofluorescence was detected by immunohistochemistry (IHC) and automatically quantified. Grn KO mice exhibited substantial lipofuscinosis throughout the brain, and ICV PR006A treatment reduced the lipofuscin score severity in the cerebral cortex, hippocampus, and thalamus (FIG. 59D). Quantitation of lipofuscin accumulation from IHC images also detected decreased lipofuscinosis with PR006A treatment in all three brain regions. Since ubiquitin-positive inclusions are a defining pathological feature of FTD-GRN patients that also accumulate in the Grn KO mouse model in an age-dependent manner, IHC was performed and quantified in the brain regions of interest (cerebral cortex, hippocampus, thalamus) to assess ubiquitin accumulation. PR006A treatment significantly reduced ubiquitin accumulation in Grn KO mice (FIG. 59E). These findings suggest that PR006A improves lysosomal dysfunction in the Grn KO mouse model of FTD-GRN.

Figure 59H:
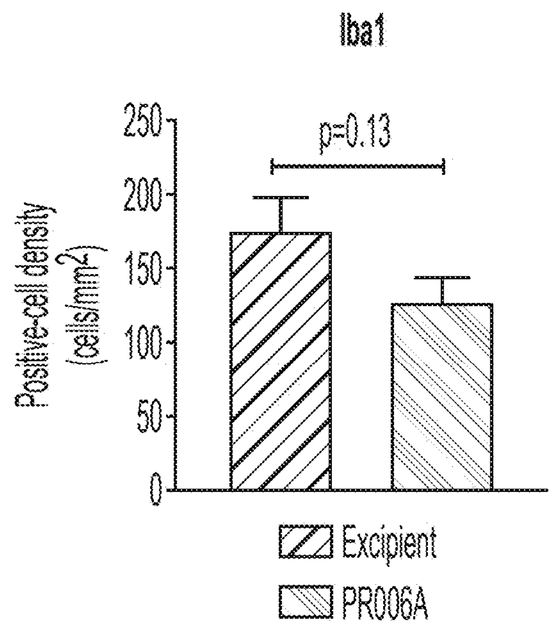
Figure 59I:
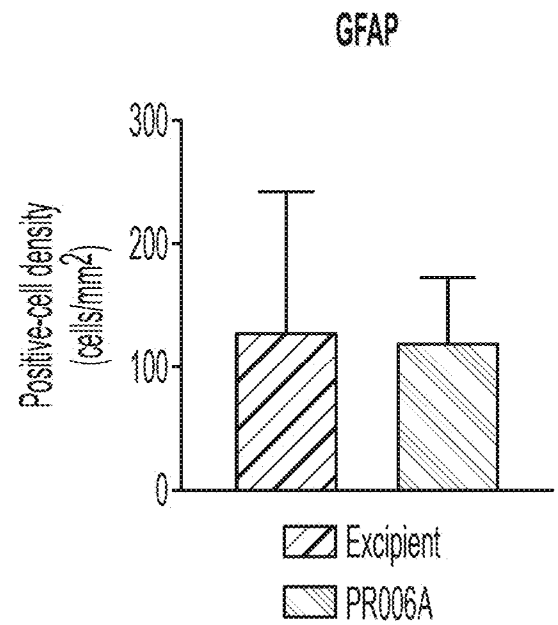

Neuroinflammation:

Chronic CNS inflammation is a pathological feature in the brain of patients with FTD-GRN that is recapitulated in Grn KO mice in an age-dependent manner. Progranulin has anti-inflammatory effects in mouse models of FTD-GRN, and loss of progranulin leads to upregulation of proinflammatory cytokines, including TNFα. In this study, treatment with PR006A suppressed inflammatory marker levels in aged Grn KO mice. ICV PR006A decreased gene expression of the proinflammatory cytokine Tnf (TNFα) and Cd68 (CD68), a marker of microglia, in the cerebral cortex (FIG. 59F). TNFα protein levels were also decreased in cerebral cortex samples from PR006A-treated Grn KO mice using the Mesoscale Discovery mouse pro-inflammatory cytokine assay (FIG. 59G). To further evaluate neuroinflammation, immunohistochemistry (IHC) was performed for Iba1, a marker of microgliosis, and GFAP, a marker of astrocytosis, and quantified in the brain regions of interest (cerebral cortex, hippocampus, thalamus). PR006A treatment resulted in a trend towards decreased microgliosis (Iba1) but did not affect astrocytosis (GFAP) in Grn KO mice (FIG. 59H; FIG. 59I). Taken together, these results indicate that PR006A treatment reduces neuroinflammation in the aged Grn KO mouse model of FTD-GRN.

Histopathology:

thorough histopathological analysis by a blinded board-certified pathologist of hematoxylin and eosin (H&E) staining of the brain, thoracic spinal cord, liver, heart, spleen, lung, and kidney of all mice from these studies revealed no adverse events related to PR006A treatment. Administration of PR006A to Grn KO mice resulted in a decreased incidence and/or severity of findings that are characteristic of the model, including a reduction in frequency and/or severity scores of neuronal necrosis in the medulla and pons. Additionally, there was a reduction in both the incidence and severity of axonal degeneration in the thoracic spinal cord with PR006A treatment. These findings are discussed in detail in the Toxicology section below.

Conclusion:

ICV PR006A at a dose of $9.7\times10^{10}$ vg ($2.4\times10^{11}$ vg/g brain) resulted in broad vector genome presence throughout the brain and peripheral tissues in aged Grn KO mice. PR006A treatment increased global progranulin expression. In addition, PR006A reduced accumulation of lipofuscin and ubiquitin in the brain, pathologies known to occur in both the Grn KO mouse model and patients with FTD-GRN. PR006A also reduced the expression of proinflammatory cytokines and immune cell activation in the cerebral cortex, phenotypes that are indicative of chronic CNS inflammation.

Dose-Ranging Efficacy in Adult Grn Knockout Mice

Figure 63:
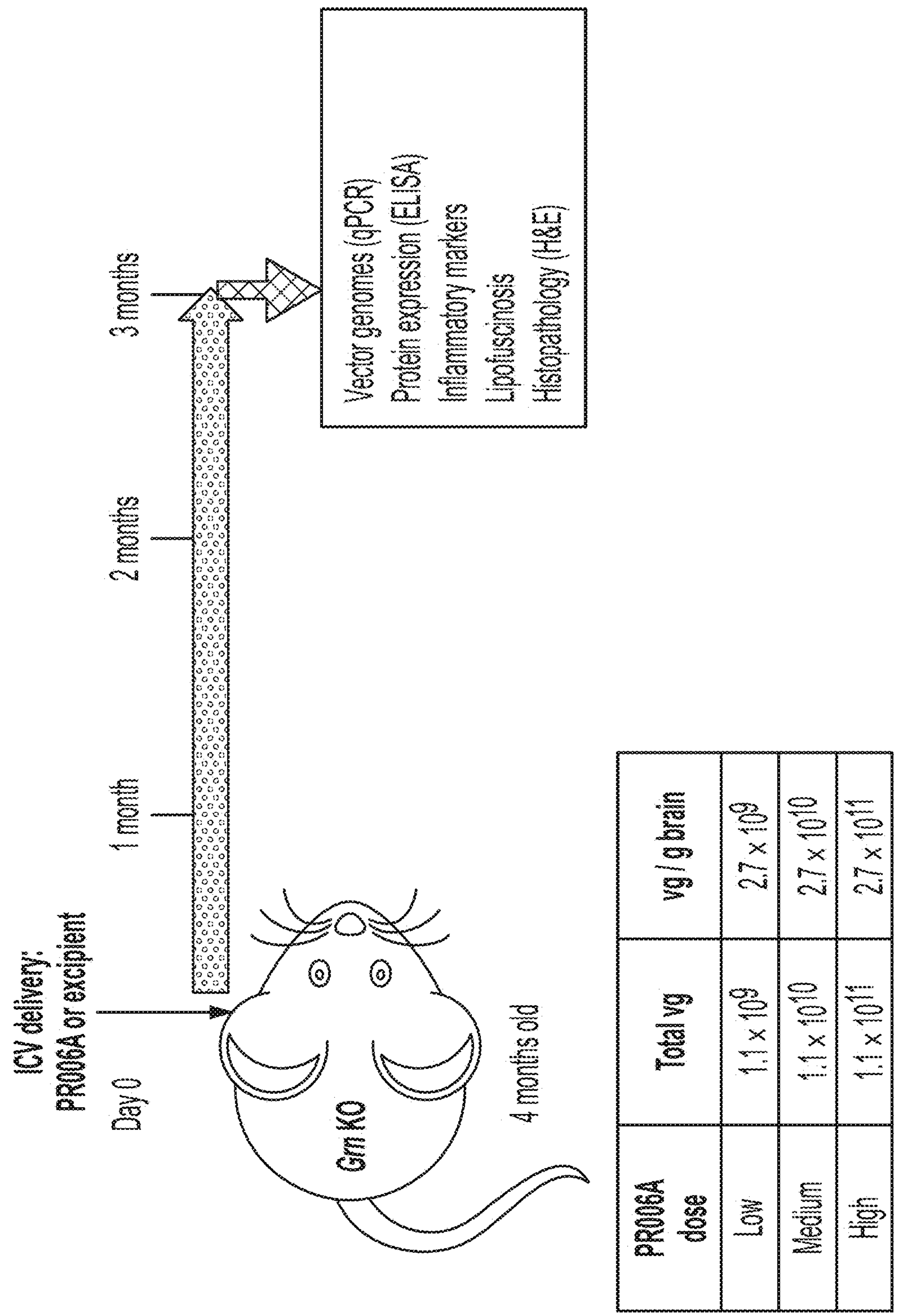
FIG. 63 is a diagram of a study design for dose-ranging PR006A in an adult FTD-GRN mouse model 10 μl excipient (control) or PR006A at dose of $1.1\times10^9$ vg ($2.7\times10^9$ vg/g brain), $1.1\times10^{10}$ vg ($2.7\times10^{10}$ vg/g brain), or $1.1\times10^{11}$ vg ($2.7\times10^{11}$ vg/g brain) PR006A was delivered by ICV injection into 4-month-old Grn KO mice (n=10/group). The animals were sacrificed three months post-injection, when the mice were 7 months old. CNS and peripheral tissues were collected to analyze PR006A biodistribution (qPCR), progranulin protein expression (ELISA), and histopathology (H&E). Expression of proinflammatory markers, lipofuscin accumulation, ubiquitin accumulation, and global gene expression changes were assessed in the brain.

To further assess efficacious doses of PR006A, a larger, dose-ranging study in adult Grn KO mice was performed. In PRV-2019-004, 10 μl excipient (the intended clinical vehicle; 20 mM Tris pH 8.0, 200 mM NaCl, and 1 mM $MgCl_2$+0.001% Pluronic F68) or PR006A was delivered via ICV to 4-month-old animals. These adult mice were used instead of the aged Grn KO mice because the latter were not available in sufficient numbers for conducting a dose-ranging study. While the adult Grn KO mice have a milder phenotype than aged mice, they still exhibit lysosomal defects and neuroinflammatory changes and therefore are suitable for evaluating the efficacious dose range of PR006A. In order to assess PR006A efficacy over a broad range of viral doses, PR006A was administered at $1.1\times10^{11}$ vg ($2.7\times10^{11}$ vg/g brain), the highest achievable dose at the time of the study due to injection volume constraints and the physical titer of the virus lot used for the study, a middle dose of $1.1\times10^{10}$ vg ($2.7\times10^{10}$ vg/g brain), or a low dose of $1.1\times10^9$ vg ($2.7\times10^9$ vg/g brain), with a full log difference spanning each dose. The details of the experimental design are given in FIG. 63.

Three doses of PR006A were assessed, with 10 mice (4M/6F) per group:

| Model | ICV | ICV dose | N |
|---|---|---|---|
| Grn KO | Excipient | N/A | 10 (4 M/6 F) |
| Grn KO | PR006A | $1.1\times10^9$ vg ($2.7\times10^9$ vg/g brain) | 10 (4 M/6 F) |
| Grn KO | PR006A | $1.1\times10^{10}$ vg ($2.7\times10^{10}$ vg/g brain) | 10 (4 M/6 F) |
| Grn KO | PR006A | $1.1\times10^{11}$ vg ($2.7\times10^{11}$ vg/g brain) | 10 (4 M/6 F) |

Age-matched mice of the same background strain as the Grn KO mice with wildtype (WT) Grn alleles (7-month old C57BL/6J) served as controls for select efficacy endpoints in this study.

| Model | ICV | ICV dose | N |
|---|---|---|---|
| WT (C57BL/6J) | N/A | N/A | 10 (5 M/5 F) |

Biodistribution and Progranulin Expression:

Biodistribution was determined by measuring vector genome presence using a qPCR assay that meets the current U.S. Food and Drug Administration CBER/OTAT standards for PCR sensitivity (with >50 vector genomes per μg genomic DNA defined as positive). Mice that received PR006A were positive for vector genomes in the cerebral cortex and spinal cord in a dose-dependent manner, indicating that ICV administration successfully results in PR006A transduction in the CNS (FIG. 53A). qRT-PCR analysis of PR006A-encoded GRN revealed that ICV dosing of PR006A resulted in a dose-dependent induction of human GRN mRNA expression in the cerebral cortex (FIG. 53B). PR006A treatment increased levels of human progranulin protein in the brain and spinal cord (FIG. 53C). In brain tissue, human progranulin levels were detected and quantified at the highest PR006A dose; at lower doses, progranulin levels were below the assay limit of detection due to the high background in brain. However, based on the log-fold difference between doses, proportional estimation of expected progranulin levels at the lower doses would be well below the lower limit of quantitation (LLOQ) of the assay in brain tissue. The level of endogenous mouse progranulin was measured in age and strain-matched mice with wildtype (WT) Grn alleles; in both the cerebral cortex and spinal cord, the levels of human progranulin in PR006A-treated Grn KO mice did not exceed the level of endogenous progranulin in WT mice at any dose. Since different detection assays employing non-species-cross-reactive anti-progranulin antibodies were used to measure human and mouse progranulin, the absolute numbers cannot be compared with accuracy.

Figure 53D:
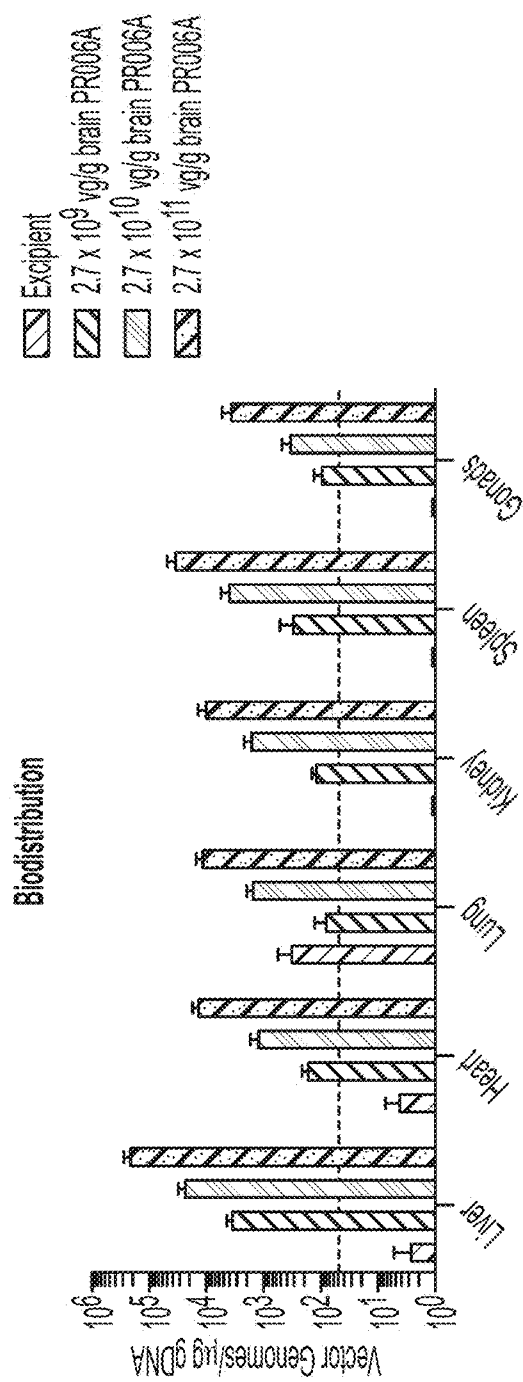
FIG. 53D-FIG. 53E are a series of bar graphs depicting the results of experiments analyzing peripheral tissue biodistribution and progranulin expression in adult dose-ranging PR006A FTD-GRN mouse model study. 4-month-old Grn KO mice were given PR006A or excipient by ICV administration. They were sacrificed 3 months after the treatment with excipient (red) or PR006A at dose of $1.1\times10^{9}$ vg ($2.7\times10^{9}$ vg/g brain), $1.1\times10^{10}$ vg ($2.7\times10^{10}$ vg/g brain), or $1.1\times10^{11}$ vg ($2.7\times10^{11}$ vg/g brain) (blue) for biochemical endpoints in the liver, heart, lung, kidney, spleen, and gonads.
Figure 53E:
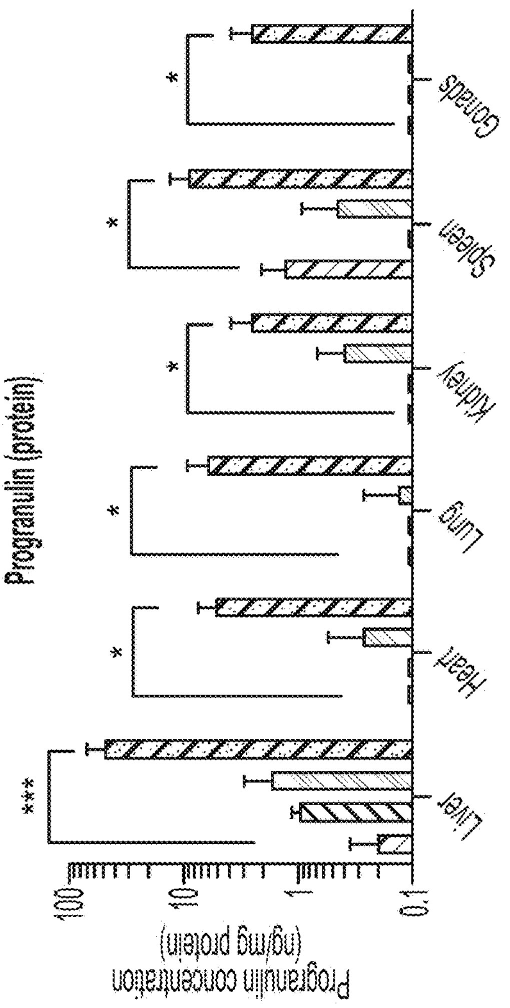

PR006A administration also resulted in broad vector genome presence and progranulin protein levels in peripheral tissues, including liver, heart, lung, kidney, spleen, and gonads (FIG. 53D; FIG. 53E).

Figure 53F:
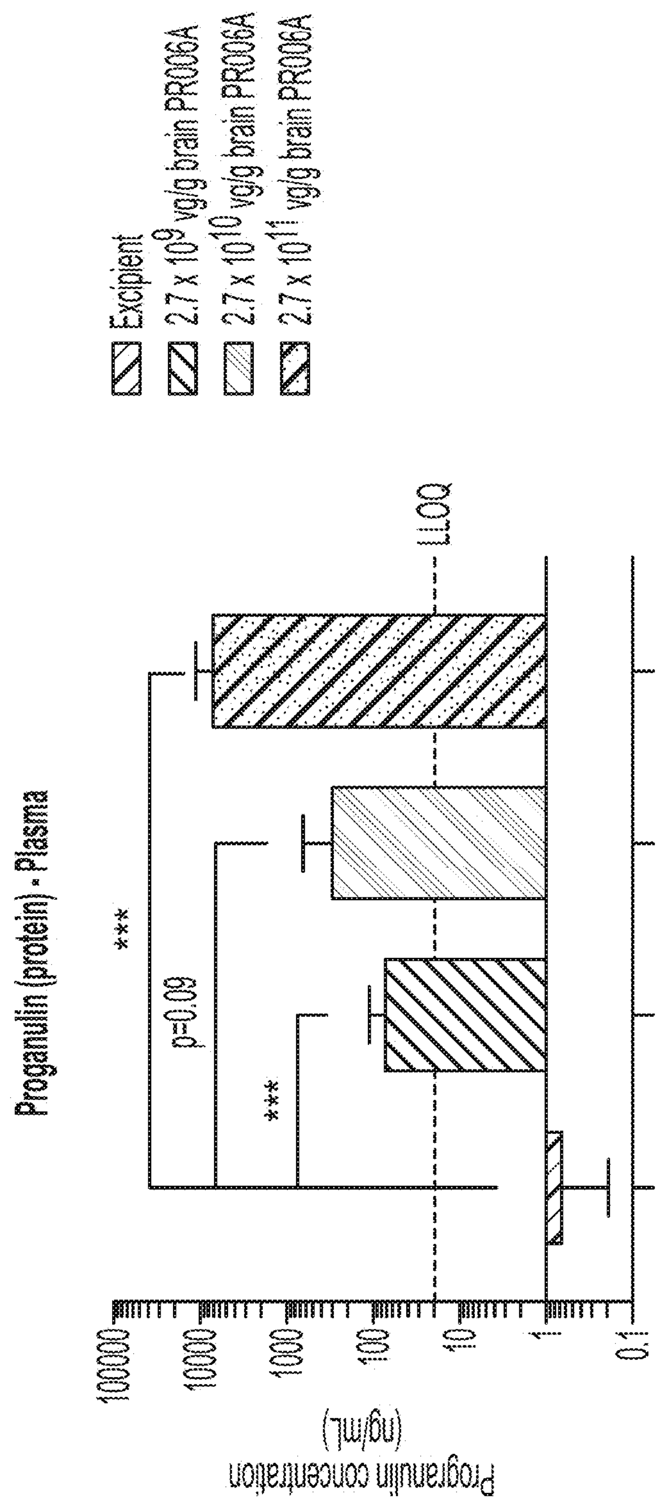
FIG. 53F is a bar graph depicting the results of experiments analyzing progranulin levels in the plasma in the adult dose-ranging PR006A FTD-GRN mouse model study. 4-month-old Grn KO mice were given PR006A or excipient by ICV administration. They were sacrificed 3 months after the treatment with excipient (red) or PR006A at dose of $1.1\times10^{9}$ vg ($2.7\times10^{9}$ vg/g brain), $1.1\times10^{10}$ vg ($2.7\times10^{10}$ vg/g brain), or $1.1\times10^{11}$ vg ($2.7\times10^{11}$ vg/g brain) (blue) for biochemical endpoints in the plasma. Progranulin protein levels were measured using a human-specific progranulin ELISA in plasma (n=8-10/group; mean±SEM). Plasma levels are shown on a log scale. The lower limit of quantitation (LLOQ) is indicated by a dashed gray line. Statistical analysis was conducted using ANOVA followed by Dunnett's test to compare to the excipient treated Grn KO mouse group; *=p<0.05, =p<0.01, *=p<0.001. LLOQ=lower limit of quantitation. vg=vector genomes.

In plasma, significant levels of human progranulin were detected in PR006A-treated Grn KO mice at all dose levels (FIG. 53F). In line with expectations, human progranulin was not detected in the excipient treated Grn KO mice. The levels of human progranulin in animals treated with the mid-dose of PR006A were in the same range as levels of mouse progranulin measured in mice with WT Grn alleles. Since different detection assays, employing non-species-cross-reactive anti-progranulin antibodies, were used to measure human and mouse progranulin, the absolute numbers cannot be compared with accuracy.

Figure 53G:
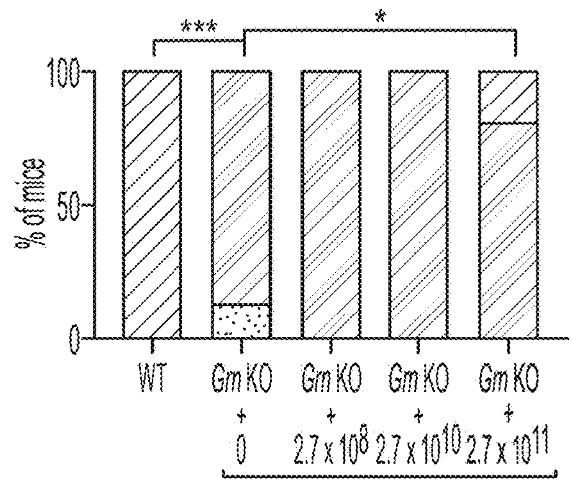
FIG. 53G-FIG. 53H are a series of bar graphs depicting the results of experiments showing reduced lysosomal and neuropathology defects in adult dose-ranging PR006A FTD-GRN adult mouse model study. 4-month-old Grn KO mice were given PR006A or excipient by ICV administration. They were sacrificed for analysis 3 months after the treatment with excipient (red) or PR006A at dose of $1.1\times10^{9}$ vg ($2.7\times10^{9}$ vg/g brain), $1.1\times10^{19}$ vg ($2.7\times10^{19}$ vg/g brain), or $1.1\times10^{11}$ vg ($2.7\times10^{11}$ vg/g brain) (blue). Lipofuscinosis was analyzed by two independent methods: (1) scoring of H&E-stained brain sections by a pathologist, and (2) quantification of lipofuscin autofluorescence from IHC sections.
Figure 53G:
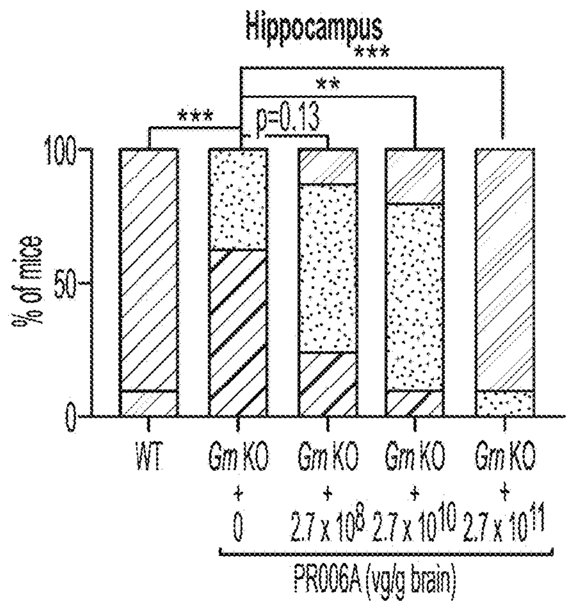
Figure 53G:
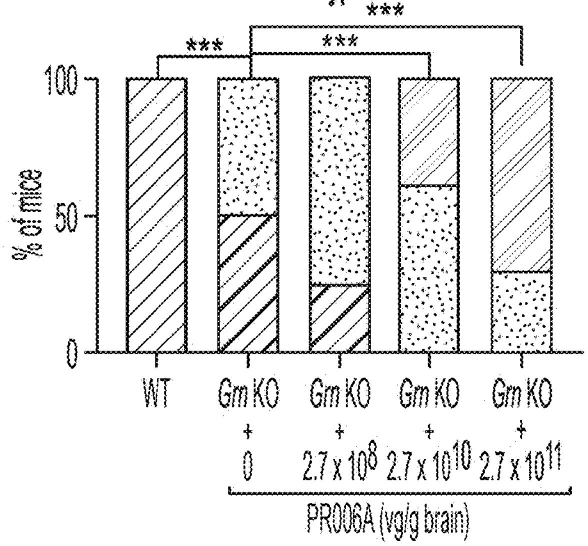
Figure 53H:
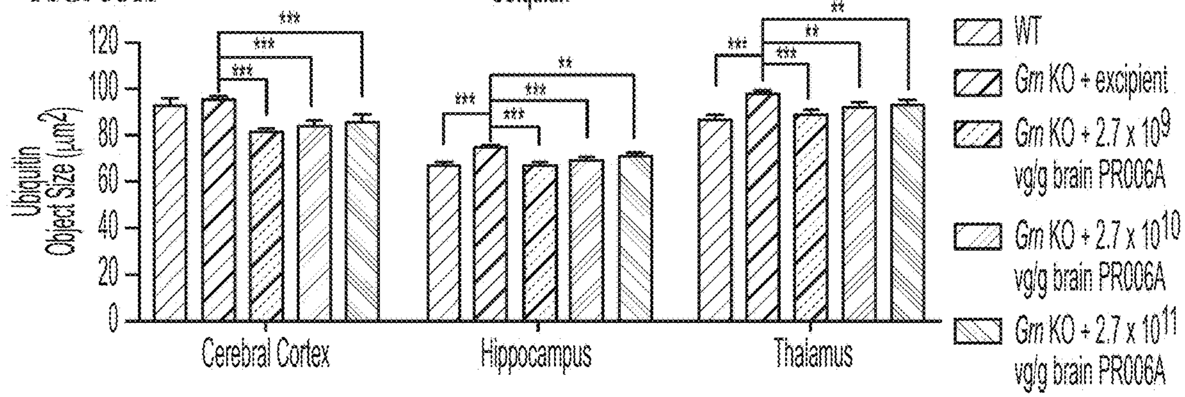

Lipofuscin Accumulation:

Lipofuscin accumulation was assessed using two independent methods in adjacent brain sections: (1) in a more clinical approach, lipofuscin accumulation in the brain was scored by a blinded pathologist on a scale of 0 (no lipofuscin observed) to 4 (widespread lipofuscin accumulation) and (2) in a more quantitative approach, lipofuscin autofluorescence was detected by IHC and automatically quantified. Grn KO mice exhibited lipofuscinosis throughout the brain, whereas WT mice did not have detectable lipofuscin in the brain (FIG. 53G). ICV administration of PR006A led to a dose-dependent reduction in the severity scores of intracellular lipofuscin accumulation in the brains of Grn KO mice (FIG. 53G). PR006A efficacy with respect to a reduction in lipofuscinosis could be most readily quantified in brain regions that display the most robust lipofuscinosis phenotype in the Grn KO mouse model of FTD-GRN, including the hippocampus and thalamus. In addition to lipofuscin scoring by a pathologist, IHC performed in brain regions of interest (i.e., cerebral cortex, hippocampus, thalamus) to quantitatively assess lipofuscinosis detected a dose-dependent reduction in the amount of lipofuscin accumulation in the cerebral cortex and thalamic brain regions, with significant decreases occurring at the middle and high PR006A doses. IHC was also performed to assess ubiquitin accumulation in the brain, an additional FTD-GRN-related pathology that occurs in Grn KO mice. Compared to WT mice, Grn KO mice exhibited an increase in ubiquitin throughout the brain (FIG. 53H). PR006A significantly reduced ubiquitin immunoreactive object size to near WT levels at all three doses (FIG. 53H).

Figure 53I:
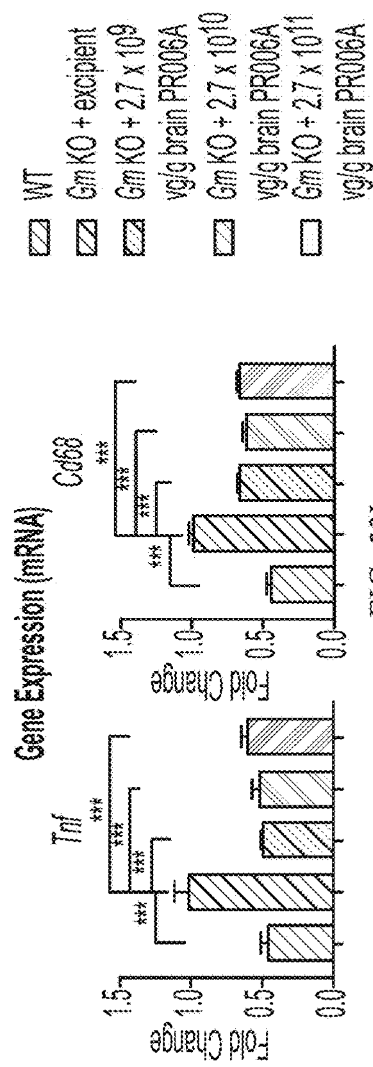
FIG. 53I-FIG. 53K are a series of bar graphs depicting the results of experiments showing decreased neuroinflammatory markers in adult dose-ranging PR006A FTD-GRN mouse model study. 4-month-old Grn KO mice were given PR006A or excipient by ICV administration. They were sacrificed for analysis 3 months after the treatment with excipient (red) or PR006A at dose of $1.1\times10^9$ vg ($2.7\times10^9$ vg/g brain), $1.1\times10^{10}$ vg ($2.7\times10^{10}$ vg/g brain), or $1.1\times10^{11}$ vg ($2.7\times10^{11}$ vg/g brain) (blue).
Figure 53J:
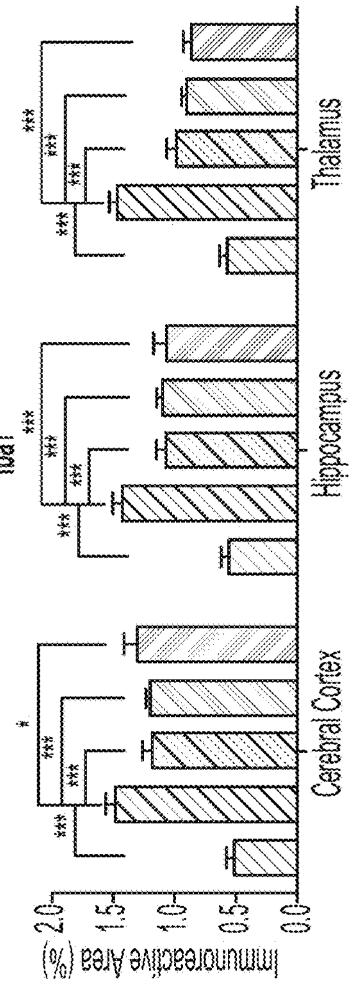
Figure 53K:
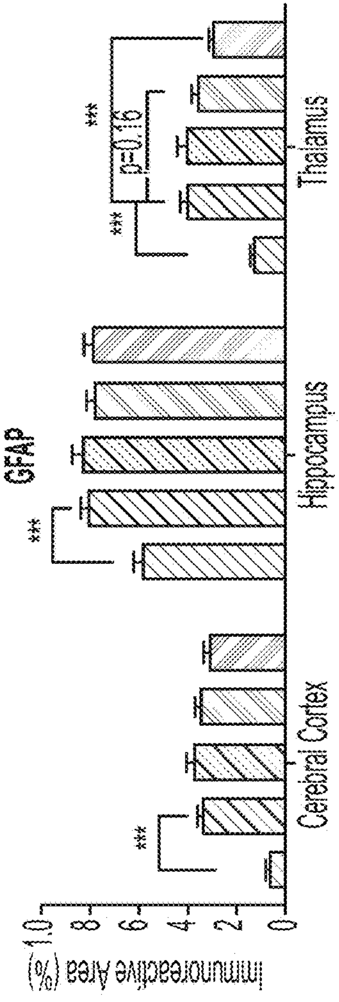

Neuroinflammation: Treatment with PR006A suppressed inflammatory marker levels in the brain of adult Grn KO mice. ICV PR006A decreased gene expression of the proinflammatory cytokine Tnf (TNFα) and Cd68 (CD68), a marker of microglia, in the cortex over a range of doses, from $2.7\times10^9$ vg/g brain to $2.7\times10^{11}$ vg/g brain (FIG. 53I). In line with published data, we observed an increase in the gene expression of these neuroinflammatory markers in excipient-treated Grn KO mice compared to age-matched mice with wildtype Grn alleles (FIG. 53I). In contrast to the observations in 18-month-old aged Grn KO mice from PRV-2018-027 and reports of TNFα abnormalities in the literature, there was no robust increase in cerebral cortex TNFα protein levels in the 7-month-old adult excipient-treated Grn KO mice; additionally, no significant changes were observed with PR006A in Grn KO mice. These findings are consistent with previously published findings that robust neuroinflammatory phenotypes do not occur in the Grn KO mouse model until 12-24 months of age. Immunohistochemistry (IHC) was performed and quantified in the brain regions of interest (cerebral cortex, hippocampus, and thalamus) to further evaluate neuronal inflammation by staining for Iba1, a marker of microgliosis, and GFAP, a marker of astrocytosis. There was a significant increase in microgliosis (Iba1) and astrocytosis (GFAP) throughout the brain in Grn KO mice compared to WT mice (FIG. 53J-FIG. 53K). PR006A treatment significantly reduced microgliosis (Iba1) at all three doses (FIG. 53J). A trend toward decreased astrocytosis (GFAP) was observed at the middle PR006A dose and a significant decrease in astrocytosis (GFAP) was observed at the high PR006A dose in the thalamus brain region (FIG. 53K).

Figure 53L:
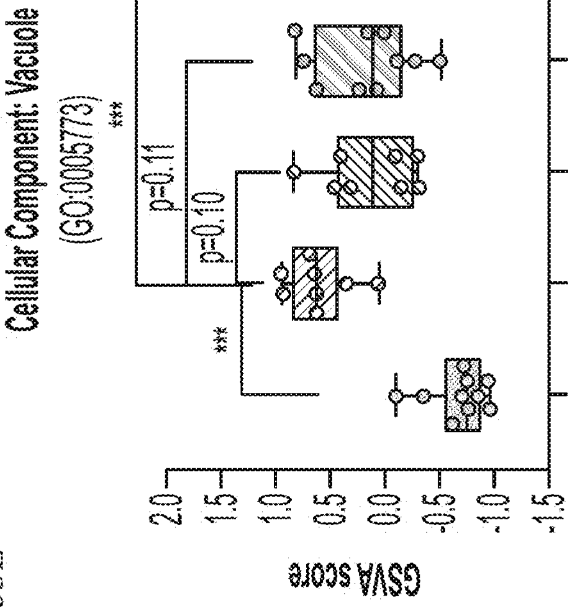
FIG. 53L-FIG. 53N are a series of bar graphs depicting the results of experiments showing decreased gene expression of lysosomal and immune pathways in adult dose-ranging PR006A FTD-GRN mouse model study. 4-month-old Grn KO mice were given PR006A or excipient by ICV administration. They were sacrificed for analysis 3 months after the treatment with excipient (red) or PR006A at dose of $1.1\times10^9$ vg ($2.7\times10^9$ vg/g brain), $1.1\times10^{10}$ vg ($2.7\times10^{10}$ vg/g brain), or $1.1\times10^{11}$ vg ($2.7\times10^{11}$ vg/g brain) (blue). RNA sequencing was performed in cerebral cortex samples from in ICV-treated Grn KO mice and from age-matched WT C57BL/6J mice (gray). Gene Set Variation Analysis (GSVA) methodology was used to compare mRNA expression levels of previously published gene signatures that are dysregulated in excipient treated Grn KO mice compared to WT mice. Data shown are the GSVA activity scores for curated gene sets from two published studies and one HALLMARK pathway.
Figure 53M:
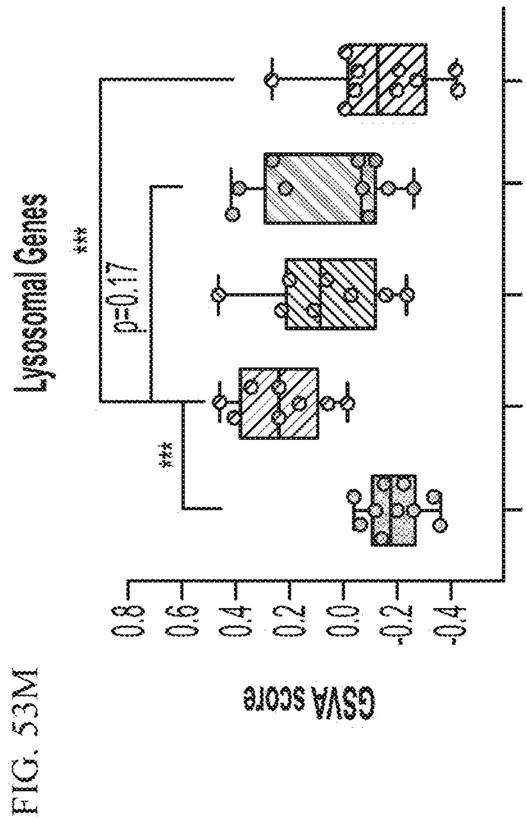
Figure 53N:
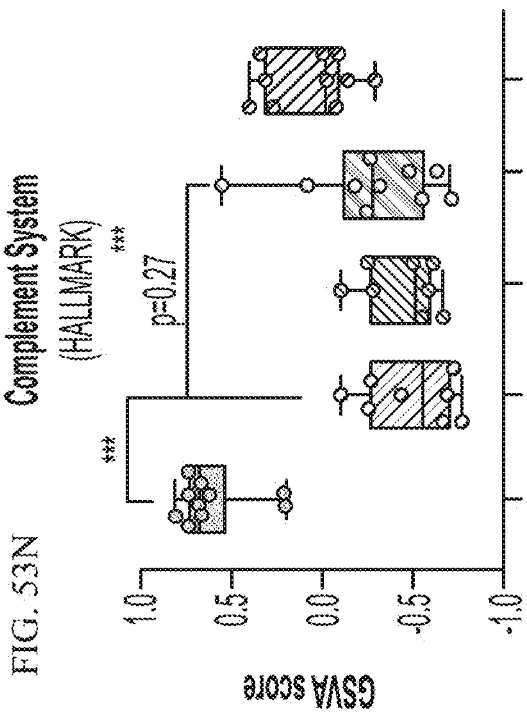

While many of the Grn KO mouse model phenotypes occur late in life, studies have reported that Grn KO mice exhibit widespread gene expression changes as early as 4 months of age, including changes in lysosomal- and immune-related pathways. Therefore, in addition to the targeted qRT-PCR analysis described above, a transcriptomics approach to evaluate changes in mRNA levels, which can be assessed globally with sensitive, high throughput technologies (RNA sequencing), and require minimal sample material, was employed. We performed RNA sequencing on cerebral cortices and used Gene Set Variation Analysis (GSVA) (Hanzelmann et al., *BMC Bioinformatics* 14, 7 (2013)) to determine which gene expression pathways are altered in the 7-month old excipient-treated Grn KO mice, as compared to age-matched WT mice of the same strain. We confirmed deficiencies in lysosomal- and immune-related pathways in mice lacking Grn, as reported in previously published studies. Significant changes were reported in a subset of the GO TERM (GO:0005773) "Vacuole" genes (contains 4 genes reported to be dysregulated in Grn KO mice described by Lui et al (*Cell* 165, 921-935 (2016))), the "Lysosomal Genes" set (a subset of 25 lysosomal-related genes shown to be dysregulated in Grn KO mice described by Evers et al (Cell Reports 20, 2565-2574 (2017))), and the "Complement" gene set from Gene Set Enrichment Analysis HALLMARK database (contains genes encoding components of the complement system, part of the innate immune system). We then measured and compared activity levels of these gene sets with PR006A treatment (FIG. 53L-FIG. 53N). Treatment with PR006A dose-dependently reversed the gene set deficiencies observed in the Grn KO mice.

Histopathology:

A thorough histopathological analysis performed by a blinded board-certified pathologist on hematoxylin and eosin (H&E) staining of the brain, thoracic spinal cord, liver, heart, spleen, lung, kidney, and gonads of all mice from these studies found no evidence of toxicity related to PR006A treatment. The details of the toxicity analysis are provided in the section below.

Conclusion:

ICV PR006A at doses ranging from $2.7\times10^{9}$ vg/g brain to $2.7\times10^{11}$ vg/g brain resulted in broad vector genome presence throughout the brain and peripheral tissues in a dose-dependent manner. PR006A treatment also led to production of progranulin mRNA and protein in the CNS. A clear dose-response relationship between PR006A and decreased lipofuscinosis, a readout of lysosomal dysfunction, was observed throughout multiple brain regions. A robust and statistically significant reduction of lipofuscinosis was observed at the middle and highest dose level of PR006A. All PR006A doses reduced ubiquitin accumulation in the brain. Starting at the lowest dose of $2.7\times10^{9}$ vg/g brain, PR006A reduced the expression of proinflammatory markers in the brain at the RNA and protein level.

Summary: In Vivo Nonclinical Studies

PR006A effectively transduced Grn KO mice, resulting in a robust, dose-dependent biodistribution of the transgene and production of progranulin mRNA and protein in the CNS. PR006A dose-dependently reversed gene expression abnormalities in lysosomal and neuroinflammatory pathways. PR006A reduced many of the phenotypes that occur in the brain_of this FTD-GRN mouse model, including lipofuscinosis, ubiquitin accumulation, and microgliosis. In the dose-ranging study, the lowest dose of $2.7\times10^{9}$ vg/g brain PR006A significantly suppressed the expression of inflammatory markers in the cerebral cortex. The middle dose of $2.7\times10^{10}$ vg/g brain PR006A improved both lysosomal defects (e.g., lipofuscinosis) and neuroinflammation, in a robust and statistically significant way. The high dose of $2.7\times10^{11}$ vg/g brain PR006A further increased progranulin expression with no evidence of toxicity.

TABLE 7

Summary of Biodistribution

| Study | Dose | Cerebral Cortex | Spinal Cord | Liver | Spleen | Heart | Kidney | Lung | Gonads |
|---|---|---|---|---|---|---|---|---|---|
| PRV-2018-027 | $9.7\times10^{10}$ vg PR006A | + | + | + | + | + | + | + | + |
| PRV-2019-004 | $1.1\times10^{9}$ vg PR006A | + | + | + | + | + | + | + | + |
| | $1.1\times10^{10}$ vg PR006A | + | + | + | + | + | + | + | + |
| | $1.1\times10^{11}$ vg PR006A | + | + | + | + | + | + | + | + |

Positive biodistribution is defined as >50 vg/μg genomic DNA.

Safety Pharmacology

Throughout these studies, there were no adverse events that can be attributed to the test article. Safety findings from in-life and histopathological analyses of the animals in PRV-2018-027, PRV-2019-002, and PRV-2019-004 are discussed in the section below.

Single-Dose Toxicity

A series of nonclinical studies with PR006A were conducted investigating safety endpoints in mice and monkeys. Three of the studies were performed in a Grn KO mouse model, where endpoints included neuropathological evaluations and assessed both protective activity as well as potential toxicity resulting from PR006A administration via intracerebroventricular (ICV) injection; ICM administration is more technically difficult in mice. These mouse models are representative of FTD-GRN in which patients have a mutation in the GRN gene resulting in reduced progranulin levels. In cynomolgus monkeys, neuropathology was also performed as part of a pilot study in which PR006A was injected into the cisterna magna (ICM). A GLP study was conducted in cynomolgus monkeys in which PR006A was delivered to the ICM, and monkeys were sacrificed at Day 7, Day 30, or Day 183. The GLP study incorporated a comprehensive list of clinical endpoints in addition to anatomical pathology evaluations on a full list of tissues. To support single-dose administration in the clinic, the following single-dose studies were conducted.

Maximal Dose PR006A in an Aged FTD-GRN Mouse Model (PRV-2018-027 and PRV-2019-002)

As part of these efficacy studies in Grn KO mice, neuropathological evaluations were conducted in mice treated ICV with either excipient or PR006A. Grn KO mice have a complete loss of progranulin and are widely used as models of FTD-GRN due to their age-dependent phenotypes, which include lysosomal alterations, neuronal lipofuscin accumulation, microgliosis, and neuroinflammation. Aspects of the pharmacology portions of the study are summarized in the sections above whereas toxicological-related endpoints assessed in this study are summarized below. Two studies of PR006A were conducted in the aged Grn KO mouse model. In the first study (PRV-2018-027), 9 mixed gender Grn KO mice 16 months of age received ICV administration of either PR006A or excipient. Animals were sacrificed 9 weeks post-administration. A single PR006A dose group was included in this study: 10 μl of undiluted virus, for a total dose of $9.7\times10^{10}$ vg ($2.4\times10^{11}$ vg/g brain), and the control group was treated with 10 μl of excipient.

TABLE 8

Study Design PRV-2018-027

| Model | Treatment | RoA (Dose Volume) | PR006A Dose (vg/g brain) | Total PR006A Dose (vg) | Number of Mice | Post-Treatment Necropsy |
|---|---|---|---|---|---|---|
| Grn KO | Excipient | ICV (10 μl) | 0 | 0 | 4 (2 M/2 F) | 9 weeks |
| Grn KO | PR006A | ICV (10 μl) | $2.4 \times 10^{11}$ | $9.7 \times 10^{10}$ | 5 (3 M/2 F) | 9 weeks |

ROA: route of administration

Various post-mortem endpoints, such as biodistribution, lysosomal alterations, and inflammatory markers, were evaluated as part of this study protocol (see section above). Animals were also checked for survival twice per day, and body weight was measured once per day. After euthanasia at 2-months post-treatment, target tissues were harvested, drop fixed in chilled 4% paraformaldehyde, and stored at 4° C. The tissues from the 8 animals that completed the study were trimmed, processed, and embedded in paraffin blocks. They were then sectioned at ~5 μm, stained with hematoxylin and eosin (H&E) and examined by a board-certified veterinary pathologist.

During this study, 1 mouse died prematurely from the treatment group; no abnormalities were recorded for the deceased animal during necropsy, and therefore there is no known cause of death. No other deaths or abnormalities were observed. All treatment groups tracked similarly in terms of body weights, with no significant differences present.

On histopathological examination, there were no PR006A-related adverse findings. There was widespread lipofuscin accumulation in the brain, consistent with expected findings in a Grn KO mouse. In PR006A-treated animals, there was a reduction in the score severity for lipofuscin accumulation in all regions of the brain. Morphologic changes also appeared to demonstrate a slight reduction in frequency and/or severity scores, particularly with respect to neuronal necrosis in the medulla and pons, with PR006A treatment. However, these trends in the morphologic changes were not as consistent as that of the lipofuscin scores.

In the thoracic spinal cord, there was axonal degeneration and, very rarely (1 out of 4 animals in each group), minimal neuronal necrosis observed. There was a minor reduction in both the incidence and severity of axonal degeneration in the animals treated with PR006A.

The following findings, which are presumably associated with the Grn homozygous knockout mouse, appeared to have a reduced incidence and/or severity in the animals treated with PR006A: dilated tubules in the medulla of the kidney, glomerulopathy in the kidney, and foreign material in the lung (characterized as linear, acellular, dark pink structures, usually within airways and frequently associated with foreign body giant cells and/or macrophages). A larger cohort of animals would be necessary for more definitive conclusions.

All other histopathologic findings observed were considered incidental and/or were of similar incidence and severity in excipient- and test article-treated animals and, therefore, were considered unrelated to administration of PR006A.

In the second study (PRV-2019-002), 5 mixed gender Grn KO mice 14 months of age received ICV administration of either PR006A or excipient. Animals were sacrificed 8 weeks post-administration. A single PR006A dose group was included in this study: 10 μl of undiluted virus, for a total dose of $9.7\times10^{10}$ vg ($2.4\times10^{11}$ vg/g brain), and the control group was treated with 10 μl of excipient.

TABLE 9

Study Design PRV-2019-002

| Model | Treatment | RoA (Dose Volume) | PR006A Dose (vg/g brain) | Total PR006A Dose (vg) | Number of Mice | Post-Treatment Necropsy |
|---|---|---|---|---|---|---|
| Grn KO | Excipient | ICV (10 μl) | 0 | 0 | 2 (0 M/2 F)* | 8 weeks |

TABLE 9-continued

| Study Design PRV-2019-002 | | | | | | |
|---|---|---|---|---|---|---|
| Model | Treatment | RoA (Dose Volume) | PR006A Dose (vg/g brain) | Total PR006A Dose (vg) | Number of Mice | Post-Treatment Necropsy |
| Grn KO | PR006A | ICV (10 μl) | $2.4 \times 10^{11}$ | $9.7 \times 10^{10}$ | 3 (1 M/2 F) | 8 weeks |

*Genotype results at the end of the study confirmed that n = 1 animal from the excipient group to be Grn heterozygous KO instead of the expected Grn homozygous KO.

The animals were analyzed in an identical manner to study PRV-2018-027. Animals were checked for survival twice per day, and body weight was measured once per day. After euthanasia at 2-months post-treatment, target tissues were harvested, drop fixed in chilled 4% paraformaldehyde, and stored at 4° C., until evaluation.

In the CNS, findings consistent with those previously observed in the Grn KO mouse were observed in the brain (Yin et al., *J Exp Med* 207(1):117-128 (2010)). Specifically, there was a widespread increase in lipofuscin accumulation throughout the brain. Rarely minimal neuronal necrosis was also observed (in the single untreated early death animal and in one Excipient animal).

Due to the low sample numbers it was not possible to demonstrate a consistent trend in the findings related to treatment. There was no consistent difference in response between the Test Article (PR006A) and Excipient.

For non-CNS tissues, findings that were considered to be consistent with the phenotype of the Grn KO mouse were observed in the kidney (tubular dilation and infiltrates of mononuclear inflammatory cells) and liver (vacuolation of Kupffer cells/sinusoidal lining cells, and Kupffer cell micro-granulomas) (Yin et al., *J Exp Med* 207(1):117-128 (2010)).

There was a finding of "glomerulopathy" observed in all animals that underwent surgery and were enrolled in the study. While published reports of this finding as a change associated with standard, unchallenged, Grn knockout mice were not found, one study has demonstrated progranulin-deficient mice treated with a diet that induces hyperhomo-cysteinemia, develop glomerular basement membrane thickening and podocyte foot process effacement (Fu et al., *Hypertension* 69(2):259-266 (2017)).

All other findings were consistent with those commonly observed in laboratory mice. Due to the low sample number, no conclusive difference related to treatment could be shown.

Dose-Ranging PR006A in an Adult FTD-GRN Mouse Model (PRV-2019-004)

To further assess the safety of PR006A, a larger, dose-ranging study in adult Grn KO mice was performed. A total of 40 mixed-gender mice were divided into 4 groups and administered either excipient or one of three doses of PR006A by a single unilateral ICV injection into the left hemisphere; all animals, regardless of treatment group, received a total dose volume of 10 μl. Mice were treated at 4 months of age and euthanized 3 months post-treatment. An additional wildtype (WT) control group, which included untreated C57BL/6J mice (the same background strain) aged to approximately 7 months, were also euthanized and subjected to a similar necropsy.

The study was conducted according to the study design below:

TABLE 10

| Study Design PRV-2019-004 | | | | | | | |
|---|---|---|---|---|---|---|---|
| Group | Model | Treatment | RoA (Dose Volume) | Dose of PR006A (vg/g brain) | Total PR006A Dose (vg) | Number of Mice | Post-Treatment Necropsy |
| 1 | Grn KO | Excipient | ICV (10 μl) | 0 | 0 | 10 (4 M/6 F) | Week 13 |
| 2 | Grn KO | PR006A | ICV (10 μl) | $2.7 \times 10^{11}$ | $1.1 \times 10^{11}$ | 10 (4 M/6 F) | Week 13 |
| 3 | Grn KO | PR006A | ICV (10 μl) | $2.7 \times 10^{10}$ | $1.1 \times 10^{10}$ | 10 (4 M/6 F) | Week 13 |
| 4 | Grn KO | PR006A | ICV (10 μl) | $2.7 \times 10^{9}$ | $1.1 \times 10^{9}$ | 10 (4 M/6 F) | Week 13 |
| N/A | WT (C57BL/6J) | None | N/A | 0 | 0 | 10 (5 M/5 F) | N/A |

During the study, animals were checked for survival twice a day and weighed once a week. Mice were euthanized 3 months post-treatment, and various post-mortem evaluations were conducted to assess efficacy of PR006A (see section above). In addition, sections stained for H&E from brain, thoracic spinal cord, liver, heart, spleen, lung, kidney, and gonads were evaluated by a board-certified pathologist.

On histopathological examination, there were no adverse PR006A-related findings in any of the mice regardless of treatment group.

There were findings consistent with the Grn KO mouse model phenotype, such as accumulation of intracellular lipofuscin in various regions of the brain: cerebral cortex, cerebral nuclei, hippocampus, thalamus/hypothalamus, cerebellum and brainstem (particularly the pons and medulla). Clear evidence of morphologic changes on the H&E stained sections (vacuolation of neurons and gliosis) was not observed. Accumulation of lipofuscin pigment can precede easily detectable morphologic changes and, therefore, serves as an adequate biomarker of efficacy. While all Grn homozygous KO groups demonstrated lipofuscin accumulation, there were differences in the severity of this finding across treatment groups. The frequency of higher scores for lipofuscin accumulation was greatest for the group of animals treated with excipient (Group 1). Of those animals treated with PR006A, the frequency of higher scores were observed in Group 4 (low dose PR006A; $2.7\times10^{9}$ vg/g brain), followed by Group 3 (middle dose PR006A; $2.7\times10^{10}$ vg/g brain). The lowest severity scores were observed with in Group 2 (high dose PR006A; $2.7\times10^{11}$ vg/g brain). These findings demonstrate a dose-dependent reduction in the severity scores of intracellular lipofuscin accumulation in the brains of Grn homozygous knock-out mice. All other histopathologic findings were considered incidental and/or were of similar incidence and severity in excipient and test article-treated animals and, therefore, were considered unrelated to administration of PR006A.

GLP Single-Dose Study in Monkeys (PRV-2018-028)

Study Design

The purpose of this GLP study was to evaluate the toxicity and biodistribution of the test article, PR006A, when administered once via ICM injection in cynomolgus monkeys with a 6-day, 29-day, or 182-day post-administration observation period; animals were sacrificed at study Day 7, Day 30, or Day 183. The study was designed to evaluate 2 dose levels: the highest dose is the maximum feasible dose achievable with 1.2 mL volume (the highest volume there was experience in administering) of undiluted PR006A, and a lower dose that is equivalent to one log unit lower than the high dose. The doses equate to a low dose of $4.8\times10^{11}$ vg and a high dose of $4.8\times10^{12}$ vg; with a brain weight estimate of 74 g in a cynomolgus monkey, the NHP species used in this study, this translates to approximately $6.5\times10^{9}$ vg/g brain and $6.5\times10^{10}$ vg/g brain. The study also includes a control arm in which animals receive 1.2 ml of excipient only (20 mM Tris pH 8.0, 200 mM NaCl, and 1 mM $MgCl_2$+0.001% [w/v] Pluronic F68). This study utilized both male and female cynomolgus macaques. The Day 7 group included 1 female at the highest dose and was designed as a sentinel for early toxicity; the remaining two timepoints (Day 30 and Day 183) included 2 males and 1 female at each dose. In addition to samples from multiple brain regions, peripheral tissue samples were collected for qPCR analysis. All samples that were positive with qPCR were analyzed for transgene expression. A tabulated summary of this study's design is provided in Table 11.

TABLE 11

Overview of the GLP NHP Study PRV-2018-028

| | | | | | |
|---|---|---|---|---|---|
| Purpose | Assess the tolerance and biodistribution of PR006A in NHPs | | | | |
| Regulatory Compliance | GLP | | | | |
| Test Article | PR006A | | | | |
| Total No. of Animals | 19 cynomolgus monkeys | | | | |
| Weight (age) | 2-5 kg (25-50 months) | | | | |
| Study Design | Group Assignments: | | | | |
| | | Dose | Number of Animals | | |
| | Group | (vg/g brain) | Necropsy (Day 7) | Necropsy (Day 30) | Necropsy (Day 183) |
| | 1 | 0 | 0 | 2M/1F | 2M/1F |
| | 2 | $6.5\times10^{9}$ | 0 | 2M/1F | 2M/1F |
| | 3 | $6.5\times10^{10}$ | 1F | 2M/1F | 2M/1F |
| Dosing Route and Frequency | Intra-cisterna magna using a polypropylene 1-3 cc syringe and spinal needle (Pencan 25 G × 2.5 cm BBraun); single slow bolus delivered at a maximum rate of 0.5 cc/min | | | | |
| Formulations | Dosing solution provided at concentration of $4.01\times10^{12}$ vg/mL | | | | |
| Clinical Signs | Daily (including food consumption); Detailed Observations weekly | | | | |
| Body weights | Weekly | | | | |
| Neurological, Ophthalmic, ECG Examinations | Once pre-dose and during Weeks 2 and 26 | | | | |
| Clinical Pathology | All groups hematology, clinical chemistry, coagulation parameters | | | | |
| Hematology | red blood cell count | | mean corpuscular volume | | |
| | hemoglobin | | platelet count | | |
| | hematocrit | | white blood cell count | | |
| | mean corpuscular | | absolute neutrophil count | | |
| | hemoglobin | | absolute lymphocyte count | | |
| | mean corpuscular | | absolute monocyte count | | |
| | hemoglobin concentration | | absolute reticulocyte count | | |
| | absolute eosinophil count | | differential blood cell count | | |
| | absolute basophil count | | blood smear | | |
| Clinical Chemistry | glucose | | alanine aminotransferase | | |
| | urea nitrogen | | alkaline phosphatase | | |
| | creatinine | | gamma glutamyltransferase | | |
| | total protein | | aspartate aminotransferase | | |
| | albumin | | calcium | | |
| | globulin | | inorganic phosphorus | | |
| | albumin/globulin ratio | | sodium | | |
| | cholesterol | | potassium | | |
| | total bilirubin | | chloride | | |
| | creatine kinase | | triglycerides | | |

TABLE 11-continued

| Overview of the GLP NHP Study PRV-2018-028 | | | |
|---|---|---|---|
| Coagulation | prothrombin time<br>fibrinogen<br>activated partial thromboplastin time | | |
| Vector Shedding (urine/feces) | At sacrifice | | |
| Necropsy | Day 7, Day 30, Day 183 | | |
| Tissue Preservation for Histopathology | The following tissues from each animal will be collected in 10% neutral-buffered formalin (unless otherwise indicated) or recorded as missing, if applicable. | | |
| Tissue Preservation, continued | Adrenal[a] | Injection site | Prostate[a] |
| | Aorta | (overlying skin) | Rectum |
| | Bone, femur with | Jejunum | Salivary gland |
| | bone marrow | Kidney[a] | Sciatic nerve |
| | Bone, sternum | Lesions | Seminal vesicle[a] |
| | with bone | Liver[a] | Skin/subcutis |
| | marrow | Lung with large | Spinal cord |
| | Brain[a] | bronchi | (cervical, |
| | Cecum | Lymph node | thoracic, lumbar) |
| | Cervix | (mandibular) | Spleen[a] |
| | Colon | Lymph node | Stomach |
| | Duodenum | (mesenteric) | Testis[a] |
| | Epididymis[a] | Mammary gland | Thymus[a] |
| | Esophagus | Muscle, biceps | Thyroid with |
| | Eye[b] | femoris | parathyroid[a] |
| | Gall bladder | Optic nerve | Tongue |
| | GALT (Peyer's | Ovary[a] | Trachea |
| | Patch) | Oviducts | Urinary bladder |
| | Heart[a] | Pancreas | Uterus[a] |
| | Ileum | Pituitary gland[a] | Vagina |
| Histopathology | All groups - all tissues | | |
| Biodistribution | The following tissues/biofluids will be analyzed for biodistribution by qPCR: | | |
| | Frontal cortex | Liver | |
| | Hippocampus | DRG (cervical) | |
| | Ventral mesencephalon | DRG (thoracic) | |
| | Periventricular gray | DRG (lumbar) | |
| | Putamen | Spinal cord (thoracic) | |
| | Testis | Spinal cord (lumbar) | |
| | Ovary | Spinal cord (cervical) | |
| | Kidney | Spleen | |
| | Stomach (pyloric) | Heart (apex) | |
| | Blood | CSF | |
| | Lung | | |
| Transgene Expression | All samples that are positive for qPCR will be evaluated for progranulin expression | | |

Abbreviations:
F, female;
ICM; intra-cisterna magna;
M, male;
MgCl2; magnesium chloride;
NaCl, sodium chloride;
vg, vector genome(s);
DRG, dorsal root ganglia;
GALT, gut-associated lymphoid tissue.
[a]Organs (when present) will be weighed or noted as missing;
[b]Collected in modified Davidson's fixative and stored in 10% neutral buffered formalin Cynomolgus NHPs were assessed by multiple in-life observations and measurements, including mortality/morbidity (daily), clinical observations (daily), body weight (baseline and weekly thereafter), visual inspection of food consumption (daily), neurological observations (baseline and during Week 2 and 26), indirect ophthalmoscopy (baseline and during Weeks 2 and 26), and electrocardiographic (ECG) measurement (baseline and during Weeks 2 and 26).

Analysis of neutralizing antibodies (nAb) to the AAV9 capsid was performed at baseline and at sacrifice on Days 7, 30, or 183. Clinical pathology consisting of hematology, coagulation, clinical chemistry, and urinalysis was performed twice at baseline (blood tests; once for urinalysis) and once during Weeks 1 and 13 of the dosing phase.

Animals were euthanized and tissues harvested on Day 7, Day 30, or Day 183. The tissues outlined in Table 11, if present, were collected from all animals, weighed (if applicable), and divided into replicates. One replicate was preserved in 10% neutral-buffered formalin (except when special fixatives are required for optimum fixation) for histopathological evaluation (all animals). Additional replicates were collected for qPCR and transgene expression analysis.

Safety and Toxicology

There were no unscheduled deaths, and all animals survived until the scheduled necropsy. There were no adverse PR006A-related clinical observations, body weight changes, ophthalmic observations, or physical or neurological examination findings; gross macroscopic examination at necropsy showed no drug-related abnormalities in any of the cohorts. In addition, there were no PR006A-related changes in PR interval, QRS duration, QT interval, corrected QT (QTc) interval, or heart rate observed in males or combined sexes administered $6.5\times10^9$ or $6.5\times10^{10}$ vg/g brain. No abnormal ECG waveforms or arrhythmias were observed during the qualitative assessment of the ECGs.

Biodistribution

Figure 54A:
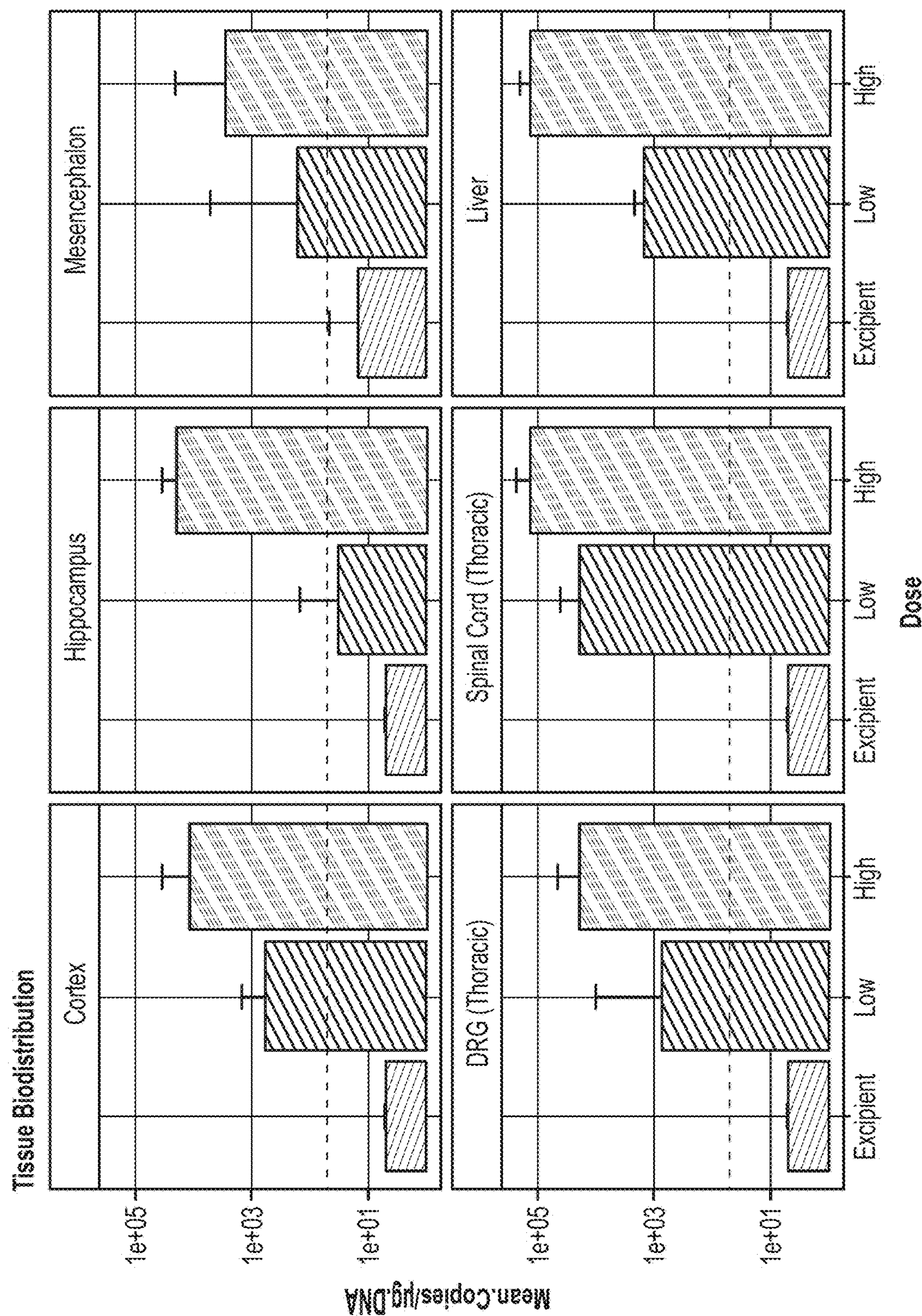
FIG. 54A is a series of bar graphs depicting the results of experiments analyzing biodistribution of PR006A transgene quantified by qPCR. Transgene levels were analyzed using qPCR methodologies in NHPs 182 days after ICM injection of either excipient, low dose of PR006A ($6.5\times10^9$ vg/g brain), or high dose of PR006A ($6.5\times10^{10}$ vg/g brain). Each bar represents the average±SEM of 3 animals per group; the yellow line indicates the lower limit of quantitation at 50 vg/μg DNA.

Biodistribution analysis of the PR006A transgene was performed using a qPCR-based assay. At Day 183 in the high dose group ($6.5\times10^{10}$ vg/g brain), there was widespread transduction throughout the CNS and periphery, with all tissues examined positive for vector presence with a cutoff of 50 vg/μg DNA, the lower limit of quantitation for the qPCR assay. Data from select representative regions from Day 183 are shown in FIG. 54A; Day 30 data is not shown. At Day 30 in the high dose group ($6.5\times10^{10}$ vg/g brain), all CNS tissues examined were positive for transduction, with the exception of the putamen. Tissues from animals treated with the low dose ($6.5\times10^{9}$ vg/g brain) were positive in the CNS at Day 183, but only the spleen and liver were positive from the peripheral tissues. In addition, the one female NHP treated with the high dose of PR006A was positive in the ovaries at Day 7, and males treated with the high dose were positive in the testes at Day 30 and Day 183. PR006A transduction was most robust in liver and tissues of the nervous system, and consistently lower in the other peripheral organs examined. In the brain, vector transduction stabilized at Day 183 when compared to Day 30, demonstrating a robust and durable transduction of the transgene.

Figure 54B:
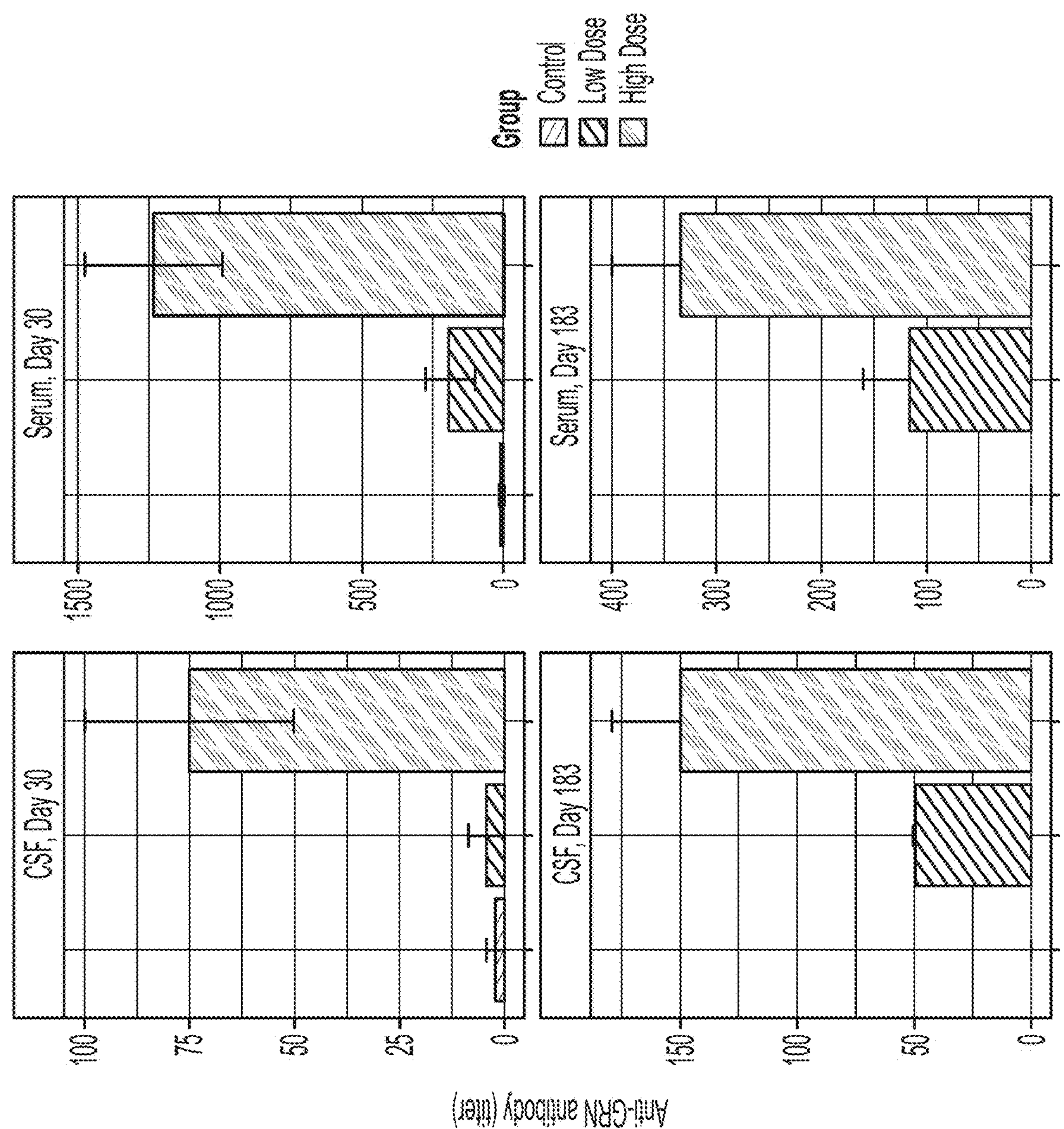
FIG. 54B is a series of bar graphs depicting the results of experiments analyzing levels of anti-drug antibody to human progranulin. Antibodies to progranulin in NHP serum and CSF samples at Day 29 and Day 182 post-treatment with either excipient, a low dose of PR006A ($6.5\times10^9$ vg/g brain), or a high dose of PR006A ($6.5\times10^{10}$ vg/g brain). Data represents the mean±SEM.

In the NHPs receiving ICM administration of PR006A, there was a significant allogeneic immune response to the transgene product, progranulin, with anti-progranulin antibodies detected in serum and CSF samples collected at Day 30 and Day 183 post-treatment; the immune response indicates that the human progranulin protein was expressed in the NHPs. The antidrug antibody (ADA) levels were determined using established immune assay technologies. The data are illustrated in FIG. 54B.

Figure 54C:
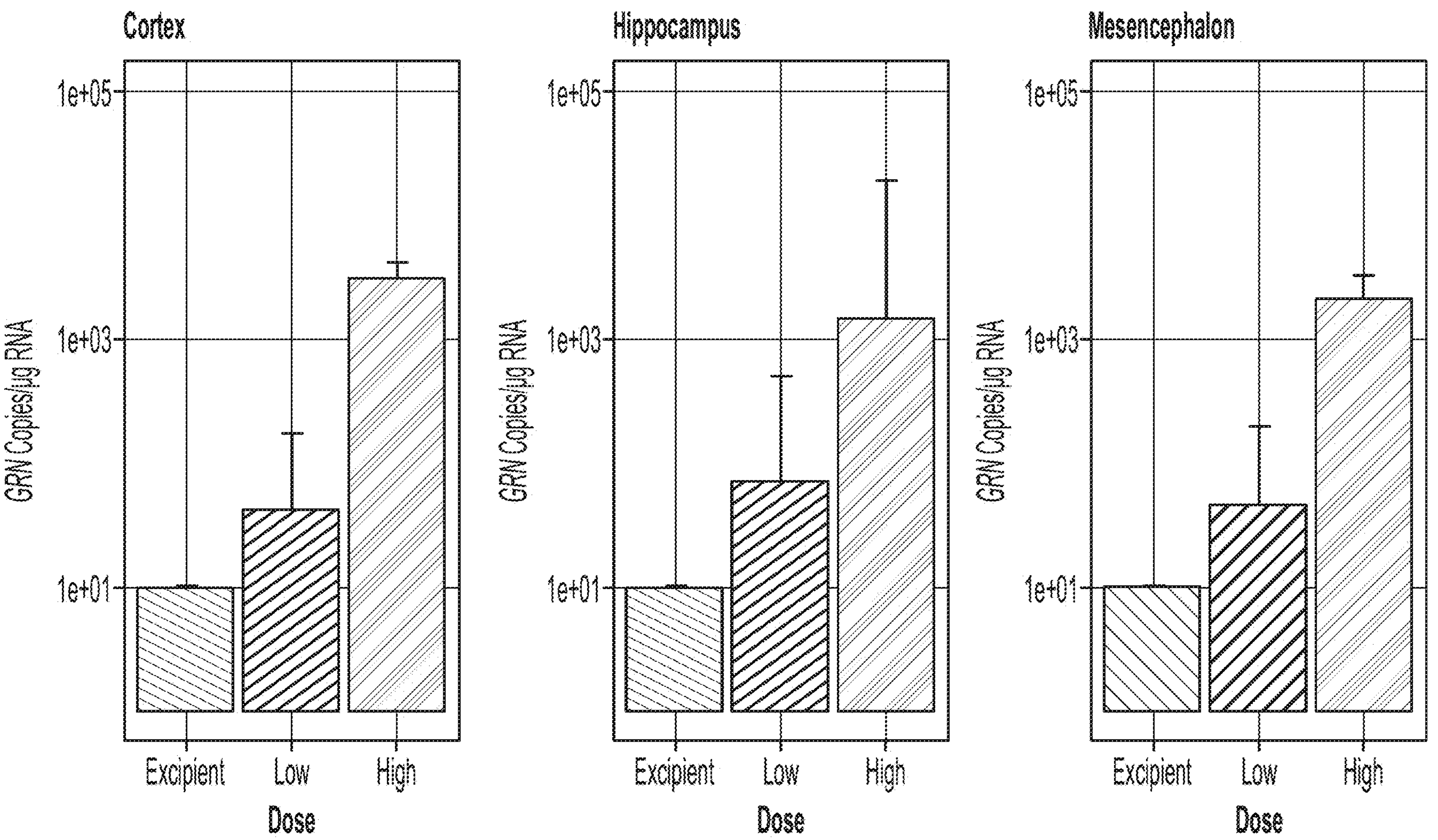
FIG. 54C is a series of bar graphs depicting the results of experiments analyzing expression of PR006A transgene (GRN). GRN expression levels were determined in NHP cortex, hippocampus and ventral mesencephalon collected on Day 183 using RT-qPCR. Data is presented as mean±SEM.

Expression of PR006A (GRN) was measured at the mRNA level using a RT-qPCR-based assay, and at the protein level using a Simple Western™ (Jess) analysis. Concomitant with levels of PR006A transduction, expression of the transgene was observed by mRNA measurements using RT-qPCR in select brain regions (FIG. 54C), liver, gonads, spinal cord and DRG collected on Day 183.

Expression of the transgene was measurable in brain and liver at both doses of PR006A, and the expression levels were both dose-dependent and durable. In gonads, expression was measurable in the males at the high dose only; at both doses in the females, expression was measurable at Day 7 and Day 30, but not at Day 183.

Figure 54D:
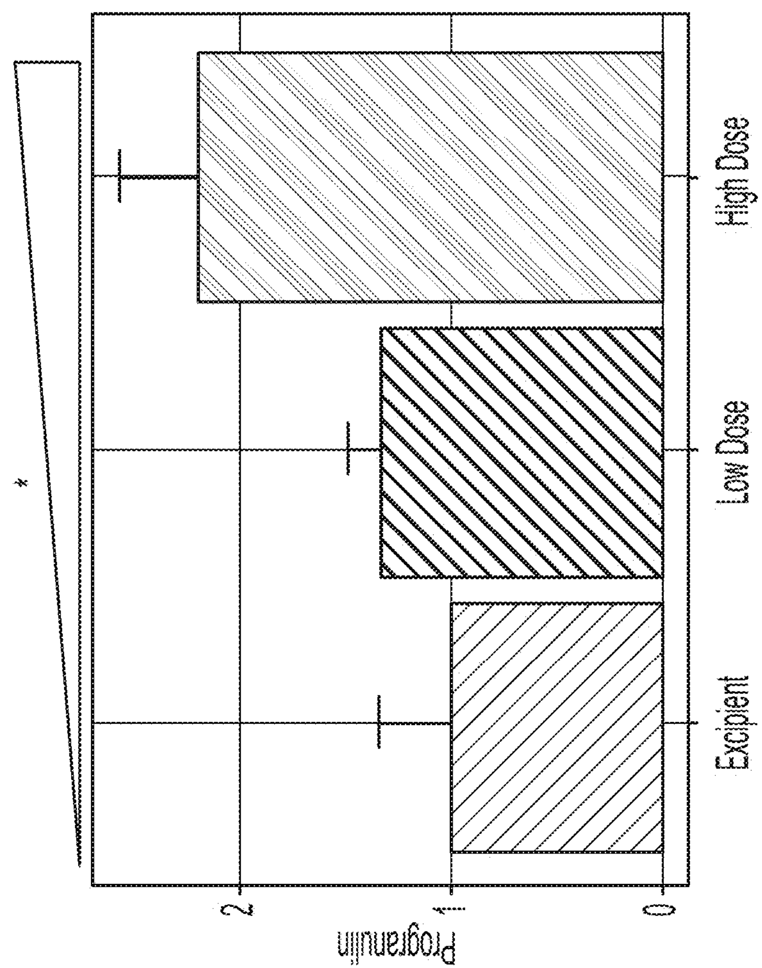
FIG. 54D is a bar graph depicting the results of experiments analyzing progranulin levels in the CSF quantified by Simple Western™ (Jess) platform. Progranulin levels were determined in NHP CSF samples that were collected at Day 183, determined by a Simple Western™ (Jess) analysis. CSF samples from NHPs treated with excipient, low dose of PR006A ($6.5\times10^9$ vg/g brain weight) or high dose of PR006A ($6.5\times10^{10}$ vg/g brain weight). Data presented is mean±SEM; P-value: *p<0.05, by one-way dose dependence response analysis using William's trend test.

To confirm that human progranulin was produced in the treated NHPs, protein levels in CSF were evaluated on a Simple Western™ (Jess) platform. Details of the method are provided in Example 14. The method was qualified by measuring progranulin levels in CSF samples from FTD-GRN patients and establishing that they were approximately half of the levels measured in CSF samples from healthy human controls and from FTD patients without a GRN mutation. Results from the CSF indicate that levels of progranulin are elevated in a dose-dependent manner in animals treated with both the low and high doses of PR006A (FIG. 54D). These results indicate that the effective and broad transduction of PR006A in NHPs following ICM administration leads to increased levels of progranulin.

Progranulin protein measurements focused on CSF because the Simple Western™ (Jess) assay is not suitable to measure progranulin levels in brain tissue due to the high level of nonspecific background bands. The assays currently available do not reliably measure levels of transgene-derived human progranulin in NHP tissues due to the high levels of nonspecific background. CSF levels are generally believed to reflect relevant brain concentrations, and they are of particular value as translational biomarkers to clinical studies.

SUMMARY

There have been no adverse safety findings or toxicity concerns in any of the nonclinical studies, including a small pilot non-GLP study in NHPs and a GLP study in NHPs through Day 183, that preclude the initiation of a clinical study. The pathology findings in the GLP study were consistently minimal in severity with a low number of affected cells across both dose groups. There were no other in-life or post-mortem PR006A-related adverse findings.

Phase 1/2 Trial in Human Subjects with FTD-GRN

Human subjects (n=15) will be enrolled in an open-label trial of the PR006 recombinant AAV. The subject inclusion criteria comprise: 30-80 years old (inclusive), has a pathogenic GRN mutation, is at a symptomatic disease stage, and has stable use of background medications prior to investigational product dosing. Each subject will receive the investigational product as a single ICM (intra-cisterna magna) injection. The trial will include a 3-month biomarker readout, a 12-month clinical readout and a 5-year safety and clinical follow-up. The trial will analyze: (1) safety and tolerability: (2) key biomarkers, including: progranulin, NfL (neurofilament light chain), and volumetric MRI (magnetic resonance imaging); and (3) Efficacy: CDR plus NACC FTLD (Clinical Dementia Rating plus National Alzheimer's Coordinating Center Frontal Temporal Lobar Dementia); measures of behavior, cognition, language, function, and QoL (quality of life).

TABLE 12

Examples of neurodegenerative diseases

Figure 4:
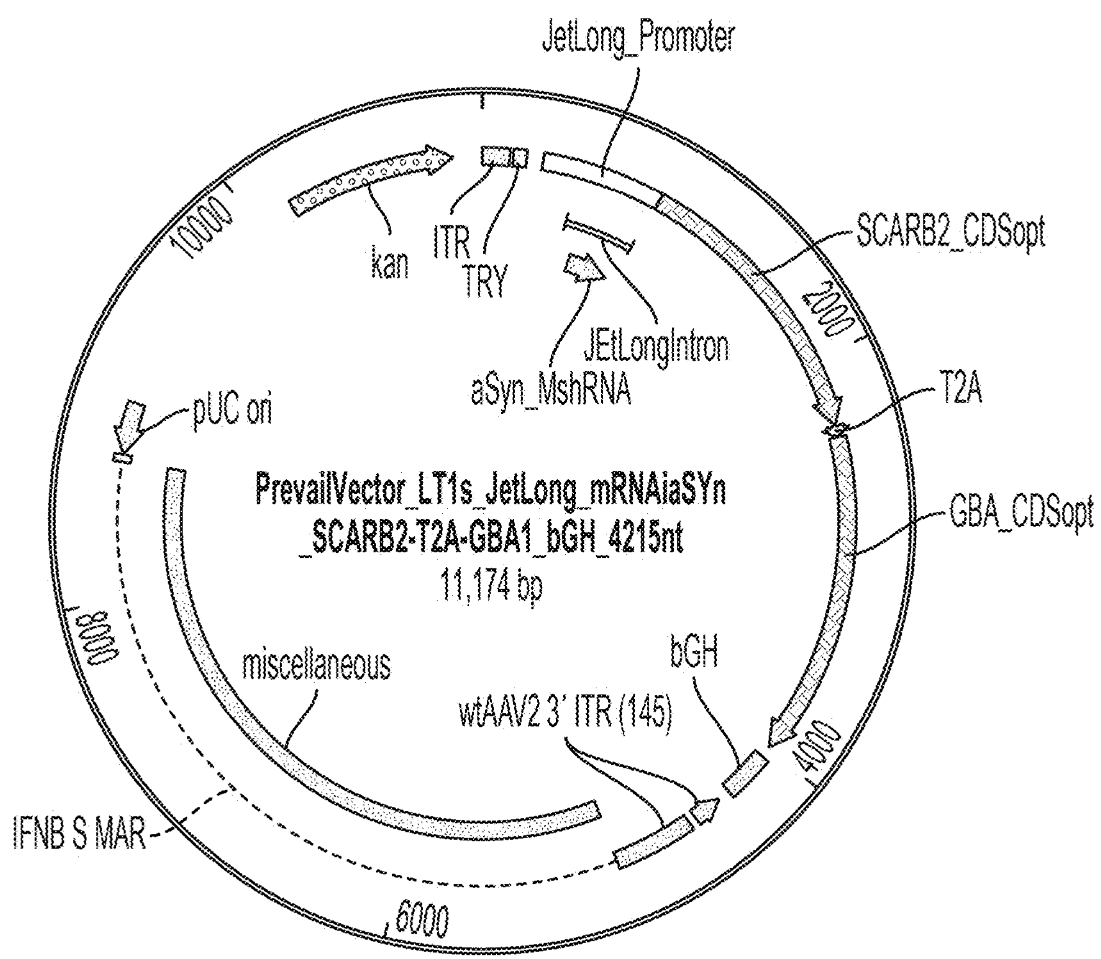
FIG. 4 is a schematic depicting one embodiment of a vector comprising an expression construct encoding Gcase (e.g., GBA1 or a portion thereof), LIMP2 (SCARB2) or a portion thereof, and an interfering RNA for α-Syn.
Figure 5:
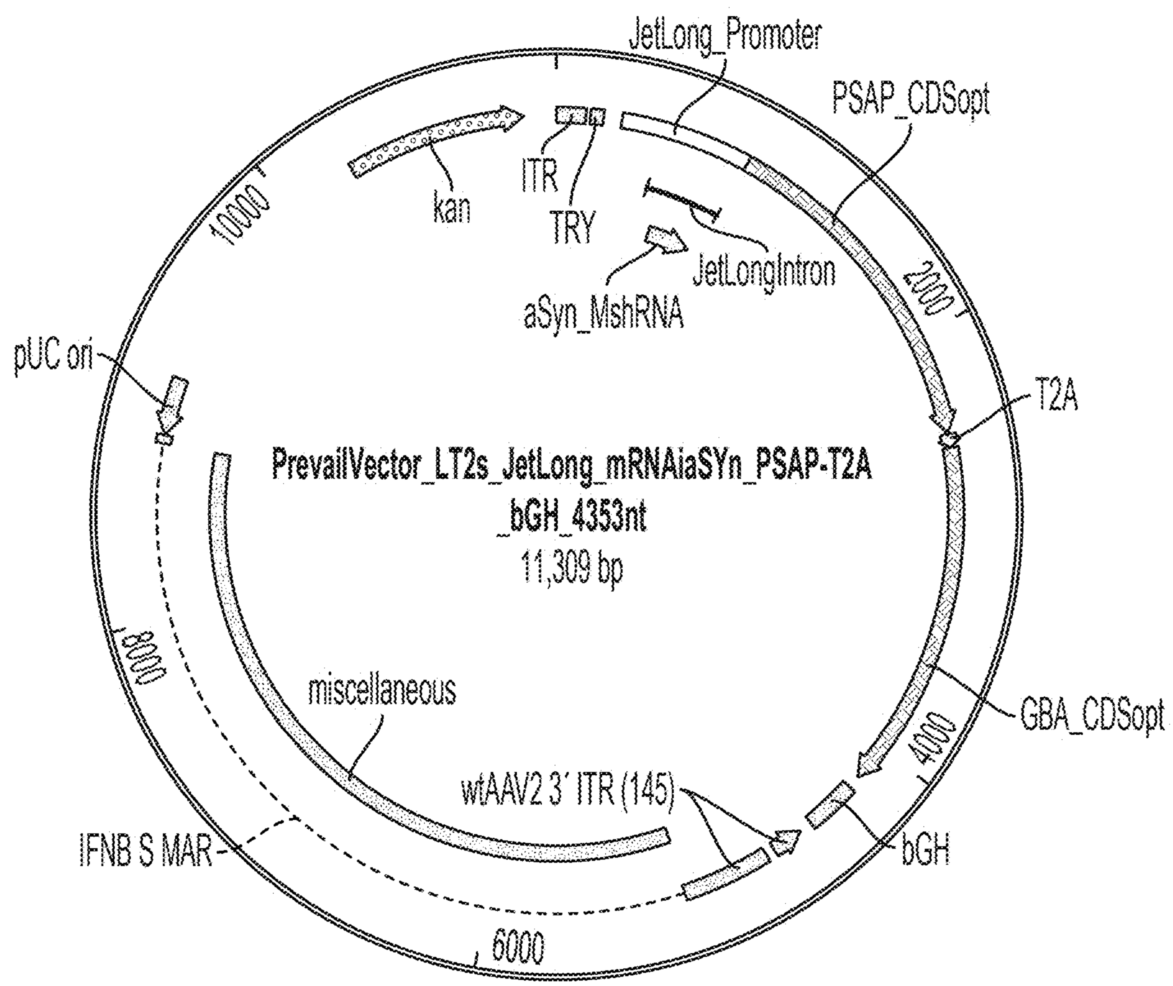
FIG. 5 is a schematic depicting one embodiment of a vector comprising an expression construct encoding Gcase (e.g., GBA1 or a portion thereof), Prosaposin (e.g., PSAP or a portion thereof), and an interfering RNA for α-Syn.
Figure 6:
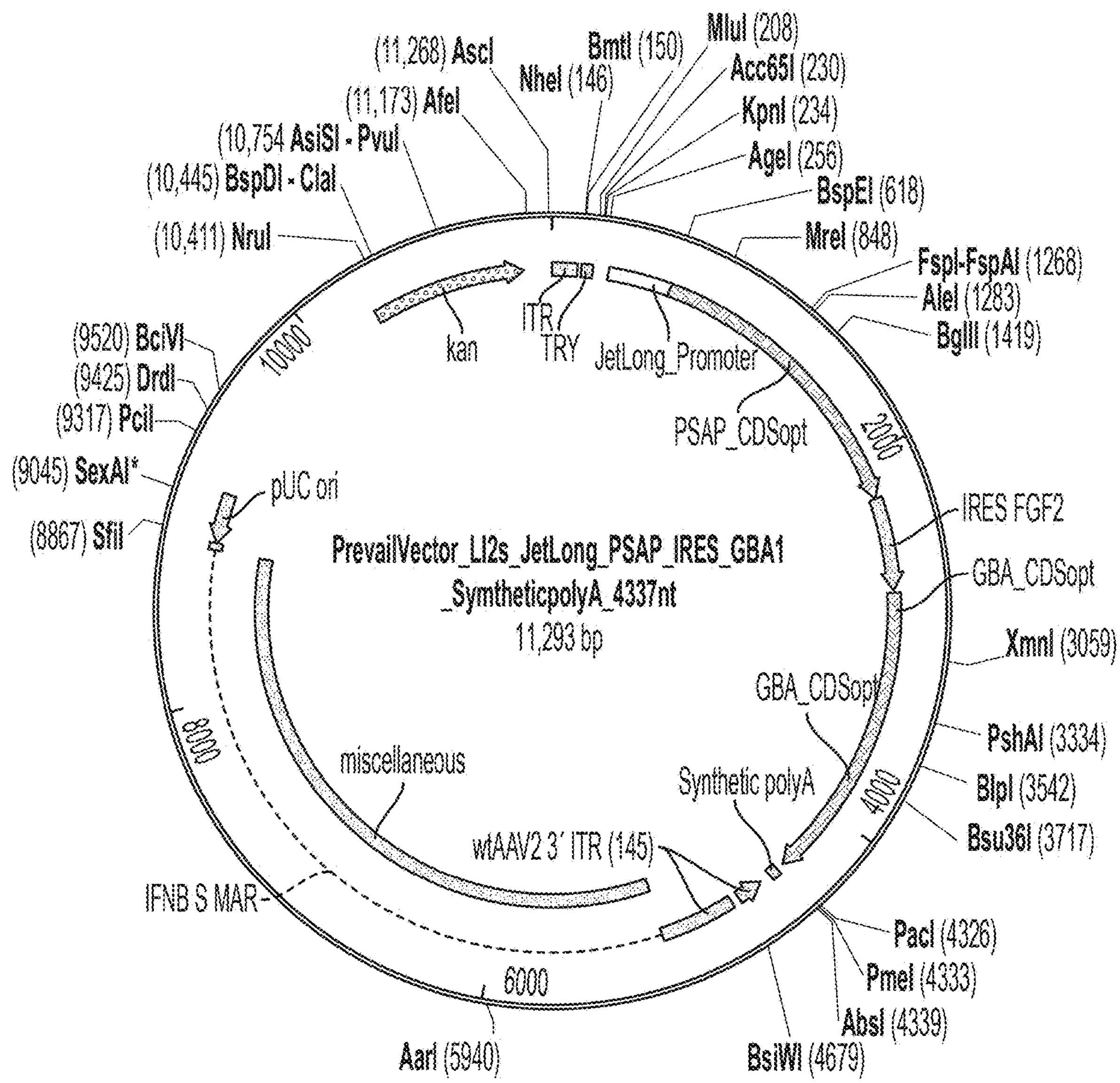
FIG. 6 is a schematic depicting one embodiment of a vector comprising an expression construct encoding Gcase (e.g., GBA1 or a portion thereof) and Prosaposin (e.g., PSAP or a portion thereof). The coding sequences of Gcase and Prosaposin are separated by an internal ribosomal entry site (IRES).

| Disease | Associated genes |
|---|---|
| Alzheimer's disease | APP, PSEN1, PSEN2, APOE |
| Parkinson's disease | LRRK2, PARK7, PINK1, PRKN, SNCA, GBA, UCHL1, ATP13A2, VPS35 |
| Huntington's disease | HTT |
| Amyotrophic lateral sclerosis | ALS2, ANG, ATXN2, C9orf72, CHCHD10, CHMP2B, DCTN1, ERBB4, FIG4, FUS, HNRNPA1, MATR3, NEFH, OPTN, PFN1, PRPH, SETX, SIGMAR1, SMN1, SOD1, SPG11, SQSTM1, TARDBP, TBK1, TRPM7, TUBA4A, UBQLN2, VAPB, VCP |
| Batten disease (Neuronal ceroid lipofunscinosis) | PPT1, TPP1, CLN3, CLN5, CLN6, MFSD8, CLN8, CTSD, DNAJC5, CTSF, ATP13A2, GRN, KCTD7 |
| Friedreich's ataxia | FXN |
| Lewy body disease | APOE, GBA, SNCA, SNCB |
| Spinal muscular atrophy | SMN1, SMN2 |
| Multiple sclerosis | CYP2781, HLA-DRB1, IL2RA, IL7R, TNFRSF1A |
| Prion disease (Creutzfeldt-Jakob disease, Fatal familial insomnia, Gertsmann-Straussler-Scheinker syndrome, Variably protease-sensitive prionopathy) | PRNP |

TABLE 13

| Examples of synucleinopathies | |
|---|---|
| Disease | Associated genes |
| Parkinson's disease | LRRK2, PARK7, PINK1, PRKN, SNCA, GBA, UCHL1, ATP13A2, VPS35 |
| Dementia with Lewy bodies | APOE, GBA, SNCA, SNCB |
| Multiple system atrophy | COQ2, SNCA |

TABLE 14

| Examples of tauopathies | |
|---|---|
| Disease | Associated genes |
| Alzheimer's disease | APP, PSEN1, PSEN2, APOE |
| Primary age-related tauopathy | MAPT |
| Progressive supranuclear palsy | MAPT |
| Corticobasal degeneration | MAPT, GRN, C9orf72, VCP, CHMP2B, TARDBP, FUS |
| Frontotemporal dementia with parkinsonism-17 | MAPT |
| Subacute sclerosing panencephalitis | SCN1A |
| Lytico-Bodig disease | |
| Gangioglioma, gangliocytoma | |
| Meningioangiomatosis | |
| Postencephalitic parkinsonism | |
| Chronic traumatic encephalopathy | |

TABLE 15

| Examples of lysosomal storage diseases | |
|---|---|
| Disease | Associated genes |
| Niemann-Pick disease | NPC1, NPC2, SMPD1 |
| Fabry disease | GLA |
| Krabbe disease | GALC |
| Gaucher disease | GBA |
| Tach-Sachs disease | HEXA |
| Metachromatic leukodystrophy | ARSA, PSAP |
| Farber disease | ASAH1 |
| Galactosialidosis | CTSA |
| Schindler disease | NAGA |
| GM1 gangliosidosis | GLB1 |
| GM2 gangliosidosis | GM2A |
| Sandhoff disease | HEXB |
| Lysosomal acid lipase deficiency | LIPA |
| Multiple sulfatase deficiency | SUMF1 |
| Mucopolysaccharidosis Type I | IDUA |
| Mucopolysaccharidosis Type II | IDS |
| Mucopolysaccharidosis Type III | GNS, HGSNAT, NAGLU, SGSH |
| Mucopolysaccharidosis Type IV | GALNS, GLB1 |
| Mucopolysaccharidosis Type VI | ARSB |
| Mucopolysaccharidosis Type VII | GUSB |
| Mucopolysaccharidosis Type IX | HYAL1 |
| Mucolipidosis Type II | GNPTAB |
| Mucolipidosis Type III alpha/beta | GNPTAB |
| Mucolipidosis Type III gamma | GNPTG |
| Mucolipidosis Type IV | MCOLN1 |
| Neuronal ceroid lipofuscinosis | PPT1, TPP1, CLN3, CLN5, CLN6, MFSD8, CLN8, CTSD, DNAJC5, CTSF, ATP13A2, GRN, KCTD7 |
| Alpha-mannosidosis | MAN2B1 |
| Beta-mannosidosis | MANBA |
| Aspartylglucosaminuria | AGA |
| Fucosidosis | FUCA1 |

Example 14: Automated Western Assay for Detection of Progranulin in Cerebrospinal Fluid The purpose of this experiment was to quantify the protein levels of progranulin (PGRN) in cerebrospinal fluid (CSF) using the ProteinSimple (San Jose, CA) Automated Western platform Jess. This test method may be used to analyze non-human primate (NHP) CSF samples. To determine the expression levels of human progranulin protein, the transgene product of PR006A, CSF samples from non-human primate subjects were analyzed on a Simple Western™ (Jess) platform using an antibody that specifically detects human progranulin protein. The Simple Western™ platform is a capillary-based automated Western blot immunoassay platform, where all steps, including protein separation, immunoprobing, washing, and detection by chemiluminescence occur in a capillary cartridge. Samples (at 4-fold dilution) and primary antibody to human progranulin (Adipogen PG-359-7, at 10-fold dilution), in addition to secondary antibodies and all buffers manufactured by ProteinSimple, were loaded onto a customized cartridge which was run on the Jess platform. Semi-quantitative data analysis occurred automatically after each run was completed, where parameters such as signal intensity, peak area, and signal-to-noise ratio were calculated using the Jess instrument. For each individual sample, the level of progranulin was measured as the peak area of immunoreactivity to the antibody. All analyses were performed with blinded samples.

The assay described here was performed on CSF samples from a non-human primate animal study. CSF samples were tested for presence and levels of progranulin protein to study efficacy of gene therapy using an rAAV construct (PR006; see FIG. 64) encoding progranulin (PGRN) protein. In this study, either the excipient or PR006 were delivered at low dose of PR006 ($1.8\times10^{10}$ vg/g brain weight) or high dose of PR006 ($1.8\times10^{11}$ vg/g brain weight) by intra-cisterna magna (ICM) injection into NHP animals. Each group consisted of 3 animals. Nine NHP animals were sacrificed at day 180 post-infection (Table 16), and CSF samples were analyzed using the Jess-based assay.

TABLE 16

| NHP animal summary with grouping and dosing | | |
|---|---|---|
| Group | Dose of PR006 (vg/g brain weight) | Number of animals Necropsy (Day 180) |
| 1 | 0 | 2 M/1 F |
| 2 | $1.8\times10^{10}$ | 2 M/1 F |
| 3 | $1.8\times10^{11}$ | 2 M/1 F |

TABLE 17

| Materials for automated Western assay | | |
|---|---|---|
| Material Description | Manufacturer | Item Number |
| 12-230 kDa Jess Separation Module, 25 capillary cartridges | ProteinSimple | SM-W004 |
| EZ Standard Pack 1, 12-230 kDa | ProteinSimple | PS-ST01EZ-8 |
| Anti-mouse detection module for Jess | ProteinSimple | DM-002 |
| Progranulin monoclonal antibody (human), clone PG359-7 (primary antibody) | Adipogen | AG-20A-0052-C100 |

Note:
all reagents should be allowed to warm to room temperature prior to opening vials.

The following procedures were followed in performing this method:

Preparation of Stock Solutions:

1. Prepare 400 mM DTT solution by adding 404 of water to clear tube in the separation module EZ Standard Pack. Mix gently.

2. To prepare master mix, add 204 of 10× sample buffer and 204 of 400 mM DTT into the EZ Pink Master Mix Tube. Mix Gently.
3. To prepare the biotinylated ladder, Pipette 204 of water into the EZ clear biotinylated ladder tube with pink pellet. Mix gently.
4. Prepare luminol and peroxide mix by adding equal amounts of each. For one run, add 2004 of luminol to 2004 of peroxide.
5. Prepare primary antibody dilution (10 fold-dilution) by mixing 254 of primary antibody and 2254 of antibody diluent 2.

Preparation of Samples:

1. Samples are diluted in 0.1× sample buffer. Prepare 0.1× sample buffer by adding 104 of 10× sample buffer into 990 μL of water.
2. Dilute samples as necessary. For example, NHP CSF samples were diluted 4-fold prior to addition of master mix. Add 54 of NHP CSF to 15 μL 0.1× sample buffer.
3. Prepare samples by adding 1× of master mix to 4× of sample. To run technical duplicates, prepare a total of 15 μL of sample plus master mix per sample. For example, add 34 of master mix to 124 of diluted sample. Mix gently.
4. Boil samples at 95° C. for 5 minutes.
5. Spin down samples briefly using desktop mini-centrifuge. Vortex before loading the sample.

Load Reagents and Samples into Cartridge:

1. Pipette all samples according to cartridge map.
   a. Pipette 154 of luminol+peroxide mix to each well in lane E.
   b. Pipette 104 of streptavidin to first well in lane D.
   c. Pipette 104 of secondary antibody to remaining 24 wells in lane D.
   d. Pipette 104 of antibody dilution to first well in lane C.
   e. Pipette 104 of primary antibody dilution to remaining 24 wells in lane C.
   f. Pipette 104 of antibody diluent to all wells in lane B.
   g. Pipette 104 of prepared EZ ladder to first well in lane A.
   h. Pipette 54 of sample and master mix solution to duplicate lanes in lane A.
2. Spin cartridge at room temperature at 2500 RPM for 5 minutes.

Load Capillaries and Cartridge into Instrument:

1. Load capillaries into slot. Make sure light turns blue.
2. Load spun cartridge into instrument.
3. Press start button after blue light stops blinking at the instrument.

The assay system suitability was considered acceptable if CV (coefficient of variance) percentage for duplicates was ≤30%.

Before the assay was used to detect progranulin in NHP CSF samples, the assay was tested as follows. Qualification of Jess assays included assessment of dilution linearity, selectivity and specificity. Normal CSF samples from BioIVT were used to determine dilution linearity of Jess assay. CSF samples from fronto-temporal dementia (FTD) patients with PGRN mutation (obtained from National Centralized Repository for Alzheimer's Disease and Related Dementias (NCRAD; Indianapolis, Indiana)) were used to determine selectivity and specificity of Jess assay.

TABLE 18

| Results summary | | | |
|---|---|---|---|
| | Elements | Acceptance Criteria | Results |
| Dilution Linearity | Investigate endogenous PGRN levels in naïve CSF samples (BioIVT). Conduct an analysis of blank sample in the matrix. Minimal required dilution (MRD) is determined by diluting a neat matrix in 2-fold serial dilution. If endogenous levels of PGRN are too low in matrix, dilutions will be performed using spiked matrix. | The MRD is defined as the lowest dilution required where a linear raw signal or concentration is observed. Within the linear range, the corrected observed concentrations should be ±30% of the MRD. | Pass All tested matrices passed by having a linear dilution range with ±30% of the MRD (see Results and Discussion section, Dilution Linearity. |
| Selectivity and Specificity | Investigate PGRN levels in FTD patient CSF samples. | The MRD is defined through Dilution Linearity test. | Pass All tested matrices passed by having a % CV of technical replicate with 20% (see Results and Discussion section, Selectivity and Specificity. |

Results and Discussion

Dilution Linearity

Dilution linearity of PGRN protein detected by Jess was tested in CSF samples from commercially available (BioIVT) normal individuals. Endogenous levels of PGRN in CSF samples were measured to determine dilution linearity. Two individuals were tested in 2-fold serial dilution that ranges from 2 to 64 fold dilution.

Table 19 reported the peak area of PGRN protein at 58 kDa detected by Jess and the % differences of each dilution from 16-fold dilution. Results within the linearity range are in bold font (within 100±30% difference). Dilution linearity was established to be within 4 to 16 fold dilution.

TABLE 19

| Dilution linearity in CSF samples | | | | |
|---|---|---|---|---|
| | CSF #1 | | CSF #2 | |
| Dilution factor | 58 kDa Peak Area (Dilution Adjusted) | % Difference | 58 kDa Peak Area (Dilution Adjusted) | % Difference |
| 1:2 | 3915099 | −41.2 | 6392991 | −38.8 |
| 1:4 | 6040885 | −9.2 | 8020821 | −23.2 |
| 1:8 | 5773987 | −13.3 | 12615004 | 20.8 |
| 1:16 | 6656474 | 0.0 | 10446186 | 0.0 |
| 1:32 | 8911479 | 33.9 | 11782404 | 12.8 |
| 1:64 | 12056943 | 81.1 | 6795118 | −35.0 |

In summary, all of the tested matrices had an acceptable linear range that passed the acceptance criteria of a % difference that is 0±30%, though the size of the range and amount of dilution varied between matrices. Sample linearity MRD was established to be 4-fold dilution. Dilution linearity was established to be within 4- to 16-fold dilution. A summary of the MRD and linear dilution range that passes acceptance criteria for CSF is depicted in Table 20.

TABLE 20

| MRD and linear dilution range of the CSF | | |
|---|---|---|
| Tissue | Linearity MRD | Linear Dilution Range |
| CSF | 1:4 | 1:4-1:16 |

Selectivity and Specificity

Selectivity and specificity of PGRN protein detected by Jess were tested in CSF samples from the PR006 FTD patient samples from NCRAD. Three groups (group A, B, and C) of CSF samples were collected form heterozygous FTD patients (group A), familial non-carrier (group B or C), and normal individuals (group B or C). Six samples were analyzed for each group. The groups of samples are listed in Table 16 FTD Patient CSF sample information.

Figures 55, 56:
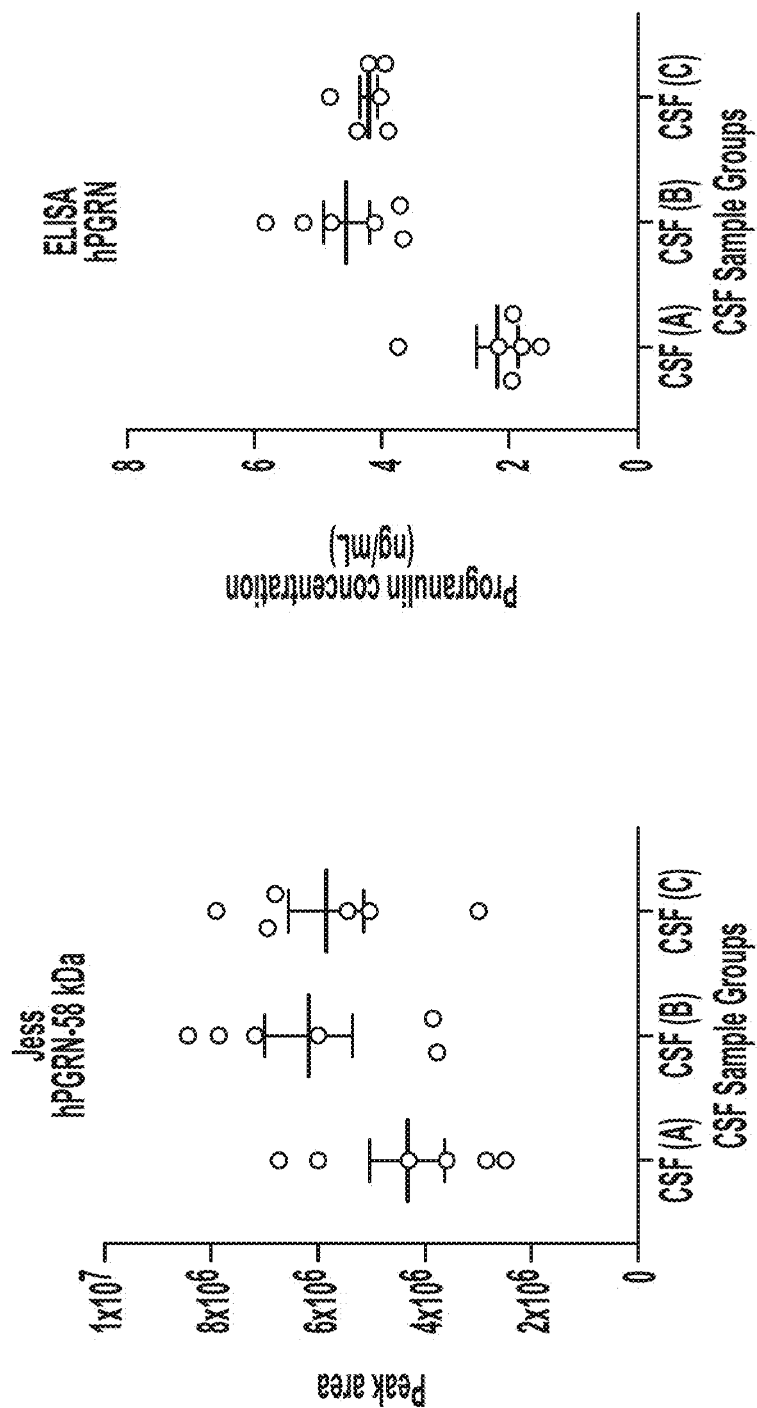
FIG. 55 is a graph showing selectivity and specificity results for the automated Western Jess assay. Progranulin protein levels in FTD patient CSF samples were detected at 58 kDa by Jess. Group (A): heterozygous FTD patients and groups (B) and (C): familial non-carrier or normal individuals. Data are presented as mean±standard error of the mean (SEM). SEM values are shown as vertical error bars.
FIG. 56 is a graph showing Progranulin levels in FTD patient CSF samples detected by ELISA. Group (A): heterozygous FTD patients and groups (B) and (C): familial non-carrier or normal individuals. Data are presented as mean±standard error of the mean (SEM). SEM values are shown as vertical error bars.
Figure 57:
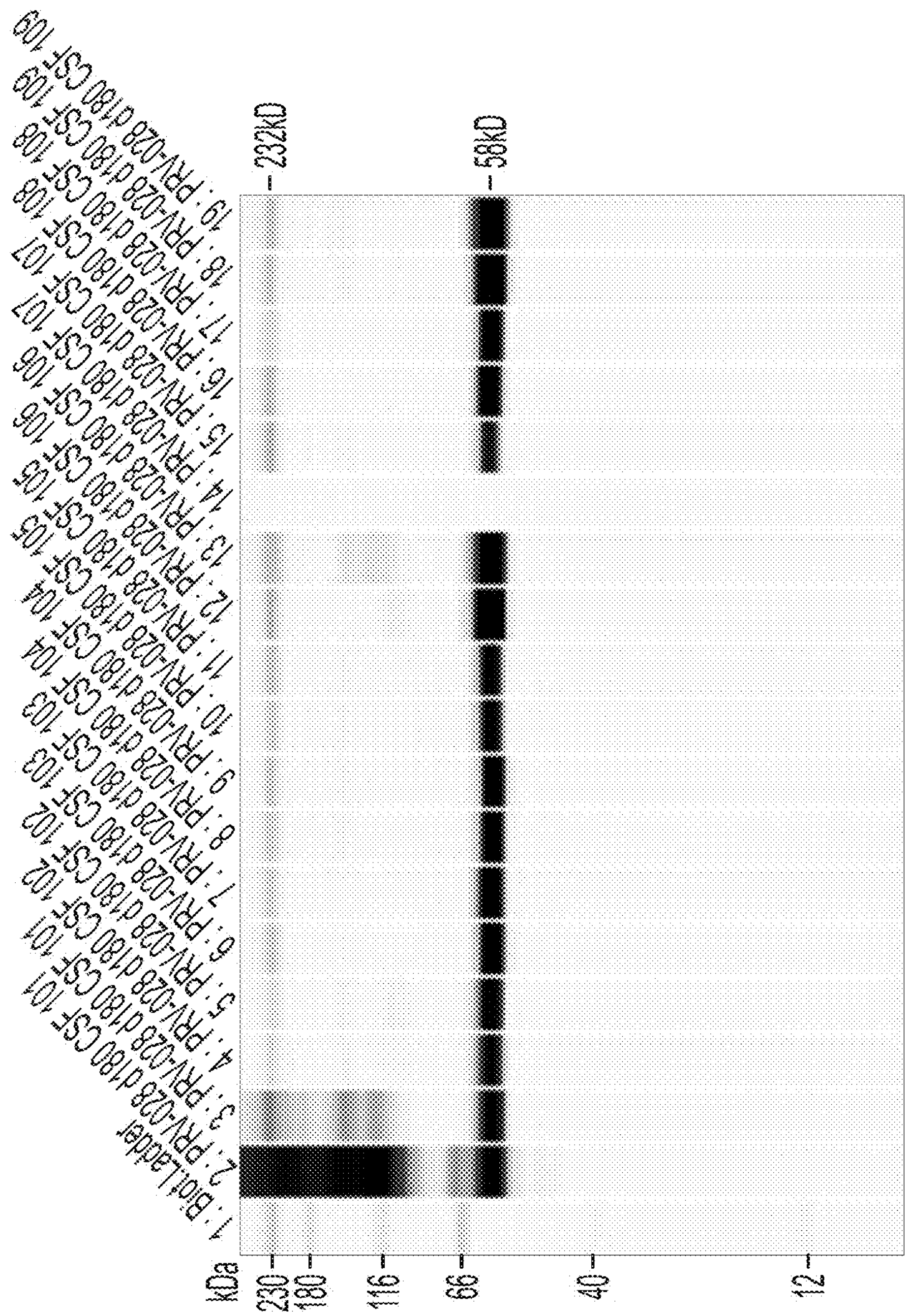
FIG. 57 is a gel image of each CSF sample run in duplicate on the Jess automated Western platform. Samples were analyzed at a 4-fold dilution using the primary antibody Adipogen PG-359-7. The first lane is the molecular weight standards, and on the right is the band identification used to calculate the immunoreactivities reported in Example 14.
Figure 58B:
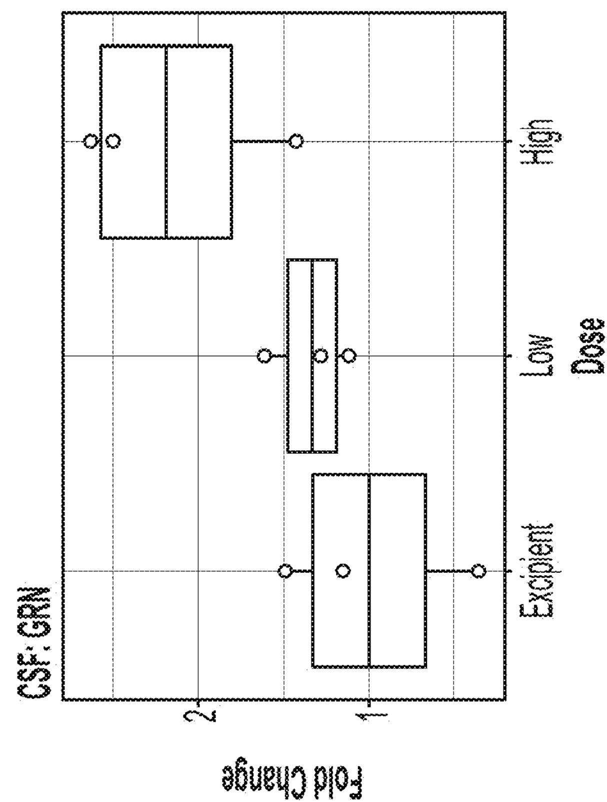
FIG. 58A-FIG. 58B are a series of plots showing the measurement of human PGRN expression levels. Human PGRN expression levels were determined in non-human primate (NHP) CSF samples that were collected at Day 180, using a Simple Western™ (Jess) analysis. CSF from NHPs treated with excipient ("Excipient"), low dose of PR006A ($6.5\times10^9$ vg/g brain weight; "low") or high dose of PR006 ($6.5\times10^{10}$ vg/g brain weight; "high") were analyzed. The data is expressed as average immunoreactivity peak area (FIG. 58A), or fold change over excipient-treated animals (FIG. 58B). Each dot represents a single CSF sample from one NHP (mean of the technical duplicate) and the box represents the mean value+/−standard error of the three individual NHPs.
Figure 58A:
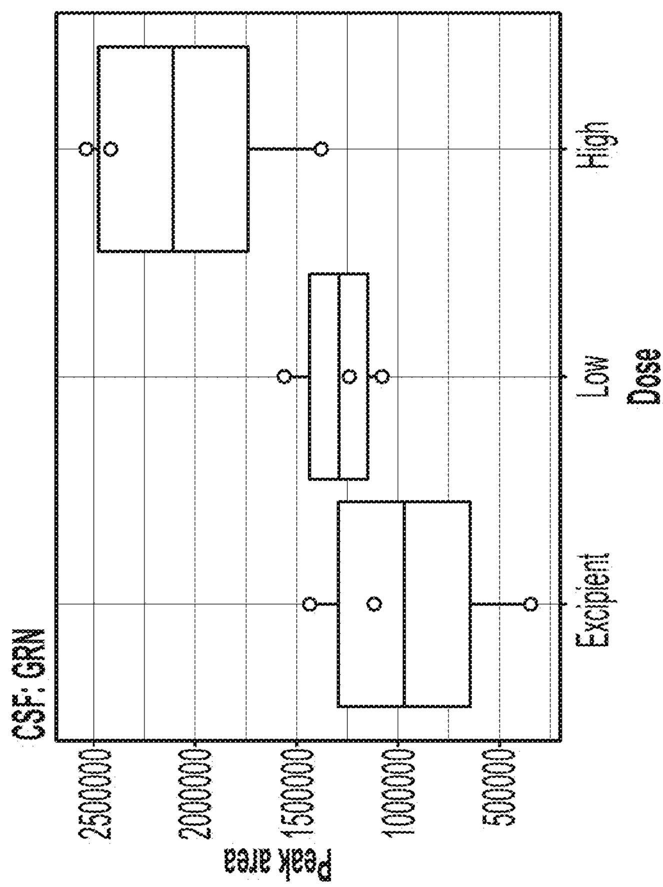

CSF samples were 4-fold diluted in 0.1× sample buffer provided by ProteinSimple and tested in technical duplicates. Samples duplicates with result % CV more than 20% were re-analyzed. Results with % CV less than 20% were reported in Table 22. Table 22 reported the peak area of PGRN protein at 58 kDa detected by Jess and the % CV between duplicates. Results showed about two fold higher of PGRN levels in group B and C as compared to group A, which indicates the selectivity and specificity of Jess assay in determine PGRN levels for CSF samples (FIG. 55).

TABLE 21

| FTD patient CSF sample information | | | | | | | |
|---|---|---|---|---|---|---|---|
| Barcode | Alternate MRN | Visit | Kit Number | Specimen Type | Box Name | Position | Group |
| 0003355598 | ST-20000108 | Cycle 2-CSF | 257282 | CSF | 27488 CSF | 1 | C |
| 0004777338 | ST-20000118 | Cycle 2-CSF | 267633 | CSF | 27488 CSF | 2 | C |
| 0004777329 | ST-20000306 | Cycle 1-CSF | 260551 | CSF | 27488 CSF | 3 | A |
| 0004777326 | ST-20000328 | Cycle 2-CSF | 260544 | CSF | 27488 CSF | 4 | C |
| 0004777335 | ST-20000386 | Cycle 1-CSF | 267110 | CSF | 27488 CSF | 5 | A |
| 0004777345 | ST-20000590 | Cycle 2-CSF | 267859 | CSF | 27488 CSF | 6 | B |
| 0004777332 | ST-20000621 | Cycle 1-CSF | 266413 | CSF | 27488 CSF | 7 | B |
| 0004628923 | ST-20000757 | Cycle 1-CSF | 269817 | CSF | 27488 CSF | 8 | B |
| 0004695103 | ST-20001142 | Cycle 1-CSF | 308149 | CSF | 27488 CSF | 9 | A |
| 0004074629 | ST-20000107 | Cycle 2-CSF | 258212 | CSF | 27488 CSF | 10 | C |
| 0003358475 | ST-20000110 | Cycle 2-CSF | 258210 | CSF | 27488 CSF | 11 | C |
| 0003358463 | ST-20000274 | Cycle 2-CSF | 257292 | CSF | 27488 CSF | 12 | A |
| 0004788828 | ST-20000309 | Cycle 2-CSF | 303093 | CSF | 27488 CSF | 13 | C |
| 0003358781 | ST-20000615 | Cycle 1-CSF | 257278 | CSF | 27488 CSF | 14 | B |
| 0003358793 | ST-20000616 | Cycle 1-CSF | 257305 | CSF | 27488 CSF | 15 | A |
| 0004777321 | ST-20000637 | Cycle 1-CSF | 257307 | CSF | 27488 CSF | 16 | B |
| 0004777341 | ST-20000768 | Cycle 1-CSF | 267857 | CSF | 27488 CSF | 17 | B |
| 0004695106 | ST-20001165 | Cycle 1-CSF | 317396 | CSF | 27488 CSF | 18 | A |

TABLE 22

| Selectivity and specificity results | | | |
|---|---|---|---|
| Groups | Sample Barcode | 58 kD Peak Area (Dilution Adjusted) | % CV |
| Group (A) | 0004777329 | 2838645 | 5.08 |
| Heterozygous | 0004777335 | 4293344 | 1.20 |
| FTD patients | 0004695103 | 6738165 | 1.08 |
| | 0003358463 | 3594249 | 11.10 |
| | 0003358793 | 5992434 | 2.49 |
| | 0004695106 | 2472462 | 10.40 |
| Group (B) | 0004777345 | 3836185 | 11.18 |
| Normal or | 0004777332 | 6006224 | 3.05 |
| familial non- | 0004628923 | 3758940 | 1.44 |
| carrier | 0003358781 | 7860294 | 17.08 |
| | 0004777321 | 7187172 | 0.69 |
| | 0004777341 | 8450410 | 0.50 |
| Group (C) | 0003355598 | 2981005 | 1.70 |
| Normal or | 0004777338 | 6803428 | 0.18 |
| familial non- | 0004777326 | 5030695 | 3.56 |
| carrier | 0004074629 | 5448863 | 3.47 |
| | 0003358475 | 7892529 | 1.17 |
| | 0004788828 | 6944800 | 1.85 |

CSF samples from FTD patient study (Table 21) were also analyzed with a human PGRN ELISA kit (Adipogen, AG-45A-0018YEK-KI01). Results from ELISA (FIG. 56) showed similar trends of PGRN levels between groups as Jess and demonstrated the Jess assay is suitable to use for the assessment of PGRN levels in CSF samples.

In conclusion, this ProteinSimple Automated Western Jess assay was determined to be suitable to use for the assessment of PGRN levels in NHP CSF samples.

Jess data for NHP CSF samples is shown in Table 23. Each sample represents the average across two technical replicates. The peak area for 58 kD band in the sample lane is reported. Data is presented as mean peak area of technical replicate and dilution folds adjusted.

TABLE 23

| Jess data for NHP CSF samples | | |
|---|---|---|
| Sample ID | Dose Group | Peak area (58 kD) |
| PRV-028 d180 CSF 101 | Low dose | 4944754 |
| PRV-028 d180 CSF 102 | Control | 4449066 |
| PRV-028 d180 CSF 103 | Low dose | 6222881 |
| PRV-028 d180 CSF 104 | High dose | 5499901 |
| PRV-028 d180 CSF 105 | Low dose | 4293853 |
| PRV-028 d180 CSF 106 | High dose | 10149400 |
| PRV-028 d180 CSF 107 | Control | 1360173 |
| PRV-028 d180 CSF 108 | Control | 5742081 |
| PRV-028 d180 CSF 109 | High dose | 9658597 |

The goal of this assay was to confirm the level of progranulin (PGRN) protein expression levels following the transduction of PR006 in tissue regions of interest for the NHP study. This was done using an automated Western platform, in which progranulin protein was detected using a monoclonal antibody. Progranulin expression was measurable in CSF in both control and PR006-treated NHP; the assay does not differentiate between endogenous progranulin protein and PR006A-induced progranulin protein.

This Application incorporates by reference the contents of the following documents in their entirety: International PCT Application Publication No. WO 2019/070893; International PCT Application Publication No. WO 2019/070891; U.S. Provisional Application Ser. No. 62/567,296, filed Oct. 3, 2017, entitled "GENE THERAPIES FOR LYSOSOMAL DISORDERS"; 62/567,311, filed Oct. 3, 2017, entitled "GENE THERAPIES FOR LYSOSOMAL DISORDERS"; 62/567,319, filed Oct. 3, 2017, entitled "GENE THERAPIES FOR LYSOSOMAL DISORDERS"; 62/567,301, filed Oct. 3, 2018, entitled "GENE THERAPIES FOR LYSOSOMAL DISORDERS"; 62/567,310, filed Oct. 3, 2017, entitled "GENE THERAPIES FOR LYSOSOMAL DISORDERS"; 62/567,303, filed Oct. 3, 2017, entitled "GENE THERAPIES FOR LYSOSOMAL DISORDERS"; and 62/567,305, filed Oct. 3, 2017, entitled "GENE THERAPIES FOR LYSOSOMAL DISORDERS".

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or"

as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

Each of the U.S. patents, U.S. patent application publications, U.S. patent applications, foreign patents, foreign patent applications and non-patent publications referred to in this application is incorporated herein by reference, in its entirety.

Sequences

In some embodiments, an expression cassette encoding one or more gene products (e.g., a first, second and/or third gene product) comprises or consists of (or encodes a peptide having) a sequence set forth in any one of SEQ ID NOs: 1-91. In some embodiments, a gene product is encoded by a portion (e.g., fragment) of any one of SEQ ID NOs: 1-91.

Numbered Embodiments

Notwithstanding the appended claims, the disclosure sets forth the following numbered embodiments:

1. An isolated nucleic acid comprising an expression construct encoding a Gcase protein flanked by two adeno-associated virus (AAV) inverted terminal repeats (ITRs), wherein
   - (i) at least one of the ITRs comprises a modified "D" region relative to a wild-type AAV2 ITR (SEQ ID NO: 29); and/or
   - (ii) the Gcase protein is encoded by a codon-optimized nucleic acid sequence.

2. The isolated nucleic acid of embodiment 1, wherein the Gcase protein comprises the amino acid sequence set forth in SEQ ID NO: 14 or a portion thereof.

3. The isolated nucleic acid of embodiment 1 or 2, wherein the Gcase protein is encoded by a codon-optimized nucleic acid sequence, optionally the nucleic acid sequence set forth in SEQ ID NO: 15.

4. The isolated nucleic acid of any one of embodiments 1 to 3, wherein the modified "D" region is a "D" sequence located on the outside of the ITR relative to the expression construct.

5. The isolated nucleic acid of any one of embodiments 1 to 4, wherein the ITR comprising the modified "D" sequence is a 3' ITR.

6. The isolated nucleic acid of any one of embodiments 1 to 5, further comprising a TRY sequence, optionally wherein the TRY sequence is set forth in SEQ ID NO: 28.

7. An isolated nucleic acid comprising an expression construct encoding a prosaposin protein flanked by two adeno-associated virus (AAV) inverted terminal repeats (ITRs), wherein
   - (i) at least one of the ITRs comprises a modified "D" region relative to a wild-type AAV2 ITR (SEQ ID NO: 29); and/or
   - (ii) the prosaposin protein is encoded by a codon-optimized nucleic acid sequence.

8. The isolated nucleic acid of embodiment 7, wherein the prosaposin protein comprises the amino acid sequence set forth in SEQ ID NO: 16 or a portion thereof.

9. The isolated nucleic acid of embodiment 7 or 8, wherein the prosaposin protein is encoded by a codon-optimized nucleic acid sequence, optionally the nucleic acid sequence set forth in SEQ ID NO: 17.

10. The isolated nucleic acid of any one of embodiments 7 to 9, wherein the modified "D" region is a "D" sequence located on the outside of the ITR relative to the expression construct.

11. The isolated nucleic acid of any one of embodiments 7 to 10, wherein the ITR comprising the modified "D" sequence is a 3' ITR.

12. The isolated nucleic acid of any one of embodiments 7 to 11, further comprising a TRY sequence, optionally wherein the TRY sequence is set forth in SEQ ID NO: 28.

13. An isolated nucleic acid comprising an expression construct encoding a SCARB2 protein flanked by two adeno-associated virus (AAV) inverted terminal repeats (ITRs), wherein
   - (i) at least one of the ITRs comprises a modified "D" region relative to a wild-type AAV2 ITR (SEQ ID NO: 29); and/or
   - (ii) the SCARB2 protein is encoded by a codon-optimized nucleic acid sequence.

14. The isolated nucleic acid of embodiment 13, wherein the SCARB2 protein comprises the amino acid sequence set forth in SEQ ID NO: 18 or a portion thereof.

15. The isolated nucleic acid of embodiment 13 or 14, wherein the SCARB2 protein is encoded by a codon-optimized nucleic acid sequence or the nucleic acid sequence set forth in SEQ ID NO: 19.

16. The isolated nucleic acid of any one of embodiments 13 to 15, wherein the modified "D" region is a "D" sequence located on the outside of the ITR relative to the expression construct.

17. The isolated nucleic acid of any one of embodiments 13 to 16, wherein the ITR comprising the modified "D" sequence is a 3' ITR.

18. The isolated nucleic acid of any one of embodiments 13 to 17, further comprising a TRY sequence, optionally wherein the TRY sequence is set forth in SEQ ID NO: 28.

19. An isolated nucleic acid comprising an expression construct encoding a GBA2 protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the GBA2 protein is encoded by a codon-optimized nucleic acid sequence.

20. The isolated nucleic acid of embodiment 19, wherein the GBA2 protein comprises the amino acid sequence set forth in SEQ ID NO: 30 or a portion thereof.

21. The isolated nucleic acid of embodiment 19 or 20, wherein the GBA2 protein is encoded by a codon-optimized nucleic acid sequence or the nucleic acid sequence set forth in SEQ ID NO: 31.

22. The isolated nucleic acid of any one of embodiments 19 to 21, wherein the modified "D" region is a "D" sequence located on the outside of the ITR relative to the expression construct.

23. The isolated nucleic acid of any one of embodiments 19 to 22, wherein the ITR comprising the modified "D" sequence is a 3' ITR.

24. The isolated nucleic acid of any one of embodiments 19 to 23, further comprising a TRY sequence, optionally wherein the TRY sequence is set forth in SEQ ID NO: 28.

25. An isolated nucleic acid comprising an expression construct encoding a GALC protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the GALC protein is encoded by a codon-optimized nucleic acid sequence.

26. The isolated nucleic acid of embodiment 25, wherein the GALC protein comprises the amino acid sequence set forth in SEQ ID NO: 33 or a portion thereof.

27. The isolated nucleic acid of embodiment 25 or 26, wherein the GALC protein is encoded by a codon-optimized nucleic acid sequence or the nucleic acid sequence set forth in SEQ ID NO: 34.

28. The isolated nucleic acid of any one of embodiments 25 to 27, wherein the modified "D" region is a "D" sequence located on the outside of the ITR relative to the expression construct.

29. The isolated nucleic acid of any one of embodiments 25 to 28, wherein the ITR comprising the modified "D" sequence is a 3' ITR.

30. The isolated nucleic acid of any one of embodiments 25 to 29, further comprising a TRY sequence, optionally wherein the TRY sequence is set forth in SEQ ID NO: 28.

31. An isolated nucleic acid comprising an expression construct encoding a CTSB protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the CTSB protein is encoded by a codon-optimized nucleic acid sequence.

32. The isolated nucleic acid of embodiment 31, wherein the CTSB protein comprises the amino acid sequence set forth in SEQ ID NO: 30 or a portion thereof.

33. The isolated nucleic acid of embodiment 31 or 32, wherein the CTSB protein is encoded by a codon-optimized nucleic acid sequence or the nucleic acid sequence set forth in SEQ ID NO: 36.

34. The isolated nucleic acid of any one of embodiments 31 to 33, wherein the modified "D" region is a "D" sequence located on the outside of the ITR relative to the expression construct.

35. The isolated nucleic acid of any one of embodiments 31 to 34, wherein the ITR comprising the modified "D" sequence is a 3' ITR.

36. The isolated nucleic acid of any one of embodiments 31 to 35, further comprising a TRY sequence, optionally wherein the TRY sequence is set forth in SEQ ID NO: 28.

37. An isolated nucleic acid comprising an expression construct encoding a SMPD1 protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the SMPD1 protein is encoded by a codon-optimized nucleic acid sequence.

38. The isolated nucleic acid of embodiment 37, wherein the SMPD1 protein comprises the amino acid sequence set forth in SEQ ID NO: 37 or a portion thereof.

39. The isolated nucleic acid of embodiment 37 or 38, wherein the SMPD1 protein is encoded by a codon-optimized nucleic acid sequence or the nucleic acid sequence set forth in SEQ ID NO: 38.

40. The isolated nucleic acid of any one of embodiments 37 to 39, wherein the modified "D" region is a "D" sequence located on the outside of the ITR relative to the expression construct.

41. The isolated nucleic acid of any one of embodiments 37 to 40, wherein the ITR comprising the modified "D" sequence is a 3' ITR.

42. The isolated nucleic acid of any one of embodiments 37 to 41, further comprising a TRY sequence, optionally wherein the TRY sequence is set forth in SEQ ID NO: 28.

43. An isolated nucleic acid comprising an expression construct encoding a GCH1 protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the GCH1 protein is encoded by a codon-optimized nucleic acid sequence.

44. The isolated nucleic acid of embodiment 43, wherein the GCH1 protein comprises the amino acid sequence set forth in SEQ ID NO: 45 or a portion thereof.

45. The isolated nucleic acid of embodiment 43 or 44, wherein the GCH1 protein is encoded by a codon-optimized nucleic acid sequence or the nucleic acid sequence set forth in SEQ ID NO: 46.

46. The isolated nucleic acid of any one of embodiments 43 to 45, wherein the modified "D" region is a "D" sequence located on the outside of the ITR relative to the expression construct.

47. The isolated nucleic acid of any one of embodiments 43 to 46, wherein the ITR comprising the modified "D" sequence is a 3' ITR.

48. The isolated nucleic acid of any one of embodiments 43 to 47, further comprising a TRY sequence, optionally wherein the TRY sequence is set forth in SEQ ID NO: 28.

49. An isolated nucleic acid comprising an expression construct encoding a RAB7L protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the RAB7L protein is encoded by a codon-optimized nucleic acid sequence.

50. The isolated nucleic acid of embodiment 49, wherein the RAB7L protein comprises the amino acid sequence set forth in SEQ ID NO: 47 or a portion thereof.

51. The isolated nucleic acid of embodiment 49 or 50, wherein the RAB7L protein is encoded by a codon-optimized nucleic acid sequence or the nucleic acid sequence set forth in SEQ ID NO: 48.

52. The isolated nucleic acid of any one of embodiments 49 to 51, wherein the modified "D" region is a "D" sequence located on the outside of the ITR relative to the expression construct.

53. The isolated nucleic acid of any one of embodiments 49 to 52, wherein the ITR comprising the modified "D" sequence is a 3' ITR.

54. The isolated nucleic acid of any one of embodiments 49 to 53, further comprising a TRY sequence, optionally wherein the TRY sequence is set forth in SEQ ID NO: 28.

55. An isolated nucleic acid comprising an expression construct encoding a VPS35 protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the VPS35 protein is encoded by a codon-optimized nucleic acid sequence.

56. The isolated nucleic acid of embodiment 55, wherein the VPS35 protein comprises the amino acid sequence set forth in SEQ ID NO: 49 or a portion thereof.

57. The isolated nucleic acid of embodiment 55 or 56, wherein the VPS35 protein is encoded by a codon-optimized nucleic acid sequence or the nucleic acid sequence set forth in SEQ ID NO: 50.

58. The isolated nucleic acid of any one of embodiments 55 to 57, wherein the modified "D" region is a "D" sequence located on the outside of the ITR relative to the expression construct.

59. The isolated nucleic acid of any one of embodiments 55 to 58, wherein the ITR comprising the modified "D" sequence is a 3' ITR.

60. The isolated nucleic acid of any one of embodiments 55 to 59, further comprising a TRY sequence, optionally wherein the TRY sequence is set forth in SEQ ID NO: 28.

61. An isolated nucleic acid comprising an expression construct encoding a IL-34 protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the IL-34 protein is encoded by a codon-optimized nucleic acid sequence.

62. The isolated nucleic acid of embodiment 61, wherein the IL-34 protein comprises the amino acid sequence set forth in SEQ ID NO: 55 or a portion thereof.

63. The isolated nucleic acid of embodiment 61 or 62, wherein the IL-34 protein is encoded by a codon-optimized nucleic acid sequence or the nucleic acid sequence set forth in SEQ ID NO: 56.

64. The isolated nucleic acid of any one of embodiments 61 to 63, wherein the modified "D" region is a "D" sequence located on the outside of the ITR relative to the expression construct.

65. The isolated nucleic acid of any one of embodiments 61 to 64, wherein the ITR comprising the modified "D" sequence is a 3' ITR.

66. The isolated nucleic acid of any one of embodiments 61 to 65, further comprising a TRY sequence, optionally wherein the TRY sequence is set forth in SEQ ID NO: 28.

67. An isolated nucleic acid comprising an expression construct encoding a TREM2 protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the TREM2 protein is encoded by a codon-optimized nucleic acid sequence.

68. The isolated nucleic acid of embodiment 67, wherein the TREM2 protein comprises the amino acid sequence set forth in SEQ ID NO: 57 or a portion thereof.

69. The isolated nucleic acid of embodiment 67 or 68, wherein the TREM2 protein is encoded by a codon-optimized nucleic acid sequence or the nucleic acid sequence set forth in SEQ ID NO: 58.

70. The isolated nucleic acid of any one of embodiments 67 to 69, wherein the modified "D" region is a "D" sequence located on the outside of the ITR relative to the expression construct.

71. The isolated nucleic acid of any one of embodiments 67 to 70, wherein the ITR comprising the modified "D" sequence is a 3' ITR.

72. The isolated nucleic acid of any one of embodiments 67 to 71, further comprising a TRY sequence, optionally wherein the TRY sequence is set forth in SEQ ID NO: 28.

73. An isolated nucleic acid comprising an expression construct encoding a TMEM106B protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the TMEM106B protein is encoded by a codon-optimized nucleic acid sequence.

74. The isolated nucleic acid of embodiment 73, wherein the TMEM106B protein comprises the amino acid sequence set forth in SEQ ID NO: 63 or a portion thereof.

75. The isolated nucleic acid of embodiment 73 or 74, wherein the TMEM106B protein is encoded by a codon-optimized nucleic acid sequence or the nucleic acid sequence set forth in SEQ ID NO: 64.

76. The isolated nucleic acid of any one of embodiments 73 to 75, wherein the modified "D" region is a "D" sequence located on the outside of the ITR relative to the expression construct.

77. The isolated nucleic acid of any one of embodiments 73 to 76, wherein the ITR comprising the modified "D" sequence is a 3' ITR.

78. The isolated nucleic acid of any one of embodiments 73 to 77, further comprising a TRY sequence, optionally wherein the TRY sequence is set forth in SEQ ID NO: 28.

79. An isolated nucleic acid comprising an expression construct encoding a Progranulin (PGRN) protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the PGRN protein is encoded by a codon-optimized nucleic acid sequence.

80. The isolated nucleic acid of embodiment 79, wherein the PGRN protein comprises the amino acid sequence set forth in SEQ ID NO: 67 or a portion thereof.

81. The isolated nucleic acid of embodiment 79 or 80, wherein the PGRN protein is encoded by a codon-optimized nucleic acid sequence or the nucleic acid sequence set forth in SEQ ID NO: 68.

82. The isolated nucleic acid of any one of embodiments 79 to 81, wherein the modified "D" region is a "D" sequence located on the outside of the ITR relative to the expression construct.

83. The isolated nucleic acid of any one of embodiments 79 to 82, wherein the ITR comprising the modified "D" sequence is a 3' ITR.

84. The isolated nucleic acid of any one of embodiments 79 to 83, further comprising a TRY sequence, optionally wherein the TRY sequence is set forth in SEQ ID NO: 28.

85. An isolated nucleic acid comprising an expression construct encoding a first gene product and a second gene product, wherein each gene product independently is selected from the gene products, or portions thereof, set forth in Table 1.

86. The isolated nucleic acid of embodiment 85, wherein the first gene product is a Gcase protein, or a portion thereof.

87. The isolated nucleic acid of embodiment 85 or 86, wherein the second gene product is LIMP2 or a portion thereof, or Prosaposin or a portion thereof.

88. The isolated nucleic acid of any one of embodiments 85 to 87, further encoding an interfering nucleic acid (e.g., shRNA, miRNA, dsRNA, etc.), optionally wherein the interfering nucleic acid inhibits expression of $\alpha$-Syn or TMEM106B.

89. The isolated nucleic acid of any one of embodiments 85 to 88, further comprising one or more promoters, optionally wherein each of the one or more promoters is independently a chicken-beta actin (CBA) promoter, a CAG promoter, a CD68 promoter, or a JeT promoter.

90. The isolated nucleic acid of any one of embodiments 85 to 89, further comprising an internal ribosomal entry site (IRES), optionally wherein the IRES is located between the first gene product and the second gene product.

91. The isolated nucleic acid of any one of embodiments 85 to 90, further comprising a self-cleaving peptide coding sequence, optionally wherein the self-cleaving peptide is T2A.

92. The isolated nucleic acid of any one of embodiments 85 to 91, wherein the expression construct comprises two adeno-associated virus (AAV) inverted terminal repeat (ITR) sequences flanking the first gene product and the second gene product, optionally wherein one of the ITR sequences lacks a functional terminal resolution site.

93. The isolated nucleic acid of embodiment 92, wherein at least one of the ITRs comprises a modified "D" region relative to a wild-type AAV2 ITR (SEQ ID NO: 29).

94. The isolated nucleic acid of embodiment 93, wherein the modified "D" region is a "D" sequence located on the outside of the ITR relative to the expression construct.

95. The isolated nucleic acid of embodiment 93 or 94, wherein the ITR comprising the modified "D" sequence is a 3' ITR.

96. The isolated nucleic acid of any one of embodiments 85 to 95, further comprising a TRY sequence, optionally wherein the TRY sequence is set forth in SEQ ID NO: 28.

97. An isolated nucleic acid having the sequence set forth in any one of SEQ ID NOs: 1 to 91.

98. A vector comprising the isolated nucleic acid of any one of embodiments 1 to 97.

99. The vector of embodiment 98, wherein the vector is a plasmid.

100. The vector of embodiment 98, wherein the vector is a viral vector, optionally wherein the viral vector is a recombinant AAV (rAAV) vector or a Baculovirus vector.

101. A composition comprising the isolated nucleic acid of any one of embodiments 1 to 97 or the vector of any one of embodiments 98 to 100.

102. A host cell comprising the isolated nucleic acid of any one of embodiments 1 to 97 or the vector of any one of embodiments 98 to 100.

103. A recombinant adeno-associated virus (rAAV) comprising:

(i) a capsid protein; and (ii) the isolated nucleic acid of any one of embodiments 1 to 97, or the vector of any one of embodiments 98 to 100.

104. The rAAV of embodiment 103, wherein the capsid protein is capable of crossing the blood-brain barrier, optionally wherein the capsid protein is an AAV9 capsid protein or an AAVrh.10 capsid protein.

105. The rAAV of embodiment 103 or 104, wherein the rAAV transduces neuronal cells and non-neuronal cells of the central nervous system (CNS).

106. A method for treating a subject having or suspected of having Parkinson's disease, the method comprising administering to the subject an isolated nucleic acid of any one of embodiments 1 to 97, the vector of any one of embodiments 98 to 100, the composition of embodiment 101, or the rAAV of any one of embodiments 103 to 105.

107. The method of embodiment 106, wherein the administration comprises direct injection to the CNS of the subject, optionally wherein the direct injection is intracerebral injection, intraparenchymal injection, intrathecal injection, intracisterna magna injection or any combination thereof.

108. The method of embodiment 107, wherein the direct injection to the CNS of the subject comprises convection enhanced delivery (CED).

109. The method of any one of embodiments 106 to 108, wherein the administration comprises peripheral injection, optionally wherein the peripheral injection is intravenous injection.

110. A method for treating a subject having or suspected of having fronto-temporal dementia with a GRN mutation, the method comprising administering to the subject a recombinant adeno-associated virus (rAAV) comprising:

(i) a rAAV vector comprising a nucleic acid comprising an expression construct comprising a promoter operably linked to a transgene insert encoding a PGRN protein, wherein the transgene insert comprises the nucleotide sequence of SEQ ID NO: 68; and (ii) an AAV9 capsid protein.

111. The method of embodiment 110, wherein the rAAV is administered to the subject at a dose ranging from about $1\times10^{13}$ vector genomes (vg) to about $7\times10^{14}$ vg.

112. The method of embodiment 110 or 111, wherein the rAAV is administered via an injection into the cisterna magna.

113. The method of any one of embodiments 110-112, wherein the promoter is a chicken beta actin (CBA) promoter.

114. The method of any one of embodiments 110-113, wherein the rAAV vector further comprises a cytomegalovirus (CMV) enhancer.

115. The method of any one of embodiments 110-114, wherein the rAAV vector further comprises a Woodchuck Hepatitis Virus Posttranscriptional Regulatory Element (WPRE).

116. The method of any one of embodiments 110-115, wherein the rAAV vector further comprises a Bovine Growth Hormone polyA signal tail.

117. The method of any one of embodiments 110-116, wherein the nucleic acid comprises two adeno-associated virus inverted terminal repeats (ITR) sequences flanking the expression construct.

118. The method of embodiment 117, wherein each ITR sequence is a wild-type AAV2 ITR sequence.

119. The method of any one of embodiments 110-118, wherein the rAAV vector further comprises a TRY region between the 5' ITR and the expression construct, wherein the TRY region comprises SEQ ID NO: 28.

120. A method for treating a subject having or suspected of having fronto-temporal dementia with a GRN mutation, the method comprising administering to the subject a rAAV comprising:

(i) a rAAV vector comprising a nucleic acid comprising, in 5' to 3' order:

(a) an AAV2 ITR;

(b) a CMV enhancer;

(c) a CBA promoter;

(d) a transgene insert encoding a PGRN protein, wherein the transgene insert comprises the nucleotide sequence of SEQ ID NO: 68;

(e) a WPRE;

(f) a Bovine Growth Hormone polyA signal tail; and (g) an AAV2 ITR; and (ii) an AAV9 capsid protein.

121. The method of embodiment 120, wherein the rAAV is administered to the subject at a dose ranging from about $1\times10^{13}$ vg to about $7\times10^{14}$ vg.

122. The method of embodiment 120 or 121, wherein the rAAV is administered via an injection into the cisterna magna.

123. The method of any one of embodiments 110-122, wherein the rAAV is administered in a formulation comprising about 20 mM Tris, pH 8.0, about 1 mM $MgCl_2$, about 200 mM NaCl, and about 0.001% w/v poloxamer 188.

124. A pharmaceutical composition comprising (i) a rAAV comprising:

(a) a rAAV vector comprising a nucleic acid comprising an expression construct comprising a promoter operably linked to a transgene insert encoding a PGRN protein, wherein the transgene insert comprises the nucleotide sequence of SEQ ID NO: 68; and (b) an AAV9 capsid protein; and (ii) about 20 mM Tris, pH 8.0, (iii) about 1 mM $MgCl_2$, (iv) about 200 mM NaCl, and (v) about 0.001% w/v poloxamer 188.

125. A rAAV comprising:

(a) a rAAV vector comprising a nucleic acid comprising an expression construct comprising a promoter operably linked to a transgene insert encoding a PGRN protein, wherein the transgene insert comprises the nucleotide sequence of SEQ ID NO: 68; and (b) an AAV9 capsid protein, for use in a method of treating fronto-temporal dementia with a GRN mutation in a subject.

126. A method of quantifying a PGRN protein level in a cerebrospinal fluid (CSF) sample, the method comprising:

(1) diluting the CSF sample in a master mix containing dithiothreitol (DTT) and sample buffer;

(2) loading the diluted CSF sample, an anti-progranulin antibody, a secondary antibody that detects the anti-progranulin antibody, luminol and peroxide into wells of a capillary cartridge;

(3) loading the capillary cartridge into an automated Western blot immunoassay instrument;

(4) using the automated Western blot immunoassay instrument to calculate signal intensity, peak area, and signal-to-noise ratio; and (5) quantifying a progranulin protein level in the CSF sample as the peak area of immunoreactivity to the anti-progranulin antibody.

What is claimed is:

1. A method for treating a subject having fronto-temporal dementia with a GRN mutation, the method comprising administering to the subject a recombinant adeno-associated virus (rAAV) comprising:

(i) a rAAV vector comprising a nucleic acid comprising an expression construct comprising a promoter operably linked to a transgene insert encoding a progranulin (PGRN) protein, wherein the transgene insert comprises the nucleotide sequence of SEQ ID NO: 68; and (ii) an AAV9 capsid protein;

wherein the rAAV is administered via an injection into the cisterna magna.

2. The method of claim 1, wherein the rAAV is administered to the subject at a dose ranging from about $1\times10^{13}$ vector genomes (vg) to about $7\times10^{14}$ vg.

3. The method of claim 1, wherein the promoter is a chicken beta actin (CBA) promoter.

4. The method of claim 1, wherein the rAAV vector further comprises a cytomegalovirus (CMV) enhancer.

5. The method of claim 1, wherein the rAAV vector further comprises a Woodchuck Hepatitis Virus Posttranscriptional Regulatory Element (WPRE).

6. The method of claim 1, wherein the rAAV vector further comprises a Bovine Growth Hormone polyA signal tail.

7. The method of claim 1, wherein the nucleic acid comprises two adeno-associated virus inverted terminal repeats (ITR) sequences flanking the expression construct, wherein the first ITR sequence is a 5' ITR, and the second ITR sequence is a 3' ITR.

8. The method of claim 7, wherein each of the two ITR sequences is a wild-type AAV2 ITR sequence.

9. The method of claim 7, wherein the rAAV vector further comprises a TRY region between the 5' ITR and the expression construct, wherein the TRY region comprises SEQ ID NO: 28.

10. The method of claim 1, wherein the rAAV is administered in a formulation comprising about 20 mM Tris, pH 8.0, about 1 mM $MgCl_2$, about 200 mM NaCl, and about 0.001% w/v poloxamer 188.

11. A method for treating a subject having fronto-temporal dementia with a GRN mutation, the method comprising administering to the subject a rAAV comprising:

(i) a rAAV vector comprising a nucleic acid comprising, in 5' to 3' order:

(a) an AAV2 ITR;

(b) a CMV enhancer;

(c) a CBA promoter;

(d) a transgene insert encoding a PGRN protein, wherein the transgene insert comprises the nucleotide sequence of SEQ ID NO: 68;

(e) a WPRE;

(f) a Bovine Growth Hormone polyA signal tail; and (g) an AAV2 ITR; and (ii) an AAV9 capsid protein;

wherein the rAAV is administered via an injection into the cisterna magna.

12. The method of claim 11, wherein the rAAV is administered to the subject at a dose ranging from about $1\times10^{13}$ vg to about $7\times10^{14}$ vg.

13. The method of claim 11, wherein the rAAV is administered in a formulation comprising about 20 mM Tris, pH 8.0, about 1 mM $MgCl_2$, about 200 mM NaCl, and about 0.001% w/v poloxamer 188.

* * * * *